(12) United States Patent
Gross et al.

(10) Patent No.: US 7,435,837 B2
(45) Date of Patent: Oct. 14, 2008

(54) DIHYDROBENZOFURANYL ALKANAMINE DERIVATIVES AND METHODS FOR USING SAME

(75) Inventors: Jonathan Laird Gross, Cranbury, NJ (US); Marla Jean Williams, Whitehouse Station, NJ (US); Gary Paul Stack, Ambler, PA (US); Hong Gao, Belle Mead, NJ (US); Dahui Zhou, East Brunswick, NJ (US)

(73) Assignee: Wyeth, Madison, NJ (US)

( * ) Notice: Subject to any disclaimer, the term of this patent is extended or adjusted under 35 U.S.C. 154(b) by 535 days.

(21) Appl. No.: 10/970,714

(22) Filed: Oct. 21, 2004

(65) Prior Publication Data

US 2005/0143452 A1 Jun. 30, 2005

Related U.S. Application Data

(60) Provisional application No. 60/514,454, filed on Oct. 24, 2003.

(51) Int. Cl.
*C07D 307/81* (2006.01)
*C07D 307/80* (2006.01)

(52) U.S. Cl. ..................................... 549/467
(58) Field of Classification Search ................... 549/467
See application file for complete search history.

(56) References Cited

U.S. PATENT DOCUMENTS

| | | | |
|---|---|---|---|
| 3,513,239 A | 5/1970 | Wiley | 424/285 |
| 3,759,927 A | 9/1973 | Huebner | 543/20 |
| 4,205,080 A | 5/1980 | Carr | |
| 4,237,144 A | 12/1980 | Cragoe et al. | |
| 4,873,325 A | 10/1989 | Olson | |
| 4,992,464 A | 2/1991 | Brooks et al. | |
| 5,110,825 A | 5/1992 | Ogata et al. | |
| 5,147,888 A | 9/1992 | Hanson et al. | |
| 5,171,751 A | 12/1992 | Hanson et al. | |
| 5,292,900 A | 3/1994 | Basha et al. | |
| 5,348,976 A | 9/1994 | Shibata et al. | |
| 5,350,748 A | 9/1994 | Boschelli et al. | |
| 5,436,246 A | 7/1995 | Bernotas et al. | |
| 5,559,127 A | 9/1996 | Hartman et al. | |
| 5,585,492 A | 12/1996 | Chandrakumar et al. | |
| 5,589,482 A | 12/1996 | Thompson | |
| 5,612,356 A | 3/1997 | Yoshimura et al. | |
| 5,616,537 A | 4/1997 | Yokota et al. | |
| 5,663,368 A | 9/1997 | Flisak et al. | |
| 5,665,722 A | 9/1997 | Kulagowski et al. | |
| 5,684,041 A | 11/1997 | Scherz | |
| 5,719,306 A | 2/1998 | Chandrakumar et al. | |
| 5,721,253 A | 2/1998 | Hartman et al. | |
| 5,767,132 A | 6/1998 | Bottcher et al. | 514/337 |
| 5,770,544 A | 6/1998 | Yokota et al. | |
| 5,798,382 A * | 8/1998 | Kogami et al. | 514/469 |
| 5,852,046 A | 12/1998 | Lang et al. | |
| 5,858,995 A | 1/1999 | Kawai et al. | |
| 5,955,495 A | 9/1999 | Bos et al. | |
| 6,011,046 A | 1/2000 | Ohkawa et al. | |
| 6,048,891 A | 4/2000 | Wechter | |
| 6,083,982 A | 7/2000 | Wechter et al. | |
| 6,147,110 A | 11/2000 | Lesieur et al. | |
| 6,150,402 A | 11/2000 | Wechter et al. | |
| 6,242,479 B1 | 6/2001 | Wechter | |
| 6,251,936 B1 | 6/2001 | Wrobel et al. | |
| 6,255,324 B1 | 7/2001 | Heindel et al. | |
| 6,410,562 B1 | 6/2002 | Jirousek et al. | |
| 6,410,578 B1 | 6/2002 | Bouvier et al. | |
| 6,433,175 B1 * | 8/2002 | Adams et al. | 546/94 |
| 6,514,996 B2 | 2/2003 | Ohshima et al. | |
| 6,569,894 B1 | 5/2003 | Takaki et al. | 514/469 |
| 6,638,972 B2 | 10/2003 | Kelly et al. | |
| 6,653,346 B1 | 11/2003 | Wang et al. | |
| 6,667,322 B2 | 12/2003 | Gross et al. | |
| 6,706,757 B2 | 3/2004 | Greenblatt et al. | |
| 6,716,987 B1 | 4/2004 | Ohshima et al. | |
| 6,812,353 B2 | 11/2004 | Bokel et al. | |
| 2002/0169188 A1 | 11/2002 | Cowart et al. | |
| 2002/0177589 A1 | 11/2002 | Cowart et al. | |
| 2002/0183309 A1 | 12/2002 | Cowart et al. | |

(Continued)

FOREIGN PATENT DOCUMENTS

| | | |
|---|---|---|
| DE | 19909760 | 10/1999 |
| EP | 254 642 A1 | 1/1988 |
| EP | 446 809 A1 | 9/1991 |
| EP | 530 149 A1 | 8/1992 |
| EP | 512 570 B1 | 11/1992 |

(Continued)

OTHER PUBLICATIONS

U.S. Appl. No. 60/621,024, filed Oct. 21, 2004, Gontcharov et al.

(Continued)

*Primary Examiner*—D. Margaret Seaman
*Assistant Examiner*—Nizal S Chandrakumar
(74) *Attorney, Agent, or Firm*—Julie Anne Knight; Andrea L. Robidoux; Choate Hall & Stewart LLP

(57) ABSTRACT

Compounds of Formula 1 or pharmaceutically acceptable salts thereof are provided:

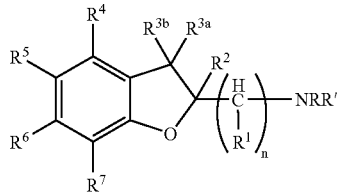

Formula 1 which are agonists or partial agonists of the 2C subtype of brain serotonin receptors. The compounds, and compositions containing the compounds, can be used to treat a variety of central nervous system disorders such as schizophrenia.

31 Claims, No Drawings

U.S. PATENT DOCUMENTS

| | | |
|---|---|---|
| 2003/0064991 A1 | 4/2003 | Harriman et al. |
| 2003/0105830 A1 | 6/2003 | Pham et al. |
| 2003/0134835 A1 | 7/2003 | Hancock et al. |
| 2003/0153548 A1 | 8/2003 | Hancock et al. |
| 2003/0203918 A1 | 10/2003 | Meade et al. |
| 2003/0225252 A1 | 12/2003 | Kim et al. |
| 2004/0009976 A1 | 1/2004 | Takeuchi et al. |
| 2004/0077867 A1 | 4/2004 | Kato et al. |
| 2004/0097433 A1 | 5/2004 | Boddupalli et al. |
| 2004/0122079 A1 | 6/2004 | Crossman et al. |
| 2004/0138286 A1 | 7/2004 | Imazaki et al. |
| 2004/0242668 A1 | 12/2004 | Sall et al. |
| 2005/0026969 A1 | 2/2005 | Cheng et al. |
| 2005/0113283 A1 | 5/2005 | Solow-Cordero et al. |
| 2005/0124692 A1 | 6/2005 | Gross et al. |
| 2005/0137234 A1 | 6/2005 | Bressi et al. |
| 2005/0137247 A1 | 6/2005 | Czeisler et al. |
| 2005/0143452 A1 | 6/2005 | Gross et al. |
| 2005/0154053 A1 | 7/2005 | Rhijn et al. |
| 2005/0250740 A1 | 11/2005 | Lanter et al. |
| 2005/0261347 A1 | 11/2005 | Gross et al. |
| 2006/0074076 A1 | 4/2006 | Termin et al. |
| 2006/0089405 A1 | 4/2006 | Zhou et al. |
| 2006/0111438 A1 | 5/2006 | Gontcharov et al. |
| 2006/0241172 A1 | 10/2006 | Zhou et al. |
| 2006/0241176 A1 | 10/2006 | Stack et al. |
| 2006/0246551 A1 | 11/2006 | Stack et al. |
| 2006/0247276 A1 | 11/2006 | Gross et al. |
| 2006/0252825 A1 | 11/2006 | Tadayon et al. |
| 2006/0258639 A1 | 11/2006 | Logue et al. |
| 2006/0258711 A1 | 11/2006 | Rosenzweig-Lipson |
| 2006/0258712 A1 | 11/2006 | Jacobson |
| 2006/0258713 A1 | 11/2006 | Rosenzweig-Lipson |
| 2006/0258714 A1 | 11/2006 | Heffernan et al. |
| 2006/0258715 A1 | 11/2006 | Jandura et al. |
| 2006/0258739 A1 | 11/2006 | Ai et al. |

FOREIGN PATENT DOCUMENTS

| | | |
|---|---|---|
| EP | 640 602 A1 | 3/1995 |
| EP | 0 707 007 A1 | 4/1996 |
| EP | 846 683 A1 | 6/1998 |
| EP | 1 211 253 A1 | 6/2002 |
| EP | 804 427 B1 | 9/2002 |
| EP | 1 348 708 A1 | 10/2003 |
| EP | 1 514 542 A1 | 3/2005 |
| EP | 1 600 447 A1 | 11/2005 |
| GB | 1 200 892 | 8/1970 |
| GB | 2165276 | 7/1972 |
| GB | 2 007 973 | 6/1977 |
| GB | 2 176 782 A | 1/1987 |
| JP | 59186969 A2 | 10/1984 |
| JP | 05/339271 | 12/1993 |
| JP | 06316563 A2 | 11/1994 |
| JP | 2000007671 | 1/2000 |
| JP | 2000080091 A2 | 3/2000 |
| JP | 2003/261557 | 9/2003 |
| JP | 2005/145859 | 6/2005 |
| WO | WO 91/17144 A1 | 11/1991 |
| WO | WO-92/03427 | 3/1992 |
| WO | WO 93/10089 A1 | 5/1993 |
| WO | WO 94/18193 A1 | 8/1994 |
| WO | WO-94/26738 | 11/1994 |
| WO | WO-96/05191 | 2/1996 |
| WO | WO-96/11192 | 4/1996 |
| WO | WO-96/15099 | 5/1996 |
| WO | WO-96/15100 | 5/1996 |
| WO | WO 96/30367 A1 | 10/1996 |
| WO | WO 97/08167 A1 | 3/1997 |
| WO | WO-98/22452 | 5/1998 |
| WO | WO-98/38188 | 9/1998 |
| WO | WO-98/52946 | 11/1998 |
| WO | WO-99/46267 | 9/1999 |
| WO | WO-99/61435 | 12/1999 |
| WO | WO 00/44737 A1 | 8/2000 |
| WO | WO-00/76990 | 12/2000 |
| WO | WO 00/76990 A1 | 12/2000 |
| WO | WO 00/77001 A1 | 12/2000 |
| WO | WO 00/77010 A2 | 12/2000 |
| WO | WO-01/21606 A1 | 3/2001 |
| WO | WO-01/55111 A1 | 8/2001 |
| WO | WO-02/24672 A2 | 3/2002 |
| WO | WO-02/074758 A2 | 9/2002 |
| WO | WO-03/016276 A2 | 2/2003 |
| WO | WO-03/016307 A1 | 2/2003 |
| WO | WO 03/022813 A1 | 3/2003 |
| WO | WO 03/022814 A1 | 3/2003 |
| WO | WO-03/027090 A2 | 4/2003 |
| WO | WO-03/059342 A1 | 7/2003 |
| WO | WO-03/062392 A2 | 7/2003 |
| WO | WO 03/074051 A1 | 9/2003 |
| WO | WO 03/082264 A1 | 10/2003 |
| WO | WO-2004/045534 A2 | 6/2004 |
| WO | WO-2004/089410 A1 | 10/2004 |
| WO | WO-2005/009389 A2 | 2/2005 |
| WO | WO-2005/011670 A1 | 2/2005 |
| WO | WO-2005/024416 A1 | 3/2005 |
| WO | WO-2005/037223 A2 | 4/2005 |
| WO | WO-2005/044812 A1 | 5/2005 |
| WO | WO-2005/058858 A1 | 6/2005 |
| WO | WO-2005/063240 A1 | 7/2005 |
| WO | WO-2005/066151 A2 | 7/2005 |
| WO | WO-2005/073210 A1 | 8/2005 |
| WO | WO-2005/110985 A2 | 11/2005 |
| WO | WO-2005/118570 A1 | 12/2005 |
| WO | WO-2005/123681 A1 | 12/2005 |
| WO | WO-2005/123731 A2 | 12/2005 |
| WO | WO-2006/000902 A1 | 1/2006 |
| WO | WO-2006/010008 A1 | 1/2006 |
| WO | WO-2006/010750 A1 | 2/2006 |
| WO | WO-2006/018184 A2 | 2/2006 |
| WO | WO-2006/030031 A1 | 3/2006 |
| WO | WO 2006/000902 | 5/2006 |
| WO | WO-2006/047228 A1 | 5/2006 |
| WO | WO-2006/047288 A2 | 5/2006 |

OTHER PUBLICATIONS

Toyoshima, S. et al., "Studies on benzoheterocyclic derivatives. VII. Synthesis and pharmacological action of benzofuran derivatives," *Yakugaku Zasshi*. May 1968;88(5):503-12. Japanese. [English abstract included].

Shinozaki, K. et al, "Synthesis and thromboxane A2 antagonistic activity activity of indane derivatives," *Bioorg Med Chem Lett.* Feb. 8, 1999;9(3):401-6.

Allison, D. B. et al., "Antipsychotic-Induced Weight Gain: A Comprehensive Research Synthesis," *Am. J. Psychiatry*, 1999, 156:1686-1696.

Masand, P. S., "Weight gain associated with psychotropic drugs," *Exp. Opin. Pharmacother.*, 2000, 1: 377-389.

Whitaker, R., "Atypical Antipsychotics: A Modest Advance in Treating Schizophrenia," *Spectrum Life Sciences*. Decision Resources, 2000, 2:1-9.

Schotte, A. et al., "Risperidone compared with new and reference antipsychotic drugs: in vitro and in vivo receptor binding," *Psychopharmacology*, 1996, 124: 57-73.

Cowen, P. J. et al., "Hypophagic, Endocrine and Subjective Responses to m-Chlorophenylpiperazine in Healthy Men and Women," *Human Psychopharmacology*, 1995, 10: 385-391.

Rosenzweig-Lipson, S. et al., "Antiobesity-like effects of the selective 5-HT2C Agonist Way," *ASPET* abstract, 2000.

Di Matteo, V. et al., "Selective blockade of serotonin$_{2C/2B}$ receptors enhances dopamine release in the rat nucleus accumbens," *Nueropharmacology*, 1998, 37: 265-272.

Fox, S. H. et al., "Behavioral Effects of 5-HT$_{2C}$ Receptor Antagonism in the Substantia Nigra Zona Reticulata of the 6-Hydroxydopamine-Lesioned Rat Model of Parkinson's Disease," *Experimental Neurology*, 1998, 151: 35-49.

Millan, M. J. et al., "Serotonin (5-HT)$_{2C}$ receptors tonically inhibit dopamine (DA) and noradrenaline (NA), but not 5-HT, release in the frontal cortex in vivo," *Neuropharmacology*, 1998, 37: 953-955.

Di Matteo, V. et al., "SB 242 084, a selective serotonin$_{2C}$ receptor antagonist, increases dopaminergic transmissions in the mesolimbic system," *Nueropharmacology*, 1999, 38: 1195-1205.

Di Giovanni, G. et al., "Preferential Modulation of Mesolimbic Vs. Nigrostriatal Dopaminergic Function by Serotonin$_{2C/2B}$ Receptor Agonists: A Combined In Vivo Electrophysiological and Microdialysis Study," *Synapse*, 2000, 35: 53-61.

Lloyd-Williams, P. et al., "Atropisomerism, biphenyls and the Suzuki coupling: peptide antibiotics," *Chem. Soc. Rev.*, 2001, 30:145-157.

Wilen, S. H. et al., *Tetrahedron*, 1977, 33:2725-2736.

Wilen, S. H., *Tables of Resolving Agents and Optical Resolutions*, pp. 268-298, E.L. Eliel, Ed., Univ. of Notre Dame Press, Notre Dame, IN 1972.

Krogsgaard-Larson, et al., (ed.) *Design and Application of Prodrugs, Textbook of Drug Design and Development*, Ch. 5, 113-191 (1991).

Bundgaard, et al., *Journal of Drug Delivery Reviews*, 8:1-38 (1992).

Bundgaard, *J. of Pharmaceutical Sciences*, 77(4):285-299 (1988).

Higuchi and Stella (eds.) *Prodrugs as Novel Drug Delivery Systems*, American Chemical Society (1975) pp. 1-115 and 196-223.

Widder, et al. (ed.), *Methods in Enzymology*, vol. 4, Academic Press (1985) pp. 309-396.

Bundgaard (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).

Eliel, E.L., *Stereochemistry of Organic Compounds*, John Wiley & Sons, 1994, pp. 1142-1155.

Al-Bojuk, N. R. et al., "Synthesis and vasorelaxant potency of monagra. A chiral 5-(2-methyl-2,3-dihydro-7-bezofuryl)pyrazolopyrimidone analog of Viagra," *Heterocycles*, 2001, 55(9): 1789-1803.

Ferorelli, S. et al., "Lipase-mediated kinetic resolution of rigid clofibrate analogues with lipid-modifying activity," *Tetrahedron: Asymmetry*, 2001, 12(6): 853-862.

Ramadas, S. et al., "Enantioselective acylation of 2-hydroxymethyl-2,3-kihydrobenzofurans catalyzed by lipase from *Pseudomas cepacia* (Amano PS) and total stereoselective synthesis of (-)-(R)-MEM-protected arthrographol," *Tetrahedron: Asymmetry*, 2000, 11(16): 3375-3393.

Kakigami, T. et al., "Serotonin 5-HT4 receptor agonistic activity of the optical isomers of (±)-4-amino-N-[2-(1-azabicyclo[3.3.0]octan-5-yl)ethyl]-5-chloro-2,3-dihydro-2-methylbenzo[b]furan-7-carboxamide," *Chemical & Pharmaceutical Bulletin*, 1998, 46(6): 1039-1043.

Kuroita, T. et al., "Synthesis and structure-activity relationships of 2,3-dihydrobenzofuran-7-carboxamide derivatives as potent serotonin-3 (5-HT3) receptor antagonists," *Chemical & Pharmaceutical Bulletin*, 1994, 42(1): 95-100.

Takehara, S. et al., "New chiral dopants for FLC materials: optically active cyclic ethers," *Ferroelectrics*, 1993, 148(1-4): 195-202.

Ceccarelli, S. et al., "Synthesis of novel 2-substituted-5-oxycoumarans via a direct route to 2,3-dihydro-5-hydroxy-2-benzofuranacetic acids," *Journal of Heterocyclic Chemistry*, May-Jun. 1993, 30(3): 679-90.

Ayer, W. et al., "Synthesis of (+/-) arthrographol," *Canadian Journal of Chemistry*, 1991, 69(12): 1909-1916.

Kemp, D. S. et al., "New templates for prior thiol capture from xanthene, dibenzo[c,h]xanthen-7-one and 2-methylenedihydrobenzofuran," *Tetrahedron Letters*, 1991, 32(26): 3009-3012.

Murakami, S. et al., "Antidopaminergic effects of the stereoisomers of N-[(1-alkyl-2-pyrrolidinyl)methyl]-5-sulfamoylbenzamides and -2,3-dihydro-benzofuran-7-carboxamides," *Journal of Medicinal Chemistry*, 1991, 34(1): 261-267.

Yodo, M. et al., "Optical resolution and chiral synthesis of methyl 6,7-dichloro-2,3-dihydrobenzo[b]furan-2-carboxylate," *Chemical & Pharmaceutical Bulletin*, 1988, 36(3): 902-913.

Chaudhuri, N. K. et al., "The absolute configuration of SU 23397: a novel neuroleptic agent," *Experientia*, 1977, 33(5): 575-577.

Grundon, M. et al., "Aysmmetric induction in the cyclization of 0-allylphenol with chiral mercury(II) carboxylates," *Journal of the Chemical Society, Chemical Communications*, 1973, 16: 573-574.

Jacques, et al., *Enantiomers, Racemates and Resolutions* Wiley Interscience, New York, 1981.

Eliel, E. L., *Stereochemistry of Carbon Compounds* McGraw-Hill, NY, 1962.

*Remington's Pharmaceutical Sciences*, 17$^{th}$ edition, ed. Alfonoso R. Gennaro, Mack Publishing Company, Easton, PA (1985).

Funke, A. et al., "Préparation et propriétéspharmacologiques de quelques aminométhylcoumaranes," *Bull. Soc. Chim. Fr.*, 1953, pp. 457-461.

Descamps et al, "Recherches dans la série des benzofurannes XLII. Synthèse de benzofuryl-2 méthylamines et d'amides d'acides coumaryliques", *Chime Therapeutique*, 5(3):169-84, 1970.

McNeel, et al., "Synthetic Approaches to 4,8-Dimethyl-5'-(N-pyridiniummethyl)-4',5'-dihydropsoralens and 4,8-Dimethyl-5'-(N-aminomethyl)-4, 5f'-dihydropsoralens [1,2]", *Journal of Heterocyclic Chem.*, 38, 909-916 (2001).

Morris J., et al., "Synthesis and Biological Activity of a Potent Antiplatelet 7-Aminofurochromone", *Bioorganic & Medicinal Chemistry Letters*, 4(21), 2621-2626 (1994).

Sviridov, et al.,, "Azido-substituted arylboronic acids: synthesis & Suzuki-Miyaura cross-coupling reactions", *ChemBridge Corporation*, 62(11): 2639-2647, 2006.

International Search Report, PCT/US2006/015141.

International Search Report, PCT/US2006/015216.

Patent Abstracts of Japan, vol. 018, No. 182, (C-1184), Mar. 29, 1994 & JP 05 339271 A (Kowa Co.), Dec. 21, 1993.

U.S. Appl. No. 11/787,929, Yu et al.

U.S. Appl. No. 11/787,860, Gontcharov et al.

U.S. Appl. No. 11/726,941, Rosenzweig-Lipson.

U.S. Appl. No. 11/787,663, Mirmehrabi.

Beilstein Reference for Struckler dissertation. Beilstein Handbook Sup Series III/IV, vol. 18, p. 7238.

English Translation of Beilstein Reference for Struckler dissertation. Beilstein Handbook Sup Series III/IV, vol. 18, p. 7238.

Trefouel, H. Strueckler and D.Bovet; Comptes Redus des Seances de la Societe de et de Ses Filiales (1939), 130, 27-9.

English Translation of Trefouel, H. Strueckler and D.Bovet; Comptes Redus des Seances de la Societe de et de Ses Filiales (1939), 130, 27-9.

D. Bouvet, Trefouel, J. Stern and H. Strickler, Action du Diethylaminoethoxy-2-Diphenyle (1262F) Sur la Fibrillation Cardiaque Provoquee.

English Translation of D. Bouvet, Trefouel, J. Stern and H. Strickler, Action du Diethylaminoethoxy-2-Diphenyle (1262F) Sur la Fibrillation Cardiaque Provoquee.

Arch. Int. Pharmacodyn., 1939, LXII, fasc. 2. Le Diethylaminoethoxy-2-Diphenyle (1262F).

U.S. Appl. No. 10/970,103, filed Oct. 21, 2004, Gross et al.

U.S. Appl. No. 60/621,023, filed Oct. 21, 2004, Zhou et al.

U.S. Appl. No. 60/621,024, filed Oct. 21, 2004, Gontcharov et al.

\* cited by examiner

DIHYDROBENZOFURANYL ALKANAMINE DERIVATIVES AND METHODS FOR USING SAME

CROSS-REFERENCE TO RELATED APPLICATIONS

The present invention claims priority benefit of U.S. Provisional Application Ser. No. 60/514,454, filed Oct. 24, 2003, which is incorporated herein by reference in its entirety for all purposes.

FIELD OF THE INVENTION

The present invention relates to novel 1-(2,3-dihydro-1-benzofuran-2-yl)alkanamine derivatives that act as agonists and partial agonists of the $5\text{-}HT_{2C}$ receptor, processes for their preparation, and their use in medicine.

BACKGROUND OF THE INVENTION

Schizophrenia affects approximately 5 million people. The most prevalent treatments for schizophrenia are currently the 'atypical' antipsychotics, which combine dopamine ($D_2$) and serotonin ($5\text{-}HT_{2A}$) receptor antagonism. Despite the reported improvements in efficacy and side-effect liability of atypical antipsychotics relative to typical antipsychotics, these compounds do not appear to adequately treat all the symptoms of schizophrenia and are accompanied by problematic side effects, such as weight gain (Allison, D. B., et. al., Am. J. Psychiatry, 156: 1686-1696, 1999; Masand, P. S., Exp. Opin. Pharmacother. I: 377-389, 2000; Whitaker, R., Spectrum Life Sciences. Decision Resources. 2: 1-9, 2000).

Atypical antipsychotics also bind with high affinity to $5\text{-}HT_{2C}$ receptors and function as $5\text{-}HT_{2C}$ receptor antagonists or inverse agonists. Weight gain is a problematic side effect associated with atypical antipsychotics such as clozapine and olanzapine, and it has been suggested that $5\text{-}HT_{2C}$ antagonism is responsible for the increased weight gain. Conversely, stimulation of the $5\text{-}HT_{2C}$ receptor is known to result in decreased food intake and body weight (Walsh et. al., Psychopharmacology 124: 57-73, 1996; Cowen, P. J., et. al., Human Psychopharmacology 10: 385-391, 1995; Rosenzweig-Lipson, S., et. al., ASPET abstract, 2000).

Several lines of evidence support a role for $5\text{-}HT_{2C}$ receptor agonism or partial agonism as a treatment for schizophrenia. Studies suggest that $5\text{-}HT_{2C}$ antagonists increase synaptic levels of dopamine and may be effective in animal models of Parkinson's disease (Di Matteo, V., et. al., Neuropharmacology 37: 265-272, 1998; Fox, S. H., et. al., Experimental Neurology 151: 35-49, 1998). Since the positive symptoms of schizophrenia are associated with increased levels of dopamine, compounds with actions opposite to those of $5\text{-}HT_{2C}$ antagonists, such as $5\text{-}HT_{2C}$ agonists and partial agonists, should reduce levels of synaptic dopamine. Recent studies have demonstrated that $5\text{-}HT_{2C}$ agonists decrease levels of dopamine in the prefrontal cortex and nucleus accumbens (Millan, M. J., et. al., Neuropharmacology 37: 953-955, 1998; Di Matteo, V., et. al., Neuropharmacology 38: 1195-1205, 1999; Di Giovanni, G., et. al., Synapse 35: 53-61, 2000), brain regions that are thought to mediate critical antipsychotic effects of drugs like clozapine. However, $5\text{-}HT_{2C}$ agonists do not decrease dopamine levels in the striatum, the brain region most closely associated with extrapyramidal side effects. In addition, a recent study demonstrates that $5\text{-}HT_{2C}$ agonists decrease firing in the ventral tegmental area (VTA), but not in the substantia nigra. The differential effects of $5\text{-}HT_{2C}$ agonists in the mesolimbic pathway relative to the nigrostriatal pathway suggest that $5\text{-}HT_{2C}$ agonists have limbic selectivity, and will be less likely to produce extrapyramidal side effects associated with typical antipsychotics.

SUMMARY OF THE INVENTION

The present invention relates to certain dihydrobenzofuranyl alkanamine derivatives and to their use in medicine. In one aspect, the invention relates to novel 1-(2,3-dihydro-1-benzofuran-2-yl)alkanamine derivatives that act as agonists or partial agonists of the $5\text{-}HT_{2C}$ receptor. The compounds can be used, for example, to treat schizophrenia and the concomitant mood disorders and cognitive impairments of schizophrenia. Compounds of the present invention are preferably less likely to produce the body weight increases associated with current atypical antipsychotics. The compounds of the present invention can also be used for the treatment of obesity and its comorbidities.

In certain embodiments, the invention relates to compounds of Formula 1:

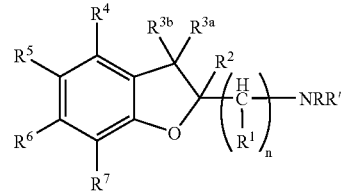

Formula 1 or pharmaceutically acceptable salts thereof;

wherein:

R and R' are, independently, hydrogen, alkyl of 1 to 6 carbon atoms, cycloalkyl of 3 to 6 carbon atoms, or alkylcycloalkyl of 4 to 12 carbon atoms having 3 to 6 carbons in the cycloalkyl ring;

alternatively R and R' can be taken together with the nitrogen to which they are attached to form a ring containing 2-5 carbon atoms, wherein one of the ring carbon atoms is optionally replaced by nitrogen, sulfur or oxygen;

$R^1$ and $R^2$ are, independently, hydrogen, alkyl of 1 to 6 carbon atoms, cycloalkyl of 3 to 6 carbon atoms, or perfluoroalkyl of 1 to 6 carbon atoms;

$R^{3a}$ and $R^{3b}$ are, independently, hydrogen, halogen, hydroxyl, alkyl of 1 to 6 carbon atoms, cycloalkyl of 3 to 6 carbon atoms, perfluoroalkyl of 1 to 6 carbon atoms, alkoxy of 1 to 6 carbon atoms, or perfluoroalkoxy of 1 to 6 carbon atoms;

$R^4$, $R^5$, $R^6$, and $R^7$ are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, aryl of 5 to 10 carbon atoms, aryloxy of 5 to 10 carbon atoms, 5 to 10 membered heteroaryl having 1 to 3 heteroatoms each independently selected from nitrogen, oxygen or sulfur, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, dialkylamino of 1 to 6 carbon atoms per alkyl moiety, cycloalkyl of 3 to 8 carbon atoms, or 3 to 8 membered heterocycloalkyl having 1 to 3 heteroatoms each independently selected from nitrogen, oxygen or sulfur, wherein the cycloalkyl and heterocycloalkyl groups are saturated or partially saturated; and n is 1, 2 or 3;

wherein at least one of $R^4$, $R^5$, $R^6$ and $R^7$ is branched alkyl of 3 to 8 carbon atoms, branched alkenyl of 3 to 8 carbon atoms, or —Y—$R^8$, wherein Y is selected from a direct bond, lower alkyl, lower ankenyl, O, and NH and $R^8$ is aryl of 5 to 10 carbon atoms, 5 to 10 membered heteroaryl, cycloalkyl of 3 to 8 carbon atoms, or 3 to 8 membered heterocycloalkyl; and wherein any aryl, heteroaryl, cycloalkyl or heterocycloalkyl may optionally be substituted with 1 to 5 substituents independently selected from halogen, hydroxyl, cyano, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

In certain other embodiments, the invention relates to methods for treating a patient suffering from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, sexual dysfunction, substance abuse, addiction to alcohol and various other drugs, including cocaine and nicotine, gastrointestinal disorders, obesity, or a central nervous system deficiency associated with trauma, stroke, or spinal cord injury that includes administering to the patient a therapeutically effective amount of a compound of formula 1, or a pharmaceutically acceptable salt thereof.

In still other embodiments, the invention relates to compositions comprising a compound of Formula 1 or a pharmaceutically acceptable salt thereof, and one or more pharmaceutically acceptable carriers, excipients, or diluents.

DETAILED DESCRIPTION OF THE INVENTION

The present invention relates to novel 1-(2,3,-dihydro-1-benzofuran-2-yl)alkanamine derivatives that are agonists or partial agonists of the 2c subtype of brain serotonin receptors.

The term "alkyl," as used herein, refers to an aliphatic hydrocarbon chain having up to 8 carbon atoms, preferably 1 to 6 carbon atoms, and more preferably 1 to 4 carbon atoms. The term "alkyl" includes, but is not limited to, straight and branched chains such as methyl, ethyl, n-propyl, isopropyl, n-butyl, isobutyl, sec-butyl, t-butyl, n-pentyl, isopentyl, neopentyl, n-hexyl, and isohexyl. In some embodiments, the alkyl group is preferably branched having 3 to 8 carbon atoms. The term "lower alkyl" refers to an alkyl group having 1 to 3 carbon atoms.

The term "alkenyl," as used herein refers to an aliphatic straight or branched hydrocarbon chain having 2 to 8 carbon atoms that may contain 1 to 3 double bonds. Examples of alkenyl groups include vinyl, prop-1-enyl, allyl, methallyl, but-1-enyl, but-2-enyl, but-3-enyl, or 3,3-dimethylbut-1-enyl. In some embodiments, the alkenyl is preferably a branched alkenyl of 3 to 8 carbon atoms. The term "lower alkenyl" refers to an alkenyl group having 1 to 3 carbon atoms.

The term "cycloalkyl," as used herein, refers to a saturated or partially saturated, hydrocarbon ring containing 3 to 8 carbon atoms and more preferably 5 to 7 carbon atoms. Cycloalkyl groups may be monocyclic or bicyclic, and more preferably monocyclic. Bicyclic cycloalkyl groups are preferably bridged. "Bridged" refers to a cycloalkyl group that contains at least one carbon-carbon bond between two non-adjacent carbon atoms of the cycloalkyl ring. "Partially saturated" refers to a nonaromatic cycloalkyl group containing at least one double bond and preferably one double bond. Preferably, the cycloalkyl group is saturated. The cycloalkyl group may be unsubstituted or substituted as described hereinafter. The term "alkylcycloalkyl," as used herein, refers to the group —R-cycloalkyl, where cycloalkyl is as defined above and R is an alkyl moiety having 1 to 6, preferably 1 to 4, and more preferably 1 to 3 carbon atoms.

The term "heterocycloalkyl," as used herein, refers to a 3 to 8 membered, and more preferably 5 to 7 membered cycloalkyl group in which one to three carbon atoms of the cycloalkyl group are replaced with a heteroatom independently selected from oxygen, nitrogen, or sulfur. The heterocycloalkyl group may be saturated or partially saturated, and may be monocyclic or bicyclic (such as bridged). Preferably, the heterocycloalkyl is monocyclic. The heterocycloalkyl group may be unsubstituted or substituted as described hereinafter.

The term "aryl," as used herein refers to a 5 to 10 membered carbocyclic aromatic ring. The aryl may be monocyclic or bicyclic, and may be substituted or unsubstituted. Monocyclic aryl groups preferably have 5, 6, or 7 members and bicyclic aryl groups preferably have 8, 9 or 10 members. Exemplary aryl groups include phenyl and naphthyl.

The term "aryloxy," as used herein, refers to the group Ar—O—, where Ar is an aryl group of 5 to 10 carbon atoms as previously described.

The term "heteroaryl," as used herein, refers to a 5 to 10 membered monocyclic or bicyclic carbon containing aromatic ring having 1 to 3 of its ring members independently selected from nitrogen, sulfur or oxygen. Monocyclic rings preferably have 5 to 6 members and bicyclic rings preferably have 8 to 10 membered ring structures. The heteroaryl group may be unsubstituted or substituted as described hereinafter. Examples of heteroaryls include, but are not limited to, thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, or quinazolinyl.

The term "perfluoroalkyl," as used herein, refers to a straight or branched aliphatic hydrocarbon chain of 1 to 6 carbon atoms and preferably 1 to 3 carbon atoms, in which all hydrogens are replaced with fluorine.

The term "alkanamido," as used herein, refers to the group R—C(=O)—NH— where R is an alkyl group of 1 to 5 carbon atoms.

The term "alkanoyl," as used herein, refers to the group R—C(=O)— where R is an alkyl group of 1 to 5 carbon atoms.

The term "alkanoyloxy," as used herein, refers to the group R—C(=O)—O— where R is an alkyl group of 1 to 5 carbon atoms.

The term "alkanesulfonamido," as used herein, refers to the group R—S(±)$_2$—NH— where R is an alkyl group of 1 to 6 carbon atoms.

The term "alkoxy," as used herein, refers to the group R—O— where R is an alkyl group of 1 to 6 carbon atoms.

The term "perfluoroalkoxy," as used herein, refers to the group R—O where R is a perfluoroalkyl group of 1 to 6 carbon atoms.

The terms "monoalkylamino" and "dialkylamino," as used herein, respectively refer to —NHR and —NRR$_a$, where R and R$_a$ are independently selected from an alkyl group of 1 to 6 carbon atoms.

The term "carboxamido," as used herein, refers to the group NH$_2$—C(=O)—.

The term "carboalkoxy," as used herein, refers to the group R—O—C(=O)— where R is an alkyl group of 1 to 5 carbon atoms.

The term "carboxy," as used herein, refers to the group —COOH.

The terms "halogen" or "halo," as used herein, refer to chlorine, bromine, fluorine or iodine.

The term "substituted," as used herein, refers to a moiety, such as an aryl, heteroaryl, cycloalkyl or heterocycloalkyl moiety having from 1 to about 5 substituents, and more preferably from 1 to about 3 substituents independently selected from a halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms. Preferred substituents are a halogen atom, a lower alkyl, a perfluoroalkyl of 1 to 3 carbon atoms, an alkoxy group of 1 to 3 carbon atoms or a perfluoroalkoxy of 1 to 3 carbon atoms.

The terms "effective amount" and "therapeutically effective amount," as used herein, refer to the amount of a compound of Formula 1 that, when administered to a patient, is effective to at least partially treat a condition from which the patient is suffering from. Such conditions include, but are not limited to, schizophrenia, schizoaffective disorder, schizophreniform disorder, L-DOPA-induced psychosis, bipolar disorder, obesity, obsessive compulsive disorder, depression, panic disorder, sleep disorders, eating disorders, and epilepsy.

The term "pharmaceutically acceptable salts" or "pharmaceutically acceptable salt" refers to salts derived from treating a compound of Formula 1 with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids.

The term "patient," as used herein, refers to a mammal.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" or "treating," as used herein, refers to partially or completely alleviating, inhibiting, preventing, ameliorating and/or relieving the condition.

The terms "suffer" or "suffering" as used herein refers to one or more conditions that a patient has been diagnosed with, or is suspected to have.

In certain embodiments, the invention relates to compounds of Formula 1:

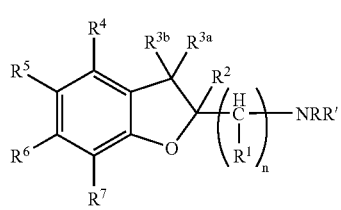

Formula 1 or pharmaceutically acceptable salts thereof;

wherein:
R and R' are, independently, hydrogen, alkyl of 1 to 6 carbon atoms, cycloalkyl of 3 to 6 carbon atoms, or alkylcycloalkyl of 4 to 12 carbon atoms having 3 to 6 carbons in the cycloalkyl ring;

alternatively R and R' can be taken together with the nitrogen to which they are attached to form a ring containing 2-5 carbon atoms, wherein one of the ring carbon atoms is optionally replaced by nitrogen, sulfur or oxygen;

$R^1$ and $R^2$ are each, independently, hydrogen, alkyl of 1 to 6 carbon atoms, cycloalkyl of 3 to 6 carbon atoms, or perfluoroalkyl of 1 to 6 carbon atoms;

$R^{3a}$ and $R^{3b}$ are, independently, hydrogen, halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms;

$R^4$, $R^5$, $R^6$, and $R^7$ are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, aryl of 5 to 10 carbon atoms, aryloxy of 5 to 10 carbon atoms, 5 to 10 membered heteroaryl having 1 to 3 heteroatoms each independently selected from nitrogen, oxygen or sulfur, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, dialkylamino of 1 to 6 carbon atoms per alkyl moiety, cycloalkyl of 3 to 8 carbon atoms, or 3 to 8 membered heterocycloalkyl having 1 to 3 heteroatoms each independently selected from nitrogen, oxygen or sulfur, wherein the cycloalkyl and heterocycloalkyl groups are saturated or partially saturated; and n is 1, 2 or 3;

wherein at least one of $R^4$, $R^5$, $R^6$ and $R^7$ is branched alkyl of 3 to 8 carbon atoms, branched alkenyl of 3 to 8 carbon atoms, or —Y—$R^8$, wherein Y is selected from a direct bond, lower alkyl, lower ankenyl, O, and NH and $R^8$ is aryl of 5 to 10 carbon atoms, 5 to 10 membered heteroaryl, cycloalkyl of 3 to 8 carbon atoms, or 3 to 8 membered heterocycloalkyl; and wherein any aryl, heteroaryl, cycloalkyl or heterocycloalkyl may optionally be substituted with 1 to 5 substituents independently selected from halogen, hydroxyl, cyano, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

As set forth above, R and R' are, independently, hydrogen, alkyl of 1 to 6 carbon atoms, cycloalkyl of 3 to 6 carbon atoms, or alkylcycloalkyl of 4 to 12 carbon atoms having 3 to 6 carbons in the cycloalkyl ring. Alternatively R and R' can be taken together with the nitrogen to which they are attached to form a ring containing 2-5 carbon atoms, wherein one of the ring carbon atoms is optionally replaced by nitrogen, sulfur or oxygen. In some embodiments, R, R', $R^1$, and $R^2$ are each, independently, hydrogen or alkyl of 1 to 6 carbon atoms. In certain embodiments, R' is hydrogen, and R, $R^1$, and $R^2$ are each independently hydrogen or alkyl of 1 to 6 carbon atoms. In certain preferred embodiments, each of R, R', $R^1$, and $R^2$ is hydrogen.

As also set forth above, $R^{3a}$ and $R^{3b}$ may each be selected, independently, from hydrogen, halogen, hydroxyl, alkyl of 1 to 6 carbon atoms, cycloalkyl of 3 to 6 carbon atoms, perfluoroalkyl of 1 to 6 carbon atoms, alkoxy of 1 to 6 carbon atoms, and perfluoroalkoxy of 1 to 6 carbon atoms. In certain embodiments, $R^{3a}$ and $R^{3b}$ are each independently hydrogen or alkyl of 1 to 3 carbon atoms and more preferably hydrogen.

$R^4$, $R^5$, $R^6$, and $R^7$ may each be selected, independently, from hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, aryl of 5 to 10 carbon atoms, aryloxy of 5 to 10 carbon atoms, 5 to 10 membered heteroaryl having 1 to 3 heteroatoms each independently selected from nitrogen, oxygen or sulfur, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, dialkylamino of 1 to 6 carbon atoms per alkyl moiety, cycloalkyl of 3 to 8 carbon atoms, and 3 to 8 membered heterocycloalkyl having 1 to 3 heteroatoms each independently selected from nitrogen, oxygen or sulfur, wherein the cycloalkyl and heterocycloalkyl groups are saturated or partially saturated. Moreover, at least one of $R^4$, $R^5$, $R^6$ and $R^7$ is —Y—$R^8$, wherein Y is selected from a direct bond, lower alkyl, lower ankenyl, O, and NH, and $R^8$ is an aryl of 5 to 10 carbon atoms, 5 to 10 membered heteroaryl, cycloalkyl of 3 to 8 carbon atoms, 3 to 8 membered heterocycloalkyl, branched alkyl of 3 to 8 carbon atoms, or branched alkenyl of 3 to 8 carbon atoms. Additionally, where any of $R^4$, $R^5$, $R^6$, and $R^7$ is aryl, heteroaryl, cycloalkyl or heterocycloalkyl, it may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, and perfluoroalkoxy of 1 to 6 carbon atoms.

In certain preferred embodiments, Y is a direct bond.

In certain embodiments, $R^4$, $R^5$, $R^6$, and $R^7$ are preferably selected from hydrogen, halogen, alkyl of 1 to 8 carbon atoms, perfluoroalkyl of 1 to 3 carbon atoms, alkoxy of 1 to 3 carbon atoms, alkenyl of 2 to 8 carbon atoms, cycloalkyl of 3 to 8 carbon atoms, 3 to 8 membered heterocycloalkyl, aryl of 5 to 10 carbon atoms, or 5 to 10 membered heteroaryl, provided that at least one of $R^4$, $R^5$, $R^6$ and $R^7$ is an aryl of 5 to 10 carbon atoms, 5 to 10 membered heteroaryl, cycloalkyl of 3 to 8 carbon atoms, 3 to 8 membered heterocycloalkyl, branched alkyl of 3 to 8 carbon atoms, or branched alkenyl of 3 to 8 carbon atoms, wherein any aryl, heteroaryl, cycloalkyl or heterocycloalkyl may optionally be substituted with 1 to 5 substituents independently selected from halogen, hydroxyl, cyano, alkyl of 1 to 6 carbon atoms, perfluoroalkyl of 1 to 6 carbon atoms, alkoxy of 1 to 6 carbon atoms, and perfluoroalkoxy of 1 to 6 carbon atoms. Preferably, at least one of $R^4$, $R^5$, $R^6$ and $R^7$ and more preferably at least one of $R^4$, $R^5$ and $R^7$ is an aryl of 5 to 10 carbon atoms, 5 to 10 membered heteroaryl, cycloalkyl of 3 to 8 carbon atoms, or 3 to 8 membered heterocycloalkyl.

In certain preferred embodiments of the invention, $R^4$, $R^5$, and $R^6$ are, independently, hydrogen, halogen, alkyl of 1 to 3 carbon atoms, alkoxy of 1 to 3 carbon atoms, perfluoroalkyl of 1 to 3 carbon atoms, or perfluoroalkoxy of 1 to 3 carbon atoms, and $R^7$ is a branched alkyl of 3 to 8 carbon atoms, branched alkenyl of 3 to 8 carbon atoms, cycloalkyl of 3 to 8 carbon atoms, 3 to 8 membered heterocycloalkyl, aryl of 5 to 10 carbon atoms, or 5 to 10 membered heteroaryl, wherein any aryl, heteroaryl, cycloalkyl or heterocycloalkyl may optionally be substituted with 1 to 5 substituents independently selected from halogen, hydroxyl, cyano, alkyl of 1 to 6 carbon atoms, perfluoroalkyl of 1 to 6 carbon atoms, alkoxy of 1 to 6 carbon atoms, and perfluoroalkoxy of 1 to 6 carbon atoms. More preferably, $R^7$ is a branched alkyl of 3 to 6 carbon atoms, branched alkenyl of 3 to 6 carbon atoms, cycloalkyl of 3 to 8 carbon atoms, aryl of 5 to 10 carbon atoms, or 5 to 10 membered heteroaryl, each of which may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, and perfluoroalkoxy of 1 to 6 carbon atoms.

In other preferred embodiments of the invention, each of $R^4$, $R^5$ and $R^7$ is, independently, aryl of 5 to 10 carbon atoms, cycloalkyl of 5 to 7 carbon atoms, or 5 to 10 membered heteroaryl, and more preferably is phenyl or napthyl, or a 5 to 10 membered heteroaryl selected from thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, or quinazolinyl, each of which may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, and perfluoroalkoxy of 1 to 6 carbon atoms.

In certain other preferred embodiments of the invention, $R^7$ is aryl of 5 to 10 carbon atoms, cycloalkyl of 5 to 7 carbon atoms, branched alkyl of 3 to 6 carbon atoms, branched alkenyl of 3 to 6 carbon atoms, or 5 to 10 membered heteroaryl, and more preferably is phenyl or napthyl, or a 5 to 10 membered heteroaryl selected from thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, or quinazolinyl, each of which may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, and perfluoroalkoxy of 1 to 6 carbon atoms. In preferred compounds of this embodiment, R, R', $R^1$, and $R^2$ are each, independently, hydrogen or alkyl of 1 to 6 carbon atoms.

In other preferred embodiments, $R^7$ is aryl of 5 to 10 carbon atoms, cycloalkyl of 5 to 7 carbon atoms, or 5 to 10 membered heteroaryl, or more preferably phenyl, wherein said aryl (including phenyl), cycloalkyl or heteroaryl may optionally be substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, and perfluoroalkoxy of 1 to 6 carbon atoms. In preferred compounds of this embodiment, at least one of $R^4$ and $R^5$ is halogen, alkyl of 1 to 6 carbon atoms, perfluoroalkyl of 1 to 3 carbon atoms, or alkoxy of 1 to 6 carbon atoms. Even more preferred compounds are those in which at least one of $R^4$ and $R^5$ is halogen, alkyl of 1 to 6 carbon atoms, perfluoroalkyl of 1 to 3 carbon atoms, or alkoxy of 1 to 6 carbon atoms, and R, R', $R^1$, and $R^2$ are each, independently, hydrogen or alkyl of 1 to 6 carbon atoms. In other preferred embodiments, $R^7$ is aryl of 5 to 10 carbon atoms, optionally substituted with 1 to 3 substituents independently selected from a halogen atom, a lower alkyl, a perfluoroalkyl of 1 to 3 carbon atoms, an alkoxy group of 1 to 3 carbon atoms or a perfluoroalkoxy of 1 to 3 carbon atoms.

In certain embodiments, $R^7$ is selected from from the group consisting of:
4-methoxy-2-methylphenyl,
2-chloro-4-(trifluoromethyl)phenyl,
2-chloro-4-methoxyphenyl,
2-chloro-4-(trifluoromethoxy)phenyl,
({7-[4-methoxy-2-(trifluoromethyl)phenyl,
4-ethoxy-2-methylphenyl,
4-ethoxy-2-(trifluoromethyl)phenylamine, 4-chloro-2-(trifluoromethyl)phenyl,
4-fluoro-2-(trifluoromethyl)phenyl,
2-ethyl-4-methoxyphenyl,
2,4-dichlorophenyl,
2,4-dimethylphenyl,
4-isopropyl-2-methoxyphenyl,
4-isopropoxy-2-(trifluoromethyl)phenyl,
2-chloro-4-isopropoxyphenyl,
4-chloro-2-methylphenyl,
2,6-difluorophenyl,
2-chloro-6-fluorophenyl,
2-fluoro-6-(trifluoromethyl)phenyl,
2,6-bis(trifluoromethyl)phenyl,
2,3-dichlorophenyl,
3-chloro-2-fluorophenyl,
2-chloro-3-methylphenyl,
2,6-dichloro-4-methoxyphenyl, and
5-fluoro-2-methoxyphenyl.

In the compounds of the present invention, n is 1, 2 or 3, preferably 1 or 2, and more preferably 1.

In still further preferred embodiments of the invention, the compounds of Formula 1 are:
(±)-1-(4-phenyl-2,3-dihydro-1-benzofuran-2-yl)methanamine,
(+)-1-(4-phenyl-2,3-dihydro-1-benzofuran-2-yl)methanamine,
(−)-1-(4-phenyl-2,3-dihydro-1-benzofuran-2-yl)methanamine,
(±)-1-[4-(2-methylphenyl)-2,3-dihydro-1-benzofuran-2-yl]methanamine,
(+)-1-[4-(2-methylphenyl)-2,3-dihydro-1-benzofuran-2-yl]methanamine,
(−)-1-[4-(2-methylphenyl)-2,3-dihydro-1-benzofuran-2-yl]methanamine,
(±)-(7-cyclopentyl-2,3-dihydro-1-benzofuran-2-yl)methylamine,
(−)-(7-cyclopentyl-2,3-dihydro-1-benzofuran-2-yl)methylamine,
(+)-(7-cyclopentyl-2,3-dihydro-1-benzofuran-2-yl)methylamine,
(±)-(5-chloro-7-cyclohexyl-2,3-dihydro-1-benzofuran-2-yl)methylamine,
(±)-N-[(5-chloro-7-cyclohexyl-2,3-dihydro-1-benzofuran-2-yl)methyl]-N-methylamine,
(±)-(7-tert-butyl-5-methoxy-2,3-dihydro-1-benzofuran-2-yl)methylamine,
(±)-(7-isopropyl-2,3-dihydro-1-benzofuran-2-yl)methylamine,
(−)-(7-isopropyl-2,3-dihydro-1-benzofuran-2-yl)methylamine,
(+)-(7-isopropyl-2,3-dihydro-1-benzofuran-2-yl)methylamine,
(±)-1-(5-chloro-7-isopropyl-4-methyl-2,3-dihydro-1-benzofuran-2-yl)methanamine,
(−)-1-(5-chloro-7-isopropyl-4-methyl-2,3-dihydro-1-benzofuran-2-yl)methanamine,
(+)-1-(5-chloro-7-isopropyl-4-methyl-2,3-dihydro-1-benzofuran-2-yl)methanamine,
(±)-1-(7-tert-butyl-2,3-dihydro-1-benzofuran-2-yl)methanamine,
(−)-1-(7-tert-butyl-2,3-dihydro-1-benzofuran-2-yl)methanamine,
(+)-1-(7-tert-butyl-2,3-dihydro-1-benzofuran-2-yl)methanamine,
(±)-1-(7-tert-butyl-5-chloro-2,3-dihydro-1-benzofuran-2-yl)methanamine,
(−)-1-(7-tert-butyl-5-chloro-2,3-dihydro-1-benzofuran-2-yl)methanamine,
(+)-1-(7-tert-butyl-5-chloro-2,3-dihydro-1-benzofuran-2-yl)methanamine,
(±)-(6-phenyl-2,3-dihydro-1-benzofuran-2-yl)methanamine,
(±)-1-{7-[3,5-bis(trifluoromethyl)phenyl]-2,3-dihydro-1-benzofuran-2-yl}methanamine,
(±)-1-[7-(1-naphthyl)-2,3-dihydro-1-benzofuran-2-yl]methanamine,
(±)-1-[7-(3-chloro-4-fluorophenyl)-2,3-dihydro-1-benzofuran-2-yl]methanamine,
(±)-1-[7-(3,5-dichlorophenyl)-2,3-dihydro-1-benzofuran-2-yl]methanamine,
(±)-1-(7-phenyl-2,3-dihydro-1-benzofuran-2-yl)methanamine,
(+)-(1-(7-phenyl-2,3-dihydro-1-benzofuran-2-yl)methanamine,
(−)-1-(7-phenyl-2,3-dihydro-1-benzofuran-2-yl)methanamine,
(±)-1-[7-(2-naphthyl)-2,3-dihydro-1-benzofuran-2-yl]methanamine,
(±)-1-(2',3'-dihydro-2,7'-bi-1-benzofuran-2'-yl)methanamine,
(±)-1-[7-(3-methylphenyl)-2,3-dihydro-1-benzofuran-2-yl]methanamine,
(+)-1-[7-(3-methylphenyl)-2,3-dihydro-1-benzofuran-2-yl]methanamine,
(−)-1-[7-(3-methylphenyl)-2,3-dihydro-1-benzofuran-2-yl]methanamine,
(±)-1-(7-thien-3-yl-2,3-dihydro-1-benzofuran-2-yl)methanamine,
(+)-1-(7-thien-3-yl-2,3-dihydro-1-benzofuran-2-yl)methanamine,
(−)-1-(7-thien-3-yl-2,3-dihydro-1-benzofuran-2-yl)methanamine,
(±)-1-[7-(2-methylphenyl)-2,3-dihydro-1-benzofuran-2-yl]methanamine,
(+)-1-[7-(2-methylphenyl)-2,3-dihydro-1-benzofuran-2-yl]methanamine,
(−)-1-[7-(2-methylphenyl)-2,3-dihydro-1-benzofuran-2-yl]methanamine,
(±)-1-[7-(2-fluorophenyl)-2,3-dihydro-1-benzofuran-2-yl]methanamine,
(+)-1-[7-(2-fluorophenyl)-2,3-dihydro-1-benzofuran-2-yl]methanamine,
(−)-1-[7-(2-fluorophenyl)-2,3-dihydro-1-benzofuran-2-yl]methanamine,
(±)-1-{7-[2-(trifluoromethyl)phenyl]-2,3-dihydro-1-benzofuran-2-yl}methanamine,
(−)-1-{7-[2-(trifluoromethyl)phenyl]-2,3-dihydro-1-benzofuran-2-yl}methanamine,
(+)-1-{7-[2-(trifluoromethyl)phenyl]-2,3-dihydro-1-benzofuran-2-yl}methanamine,
(±)-1-[7-(2,6-dimethylphenyl)-2,3-dihydro-1-benzofuran-2-yl]methanamine,
(−)-1-[7-(2,6-dimethylphenyl)-2,3-dihydro-1-benzofuran-2-yl]methanamine,
(+)-1-[7-(2,6-dimethylphenyl)-2,3-dihydro-1-benzofuran-2-yl]methanamine,
(±)-1-[7-(2-methoxyphenyl)-2,3-dihydro-1-benzofuran-2-yl]methanamine,
(±)-[7-(2-chlorophenyl)-2,3-dihydro-1-benzofuran-2-yl]methanamine,
(±)-[7-(2-isopropylphenyl)-2,3-dihydro-1-benzofuran-2-yl]methylamine, (+)-[7-(2-isopropylphenyl)-2,3-dihydro-1-benzofuran-2-yl]methylamine,
(−)-[7-(2-isopropylphenyl)-2,3-dihydro-1-benzofuran-2-yl]methylamine,
(±)-1-[7-(3-fluorophenyl)-2,3-dihydro-1-benzofuran-2-yl]methanamine,
(±)-1-[7-(3-chlorophenyl)-2,3-dihydro-1-benzofuran-2-yl]methanamine,
(+)-1-[7-(3-chlorophenyl)-2,3-dihydro-1-benzofuran-2-yl]methanamine,
(−)-1-[7-(3-chlorophenyl)-2,3-dihydro-1-benzofuran-2-yl]methanamine,
(±)-1-[7-(3-methoxyphenyl)-2,3-dihydro-1-benzofuran-2-yl]methanamine,
(±)-1-{7-[3-(trifluoromethyl)phenyl]-2,3-dihydro-1-benzofuran-2-yl}methanamine,
(±)-1-[7-(4-methylphenyl)-2,3-dihydro-1-benzofuran-2-yl]methanamine,
(+)-1-[7-(4-methylphenyl)-2,3-dihydro-1-benzofuran-2-yl]methanamine,
(−)-1-[7-(4-methylphenyl)-2,3-dihydro-1-benzofuran-2-yl]methanamine,
(±)-1-[7-(4-fluorophenyl)-2,3-dihydro-1-benzofuran-2-yl]methanamine,
(+)-1-[7-(4-fluorophenyl)-2,3-dihydro-1-benzofuran-2-yl]methanamine,
(−)-1-[7-(4-fluorophenyl)-2,3-dihydro-1-benzofuran-2-yl]methanamine,
(±)-1-[7-(4-chlorophenyl)-2,3-dihydro-1-benzofuran-2-yl]methanamine,
(+)-1-[7-(4-chlorophenyl)-2,3-dihydro-1-benzofuran-2-yl]methanamine,
(−)-1-[7-(4-chlorophenyl)-2,3-dihydro-1-benzofuran-2-yl]methanamine,
(±)-1-[7-(4-methoxyphenyl)-2,3-dihydro-1-benzofuran-2-yl]methanamine,
(+)-1-[7-(4-methoxyphenyl)-2,3-dihydro-1-benzofuran-2-yl]methanamine,
(−)-1-[7-(4-methoxyphenyl)-2,3-dihydro-1-benzofuran-2-yl]methanamine,
(±)-1-{7-[4-(trifluoromethyl)]-2,3-dihydro-1-benzofuran-2-yl}methanamine,
(±)-1-[7-(2,4-dichlorophenyl)-2,3-dihydro-1-benzofuran-2-yl]methanamine,
(±)-1-(5-chloro-7-phenyl-2,3-dihydro-1-benzofuran-2-yl)methanamine,
(+)-1-(5-chloro-7-phenyl-2,3-dihydro-1-benzofuran-2-yl)methanamine,
(−)-1-(5-chloro-7-phenyl-2,3-dihydro-1-benzofuran-2-yl)methanamine,
(±)-1-[5-chloro-7-(2-chlorophenyl)-2,3-dihydro-1-benzofuran-2-yl]methanamine,
(±)-1-[5-chloro-7-(3-methylphenyl)-2,3-dihydro-1-benzofuran-2-yl]methanamine,
(±)-1-[5-chloro-7-(3-chlorophenyl)-2,3-dihydro-1-benzofuran-2-yl]methanamine,
(±)-(5-chloro-7-thien-3-yl-2,3-dihydro-1-benzofuran-2-yl)methylamine,
(−)-(5-chloro-7-thien-3-yl-2,3-dihydro-1-benzofuran-2-yl)methylamine,
(+)-(5-chloro-7-thien-3-yl-2,3-dihydro-1-benzofuran-2-yl)methylamine,
(+)-N-[(5-chloro-7-thien-3-yl-2,3-dihydro-1-benzofuran-2-yl)methyl]-N-methylamine,
(−)-N-[(5-chloro-7-thien-3-yl-2,3-dihydro-1-benzofuran-2-yl)methyl]-N-methylamine,
(±)-1-[5-chloro-7-(2-methylphenyl)-2,3-dihydro-1-benzofuran-2-yl]methanamine,
(+)-1-[5-chloro-7-(2-methylphenyl)-2,3-dihydro-1-benzofuran-2-yl]methanamine,
(−)-1-[5-chloro-7-(2-methylphenyl)-2,3-dihydro-1-benzofuran-2-yl]methanamine,
(±)-1-(4-fluoro-7-phenyl-2,3-dihydro-1-benzofuran-2-yl)methanamine,
(±)-1-[4-fluoro-7-(2-methylphenyl)-2,3-dihydro-1-benzofuran-2-yl]methanamine,
(±)-1-[7-(2-chlorophenyl)-5-fluoro-2,3-dihydro-1-benzofuran-2-yl]methanamine,
(+)-1-[7-(2-chlorophenyl)-5-fluoro-2,3-dihydro-1-benzofuran-2-yl]methanamine,
(−)-1-[7-(2-chlorophenyl)-5-fluoro-2,3-dihydro-1-benzofuran-2-yl]methanamine,
(±)-1-(5-fluoro-7-phenyl-2,3-dihydro-1-benzofuran-2-yl)methanamine,
(±)-1-[5-fluoro-7-(2-methylphenyl)-2,3-dihydro-1-benzofuran-2-yl]methanamine,
(+)-1-[5-fluoro-7-(2-methylphenyl)-2,3-dihydro-1-benzofuran-2-yl]methanamine,
(−)-1-[5-fluoro-7-(2-methylphenyl)-2,3-dihydro-1-benzofuran-2-yl]methanamine,
(±)-1-[5-fluoro-7-(2-fluorophenyl)-2,3-dihydro-1-benzofuran-2-yl]methanamine,
(±)-1-{5-fluoro-7-[2-(trifluoromethyl)phenyl]-2,3-dihydro-1-benzofuran-2-yl}methanamine,
(±)-(4,5-difluoro-7-phenyl-2,3-dihydro-1-benzofuran-2-yl)methylamine,
(±)-1-[4,5-difluoro-7-(2-methylphenyl)-2,3-dihydro-1-benzofuran-2-yl]methanamine,
(±)-1-(5-chloro-2-methyl-7-phenyl-2,3-dihydro-1-benzofuran-2-yl)methanamine,
(±)-(5-chloro-2-methyl-7-thien-3-yl-2,3-dihydro-1-benzofuran-2-yl)methylamine,
(±)-(5-chloro-2-methyl-7-thien-2-yl-2,3-dihydro-1-benzofuran-2-yl)methylamine,
(−)-1-(7-tert-butyl-5-methoxy-2,3-dihydro-1-benzofuran-2-yl)methanamine,
(+)-1-(7-tert-butyl-5-methoxy-2,3-dihydro-1-benzofuran-2-yl)methanamine,
(±)-1-{7-[(1E)-3,3-dimethylbut-1-enyl]-2,3-dihydro-1-benzofuran-2-yl}methanamine,
(±)-1-[7-(3,3-dimethylbutyl)-2,3-dihydro-1-benzofuran-2-yl]methanamine,
(±)-1-[4-(4-methylphenyl)-2,3-dihydro-1-benzofuran-2-yl]methanamine,
(±)-1-{4-[2-(trifluoromethyl)phenyl]-2,3-dihydro-1-benzofuran-2-yl}methanamine,
(−)-1-{4-[2-(trifluoromethyl)phenyl]-2,3-dihydro-1-benzofuran-2-yl}methanamine,
(+)-1-{4-[2-(trifluoromethyl)phenyl]-2,3-dihydro-1-benzofuran-2-yl}methanamine,
(±)-1-[4-(2,6-dimethylphenyl)-2,3-dihydro-1-benzofuran-2-yl]methanamine,
(+)-1-[4-(2,6-dimethylphenyl)-2,3-dihydro-1-benzofuran-2-yl]methanamine,
(−)-1-[4-(2,6-dimethylphenyl)-2,3-dihydro-1-benzofuran-2-yl]methanamine,
(+)-1-[7-(2-methoxyphenyl)-2,3-dihydro-1-benzofuran-2-yl]methanamine,
(−)-1-[7-(2-chlorophenyl)-2,3-dihydro-1-benzofuran-2-yl]methanamine,
(+)-1-[7-(2-chlorophenyl)-2,3-dihydro-1-benzofuran-2-yl]methanamine, (+)-1-[7-(3-fluorophenyl)-2,3-dihydro-1-benzofuran-2-yl]
methanamine,
(−)-1-[7-(3-fluorophenyl)-2,3-dihydro-1-benzofuran-2-yl]
methanamine,
(+)-1-[7-(3-methoxyphenyl)-2,3-dihydro-1-benzofuran-2-yl]methanamine,
(−)-1-[7-(3-methoxyphenyl)-2,3-dihydro-1-benzofuran-2-yl]methanamine,
(−)-1-{7-[3-(trifluoromethyl)phenyl]-2,3-dihydro-1-benzofuran-2-yl}methanamine,
(+)-1-{7-[3-(trifluoromethyl)phenyl]-2,3-dihydro-1-benzofuran-2-yl}methanamine,
(+)-1-{7-[4-(trifluoromethyl)phenyl]-2,3-dihydro-1-benzofuran-2-yl}methanamine,
(−)-1-{7-[4-(trifluoromethyl)phenyl]-2,3-dihydro-1-benzofuran-2-yl}methanamine,
(±)-1-[7-(2,6-difluorophenyl)-2,3-dihydro-1-benzofuran-2-yl]methanamine,
(±)-1-[7-(2,6-dichlorophenyl)-2,3-dihydro-1-benzofuran-2-yl]methanamine,
(−)-1-[7-(2,6-dichlorophenyl)-2,3-dihydro-1-benzofuran-2-yl]methanamine,
(+)-1-[7-(2,6-dichlorophenyl)-2,3-dihydro-1-benzofuran-2-yl]methanamine,
(±)-1-[7-(2,4-dimethoxyphenyl)-2,3-dihydro-1-benzofuran-2-yl]methanamine,
(−)-1-[7-(2,4-dimethoxyphenyl)-2,3-dihydro-1-benzofuran-2-yl]methanamine,
(+)-1-[7-(2,4-dimethoxyphenyl)-2,3-dihydro-1-benzofuran-2-yl]methanamine,
(±)-1-[7-(2,4-difluorophenyl)-2,3-dihydro-1-benzofuran-2-yl]methanamine,
(+)-1-[7-(2,4-difluorophenyl)-2,3-dihydro-1-benzofuran-2-yl]methanamine,
(−)-1-[7-(2,4-difluorophenyl)-2,3-dihydro-1-benzofuran-2-yl]methanamine,
(−)-1-[7-(2,4-dichlorophenyl)-2,3-dihydro-1-benzofuran-2-yl]methanamine,
(+)-1-[7-(2,4-dichlorophenyl)-2,3-dihydro-1-benzofuran-2-yl]methanamine,
(−)-1-{5-fluoro-7-[2-(trifluoromethyl)phenyl]-2,3-dihydro-1-benzofuran-2-yl}methanamine,
(+)-1-{5-fluoro-7-[2-(trifluoromethyl)phenyl]-2,3-dihydro-1-benzofuran-2-yl}methanamine,
(±)-1-(7-benzyl-2,3-dihydro-1-benzofuran-2-yl)methanamine,
(+)-1-(7-benzyl-2,3-dihydro-1-benzofuran-2-yl)methanamine,
(−)-1-(7-benzyl-2,3-dihydro-1-benzofuran-2-yl)methanamine,
(±)-1-{7-[(E)-2-phenylvinyl]-2,3-dihydro-1-benzofuran-2-yl}methanamine, or
(±)-1-[7-(2-phenylethyl)-2,3-dihydro-1-benzofuran-2-yl]methanamine, or a pharmaceutically acceptable salt thereof.

In other preferred embodiments of the invention, the compounds of Formula 1 are:
(±)-1-[7-(2,3-dimethylphenyl)-2,3-dihydro-1-benzofuran-2-yl]methanamine,
(±)-{[7-(2,3-dimethoxyphenyl)-2,3-dihydro-1-benzofuran-2-yl]methyl}amine,
(−)-{[(7-(2,3-dimethoxyphenyl)-2,3-dihydro-1-benzofuran-2-yl]methyl}amine,
(+)-{[(7-(2,3-dimethoxyphenyl)-2,3-dihydro-1-benzofuran-2-yl]methyl}amine,
(+)-{[7-(4-chloro-2-methylphenyl)-2,3-dihydro-1-benzofuran-2-yl]methyl}amine,
(−)-{[7-(4-chloro-2-methylphenyl)-2,3-dihydro-1-benzofuran-2-yl]methyl}amine,
(±)-{[7-(2,3-difluorophenyl)-2,3-dihydro-1-benzofuran-2-yl]methyl}amine,
(±)-{[7-(2,5-dimethylphenyl)-2,3-dihydro-1-benzofuran-2-yl]methyl}amine,
(±)-{[7-(2,5-dimethoxyphenyl)-2,3-dihydro-1-benzofuran-2-yl]methyl}amine,
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(−)-{[7-(2,5-dichlorophenyl)-2,3-dihydro-1-benzofuran-2-yl]methyl}amine,
(±)-{[7-(2,4,6-trichlorophenyl)-2,3-dihydro-1-benzofuran-2-yl]methyl}amine,
(±)-{[7-(4-chloro-2-methylphenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(±)-{[7-(5-chloro-2-methoxyphenyl)-2,3-dihydro-1-benzofuran-2-yl]methyl}amine,
(±)-[(7-pyridin-3-yl-2,3-dihydro-1-benzofuran-2-yl)methyl]amine,
(+)-{[7-pyridin-3-yl-2,3-dihydro-1-benzofuran-2-yl]methyl}amine,
(−)-{[7-pyridin-3-yl-2,3-dihydro-1-benzofuran-2-yl]methyl}amine,
(±)-N-[2-(aminomethyl)-2,3-dihydro-1-benzofuran-7-yl]-N-phenylamine,
(±)-N-[2-(aminomethyl)-2,3-dihydro-1-benzofuran-7-yl]-N-(4-methylphenyl)amine,
(±)-N-[2-(aminomethyl)-2,3-dihydro-1-benzofuran-7-yl]-N-(4-chlorophenyl)amine,
(±)-N-[2-(aminomethyl)-2,3-dihydro-1-benzofuran-7-yl]-N-(4-methoxyphenyl)amine,
(±)-N-[2-(aminomethyl)-2,3-dihydro-1-benzofuran-7-yl]-N-[4-(trifluoromethyl)phenyl]amine,
(±)-N-[2-(aminomethyl)-2,3-dihydro-1-benzofuran-7-yl]-N-(4-fluorophenyl)amine,
(±)-N-[2-(aminomethyl)-2,3-dihydro-1-benzofuran-7-yl]-N-(3,4-dichlorophenyl)amine,
(±)-N-[2-(aminomethyl)-2,3-dihydro-1-benzofuran-7-yl]-N-(2,4-dimethylphenyl)amine,
(±)-N-[2-(aminomethyl)-2,3-dihydro-1-benzofuran-7-yl]-N-(3,4-dimethylphenyl)amine,
(±)-N-[2-(aminomethyl)-2,3-dihydro-1-benzofuran-7-yl]-N-(3-methylphenyl)amine,
(±)-N-[2-(aminomethyl)-2,3-dihydro-1-benzofuran-7-yl]-N-(3-fluorophenyl)amine,
(±)-N-2-(aminomethyl)-N-[3-(trifluoromethyl)phenyl]-2,3-dihydro-1-benzofuran-7-amine,
(±)-N-[2-(aminomethyl)-2,3-dihydro-1-benzofuran-7-yl]-N-(4-methoxy-3-methylphenyl)amine,
(±)-N-[2-(aminomethyl)-2,3-dihydro-1-benzofuran-7-yl]-N-(3,5-difluorophenyl)amine,
(±)-N-[2-(aminomethyl)-2,3-dihydro-1-benzofuran-7-yl]-N-(3-trifluoromethoxy)phenyl]amine,
(±)-N-[2-(aminomethyl)-2,3-dihydro-1-benzofuran-7-yl]-N-(3-chloro-4-methylphenyl)amine,
(±)-N-[2-(aminomethyl)-2,3-dihydro-1-benzofuran-7-yl]-N-(3,5-dichlorophenyl)amine,
(±)-N-[2-(aminomethyl)-2,3-dihydro-1-benzofuran-7-yl]-N-(3-chlorophenyl)amine, (±)-N-[2-(aminomethyl)-2,3-dihydro-1-benzofuran-7-yl]-N-(4-chloro-3-methylphenyl)amine,
(±)-N-[2-(aminomethyl)-2,3-dihydro-1-benzofuran-7-yl]-N-(3,5-dimethylphenyl)amine,
(±)-N-[2-(aminomethyl)-2,3-dihydro-1-benzofuran-7-yl]-N-(3-chloro-4-fluorophenyl)amine,
(±)-N-[2-(aminomethyl)-2,3-dihydro-1-benzofuran-7-yl]-N-(2-fluorophenyl)amine,
(±)-{[5-fluoro-7-(2-methoxyphenyl)-2,3-dihydro-1-benzofuran-2-yl]methyl}amine,
(±)-{[5-fluoro-7-(3-fluorophenyl)-2,3-dihydro-1-benzofuran-2-yl]methyl}amine,
(±)-{[5-fluoro-7-(3-methoxyphenyl)-2,3-dihydro-1-benzofuran-2-yl]methyl}amine,
(±)-{[5-fluoro-7-(3-methylphenyl)-2,3-dihydro-1-benzofuran-2-yl]methyl}amine,
(±)-{[5-fluoro-7-(4-fluorophenyl)-2,3-dihydro-1-benzofuran-2-yl]methyl}amine,
(±)-{[5-fluoro-7-(4-chlorophenyl)-2,3-dihydro-1-benzofuran-2-yl]methyl}amine,
(±)-{[5-fluoro-7-(4-methylphenyl)-2,3-dihydro-1-benzofuran-2-yl]methyl}amine,
(±)-{[5-fluoro-7-(4-methoxyphenyl)-2,3-dihydro-1-benzofuran-2-yl]methyl}amine,
(±)-[(5-fluoro-7-thien-3-yl-2,3-dihydro-1-benzofuran-2-yl)methyl]amine,
(±)-{[5-fluoro-7-(3-furyl)-2,3-dihydro-1-benzofuran-2-yl]methyl}amine,
(±)-[(5-fluoro-7-pyridin-2-yl-2,3-dihydro-1-benzofuran-2-yl)methyl]amine,
(±)-[(5-fluoro-7-pyridin-3-yl-2,3-dihydro-1-benzofuran-2-yl)methyl]amine,
(−)-[(5-fluoro-7-pyridin-3-yl-2,3-dihydro-1-benzofuran-2-yl)methyl]amine,
(+)-{[5-fluoro-7-pyridin-3-yl-2,3-dihydro-1-benzofuran-2-yl]methyl}amine,
(±)-[(5-fluoro-7-pyridin-4-yl-2,3-dihydro-1-benzofuran-2-yl)methyl]amine,
(±)-[(5-fluoro-7-pyrimidin-5-yl-2,3-dihydro-1-benzofuran-2-yl)methyl]amine,
(±)-{[7-(2,3-dichlorophenyl)-5-fluoro-2,3-dihydro-1-benzofuran-2-yl]methyl}amine,
(±)-{[7-(2,3-dimethoxyphenyl)-5-fluoro-2,3-dihydro-1-benzofuran-2-yl]methyl}amine,
(−)-{[7-(2,3-dimethoxyphenyl)-5-fluoro-2,3-dihydro-1-benzofuran-2-yl]methyl}amine,
(+)-{[7-(2,3-dimethoxyphenyl)-5-fluoro-2,3-dihydro-1-benzofuran-2-yl]methyl}amine,
(±)-{[7-(2,4-difluorophenyl)-5-fluoro-2,3-dihydro-1-benzofuran-2-yl]methyl}amine,
(±)-{[7-(2,4-dichlorophenyl)-5-fluoro-2,3-dihydro-1-benzofuran-2-yl]methyl}amine,
(−)-{[5-fluoro-7-(2,4-dichlorophenyl)-2,3-dihydro-1-benzofuran-2-yl]methyl}amine,
(+)-{[5-fluoro-7-(2,4-dichlorophenyl)-2,3-dihydro-1-benzofuran-2-yl]methyl}amine,
(±)-{[7-(2,4-dimethoxyphenyl)-5-fluoro-2,3-dihydro-1-benzofuran-2-yl]methyl}amine,
(±)-{[7-(2,5-difluorophenyl)-5-fluoro-2,3-dihydro-1-benzofuran-2-yl]methyl}amine,
(±)-{[7-(2,5-dichlorophenyl)-5-fluoro-2,3-dihydro-1-benzofuran-2-yl]methyl}amine,
(±)-{[7-(2,5-dimethylphenyl)-5-fluoro-2,3-dihydro-1-benzofuran-2-yl]methyl}amine,
(±)-{[7-(2,5-dimethoxyphenyl)-5-fluoro-2,3-dihydro-1-benzofuran-2-yl]methyl}amine,
(±)-{[5-fluoro-7-(5-methoxy-2-methylphenyl)-2,3-dihydro-1-benzofuran-2-yl]methyl}amine,
(±)-{[5-fluoro-7-(2-methoxy-5-methylphenyl)-2,3-dihydro-1-benzofuran-2-yl]methyl}amine,
(±)-{[7-(2,6-difluorophenyl)-5-fluoro-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(+)-{[7-(2,6-dimethylphenyl)-5-fluoro-2,3-dihydro-1-benzofuran-2-yl]methyl}amine,
(−)-{[7-(2,6-dimethylphenyl)-5-fluoro-2,3-dihydro-1-benzofuran-2-yl]methyl}amine,
(±)-{[7-(2,6-dichlorophenyl)-5-fluoro-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine,
(±)-1-cyclopropyl-N-{[7-(2,6-dichlorophenyl)-5-fluoro-2,3-dihydro-1-benzofuran-2-yl]methyl}methanamine,
(±)-N-{[7-(2,6-dichlorophenyl)-5-fluoro-2,3-dihydro-1-benzofuran-2-yl]methyl}cyclobutanamine,
(±)-N-{[7-(2,6-dichlorophenyl)-5-fluoro-2,3-dihydro-1-benzofuran-2-yl]methyl}ethanamine,
(±)-N-{[7-(2,6-dichlorophenyl)-5-fluoro-2,3-dihydro-1-benzofuran-2-yl]methyl}propan-1-amine,
(±)-N-{[7-(2,6-dichlorophenyl)-5-fluoro-2,3-dihydro-1-benzofuran-2-yl]methyl}propan-2-amine,
(±)-{[7-(2,6-dichlorophenyl)-5-fluoro-2,3-dihydro-1-benzofuran-2-yl]methyl}dimethylamine,
(±)-1-{[7-(2,6-dichlorophenyl)-5-fluoro-2,3-dihydro-1-benzofuran-2-yl]methyl}piperidine
(±)-1-{[7-(2,6-dichlorophenyl)-5-fluoro-2,3-dihydro-1-benzofuran-2-yl]methyl}morpholine
(±)-1-{[7-(2,6-dichlorophenyl)-5-fluoro-2,3-dihydro-1-benzofuran-2-yl]methyl}pyrrolidine
(±)-{[5-chloro-7-(2-fluorophenyl)-2,3-dihydro-1-benzofuran-2-yl]methyl}amine,
(±)-{[5-chloro-7-(2-methoxyphenyl)-2,3-dihydro-1-benzofuran-2-yl]methyl}amine,
(±)-{[5-chloro-7-(3-furyl)-2,3-dihydro-1-benzofuran-2-yl]methyl}amine,
(±)-{[5-chloro-7-(2,3-difluorophenyl)-2,3-dihydro-1-benzofuran-2-yl]methyl}amine,
(−)-{[5-chloro-7-(2,3-difluorophenyl)-2,3-dihydro-1-benzofuran-2-yl]methyl}amine,
(+)-{[5-chloro-7-(2,3-difluorophenyl)-2,3-dihydro-1-benzofuran-2-yl]methyl}amine,
(±)-{[5-chloro-7-(2,3-dichlorophenyl)-2,3-dihydro-1-benzofuran-2-yl]methyl}amine,
(±)-{[5-chloro-7-(2,3-dimethylphenyl)-2,3-dihydro-1-benzofuran-2-yl]methyl}amine,
(±)-{[5-chloro-7-(2,3-dimethoxyphenyl)-2,3-dihydro-1-benzofuran-2-yl]methyl}amine,
(±)-{[5-chloro-7-(2,4-difluorophenyl)-2,3-dihydro-1-benzofuran-2-yl]methyl}amine,
(±)-{[5-chloro-7-(2,4-dichlorophenyl)-2,3-dihydro-1-benzofuran-2-yl]methyl}amine,
(−)-{[5-chloro-7-(2,4-dichlorophenyl)-2,3-dihydro-1-benzofuran-2-yl]methyl}amine,
(+)-{[5-chloro-7-(2,4-dichlorophenyl)-2,3-dihydro-1-benzofuran-2-yl]methyl}amine,
(±)-{[5-chloro-7-(2,4-dimethoxyphenyl)-2,3-dihydro-1-benzofuran-2-yl]methyl}amine,
(±)-{[5-chloro-7-(2,5-difluorophenyl)-2,3-dihydro-1-benzofuran-2-yl]methyl}amine,
(±)-{[5-chloro-7-(2,5-dichlorophenyl)-2,3-dihydro-1-benzofuran-2-yl]methyl}amine, (±)-{[5-chloro-7-(5-chloro-2-methoxyphenyl)-2,3-dihydro-1-benzofuran-2-yl]methyl}amine,
(±)-{[5-chloro-7-(3,4-difluorophenyl)-2,3-dihydro-1-benzofuran-2-yl]methyl}amine,
(±)-{[5-chloro-7-(3-chloro-4-fluorophenyl)-2,3-dihydro-1-benzofuran-2-yl]methyl}amine,
(±)-{[5-chloro-7-(2,6-dimethylphenyl)-2,3-dihydro-1-benzofuran-2-yl]methyl}amine,
(−)-{[5-chloro-7-(2,6-dimethylphenyl)-2,3-dihydro-1-benzofuran-2-yl]methyl}amine,
(+)-{[5-chloro-7-(2,6-dimethylphenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(+)-{[5-chloro-7-(2,6-dichlorophenyl)-2,3-dihydro-1-benzofuran-2-yl]methyl}amine,
(−)-{[5-chloro-7-(2,6-dichlorophenyl)-2,3-dihydro-1-benzofuran-2-yl]methyl}amine,
(±)-{[(5-chloro-7-pyridin-3-yl-2,3-dihydro-1-benzofuran-2-yl)methyl]amine,
(±)-N-{[5-chloro-7-(2,6-dimethylphenyl)-2,3-dihydro-1-benzofuran-2-yl]methyl}cyclopropanamine,
(±)-N-{[5-chloro-7-(2,6-dimethylphenyl)-2,3-dihydro-1-benzofuran-2-yl]methyl}(cyclopropylmethyl)amine,
(±)-N-{[5-chloro-7-(2,6-dimethylphenyl)-2,3-dihydro-1-benzofuran-2-yl]methyl}cyclobutanamine,
(±)-N-{[5-chloro-7-(2,6-dimethylphenyl)-2,3-dihydro-1-benzofuran-2-yl]methyl}ethanamine,
(±)-N-{[5-chloro-7-(2,6-dimethylphenyl)-2,3-dihydro-1-benzofuran-2-yl]methyl}propan-2-amine,
(±)-{[5-chloro-7-(2,6-dimethylphenyl)-2,3-dihydro-1-benzofuran-2-yl]methyl}dimethylamine,
(±)-1-{[5-chloro-7-(2,6-dimethylphenyl)-2,3-dihydro-1-benzofuran-2-yl]methyl}piperidine,
(±)-4-{[5-chloro-7-(2,6-dimethylphenyl)-2,3-dihydro-1-benzofuran-2-yl]methyl}morpholine,
(±)-4-{[5-chloro-7-(2,6-dimethylphenyl)-2,3-dihydro-1-benzofuran-2-yl]methyl}thiomorpholine
(±)-N-{[5-chloro-7-(2,6-dimethylphenyl)-2,3-dihydro-1-benzofuran-2-yl]methyl}propan-1-amine,
(±)-1-{[5-chloro-7-(2,6-dimethylphenyl)-2,3-dihydro-1-benzofuran-2-yl]methyl}piperazine
(±)-1-{[5-chloro-7-(2,6-dimethylphenyl)-2,3-dihydro-1-benzofuran-2-yl]methyl}pyrrolidine
(±)-{[(5-methyl-7-phenyl-2,3-dihydro-1-benzofuran-2-yl)methyl]amine,
(±)-{[7-(2-methylphenyl)-5-methyl-2,3-dihydro-1-benzofuran-2-yl]methyl}amine,
(±)-{[7-(2-fluorophenyl)-5-methyl-2,3-dihydro-1-benzofuran-2-yl]methyl}amine,
(±)-{[7-(2-methoxyphenyl)-5-methyl-2,3-dihydro-1-benzofuran-2-yl]methyl}amine,
(±)-{[7-(2-chlorophenyl)-5-methyl-2,3-dihydro-1-benzofuran-2-yl]methyl}amine,
(±)-({5-methyl-7-[2-(trifluoromethyl)phenyl]-2,3-dihydro-1-benzofuran-2-yl}methyl)amine,
(±)-{[7-(3-chlorophenyl)-5-methyl-2,3-dihydro-1-benzofuran-2-yl]methyl}amine,
(±)-{[7-(3-methylphenyl)-5-methyl-2,3-dihydro-1-benzofuran-2-yl]methyl}amine,
(±)-{[7-(4-methylphenyl)-5-methyl-2,3-dihydro-1-benzofuran-2-yl]methyl}amine,
(±)-{[7-(4-fluorophenyl)-5-methyl-2,3-dihydro-1-benzofuran-2-yl]methyl}amine,
(±)-{[7-(4-chlorophenyl)-5-methyl-2,3-dihydro-1-benzofuran-2-yl]methyl}amine,
(±)-{[7-(4-methoxyphenyl)-5-methyl-2,3-dihydro-1-benzofuran-2-yl]methyl}amine,
(±)-{[7-(2,3-dimethoxyphenyl)-5-methyl-2,3-dihydro-1-benzofuran-2-yl]methyl}amine,
(−)-{[7-(2,3-dimethoxyphenyl)-5-methyl-2,3-dihydro-1-benzofuran-2-yl]methyl}amine,
(+)-{[7-(2,3-dimethoxyphenyl)-5-methyl-2,3-dihydro-1-benzofuran-2-yl]methyl}amine,
(±)-{[7-(2,4-dichlorophenyl)-5-methyl-2,3-dihydro-1-benzofuran-2-yl]methyl}amine,
(−)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dimethylphenyl)-5-methyl-2,3-dihydro-1-benzofuran-2-yl]methyl}amine,
(±)-{[7-(2,6-dichlorophenyl)-5-methyl-2,3-dihydro-1-benzofuran-2-yl]methyl}amine,
(−)-{[7-(2,6-dichlorophenyl)-5-methyl-2,3-dihydro-1-benzofuran-2-yl]methyl}amine,
(+)-{[7-(2,6-dichlorophenyl)-5-methyl-2,3-dihydro-1-benzofuran-2-yl]methyl}amine,
(±)-{[5-ethyl-7-(2-methylphenyl)-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[5-isopropyl-7-(2-methylphenyl)-2,3-dihydro-1-benzofuran-2-yl]methyl}amine,
(±)-{[5-isopropyl-7-(2-chlorophenyl)-2,3-dihydro-1-benzofuran-2-yl]methyl}amine,
(±)-{[5-cyclopentyl-7-(2-methylphenyl)-2,3-dihydro-1-benzofuran-2-yl]methyl}amine,
(±)-{[5-cyclopentyl-7-(2-chlorophenyl)-2,3-dihydro-1-benzofuran-2-yl]methyl}amine,
(±)-{[5-isocyano-7-(2-methylphenyl)-2,3-dihydro-1-benzofuran-2-yl]methyl}amine,
(±)-{[5-isocyano-7-(2-chlorophenyl)-2,3-dihydro-1-benzofuran-2-yl]methyl}amine,
(±)-{[5-(trifluoromethyl)-7-(2-fluorophenyl)-2,3-dihydro-1-benzofuran-2-yl]methyl}amine,
(±)-{[5-(trifluoromethyl)-7-(2-methylphenyl)-2,3-dihydro-1-benzofuran-2-yl]methyl}amine,
(±)-{[5-(trifluoromethyl)-7-(2-chlorophenyl)-2,3-dihydro-1-benzofuran-2-yl]methyl}amine,
(±)-{[5-(trifluoromethyl)-7-(2-methoxyphenyl)-2,3-dihydro-1-benzofuran-2-yl]methyl}amine,
(±)-{[5-(trifluoromethyl)-7-(2-(trifluoromethyl)phenyl)-2,3-dihydro-1-benzofuran-2-yl]methyl}amine,
(±)-{[5-(trifluoromethyl)-7-(3-methylphenyl)-2,3-dihydro-1-benzofuran-2-yl]methyl}amine,
(±)-{[5-(trifluoromethyl)-7-(3-fluorophenyl)-2,3-dihydro-1-benzofuran-2-yl]methyl}amine,
(±)-{[5-(trifluoromethyl)-7-(3-chlorophenyl)-2,3-dihydro-1-benzofuran-2-yl]methyl}amine,
(±)-{[5-(trifluoromethyl)-7-(3-methoxyphenyl)-2,3-dihydro-1-benzofuran-2-yl]methyl}amine,
(±)-{[5-(trifluoromethyl)-7-(3-(trifluoromethyl)phenyl)-2,3-dihydro-1-benzofuran-2-yl]methyl}amine,
(±)-{[5-(trifluoromethyl)-7-(4-methylphenyl)-2,3-dihydro-1-benzofuran-2-yl]methyl}amine,
(±)-{[5-(trifluoromethyl)-7-(4-fluorophenyl)-2,3-dihydro-1-benzofuran-2-yl]methyl}amine,
(±)-{[5-(trifluoromethyl)-7-(4-chlorophenyl)-2,3-dihydro-1-benzofuran-2-yl]methyl}amine, (±)-{[5-(trifluoromethyl)-7-(4-methoxyphenyl)-2,3-dihydro-1-benzofuran-2-yl]methyl}amine,
(±)-{[5-(trifluoromethyl)-7-(4-(trifluoromethyl)phenyl)-2,3-dihydro-1-benzofuran-2-yl]methyl}amine,
(±)-{[7-(2,3-dimethylphenyl)-5-(trifluoromethyl)-2,3-dihydro-1-benzofuran-2-yl]methyl}amine,
(±)-{[7-(2,3-difluorophenyl)-5-(trifluoromethyl)-2,3-dihydro-1-benzofuran-2-yl]methyl}amine,
(±)-{[7-(2,3-dichlorophenyl)-5-(trifluoromethyl)-2,3-dihydro-1-benzofuran-2-yl]methyl}amine,
(±)-{[7-(2,3-dimethoxyphenyl)-5-(trifluoromethyl)-2,3-dihydro-1-benzofuran-2-yl]methyl}amine,
(±)-{[7-(2,4-difluorophenyl)-5-(trifluoromethyl)-2,3-dihydro-1-benzofuran-2-yl]methyl}amine,
(±)-{[7-(2,4-dimethoxyphenyl)-5-(trifluoromethyl)-2,3-dihydro-1-benzofuran-2-yl]methyl}amine,
(±)-{[7-(3,4-difluorophenyl)-5-(trifluoromethyl)-2,3-dihydro-1-benzofuran-2-yl]methyl}amine,
(±)-{[7-(3-chloro-4-fluorophenyl)-5-(trifluoromethyl)-2,3-dihydro-1-benzofuran-2-yl]methyl}amine,
(±)-{[7-(2,5-difluorophenyl)-5-(trifluoromethyl)-2,3-dihydro-1-benzofuran-2-yl]methyl}amine,
(±)-{[7-(2,5-dichlorophenyl)-5-(trifluoromethyl)-2,3-dihydro-1-benzofuran-2-yl]methyl}amine,
(±)-{[7-(2,6-dimethylphenyl)-5-(trifluoromethyl)-2,3-dihydro-1-benzofuran-2-yl]methyl}amine,
(±)-{[7-(4-butylphenyl)-5-(trifluoromethyl)-2,3-dihydro-1-benzofuran-2-yl]methyl}amine,
(±)-4-[2-(aminomethyl)-5-(trifluoromethyl)-2,3-dihydro-1-benzofuran-7-yl]benzonitrile
(±)-{[7-(3-furyl)-5-(trifluoromethyl)-2,3-dihydro-1-benzofuran-2-yl]methyl}amine,
(±)-{[7-thien-3-yl-5-(trifluoromethyl)-2,3-dihydro-1-benzofuran-2-yl]methyl}amine,
(±)-{[7-pyridin-3-yl-5-(trifluoromethyl)-2,3-dihydro-1-benzofuran-2-yl]methyl}amine,
(±)-[(5,7-diphenyl-2,3-dihydro-1-benzofuran-2-yl)methyl]amine,
(±)-{[7-(2-chlorophenyl)-5-phenyl-2,3-dihydro-1-benzofuran-2-yl]methyl}amine,
(±)-{[7-(3-chlorophenyl)-5-phenyl-2,3-dihydro-1-benzofuran-2-yl]methyl}amine,
(±)-{[7-(4-chlorophenyl)-5-phenyl-2,3-dihydro-1-benzofuran-2-yl]methyl}amine,
(±)-{[7-(2-fluorophenyl)-5-phenyl-2,3-dihydro-1-benzofuran-2-yl]methyl}amine,
(±)-{[7-(3-fluorophenyl)-5-phenyl-2,3-dihydro-1-benzofuran-2-yl]methyl}amine,
(±)-{[7-(4-fluorophenyl)-5-phenyl-2,3-dihydro-1-benzofuran-2-yl]methyl}amine,
(±)-{[7-(2-methylphenyl)-5-phenyl-2,3-dihydro-1-benzofuran-2-yl]methyl}amine,
(±)-{[7-(3-methylphenyl)-5-phenyl-2,3-dihydro-1-benzofuran-2-yl]methyl}amine,
(±)-{[7-(4-methylphenyl)-5-phenyl-2,3-dihydro-1-benzofuran-2-yl]methyl}amine,
(±)-{[7-(2,4-difluorophenyl)-5-phenyl-2,3-dihydro-1-benzofuran-2-yl]methyl}amine,
(±)-{[7-(2,5-dichlorophenyl)-5-phenyl-2,3-dihydro-1-benzofuran-2-yl]methyl}amine,
(±)-{[7-(2-fluorophenyl)-5-methoxy-2,3-dihydro-1-benzofuran-2-yl]methyl}amine,
(±)-{[7-(2-chlorophenyl)-5-methoxy-2,3-dihydro-1-benzofuran-2-yl]methyl}amine,
(±)-{[7-(2-methylphenyl)-5-methoxy-2,3-dihydro-1-benzofuran-2-yl]methyl}amine,
(±)-{[7-(2-methoxyphenyl)-5-methoxy-2,3-dihydro-1-benzofuran-2-yl]methyl}amine,
(±)-{[5-methoxy-7-(3-thienyl)-2,3-dihydro-1-benzofuran-2-yl]methyl}amine,
(±)-{[7-(2,3-difluorophenyl)-5-methoxy-2,3-dihydro-1-benzofuran-2-yl]methyl}amine,
(±)-{[7-(2,3-dichlorophenyl)-5-methoxy-2,3-dihydro-1-benzofuran-2-yl]methyl}amine,
(±)-{[7-(2,3-dimethylphenyl)-5-methoxy-2,3-dihydro-1-benzofuran-2-yl]methyl}amine,
(±)-{[7-(2,4-difluorophenyl)-5-methoxy-2,3-dihydro-1-benzofuran-2-yl]methyl}amine,
(±)-{[7-(2,4-dichlorophenyl)-5-methoxy-2,3-dihydro-1-benzofuran-2-yl]methyl}amine,
(±)-{[7-(2,5-difluorophenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(−)-{[7-(2,5-dichlorophenyl)-5-methoxy-2,3-dihydro-1-benzofuran-2-yl]methyl}amine,
(±)-{[7-(2,5-dimethylphenyl)-5-methoxy-2,3-dihydro-1-benzofuran-2-yl]methyl}amine,
(±)-{[7-(2,5-dimethoxylphenyl)-5-methoxy-2,3-dihydro-1-benzofuran-2-yl]methyl}amine,
(±)-{[7-(5-chloro-2-methoxyphenyl)-5-methoxy-2,3-dihydro-1-benzofuran-2-yl]methyl}amine,
(±)-{[7-(3-chloro-4-fluorophenyl)-5-methoxy-2,3-dihydro-1-benzofuran-2-yl]methyl}amine,
(±)-{[7-(2,6-dimethylphenyl)-5-methoxy-2,3-dihydro-1-benzofuran-2-yl]methyl}amine,
(±)-{[7-fluoro-5-(2-methylphenyl)-2,3-dihydro-1-benzofuran-2-yl]methyl}amine,
(±)-{[7-fluoro-5-(2-chlorophenyl)-2,3-dihydro-1-benzofuran-2-yl]methyl}amine,
(±)-{[7-fluoro-5-(2-fluorophenyl)-2,3-dihydro-1-benzofuran-2-yl]methyl}amine,
(±)-({7-fluoro-5-[2-(trifluoromethyl)phenyl]-2,3-dihydro-1-benzofuran-2-yl}methyl)amine,
(±)-{[7-fluoro-5-(2-methoxyphenyl)-2,3-dihydro-1-benzofuran-2-yl]methyl}amine,
(±)-{[7-fluoro-5-(3-methylphenyl)-2,3-dihydro-1-benzofuran-2-yl]methyl}amine,
(±)-{[7-fluoro-5-(3-fluorophenyl)-2,3-dihydro-1-benzofuran-2-yl]methyl}amine,
(±)-{[7-fluoro-5-(3-chlorophenyl)-2,3-dihydro-1-benzofuran-2-yl]methyl}amine,
(±)-({7-fluoro-5-[3-(trifluoromethyl)phenyl]-2,3-dihydro-1-benzofuran-2-yl}methyl)amine,
(±)-{[7-fluoro-5-(3-methoxyphenyl)-2,3-dihydro-1-benzofuran-2-yl]methyl}amine,
(±)-{[7-fluoro-5-(4-methylphenyl)-2,3-dihydro-1-benzofuran-2-yl]methyl}amine,
(±)-{[7-fluoro-5-(4-chlorophenyl)-2,3-dihydro-1-benzofuran-2-yl]methyl}amine,
(±)-{[7-fluoro-5-(4-fluorophenyl)-2,3-dihydro-1-benzofuran-2-yl]methyl}amine,
(±)-({7-fluoro-5-[4-(trifluoromethyl)phenyl]-2,3-dihydro-1-benzofuran-2-yl}methyl)amine,
(±)-{[7-fluoro-5-(4-methoxyphenyl)-2,3-dihydro-1-benzofuran-2-yl]methyl}amine,
(±)-N-{[7-(2,6-dichlorophenyl)-2,3-dihydro-1-benzofuran-2-yl]methyl}ethanamine,
(±)-N-{[7-(2,6-dichlorophenyl)-2,3-dihydro-1-benzofuran-2-yl]methyl}cyclopropanamine, (±)-N-{[7-(2,6-dichlorophenyl)-2,3-dihydro-1-benzofuran-2-yl]methyl}cyclobutanamine,
(±)-N-{[7-(2,6-dichlorophenyl)-2,3-dihydro-1-benzofuran-2-yl]methyl}propan-2-amine,
(±)-{[6-fluoro-7-(2-methylphenyl)-2,3-dihydro-1-benzofuran-2-yl]methyl}amine,
(+)-{[6-fluoro-7-(2-methylphenyl)-2,3-dihydro-1-benzofuran-2-yl]methyl}amine,
(−)-{[6-fluoro-7-(2-methylphenyl)-2,3-dihydro-1-benzofuran-2-yl]methyl}amine,
(±)-{[{[7-(2-chlorophenyl)-6-fluoro-2,3-dihydro-1-benzofuran-2-yl]methyl}amine,
(±)-{[6-chloro-7-(2-methylphenyl)-2,3-dihydro-1-benzofuran-2-yl]methyl}amine,
(±)-{[6-chloro-7-(2-chlorophenyl)-2,3-dihydro-1-benzofuran-2-yl]methyl}amine,
(±)-{[6-fluoro-7-(2-methylphenyl)-2,3-dihydro-1-benzofuran-2-yl]methyl}methylamine,
(±)-{[6-fluoro-7-(2-chlorophenyl)-2,3-dihydro-1-benzofuran-2-yl]methyl}methylamine,
(±)-{[6-chloro-7-(2-methylphenyl)-2,3-dihydro-1-benzofuran-2-yl]methyl}methylamine,
(±)-{[6-chloro-7-(2-chlorophenyl)-2,3-dihydro-1-benzofuran-2-yl]methyl}methylamine,
(±)-[(N-methyl-1-[7-(2-methylphenyl)-2,3-dihydro-1-benzofuran-2-yl]methanamine,
(−)-N-methyl-1-[7-(2-methylphenyl)-2,3-dihydro-1-benzofuran-2-yl]methanamine,
(+)-N-methyl-1-[7-(2-methylphenyl)-2,3-dihydro-1-benzofuran-2-yl]methanamine,
(±)-[(N-methyl-1-[7-(2-chlorophenyl)-2,3-dihydro-1-benzofuran-2-yl]methanamine,
(+)-N-methyl-1-[7-(2-chlorophenyl)-2,3-dihydro-1-benzofuran-2-yl]methanamine,
(−)-N-methyl-1-[7-(2-chlorophenyl)-2,3-dihydro-1-benzofuran-2-yl]methanamine,
(±)-[(N-methyl-1-[7-(2-fluorophenyl)-2,3-dihydro-1-benzofuran-2-yl]methanamine,
(±)-[(N-methyl-1-[7-(2-methoxyphenyl)-2,3-dihydro-1-benzofuran-2-yl]methanamine,
(±)-[(N-methyl-1-[7-(3-methylphenyl)-2,3-dihydro-1-benzofuran-2-yl]methanamine,
(±)-[(N-methyl-1-[7-(3-fluorophenyl)-2,3-dihydro-1-benzofuran-2-yl]methanamine,
(±)-[(N-methyl-1-[7-(3-chlorophenyl)-2,3-dihydro-1-benzofuran-2-yl]methanamine,
(±)-[(N-methyl-1-[7-(3-methoxyphenyl)-2,3-dihydro-1-benzofuran-2-yl]methanamine,
(±)-[(N-methyl-1-[7-(4-methylphenyl)-2,3-dihydro-1-benzofuran-2-yl]methanamine,
(±)-[(N-methyl-1-[7-(4-fluorophenyl)-2,3-dihydro-1-benzofuran-2-yl]methanamine,
(±)-[(N-methyl-1-[7-(4-chlorophenyl)-2,3-dihydro-1-benzofuran-2-yl]methanamine,
(±)-[(N-methyl-1-[7-(4-methoxyphenyl)-2,3-dihydro-1-benzofuran-2-yl]methanamine,
(±)-[(N-methyl-1-[7-(2,3-dimethylphenyl)-2,3-dihydro-1-benzofuran-2-yl]methanamine,
(±)-[(N-methyl-1-[7-(2,3-dimethoxyphenyl)-2,3-dihydro-1-benzofuran-2-yl]methanamine,
(±)-[(N-methyl-1-[7-(2,4-difluorophenyl)-2,3-dihydro-1-benzofuran-2-yl]methanamine,
(±)-[(N-methyl-1-[7-(2,4-dichlorophenyl)-2,3-dihydro-1-benzofuran-2-yl]methanamine,
(±)-[(N-methyl-1-[7-(2,4-dimethoxyphenyl)-2,3-dihydro-1-benzofuran-2-yl]methanamine,
(±)-[(N-methyl-1-[7-(2,5-dimethylphenyl)-2,3-dihydro-1-benzofuran-2-yl]methanamine,
(±)-[(N-methyl-1-[7-(2,5-difluorophenyl)-2,3-dihydro-1-benzofuran-2-yl]methanamine,
(±)-[(N-methyl-1-[7-(2,5-dichlorophenyl)-2,3-dihydro-1-benzofuran-2-yl]methanamine,
(±)-[(N-methyl-1-[7-(5-chloro-2-methoxyphenyl)-2,3-dihydro-1-benzofuran-2-yl]methanamine,
(±)-[(N-methyl-1-[7-(5-chloro-2-methylphenyl)-2,3-dihydro-1-benzofuran-2-yl]methanamine,
(±)-[(N-methyl-1-[7-(2,6-dimethylphenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(+)-{[7-(2,6-dichlorophenyl)-2,3-dihydro-1-benzofuran-2-yl]methyl}methylamine,
(±)-N-methyl-1-(7-pyridin-3-yl-2,3-dihydro-1-benzofuran-2-yl)methanamine,
(±)-[(N-methyl-1-[7-(2,3-difluorophenyl)-2,3-dihydro-1-benzofuran-2-yl]methanamine,
(±)-{[5-fluoro-7-(2-fluorophenyl)-2,3-dihydro-1-benzofuran-2-yl]methyl}methylamine,
(±)-{[5-fluoro-7-(2-chlorophenyl)-2,3-dihydro-1-benzofuran-2-yl]methyl}methylamine,
(±)-{[5-fluoro-7-(2-methylphenyl)-2,3-dihydro-1-benzofuran-2-yl]methyl}methylamine,
(−)-{[5-fluoro-7-(2-methylphenyl)-2,3-dihydro-1-benzofuran-2-yl]methyl}methylamine,
(+)-{[5-fluoro-7-(2-methylphenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-{[7-(2,3-dimethoxyphenyl)-5-fluoro-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(−)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-difluorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(−)-{[5-fluoro-7-(2,5-dichlorophenyl)-2,3-dihydro-1-benzofuran-2-yl]methyl}methylamine,
(±)-{[7-(2,5-dimethylphenyl)-5-fluoro-2,3-dihydro-1-benzofuran-2-yl]methyl}methylamine,
(±)-{[7-(2,6-dimethylphenyl)-5-fluoro-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-{[5-fluoro-7-(5-methoxy-2-methylphenyl)-2,3-dihydro-1-benzofuran-2-yl]methyl}methylamine,
(±)-{[5-fluoro-7-(2-methoxy-5-methylphenyl)-2,3-dihydro-1-benzofuran-2-yl]methyl}methylamine,
(±)-{[7-(5-chloro-2-methoxyphenyl)-5-fluoro-2,3-dihydro-1-benzofuran-2-yl]methyl}methylamine,
(±)-[(5-fluoro-7-pyridin-3-yl-2,3-dihydro-1-benzofuran-2-yl)methyl]methylamine,
(±)-[(5-chloro-7-(2-methoxyphenyl)-2,3-dihydro-1-benzofuran-2-yl]methyl}methylamine, (±)-{[5-chloro-7-(2,6-dimethylphenyl)-2,3-dihydro-1-benzofuran-2-yl]methyl}methylamine,
(±)-[(5-chloro-7-(2-fluorophenyl)-2,3-dihydro-1-benzofuran-2-yl]methyl}methylamine,
(±)-{[5-chloro-7-(2,3-difluorophenyl)-2,3-dihydro-1-benzofuran-2-yl]methyl}methylamine,
(±)-{[5-chloro-7-(2,3-dichlorophenyl)-2,3-dihydro-1-benzofuran-2-yl]methyl}methylamine,
(±)-{[5-chloro-7-(2,3-dimethylphenyl)-2,3-dihydro-1-benzofuran-2-yl]methyl}methylamine,
(±)-{[5-chloro-7-(2,3-dimethoxyphenyl)-2,3-dihydro-1-benzofuran-2-yl]methyl}methylamine,
(±)-{[5-chloro-7-(2,4-difluorophenyl)-2,3-dihydro-1-benzofuran-2-yl]methyl}methylamine,
(±)-{[5-chloro-7-(2,4-dichlorophenyl)-2,3-dihydro-1-benzofuran-2-yl]methyl}methylamine,
(±)-{[5-chloro-7-(2,4-dimethoxyphenyl)-2,3-dihydro-1-benzofuran-2-yl]methyl}methylamine,
(±)-{[5-chloro-7-(2,5-difluorophenyl)-2,3-dihydro-1-benzofuran-2-yl]methyl}methylamine,
(±)-{[5-chloro-7-(2,5-dichlorophenyl)-2,3-dihydro-1-benzofuran-2-yl]methyl}methylamine,
(±)-{[5-chloro-7-(5-chloro-2-methoxyphenyl)-2,3-dihydro-1-benzofuran-2-yl]methyl}methylamine,
(±)-{[5-chloro-7-(3,4-difluorophenyl)-2,3-dihydro-1-benzofuran-2-yl]methyl}methylamine,
(±)-[5-chloro-7-(3-chloro-4-fluorophenyl)-2,3-dihydro-1-benzofuran-2-yl]methyl}methylamine,
(±)-{[7-(2-fluorophenyl)-5-methyl-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2-methoxyphenyl)-5-methyl-2,3-dihydro-1-benzofuran-2-yl]methyl}methylamine,
(±)-{[7-(3-methylphenyl)-5-methyl-2,3-dihydro-1-benzofuran-2-yl]methyl}methylamine,
(±)-{[7-(3-chlorophenyl)-5-methyl-2,3-dihydro-1-benzofuran-2-yl]methyl}methylamine,
(±)-{[7-(4-methylphenyl)-5-methyl-2,3-dihydro-1-benzofuran-2-yl]methyl}methylamine,
(±)-{[7-(4-chlorophenyl)-5-methyl-2,3-dihydro-1-benzofuran-2-yl]methyl}methylamine,
(±)-{[7-(4-fluorophenyl)-5-methyl-2,3-dihydro-1-benzofuran-2-yl]methyl}methylamine,
(±)-{[7-(4-methoxyphenyl)-5-methyl-2,3-dihydro-1-benzofuran-2-yl]methyl}methylamine,
(±)-{[7-(2,3-dimethoxyphenyl)-5-methyl-2,3-dihydro-1-benzofuran-2-yl]methyl}methylamine,
(±)-{[7-(2,4-dichlorophenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(−)-{[7-(2,5-dichlorophenyl)-5-methyl-2,3-dihydro-1-benzofuran-2-yl]methyl}methylamine,
(±)-{[7-(2,6-dimethylphenyl)-5-methyl-2,3-dihydro-1-benzofuran-2-yl]methyl}methylamine,
(±)-{[7-(2,6-dichlorophenyl)-5-methyl-2,3-dihydro-1-benzofuran-2-yl]methyl}methylamine,
(±)-{[7-(2-fluorophenyl)-5-methoxy-2,3-dihydro-1-benzofuran-2-yl]methyl}methylamine,
(±)-{[7-(2-chlorophenyl)-5-methoxy-2,3-dihydro-1-benzofuran-2-yl]methyl}methylamine,
(±)-{[7-(2-meth ylphenyl)-5-methoxy-2,3-dihydro-1-benzofuran-2-yl]methyl}methylamine,
(±)-{[7-(2,3-difluorophenyl)-5-methoxy-2,3-dihydro-1-benzofuran-2-yl]methyl}methylamine,
(±)-{[7-(2,3-dichlorophenyl)-5-methoxy-2,3-dihydro-1-benzofuran-2-yl]methyl}methylamine,
(±)-{[7-(2,3-dimethylphenyl)-5-methoxy-2,3-dihydro-1-benzofuran-2-yl]methyl}methylamine,
(±)-{[7-(2,4-difluorophenyl)-5-methoxy-2,3-dihydro-1-benzofuran-2-yl]methyl}methylamine,
(±)-{[7-(2,5-difluorophenyl)-5-methoxy-2,3-dihydro-1-benzofuran-2-yl]methyl}methylamine,
(±)-{[7-(2,5-dichlorophenyl)-5-methoxy-2,3-dihydro-1-benzofuran-2-yl]methyl}methylamine,
(±)-{[7-(2,5-dimethylphenyl)-5-methoxy-2,3-dihydro-1-benzofuran-2-yl]methyl}methylamine,
(±)-{[7-(2,5-dimethoxyphenyl)-5-methoxy-2,3-dihydro-1-benzofuran-2-yl]methyl}methylamine,
(±)-{[7-(5-chloro-2-methoxyphenyl)-5-methoxy-2,3-dihydro-1-benzofuran-2-yl]methyl}methylamine,
(±)-{[7-(3-chloro-4-fluorophenyl)-5-methoxy-2,3-dihydro-1-benzofuran-2-yl]methyl}methylamine,
(±)-{[7-(2,6-dimethylphenyl)-5-methoxy-2,3-dihydro-1-benzofuran-2-yl]methyl}methylamine,
(±)-{[7-(2-chlorophenyl)-5-phenyl-2,3-dihydro-1-benzofuran-2-yl]methyl}methylamine,
(±)-{[7-(3-chlorophenyl)-5-phenyl-2,3-dihydro-1-benzofuran-2-yl]methyl}methylamine,
(±)-{[7-(4-chlorophenyl)-5-phenyl-2,3-dihydro-1-benzofuran-2-yl]methyl}methylamine,
(±)-{[7-(2-fluorophenyl)-5-phenyl-2,3-dihydro-1-benzofuran-2-yl]methyl}methylamine,
(±)-{[7-(3-fluorophenyl)-5-phenyl-2,3-dihydro-1-benzofuran-2-yl]methyl}methylamine,
(±)-{[7-(4-fluorophenyl)-5-phenyl-2,3-dihydro-1-benzofuran-2-yl]methyl}methylamine,
(±)-{[7-(2-methylphenyl)-5-phenyl-2,3-dihydro-1-benzofuran-2-yl]methyl}methylamine,
(±)-{[7-(3-methylphenyl)-5-phenyl-2,3-dihydro-1-benzofuran-2-yl]methyl}methylamine,
(±)-{[7-(4-methylphenyl)-5-phenyl-2,3-dihydro-1-benzofuran-2-yl]methyl}methylamine,
(±)-{[7-(2-methoxyphenyl)-5-phenyl-2,3-dihydro-1-benzofuran-2-yl]methyl}methylamine,
(±)-{[7-(3-methoxyphenyl)-5-phenyl-2,3-dihydro-1-benzofuran-2-yl]methyl}methylamine,
(±)-{[7-(4-methoxyphenyl)-5-phenyl-2,3-dihydro-1-benzofuran-2-yl]methyl}methylamine,
(±)-{[7-(2,4-difluorophenyl)-5-phenyl-2,3-dihydro-1-benzofuran-2-yl]methyl}methylamine,
(±)-{[N-methyl-1-[7-phenyl-5-(trifluoromethyl)-2,3-dihydro-1-benzofuran-2-yl]methanamine,
(±)-N-methyl-1-[7-(3-methylphenyl)-5-(trifluoromethyl)-2,3-dihydro-1-benzofuran-2-yl]methanamine,
(±)-N-methyl-1-[7-(3-fluorophenyl)-5-(trifluoromethyl)-2,3-dihydro-1-benzofuran-2-yl]methanamine,
(±)-N-methyl-1-[7-(2,3-difluorophenyl)-5-(trifluoromethyl)-2,3-dihydro-1-benzofuran-2-yl]methanamine,
(±)-N-methyl-1-[7-(3,4-difluorophenyl)-5-(trifluoromethyl)-2,3-dihydro-1-benzofuran-2-yl]methanamine,
(±)-N-methyl-1-[7-(2,5-difluorophenyl)-5-(trifluoromethyl)-2,3-dihydro-1-benzofuran-2-yl]methanamine,
(±)-N-methyl-1-[7-(2,3-dichlorophenyl)-5-(trifluoromethyl)-2,3-dihydro-1-benzofuran-2-yl]methanamine,
(±)-{[7-(3-chloro-4-fluorophenyl)-5-(trifluoromethyl)-2,3-dihydro-1-benzofuran-2-yl]methyl}methylamine,
(±)-N-methyl-1-[7-(2,4-dimethoxyphenyl)-5-(trifluoromethyl)-2,3-dihydro-1-benzofuran-2-yl]methanamine, (±)-{[7-[3,5-bis(trifluoromethyl)phenyl]-5-(trifluoromethyl)-2,3-dihydro-1-benzofuran-2-yl]methyl}methylamine,
(±)-{[7-fluoro-5-(2-methylphenyl)-2,3-dihydro-1-benzofuran-2-yl]methyl}methylamine,
(±)-{[7-fluoro-5-(2-chlorophenyl)-2,3-dihydro-1-benzofuran-2-yl]methyl}methylamine,
(±)-{[7-fluoro-5-(2-fluorophenyl)-2,3-dihydro-1-benzofuran-2-yl]methyl}methylamine,
(±)-{7-fluoro-5-[2-(trifluoromethyl)phenyl]-2,3-dihydro-1-benzofuran-2-yl}methyl)methylamine,
(±)-{7-fluoro-5-[2-methoxyphenyl]-2,3-dihydro-1-benzofuran-2-yl}methyl)methylamine,
(±)-{7-fluoro-5-[3-methylphenyl]-2,3-dihydro-1-benzofuran-2-yl}methyl)methylamine,
(±)-{7-fluoro-5-[3-chlorophenyl]-2,3-dihydro-1-benzofuran-2-yl}methyl)methylamine,
(±)-{[7-fluoro-5-(3-fluorophenyl)-2,3-dihydro-1-benzofuran-2-yl]methyl}methylamine,
(±)-{7-fluoro-5-[3-(trifluoromethyl)phenyl]-2,3-dihydro-1-benzofuran-2-yl}methyl)methylamine,
(±)-{7-fluoro-5-[3-methoxyphenyl]-2,3-dihydro-1-benzofuran-2-yl}methyl)methylamine,
(±)-{7-fluoro-5-[4-methylphenyl]-2,3-dihydro-1-benzofuran-2-yl}methyl)methylamine,
(±)-{7-fluoro-5-[4-chlorophenyl]-2,3-dihydro-1-benzofuran-2-yl}methyl)methylamine,
(±)-{[7-fluoro-5-(4-fluorophenyl)-2,3-dihydro-1-benzofuran-2-yl]methyl}methylamine,
(±)-{7-fluoro-5-[4-(trifluoromethyl)phenyl]-2,3-dihydro-1-benzofuran-2-yl}methyl)methylamine,
(±)-{7-fluoro-5-[4-methoxyphenyl]-2,3-dihydro-1-benzofuran-2-yl}methyl)methylamine,
(+) {[7-(2,6-dichlorophenyl)-5-fluoro-2,3-dihydro-1-benzofuran-2-yl]methyl}methylamine,
(−) {[7-(2,6-dichlorophenyl)-5-fluoro-2,3-dihydro-1-benzofuran-2-yl]methyl}methylamine,
(R)-[7-(2-chloro-phenyl)-(5-Fluoro-2,3-dihydro-benzofuran-2-ylmethyl)methyl-amine,
(R)-[7-(2,6-dichloro-phenyl)-5-Fluoro-2,3-dihydro-benzofuran-2-ylmethyl]ethylamine,
(R)-[7-(2,6-dichloro-phenyl)-5-Fluoro-2,3-dihydro-benzofuran-2-ylmethyl]dimethylamine,
{[(2R)-7-(5-chloro-2-methylphenyl)-5-fluoro-2,3-dihydro-1-benzofuran-2-yl]methyl}amine,
{[(2R)-7-(4-chloro-2-methylphenyl)-5-fluoro-2,3-dihydro-1-benzofuran-2-yl]methyl}amine,
(−)-{[7-(2,6-dichlorophenyl)-5-fluoro-2,3-dihydro-1-benzofuran-2-yl]methyl}amine,
(+)-{[7-(2,6 dichlorophenyl)-5-fluoro-2,3-dihydro-1-benzofuran-2-yl]methyl}amine,
(±)-{2-[6-chloro-7-(2-chlorophenyl)-2,3-dihydro-1-benzofuran-2-yl]ethyl}amine,
(±)-{2-[7-(2,6-dichlorophenyl)-5-fluoro-2,3-dihydro-1-benzofuran-2-yl]ethyl}amine,
(±)-{2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(+)-{N-methyl-1-[(7-(2,4,6-trichlorophenyl)-2,3-dihydro-1-benzofuran-2-yl]methanamine,
(−)-{N-methyl-1-[(7-(2,4,6-trichlorophenyl)-2,3-dihydro-1-benzofuran-2-yl]methanamine,
(+)-{[7-(2,6-dimethylphenyl)-5-fluoro-2,3-dihydro-1-benzofuran-2-yl]methyl}methylamine,
(−)-{[7-(2,6-dimethylphenyl)-5-fluoro-2,3-dihydro-1-benzofuran-2-yl]methyl}methylamine,
(−)-{[7-(2,6-dimethylphenyl)-5-methoxy-2,3-dihydro-1-benzofuran-2-yl]methyl}methylamine,
(+)-{[7-(2,6-dimethylphenyl)-5-methoxy-2,3-dihydro-1-benzofuran-2-yl]methyl}methylamine,
(+)-{[5-chloro-7-(2,5-dichlorophenyl)-2,3-dihydro-1-benzofuran-2-yl]methyl}methylamine,
(−)-{[5-chloro-7-(2,5-dichlorophenyl)-2,3-dihydro-1-benzofuran-2-yl]methyl}methylamine,
(−)-{[5-chloro-7-(2,6-dimethylphenyl)-2,3-dihydro-1-benzofuran-2-yl]methyl}methylamine,
(+)-{[5-chloro-7-(2,6-dimethylphenyl)-2,3-dihydro-1-benzofuran-2-yl]methyl}methylamine,
(+)-{[7-(2,3-dimethoxyphenyl)-5-methyl-2,3-dihydro-1-benzofuran-2-yl]methyl}methylamine,
(−)-{[7-(2,3-dimethoxyphenyl)-5-methyl-2,3-dihydro-1-benzofuran-2-yl]methyl}methylamine,
(−)-{[7-(2,3-dimethoxyphenyl)-5-fluoro-2,3-dihydro-1-benzofuran-2-yl]methyl}methylamine, or
(+)-{[7-(2,3-dimethoxyphenyl)-5-fluoro-2,3-dihydro-1-benzofuran-2-yl]methyl}methylamine;

or a pharmaceutically acceptable salt thereof.

The compounds of Formula 1 have affinity for and agonist or partial agonist activity at the 2c subtype of brain serotonin receptors and are thus of interest for the treatment of mental disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified; adjustment disorders such as adjustment disorders with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders such as depressive disorders or bipolar disorders often accompany psychotic disorders such as schizophrenia. A more complete description of the aforementioned mental disorders can be found in the Diagnostic and Statistical Manual of Mental Disorders, $4^{th}$ edition, Washington, D.C., American Psychiatric Association (1994), incorporated herein by reference in its entirety.

The compounds of formula 1 are also of interest for the treatment of epilepsy; migraines; sexual dysfunction; sleep disorders; substance abuse, including addiction to alcohol and various drugs, including cocaine and nicotine; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality.

The compounds of Formula 1 can also be used to treat central nervous system deficiencies associated, for example, with trauma, stroke, and spinal cord injuries. The compounds of Formula 1 can therefore be used to improve or inhibit further degradation of central nervous system activity during or following the malady or trauma in question. Included in these improvements are maintenance or improvement in motor and motility skills, control, coordination and strength.

In certain embodiments, the present invention therefore provides methods of treating, each of the conditions listed above in a patient, preferably in a human, the methods including administering a therapeutically effective amount of at least one compound of Formula 1 or a pharmaceutically acceptable salt thereof to a patient suffering from such a condition.

In other embodiments, the invention relates to compositions comprising at least one compound of Formula 1, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of Formula 1.

Certain of the compounds of Formula 1 contain stereogenic carbon atoms or other chiral elements (i.e. chirality axis) and thus give rise to stereoisomers, including enantiomers, diastereomers, and in the case of biphenyls, the formation of atropisomers. For definitions and an extensive discourse on atropisomers, see: Eliel, E. L. Stereochemistry of Organic Compounds (John Wiley & Sons, 1994, p 1142), which is incorporated herein by reference in its entirety. Although the stereochemistry is not shown in Formula 1, Formula 1 includes all of the stereoisomers of the 1-(2,3-dihydro-1-benzofuran-2-yl)alkanamine derivatives, as well as mixtures of the stereoisomers. Throughout this application, the name of the product, where the absolute configuration of an asymmetric center is not indicated, is intended to embrace the individual stereoisomers as well as mixtures of stereoisomers. When it is necessary to distinguish the enantiomers from one another and from the racemate, the sign of the optical rotation [(+), (−) and (±)] is utilized. Furthermore, throughout this application, the designations R* and S* are used to indicate relative stereochemistry, employing the Chemical Abstracts convention which automatically assigns R* to the lowest numbered asymmetric center.

Where a stereoisomer is preferred, it may, in some embodiments, be provided substantially free of the corresponding stereoisomer. Thus, a stereoisomer substantially free of the corresponding stereoisomer refers to a compound that is isolated or separated via separation techniques or prepared free of the corresponding stereoisomer. "Substantially free," as used herein, means that the compound is made up of a significantly greater proportion of one stereoisomer. In preferred embodiments, the compound is made up of at least about 90% by weight of a preferred stereoisomer. In other embodiments of the invention, the compound is made up of at least about 99% by weight of a preferred stereoisomer. Preferred stereoisomers can be isolated from racemic mixtures by any method known to those skilled in the art, including high performance liquid chromatography (HPLC) and the formation and crystallization of chiral salts, or preferred stereoisomers can be prepared by methods described herein. Methods for the preparation of preferred stereoisomers are described, for example, in Jacques, et al., *Enantiomers, Racemates and Resolutions* (Wiley Interscience, New York, 1981); Wilen, S. H., et al., *Tetrahedron* 33: 2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972), each of which is hereby incorporated by reference in its entirety.

This invention also provides processes for preparing compounds of formula I which processes include one of the following:

a) reacting a compound of formula 7

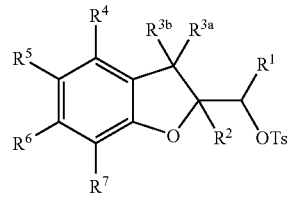

wherein $R^1$, $R^2$, $R^3$, $R^4$, $R^5$, $R^6$, and $R^7$ are as defined herein, with sodium azide and reducing the product to give a compound of formula 1 wherein n is 1 and R and R' are both H;

or b) reacting a compound of formula 7 as defined above with an amine of formula NHRR' where R and R' are as defined herein to give a corresponding compound of formula 1 wherein n is 1;

or c) reacting a compound of formula 7 as defined above with sodium cyanide followed by reduction to give a compound of formula 1 wherein n is 2 and R and R' are both H;

d) converting a compound of formula 1 as defined herein to a pharmaceutically acceptable salt or vice versa;

or e) isolating a specific enantiomer or diastereomer of a compound of formula 1 or a pharmaceutically acceptable salt thereof as defined herein from a mixture thereof.

The 1-(2,3-dihydro-1-benzofuran-2-yl)alkanamine derivatives of Formula 1 may be prepared as illustrated in Scheme I.

Scheme I

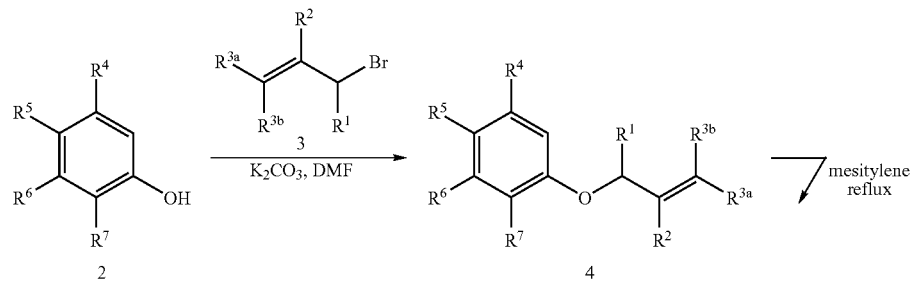

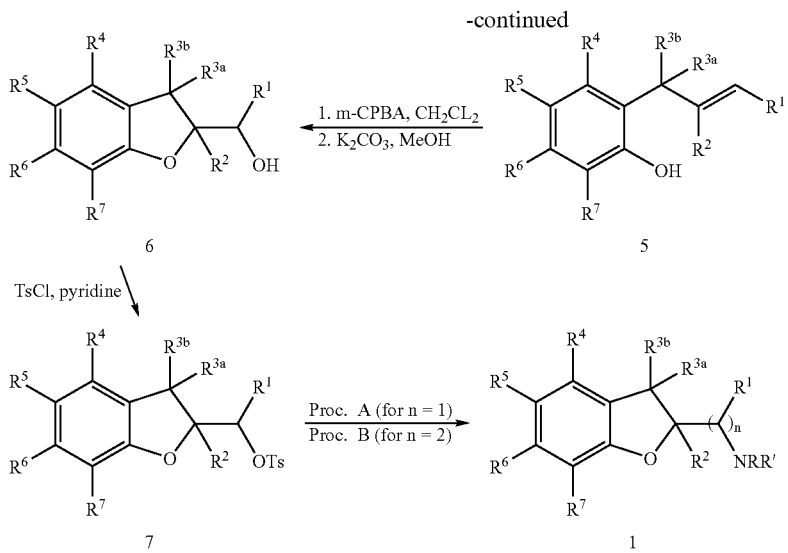

Proc. A: 1. a) NaN3, DMSO and b) reduction, or 2. NHRR'/DMSO
Proc. B: 1. a) NaCN/DMSO and b) H2/5% Rh on Al2O3, NH4OH Variables used are as defined for Formula 1, unless otherwise noted. The appropriately substituted phenol (2) is alkylated with an appropriately substituted allyl bromide or alcohol (3) in the presence of a suitable base such as potassium carbonate in a solvent such as N,N-dimethylformamide. The phenols, allyl bromides, and allyl alcohols appropriate for the synthesis of the compounds of formula I are either commercially available or can readily be prepared by one skilled in the art. The resulting allyl ether (4) is treated in refluxing mesitylene or other suitable high boiling solvent to afford the desired Claisen rearrangement product. The 2-allyl phenol (5) intermediate is subjected to epoxidation of the double bond with 3-chloroperoxybenzoic acid in dichloromethane. The resulting epoxy phenol intermediate is treated with a suitable base such as potassium carbonate in a solvent such as methanol to induce cyclization to give the 2,3-dihydro-1-benzofuran-2-yl)methanol (6). Treatment of (6) with p-toluenesulfonyl chloride and a suitable base such as pyridine affords the tosylate (7). Conversion of (7) to the amine (1) can be accomplished, for example, by treatment with sodium azide in a solvent such as dimethylsulfoxide followed by reduction of the azide or direct treatment with an appropriately substituted amine to provide the compounds of Formula 1. Additionally, longer alkyl chains (i.e. 2-aminoethyl) may be prepared, for example, via treatment of (7) with sodium cyanide in a solvent such as dimethylsulfoxide followed by reduction of the nitrile.

The preparation of appropriately substituted phenols (2) in Scheme I; in particular the 7-aryl substituted phenols, is illustrated in Scheme Ia.

Scheme Ia

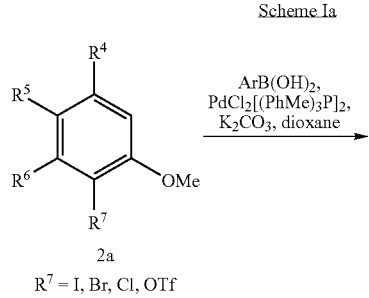

Utilization of a 2-halogenated methoxy benzene or a suitably protected 2-halogenated phenol (2a) permits the introduction of the aromatic substitutent through a palladium-catalyzed cross coupling reaction (i.e Suzuki reaction) with the desired boronic acid. Treatment of (2a) with a catalyst such as dichlorobis(tri-o-tolylphosphine)-palladium(II) in the presence of a suitable base such as potassium carbonate in a solvent such as dioxane provides the biaryl system. Subsequent removal of the protecting group, in this example demethylation of (2b) via reaction with borontribromide in dichloromethane affords the phenol (2).

Alternatively, the phenols (2) may be prepared by a reversal of the inherent reactivity associated with the partners in the cross-coupling reaction as shown in Scheme Ib.

Scheme Ib

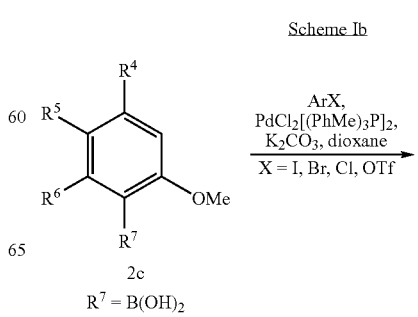

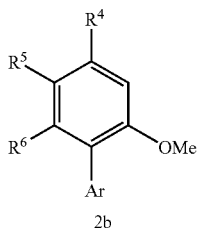

Installation of the biaryl system may also be accomplished via a palladium-catalyzed cross coupling reaction (i.e. Suzuki reaction) of appropriate derivatives of 2,3-dihydro-1-benzofuran-2-yl)methyl 4-methylbenzenesulfonate (7) with the desired boronic acid (Scheme Ic). Treatment of (7) with a catalyst such as dichlorobis(tri-o-tolylphosphine)-palladium (II) in the presence of a suitable base such as potassium carbonate in a solvent such as dioxane provides the biaryl system.

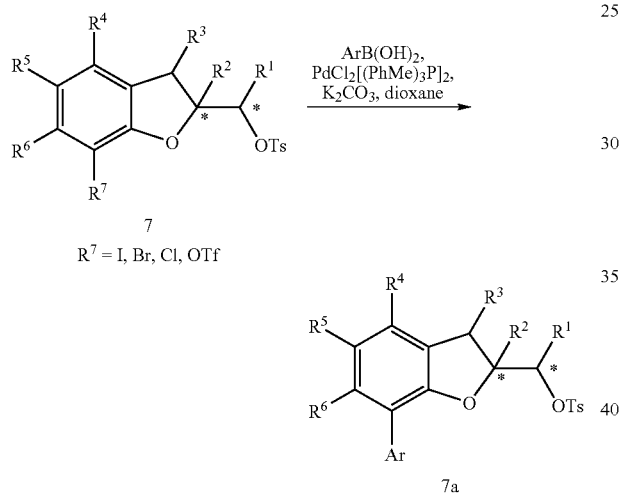

Alternatively, installation of the biaryl system may be accomplished via a palladium-catalyzed cross coupling reaction (i.e Suzuki reaction) of appropriate 1-(2,3-dihydro-1-benzofuran-2-yl) derivatives (1a) in either racemic or stereochemically pure form following separation of the enantiomers. For example, treatment of 1a and a boronic acid (Scheme Id) with a catalyst such as dichlorobis(tri-o-tolylphosphine)-palladium(II) in the presence of a suitable base such as potassium carbonate (as described previously) provides the desired biaryl system. Deprotection of the resultant product from the coupling procedure with, for example, iodotrimethylsilane in a solvent such as acetonitrile (foir X=NRCbz) then affords the title compounds of Formula 1.

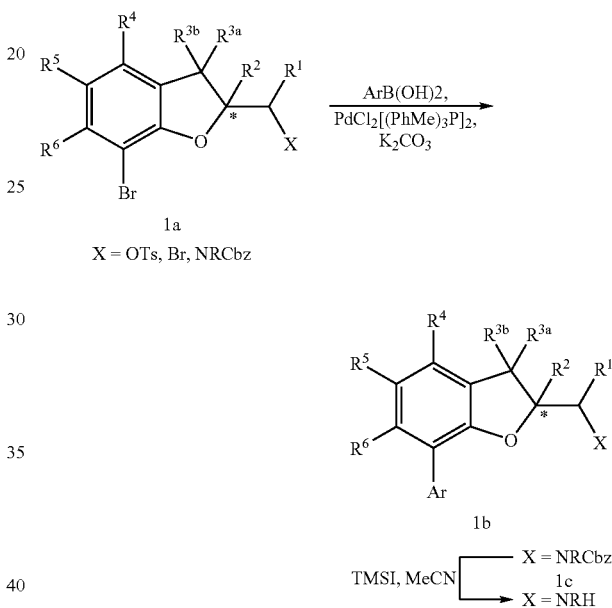

The compounds of Formula 1 can also be prepared in a stereoselective manner as illustrated in Scheme II.

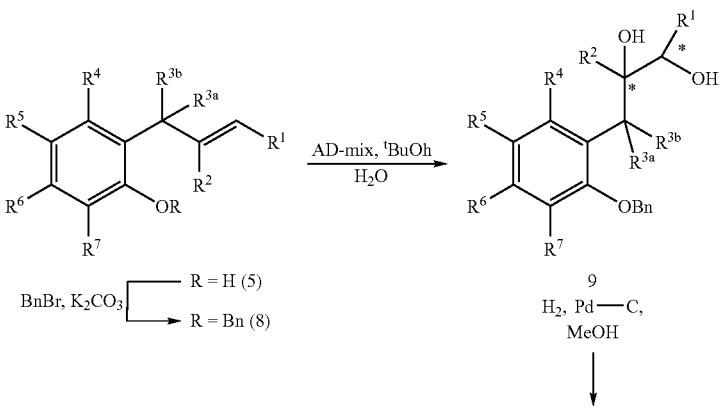

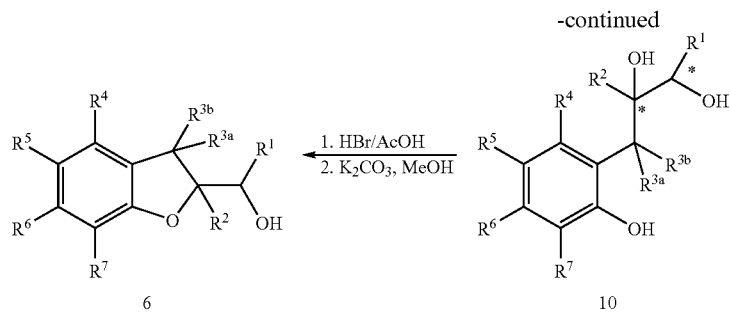

Protection of the 2-allyl phenol (5) with a suitable protecting group such as benzyl by treatment with benzyl bromide in the presence of a suitable base such as potassium carbonate in a solvent such as N,N-dimethylformamide gives the benzyl ether (8). Treatment of (8) utilizing extant methodology known to one skilled in the art for the stereoselective oxidation of double bonds such as the Sharpless Asymmetric Dihydroxylation (A-D) provides the diol (9) in stereochemically enriched form. Many methods are available to one skilled in the art for the transfer of the stereochemical information present in (9) into the compounds of formula (1) with retention of stereochemical integrity. One such method involves deprotection of the benzyl ether with catalytic palladium on carbon under a hydrogen atmosphere (45 psi) in a solvent, such as methanol, to provide triol (10). Formation to the previously described 2,3-dihydro-1-benzofuran-2-yl)methanol (6) can be accomplished by treatment of (9) with hydrogen bromide in acetic acid to provide the intermediate vicinal acetoxy bromide followed by cyclization with a suitable base such as potassium carbonate in a solvent such as methanol.

Alternatively, the compounds of Formula 1 can be prepared via selective mono-protection of diol (9) with a suitable protecting group as illustrated in Scheme III.

Treatment of (9) with tert-butyldimethylsilyl chloride in the presence of a suitable base such as imidazole in a solvent such as N,N,-dimethylformamide followed by deprotection of the benzyl ether (as previously described) with catalytic palladium on carbon under a hydrogen atmosphere gives phenol (12). Cyclodehydration of (12) using standard Mitsunobu conditions, such as triphenylphosphine in the presence of diethylazodicarboxylate in a solvent such as toluene, provides the 2,3-dihydro-1-benzofuran-2-yl)methanol (13) protected as the silyl ether. Removal of the silyl ether in (13) using standard conditions such as tetrabutylamonnium fluoride in a solvent such as tetrahydrofuran then provides the alcohol (6) which can be converted to the compounds of the current invention as previously described (Scheme I).

In lieu of a protecting group, diol (9) can be converted to the mono-tosylated derivative (12a) by treatment with p-toluenesulfonyl chloride and a suitable base such as pyridine to give the desired product, as illustrated in Scheme IV.

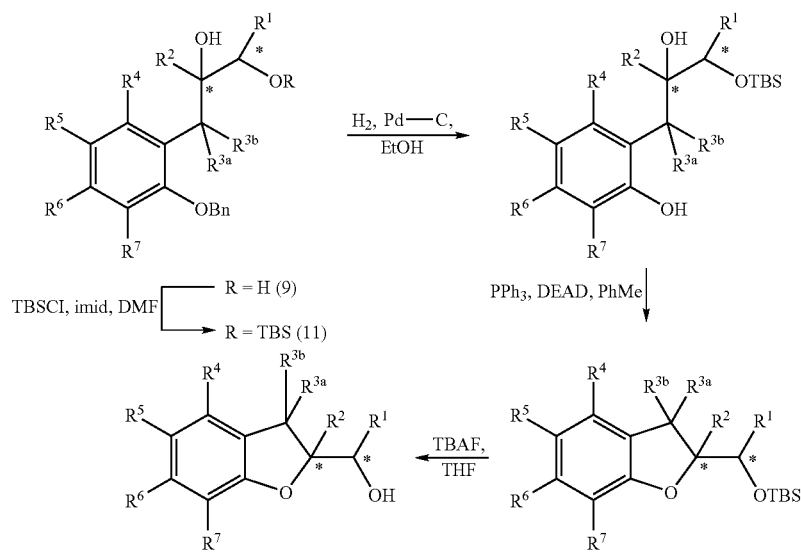

Scheme IV

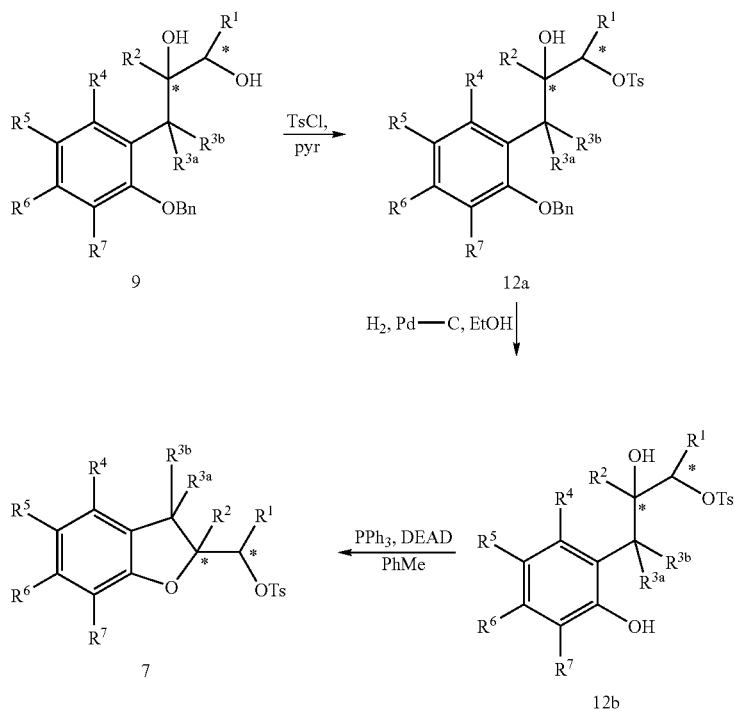

Deprotection of the benzyl ether with catalytic palladium on carbon gives phenol (12b) followed by cyclodehydration with triphenylphosphine in the presence of diethylazodicarboxylate (as previously described) provides the aforementioned 2,3-dihydro-1-benzofuran-2-yl)methyl 4-methylbenzenesulfonate (7).

An additional route to the production of stereochemically enriched compounds of Formula 1 is illustrated in Scheme V.

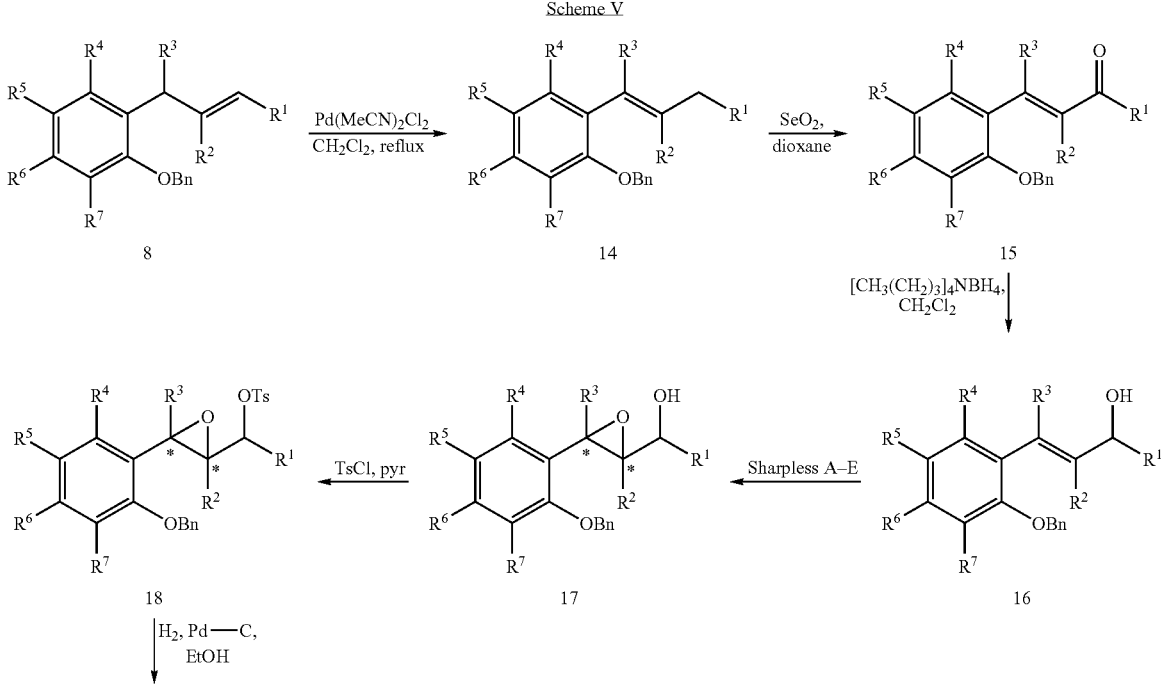

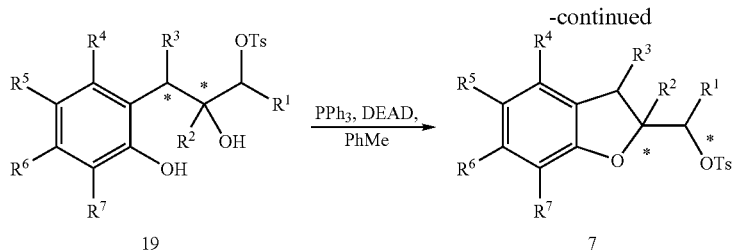

Palladium or transition metal catalyzed transposition of the double bond present in the previously described 2-allyl benzyl ether (8) using an appropriate catalyst such as dichlorobis (acetonitrile)palladium(II) in dichloromethane provides styrene derivative (14). Treatment of (14) with selenium dioxide in dioxane provides the carbonyl derivative (15). Reduction of the carbonyl to the allylic alcohol (16) can be accomplished by treatment with an appropriate reducing agent such as tetrabutylammonium borohydride in a solvent such as dichloromethane. The allylic alcohol (16) provides a suitable intermediate for the stereoselective introduction of oxygenation that permits transfer of this stereochemical integrity into the compounds of formula (1). The Sharpless Asymmetric Epoxidation (A-E) reaction is a general method for the stereoselective epoxidation of allylic alcohols and treatment of (16) under the appropriate conditions provides epoxy alcohol (17) with a high degree of stereoselectivity. The alcohol present in (17) can then be tosylated with p-toluenesulfonyl chloride as previously described to give derivative (18). Deprotection of the benzyl ether with concomitant regioselective opening of the epoxide maintaining the stereochemical information introduced by the Sharpless A-E is accomplished under the appropriate conditions by treatment of (18) with palladium on carbon under a hydrogen atmosphere in a solvent such as ethanol. Cyclodehydration using Mitsunobu conditions as previously described then affords 2,3-dihydro-1-benzofuran-2-yl)methyl 4-methylbenzenesulfonate (7).

The preparation of compounds of Formula 1 can also be accomplished in a stereospecific manner utilizing an optically pure commercially available intermediate. This method is described in detail in a copending U.S. provisional patent application entitled "Process For Stereospecific Synthesis of Dihydrobenzofuran Derivatives," filed in the name of Dahui Zhou, et al. on the same date as the instant application. That application is incorporated herein by reference in its entirety for all purposes. As shown in Scheme VI, below, for example, reaction of benzyl (S)-(+)-glycidyl ether with the anion obtained by treatment of 2-bromoanisole with an alkyllithium such as n-butyllithium provides the resultant epoxy intermediate. Ring opening of the epoxide with a Lewis acid such as borontrifluoride diethyletherate provides diol (9a) with the primary alcohol protected as the benzyl ether. Deprotection of the methoxy group in 9a by treatment with 30% hydrogen bromide in acetic acid results in concomitant formation of intermediate vicinal acetoxy bromide (10a) followed by removal of the acetate with aqueous hydrogen chloride to provide diol (13a). Cyclodehydration with triphenylphosphine in the presence of diethylazodicarboxylate (as previously described) provides the desired 2-(bromomethyl)-2,3-dihydro-1-benzofuran (7b) that can be converted to the 7-bromo derivative (7c) by treatment with bromine in acetic acid.

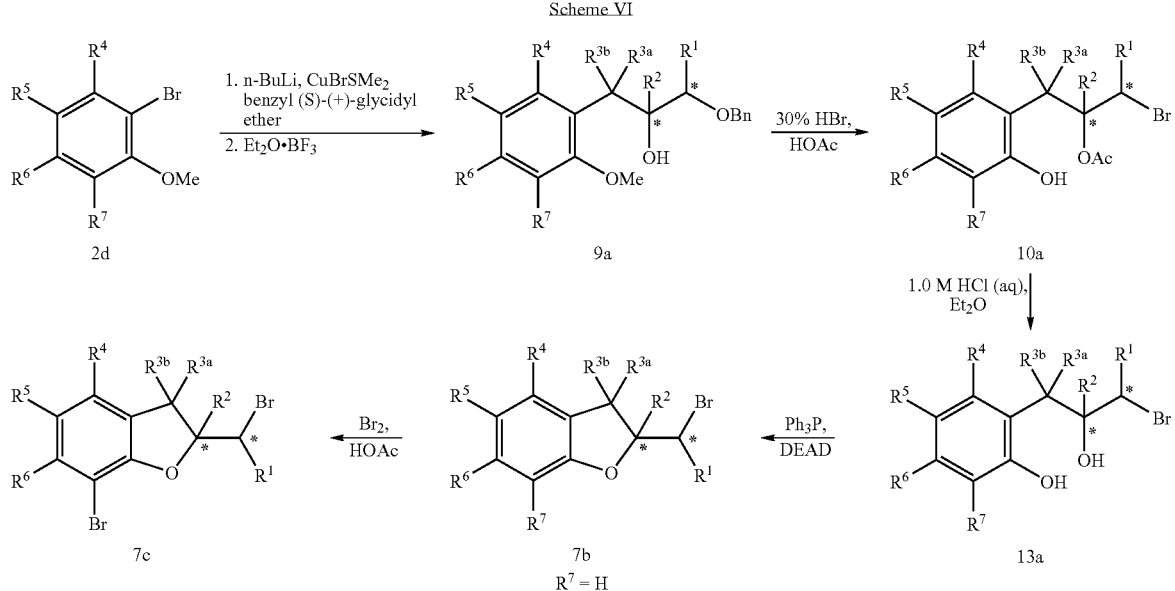

Scheme VI

A further method for the synthesis of stereochemically enriched compounds of Formula 1 is described in detail in copending U.S. provisional patent application entitled "Asymmetric Synthesis of 2-(methylamino)dihydrobenzofurans," filed in the name of Alexander Gontcharov, et al. on the same date as the instant application. That application is incorporated herein by reference in its entirety for all purposes. That method is illustrated in the preparation of the compound 2R-(−)-7-(2,6-dichlorophenyl)-5-fluoro-2,3-dihydro-2-aminomethylbenzofuran hydrochloride shown in Scheme VII.

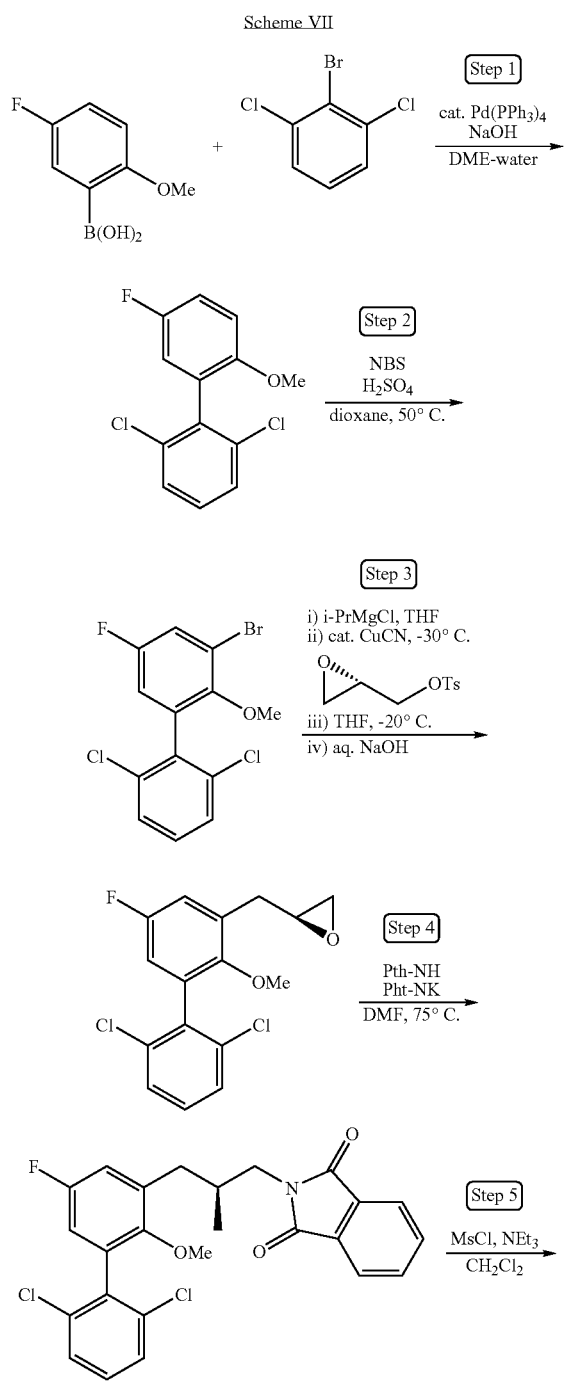

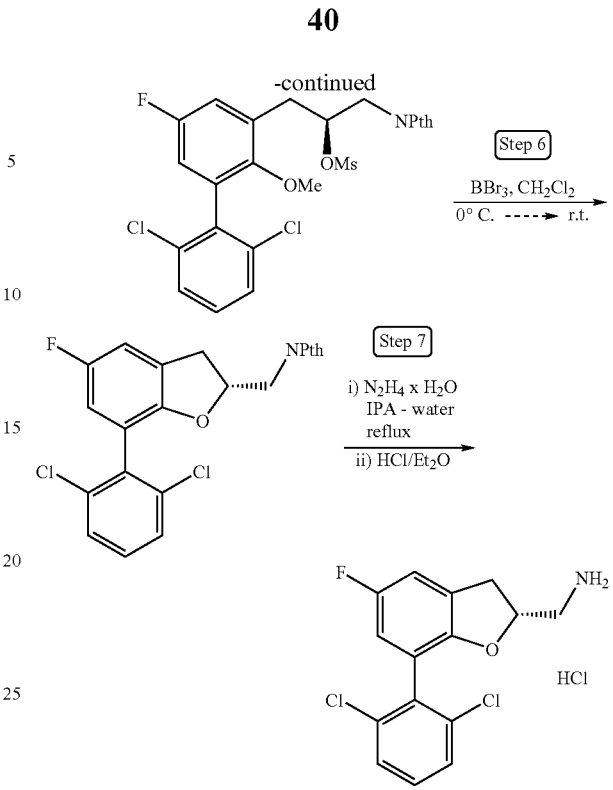

In certain embodiments, the invention relates to compositions comprising at least one compound of Formula 1, or a pharmaceutically acceptable salt thereof, and one or more pharmaceutically acceptable carriers, excipients, or diluents. Such compositions are prepared in accordance with acceptable pharmaceutical procedures, such as, for example, those described in *Remingtons Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those carriers that are compatible with the other ingredients in the formulation and are biologically acceptable.

The compounds of Formula 1 can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of Formula 1 can be administered rectally or vaginally in the form of a conventional suppository. For administration by intranasal or intrabronchial inhalation or insufflation, the compounds of Formula 1 can be formulated into an aqueous or partially aqueous solution, which can then be utilized in the form of an aerosol. The compounds of Formula 1 can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount of compound of formula 1 provided to a patient will vary depending upon what is being administered, the purpose of the administration, such as prophylaxis or therapy, the state of the patient, the manner of administration, and the like. In therapeutic applications, compounds of formula 1 are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. The treatment of substance abuse follows the same method of subjective drug administration under the guidance of the attending physician. Generally, a starting dose is about 5 mg per day with gradual increase in the daily dose to about 150 mg per day, to provide the desired dosage level in the patient.

In certain embodiments, the present invention is directed to prodrugs of compounds of Formula 1. The term "prodrug," as used herein, means a compound that is convertible in vivo by metabolic means (e.g. by hydrolysis) to a compound of Formula 1. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is hereby incorporated by reference in its entirety.

Intermediate 1

1-allyl-2-(benzyloxy)-4-methoxybenzene

To a solution of 2-allyl-5-methoxyphenol (20.30 g, 0.124 mol) in DMF (500 mL) was added potassium carbonate (68.35 g, 0.495 mol) followed by benzyl bromide (23.26 g, 0.136 mol) and tetrabutylammonium iodide (4.57 g, 0.012 mol). The reaction mixture was allowed to stir at room temperature for 12 h. The reaction mixture was diluted with water (1000 mL) to dissolve any solids and extracted with diethyl ether (3×250 mL). The combined organic layers were washed with water (4×500 mL), saturated aqueous sodium chloride (400 mL), dried (magnesium sulfate) and the solvent removed in vacuo to give a crude oil. Purification by flash column chromatography (silica, ethyl acetate:hexanes 1:19) provided 28.44 g (90%) of 1-allyl-2-(benzyloxy)-4-methoxybenzene as a colorless oil. $R_f$=0.88 (silica, ethyl acetate:hexanes 1:9); Anal. calcd. for $C_{17}H_{18}O_2$: C, 80.28; H, 7.13. Found: C, 82.43; H, 7.09.

Intermediate 2

(±)-3-[2-(benzyloxy)-4-methoxyphenyl]propane-1,2-diol

To a suspension of AD-mix-α (156.55 g) in water:tert-butyl alcohol (1:1,800 mL) cooled to 0° C. was slowly added via an addition funnel a solution of 1-allyl-2-(benzyloxy)-4-methoxybenzene (28.44 g, 0.112 mol) in water:tert-butyl alcohol (1:1,200 mL) and the reaction mixture was allowed to stir at 0° C. for 12 h. The reaction mixture was quenched by the addition of sodium sulfite. The reaction mixture was diluted with water (500 mL) and ethyl acetate (500 mL). The aqueous phase was separated and extracted with ethyl acetate (2×200 mL). The combined organic extracts were washed with saturated aqueous sodium chloride (400 mL), dried (magnesium sulfate) and the solvent was removed in vacuo to give a crude oil. Purification by flash column chromatography (silica, ethyl acetate:hexanes 3:2) gave 30.50 g (95%, 27% ee) of (±)-3-[2-(benzyloxy)-4-methoxyphenyl]propane-1,2-diol as a white crystalline solid. mp 82-86° C.; Anal. calcd. for $C_{17}H_{20}O_4$: C, 70.81; H, 6.99. Found: C, 70.78; H, 7.16.

Intermediate 3

(±)-3-[2-(benzyloxy)-4-methoxyphenyl]-2-hydroxypropyl 4-methylbenzenesulfonate

To a solution of (±)-3-[2-(benzyloxy)-4-methoxyphenyl] propane-1,2-diol (30.50 g, 0.106 mol) in anhydrous pyridine (600 mL) cooled to 0° C. under a nitrogen atmosphere was added p-toluenesulfonyl chloride (22.18 g, 0.116 mol). The reaction mixture was allowed to stir at 0° C. for 12 h. The reaction mixture was quenched by the addition of water (10 mL). The reaction mixture was diluted with ethyl acetate (750 mL) and the organic layer was washed with aqueous hydrogen chloride (6 N, 4×400 mL), saturated aqueous sodium chloride (300 mL), dried (magnesium sulfate) and the solvent was removed in vacuo to give a crude oil. Purification by flash column chromatography (silica, ethyl acetate:hexanes 2:8) gave 42.84 g (91%) of (±)-3-[2-(benzyloxy)-4-methoxyphenyl]-2-hydroxypropyl 4-methylbenzenesulfonate as a colorless oil. $R_f$=0.28 (silica, ethyl acetate:hexanes 2:8); Anal. calcd. for $C_{24}H_{26}O_6S$: C, 65.14; H, 5.92. Found: C, 64.59; H, 5.72.

Intermediate 4

(±)-2-hydroxy-3-(2-hydroxy-4-methoxyphenyl)propyl 4-methylbenzenesulfonate

To a solution of (±)-3-[2-(benzyloxy)-4-methoxyphenyl]-2-hydroxypropyl 4-methylbenzenesulfonate (42.84 g, 0.097 mol) in ethanol (600 mL) was added palladium on carbon (10 wt. %, 5.81 g) and the reaction mixture was shaken under an $H_2$ atmosphere (50 psi) for 6 h. The reaction mixture was filtered (celite) and the solvent removed in vacuo to provide 32.27 g (95%) of (±)-2-hydroxy-3-(2-hydroxy-4-methoxyphenyl)propyl 4-methylbenzenesulfonate as a colorless oil. $R_f$=0.34 (silica, ethyl acetate:hexanes 2:8); Anal. calcd. for $C_{17}H_{18}O_5S$: C, 61.06; H, 5.43. Found: C, 60.70; H, 5.37.

Intermediate 5

(±)-(6-methoxy-2,3-dihydro-1-benzofuran-2-yl)methyl 4-methylbenzenesulfonate

To a solution of (±)-2-hydroxy-3-(2-hydroxy-4-methoxyphenyl)propyl 4-methylbenzenesulfonate (32.27 g, 0.092 mol) in toluene (1000 mL) cooled to 0° C. was added triphenylphosphine (27.62 g, 0.105 mol) followed by dropwise addition of diethylazodicarboxylate (18.34 g, 0.105 mol) and the reaction mixture was allowed to stir at 0° C. for 15 min. The reaction mixture was quenched by the addition of water (10 mL). The solvent was removed in vacuo to give a crude solid. Purification by flash column chromatography (silica, ethyl acetate:hexanes 1:19) provided 22.53 g (74%) of (±)-(6-methoxy-2,3-dihydro-1-benzofuran-2-yl)methyl 4-methylbenzenesulfonate as a colorless oil. $R_f$=0.67 (silica, ethyl acetate:hexanes 1:9); Anal. calcd. for $C_{17}H_{18}O_5S$: C, 61.06; H, 5.43. Found: C, 60.70; H, 5.37.

Intermediate 6

(±)-(6-hydroxy-2,3-dihydro-1-benzofuran-2-yl)methyl 4-methylbenzenesulfonate

To a solution of (±)-(5-methoxy-2,3-dihydro-1H-inden-2-yl)methyl 4-methylbenzenesulfonate (13.5 g, 40.5 mmol) in dichloromethane (250 mL) at −70° C. was added boron tribromide (27.0 mL, 1.0 N in dichloromethane) over 15 min. The reaction mixture was allowed to stir at −70° C. for an additional 15 minutes and allowed to warm to room temperature over 6 h. The reaction mixture was quenched with ice water and the product extracted with ethyl acetate (600 mL). The organic layer dried (magnesium sulfate), and the solvent removed in vacuo to provide a crude oil. Purification by flash column chromatography (silica, ethyl acetate:hexanes 1:4→1:1) afforded 10.15 g (79%) of (±)-(6-hydroxy-2,3-dihydro-1-benzofuran-2-yl)methyl 4-methylbenzenesulfonate as a yellow solid. mp 107-110° C.; Anal. calcd. for $C_{16}H_{16}O_5S$: C, 59.99; H, 5.03. Found: C, 59.21; H, 5.05.

Intermediate 7

(±)-(6-phenyl-2,3-dihydro-1-benzofuran-2-yl)methyl 4-methylbenzenesulfonate

To a solution of (±)-(6-hydroxy-2,3-dihydro-1-benzofuran-2-yl)methyl 4-methylbenzenesulfonate (8.67 g, 27.2 mmol) in anhydrous dichloromethane (300 mL) at 0° C. was added diisopropylethylamine (4.22 g, 32.6 mmol) followed by trifluoromethanesulfonic anhydride (8.45 g, 29.9 mmol) and the reaction mixture was allowed to stir at 0° C. for 1 h. The reaction mixture was quenched with water (300 mL) and diluted with dichloromethane (400 mL), The combined organic layers were washed with saturated aqueous sodium chloride, dried (magnesium sulfate), and the solvent removed in vacuo to provide a crude solid. Purification by flash column chromatography (silica, ethyl acetate:hexanes 1:4→2:3) afforded 10.3 g (84%) of (±)-(6-{[(trifluoromethyl)sulfonyl]oxy}-2,3-dihydro-1-benzofuran-2-yl)methyl 4-methylbenzenesulfonate as a tan solid. To a solution of (±)-(6-{[(trifluoromethyl)sulfonyl]oxy}-2,3-dihydro-1-benzofuran-2-yl)methyl 4-methylbenzenesulfonate (2.0 g, 4.43 mmol) in dioxane (50 mL) was added phenylboronic acid (1.08 g, 8.86 mmol), tetrakis(triphenylphosphine)palladium(0) (1.0 g, 0.884 mmol), and lithium chloride (0.787 g, 17.43 mmol) and the reaction mixture was heated at 90° C. for 12 h. The reaction mixture was cooled to room temperature and diluted with water (500 mL) and ethyl acetate (500 mL). The organic layer was separated and washed with water (200 mL), saturated aqueous sodium chloride (200 mL), dried (magnesium sulfate) and the solvent removed in vacuo to give a crude solid. Purification by flash column chromatography (silica, ethyl acetate:hexanes 1:9) provided 0.170 g (10%) of (±)-(6-phenyl-2,3-dihydro-1-benzofuran-2-yl)methyl 4-methylbenzenesulfonate as an oil. $^1$H NMR (DMSO $d_6$) $\delta_H$ 7.75 (d, 2H); 7.56 (d, 2H); 7.42 (m, 4H); 7.28 (t, 1H); 7.21 (d, 1H); 7.08 (d, 1H); 6.92 (s, 1H); 4.98 (m, 1H); 4.24 (dd, 1H); 4.18 (q, 1H); 3.29 (dd, 1H); 2.88 (dd, 1H); 2.46 (s, 3H).

Intermediate 8

2-allyl-6-chloro-3-(trifluoromethyl)phenol

To a solution of 2-chloro-5-trifluoromethyl-phenol (10.00 g, 0.05 mol) in N,N-dimethylformamide (500 mL) was added potassium carbonate (28.12 g, 0.209 mol) followed by allyl bromide (7.38 g, 0.061 mol) and the reaction was allowed to stir at room temperature for 12 h. The reaction mixture was diluted with water (500 mL) to dissolve any solids and extracted with ethyl acetate (3×250 mL). The combined organic layers were washed with water (4×500 mL), saturated aqueous sodium chloride (400 mL), dried (magnesium sulfate) and the solvent removed in vacuo to give 2-(allyloxy)-1-chloro-4-(trifluoromethyl)benzene as a colorless oil. The oil was re-dissolved in mesitylene (35 mL) and heated at reflux for 12 h. Removal of the solvent in vacuo provided a crude oil. Purification by flash column chromatography (silica, ethyl acetate:hexanes 2:8) provided 9.6 g (96%) of 2-allyl-6-chloro-3-(trifluoromethyl)phenol as a amber oil. $R_f$=0.66 (silica, ethyl acetate:hexanes 1:4); $^1$H NMR (DMSO-$d_6$) $\delta_H$ 9.84 (s, 1H); 7.43 (d, 2H); 7.16 (d, 1H); 5.84 (m, 1H); 4.95 (d, 1H); 4.89 (d, 1H); 3.46 (d, 2H).

Intermediate 9

(±)-[7-chloro-4-(trifluoromethyl)-2,3-dihydro-1-benzofuran-2-yl]methanol

To a solution of 6-chloro-3-(trifluoromethyl)-2-vinylphenol (9.67 g, 0.043 mol) in dichloromethane 225 mL) was added 3-chloroperoxybenzoic acid (77%, 21.15 g, 0.122 mol). The reaction mixture was allowed to stir at room temperature for 8 h. The reaction mixture was washed with a 1:1 solution of 10% sodium sulfite:saturated sodium bicarbonate (2×200 mL). The solvent was removed in vacuo to give crude yellow oil. The oil was diluted with methanol (100 mL) and added to a solution of potassium carbonate (16.5 g, 0.119 mol) and methanol (825 mL) and the solution was allowed to stir at room temperature 2 h. The solvent was removed in vacuo. The residue was washed with water (1000 mL) and ethyl acetate (500 mL). The aqueous layer was acidified with 1 N aqueous hydrogen chloride and washed with ethyl acetate (500 mL). The combined organics were washed with water (500 mL), saturated aqueous sodium chloride (500 mL), dried (magnesium sulfate) and the solvent removed in vacuo to provide a crude solid. Purification by flash column chromatography (silica, ethyl acetate:hexanes 1:4) provided 6.71 g (70%) of (±)-(7-bromo-4-fluoro-2,3-dihydro-1-benzofuran-2-yl)methanol as a yellow oil. $R_f$=0.20 (silica, ethyl acetate: hexanes 1:4). Anal. calcd. for $C_{10}H_8ClF_3O_2$ C, 47.55; H, 3.19. Found C, 49.39; H, 3.57.

Intermediate 10

(±)-[7-chloro-4-(trifluoromethyl)-2,3-dihydro-1-benzofuran-2-yl]methyl 4-methylbenzenesulfonate To a solution of (±)-(7-bromo-4-fluoro-2,3-dihydro-1-benzofuran-2-yl)methanol (8.5, g, 0.034 mol) in pyridine (150 mL) cooled to 0° C. was added p-toluenesulfonyl chloride (7.06 g, 0.037 mol) and the reaction mixture was allowed to stir at 0° C. for 12 h. The reaction mixture was quenched by the addition of water (75 mL), diluted with diethyl ether (600 mL), washed with aqueous hydrogen chloride (1.0 M, 750 mL), water (200 mL), saturated aqueous sodium chloride (200 mL), dried (magnesium sulfate) and the solvent removed in vacuo to give a crude oil. Purification by flash column chromatography (silica, ethyl acetate:hexanes 2:8) afforded 7.0 g (51%) of (±)-[7-chloro-4-(trifluoromethyl)-2,3-dihydro-1-benzofuran-2-yl]methyl 4-methylbenzenesulfonate as a white solid $R_f$=0.60 (silica, ethyl acetate:hexanes 3:7); mp 89-92° C.; Anal. calcd. for $C_{17}H_{14}ClF_3O_4S$ C, 50.19; H, 3.47. Found C, 50.30; H, 3.35.

Intermediate 11

(±)-(7-cyclopentyl-2,3-dihydro-1-benzofuran-2-yl)methanol

Treatment of 2-allyl-6-cyclopentylphenol (6.97 g, 0.0344 mol) with 3-chloroperoxybenzoic acid (17.83 g, 0.1033 mol, 77%) and potassium carbonate (14.0 g, 0.1013 mol) generally according to the procedure described for Intermediate 9 afforded 4.1 g (54%) of (±)-(7-cyclopentyl-2,3-dihydro-1-benzofuran-2-yl)methanol as a yellow oil. $R_f$=0.58 (silica, ethyl acetate:hexanes 3:7); Anal. calcd. for $C_{14}H_{18}O_2$ C, 77.03; H, 8.31. Found C, 76.5; H, 8.44.

Intermediate 12

(±)-benzyl(7-cyclopentyl-2,3-dihydro-1-benzofuran-2-yl)methylcarbamate

To a suspension of (7-cyclopentyl-2,3-dihydro-1-benzofuran-2-yl)methylamine (2.4 g, 9.46 mmol) in tetrahydrofuran (100 mL) cooled to 0° C. was added diisopropylethylamine (2.14 g, 16.58 mmol) followed by benzyl chloroformate (2.08 g, 12.19 mmol) and the reaction mixture was allowed to stir for 15 min. The reaction mixture was quenched with water (100 mL). The aqueous layer was extracted with ethyl acetate (2×200 mL) and the combined organic extracts were washed with saturated aqueous sodium chloride (100 mL), dried (magnesium sulfate) and the solvent removed in vacuo. Purification by flash column chromatography (silica, ethyl acetate:hexanes 1:9) provided 2.52 g (76%) of (±)-benzyl(7-cyclopentyl-2,3-dihydro-1-benzofuran-2-yl)methylcarbamate as a yellow oil. $R_f$=0.21 (silica, ethyl acetate:hexanes 2:8); Anal. calcd. for $C_{22}H_{25}NO_3$ C, 75.19; H, 7.17; N, 3.99. Found C, 74.74; H, 7.02; N, 3.85. Chiral HPLC separation of (±)-benzyl(7-cyclopentyl-2,3-dihydro-1-benzofuran-2-yl)methylcarbamate (Chiralcel OJ, ethanol:hexane 1:1) provided two fractions. Fraction 1 ($R_t$=9.678 min, Chiralcel OJ, ethanol:hexane 1:1); Fraction 2 ($R_t$=12.824 min, Chiralcel OJ, ethanol:hexane 1:1).

Intermediate 13

(±)-(5-chloro-7-cyclohexyl-2,3-dihydro-1-benzofuran-2-yl)methanol

To a solution of 4-chloro-2-cyclohexylphenol (23.00 g, 0.109 mol) in N,N-dimethylformamide (600 mL) was added sodium hydride (4.56 g, 0.114 mol, 60 wt. %) followed by allyl bromide (14.51 g, 0.120 mol) and the reaction mixture was allowed to stir at room temperature for 5 h. The solvent was removed in vacuo and the residue diluted with water (500 mL) and extracted with ethyl acetate (2×300 mL). The combined organic layers were washed with water (500 mL), saturated aqueous sodium chloride (500 mL), dried (magnesium sulfate), and the solvent removed in vacuo to give 29.0 g of 1-(allyloxy)-4-chloro-2-cyclohexylbenzene as a brown oil. Treatment of the allyl ether in refluxing mesitylene generally according to the procedure described for Intermediate 8 provided 18.0 g of 2-allyl-4-chloro-6-cyclohexylphenol. Treatment of the phenol (6.5 g, 0.026 mol) with 3-chloroperoxybenzoic acid (9.88 g, 0.045 mol, 77%) followed by potassium carbonate (10.00 g, 0.072 mol) generally according to the procedure described for Intermediate 9 afforded 4.6 g (67%) of (±)-(5-chloro-7-cyclohexyl-2,3-dihydro-1-benzofuran-2-yl)methanol as a white solid. mp 67-69° C.; Anal. calcd. for $C_{15}H_{19}ClO_2$: C, 67.54; H, 7.18. Found: C, 67.81; H, 6.98.

Intermediate 14

(±)-methyl(5-chloro-7-cyclohexyl-2,3-dihydro-1-benzofuran-2-yl)methylcarbamate

Treatment of (±)-(5-chloro-7-cyclohexyl-2,3-dihydro-1-benzofuran-2-yl)methylamine (2.20 g, 7.28 mmol) with diisopropylethylamine (2.94 g, 22.7 mmol) and methyl chloroformate (1.08 g, 11.4 mmol) generally according to the procedure described for Intermediate 12 provided 2.30 g (93%) of (±)-methyl(5-chloro-7-cyclohexyl-2,3-dihydro-1-benzofuran-2-yl)methylcarbamate as a white solid. mp 100-103° C.; Anal. calcd. for $C_{17}H_{22}ClNO_3$: C, 63.06; H, 6.85; N, 4.33. Found: C, 63.16; H, 6.3; N, 4.25.

Intermediate 15

(±)-3-[3-benzyl-2-(benzyloxy)phenyl]propane-1,2-diol

Treatment of 2-allyl-6-benzylphenol (12.11 g, 0.054 mol) with potassium carbonate (30.00 g, 0.217 mol), benzyl bromide (10.67 g, 0.062 mol), and tetrabutylammonium iodide (2.01 g, 0.005 mol) generally according to the procedure described for Intermediate 1 provided 1-allyl-3-benzyl-2-(benzyloxy)benzene. Treatment of 1-allyl-3-benzyl-2-(benzyloxy)benzene (16.35 g, 0.052 mol) with AD-mix-ox (76.02 g) generally according to the procedure described for Intermediate 2 gave 9.82 (54%, 25% ee) of (±)-3-[3-benzyl-2-(benzyloxy)phenyl]propane-1,2-diol as a white crystalline solid. mp 55-58° C.; Anal. calcd. for $C_{23}H_{24}O_3$: C, 79.28; H, 6.94. Found: C, 78.89; H, 6.96.

Intermediate 16

(±)-3-[3-benzyl-2-(benzyloxy)phenyl]-2-hydroxypropyl 4-methylbenzenesulfonate

Treatment of (±)-3-[3-benzyl-2-(benzyloxy)phenyl]propane-1,2-diol (9.76 g, 0.028 mol) with p-toluenesulfonyl chloride (5.87 g, 0.031 mol) in pyridine (250 mL) generally according to the procedure described for Intermediate 3 gave 9.88 g (70%) of (±)-3-[3-benzyl-2-(benzyloxy)phenyl]-2-hydroxypropyl 4-methylbenzenesulfonate as a colorless oil. Anal. calcd. for $C_{30}H_{30}O_5S$: C, 71.69; H, 6.02. Found: C, 70.41; H, 6.14.

Intermediate 17

(±)-3-(3-benzyl-2-hydroxyphenyl)-2-hydroxypropyl 4-methylbenzenesulfonate

Treatment of (±)-3-[3-benzyl-2-(benzyloxy)phenyl]-2-hydroxypropyl 4-methylbenzenesulfonate (9.72 g, 0.019 mol) with palladium on carbon (0.97 g, 10 wt. %) generally according to the procedure described for Intermediate 4 provided 7.34 g (92%) of (±)-3-(3-benzyl-2-hydroxyphenyl)-2-hydroxypropyl 4-methylbenzenesulfonate as a colorless oil. Anal. calcd. for $C_{23}H_{24}O_5S$: C, 66.97; H, 5.86. Found: C, 66.11; H, 5.95.

Intermediate 18

(±)-(7-benzyl-2,3-dihydro-1-benzofuran-2-yl)methyl 4-methylbenzenesulfonate

Treatment of (±)-3-(3-benzyl-2-hydroxyphenyl)-2-hydroxypropyl 4-methylbenzenesulfonate (7.29 g, 0.018 mol) with triphenylphosphine (5.10 g, 0.019 mol) and diethylazodicarboxylate (3.39 g, 0.019 mol) generally according to the procedure described for Intermediate 5 afforded 6.57 g (94%) of (±)-(7-benzyl-2,3-dihydro-1-benzofuran-2-yl)methyl 4-methylbenzenesulfonate as a colorless oil. Anal. calcd. for $C_{23}H_{22}O_4S$: C, 70.03; H, 5.62. Found: C, 68.97; H, 5.42.

Intermediate 19

(±)-benzyl(7-benzyl-2,3-dihydro-1-benzofuran-2-yl)methylcarbamate

Treatment of (±)-1-(7-benzyl-2,3-dihydro-1-benzofuran-2-yl)methanamine (2.0 g, 8.36 mmol) with disopropylethylamine (1.62 g, 12.56 mmol) and benzyl chloroformate (1.64 g, 9.61 mmol) generally according to the procedure described for Intermediate 12 provided 2.96 g (95%) of (±)-benzyl(7-benzyl-2,3-dihydro-1-benzofuran-2-yl)methylcarbamate as a colorless oil. Anal. calcd. for $C_{24}H_{23}NO_3$ C, 77.19; H, 6.21; N, 3.75. Found C, 75.58; H, 6.42; N, 3.55. Chiral HPLC eparation of (±)-benzyl(7-benzyl-2,3-dihydro-1-benzofuran-2-yl)methylcarbamate (Chiralcel OD, methanol) provided two fractions. Fraction 1 ($R_t$=12.085 min, Chiralcel OD, methanol); Fraction 2 ($R_t$=17.945 min, Chiralcel OD, methanol).

Intermediate 20

(±)-(7-isopropyl-2,3-dihydro-1-benzofuran-2-yl)methyl 4-methylbenzenesulfonate

Treatment of 2-allyl-6-isopropylphenol (8.81 g, 0.05 mmol) with 3-chloroperoxybenzoic acid (22.43 g, 0.13 mol, 77%)) followed by potassium carbonate (13.82 g, 0.1 mol) generally according to the procedure described for Intermediate 9 provided (±)-(7-isopropyl-2,3-dihydro-1-benzofuran-2-yl)methanol. Treatment of (±)-(7-isopropyl-2,3-dihydro-1-benzofuran-2-yl)methanol (3.45 g, 0.018 mol) with p-toluenesulfonyl chloride (3.92 g, 0.021 mol) generally according to the procedure described for Intermediate 10 afforded 4.91 g (79%) (±)-(7-isopropyl-2,3-dihydro-1-benzofuran-2-yl)methyl 4-methylbenzenesulfonate as a colorless oil. Anal. calcd. for $C_{19}H_{22}O_4S$ C, 65.87; H, 6.4. Found C, 65.63; H, 6.32.

Intermediate 21

(±)-benzyl(7-isopropyl-2,3-dihydro-1-benzofuran-2-yl)methylcarbamate

Treatment of (±)-(7-isopropyl-2,3-dihydro-1-benzofuran-2-yl)methylamine (2.2 g, 9.66 mmol) with diisopropylethylamine (3.12 g, 24.15 mmol) and benzyl chloroformate (1.81 g, 10.63 mmol) generally according to the procedure described for Intermediate 12 gave 1.2 g (59%) of (±)-benzyl (7-isopropyl-2,3-dihydro-1-benzofuran-2-yl)methylcarbamate as a colorless oil. Anal. calcd. for $C_{20}H_{23}NO_3$ C, 73.82; H, 7.12; N, 4.3. Found C, 73.32; H, 7.33; N, 4.15. Chiral HPLC separation of (±)-benzyl(7-isopropyl-2,3-dihydro-1-benzofuran-2-yl)methylcarbamate (Chiralcel OJ, ethanol) provided two fractions. Fraction 1 ($R_t$=9.319 min, Chiralcel OJ, ethanol); Fraction 2 ($R_t$=11.868 min, Chiralcel OJ, ethanol).

Intermediate 22

2-allyl-4-chloro-6-isopropyl-3-methylphenol

Treatment of 4-chloro-2-isopropyl-5-methylphenol (10.00 g, 0.054 mol) with potassium carbonate (29.94 g, 0.217 mol) and allyl bromide (7.86 g, 0.065 mol), followed by refluxing the resultant allyl ether in mesitylene generally according to the procedure described for Intermediate 8 provided 8.92 g (73%) of 2-allyl-4-chloro-6-isopropyl-3-methylphenol as a colorless oil. $R_f$=0.85 (silica, ethyl acetate:hexanes 1:9); Anal. calcd. for $C_{13}H_{17}ClO$: C, 69.48; H, 7.62. Found: C, 69.87; H, 7.43.

Intermediate 23

(±)-(5-chloro-7-isopropyl-4-methyl-2,3-dihydro-1-benzofuran-2-yl)methyl 4-methylbenzenesulfonate Treatment of 2-allyl-4-chloro-6-isopropyl-3-methylphenol (8.88 g, 0.04 mmol) with 3-chloroperoxybenzoic acid (13.63 g, 0.079 mol, 77%)) followed by potassium carbonate (10.92 g, 0.079 mol) generally according to the procedure described for Intermediate 9 provided (±)-(5-chloro-7-isopropyl-4-methyl-2,3-dihydro-1-benzofuran-2-yl)methanol. Treatment of (±)-(5-chloro-7-isopropyl-4-methyl-2,3-dihydro-1-benzofuran-2-yl)methanol (5.95 g, 0.025 mol) with p-toluenesulfonyl chloride (5.66 g, 0.03 mol) generally according to the procedure described for Intermediate 10 afforded 6.71 g (69%) (±)-(5-chloro-7-isopropyl-4-methyl-2, 3-dihydro-1-benzofuran-2-yl)methyl 4-methylbenzenesulfonate as a white solid. mp 103-105° C.; Anal. calcd. for $C_{20}H_{23}ClO_4S$ C, 60.83; H, 5.87. Found C, 60.67; H, 5.88.

Intermediate 24

(±)-benzyl(5-chloro-7-isopropyl-4-methyl-2,3-dihydro-1-benzofuran-2-yl)methylcarbamate Treatment of (±)-1-(5-chloro-7-isopropyl-4-methyl-2,3-dihydro-1-benzofuran-2-yl)methanamine (3.41 g, 12.3 mmol) with diisopropylethylamine (1.99 g, 14.2 mmol) and benzyl chloroformate (2.42 g, 14.2 mmol) generally according to the procedure described for Intermediate 12 gave 3.74 g (81%) of (±)-benzyl(5-chloro-7-isopropyl-4-methyl-2,3-dihydro-1-benzofuran-2-yl)methylcarbamate as a colorless oil. Anal. calcd. for $C_{21}H_{24}ClNO_3$ C, 67.46; H, 6.47; N, 3.75. Found C, 67.01; H, 6.52; N, 3.56. Chiral HPLC separation of (±)-benzyl(5-chloro-7-isopropyl-4-methyl-2,3-dihydro-1-benzofuran-2-yl)methylcarbamate (Chiralpak AD, ethanol) provided two fractions.

Intermediate 25

(−)-benzyl(5-chloro-7-isopropyl-4-methyl-2,3-dihydro-1-benzofuran-2-yl)methylcarbamate Fraction 1 obtained as a white solid from the separation of (±)-benzyl(5-chloro-7-isopropyl-4-methyl-2,3-dihydro-1-benzofuran-2-yl)methylcarbamate ($R_t$=4.132 min, Chiralpak AD, ethanol). $[\alpha]_D^{25}$=−38.52 (c 10.0 in methanol); mp 59-62° C.; Anal. calcd. for $C_{21}H_{24}ClNO_3$ C, 67.46; H, 6.47; N, 3.75. Found C, 67.26; H, 6.41; N, 3.36.

Intermediate 26

(±)-benzyl(5-chloro-7-isopropyl-4-methyl-2,3-dihydro-1-benzofuran-2-yl)methylcarbamate Fraction 2 obtained as a white solid from the separation of (±)-benzyl(5-chloro-7-isopropyl-4-methyl-2,3-dihydro-1-benzofuran-2-yl)methylcarbamate ($R_t$=5.393 min, Chiralpak AD, ethanol). $[\alpha]_D^{25}$=+37.84 (c 10.0 in methanol); mp 59-62° C.; Anal. calcd. for $C_{21}H_{24}ClNO_3$ C, 67.46; H, 6.47; N, 3.75. Found C, 67.2; H, 6.49; N, 3.58.

Intermediate 27

1-allyl-2-(benzyloxy)-3-tert-butylbenzene

Treatment of 2-allyl-6-tert-butylphenol (12.5 g, 0.066 mol) with potassium carbonate (27.24 g, 0.197 mol), benzyl bromide (11.80 g, 0.069 mol), and tetrabutylammonium iodide (2.43 g, 6.57 mmol) generally according to the procedure described for Intermediate 1 provided 16.2 g (88%) of 1-allyl-2-(benzyloxy)-3-tert-butylbenzene as a colorless oil. Anal. calcd. for $C_{20}H_{24}O$: C, 85.67; H, 8.63. Found: C, 86.27; H, 8.77.

Intermediate 28

(±)-3-[2-(benzyloxy)-3-tert-butylphenyl]propane-1, 2-diol

To a suspension of potassium ferricyanide (57.00 g, 0.173 mol), potassium carbonate (24.00 g, 0.174 mol), hydroquinine anthraquinone-1,4-diyl diether (0.495 g, 0.578 mmol), and potassium osmate dihydrate (0.043 g, 0.117 mmol) in water:tert-butyl alcohol (1:1, 600 mL) cooled to 0° C. was slowly added via an addition funnel a solution of 1-allyl-2-(benzyloxy)-3-tert-butylbenzene (16.2 g, 0.058 mol) in tert-butyl alcohol (50 mL) and the reaction mixture was allowed to stir at 0° C. for 12 h. The reaction mixture was quenched by the addition of sodium sulfite. The reaction mixture was diluted with water (500 mL) and ethyl acetate (500 mL). The aqueous phase was separated and extracted with ethyl acetate (2×200 mL). The combined organic extracts were washed with saturated aqueous sodium chloride (400 mL), dried (magnesium sulfate) and the solvent was removed in vacuo to give a crude oil. Purification by flash column chromatography (silica, ethyl acetate:hexanes 3:2) gave 16.75 g (92%, 32% ee) of (±)-3-[2-(benzyloxy)-3-tert-butylphenyl]propane-1,2-diol as a white solid. mp 79-81° C.; Anal. calcd. for $C_{20}H_{26}O_3$: C, 76.4; H, 8.33. Found: C, 76.39; H, 8.22.

Intermediate 29

(±)-3-(3-tert-butyl-2-hydroxyphenyl)-2-hydroxypropyl 4-methylbenzenesulfonate

Treatment of (±)-3-[2-(benzyloxy)-3-tert-butylphenyl] propane-1,2-diol (16.50 g, 0.053 mol) with p-toluenesulfonyl chloride (10.51 g, 0.055 mol) in pyridine (400 mL) generally according to the procedure described for Intermediate 3 gave 42.84 g (91%) of (±)-3-[2-(benzyloxy)-4-methoxyphenyl]-2-hydroxypropyl 4-methylbenzenesulfonate. Treatment of the tosylate with palladium on carbon (2.4 g, 10 wt. %) generally according to the procedure described for Intermediate 4 provided 14.71 g (74%) of (±)-3-(3-tert-butyl-2-hydroxyphenyl)-2-hydroxypropyl 4-methylbenzenesulfonate as a white solid. mp 98-101° C.; Anal. calcd. for $C_{20}H_{26}O_5S$: C, 63.47; H, 6.92. Found: C, 63.24; H, 6.99.

Intermediate 30

(±)-(7-tert-butyl-2,3-dihydro-1-benzofuran-2-yl) methyl 4-methylbenzenesulfonate Treatment of (±)-3-(3-tert-butyl-2-hydroxyphenyl)-2-hydroxypropyl 4-methylbenzenesulfonate (14.66 g, 0.039 mol) with triphenylphosphine (11.18 g, 0.043 mol) and diethylazodicarboxylate (7.42 g, 0.043 mol) generally according to the procedure described for Intermediate 5 afforded 12.48 g (89%) of (±)-(7-tert-butyl-2,3-dihydro-1-benzofuran-2-yl) methyl 4-methylbenzenesulfonate as a colorless oil. Anal. calcd. for $C_{20}H_{24}O_4S$: C, 66.64; H, 6.71. Found: C, 66.28; H, 6.95.

Intermediate 31

(±)-benzyl(7-tert-butyl-2,3-dihydro-1-benzofuran-2-yl)methylcarbamate

Treatment of (±)-1-(7-tert-butyl-2,3-dihydro-1-benzofuran-2-yl)methanamine (3.25 g, 13.4 mmol) with diisopropylethylamine (4.34 g, 33.6 mmol) and benzyl chloroformate (2.64 g, 15.5 mmol) generally according to the procedure described for Intermediate 12 gave 4.37 g (96%) of (±)-benzyl(7-tert-butyl-2,3-dihydro-1-benzofuran-2-yl)methylcarbamate as a white solid. mp 73-76° C.; Anal. Calcd. for $C_{21}H_{25}NO_3$ C, 74.31; H, 7.42; N, 4.13. Found C, 74.95; H, 7.51; N, 4.18. Chiral HPLC separation of (±)-benzyl(7-tert-butyl-2,3-dihydro-1-benzofuran-2-yl)methylcarbamate (Chiralcel OJ, ethanol) provided two fractions. Fraction 1 ($R_t$=9.100 min, Chiralcel OJ, ethanol); Fraction 2 ($R_t$=14.428 min, Chiralcel OJ, ethanol).

Intermediate 32

(±)-(7-tert-butyl-5-chloro-2,3-dihydro-1-benzofuran-2-yl)methyl 4-methylbenzenesulfonate Treatment of 2-tert-butyl-4-chlorophenol (12.73 g, 0.070 mol) with allyl bromide (10.01 g, 0.083 mol) and potassium carbonate (38.11 g, 0.276 mol) followed by refluxing the resultant allyl ether in mesitylene generally according to the procedure described for Intermediate 8 gave 2-allyl-6-tert-butyl-4-chlorophenol. Treatment of the phenol with 3-chloroperoxybenzoic acid (35.90 g, 0.146 mol, 77%) followed by potassium carbonate (28.18 g, 0.204 mol) generally according to the procedure described for Intermediate 9 provided (±)-(7-tert-butyl-5-chloro-2,3-dihydro-1-benzofuran-2-yl)methanol. Treatment of the alcohol with with p-toluenesulfonyl chloride (10.27 g, 0.054 mol) generally according to the procedure described for Intermediate 10 afforded 13.84 g (51%) (±)-(7-tert-butyl-5-chloro-2,3-dihydro-1-benzofuran-2-yl)methyl 4-methylbenzenesulfonate as a white solid. mp 74-77° C.; Anal. calcd. for $C_{20}H_{23}ClO_4S$ C, 60.83; H, 5.87. Found C, 60.79; H, 5.80.

Intermediate 33

(±)-benzyl(7-tert-butyl-5-chloro-2,3-dihydro-1-benzofuran-2-yl)methylcarbamate

Treatment of (±)-1-(7-tert-butyl-5-chloro-2,3-dihydro-1-benzofuran-2-yl)methanamine (1.80 g, 6.52 mmol) with diisopropylethylamine (2.11 g, 16.29 mmol) and benzyl chloroformate (1.28 g, 7.49 mmol) generally according to the procedure described for Intermediate 12 gave 2.33 g (95%) of (±)-benzyl(7-tert-butyl-5-chloro-2,3-dihydro-1-benzofuran-2-yl)methylcarbamate as a colorless oil. Anal. calcd. for $C_{21}H_{24}ClNO_3$ C, 67.46; H, 6.47; N, 3.75. Found C, 67.27; H, 6.62; N, 3.66. Chiral HPLC separation of (±)-benzyl(7-tert-butyl-5-chloro-2,3-dihydro-1-benzofuran-2-yl)methylcarbamate (Chiralpak AD, hexane:isopropanol 9:1) provided two fractions. Fraction 1 ($R_t$=5.642 min, Chiralpak AD, hexane:isopropanol 9:1); Fraction 2 ($R_t$=6.494 min, Chiralpak AD, hexane:isopropanol 9:1).

Intermediate 34

(±)-benzyl(7-tert-butyl-5-methoxy-2,3-dihydro-1-benzofuran-2-yl)methylcarbamate

Treatment of (±)-(7-tert-butyl-5-methoxy-2,3-dihydro-1-benzofuran-2-yl)methylamine (1.03 g, 3.8 mmol) with diisopropylethylamine (0.735 g, 5.7 mmol) and benzyl chloroformate (0.711 g, 4.2 mmol) generally according to the procedure described for Intermediate 12 gave 1.2 g (59%) of (±)-benzyl(7-tert-butyl-5-methoxy-2,3-dihydro-1-benzofuran-2-yl)methylcarbamate as a colorless oil. $R_f$=0.51 (silica, ethyl acetate:hexanes 2:8); Anal. calcd. for $C_{22}H_{27}NO_4$ C, 71.52; H, 7.37; N, 3.79. Found C, 71.2; H, 7.44; N, 3.77.

Intermediate 35

2-(2-isopropylphenyl)-4,4,5,5-tetramethyl-1,3,2-dioxaborolane

To a solution of dichloro[1,1'-bis(diphenylphosphino)ferrocene]palladium(II)dichloromethane adduct (0.92 g, 1.12 mmol) and 1,1'-bis(diphenylphosphino) ferrocene (0.62 g, 1.12 mmol) in dioxane (275 mL) was added 2-isopropylphenyl trifluoromethanesulfonate (10.0 g, 37.5 mmol), bis(pinacolato)diboron (10.48 g, 41.26 mmol) and potassium acetate (10.96 g, 55.83 mmol) and the reaction mixture was heated to 90° C. and allowed to stir for 36 h. The reaction mixture was cooled to room temperature and diluted with water (300 mL) and extracted with diethyl ether (2×300 mL). The combined organic layers were washed with water (2×200 mL) and saturated aqueous sodium chloride (200 mL), were dried (magnesium sulfate), and the solvent was removed in vacuo to provide a crude oil. Purification by flash column chromatography (silica, ethyl acetate:hexane 1:1) provided 3.9 g (43%) of 2-(2-isopropylphenyl)-4,4,5,5-tetramethyl-1,3,2-dioxaborolane as a pale yellow oil. $^1$H NMR (DMSO-d$_6$) $\delta_H$ 7.57 (d, 1H); 7.38 (t, 1H); 7.30 (d, 1H); 7.13 (t, 1H); 3.57 (m, 1H); 1.27 (s, 12H); 1.14 (d, 6H).

Intermediate 36

(±)-(4-bromo-2,3-dihydro-1-benzofuran-2-yl)methyl 4-methylbenzenesulfonate

Treatment of 2-allyl-5-bromophenol (27.25 g, 0.128 mmol), with 3-chloroperoxybenzoic acid (66.20 g, 0.384 mol, 77%)) followed by potassium carbonate (44.18 g, 0.319 mol) generally according to the procedure described for Intermediate 9 provided (±)-(4-bromo-2,3-dihydro-1-benzofuran-2-yl)methanol as a yellow oil. Treatment of the oil with p-toluenesulfonyl chloride (15.65 g, 0.082 mol) generally according to the procedure described for Intermediate 10 afforded 24.7 g (78%) of (±)-(4-bromo-2,3-dihydro-1-benzofuran-2-yl)methyl 4-methylbenzenesulfonate as a white solid. mp 90-91° C.; Anal. calcd. for $C_{16}H_{15}BrO_4S$: C, 50.14; H, 3.94. Found: C, 50.09; H, 3.82.

Intermediate 37

(±)-(4-phenyl-2,3-dihydro-1-benzofuran-2-yl)methyl 4-methylbenzenesulfonate

To a solution of (±)-(4-bromo-2,3-dihydro-1-benzofuran-2-yl)methyl 4-methylbenzenesulfonate (2.05 g, 5.21 mmol) and phenylboronic acid (0.952 g, 7.81 mmol) in dioxane (50 mL) heated to 100° C. was added dichlorobis(tri-o-tolylphosphine)-palladium(II) (0.205 g, 0.261 mmol) and potassium carbonate (1.80 g, 13.04 mmol) and the reaction mixture was allowed to stir at 100° C. for 12 h. The reaction mixture was cooled to room temperature, diluted with diethyl ether (250 mL), and filtered (celite). The organic layer was washed with water (2×100 mL) and saturated aqueous sodium chloride (100 mL), was dried (magnesium sulfate), and the solvent was removed in vacuo to provide a crude oil. Purification by flash column chromatography (silica, ethyl acetate:hexanes 1:9) provided 1.45 g (73%) of (±)-(4-phenyl-2,3-dihydro-1-benzofuran-2-yl)methyl 4-methylbenzenesulfonate as a clear oil. $R_f$=0.34 (silica, ethyl acetate:hexanes 1:4); Anal. calcd. for $C_{22}H_{20}O_4S$: C, 69.45; H, 5.30. Found: C, 69.17; H, 5.30.

Intermediate 38

(±)-benzyl(4-phenyl-2,3-dihydro-1-benzofuran-2-yl)methylcarbamate

Treatment of (±)-(4-phenyl-2,3-dihydro-1-benzofuran-2-yl)methanamine (0.622 g, 2.38 mmol) with diisopropylethylamine (0.447 g, 3.57 mmol) and benzyl chloroformate (0.462 g, 2.62 mmol) generally according to the procedure described for Intermediate 12 provided 0.601 g (70%) of (±)-benzyl(4-phenyl-2,3-dihydro-1-benzofuran-2-yl)methylcarbamate as a white solid. mp 132-134° C.; Anal. calcd. for $C_{23}H_{21}NO_3$: C, 76.86H, 5.89; N, 3.90. Found: C, 75.98H, 5.80; N, 3.72. Chiral HPLC separation of (±)-benzyl(4-phenyl-2,3-dihydro-1-benzofuran-2-yl)methylcarbamate (Chiralcel OD, ethanol:water 15:85) provided two fractions. Fraction 1 ($R_t$=6.651 min Chiralcel OD, ethanol:water 1:3); Fraction 2 ($R_t$=7.395 min, Chiralcel OD, ethanol:water 1:3).

Intermediate 39

(±)-[4-(2-methylphenyl)-2,3-dihydro-1-benzofuran-2-yl]methyl 4-methylbenzenesulfonate Treatment of (±)-(4-bromo-2,3-dihydro-1-benzofuran-2-yl)methyl 4-methylbenzenesulfonate (2.0 g, 5.21 mmol), 2-methylphenyl boronic acid (1.06 g, 7.82 mmol), dichlorobis(tri-o-tolylphosphine)-palladium(II) (0.205 g, 0.261 mmol), and potassium carbonate (1.80 g, 13.04 mmol) generally according to the procedure described for Intermediate 37 provided 1.41 g (69%) of (±)-[4-(2-methylphenyl)-2,3-dihydro-1-benzofuran-2-yl]methyl 4-methylbenzenesulfonate as a yellow oil. $R_f$=0.42 (silica, ethyl acetate:hexanes 1:4); Anal. calcd. for $C_{23}H_{22}O_4S$: C, 70.03; H, 5.62. Found: C, 69.70; H, 5.45.

Intermediate 40

(±)-benzyl[4-(2-methylphenyl)-2,3-dihydro-1-benzofuran-2-yl]methylcarbamate

Treatment of (±)-1-[4-(2-methylphenyl)-2,3-dihydro-1-benzofuran-2-yl]methanamine (0.533 g, 1.94 mmol) with diisopropylethylamine (0.375 g, 2.90 mmol) and benzyl chloroformate (0.363 g, 2.13 mmol) generally according to the procedure described for Intermediate 12 provided 0.594 g (82%) of (±)-benzyl[4-(2-methylphenyl)-2,3-dihydro-1-benzofuran-2-yl]methylcarbamate as colorless oil. $R_f$=0.42 (silica, ethyl acetate:hexanes 1:4); Anal. calcd. for $C_{24}H_{23}NO_3$: C, 77.19H, 6.21; N, 3.75. Found: C, 76.0H, 6.01; N, 3.55. Chiral HPLC separation of (±)-benzyl[4-(2-methylphenyl)-2,3-dihydro-1-benzofuran-2-yl]methylcarbamate (Chiralcel OD, methanol) provided two fractions. Fraction 1 ($R_t$=5.952 min Chiralcel OD, methanol); Fraction 2 ($R_t$=7.345 min, Chiralcel OD, methanol).

Intermediate 41

1-allyl-2-(benzyloxy)-3-methoxybenzene

Treatment of guaiacol (25.00 g, 0.201 mol) with allyl bromide (29.24 g, 0.242 mol) and potassium carbonate (83.50 g, 0.604 mol) followed by refluxing the resultant allyl ether in mesitylene generally according to the procedure described for Intermediate 8 afforded 2-allyl-6-methoxyphenol as a brown oil. Treatment of the phenol with potassium carbonate (83.5 g, 0.604 mol), benzyl bromide (36.19 g, 0.212 mol), and tetrabutylammonium iodide (7.42 g, 0.020 mol) generally according to the procedure described for Intermediate 1 gave 23.61 g (45%) of 1-allyl-2-(benzyloxy)-3-methoxybenzene as a pale yellow oil. $R_f$=0.71 (silica, ethyl acetate:hexanes 1:9); Anal. calcd. for $C_{17}H_{18}O_2$: C, 80.28; H, 7.13. Found: C, 79.09; H, 6.93.

Intermediate 42

(±)-3-[2-(benzyloxy)-3-methoxyphenyl]propane-1,2-diol

Treatment of (4-methoxy-1,3-benzodioxol-2-yl)methanol (23.61 g, 0.093 mol) with AD-mix-α (129.97 g) generally according to the procedure described for Intermediate 2 provided 26.49 g (99%, 34% ee) of (±)-3-[2-(benzyloxy)-3-methoxyphenyl]propane-1,2-diol as a colorless oil. $R_f$=0.63 (silica, ethyl acetate:hexanes 3:2); Anal. calcd. for $C_{17}H_{20}O_4$: C, 70.81; H, 6.99. Found: C, 69.33; H, 7.12.

Intermediate 43

(±)-1-[2-(benzyloxy)-3-methoxyphenyl]-3-{[tert-butyl(dimethyl)silyl]oxy}propan-2-ol To a solution of (±)-3-[2-(benzyloxy)-3-methoxyphenyl]propane-1,2-diol (50.23 g, 0.174 mol) in N,N-dimethylformamide (600 mL) was added tert-butyldimethylsilyl chloride (28.88 g, 0.192 mol) followed by triethylamine (22.03 g, 0.218 mol) and 4-(dimethylamino)pyridine (2.12 g, 0.017 mol) and the reaction mixture was allowed to stir at room temperature for 6 h. The reaction mixture was quenched by the addition of water (1000 mL) and was extracted with ethyl acetate (3×300 mL). The combined organic extracts were washed with water (4×300 mL), aqueous hydrogen chloride (1.0 N, 400 mL), saturated aqueous sodium chloride (300 mL), dried (magnesium sulfate) and the solvent was removed in vacuo to give a crude oil. Purification by flash column chromatography (silica, ethyl acetate:hexanes 3:7) provided 58.14 g (83%) of (±)-1-[2-(benzyloxy)-3-methoxyphenyl]-3-{[tert-butyl(dimethyl)silyl]oxy}propan-2-ol as a colorless oil. $R_f$=0.48 (silica, ethyl acetate:hexanes 3:7); Anal. calcd. for $C_{23}H_{34}O_4Si$: C, 68.62; H, 8.51. Found: C, 69.20; H, 8.91.

Intermediate 44

(±)-tert-butyl[(7-methoxy-2,3-dihydro-1-benzofuran-2-yl)methoxy]dimethylsilane

Treatment of (±)-1-[2-(benzyloxy)-3-methoxyphenyl]-3-{[tert-butyl(dimethyl)silyl]oxy}propan-2-ol (58.14 g, 0.144 mol) with palladium on carbon (5.81 g, 10 wt. %) generally according to the procedure described for Intermediate 4 provided (±)-2-(3-[tert-butyl(dimethyl)silyl]oxy}-2-hydroxypropyl)-6-methoxyphenol as a crude oil. Treatment of the phenol with triphenylphosphine (44.52 g, 0.170 mol) and diethylazodicarboxylate (29.56 g, 0.170 mol) generally according to the procedure described for Intermediate 5 gave 34.12 g (80%) of (±)-tert-butyl[(7-methoxy-2,3-dihydro-1-benzofuran-2-yl)methoxy]dimethylsilane as a colorless oil. $R_f$=0.67 (silica, ethyl acetate:hexanes 1:9); Anal. calcd. for $C_{16}H_{26}O_3Si$: C, 65.26; H, 8.90. Found: C, 64.26; H, 9.24.

Intermediate 45

(±)-(7-methoxy-2,3-dihydro-1-benzofuran-2-yl)methyl 4-methylbenzenesulfonate

To a solution of (±)-tert-butyl[(7-methoxy-2,3-dihydro-1-benzofuran-2-yl)methoxy]dimethylsilane (34.12 g; 0.116 mol) in tetrahydrofuran (700 mL) cooled to 0° C. was added via an addition funnel tetrabutylammonium fluoride (140 mL, 1.0 M solution in tetrahydrofuran) and the reaction mixture was allowed to stir at room temperature for 6 h. The reaction was diluted with water (500 mL) and extracted with ethyl acetate (2×300 mL). The combined organic extracts were washed with saturated aqueous sodium chloride (400 mL), dried (magnesium sulfate) and the solvent was removed in vacuo to give (±)-(7-methoxy-2,3-dihydro-1-benzofuran-2-yl)methanol, a crude oil. The alcohol was dissolved in dichloromethane (700 mL) and p-toluenesulfonyl chloride (33.14 g, 0.174 mol) was added followed by triethylamine (21.11 g, 0.209 mol) and then 4-(dimethylamino)pyridine (2.12 g, 0.017 mol). The reaction mixture was allowed to stir at 50° C. for 12 h. The reaction mixture was cooled to room temperature and the solvent was removed in vacuo to give a crude solid. Purification by flash column chromatography (silica, ethyl acetate:hexanes 3:7) provided 26.45 g (68%) of (±)-(7-methoxy-2,3-dihydro-1-benzofuran-2-yl)methyl 4-methylbenzenesulfonate as a white crystalline solid. $R_f$=0.38 (silica, ethyl acetate:hexanes 3:7); mp 98-103° C.; Anal. calcd. for $C_{17}H_{18}O_5S$: C, 61.06; H, 5.43. Found: C, 60.80; H, 5.37.

Intermediate 46

(±)-(7-hydroxy-2,3-dihydro-1-benzofuran-2-yl)methyl 4-methylbenzenesulfonate

To (±)-(7-methoxy-2,3-dihydro-1-benzofuran-2-yl)methyl 4-methylbenzenesulfonate (10.00 g, 0.030 mol) was added hydrogen bromide (20 mL, 30 wt. % in acetic acid) and the resulting solution was heated to 40° C. The reaction mixture was allowed to stir at 40° C. for 4 h. The reaction mixture was cooled to room temperature and was diluted with water (250 mL) and extracted with diethyl ether (3×200 mL). The combined organic extracts were washed with saturated sodium bicarbonate (3×300 mL), water (200 mL), and saturated aqueous sodium chloride (200 mL), were dried (magnesium sulfate), and the solvent was removed in vacuo to provide a crude oil. Purification by flash column chromatography (silica, ethyl acetate:hexanes 1:3) provided 7.34 g (77%) of (±)-(7-hydroxy-2,3-dihydro-1-benzofuran-2-yl)methyl 4-methylbenzenesulfonate as white solid. $R_f$=0.31 (silica, ethyl acetate:hexanes 1:3); mp 122-125° C.; Anal. calcd. for $C_{16}H_{16}O_5S$: C, 59.99; H, 5.03. Found: C, 59.8; H, 4.73.

Intermediate 47

(±)-(7-{[(trifluoromethyl)sulfonyl]oxy}-2,3-dihydro-1-benzofuran-2-yl)methyl 4-methylbenzenesulfonate Treatment of (±)-(7-hydroxy-2,3-dihydro-1-benzofuran-2-yl)methyl 4-methylbenzenesulfonate (1.00 g, 3.12 mmol) with diisopropylethylamine (0.44 g, 3.43 mmol) and trifluoromethanesulfonic anhydride (0.92 g, 3.28 mmol) generally according to the procedure described for Intermediate 7 gave 1.05 g (74%) of (±)-(7-{[(trifluoromethyl)sulfonyl]oxy}-2,3-dihydro-1-benzofuran-2-yl)methyl 4-methylbenzenesulfonate as a white solid. $R_f$=0.45 (silica, ethyl acetate:hexanes 1:3); mp 60-63° C.; Anal. calcd. for $C_{17}H_{15}F_3O_7S_2$: C, 45.13; H, 3.34. Found: C, 44.85; H, 3.04.

Intermediate 48

(±)-(7-bromo-2,3-dihydro-1-benzofuran-2-yl)methanol

Treatment of 2-allyl-6-bromophenol (61.4 g 0.288 mol) with 3-chloroperoxybenzoic acid (77%, 149.18 g, 0.864 mol)) followed by potassium carbonate (99.56 g, 0.72 mol) generally according to the procedure described for Intermediate 9 provided 49.00 g (78%) (86%) of (±)-(7-bromo-2,3-dihydro-1-benzofuran-2-yl)methanol as an amber oil. $R_f$=0.66 (silica, ethyl acetate:hexanes 1:9) $^1$H NMR (DMSO-$d_6$) $\delta_H$ 7.23 (dd, 1H); 7.14 (dd, 1H); 6.71 (t, 1H); (5.01 m, 1H); 4.85 (m, 1H); 4.99 (m, 2H); 3.36 (d, 2H).

Intermediate 49

(±)-(7-bromo-2,3-dihydro-1-benzofuran-2-yl)methyl 4-methylbenzenesulfonate

Treatment of (±)-(7-bromo-2,3-dihydro-1-benzofuran-2-yl)methanol (49.0 g, 0.214 mol) with p-toluenesulfonyl chloride (44.9 g, 0.235 mol) generally according to the procedure described for Intermediate 10 gave 66.00 g (80%) (±)-(7-bromo-2,3-dihydro-1-benzofuran-2-yl)methyl 4-methylbenzenesulfonate as a white solid. $R_f$=0.44 (silica, ethyl acetate: hexanes 1:4); mp 120-122° C.; Anal. calcd. for $C_{16}H_{15}BrO_4S$: C, 50.14; H, 3.94. Found: C, 48.47; H, 4.03.

Intermediate 50

(±)-{7-[3,5-bis(trifluoromethyl)phenyl]-2,3-dihydro-1-benzofuran-2-yl}methyl 4-methylbenzenesulfonate To a solution of (±)-(7-{[(trifluoromethyl)sulfonyl]oxy}-2,3-dihydro-1-benzofuran-2-yl)methyl 4-methylbenzenesulfonate (1.0 g, 2.21 mmol) and 3,5-bis(trifluoromethyl)phenylboronic acid (0.86 g, 3.32 mmol) in dioxane (25 mL) heated to 90° C. was added tetrakis(triphenylphosphine)palladium(0) (0.26 g, 0.22 mmol) and potassium phosphate (0.94 g, 4.42 mmol). The reaction mixture was allowed to stir at 90° C. for 12 h. The reaction mixture was allowed to cool and was diluted with diethyl ether (100 mL), filtered (celite), and the solvent was removed in vacuo to provide a crude solid. Purification by flash column chromatography (silica, ethylacetate:hexanes 1:9) afforded 0.75 g (66%) of (±)-{7-[3,5-bis(trifluoromethyl)phenyl]-2,3-dihydro-1-benzofuran-2-yl]methyl 4-methylbenzenesulfonate as a white solid. $R_f$=0.49 (silica, ethyl acetate:hexanes 1:3); mp 100-105° C.; Anal. calcd. for $C_{24}H_{18}F_6O_4S_2$: C, 55.82; H, 3.51. Found: C, 55.75; H, 3.35.

Intermediate 51

(±)-[7-(3-chloro-4-fluorophenyl)-2,3-dihydro-1-benzofuran-2-yl]methyl 4-methylbenzenesulfonate Treatment of (±)-(7-{[(trifluoromethyl)sulfonyl]oxy}-2,3-dihydro-1-benzofuran-2-yl)methyl 4-methylbenzenesulfonate (1.5 g, 3.32 mmol) with 3-chloro-4-fluorophenylboronic acid (0.87 g, 4.97 mmol), tetrakis(triphenylphosphine)palladium(0) (0.38 g, 0.33 mmol), and potassium phosphate (1.41 g, 6.64 mmol) generally according to the procedure described for Intermediate 50 provided 0.68 g (48%) of (±)-[7-(3-chloro-4-fluorophenyl)-2,3-dihydro-1-benzofuran-2-yl]methyl 4-methylbenzenesulfonate as a white solid. $R_f$=0.43 (silica, ethyl acetate:hexanes 1:3); mp 104-108° C.; Anal. calcd. for $C_{22}H_{18}ClFO_4S_2$: C, 61.04; H, 4.19. Found: C, 60.74; H, 4.13.

Intermediate 52

(±)-(7-phenyl-2,3-dihydro-1-benzofuran-2-yl)methyl 4-methylbenzenesulfonate

Treatment of (±)-(7-{[(trifluoromethyl)sulfonyl]oxy}-2,3-dihydro-1-benzofuran-2-yl)methyl 4-methylbenzenesulfonate (1.5 g, 3.32 mmol) with phenylboronic acid (0.95 g, 4.97 mmol), tetrakis(triphenylphosphine)palladium(0) (0.38 g, 0.33 mmol), and potassium phosphate (1.41 g, 6.64 mmol) generally according to the procedure described for Intermediate 50 provided 0.40 g (32%) of (±)-(7-phenyl-2,3-dihydro- 1-benzofuran-2-yl)methyl 4-methylbenzenesulfonate as a white solid. $R_f$=0.48 (silica, ethyl acetate:hexanes 1:3); Anal. calcd. for $C_{22}H_{20}O_4S.0.2H_2O$: C, 68.8; H, 5.35. Found: C, 68.78; H, 5.08.

Intermediate 53

(±)-benzyl(7-phenyl-2,3-dihydro-1-benzofuran-2-yl) methylcarbamate

Treatment of (±)-benzyl(7-phenyl-2,3-dihydro-1-benzofuran-2-yl)methanamine (1.5 g, 1.43 mmol) with diisopropylethylamine (0.277 g, 2.14 mmol) followed by benzyl chloroformate (0.268 g, 1.572 mmol) generally according to the procedure described for Intermediate 12 provided 1.64 (79%) of (±)-benzyl[7-phenyl-2,3-dihydro-1-benzofuran-2-yl]methylcarbamate as a clear oil. $R_f$=0.68 (silica, ethyl acetate:hexanes 1:2); Anal. calcd. for $C_{23}H_{21}NO_3$: C, 76.86; H, 5.89; N, 3.90. Found: C, 75.10H, 5.71; N, 3.90. Chiral HPLC separation of (±)-benzyl[7-phenyl-2,3-dihydro-1-benzofuran-2-yl]methylcarbamate (Chiralpak AD, ethanol:hexane 1:1) provided two fractions. Fraction 1 ($R_t$=10.746 min, Chiralpak AD, ethanol:hexane 1:1); Fraction 2 ($R_t$=13.433 min, Chiralpak AD ethanol:hexane 1:1).

Intermediate 54

(±)-[7-(2-naphthyl)-2,3-dihydro-1-benzofuran-2-yl] methyl 4-methylbenzenesulfonate Treatment of (±)-(7-{[(trifluoromethyl)sulfonyl]oxy}-2,3-dihydro-1-benzofuran-2-yl)methyl 4-methylbenzenesulfonate (1.5 g, 3.32 mmol) with 2-naphthaleneboronic acid (0.86 g, 4.97 mmol), tetrakis(triphenylphosphine)palladium (0) (0.38 g, 0.33 mmol), and potassium phosphate (1.41 g, 6.64 mmol) generally according to the procedure described for Intermediate 50 provided 0.513 g (36%) of (±)-[7-(2-naphthyl)-2,3-dihydro-1-benzofuran-2-yl]methyl 4-methylbenzenesulfonate as a white solid. $R_f$=0.42 (silica, ethyl acetate:hexanes 1:3); Anal. calcd. for $C_{26}H_{22}O_4S$: C, 72.54; H, 5.15. Found: C, 72.04; H, 5.04.

Intermediate 55

(±)-[7-(3,5-dichlorophenyl)-2,3-dihydro-1-benzofuran-2-yl]methyl 4-methylbenzenesulfonate Treatment of (±)-(7-{[(trifluoromethyl)sulfonyl]oxy}-2,3-dihydro-1-benzofuran-2-yl)methyl 4-methylbenzenesulfonate (1.5 g, 3.32 mmol) with 3,5-dichlorophenylboronic acid (0.95 g, 4.97 mmol), tetrakis(triphenylphosphine)palladium(0) (0.38 g, 0.33 mmol), and potassium phosphate (1.41 g, 6.64 mmol) generally according to the procedure described for Intermediate 50 provided 0.22 g (15%) of (±)-[7-(3,5-dichlorophenyl)-2,3-dihydro-1-benzofuran-2-yl]methyl 4-methylbenzenesulfonate as a white solid. $R_f$=0.48 (silica, ethyl acetate:hexanes 1:3); mp 113-115° C.; Anal. calcd. for $C_{22}H_{18}Cl_2O_4S$: C, 58.8: H, 4.04. Found: C, 58.73; H, 3.77.

Intermediate 56

(+t)-[7-(2-methylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 2-methylphenyl boronic acid (0.266 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.358 g (70%) of (±)-[7-(2-methylphenyl)-2,3-dihydro-1-benzofuran-2-yl]methyl 4-methylbenzenesulfonate as a white solid. $R_f$=0.43 (silica, ethyl acetate:hexanes 1:3); mp 98-100° C.; Anal. calcd. for $C_{23}H_{22}O_4S$: C, 70.03; H, 5.62. Found: C, 69.83; H, 5.61.

Intermediate 57

(±)-benzyl[7-(2-methylphenyl)-2,3-dihydro-1-benzofuran-2-yl]methylcarbamate

Treatment of (±)-[7-(2-methylphenyl)-2,3-dihydro-1-benzofuran-2-yl]methanamine (3.55 g, 12.9 mmol) with diisopropylethylamine (2.5 g, 19.4 mmol) and benzyl chloroformate (2.42 g, 14.2 mmol) generally according to the procedure described for Intermediate 12 provided 4.1 g (85%) of (±)-benzyl[7-(2-methylphenyl)-2,3-dihydro-1-benzofuran-2-yl]methylcarbamate as a clear oil $R_f$=0.64 (silica, ethyl acetate:hexanes 1:4); Anal. calcd. for $C_{24}H_{23}F_4NO_3$: C, 77.19; H, 6.21; N, 3.75. Found: C, 76.95; H, 6.18; N, 3.53. Chiral HPLC separation of (±)-benzyl[7-(2-methylphenyl)-2,3-dihydro-1-benzofuran-2-yl]methylcarbamate (Chiralcel OD, isopropanol:hexane 1:4) provided two fractions. Fraction 1 ($R_t$=7.285 min, isopropanol:hexane 1:4); Fraction 2 ($R_t$=9.361 min, Chiralcel OD, isopropanol:hexane 1:4).

Intermediate 58

(±)-(7-thien-3-yl-2,3-dihydro-1-benzofuran-2-yl) methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 3-thiophene boronic acid (0.334 g, 2.61 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.389 g (77%) of (±)-(7-thien-3-yl-2,3-dihydro-1-benzofuran-2-yl)methyl 4-methylbenzenesulfonate as a yellow solid. mp 90-92° C.; Anal. calcd. for $C_{20}H_{18}O_4S_2$: C, 62.15; H, 4.69. Found: C, 62.2; H, 4.72.

Intermediate 59

(±)-benzyl(7-thien-3-yl-2,3-dihydro-1-benzofuran-2-yl)methylcarbamate

Treatment of (±)-1-(7-thien-3-yl-2,3-dihydro-1-benzofuran-2-yl)methanamine (0.56 g, 2.09 mmol) with diisopropylethylamine (0.406 g, 3.14 mmol) and benzyl chloroformate (0.393 g, 2.30 mmol) generally according to the procedure described for Intermediate 12 provided 0.54 g (71%) of (±)-benzyl(7-thien-3-yl-2,3-dihydro-1-benzofuran-2-yl)methylcarbamate as a colorless oil. $R_f$=0.49 (silica, ethyl acetate:hexanes 2:8); Anal. calcd. for $C_{21}H_{19}NO_3S.0.3H_2O$: C, 68.01; H, 5.33; N, 3.78. Found: C, 67.88; H, 5.18; N, 3.72. Chiral HPLC separation of (±)-benzyl(7-thien-3-yl-2,3-dihydro-1-benzofuran-2-yl)methylcarbamate (Chiralcel AD, water:methanol 1:9) provided two fractions. Fraction 1 ($R_t$=13.00 min, (Chiralcel AD, water:methanol 1:9); Fraction 2 ($R_t$=14.1 min, (Chiralcel AD, water:methanol 1:9).

Intermediate 60

(±)-[7-(2-fluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 2-fluorophenylboronic acid (0.274 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.422 g (81%) of (±)-[7-(2-fluorophenyl)-2,3-dihydro-1-benzofuran-2-yl]methyl 4-methylbenzenesulfonate as a yellow solid. mp 99-101° C.; Anal. calcd. for $C_{22}H_{19}FO_4S$: C, 66.32; H, 4.81. Found: C, 65.16; H, 4.86.

Intermediate 61

(±)-benzyl[7-(2-fluorophenyl)-2,3-dihydro-1-benzofuran-2-yl]methylcarbamate

Treatment of (±)-1-[7-(2-fluorophenyl)-2,3-dihydro-1-benzofuran-2-yl]methanamine (1.5 g, 5.36 mmol) with diisopropylethylamine (1.04 g, 8.04 mmol) and benzyl chloroformate (1.01 g, 5.89 mmol) generally according to the procedure described for Intermediate 12 afforded 1.7 g (84%) of (±)-benzyl[7-(2-fluorophenyl)-2,3-dihydro-1-benzofuran-2-yl]methylcarbamate as a colorless oil $R_f$=0.68 (silica, ethyl acetate:hexanes 1:9); Anal. calcd. for $C_{22}H_{18}FNO_3$: C, 72.72; H, 4.99; N, 3.85. Found: C, 72.65H, 5.41; N, 3.47. Chiral HPLC separation of (±)-benzyl[7-(2,6-dimethylphenyl)-2,3-dihydro-1-benzofuran-2-yl]methylcarbamate (Chiralcel OJ, hexane:isopropanol 9:1) provided two fractions. Fraction 1 ($R_t$=13.628 min, Chiralcel OJ, hexane:isopropanol 9:1); Fraction 2 ($R_t$=17.247 min, Chiralcel OJ, hexane:isopropanol 9:1).

Intermediate 62

(±)-{7-[2-(trifluoromethyl)phenyl]-2,3-dihydro-1-benzofuran-2-yl}methyl 4-methylbenzenesulfonate Treatment of (±)-(7-bromo-2,3-dihydro-1-benzofuran-2-yl)methyl 4-methylbenzenesulfonate (10.00 g, 26.10 mmol) with 2-(trifluoromethy)phenylboronic acid (7.43 g, 39.14 mmol), dichlorobis(tri-o-tolylphosphine)palladium(II) (0.786 g, 1.3 mmol), and potassium carbonate (9.01 g, 65.19 mmol) generally according to the procedure described for Intermediate 37 afforded 8.46 g (72%) of (±)-{7-[2-(trifluoromethyl)phenyl]-2,3-dihydro-1-benzofuran-2-yl}methyl 4-methylbenzenesulfonate as a tan solid. mp 116-118° C.; Anal. calcd. for $C_{23}H_{19}F_3O_4S$: C, 61.6; H, 4.27. Found: C, 61.91; H, 4.23.

Intermediate 63

(±)-benzyl {7-[2-(trifluoromethyl)phenyl]-2,3-dihydro-1-benzofuran-2-yl}methylcarbamate Treatment of (±)-1-{7-[2-(trifluoromethyl)phenyl]-2,3-dihydro-1-benzofuran-2-yl}methanamine (0.813 g, 2.46 mmol) with diisopropylethylamine (0.478 g, 3.69 mmol) and benzyl chloroformate (0.462 g, 2.71 mmol) generally according to the procedure described for Intermediate 12 gave 0.99 g (94%) of (±)-benzyl {7-[2-(trifluoromethyl)phenyl]-2,3-dihydro-1-benzofuran-2-yl}methylcarbamate as a pale yellow oil $R_f$=0.60 (silica, ethyl acetate:hexanes 2:8); Anal. calcd. for $C_{24}H_{20}F_3NO_3$: C, 67.44; H, 4.71; N, 3.15. Found: C, 67.43H, 4.76; N, 3.15. Chiral HPLC separation of (±)-benzyl[7-(2-(trifluoromethyl))-2,3-dihydro-1-benzofuran-2-yl]methylcarbamate (Chiralcel OJ, isopropanol:carbon dioxide 3:17) provided two fractions. Fraction 1 ($R_t$=5.252 min, Chiralcel OJ, isopropanol:carbon dioxide 3:17); Fraction 2 ($R_t$=6.280 min, Chiralcel OJ, isopropanol:carbon dioxide 3:17).

Intermediate 64

(±)-[7-(2,6-dimethylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (1.00 g, 2.61 mmol) with 2,6-dimethylphenylboronic acid (0.783 g, 5.22 mmol), dichlorobis(tri-o-tolylphosphine)-palladium(II) (0.103 g, 0.135 mmol), and potassium carbonate (0.90 g, 6.52 mmol) generally according to the procedure described for Intermediate 37 provided 0.192 g (18%) of (±)-[7-(2,6-dimethylphenyl)-2,3-dihydro-1-benzofuran-2-yl]methyl 4-methylbenzenesulfonate as a yellow oil. Anal. calcd. for $C_{24}H_{24}O_4S$: C, 70.56; H, 5.92. Found: C, 68.01; H, 5.6.

Intermediate 65

(±)-benzyl[7-(2,6-dimethylphenyl)-2,3-dihydro-1-benzofuran-2-yl]methylcarbamate

Treatment of (±)-1-[7-(2,6-dimethylphenyl)-2,3-dihydro-1-benzofuran-2-yl]methanamine (0.947 g, 3.73 mmol) with diisopropylethylamine (0.725 g, 5.60 mmol) and benzyl chloroformate (0.7647 g, 4.48 mmol) generally according to the procedure described for Intermediate 12 gave 1.26 g (87%) of (±)-benzyl[7-(2,6-dimethylphenyl)-2,3-dihydro-1-benzofuran-2-yl]methylcarbamate as a colorless oil $R_f$=0.56 (silica, ethyl acetate:hexanes 1:4); Anal. calcd. for $C_{25}H_{25}NO_3$: C, 77.49; H, 6.50; N, 3.61. Found: C, 77.42H, 6.57; N, 3.62. Chiral HPLC separation of (±)-benzyl[7-(2,6-dimethylphenyl)-2,3-dihydro-1-benzofuran-2-yl]methylcarbamate (Chiralcel OJ, methanol:carbon dioxide 4:6) provided two fractions. Fraction 1 ($R_t$=2.89 min, Chiralcel OJ, methanol:carbon dioxide 4:6); Fraction 2 ($R_t$=3.84 min, Chiralcel OJ, methanol:carbon dioxide 4:6).

Intermediate 66

(±)-[7-(2-methoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.5 g, 1.31 mmol) with 2-methoxyphenylboronic acid (0.297 g, 1.96 mmol), dichlorobis(tri-o-tolylphosphine)palladium(II) (0.051 g, 0.065 mmol), and potassium carbonate (0.45 g, 3.26 mmol) generally according to the procedure described for Intermediate 37 gave 0.399 g (74%) of (±)-[7-(2-methoxyphenyl)-2,3-dihydro-1-benzofuran-2-yl]methyl 4-methylbenzenesulfonate as a tan solid. mp 100-103° C.; Anal. calcd. for $C_{23}H_{22}O_5S$: C, 67.3; H, 5.4. Found: C, 66.95; H, 5.43.

Intermediate 67

(±)-benzyl[7-(2-methoxyphenyl)-2,3-dihydro-1-benzofuran-2-yl]methylcarbamate

Treatment of (±)-1-[7-(2-methoxyphenyl)-2,3-dihydro-1-benzofuran-2-yl]methanamine (0.296 g, 1.01 mmol) with diisopropylethylamine (1.52 g, 1.5 mmol) and benzyl chloroformate (0.190 g, 1.11 mmol) generally according to the procedure described for Intermediate 12 afforded 0.33 g (84%) (±)-benzyl[7-(2-methoxyphenyl)-2,3-dihydro-1-benzofuran-2-yl]methylcarbamate of a colorless oil $R_f$=0.72 (silica, ethyl acetate:hexanes 2:8); Anal. calcd. for $C_{24}H_{23}NO_4$: C, 74.02; H, 5.95; N, 3.6. Found: C, 73.68H, 5.81; N, 3.43.

Intermediate 68

(±)-[7-(2-chlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 2-chlorophenylboronic acid (0.306 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.380 g (70%) of (±)-[7-(2-chlorophenyl)-2,3-dihydro-1-benzofuran-2-yl]methyl 4-methylbenzenesulfonate as a tan solid. mp 100-103° C.; Anal. calcd. for $C_{22}H_{19}ClO_4S$: C, 63.69; H, 4.62. Found: C, 63.43; H, 4.69.

Intermediate 69

(±)-benzyl[7-(2-chlorophenyl)-2,3-dihydro-1-benzofuran-2-yl]methylcarbamate

Treatment of (±)-1-[7-(2-chlorophenyl)-2,3-dihydro-1-benzofuran-2-yl]methanamine (0.743 g 2.52 mmol) with diisopropylethylamine (0.488 g, 3.77 mmol) and benzyl chloroformate (0.472 g, 2.77 mmol) generally according to the procedure described for Intermediate 12 afforded 0.749 g (76%) (±)-benzyl[7-(2-chlorophenyl)-2,3-dihydro-1-benzofuran-2-yl]methylcarbamate as a white solid. mp 155-157° C.; Anal. calcd. for $C_{23}H_{20}ClNO_3$: C, 70.14; H, 5.12; N, 3.56. Found: C, 70.1; H, 5.15; N, 3.37. Chiral HPLC separation of (±)-benzyl[7-(2-chlorophenyl)-2,3-dihydro-1-benzofuran-2-yl]methylcarbamate (Chiralcel OJ, hexane:ethanol 1:1) provided two fractions. Fraction 1 ($R_t$=9.655 min, Chiralcel OJ, hexane:ethanol 1:1); Fraction 2 ($R_t$=16.300 min, Chiralcel OJ, hexane:ethanol 1:1).

Intermediate 70

(±)-benzyl[7-(2-isopropylphenyl)-2,3-dihydro-1-benzofuran-2-yl]methylcarbamate

Treatment of (±)-[7-(2-isopropylphenyl)-2,3-dihydro-1-benzofuran-2-yl]methylamine (1.69 g, 5.56 mmol) with diisopropylethylamine (1.08 g, 8.34 mmol) and benzyl chloroformate (1.04 g, 6.12 mmol) generally according to the procedure described for Intermediate 12 gave 1.92 (89%) of (±)-benzyl[7-(2-isopropylphenyl)-2,3-dihydro-1-benzofuran-2-yl]methylcarbamate as a yellow oil. $R_f$=0.66 (silica, ethyl acetate:hexanes 1:4); Anal. calcd. for $C_{26}H_{27}NO_3$: C, 77.78; H, 6.78; N, 3.49. Found: C, 77.5; H, 6.7; N, 3.33. Chiral HPLC separation of (±)-[7-(2-isopropylphenyl)-2,3-dihydro-1-benzofuran-2-yl]methylcarbamate (Chiralcel OD, hexane:isopropanol 9:1) provided two fractions. Fraction 1 ($R_t$=8.131 min, Chiralcel OD, hexane:isopropanol 9:1); Fraction 2 ($R_t$=11.048 min, Chiralcel OD, hexane:isopropanol 9:1).

Intermediate 71

(±)-[7-(3-methylphenyl)-2,3-dihydro-1-benzofuran-2-yl]methyl 4-methylbenzenesulfonate Treatment of (±)-(7-{[(trifluoromethyl)sulfonyl]oxy}-2,3-dihydro-1-benzofuran-2-yl)methyl 4-methylbenzenesulfonate (1.5 g, 3.32 mmol) with 3-methylbenzeneboronic (0.68 g, 4.97 mmol), tetrakis(triphenylphosphine)palladium (0) (0.38 g, 0.33 mmol), and potassium phosphate (1.41 g, 6.64 mmol) generally according to the procedure described for Intermediate 50 provided 0.899 g (69%) of (±)-[7-(3-methylphenyl)-2,3-dihydro-1-benzofuran-2-yl]methyl 4-methylbenzenesulfonate as a white solid. $R_f$=0.44 (silica, ethyl acetate:hexanes 1:3); mp 81-82° C.; Anal. calcd. for $C_{23}H_{22}O_4S.0.2H_2O$: C, 69.39; H, 5.67. Found: C, 69.42; H, 5.49.

Intermediate 72

(±)-benzyl[7-(3-methylphenyl)-2,3-dihydro-1-benzofuran-2-yl]methylcarbamate

Treatment of (±)-[7-(3-methylphenyl)-2,3-dihydro-1-benzofuran-2-yl]methanamine (1.76 g, 6.38 mmol) with diisopropylethylamine (2.47 g, 19.17 mmol) followed by benzyl chloroformate (1.19 g, 7.02 mmol) generally according to the procedure described for Intermediate 12 provided 1.4 g (58%) of (±)-benzyl[7-(3-methylphenyl)-2,3-dihydro-1-benzofuran-2-yl]methylcarbamate as a clear oil. $R_f$=0.68 (silica, ethyl acetate:hexanes 1:2); Anal. calcd. for $C_{24}H_{23}NO_3$: C, 77.19; H, 6.20; N, 3.75. Found: C, 76.88H, 6.25; N, 3.51. Chiral HPLC separation of (±)-benzyl[7-(3-methylphenyl)-2,3-dihydro-1-benzofuran-2-yl]methylcarbamate (Chiralpak AD, ethanol:hexane 1:1) provided two fractions. Fraction 1 ($R_t$=10.439 min, Chiralpak AD, ethanol:hexane 1:1); Fraction 2 ($R_t$=11.833 min, Chiralpak AD ethanol:hexane 1:1).

Intermediate 73

(±)-[7-(3-fluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 3-fluorophenylboronic acid (0.274 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.392 g (75%) of (±)-[7-(3-fluorophenyl)-2,3-dihydro-1-benzofuran-2-yl]methyl 4-methylbenzenesulfonate as a light yellow solid. mp 88-90° C.; Anal. calcd. for $C_{22}H_{19}FO_4S$: C, 66.32; H, 4.81. Found: C, 65.63; H, 4.84.

Intermediate 74

(±)-benzyl[7-(3-fluorophenyl)-2,3-dihydro-1-benzofuran-2-yl]methylcarbamate

Treatment of (±)-[7-(3-fluorophenyl)-2,3-dihydro-1-benzofuran-2-yl]methanamine (0.798 g, 2.856 mmol) with diisopropylethylamine (0.554 g, 4.286 mmol) and benzyl chloroformate (0.536 g, 3.143 mmol) generally according to the procedure described for Intermediate 12 afforded 1.01 g (94%) of (±)-benzyl[7-(3-fluorophenyl)-2,3-dihydro-1-benzofuran-2-yl]methylcarbamate as a white solid. $R_f$=0.40 (silica, ethyl acetate:hexanes 1:4); Anal. Calcd. for $C_{23}H_{20}FNO_3$: C, 73.2; H, 5.34; N, 3.71. Found: C, 92.96; H, 5.38; N, 3.59.

Intermediate 75

(±)-[7-(3-chlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol)

with 3-chlorophenylboronic acid (0.306 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.404 g (75%) of (±)-[7-(3-chlorophenyl)-2,3-dihydro-1-benzofuran-2-yl]methyl 4-methylbenzenesulfonate as a light yellow solid. mp 101-103° C.; Anal. calcd. for $C_{22}H_{19}ClO_4S$: C, 63.69; H, 4.62. Found: C, 63.59; H, 4.52.

Intermediate 76

(±)-benzyl[7-(3-chlorophenyl)-2,3-dihydro-1-benzofuran-2-yl]methylcarbamate

Treatment of (±)-1-[7-(3-chlorophenyl)-2,3-dihydro-1-benzofuran-2-yl]methanamine (1.6 g, 5.4 mmol) with diisopropylethylamine (1.197 g, 9.26 mmol) and benzyl chloroformate (1.02 g, 5.96 mmol) generally according to the procedure described for Intermediate 12 afforded 1.59 g (75%) of (±)-benzyl[7-(3-chlorophenyl)-2,3-dihydro-1-benzofuran-2-yl]methylcarbamate as a colorless oil. $R_f$=0.56 (silica, ethyl acetate:hexanes 1:9); Anal. calcd. for $C_{23}H_{20}ClNO_3$: C, 70.14; H, 5.12; N, 3.56. Found: C, 69.11; H, 5.07; N, 3.37. Chiral HPLC separation of (±)-benzyl[7-(3-chlorophenyl)-2,3-dihydro-1-benzofuran-2-yl]methylcarbamate (Chiralcel OD, hexane:isopropanol 9:1) provided two fractions. Fraction 1 ($R_t$=15.935 min Chiralcel OD, hexane:isopropanol 9:1); Fraction 2 ($R_t$=18.546 min, Chiralcel OD, hexane:isopropanol 9:1).

Intermediate 77

(±)-[7-(3-methoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (5.00 g, 13.04 mmol) with 3-methoxyphenylboronic acid (2.97 g, 19.57 mmol), dichlorobis(tri-o-tolylphosphine)palladium(II) (0.512 g, 0.652 mmol) and potassium carbonate (4.51 g, 32.62 mmol) generally according to the reaction conditions described for Intermediate 37 gave 4.48 g (84%) of (±)-[7-(3-methoxyphenyl)-2,3-dihydro-1-benzofuran-2-yl]methyl 4-methylbenzenesulfonate as a white solid. mp 141-142° C.; Anal. calcd. for $C_{23}H_{22}O_5S$: C, 67.3; H, 5.4. Found: C, 66.51; H, 5.41.

Intermediate 78

(±)-benzyl[7-(3-methoxyphenyl)-2,3-dihydro-1-benzofuran-2-yl]methylcarbamate

Treatment of (±)-1-[7-(3-methoxyphenyl)-2,3-dihydro-1-benzofuran-2-yl]methanamine (2.4 g, 9.4 mmol) with diisopropylethylamine (1.82 g, 14.10 mmol) and benzyl chloroformate (1.92 g, 11.28 mmol) generally according to the reaction conditions described for Intermediate 12 afforded 3.42 g (93%) of (±)-benzyl[7-(3-methoxyphenyl)-2,3-dihydro-1-benzofuran-2-yl]methylcarbamate as a colorless oil. $R_f$=0.78 (silica, ethyl acetate:hexanes 1:4); Anal. calcd. for $C_{24}H_{23}NO_4$: C, 74.02; H, 5.95; N, 3.6. Found: C, 73.52; H, 6.06; N, 3.28.

Intermediate 79

(±)-{7-[3-(trifluoromethyl)phenyl]-2,3-dihydro-1-benzofuran-2-yl}methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 3-(trifluoromethyl)phenylboronic acid (0.372 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.383 g (65%) of (±)-{7-[3-(trifluoromethyl)phenyl]-2,3-dihydro-1-benzofuran-2-yl}methyl 4-methylbenzenesulfonate as a white solid. mp 90-93° C.; Anal. calcd. for $C_{23}H_{19}F_3O_4S$: C, 61.6; H, 4.27. Found: C, 61.52; H, 4.21.

Intermediate 80

(±)-benzyl {7-[3-(trifluoromethyl)phenyl]-2,3-dihydro-1-benzofuran-2-yl}methylcarbamate Treatment of (±)-[7-(3-trifluoromethylphenyl)-2,3-dihydro-1-benzofuran-2-yl]methanamine (1.67 g, 5.06 mmol) with diisopropylethylamine (0.98 g, 7.59 mmol) and benzyl chloroformate (1.04 g, 6.07 mmol) generally according to the procedure described for Intermediate 12 provided 2.1 g (97%) of (±)-benzyl {7-[3-(trifluoromethyl)phenyl]-2,3-dihydro-1-benzofuran-2-yl}methylcarbamate as a colorless oil. $R_f$=0.51; Anal. calcd. for $C_{24}H_{20}F_3NO_3$: C, 67.44; H, 4.72; N, 3.28. Found: C, 67.08; H, 5.05; N, 3.22.

Intermediate 81

(±)-[7-(4-methylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (11.2 g, 29.22 mmol) with 4-methylphenylboronic acid (5.96 g, 43.84 mmol), dichlorobis(tri-o-tolylphosphine)-palladium(II) (1.148 g, 1.46 mmol), and potassium carbonate (10.10 g, 73.07 mmol) generally according to the procedure described for Intermediate 37 afforded 9.8 g (85%) of (±)-[7-(4-methylphenyl)-2,3-dihydro-1-benzofuran-2-yl]methyl 4-methylbenzenesulfonate a white solid. mp 145-147° C.; Anal. calcd. for $C_{23}H_{22}O_4S$: C, 70.03; H, 5.62. Found: C, 69.91; H, 5.70.

Intermediate 82

(±)-benzyl[7-(4-methylphenyl)-2,3-dihydro-1-benzofuran-2-yl]methylcarbamate

Treatment of (±)-[7-(4-methylphenyl)-2,3-dihydro-1-benzofuran-2-yl]methanamine (0.385 g, 1.396 mmol) with diisopropylethylamine (0.270 g, 2.09 mmol) and benzyl chloroformate (0.285 g, 1.675 mmol) generally according to the procedure described for Intermediate 12 provided 0.483 g (93%) of (±)-benzyl[7-(4-methylphenyl)-2,3-dihydro-1-benzofuran-2-yl]methylcarbamate as colorless oil. $R_f$=0.47 (silica, ethyl acetate:hexane 2:8); mp 83-86° C.; Anal. calcd. for $C_{24}H_{23}NO_3$: C, 77.19; H, 6.21; N, 3.75. Found: C, 76.97; H, 5.99; N, 3.68. Chiral HPLC separation of (±)-benzyl[7-(4-methylphenyl)-2,3-dihydro-1-benzofuran-2-yl]methylcarbamate (Chiralpak OD, methanol:carbon dioxide 1:1) provided two fractions. Fraction 1 ($R_t$=3.788 min Chiralpak OD, methanol:carbon dioxide 1:1); Fraction 2 ($R_t$=4.398 min, Chiralpak OD, methanol:carbon dioxide 1:1).

Intermediate 83

(±)-[7-(4-methoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (3.0 g, 7.82 mmol) with 4-methoxyphenylboronic acid (1.78 g, 11.74 mmol), dichlorobis(tri-o-tolylphosphine)-palladium(II) (0.307 g, 0.391 mmol), and potassium carbonate (2.70 g, 19.57 mmol) generally according to the procedure described for Intermediate 37 provided 2.2 g (68%) of (±)-[7-(4-methoxyphenyl)-2,3-dihydro-1-benzofuran-2-yl]methyl 4-methylbenzenesulfonate as a yellow solid. mp 116-117° C.; Anal. calcd. for $C_{23}H_{22}O_5S$: C, 67.30; H, 5.40. Found: C, 67.31; H, 5.35.

Intermediate 84

(±)-benzyl[7-(4-methoxyphenyl)-2,3-dihydro-1-benzofuran-2-yl]methylcarbamate

Treatment of 1-[7-(4-methoxyphenyl)-2,3-dihydro-1-benzofuran-2-yl]methanamine (0.727 g, 2.49 mmol) with diisopropylethylamine (0.483 g, 3.73) and benzyl chloroformate (0.510 g, 2.99 mmol) generally according to the procedure described for Intermediate 12 provided 0.820 g of (±)-benzyl [7-(4-methoxyphenyl)-2,3-dihydro-1-benzofuran-2-yl]methylcarbamate as a colorless oil. $R_f$=0.48 (silica, ethyl acetate:hexanes 1:5); Anal. calcd. for $C_{24}H_{23}NO_4$: C, 74.02; H, 5.95; N, 3.60. Found: C, 73.66H, 6.13; N, 3.42. Chiral HPLC separation of (±)-benzyl[7-(4-methoxyphenyl)-2,3-dihydro-1-benzofuran-2-yl]methylcarbamate (Chiralcel AD, methanol) provided two fractions. Fraction 1 ($R_t$=7.386 min, Chiralcel AD, methanol); Fraction 2 ($R_t$=10.882 min, Chiralcel AD, methanol).

Intermediate 85

(±)-(7-[4-(trifluoromethyl)phenyl]-2,3-dihydro-1-benzofuran-2-yl}methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 4-(trifluoromethyl)phenylboronic acid (0.372 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.435 g (74%) of (±)-{7-[4-(trifluoromethyl)phenyl]-2,3-dihydro-1-benzofuran-2-yl methyl 4-methylbenzenesulfonate as a light yellow solid. mp 116-118° C.; Anal. calcd. for $C_{23}H_{19}F_3O_4S$: C, 61.6; H, 4.27. Found: C, 61.37; H, 4.36.

Intermediate 86

(±)-benzyl {7-[4-(trifluoromethyl)phenyl]-2,3-dihydro-1-benzofuran-2-yl}methylcarbamate Treatment of (±)-1-{7-[4-(trifluoromethyl)phenyl]-2,3-dihydro-1-benzofuran-2-yl}methanamine (1.8 g, 6.14 mmol) with diisopropylethylamine (1.06 g, 8.20) and benzyl chloroformate (1.12 g, 6.56 mmol) generally according to the procedure described for Intermediate 12 afforded 2.38 g (91%) of (±)-benzyl {7-[4-(trifluoromethyl)phenyl]-2,3-dihydro-1-benzofuran-2-yl}methylcarbamate as a white solid. $R_f$=0.48 (silica, ethyl acetate:hexanes 1:4); mp 100-102° C.; Anal. calcd. for $C_{24}H_{20}F_3NO_3$: C, 67.44; H, 4.72; N, 3.28. Found: C, 67.37; H, 4.69; N, 3.15.

Intermediate 87

(±)-[7-(4-fluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 4-fluorophenylboronic acid (0.274 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.408 g (78%) of (±)-[7-(4-fluorophenyl)-2,3-dihydro-1-benzofuran-2-yl]methyl 4-methylbenzenesulfonate as a light yellow solid. mp 83-86° C.; Anal. calcd. for $C_{22}H_{19}FO_4S$: C, 66.32; H, 4.81. Found: C, 66.11; H, 4.61.

Intermediate 88

(±)-[7-(4-chlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 4-chlorophenylboronic acid (0.306 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.367 g (68%) of (±)-[7-(4-chlorophenyl)-2,3-dihydro-1-benzofuran-2-yl]methyl 4-methylbenzenesulfonate as an orange solid. mp 130-133° C.; Anal. calcd. for $C_{22}H_{19}ClO_4S$: C, 63.69; H, 4.62. Found: C, 62.82; H, 4.56.

Intermediate 89

(±)-[7-(2,4-dichlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (5.0 g, 13.05 mmol) with 2,4-dichlorophenylboronic acid (3.73 g, 19.57 mmol), dichlorobis(tri-o-tolylphosphine)-palladium(II) (0.512 g, 0.652 mmol), and potassium carbonate (4.51 g, 32.62 mmol) generally according to the procedure described for Intermediate 37 provided 4.5 g (75%) of (±)-[7-(2,4-dichlorophenyl)-2,3-dihydro-1-benzofuran-2-yl]methyl 4-methylbenzenesulfonate as a yellow oil. Anal. calcd. for $C_{22}H_{18}Cl_2O_4S$: C, 58.8; H, 4.04. Found: C, 59.01; H, 4.09.

Intermediate 90

(±)-benzyl[7-(2,4-dichlorophenyl)-2,3-dihydro-1-benzofuran-2-yl]methylcarbamate

Treatment of (±)-1-[7-(2,4-dichlorophenyl)-2,3-dihydro-1-benzofuran-2-yl]methanamine (1.9 g, 5.75 mmol) with diisopropylethylamine (1.11 g, 8.62) and benzyl chloroformate (1.18 g, 6.89 mmol) generally according to the procedure described for Intermediate 12 afforded 2.14 g (87%) of (±)-benzyl[7-(2,4-dichlorophenyl)-2,3-dihydro-1-benzofuran-2-yl]methylcarbamate as a white solid. mp 87-89° C.; Anal. calcd. for $C_{23}H_{19}Cl_2NO_3$: C, 64.5; H, 4.47; N, 3.27. Found: C, 64.65; H, 4.78; N, 3.08.

Intermediate 91

(±)-3-[2-(benzyloxy)-5-chloro-3-methoxyphenyl] propane-1,2-diol

Treatment of 4-chloro-2-methoxyphenol (30.0 g, 0.19 mol) with sodium hydride (9.1 g, 0.23 mol, 60 wt. %) and allyl bromide (27.46 g, 0.23 mol) followed by treatment of the resultant allyl ether in refluxing mesitylene generally according to the procedure described for Intermediate 8 gave 2-allyl-4-chloro-6-methoxyphenol as a yellow oil. Treatment of 2-allyl-4-chloro-6-methoxyphenol with sodium hydride (7.08 g, 0.177 mol, 60 wt. %) and benzyl bromide (30.27 g, 0.177 mol) generally according to the procedure described for Intermediate 13 provided 1-allyl-2-(benzyloxy)-5-chloro-3-methoxybenzene as a pale yellow oil. Treatment of the olefin (35.5 g, 0.123 mol) of with AD-mix-α (132.0 g) generally according to the procedure described for Intermediate 2 gave 35 g (54%) of (±)-3-[2-(benzyloxy)-5-chloro-3-methoxyphenyl] propane-1,2-diol as a white solid. mp. 65-68° C. Anal. calcd. for $C_{17}H_{19}ClO_4$: C, 63.26; H, 5.93. Found: C, 65.29; H, 6.23.

Intermediate 92

(±)-(5-chloro-7-methoxy-2,3-dihydro-1-benzofuran-2-yl)methyl 4-methylbenzenesulfonate Treatment of (±)-3-[2-(benzyloxy)-5-chloro-3-methoxyphenyl]-1,2-propanediol (32 g, 0.1 mol) with p-toluenesulfonyl chloride (21 g, 0.11 mol) in pyridine generally according to the procedure described for intermediate 3 provided (±)-3-[2-(benzyloxy)-5-chloro-3-methoxyphenyl]-2-hydroxypropyl 4-methylbenzenesulfonate. Treatment of the tosylate with palladium on carbon (2.32 g, 5 wt. %) generally according to the procedure described for Intermediate 4 afforded (±)-3-(5-chloro-2-hydroxy-3-methoxyphenyl)-2-hydroxypropyl 4-methylbenzenesulfonate. Treatment of the phenol with triphenylphosphine (23.6 g, 0.09 mol) and diisopropyl azodicarboxylate (18.2 g, 0.09 mol) generally according to the procedure described for Intermediate 5 afforded 28 g (76%) of (±)-(5-chloro-7-methoxy-2,3-dihydro-1-benzofuran-2-yl)methyl 4-methylbenzenesulfonate as a pale yellow solid. mp 99-102° C.; Anal. calcd. for $C_{17}H_{17}ClO_5S$: C, 55.36; H, 4.65. Found: C, 55.35; H, 4.62.

Intermediate 93

(±)-(5-chloro-7-{[(trifluoromethyl)sulfonyl]oxy}-2,3-dihydro-1-benzofuran-2-yl)methyl 4-methylbenzenesulfonate Treatment of (±)-(5-chloro-7-methoxy-2,3-dihydro-1-benzofuran-2-yl)methyl 4-methylbenzenesulfonate (22.1 g, 0.06 mol) with hydrogen bromide (400 mL, 30 wt. % in acetic acid) generally according to the procedure described for Intermediate 46 gave 14.6 g of (±)-(5-chloro-7-hydroxy-2,3-dihydro-1-benzofuran-2-yl)methyl 4-methylbenzenesulfonate as a colorless oil. Treatment of (±)-(5-chloro-7-hydroxy-2,3-dihydro-1-benzofuran-2-yl)methyl 4-methylbenzenesulfonate (4.5 g, 12.68 mmol) with trifluoromethanesulfonic anhydride (2.34 mL, 13.9 mmol) and diisopropylethylamine (2.43 mL, 13.9 mmol) generally according to the procedure described for Intermediate 7 provided 6.27 g (99%) of (±)-(5-chloro-7-{[(trifluoromethyl)sulfonyl]oxy}-2,3-dihydro-1-benzofuran-2-yl)methyl 4-methylbenzenesulfonate as a light yellow solid. mp 55-57° C.; Anal. calcd. for $C_{17}H_{14}ClF_3O_7S_2$: C, 41.94; H, 2.90. Found: C, 42.10; H, 2.76.

Intermediate 94

(±)-(5-chloro-7-phenyl-2,3-dihydro-1-benzofuran-2-yl)methyl 4-methylbenzenesulfonate Treatment of (±)-(5-chloro-7-{[(trifluoromethyl)sulfonyl]oxy}-2,3-dihydro-1-benzofuran-2-yl)methyl 4-methylbenzenesulfonate (1.50 g, 3.10 mmol) with phenyl boronic acid (0.564 g, 4.60 mmol), dichloro[1,1'-bis(diphenylphosphino)ferrocene]palladium(II) dichloromethane adduct (0.252 g, 0.30 mmol), and potassium carbonate (0.829 g, 6.0 mmol) generally according to the procedure described for Intermediate 35 provided 0.94 g of a white paste. Re-crystallization from methanol afforded 0.6 g (47%) of (±)-(5-chloro-7-phenyl-2,3-dihydro-1-benzofuran-2-yl)methyl 4-methylbenzenesulfonate as a white solid. mp 127-130° C.; Anal. calcd. for $C_{22}H_{19}ClO_4S$: C, 63.69; H, 4.62. Found: C, 62.51; H, 4.48.

Intermediate 95

(±)-[5-chloro-7-(3-chlorophenyl)-2,3-dihydro-1-benzofuran-2-yl]methyl 4-methylbenzenesulfonate Treatment of (±)-(5-chloro-7-{[(trifluoromethyl)sulfonyl]oxy}-2,3-dihydro-1-benzofuran-2-yl)methyl 4-methylbenzenesulfonate (1.50 g, 3.10 mmol) with 3-chlorophenylboronic acid (0.72 g, 4.60 mmol), dichloro[1,1'-bis(diphenylphosphino)ferrocene]palladium(II) dichloromethane adduct (0.252 g, 0.30 mmol), and potassium carbonate (0.829 g, 6.0 mmol) generally according to the procedure described for Intermediate 35 gave 1.1 g (80%) of (±)-[5-chloro-7-(3-chlorophenyl)-2,3-dihydro-1-benzofuran-2-yl]methyl 4-methylbenzenesulfonate as a white solid. mp 80-82° C. Anal. calcd. for $C_{22}H_{18}Cl_2O_4S$: C, 58.8; H, 4.04. Found: C, 56.91; H, 3.82.

Intermediate 96

(±)-(5-chloro-7-thien-3-yl-2,3-dihydro-1-benzofuran-2-yl)methyl 4-methylbenzenesulfonate Treatment of (±)-(5-chloro-7-{[(trifluoromethyl)sulfonyl]oxy}-2,3-dihydro-1-benzofuran-2-yl)methyl 4-methylbenzenesulfonate (1.50 g, 3.10 mmol) with thiophene-3-boronic acid (0.62 g, 4.88 mmol), dichloro[1,1'-bis(diphenylphosphino)ferrocene]palladium(II) dichloromethane adduct (0.265 g, 0.325 mmol), and potassium carbonate (0.898 g, 6.5 mmol) generally according to the procedure described for Intermediate 35 provided 0.22 g (17%) of (±)-(5-chloro-7-thien-3-yl-2,3-dihydro-1-benzofuran-2-yl)methyl 4-methylbenzenesulfonate as a white solid. mp 115-117° C.; Anal. calcd. for $C_{20}H_{17}ClO_4S_2$: C, 57.07; H, 4.07. Found: C, 56.17; H, 3.85.

Intermediate 97

(±)-2-(azidomethyl)-5-chloro-7-(3-methylphenyl)-2,3-dihydro-1-benzofuran

Treatment of (±)-(5-chloro-7-{[(trifluoromethyl)sulfonyl]oxy}-2,3-dihydro-1-benzofuran-2-yl)methyl 4-methylbenzenesulfonate (1.50 g, 3.10 mmol) with 3-methylphenylboronic acid (0.63 g, 4.60 mmol), dichloro[1,1'-bis(diphenylphosphino)ferrocene]palladium(II) dichloromethane adduct (0.252 g, 0.30 mmol), and potassium carbonate (0.829 g, 6.0 mmol) generally according to the procedure described for Intermediate 35 gave (±)-[5-chloro-7-(3-methylphenyl)-2,3-dihydro-1-benzofuran-2-yl]methyl 4-methylbenzenesulfonate as a colorless oil. Treatment of the tosylate with sodium azide (0.31 g, 4.78 mmol) generally according to the procedure described for Intermediate 98 afforded 0.32 g (34%) of (±)-2-(azidomethyl)-5-chloro-7-(3-methylphenyl)-2,3-dihydro-1-benzofuran as a tan solid. mp 48-50° C.; Anal. calcd. for $C_{16}H_{14}ClN_3O$: C, 64.11; H, 4.71; N, 14.02. Found: C, 62.95; H, 4.62; N, 13.72.

Intermediate 98

(±)-2-(azidomethyl)-5-chloro-7-thien-3-yl-2,3-dihydro-1-benzofuran

To a solution of (±)-(5-chloro-7-thien-3-yl-2,3-dihydro-1-benzofuran-2-yl)methyl 4-methylbenzenesulfonate (4.5 g, 10.69 mmol) in dimethylsulfoxide (150 mL) was added sodium azide (3.6 g, 55.38 mmol) and the reaction mixture was heated to 70° C. and allowed to stir for 6 h. The reaction mixture was cooled to room temperature and diluted with water (300 mL) and diethyl ether (200 mL). The aqueous layer was separated and extracted with diethyl ether (200 mL). The combined organic layers were washed with water (3×200 mL), saturated aqueous sodium chloride (100 mL), dried (magnesium sulfate), and the solvent removed in vacuo to afford 2.6 g (83%) of (±)-2-(azidomethyl)-5-chloro-7-thien-3-yl-2,3-dihydro-1-benzofuran as a white solid. mp 50-52° C.; Anal. calcd. for $C_{13}H_{10}ClN_3OS$: C, 53.52; H, 3.45; N, 14.40. Found: C, 53.50; H, 3.33; N, 14.26.

Intermediate 99

(±)-benzyl(5-chloro-7-thien-3-yl-2,3-dihydro-1-benzofuran-2-yl)methylcarbamate

Treatment of (±)-(5-chloro-7-thien-3-yl-2,3-dihydro-1-benzofuran-2-yl)methylamine (2.45 g, 8.11 mmol) with benzyl chloroformate (2.07 g, 12.15 mmol) and diisopropylethylamine (3.43 g, 24.32 mmol) generally according to the procedure described for Intermediate 12 provided 2.6 g (81%) of (±)-benzyl(5-chloro-7-thien-3-yl-2,3-dihydro-1-benzofuran-2-yl)methylcarbamate as a white solid. mp 90-92° C.; Anal. calcd. for $C_{21}H_{18}ClNO_3S$: C, 63.07; H, 4.54; N, 3.50. Found: C, 63.44; H, 4.51; N, 3.43. Chiral HPLC separation of (±)-benzyl(5-chloro-7-thien-3-yl-2,3-dihydro-1-benzofuran-2-yl)methylcarbamate (Chiralpak AD, hexane:ethanol 1:1) provided two fractions. Fraction 1 ($R_t$=11.538 min, (Chiralpak AD, hexane:ethanol 1:1); Fraction 2 ($R_t$=17.694 min, (Chiralpak AD, hexane:ethanol 1:1).

Intermediate 100

2-(allyloxy)-1-bromo-4-fluorobenzene

Treatment of 2-bromo-5-fluorophenol (10.00 g, 0.052 mol) with potassium carbonate (29.30 g, 0.209 mol) and allyl bromide (7.60 g, 0.063 mol) generally according to the reaction procedure described for Intermediate 8 provided 12.1 g (99%) of 2-(allyloxy)-1-bromo-4-fluorobenzene as a colorless oil. $R_f$=0.37 (silica, ethyl acetate:hexanes 1:9); $^1$H NMR (DMSO-$d_6$) $\delta_H$ 7.58 (dd, 1H); 7.05 (dd, 1H); 6.75 (dt, 1H); 6.02 (m, 1H); 5.43 (d, 1H); 5.27 (d, 1H); 4.65 (m, 2H).

Intermediate 101

2-allyl-6-bromo-3-fluorophenol

Treatment of 2-(allyloxy)-1-bromo-4-fluorobenzene (12.00 g, 0.052 mol) in refluxing mesitylene generally according to the reaction procedure described for Intermediate 8 provided 11.5 g (95%) of 2-allyl-6-bromo-3-fluorophenol as a pale yellow oil. $R_f$=0.48 (silica, ethyl acetate:hexanes 1:4); Anal. calcd. for $C_9H_8BrFO$: C, 46.78; H, 3.49. Found: C, 47.59; H, 3.47.

Intermediate 102

(±)-(7-bromo-4-fluoro-2,3-dihydro-1-benzofuran-2-yl)methanol

Treatment of 2-allyl-6-bromo-3-fluorophenol (9.01 g, 0.039 mol) with 3-chloroperoxybenzoic acid (77%, 13.46 g, 0.06 mol) followed by potassium carbonate (13.82 g, 0.10 mol) generally according to the reaction procedure described for Intermediate 9 gave 6.71 g (70%) of (±)-(7-bromo-4-fluoro-2,3-dihydro-1-benzofuran-2-yl)methanol as a white solid. $R_f$=0.20 (silica, ethyl acetate:hexanes 1:4); mp 40-43° C.; Anal. calcd. for $C_9H_8BrFO_2 \cdot 0.2H_2O$: C, 43.13; H, 3.38. Found: C, 42.94; H, 3.15.

Intermediate 103

(±)-(7-bromo-4-fluoro-2,3-dihydro-1-benzofuran-2-yl)methyl 4-methylbenzenesulfonate Treatment of (±)-(7-bromo-4-fluoro-2,3-dihydro-1-benzofuran-2-yl)methanol (6.21 g, 0.025 mol) with p-toluenesulfonyl chloride (5.26 g, 0.028 mol) in pyridine (120 mL) generally according to the procedure described for Intermediate 10 afforded 8.85 g (88%) of (±)-(7-bromo-4-fluoro-2,3-dihydro-1-benzofuran-2-yl)methyl 4-methylbenzenesulfonate as a white solid. $R_f$=0.60 (silica, ethyl acetate:hexanes 1:1); mp 100-103° C.; Anal. calcd. for $C_{16}H_{14}BrFO_4S$: C, 47.89; H, 3.52. Found: C, 47.89; H, 3.68.

Intermediate 104

(±)-(4-fluoro-7-phenyl-2,3-dihydro-1-benzofuran-2-yl)methyl 4-methylbenzenesulfonate Treatment of (±)-(7-bromo-4-fluoro-2,3-dihydro-1-benzofuran-2-yl)methyl 4-methylbenzenesulfonate (2.0 g, 4.98 mmol) with phenyl boronic acid (0.91 g, 7.22 mmol), dichlorobis(tri-o-tolylphosphine)-palladium(II) (0.392 g, 0.498 mmol), and potassium carbonate (1.72 g, 12.46 mmol) acording to the procedure described for Intermediate 37 gave 1.07 g (54%) of (±)-(4-fluoro-7-phenyl-2,3-dihydro-1-benzofuran-2-yl)methyl 4-methylbenzenesulfonate as a white solid. $R_f$=0.46 (silica, ethyl acetate:hexanes 1:4); $^1$H NMR (DMSO-$d_6$) $\delta_H$ 7.70 (d, 2H); 7.53 (d, 2H); 7.40 (t, 2H); 7.32 (m, 4H); 6.77 (t, 1H); 5.15 (m, 1H); 4.31 (dd, 1H); 4.22 (dd, 1H); 3.30 (dd, 1H, obscured by $H_2O$ peak); 3.01 (dd, 1H).

Intermediate 105

(±)-[4-fluoro-7-(2-methylphenyl)-2,3-dihydro-1-benzofuran-2-yl]methyl 4-methylbenzenesulfonate Treatment of (±)-(7-bromo-4-fluoro-2,3-dihydro-1-benzofuran-2-yl)methyl 4-methylbenzenesulfonate (2.05 g, 5.11 mmol) with 2-methylphenyl boronic acid (1.04 g, 7.66 mmol), dichlorobis(tri-o-tolylphosphine)-palladium(II) (0.201 g, 0.255 mmol), and potassium carbonate (1.77 g, 12.77 mmol) generally according to the procedure described for Intermediate 37 provided 1.38 g (65%) of (±)-[4-fluoro-7-(2-methylphenyl)-2,3-dihydro-1-benzofuran-2-yl]methyl 4-methylbenzenesulfonate as a white solid. $R_f$=0.34 (silica, ethyl acetate:hexanes 1.5:8.5); Anal. calcd. for $C_{23}H_{21}FO_4S$: C, 66.97; H, 5.13. Found: C, 66.95; H, 4.76.

Intermediate 106

2-allyl-6-bromo-4-fluorophenol

Treatment of 1-(allyloxy)-2-bromo-4-fluorobenzene (23.90 g, 0.103 mol) in refluxing mesitylene (50 mL) generally according to the procedure described for Intermediate 8 provided 23.44 g (99%) 2-allyl-6-bromo-4-fluorophenol as a brown oil. $R_f$=0.64 (silica, ethyl acetate:hexanes 1:19); Anal. calcd. for $C_9H_8BrFO$: C, 46.78; H, 3.49. Found: C, 49.19; H, 3.59.

Intermediate 107

(±)-(7-bromo-5-fluoro-2,3-dihydro-1-benzofuran-2-yl)methanol

Treatment of 2-allyl-6-bromo-4-fluorophenol (25.1 g, 0.109 mol) with 3-chloroperoxybenzoic acid (77%, 56.24 g, 0.326 mol) followed by potassium carbonate (62.19 g, 0.45 mol) generally according to the procedure described for Intermediate 9 provided 20.98 g (78%) of (±)-(7-bromo-5-fluoro-2,3-dihydro-1-benzofuran-2-yl)methanol as a white solid. $R_f$=0.54 (silica, ethyl acetate:hexanes 1:1); mp 53-57° C.; Anal. calcd. for $C_9H_8BrFO_2$·0.1 $C_4H_8O_2$: C, 44.13; H, 3.47. Found: C, 44.17; H, 3.16.

Intermediate 108

(±)-(7-bromo-5-fluoro-2,3-dihydro-1-benzofuran-2-yl)methyl 4-methylbenzenesulfonate Treatment of (±)-(7-bromo-5-fluoro-2,3-dihydro-1-benzofuran-2-yl)methanol (11.5 g, 0.047 mol) with p-toluenesulfonyl chloride (9.76 g, 0.051 mol) generally according to the procedure described for Intermediate 10 gave 12.50 g (66%) (±)-(7-bromo-5-fluoro-2,3-dihydro-1-benzofuran-2-yl)methyl 4-methylbenzenesulfonate as a white solid. $R_f$=0.44 (silica, ethyl acetate:hexanes 1:4); mp 84-86° C.; Anal. calcd. for $C_{16}H_{14}BrFO_4S$: C, 47.89; H, 3.52. Found: C, 47.65; H, 3.63.

Intermediate 109

(±)-(5-fluoro-7-phenyl-2,3-dihydro-1-benzofuran-2-yl)methyl 4-methylbenzenesulfonate Treatment of (±)-(7-bromo-5-fluoro-2,3-dihydro-1-benzofuran-2-yl)methyl 4-methylbenzenesulfonate (2.00 g, 4.98 mmol) with phenyl boronic acid (0.912 g, 7.48 mmol), dichlorobis(tri-o-tolylphosphine)palladium(II) (0.196 g, 0.249 mmol), and potassium carbonate (1.72 g, 12.46 mmol) generally according to the procedure described for Intermediate 37 gave 1.62 g (82%) of (±)-(5-fluoro-7-phenyl-2,3-dihydro-1-benzofuran-2-yl)methyl 4-methylbenzenesulfonate as a yellow oil. $R_f$=0.54 (silica, ethyl acetate:hexanes 1:4); Anal. calcd. for $C_{22}H_{19}FO_4S$·0.2 $C_4H_8O_2$: C, 65.82; H, 4.99. Found: C, 65.77; H, 4.99.

Intermediate 110

(±)-[5-fluoro-7-(2-methylphenyl)-2,3-dihydro-1-benzofuran-2-yl]methyl 4-methylbenzenesulfonate Treatment of (±)-(7-bromo-5-fluoro-2,3-dihydro-1-benzofuran-2-yl)methyl 4-methylbenzenesulfonate (2.00 g, 4.98 mmol) with 2-methylphenyl boronic acid (1.017 g, 7.48 mmol), dichlorobis(tri-o-tolylphosphine)palladium(II) (0.196 g, 0.249 mmol), and potassium carbonate (1.72 g, 12.46 mmol) generally according to the procedure described for Intermediate 37 provided 1.58 g (77%) of (±)-[5-fluoro-7-(2-methylphenyl)-2,3-dihydro-1-benzofuran-2-yl]methyl 4-methylbenzenesulfonate as a colorless oil. $R_f$=0.47 (silica, ethyl acetate:hexanes 3:17); Anal. calcd. for $C_{22}H_{19}FO_4S$·0.2 $C_4H_8O_2$: C, 66.46; H, 5.30. Found: C, 66.25; H, 4.98.

Intermediate 111

(±)-[7-(2-chlorophenyl)-5-fluoro-2,3-dihydro-1-benzofuran-2-yl]methyl 4-methylbenzenesulfonate Treatment of (±)-(7-bromo-5-fluoro-2,3-dihydro-1-benzofuran-2-yl)methyl 4-methylbenzenesulfonate (2.00 g, 4.98 mmol) with 2-chlorophenyl boronic acid (1.17 g, 7.48 mmol), dichlorobis(tri-o-tolylphosphine)palladium(II) (0.196 g, 0.249 mmol), and potassium carbonate (1.72 g, 12.46 mmol) generally according to the procedure described for Intermediate 37 afforded 1.44 g (67%) of (±)-[7-(2-chlorophenyl)-5-fluoro-2,3-dihydro-1-benzofuran-2-yl]methyl 4-methylbenzenesulfonate as a white solid. $R_f$=0.26 (silica, ethyl acetate:hexanes 3:17); Anal. calcd. for $C_{22}H_{18}ClFO_4S$: C, 61.04; H, 4.19. Found: C, 61.02; H, 3.95.

Intermediate 112

(±)-[5-fluoro-7-(2-fluorophenyl)-2,3-dihydro-1-benzofuran-2-yl]methyl 4-methylbenzenesulfonate Treatment of (±)-(7-bromo-5-fluoro-2,3-dihydro-1-benzofuran-2-yl)methyl 4-methylbenzenesulfonate (2.00 g, 4.98 mmol) with 2-fluorophenyl boronic acid (1.05 g, 7.48 mmol), dichlorobis(tri-o-tolylphosphine)palladium(II) (0.196 g, 0.249 mmol), and potassium carbonate (1.72 g, 12.46 mmol) generally according to the procedure described for Intermediate 37 gave 1.94 g (94%) of (±)-[5-fluoro-7-(2-fluorophenyl)-2,3-dihydro-1-benzofuran-2-yl]methyl 4-methylbenzenesulfonate as a yellow oil. $R_f$=0.38 (silica, ethyl acetate:hexanes 3:17); Anal. calcd. for $C_{22}H_{18}F_2O_4S$: C, 63.45; H, 4.36. Found: C, 63.13; H, 4.19.

Intermediate 113

(±)-{5-fluoro-7-[2-(trifluoromethyl)phenyl]-2,3-dihydro-1-benzofuran-2-yl}methyl 4-methylbenzenesulfonate Treatment of (±)-(7-bromo-5-fluoro-2,3-dihydro-1-benzofuran-2-yl)methyl 4-methylbenzenesulfonate (4.01 g, 10.0 mmol) with 2-(trifluoromethyl)-phenyl boronic acid (2.85 g, 15.0 mmol), dichlorobis(tri-o-tolylphosphine)palladium(II) (0.786 g, 1.00 mmol), and potassium carbonate (3.46 g, 25.00 mmol) generally according to the procedure described for Intermediate 37 provided 4.34 g (93%) of (±)-{5-fluoro-7-[2-(trifluoromethyl)phenyl]-2,3-dihydro-1-benzofuran-2-yl}methyl 4-methylbenzenesulfonate as a yellow oil. $R_f$=0.54 (silica, ethyl acetate:hexanes 3:7); Anal. calcd. for $C_{23}H_{18}F_4O_4S$: C, 59.22; H, 3.89. Found: C, 60.19; H, 4.29.

Intermediate 114

(±)-benzyl[5-fluoro-7-(2-methylphenyl)-2,3-dihydro-1-benzofuran-2-yl]methylcarbamate Treatment of (±)-1-[5-fluoro-7-(2-methylphenyl)-2,3-dihydro-1-benzofuran-2-yl]methanamine (3.11 g, 12.1 mmol) with diisopropylethylamine (2.34 g, 18.1 mmol) and benzyl chloroformate (2.27 g, 13.3 mmol) generally according to the procedure described for Intermediate 12 gave 4.35 (92%) of (±)-benzyl[5-fluoro-7-(2-methylphenyl)-2,3-dihydro-1-benzofuran-2-yl]methylcarbamate as a colorless oil. $R_f$=0.83 (silica, ethyl acetate:hexanes 1:9); Anal. calcd. for $C_{24}H_{22}FO_3 \cdot 0.2H_2O$: C, 72.97; H, 5.72; N, 3.55. Found: C, 72.8; H, 5.72; N, 3.48. Chiral HPLC separation of (±)-benzyl [5-fluoro-7-(2-methylphenyl)-2,3-dihydro-1-benzofuran-2-yl]methylcarbamate (Chiralcel OD, hexane:isopropanol 8:2) provided two fractions. Fraction 1 ($R_t$=7.269 min, Chiralcel OD, hexane:isopropanol 8:2); Fraction 2 ($R_t$=8.449 min, Chiralcel OD, hexane:isopropanol 8:2).

Intermediate 115

(±)-benzyl[7-(2-chlorophenyl)-5-fluoro-2,3-dihydro-1-benzofuran-2-yl]methylcarbamate Treatment of (±)-1-[7-(2-chlorophenyl)-5-fluoro-2,3-dihydro-1-benzofuran-2-yl]methanamine (2.92 g, 10.5 mmol) with diisopropylethylamine (1.70 g, 13.1 mmol) and benzyl chloroformate (1.97 g, 11.6 mmol) generally according to the procedure described for Intermediate 12 provided 3.02 (70%) of (±)-benzyl[7-(2-chlorophenyl)-5-fluoro-2,3-dihydro-1-benzofuran-2-yl]methylcarbamate as a colorless oil. $R_f$=0.76 (silica, ethyl acetate:hexanes 1:9); Anal. calcd. for $C_{23}H_{19}ClFNO_3 \cdot 0.5H_2O$: C, 65.64; H, 4.79; N, 3.33. Found: C, 65.28; H, 4.73; N, 3.18. Chiral HPLC separation of (±)-benzyl[7-(2-chlorophenyl)-5-fluoro-2,3-dihydro-1-benzofuran-2-yl]methylcarbamate (Chiralcel OJ, hexane:ethanol 1:1) provided two fractions. Fraction 1 ($R_t$=9.322 min, Chiralcel OJ, hexane:ethanol 1:1); Fraction 2 ($R_t$=13.646 min, Chiralcel OJ, hexane:ethanol 1:1).

Intermediate 116

(±)-benzyl {5-fluoro-7-[2-(trifluoromethyl)phenyl]-2,3-dihydro-1-benzofuran-2-yl}methylcarbamate Treatment of (±)-1-{5-fluoro-7-[2-(trifluoromethyl)phenyl]-2,3-dihydro-1-benzofuran-2-yl}methanamine (1.87 g, 5.38 mmol) with diisopropylethylamine (1.74 g, 13.4 mmol) and benzyl chloroformate (1.01 g, 5.92 mmol) following the procedure described for Intermediate 12 provided 2.03 (85%) of (±)-benzyl {5-fluoro-7-[2-(trifluoromethyl)phenyl]-2,3-dihydro-1-benzofuran-2-yl}methylcarbamate as a white solid. $R_f$=0.69 (silica, ethyl acetate:hexanes 1:9); mp 76-80° C.; Anal. calcd. for $C_{24}H_{19}F_4NO_3$: C, 64.72; H, 4.3; N, 3.14. Found: C, 65.01; H, 4.3; N, 2.99.

Intermediate 117

(±)-(7-bromo-4,5-difluoro-2,3-dihydro-1-benzofuran-2-yl)methyl 4-methylbenzenesulfonate Treatment of 2-allyl-6-bromo-3,4-difluorophenol (5.0 g, 0.020 mol) with 3-chloroperoxybenzoic acid (77%, 8.1 g, 0.036 mol) followed by potassium carbonate (6.94 g, 0.050 mol) generally according to the procedure described for Intermediate 9 afforded (±)-(7-bromo-4,5-difluoro-2,3-dihydro-1-benzofuran-2-yl)methanol a brown oil. Treatment of the alcohol with diisopropylethylamine (2.57 g, 0.020 mol), p-toluenesulfonyl chloride (2.28 g, 0.012 mol), and 4-(dimethylamino)pyridine (0.29 g, 2.375 mmol) generally according to the procedure described for Intermediate 45 gave 2.9 g (35%) of (±)-(7-bromo-4,5-difluoro-2,3-dihydro-1-benzofuran-2-yl)methyl 4-methylbenzenesulfonate as a white solid.

$R_f$=0.46 (silica, ethyl acetate:hexanes 1:3); $^1$H NMR (DMSO-$d_6$) $\delta_H$ 7.73 (d, 2H); 7.50 (dd, 1H); 7.43 (d, 2H); 5.15 (m, 1H); 4.3 (dd, 1H); 4.22 (dd, 1H); 3.45 (dd, 1H); 3.08 (dd, 1H).

Intermediate 118

(±)-(4,5-difluoro-7-phenyl-2,3-dihydro-1-benzofuran-2-yl)methyl 4-methylbenzenesulfonate To a solution of (±)-(7-bromo-4,5-difluoro-2,3-dihydro-1-benzofuran-2-yl)methyl 4-methylbenzenesulfonate (1.5 g, 3.59 mmol) in dioxane (30 mL) was added phenylboronic acid (0.656 g, 5.38 mmol), dichloro[1,1'-bis(diphenylphosphino)ferrocene]palladium(II)dichloromethane adduct (0.293 g, 0.359 mmol), and potassium carbonate (0.993 g, 7.18 mmol) and the reaction mixture was heated at reflux for 48 h. The reaction mixture was filtered (celite), rinsed (ethyl acetate), and the combined organic layers were washed with water (100 mL), aqueous sodium chloride (75 mL), dried (sodium sulfate) and the solvent was removed in vacuo to provide a crude solid. Purification by column chromatography (silica, ethyl acetate:hexane 1:9) afforded 1.19 g (80%) of (±)-(4,5-difluoro-7-phenyl-2,3-dihydro-1-benzofuran-2-yl) methyl 4-methylbenzenesulfonate as a white solid. $R_f$=0.76 (silica, ethyl acetate:hexanes 1:9); $^1$H NMR (DMSO-$d_6$) $\delta_H$ 7.69 (d, 2H); 7.50 (dd, 1H); 7.56 (d, 2H); 7.35 (m, 6H); 5.14 (m, 1H); 4.30 (dd, 1H); 4.20 (dd, 1H); 3.39 (dd, 1H); 3.05 (dd, 1H).

Intermediate 119

(±)-(4,5-difluoro-7-phenyl-2,3-dihydro-1-benzofuran-2-yl)methyl azide

To a solution of (±)-(4,5-difluoro-7-phenyl-2,3-dihydro-1-benzofuran-2-yl)methyl 4-methylbenzenesulfonate (1.0 g, 2.40 mmol) in N,N-dimethylformamide (25 mL) was added sodium azide (0.781 g, 12.02 mmol) and the reaction mixture was heated to 70° C. and allowed to stir for 3 h. The reaction mixture was allowed to cool and the solvent was removed in vacuo to provide a crude solid. The residue was suspended in ethyl acetate (100 mL) and washed with water (50 mL) and aqueous sodium chloride (50 mL), was dried (sodium sulfate) and the solvent was removed in vacuo to give a crude solid. Purification by flash column chromatography (silica, ethyl acetate:hexanes 1:9) provided 0.68 g (99%) of (±)-(4,5-difluoro-7-phenyl-2,3-dihydro-1-benzofuran-2-yl)methyl azide as a white solid. $R_f$=0.93 (silica, ethyl acetate:hexanes 1:9); $^1$H NMR (DMSO-$d_6$) $\delta_H$ 7.65 (d, 2H); 7.41 (m, 3H); 7.31 (t, 1H); 5.15 (m, 1H); 3.64 (m, 2H); 3.46 (dd, 1H); 3.10 (dd, 1H).

Intermediate 120

(±)-[4,5-difluoro-7-(2-methylphenyl)-2,3-dihydro-1-benzofuran-2-yl]methyl 4-methylbenzenesulfonate Treatment of (±)-(7-bromo-4,5-difluoro-2,3-dihydro-1-benzofuran-2-yl)methyl 4-methylbenzenesulfonate (1.5 g, 3.59 mmol) with 2-methylphenyl boronic acid (0.732 g, 5.38 mmol), dichloro[1,1'-bis(diphenylphosphino)ferrocene]palladium(II)dichloromethane adduct (0.293 g, 0.359 mmol), and potassium carbonate (0.993 g, 7.18 mmol) generally according to the procedure described for Intermediate 118 afforded 1.3 g (84%) of (±)-[4,5-difluoro-7-(2-methylphenyl)-2,3-dihydro-1-benzofuran-2-yl]methyl 4-methylbenzenesulfonate as a white solid. $R_f$=0.72 (silica, ethyl acetate:

hexanes 1:4); $^1$H NMR (DMSO-d$_6$) $\delta_H$ 7.67 (d, 2H); 7.38 (d, 2H); 7.20 (m, 3H); 7.05 (m, 2H); 5.05 (m, 1H); 4.22 (dd, 2H); 4.13 (dd, 1H); 3.40 (dd, 1H); 3.02 (dd, 1H); 2.05 (s, 3H).

Intermediate 121

(±)-[4,5-difluoro-7-(2-methylphenyl)-2,3-dihydro-1-benzofuran-2-yl]methyl azide

Treatment of (±)-[4,5-difluoro-7-(2-methylphenyl)-2,3-dihydro-1-benzofuran-2-yl]methyl 4-methylbenzenesulfonate (1.3 g, 3.02 mmol) with sodium azide (0.983 g, 15.11 mmol) generally according to the procedure described for intermediate 98 gave 0.82 g (90%) of (±)-[4,5-difluoro-7-(2-methylphenyl)-2,3-dihydro-1-benzofuran-2-yl]methyl azide as a colorless oil. R$_f$=0.69 (silica, ethyl acetate:hexanes 1:4); $^1$H NMR (DMSO-d$_6$) $\delta_H$ 7.25 (d, 2H); 7.14 (m, 3H); 5.06 (m, 1H); 3.67 (dd, 1H); 3.55 (dd, 1H); 3.46 (dd, 1H); 3.11 (dd, 1H); 2.15 (s, 3H).

Intermediate 122

(±)-(5-chloro-7-methoxy-2-methyl-2,3-dihydro-1-benzofuran-2-yl)methyl 4-methylbenzenesulfonate Treatment of 4-chloro-2-methoxyphenol (15.00 g, 0.10 mol) with sodium hydride (4.4 g, 0.11 mol, 60 wt. %) and 3-chloro-2-methylpropene (12.00 g, 0.12 mol) generally according to the procedure described for Intermediate 13 provided 19.3 g (91%) of 4-chloro-2-methoxy-1-[(2-methylprop-2-enyl)oxy]benzene as a colorless oil. Treatment of the allyl ether in refluxing mesitylene generally according to the procedure described for Intermediate 8 afforded 15.5 g (78%) of 4-chloro-2-methoxy-6-(2-methylprop-2-enyl)phenol as a pale yellow oil. Treatment of 4-chloro-2-methoxy-6-(2-methylprop-2-enyl)phenol (10.00 g, 0.047 mol) with 3-chloroperoxybenzoic acid (20.00 g, 0.089 mol, 77%) followed by potassium carbonate (20.00 g, 0.145 mol) generally according to the Procedure described for Intermediate 9 provided 8.00 g (74%) of (±)-(5-chloro-7-methoxy-2-methyl-2,3-dihydro-1-benzofuran-2-yl)methanol as a light yellow oil. Treatment of (±)-(5-chloro-7-methoxy-2-methyl-2,3-dihydro-1-benzofuran-2-yl)methanol (10.8 g, 0.047 mol) with p-toluenesulfonyl chloride (13.5 g, 0.071 mol), diisopropylethylamine (12.15 g, 0.094 mol), and 4-(dimethylamino)pyridine (0.35 g, 2.83 mmol) generally according to the procedure described for Intermediate 45 gave 13.8 g (76%) of (±)-(5-chloro-7-methoxy-2-methyl-2,3-dihydro-1-benzofuran-2-yl)methyl 4-methylbenzenesulfonate as a white solid. mp 113-115° C.; Anal. calcd. for C$_{18}$H$_{19}$ClO$_5$S: C, 56.47; H, 5.00. Found: C, 55.82; H, 4.94.

Intermediate 123

(±)-(5-chloro-7-hydroxy-2-methyl-2,3-dihydro-1-benzofuran-2-yl)methyl 4-methylbenzenesulfonate Treatment of (±)-(5-chloro-7-methoxy-2-methyl-2,3-dihydro-1-benzofuran-2-yl)methyl 4-methylbenzenesulfonate (13.80 g, 0.036 mol) with hydrogen bromide (200 mL, 30 wt. % in acetic acid) generally according to the procedure described for Intermediate 46 afforded 11.7 g (80%) of (±)-(5-chloro-7-hydroxy-2-methyl-2,3-dihydro-1-benzofuran-2-yl)methyl 4-methylbenzenesulfonate as a white solid. mp 135-137° C.; Anal. calcd. for C$_{17}$H$_{17}$ClO$_5$S: C, 55.36; H, 4.65. Found: C, 54.35; H, 4.52.

Intermediate 124

(±)-(5-chloro-2-methyl-7-{[(trifluoromethyl)sulfonyl]oxy}-2,3-dihydro-1-benzofuran-2-yl)methyl 4-methylbenzenesulfonate Treatment of (±)-(5-chloro-7-hydroxy-2-methyl-2,3-dihydro-1-benzofuran-2-yl)methyl 4-methylbenzenesulfonate (11.7 g, 0.032 mol) with trifluoromethanesulfonic anhydride (10.34 g, 0.037 mol) and diisopropylethylamine (4.74 g, 0.037 mol) generally according to the procedure described for Intermediate 7 provided 13.0 g (82%) of (±)-(5-chloro-2-methyl-7-{[(trifluoromethyl)sulfonyl]oxy}-2,3-dihydro-1-benzofuran-2-yl)methyl 4-methylbenzenesulfonate as a white solid. mp 100-102° C.; Anal. calcd. for C$_{18}$H$_{16}$ClF$_3$O$_7$S$_2$: C, 43.16; H, 3.22. Found: C, 43.07; H, 3.04.

Intermediate 125

(−)-benzyl [(7-tert-butyl-5-methoxy-2,3-dihydro-1-benzofuran-2-yl)methyl]carbamate Fraction 1 obtained as a colorless oil from the chiral HPLC separation of (±)-benzyl (7-tert-butyl-5-methoxy-2,3-dihydro-1-benzofuran-2-yl)methylcarbamate (R$_t$=4.39 min, Chiralpak OD, 2-butanol:carbon dioxide 2:8). [α]$_D^{25}$= −17.46 (c 10.0 in methanol); Anal. calcd. for C$_{22}$H$_{27}$NO$_4$ C, 71.52; H, 7.37; N, 3.79. Found C, 71.2; H, 7.61; N, 3.62.

Intermediate 126

(+)-benzyl [(7-tert-butyl-5-methoxy-2,3-dihydro-1-benzofuran-2-yl)methyl]carbamate Fraction 2 obtained as a colorless oil from the chiral HPLC separation of (±)-benzyl [(7-tert-butyl-5-methoxy-2,3-dihydro-1-benzofuran-2-yl)methyl]carbamate (R$_t$=5.07 min, Chiralpak OD, 2-butanol:carbon dioxide 2:8). [α]$_D^{25}$= +22.18 (c 10.0 in methanol); Anal. calcd. for C$_{22}$H$_{27}$NO$_4$ C, 71.52; H, 7.37; N, 3.79. Found C, 70.33; H, 7.49; N, 3.5.

Intermediate 127

(±)-{7-[(1E)-3,3-dimethylbut-1-enyl]-2,3-dihydro-1-benzofuran-2-yl}methyl 4-methylbenzenesulfonate Treatment of (±)-(7-bromo-2,3-dihydro-1-benzofuran-2-yl)methyl 4-methylbenzenesulfonate (8.0 g, 20.87 mmol) with [E]-2-tert-butylvinylboronic acid (4.01 g, 31.31 mmol), dichlorobis(tri-o-tolylphosphine)-palladium(II) (0.82 g, 1.04 mmol), and potassium carbonate (7.21 g, 52.19 mmol) generally according to the procedure described for Intermediate 37 provided 6.54 g (81%) of (±)-{7-[(1E)-3,3-dimethylbut-1-enyl]-2,3-dihydro-1-benzofuran-2-yl}methyl 4-methylbenzenesulfonate as a white solid. mp 85-88° C.; Anal. calcd. for C$_{22}$H$_{26}$O$_4$S: C, 68.37; H, 6.78. Found: C, 68.27; H, 6.86.

Intermediate 128

(±)-{7-[(E)-2-phenylvinyl]-2,3-dihydro-1-benzofuran-2-yl}methyl 4-methylbenzenesulfonate Treatment of (±)-(7-bromo-2,3-dihydro-1-benzofuran-2-yl)methyl 4-methylbenzenesulfonate (8.0 g, 20.9 mmol) with trans-2-phenylvinylboronic acid (4.63 g, 31.3 mmol), dichlorobis(tri-o-tolylphosphine)-palladium(II) (0.82 g, 1.04 mmol), and potassium carbonate (7.21 g, 52.2 mmol) generally according to the procedure described for Intermediate 37 provided 6.59 g (78%) of (±)-{7-[(E)-2-phenylvinyl]-2,3-dihydro-1-benzofuran-2-yl}methyl 4-methylbenzenesulfonate as a light yellow solid. mp 120-122° C.; Anal. calcd. for $C_{24}H_{22}O_4S$: C, 70.91; H, 5.45. Found: C, 70.78; H, 5.56.

Intermediate 129

(±)-benzyl {[4-(4-methylphenyl)-2,3-dihydro-1-benzofuran-2-yl]methyl}carbamate

Treatment of (±)-1-[4-(4-methylphenyl)-2,3-dihydro-1-benzofuran-2-yl]methanamine (1.94 g, 7.03 mmol) with diisopropylethylamine (1.36 g, 10.55 mmol) followed by benzyl chloroformate (1.32 g, 7.74 mmol) generally according to the procedure described for Intermediate 12 provided 2.36 g (90%) of (±)-benzyl {[4-(4-methylphenyl)-2,3-dihydro-1-benzofuran-2-yl]methyl}carbamate as a white solid. mp 134-136° C.; Anal. calcd. for $C_{24}H_{23}NO_3$: C, 77.19; H, 6.21; N, 3.75. Found: C, 77.08; H, 6.3; N, 3.69.

Intermediate 130

(±)-benzyl({4-[2-(trifluoromethyl)phenyl]-2,3-dihydro-1-benzofuran-2-yl}methyl)carbamate Treatment of (±)-1-{4-[2-(trifluoromethyl)phenyl]-2,3-dihydro-1-benzofuran-2-yl}methanamine (2.21 g, 6.7 mmol) with diisopropylethylamine (1.3 g, 10.05 mmol) followed by benzyl chloroformate (1.25 g, 7.37 mmol) generally according to the procedure described for Intermediate 12 provided 2.6 g (91%) of (±)-benzyl({4-[2-(trifluoromethyl)phenyl]-2,3-dihydro-1-benzofuran-2-yl}methyl)carbamate as a colorless oil. Anal. calcd. for $C_{24}H_{20}F_3NO_3$: C, 67.44; H, 4.72; N, 3.28. Found: C, 67.5; H, 4.7; N, 3.13. Chiral HPLC separation of (±)-benzyl ({4-[2-(trifluoromethyl)phenyl]-2,3-dihydro-1-benzofuran-2-yl}methyl)carbamate (Chiralcel OJ, ethanol: hexane 1:1) provided two fractions. Fraction 1 ($R_t$=5.701 min, Chiralcel OJ, ethanol:hexane 1:1); Fraction 2 ($R_t$=7.122 min, Chiralcel OJ, ethanol:hexane 1:1).

Intermediate 131

(−)-benzyl({4-[2-(trifluoromethyl)phenyl]-2,3-dihydro-1-benzofuran-2-yl}methyl)carbamate Fraction 1 obtained as a colorless oil from the chiral HPLC separation of (±)-benzyl ({4-[2-(trifluoromethyl)phenyl]-2,3-dihydro-1-benzofuran-2-yl}methyl)carbamate ($R_t$=5.701 min, Chiralcel OJ, ethanol:hexane 1:1). $[\alpha]_D^{25}$=−61.46 (c 10.0 in methanol); Anal. calcd. for $C_{24}H_{20}F_3NO_3$: C, 67.44; H, 4.72; N, 3.28. Found C, 67.52; H, 4.67; N, 3.11.

Intermediate 132

(±)-benzyl({4-[2-(trifluoromethyl)phenyl]-2,3-dihydro-1-benzofuran-2-yl}methyl)carbamate Fraction 2 obtained as a colorless oil from the chiral HPLC separation of (±)-benzyl ({4-[2-(trifluoromethyl)phenyl]-2,3-dihydro-1-benzofuran-2-yl}methyl)carbamate ($R_t$=7.122 min, Chiralcel OJ, ethanol:hexane 1:1). $[\alpha]_D^{25}$=+60.44 (c 10.0 in methanol); Anal. calcd. for $C_{24}H_{20}F_3NO_3$: C, 67.44; H, 4.72; N, 3.28. Found: C, 67.03; H, 4.62; N, 3.2.

Intermediate 133

(±)-[4-(2,6-dimethylphenyl)-2,3-dihydro-1-benzofuran-2-yl]methyl 4-methylbenzenesulfonate Treatment of (±)-(4-bromo-2,3-dihydro-1-benzofuran-2-yl)methyl 4-methylbenzenesulfonate (1.5 g, 3.32 mmol) with 2,6-dimethylphenylboronic acid (2.35 g, 15.66 mmol), tetrakis(triphenylphosphine)palladium(0) (0.452 g, 0.394 mmol), and barium hydroxide octahydrate (6.17 g, 19.57 mmol) generally according to the procedure described for Intermediate 50 provided 2.27 g (71%) of (±)-[4-(2,6-dimethylphenyl)-2,3-dihydro-1-benzofuran-2-yl]methyl 4-methylbenzenesulfonate as a colorless oil. Anal. calcd. for $C_{24}H_{24}O_4S$: C, 70.56; H, 5.92. Found: C, 69.72; H, 5.87.

Intermediate 134

(±)-benzyl {[4-(2,6-dimethylphenyl)-2,3-dihydro-1-benzofuran-2-yl]methyl}carbamate Treatment of (±)-1-[4-(2,6-dimethylphenyl)-2,3-dihydro-1-benzofuran-2-yl]methanamine (1.2 g, 4.14 mmol) with diisopropylethylamine (0.803 g, 6.21 mmol) followed by benzyl chloroformate (0.848 g, 4.97 mmol) generally according to the procedure described for Intermediate 12 provided 1.52 g (95%) of (±)-benzyl {[4-(2,6-dimethylphenyl)-2,3-dihydro-1-benzofuran-2-yl]methyl}carbamate as a colorless oil. Anal. calcd. for $C_{25}H_{25}NO_3$: C, 77.49; H, 6.5; N, 3.61. Found: C, 76.66; H, 6.31; N, 3.44. Chiral HPLC separation of (±)-benzyl {[4-(2,6-dimethylphenyl)-2,3-dihydro-1-benzofuran-2-yl]methyl}carbamate (Chiralcel OD, ethanol) provided two fractions. Fraction 1 ($R_t$=4.818 min, Chiralcel OD, ethanol); Fraction 2 ($R_t$=6.985 min, Chiralcel OD, ethanol).

Intermediate 135

(+)-benzyl {[4-(2,6-dimethylphenyl)-2,3-dihydro-1-benzofuran-2-yl]methyl}carbamate Fraction 1 obtained as a colorless oil from the chiral HPLC separation of (±)-benzyl {[4-(2,6-dimethylphenyl)-2,3-dihydro-1-benzofuran-2-yl]methyl}carbamate ($R_t$=4.818 min, Chiralcel OD, ethanol). $[\alpha]_D^{25}$=+60.96 (c 10.0 in methanol); Anal. calcd. for $C_{25}H_{25}NO_3$: C, 77.49; H, 6.5; N, 3.61. Found: C, 77.11; H, 6.26; N, 3.38.

Intermediate 136

(−)-benzyl {[4-(2,6-dimethylphenyl)-2,3-dihydro-1-benzofuran-2-yl]methyl}carbamate Fraction 2 obtained as a colorless oil from the chiral HPLC separation of (±)-benzyl {[4-(2,6-dimethylphenyl)-2,3-dihydro-1-benzofuran-2-yl]methyl}carbamate ($R_t$=6.985 min, Chiralcel OD, ethanol). $[\alpha]_D^{25}$=−59.24 (c 10.0 in methanol); Anal. calcd. for $C_{25}H_{25}NO_3$: C, 77.49; H, 6.5; N, 3.61. Found: C, 76.91; H, 6.37; N, 3.46.

Intermediate 137

(±)-(7-thien-3-yl-2,3-dihydro-1-benzofuran-2-yl) methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 3-thiopheneboronic acid (0.334 g, 2.61 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.389 g (77%) of (±)-(7-thien-3-yl-2,3-dihydro-1-benzofuran-2-yl)methyl 4-methylbenzenesulfonate as a light yellow solid. mp 90-92° C.; Anal. calcd. for $C_{20}H_{18}O_4S_2$: C, 62.15; H, 4.69. Found: C, 62.2; H, 4.72.

Intermediate 138

(±)-{7-[2-(trifluoromethyl)phenyl]-2,3-dihydro-1-benzofuran-2-yl}methyl 4-methylbenzenesulfonate Treatment of (±)-(7-bromo-2,3-dihydro-1-benzofuran-2-yl)methyl 4-methylbenzenesulfonate (10.0 g, 26.10 mmol) with 2-(trifluoromethyl)phenylboronic acid (7.43 g, 39.12 mmol), dichlorobis(tri-o-tolylphosphine)-palladium(II) (1.02 g, 1.30 mmol), and potassium carbonate (9.01 g, 65.19 mmol) generally according to the procedure described for Intermediate 37 provided 8.46 g (75%) of (±)-{7-[2-(trifluoromethyl)phenyl]-2,3-dihydro-1-benzofuran-2-yl}methyl 4-methylbenzenesulfonate as a tan solid. mp 116-118° C.; Anal. calcd. for $C_{23}H_{19}F_3O_4S$: C, 61.60; H, 4.27. Found: C, 61.91; H, 4.23.

Intermediate 139

(±)-[7-(2-chlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (3.00 g, 7.83 mmol) with 3-chlorophenylboronic acid (1.84 g, 11.74 mmol), dichlorobis(tri-o-tolylphosphine)-palladium(II) (0.308 g, 0.391 mmol), and potassium carbonate (2.70 g, 19.57 mmol) generally according to the procedure described for Intermediate 37 provided 2.35 g (72%) of (±)-[7-(2-chlorophenyl)-2,3-dihydro-1-benzofuran-2-yl]methyl 4-methylbenzenesulfonate as a tan solid. mp 100-103° C.; Anal. calcd. for $C_{22}H_{19}ClO_4S$: C, 63.69; H, 4.62. Found: C, 63.43; H, 4.69.

Intermediate 140

(+)-benzyl {[7-(2-chlorophenyl)-2,3-dihydro-1-benzofuran-2-yl]methyl}carbamate

Fraction 1 obtained as a colorless oil from the chiral HPLC separation of (±)-benzyl {[7-(2-chlorophenyl)-2,3-dihydro-1-benzofuran-2-yl]methyl}carbamate ($R_t$=9.655 min, Chiralcel OJ, hexane:ethanol 1:1). $[\alpha]_D^{25}$=+10.48 (c 10.0 in methanol); Anal. calcd. for $C_{23}H_{20}ClNO_3$: C, 70.14; H, 5.12; N, 3.56. Found C, 69.45; H, 4.92; N, 2.94.

Intermediate 141

(−)-benzyl {[7-(2-chlorophenyl)-2,3-dihydro-1-benzofuran-2-yl]methyl}carbamate

Fraction 2 obtained as a colorless oil from the chiral HPLC separation of (±)-benzyl {[7-(2-chlorophenyl)-2,3-dihydro-1-benzofuran-2-yl]methyl}carbamate ($R_t$=16.300 min, Chiralcel OJ, hexane:ethanol 1:1). $[\alpha]_D^{25}$=−9.64 (c 10.0 in methanol); Anal. calcd. for $C_{23}H_{20}ClNO_3$: C, 70.14; H, 5.12; N, 3.56. Found C, 69.43; H, 5.06; N, 3.19.

Intermediate 142

(±)-[7-(2-methylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 3-methylphenylboronic acid (0.266 g, 1.96 mmol), dichlorobis(tri-o-tolylphosphine)-palladium(II) (0.051 g, 0.065 mmol), and potassium tert-butoxide (0.366 g, 3.26 mmol) generally according to the procedure described for Intermediate 37 provided 0.358 g (70%) of (±)-[7-(2-methylphenyl)-2,3-dihydro-1-benzofuran-2-yl]methyl 4-methylbenzenesulfonate as a white solid. mp 98-100° C.; Anal. calcd. for $C_{23}H_{22}O_4S$: C, 70.03; H, 5.62. Found: C, 69.83; H, 5.61.

Intermediate 143

(±)-[7-(2-fluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.500 g, 1.305 mmol) with 2-fluorophenylboronic acid (0.274 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.422 g (81%) of (±)-[7-(2-fluorophenyl)-2,3-dihydro-1-benzofuran-2-yl]methyl 4-methylbenzenesulfonate as a yellow solid. mp 99-101° C.; Anal. calcd. for $C_{22}H_{19}FO_4S$: C, 66.32; H, 4.81. Found: C, 65.16; H, 4.86.

Intermediate 144

(±)-[7-(2-methoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (5.00 g, 13.04 mmol) with 2-methoxyphenylboronic acid (3.96 g, 26.09 mmol), dichlorobis(tri-o-tolylphosphine)-palladium(II) (0.532 g, 0.652 mmol), and potassium carbonate (4.5 g, 32.62 mmol) generally according to the procedure described for Intermediate 37 provided 3.63 g (68%) of (±)-[7-(2-methoxyphenyl)-2,3-dihydro-1-benzofuran-2-yl]methyl 4-methylbenzenesulfonate as a yellow solid. mp 151-153° C.; Anal. calcd. for $C_{23}H_{22}O_5S$: C, 67.3; H, 5.4. Found: C, 66.95; H, 5.43.

Intermediate 145

(±)-[7-(3-fluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 3-fluorophenylboronic acid (0.274 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.392 g (75%) of (±)-[7-(3-fluorophenyl)-2,3-dihydro-1-benzofuran-2-yl]methyl 4-methylbenzenesulfonate as a light yellow solid. mp 88-90° C.; Anal. calcd. for $C_{22}H_{19}FO_4S$: C, 66.32; H, 4.81. Found: C, 65.63; H, 4.84.

Intermediate 146

(±)-benzyl {[7-(3-fluorophenyl)-2,3-dihydro-1-benzofuran-2-yl]methyl}carbamate

Treatment of (±)-1-[7-(3-fluorophenyl)-2,3-dihydro-1-benzofuran-2-yl]methanamine (798 g, 6.382.86 mmol) with diisopropylethylamine (0.554 g, 4.29 mmol) followed by benzyl chloroformate (0.536 g, 3.14 mmol) generally according to the procedure described for Intermediate 12 provided 1.01 g (94%) of (±)-benzyl {[7-(3-fluorophenyl)-2,3-dihydro-1-benzofuran-2-yl]methyl}carbamate as a white solid.

$R_f$=0.41 (silica, ethyl acetate:hexanes 2:8); Anal. calcd. for $C_{23}H_{20}FNO_3$: C, 73.2; H, 5.34; N, 3.71. Found: C, 72.96H, 5.38; N, 3.59. Chiral HPLC separation of (±)-benzyl {[7-(3-fluorophenyl)-2,3-dihydro-1-benzofuran-2-yl]methyl}carbamate (Chiralpak OD, isopropanol:hexane 2:8) provided two fractions. Fraction 1 ($R_t$=7.675 min, Chiralpak OD, isopropanol:hexane 2:8); Fraction 2 ($R_t$=9.182 min, Chiralpak OD, isopropanol:hexane 2:8).

Intermediate 147

(±)-benzyl {[7-(3-fluorophenyl)-2,3-dihydro-1-benzofuran-2-yl]methyl}carbamate

Fraction 1 obtained as a colorless oil from the chiral HPLC separation of (±)-benzyl {[7-(3-fluorophenyl)-2,3-dihydro-1-benzofuran-2-yl]methyl}carbamate ($R_t$=7.675 min, Chiralpak OD, isopropanol:hexane 2:8). $[\alpha]_D^{25}$=+41.76 (c 10.0 in methanol); Anal. calcd. for $C_{23}H_{20}FNO_3$: C, 73.2; H, 5.34; N, 3.71. Found C, 73.01; H, 5.28; N, 3.75.

Intermediate 148

(−)-benzyl {[7-(3-fluorophenyl)-2,3-dihydro-1-benzofuran-2-yl]methyl}carbamate

Fraction 2 obtained as a colorless oil from the chiral HPLC separation of (±)-benzyl {[7-(3-fluorophenyl)-2,3-dihydro-1-benzofuran-2-yl]methyl}carbamate ($R_t$=9.182 min, Chiralpak OD, isopropanol:hexane 2:8). $[\alpha]_D^{25}$=−34.44 (c 10.0 in methanol); Anal. calcd. for $C_{23}H_{20}FNO_3$: C, 73.2; H, 5.34; N, 3.71. Found C, 73.2; H, 5.39; N, 3.62.

Intermediate 149

(±)-[7-(3-methoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (5.00 g, 13.05 mmol) with 3-methoxyphenylboronic acid (2.97 g, 19.57 mmol), dichlorobis(tri-o-tolylphosphine)-palladium(II) (0.512 g, 0.652 mmol), and potassium carbonate (4.51 g, 32.62 mmol) generally generally according to the procedure described for Intermediate 37 provided 4.48 g (84%) of (±)-[7-(3-methoxyphenyl)-2,3-dihydro-1-benzofuran-2-yl]methyl 4-methylbenzenesulfonate as a white solid. mp 141-142° C.; Anal. calcd. for $C_{23}H_{22}O_5S$: C, 67.3; H, 5.4. Found: C, 66.51; H, 5.41.

Intermediate 150

(±)-benzyl {[7-(3-methoxyphenyl)-2,3-dihydro-1-benzofuran-2-yl]methyl}carbamate

Treatment of (±)-1-[7-(3-methoxyphenyl)-2,3-dihydro-1-benzofuran-2-yl]methanamine (2.4 g, 9.4 mmol) with diisopropylethylamine (1.82 g, 14.10 mmol) followed by benzyl chloroformate (1.92 g, 11.28 mmol) generally according to the procedure described for Intermediate 12 provided 3.28 g (90%) of (±)-benzyl {[7-(3-methoxyphenyl)-2,3-dihydro-1-benzofuran-2-yl]methyl}carbamate as a colorless oil. $R_f$=0.51 (silica, ethyl acetate:hexanes 2:8); Anal. calcd. for $C_{24}H_{23}NO_4$: C, 74.02; H, 5.95; N, 3.6. Found: C, 73.52; H, 6.06; N, 3.28. Chiral HPLC separation of (±)-benzyl {[7-(3-methoxyphenyl)-2,3-dihydro-1-benzofuran-2-yl]methyl}carbamate (Chiralpak OD, ethanol) provided two fractions. Fraction 1 ($R_t$=6.220 min, Chiralpak OD, ethanol); Fraction 2 ($R_t$=8.373 min, Chiralpak OD ethanol).

Intermediate 151

(+)-benzyl {[7-(3-methoxyphenyl)-2,3-dihydro-1-benzofuran-2-yl]methyl}carbamate

Fraction 1 obtained as a colorless oil from the chiral HPLC separation of (±)-benzyl {[7-(3-methoxyphenyl)-2,3-dihydro-1-benzofuran-2-yl]methyl}carbamate ($R_t$=6.220 min, Chiralpak OD, ethanol). $[\alpha]_D^{25}$=+26.94 (c 10.0 in methanol); Anal. calcd. for $C_{24}H_{23}NO_4$: C, 74.02; H, 5.95; N, 3.6. Found: C, 73.48; H, 5.98; N, 3.46.

Intermediate 152

(−)-benzyl {[7-(3-methoxyphenyl)-2,3-dihydro-1-benzofuran-2-yl]methyl}carbamate

Fraction 2 obtained as a colorless oil from the chiral HPLC separation of (±)-benzyl {[7-(3-methoxyphenyl)-2,3-dihydro-1-benzofuran-2-yl]methyl}carbamate ($R_t$=8.373 min, Chiralpak OD ethanol). $[\alpha]_D^{25}$=−26.96 (c 10.0 in methanol); Anal. calcd. for $C_{24}H_{23}NO_4$: C, 74.02; H, 5.95; N, 3.6. Found: C, 73.52; H, 6.01; N, 3.45.

Intermediate 153

(±)-[7-(3-chlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 3-chlorophenylboronic acid (0.306 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.404 g (75%) of (±)-[7-(3-chlorophenyl)-2,3-dihydro-1-benzofuran-2-yl]methyl 4-methylbenzenesulfonate as a light yellow solid. mp 101-103° C.; Anal. calcd. for $C_{22}H_{19}ClO_4S$: C, 63.69; H, 4.62. Found: C, 63.59; H, 4.52.

Intermediate 154

(±)-{7-[3-(trifluoromethyl)phenyl]-2,3-dihydro-1-benzofuran-2-yl}methyl 4-methylbenzenesulfonate Treatment of (±)-(7-bromo-2,3-dihydro-1-benzofuran-2-yl)methyl 4-methylbenzenesulfonate (5.0 g, 13.05 mmol) with 3-(trifluoromethyl)phenylboronic acid (3.72 g, 19.57 mmol), dichlorobis(tri-o-tolylphosphine)-palladium(II) (0.512 g, 0.652 mmol), and potassium carbonate (4.5 g, 32.62 mmol) generally according to the procedure described for Intermediate 37 provided 5.28 g (90%) of (±)-{7-[3-(trifluoromethyl)phenyl]-2,3-dihydro-1-benzofuran-2-yl}methyl 4-methylbenzenesulfonate as a white solid. mp 90-93° C.; Anal. calcd. for $C_{23}H_{19}F_3O_4S$: C, 61.6; H, 4.27. Found: C, 61.52; H, 4.21.

Intermediate 155

(±)-benzyl({7-[3-(trifluoromethyl)phenyl]-2,3-dihydro-1-benzofuran-2-yl}methyl)carbamate Treatment of (±)-1-{7-[3-(trifluoromethyl)phenyl]-2,3-dihydro-1-benzofuran-2-yl}methanamine (1.67 g, 5.06 mmol) with diisopropylethylamine (0.98 g, 7.59 mmol) followed by benzyl chloroformate (1.04 g, 7.59 mmol) generally according to the procedure described for Intermediate 12 provided 2.1 g (97%) of (±)-benzyl({7-[3-(trifluoromethyl)phenyl]-2,3-dihydro-1-benzofuran-2-yl}methyl)carbamate as a colorless oil. Anal. calcd. for $C_{24}H_{20}F_3NO_3$: C, 67.44; H, 4.72; N, 3.28. Found: C, 67.08; H, 5.05; N, 3.22. Chiral HPLC separation of (±)-benzyl ({7-[3-(trifluoromethyl)phenyl]-2,3-dihydro-1-benzofuran-2-yl}methyl)carbamate (Chiralpak OJ, isopropanol:carbon dioxide 15:85) provided two fractions. Fraction 1 ($R_t$=6.12 min, Chiralpak OJ, isopropanol:carbon dioxide 15:85); Fraction 2 ($R_t$=7.17 min, Chiralpak OJ, isopropanol:carbon dioxide 15:85).

Intermediate 156

(±)-[7-(4-methylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (11.2 g, 29.22 mmol) with 4-methylphenylboronic acid (5.96 g, 43.84 mmol), dichlorobis(tri-o-tolylphosphine)-palladium(II) (1.15 g, 1.46 mmol), and potassium carbonate (10.10 g, 73.07 mmol) generally according to the procedure described for Intermediate 37 provided 9.8 g (85%) of (±)-[7-(4-methylphenyl)-2,3-dihydro-1-benzofuran-2-yl]methyl 4-methylbenzenesulfonate as a white solid. mp 145-147° C.; Anal. calcd. for $C_{23}H_{22}O_4S$: C, 70.03; H, 5.62. Found: C, 69.91; H, 5.7.

Intermediate 157

(±)-benzyl {[7-(4-methylphenyl)-2,3-dihydro-1-benzofuran-2-yl]methyl}carbamate

Treatment of (±)-1-[7-(4-methylphenyl)-2,3-dihydro-1-benzofuran-2-yl]methanamine (5.8 g, 24.24 mmol) with diisopropylethylamine (4.69 g, 36.35 mmol) followed by benzyl chloroformate (5.17 g, 30.30 mmol) generally according to the procedure described for Intermediate 12 provided 5.05 g (56%) of (±)-benzyl {[7-(4-methylphenyl)-2,3-dihydro-1-benzofuran-2-yl]methyl}carbamate as a clear oil. Anal. calcd. for $C_{24}H_{23}NO_3$: C, 77.19; H, 6.21; N, 3.75. Found: C, 76.97; H, 5.99; N, 3.68. Chiral HPLC separation of (±)-benzyl {[7-(4-methylphenyl)-2,3-dihydro-1-benzofuran-2-yl]methyl}carbamate (Chiralpak OD, methanol:carbon dioxide 1:1) provided two fractions. Fraction 1 ($R_t$=3.735 min, Chiralpak OD, methanol:carbon dioxide 1:1); Fraction 2 ($R_t$=4.381 min, Chiralpak OD, methanol:carbon dioxide 1:1).

Intermediate 158

(±)-[7-(4-fluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 4-fluorophenylboronic acid (0.274 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.408 g (78%) of (±)-[7-(4-fluorophenyl)-2,3-dihydro-1-benzofuran-2-yl]methyl 4-methylbenzenesulfonate as a light yellow solid. mp 83-86° C.; Anal. calcd. for $C_{22}H_{19}FO_4S$: C, 66.32; H, 4.81. Found: C, 66.11; H, 4.61.

Intermediate 159

(±)-[7-(4-chlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 4-chlorophenylboronic acid (0.306 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.367 g (68%) of (±)-[7-(4-chlorophenyl)-2,3-dihydro-1-benzofuran-2-yl]methyl 4-methylbenzenesulfonate as an orange solid. mp 130-133° C.; Anal. calcd. for $C_{22}H_{19}ClO_4S$: C, 63.69; H, 4.62. Found: C, 62.82; H, 4.56.

Intermediate 160

(±)-{7-[4-(trifluoromethyl)phenyl]-2,3-dihydro-1-benzofuran-2-yl}methyl 4-methylbenzenesulfonate Treatment of (±)-(7-bromo-2,3-dihydro-1-benzofuran-2-yl)methyl 4-methylbenzenesulfonate (0.50 g, 1.305 mmol) with 4-(trifluoromethyl)phenylboronic acid (0.372 g, 1.96 mmol), dichlorobis(tri-o-tolylphosphine)-palladium(II) (0.051 g, 0.065 mmol), and potassium carbonate (0.45 g, 3.26 mmol) generally according to the procedure described for Intermediate 37 provided 0.435 g (74%) of (±)-{7-[4-(trifluoromethyl)phenyl]-2,3-dihydro-1-benzofuran-2-yl}methyl 4-methylbenzenesulfonate as a light yellow solid. mp 116-118° C.; Anal. calcd. for $C_{23}H_{19}F_3O_4S$: C, 61.6; H, 4.27. Found: C, 61.37; H, 4.36.

Intermediate 161

(±)-[7-(2,6-dimethylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (1.0 g, 2.61 mmol) with 2,6-dimethylphenylboronic acid (0.783 g, 5.22 mmol), dichlorobis(tri-o-tolylphosphine)-palladium(II) (0.103 g, 0.131 mmol), and potassium carbonate (0.902 g, 6.52 mmol) generally according to the procedure described for Intermediate 37 provided 0.192 g (18%) of (±)-[7-(2,6-dimethylphenyl)-2,3-dihydro-1-benzofuran-2-yl]methyl 4-methylbenzenesulfonate as a yellow oil. Anal. calcd. for $C_{24}H_{24}O_4S$: C, 70.56; H, 5.92. Found: C, 68.01; H, 5.6.

Intermediate 162

(±)-benzyl {[7-(2,6-dimethylphenyl)-2,3-dihydro-1-benzofuran-2-yl]methyl}carbamate Treatment of (±)-1-[7-(2,6-dimethylphenyl)-2,3-dihydro-1-benzofuran-2-yl]methanamine (0.947 g, 3.73 mmol) with diisopropylethylamine (0.725 g, 5.60 mmol) followed by benzyl chloroformate (0.765 g, 4.48 mmol) generally according to the procedure described for Intermediate 12 provided 1,26 g (87%) of (±)-benzyl {[7-(2,6-dimethylphenyl)-2,3-dihydro-1-benzofuran-2-yl]methyl}carbamate as a colorless oil. Anal. calcd. for $C_{25}H_{25}NO_3$: C, 77.49; H, 6.5; N, 3.61. Found: C, 77.42; H, 6.57; N, 3.62. Chiral HPLC separation of (±)-benzyl {[7-(2,6-dimethylphenyl)-2,3-dihydro-1-benzofuran-2-yl]methyl}carbamate (Chiralcel OJ, methanol:carbon dioxide 4:6) provided two fractions. Fraction 1 ($R_t$=3.12 min, Chiralcel OJ, methanol:carbon dioxide 4:6); Fraction 2 ($R_t$=4.28 min, Chiralcel OJ methanol:carbon dioxide 4:6).

Intermediate 163

2',6'-difluoro-1,1'-biphenyl-2-ol

Treatment of 2,6-difluorobromobenzene (8.9 g, 46.1 mmol) with 2-methoxybenzeneboronic acid (10.51 g, 69.2 mmol), dichlorobis(tri-o-tolylphosphine)-palladium(II) (1.81 g, 2.3 mmol), and potassium carbonate (15.9 g, 115.3 mmol) generally according to the procedure described for Intermediate 37 provided 4.6 g (45%) of 2',6'-difluoro-1,1'-biphenyl-2-yl methyl ether. To a solution of 2',6'-difluoro-1, 1'-biphenyl-2-yl methyl ether (4.5 g, 20.4 mmol) in dichloromethane (100 mL) cooled to −78° C. was added boron tribromide (5.11 g, 1.0 M in dichloromethane) and the reaction mixture was allowed to stir for 30 min. The reaction mixture was allowed to warm to room temperature and was quenched by the addition of ice (150 mL). The organic layer was separated and the aqueous layer was extracted with dichloromethane (500 mL). The combined organic layers were washed with water (400 mL), saturated aqueous sodium chloride (100 mL), dried (magnesium sulfate), and the solvent removed in vacuo to provide a crude oil. Purification by flash column chromatography (silica, hexanes:ethyl acetate 95:5) provided 3.95 g (94%) of 2',6'-difluoro-1,1'-biphenyl-2-ol as a colorless oil. Anal. calcd. for $C_{12}H_8F_2O$: C, 69.9; H, 3.91. Found: C, 68.51; H, 4.06.

Intermediate 164

(±)-[7-(2,6-difluorophenyl)-2,3-dihydro-1-benzofuran-2-yl]methanol

Treatment of 2',6'-difluoro-1,1'-biphenyl-2-ol (3.8 g, 18.43 mmol) with potassium carbonate (10.19 g, 73.72 mmol) and allyl bromide (2.67 g, 22.11 mol), followed by refluxing the resultant allyl ether in mesitylene generally according to the procedure described for Intermediate 8 provided 3-allyl-2',6'-difluoro-1,1'-biphenyl-2-ol. Treatment of the 3-allyl-2',6'-difluoro-1,1'-biphenyl-2-ol (3.41 g, 13.85 mmol) with 3-chloroperoxybenzoic acid (7.25 g, 41.54 mmol, 77%) followed by potassium carbonate (4.78 g, 34.62 mmol) generally according to the procedure described for Intermediate 9 afforded 3.5 g (72%) of (±)-[7-(2,6-difluorophenyl)-2,3-dihydro-1-benzofuran-2-yl]methanol as an amber oil. Anal. calcd. for $C_{15}H_{12}F_2O_2$: C, 68.7; H, 4.61. Found C, 67.26; H, 4.5.

Intermediate 165

(±)-benzyl {[7-(2,6-difluorophenyl)-2,3-dihydro-1-benzofuran-2-yl]methyl}carbamate Treatment of (±)-1-[7-(2,6-difluorophenyl)-2,3-dihydro-1-benzofuran-2-yl]methanamine (1.54 g, 5.17 mmol) with diisopropylethylamine (1.02 g, 7.76 mmol) and benzyl chloroformate (0.971 g, 5.69 mmol) generally according to the procedure described for Intermediate 12 gave 2.02 g (98%) of (±)-benzyl {[7-(2,6-difluorophenyl)-2,3-dihydro-1-benzofuran-2-yl]methyl}carbamate as a colorless oil. Anal. calcd. for $C_{23}H_{19}F_2NO_3$: C, 69.87; H, 4.84; N, 3.54. Found C, 69.54; H, 4.87; N, 3.31.

Intermediate 166

2',6'-dichloro-1,1'-biphenyl-2-ol

Treatment of 2,6-dichlorobromobenzene (25.0 g, 0.110 mol) with 2-methoxybenzeneboronic acid (25.22 g, 0.166 mol), dichlorobis(tri-o-tolylphosphine)-palladium(II) (2.33 g, 2.96 mmol), and potassium carbonate (34.15 g, 0.247 mmol) generally according to the procedure described for Intermediate 37 provided 21.5 g (77%) of 2',6'-dichloro-1,1'-biphenyl-2-yl methyl ether. Treatment of 2',6'-dichloro-1,1'-biphenyl-2-yl methyl ether (19.0 g, 75.06 mmol) with boron tribromide (18.78 g, 1.0 M in dichloromethane) generally according to the procedure described for Intermediate 163 provided 17.89 g (99%) of 2',6'-dichloro-111'-biphenyl-2-ol as a light yellow solid. mp 100-103° C.; Anal. calcd. for $C_{12}H_8Cl_2O$: C, 60.28H, 3.37. Found: C, 60.29; H, 3.13.

Intermediate 167

(±)-[7-(2,6-dichlorophenyl)-2,3-dihydro-1-benzofuran-2-yl]methyl 4-methylbenzenesulfonate Treatment of 2',6'-dichloro-1,1'-biphenyl-2-ol (17.95 g, 75.06 mmol) with potassium carbonate (41.38 g, 299.43 mmol) and allyl bromide (10.89 g, 90.08 mol), followed by refluxing the resultant allyl ether in mesitylene generally according to the procedure described for Intermediate 8 provided 3-allyl-2',6'-dichloro-1,1'-biphenyl-2-ol. Treatment of 3-allyl-2',6'-dichloro-1,1'-biphenyl-2-ol (16.5 g, 59.10 mmol) with 3-chloroperoxybenzoic acid (30.59 g, 177.3 mmol, 77%) followed by potassium carbonate (20.41 g, 14.77 mmol) generally according to the procedure described for Intermediate 9 afforded 11.2 g (64%) of (±)-[7-(2,6-dichlorophenyl)-2,3-dihydro-1-benzofuran-2-yl]methanol. Treatment of (±)-[7-(2,6-dichlorophenyl)-2,3-dihydro-1-benzofuran-2-yl]methanol (11.2 g, 37.94 mmol) with p-toluenesulfonyl chloride (8.68 g, 45.53 mol) generally according to the procedure described for Intermediate 10 gave 15.2 g (89%) of (±)-[7-(2,6-dichlorophenyl)-2,3-dihydro-1-benzofuran-2-yl]methyl 4-methylbenzenesulfonate as a yellow oil. Anal. calcd. for $C_{22}H_{18}Cl_2O_4S$: C, 58.8; H, 4.04. Found: C, 58.1; H, 4.05.

Intermediate 168

(±)-benzyl {[7-(2,6-dichlorophenyl)-2,3-dihydro-1-benzofuran-2-yl]methyl}carbamate Treatment of (±)-1-[7-(2,6-dichlorophenyl)-2,3-dihydro-1-benzofuran-2-yl]methanamine (0.290 g, 0.877 mmol) with diisopropylethylamine (0.170 g, 1.315 mmol) followed by benzyl chloroformate (0.165 g, 0.965 mmol) generally according to the procedure described for Intermediate 12 provided 0.352 g (94%) of (±)-benzyl {[7-(2,6-dichlorophenyl)-2,3-dihydro-1-benzofuran-2-yl]methyl}carbamate as a white solid. mp 198-200° C.; Anal. calcd. for $C_{23}H_{19}Cl_2NO_3$: C, 64.5; H, 4.47; N, 3.27. Found: C, 64.2; H, 4.43; N, 3.21. Chiral HPLC separation of (±)-benzyl {[7-(2,6-dichlorophenyl)-2,3-dihydro-1-benzofuran-2-yl]methyl]carbamate (Chiralcel AD, ethanol:hexane 1:1) provided two fractions. Fraction 1 ($R_t$=5.174 min, Chiralcel AD, ethanol:hexane 1:1); Fraction 2 ($R_t$=6.229 min, Chiralcel AD, ethanol:hexane 1:1).

Intermediate 169

(±)-[7-(2,4-dichlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (5.0 g, 13.05 mmol) with 2,4-dichlorophenylboronic acid (3.73 g, 19.57 mmol), dichlorobis(tri-o-tolylphosphine)-palladium(II) (0.512 g, 0.652 mmol), and potassium carbonate (4.51 g, 32.62 mmol) generally according to the procedure described for Intermediate 37 provided 4.5 g (75%) of (±)-[7-(2,4-dichlorophenyl)-2,3-dihydro-1-benzofuran-2-yl]methyl 4-methylbenzenesulfonate as a yellow oil. Anal. calcd. for $C_{22}H_{18}Cl_2O_4S$: C, 58.8; H, 4.04. Found: C, 59.01; H, 4.09.

Intermediate 170

(±)-benzyl {[7-(2,4-dichlorophenyl)-2,3-dihydro-1-benzofuran-2-yl]methyl}carbamate Treatment of (±)-1-[7-(2,4-dichlorophenyl)-2,3-dihydro-1-benzofuran-2-yl]methanamine (1.9 g, 5.75 mmol) with diisopropylethylamine (1.11 g, 8.62 mmol) followed by benzyl chloroformate (1.18 g, 6.89 mmol) generally according to the procedure described for Intermediate 12 gave 2.14 g (87%) of (±)-benzyl {[7-(2,4-dichlorophenyl)-2,3-dihydro-1-benzofuran-2-yl]methyl}carbamate as a white solid. mp 87-89° C.; Anal. calcd. for $C_{23}H_{19}Cl_2NO_3$: C, 64.5; H, 4.47; N, 3.27. Found: C, 64.65; H, 4.78; N, 3.08. Chiral HPLC separation of (±)-benzyl {[7-(2,4-dichlorophenyl)-2,3-dihydro-1-benzofuran-2-yl]methyl}carbamate (Chiralcel AD, methanol:water 95:5) provided two fractions. Fraction 1 ($R_t$=8.094 min, Chiralcel AD, methanol:water 95:5); Fraction 2 ($R_t$=9.152 min, Chiralcel AD methanol:water 95:5).

Intermediate 171

(+)-benzyl {[7-(2,4-dichlorophenyl)-2,3-dihydro-1-benzofuran-2-yl]methyl}carbamate Fraction 1 obtained as a colorless oil from the chiral HPLC separation of (±)-benzyl {[7-(2,4-dichlorophenyl)-2,3-dihydro-1-benzofuran-2-yl]methyl}carbamate ($R_t$=8.094 min, Chiralcel AD, methanol:water 95:5). $[\alpha]_D^{25}$=+14.36 (c 10.0 in methanol); Anal. calcd. for $C_{23}H_{19}Cl_2NO_3$: C, 64.5; H, 4.47; N, 3.27. Found: C, 64.71; H, 4.76; N, 3.34.

Intermediate 172

(−)-benzyl {[7-(2,4-dichlorophenyl)-2,3-dihydro-1-benzofuran-2-yl]methyl}carbamate Fraction 2 obtained as a colorless oil from the chiral HPLC separation of (±)-benzyl {[7-(2,4-dichlorophenyl)-2,3-dihydro-1-benzofuran-2-yl]methyl}carbamate ($R_t$=9.152 min, Chiralcel AD methanol:water 95:5). $[\alpha]_D^{25}$=−14.66 (c 10.0 in methanol); Anal. calcd. for $C_{23}H_{19}Cl_2NO_3$: C, 64.5; H, 4.47; N, 3.27. Found: C, 63.95; H, 4.68; N, 3.27.

Intermediate 173

(±)-[7-(2,4-dimethoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (5.0 g, 13.05 mmol) with 2,4-dimethoxyphenylboronic acid (3.56 g, 19.57 mmol), dichlorobis(tri-o-tolylphosphine)-palladium(II) (0.512 g, 0.652 mmol), and potassium carbonate (4.5 g, 32.62 mmol) generally according to the procedure described for Intermediate 37 provided 3.3 g (57%) of (±)-[7-(2,4-dimethoxyphenyl)-2,3-dihydro-1-benzofuran-2-yl]methyl 4-methylbenzenesulfonate as a light yellow solid. mp 120-123° C.; Anal. calcd. for $C_{24}H_{24}O_6S$: C, 65.44; H, 5.49. Found: C, 64.99; H, 5.46.

Intermediate 174

(±)-benzyl {[7-(2,4-dimethoxyphenyl)-2,3-dihydro-1-benzofuran-2-yl]methyl}carbamate Treatment of (±)-1-[7-(2,4-dimethoxyphenyl)-2,3-dihydro-1-benzofuran-2-yl]methanamine (1.42 g, 4.41 mmol) with diisopropylethylamine (0.855 g, 6.62 mmol) followed by benzyl chloroformate (0.828 g, 4.85 mmol) generally according to the procedure described for Intermediate 12 provided 1.58 g (85%) of (±)-benzyl {[7-(2,4-dimethoxyphenyl)-2,3-dihydro-1-benzofuran-2-yl]methyl}carbamate as a colorless oil. Anal. calcd. for $C_{25}H_{25}NO_5$: C, 71.58; H, 6.01; N, 3.34. Found: C, 71.24; H, 5.92; N, 3.09. Chiral HPLC separation of (±)-benzyl {[7-(2,4-dimethoxyphenyl)-2,3-dihydro-1-benzofuran-2-yl]methyl}carbamate (Chiralcel OD, ethanol) provided two fractions. Fraction 1 ($R_t$=5.107 min, Chiralcel OD, ethanol); Fraction 2 ($R_t$=6.134 min, Chiralcel OD, ethanol).

Intermediate 175

(+)-benzyl {[7-(2,4-dimethoxyphenyl)-2,3-dihydro-1-benzofuran-2-yl]methyl}carbamate Fraction 1 obtained as a colorless oil from the chiral HPLC separation of (±)-benzyl {[7-(2,4-dimethoxyphenyl)-2,3-dihydro-1-benzofuran-2-yl]methyl}carbamate ($R_t$=5.107 min, Chiralcel OD, ethanol). $[\alpha]_D^{25}$=+21.96 (c 10.0 in methanol); Anal. calcd. for $C_{25}H_{25}NO_5$: C, 71.58; H, 6.01; N, 3.34. Found: C, 70.12; H, 6.11; N, 3.12.

Intermediate 176

(−)-benzyl {[7-(2,4-dimethoxyphenyl)-2,3-dihydro-1-benzofuran-2-yl]methyl}carbamate Fraction 2 obtained as a colorless oil from the chiral HPLC separation of (±)-benzyl {[7-(2,4-dimethoxyphenyl)-2,3-dihydro-1-benzofuran-2-yl]methyl}carbamate ($R_t$=6.134 min, Chiralcel OD, ethanol). $[\alpha]_D^{25}$=−23.20 (c 10.0 in methanol); Anal. calcd. for $C_{25}H_{25}NO_5$: C, 71.58; H, 6.01; N, 3.34. Found: C, 70.22; H, 6.1; N, 3.28.

Intermediate 177

(±)-[7-(2,4-difluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (5.0 g, 13.05 mmol) with 2,4-difluorophenylboronic acid (3.09 g, 19.57 mmol), dichlorobis(tri-o-tolylphosphine)-palladium(II) (0.512 g, 0.651 mmol), and potassium carbonate (4.51 g, 32.62 mmol) generally according to the procedure described for Intermediate 37 afforded 4.43 g (82%) of (±)-[7-(2,4-difluorophenyl)-2,3-dihydro-1-benzofuran-2-yl]methyl 4-methylbenzenesulfonate as a white solid. mp 116-118° C.; Anal. calcd. for $C_{22}H_{18}F_2O_4S$: C, 63.45; H, 4.36. Found: C, 63.3; H, 4.11.

Intermediate 178

(±)-benzyl {[7-(2,4-difluorophenyl)-2,3-dihydro-1-benzofuran-2-yl]methyl}carbamate Treatment of (±)-1-[7-(2,4-difluorophenyl)-2,3-dihydro-1-benzofuran-2-yl]methanamine (2.0 g, 6.72 mmol) with diisopropylethylamine (1.30 g, 10.07 mmol) followed by benzyl chloroformate (1.26 g, 7.37 mmol) generally according to the procedure described for Intermediate 12 gave 2.14 g (81%) of (±)-benzyl {[7-(2,4-difluorophenyl)-2,3-dihydro-1-benzofuran-2-yl]methyl}carbamate as a white solid. mp 78-80° C.; Anal. calcd. for $C_{23}H_{19}F_2NO_3$: C, 69.87; H, 4.84; N, 3.54. Found: C, 69.76; H, 4.8; N, 3.35. Chiral HPLC separation of (±)-benzyl {[7-(2,4-difluorophenyl)-2,3-dihydro-1-benzofuran-2-yl]methyl}carbamate (Chiralpak AD, ethanol:hexane 1:1) provided two fractions. Fraction 1 ($R_t$=9.117 min, Chiralpak AD, ethanol:hexane 1:1); Fraction 2 ($R_t$=9.424 min, Chiralpak AD ethanol:hexane 1:1).

Intermediate 179

(+)-benzyl {[7-(2,4-difluorophenyl)-2,3-dihydro-1-benzofuran-2-yl]methyl}carbamate Fraction 1 obtained as a colorless oil from the chiral HPLC separation of (±)-benzyl {[7-(2,4-difluorophenyl)-2,3-dihydro-1-benzofuran-2-yl]methyl}carbamate ($R_t$=9.117 min, Chiralpak AD, ethanol:hexane 1:1). $[\alpha]_D^{25}$=+13.0 (c 10.0 in methanol); Anal. calcd. for $C_{23}H_{19}F_2NO_3$: C, 69.87; H, 4.84; N, 3.54. Found: C, 69.28; H, 5.23; N, 3.47.

Intermediate 180

(−)-benzyl {[7-(2,4-difluorophenyl)-2,3-dihydro-1-benzofuran-2-yl]methyl}carbamate Fraction 2 obtained as a colorless oil from the chiral HPLC separation of (±)-benzyl {[7-(2,4-difluorophenyl)-2,3-dihydro-1-benzofuran-2-yl]methyl}carbamate ($R_t$=9.424 min, Chiralpak AD ethanol:hexane 1:1). $[\alpha]_D^{25}$=−13.68 (c 10.0 in methanol); Anal. calcd. for $C_{23}H_{19}F_2NO_3$: C, 69.87; H, 4.84; N, 3.54. Found: C, 69.65; H, 5.06; N, 3.57.

Intermediate 181

4'-chloro-2'-methyl-1,1'-biphenyl-2-ol

Treatment of 2-bromo-5-chlorotoluene (5.0 g, 24.33 mmol) with 2-methoxybenzeneboronic acid (4.8 g, 31.63 mmol), dichlorobis(tri-o-tolylphosphine)-palladium(II) (0.478 g, 0.608 mmol), and potassium carbonate (8.41 g, 60.83 mmol) generally according to the procedure described for Intermediate 37 provided 5.05 g (89%) of 4'-chloro-2'-methyl-1,1'-biphenyl-2-yl methyl ether. Treatment of 4'-chloro-2'-methyl-1,1'-biphenyl-2-yl methyl ether (5.05 g, 21.48 mmol) with boron tribromide (5.37 g, 1.0 M in dichloromethane) generally according to the procedure described for Intermediate 163 provided 4.58 g (97%) of 4'-chloro-2'-methyl-1,1'-biphenyl-2-ol as a yellow oil. Anal. calcd. for $C_{13}H_{11}ClO$: C, 71.4; H, 5.07. Found: C, 71.03; H, 4.84.

Intermediate 182

(±)-[7-(4-chloro-2-methylphenyl)-2,3-dihydro-1-benzofuran-2-yl]methanol

Treatment of 4'-chloro-2'-methyl-1,1'-biphenyl-2-ol (4.54 g, 20.78 mmol) with potassium carbonate (11.47 g, 83.04 mmol) and allyl bromide (3.01 g, 24.91 mol), followed by refluxing the resultant allyl ether in mesitylene generally according to the procedure described for Intermediate 8 provided 3-allyl-4'-chloro-2'-methyl-1,1'-biphenyl-2-ol. Treatment of 3-allyl-4'-chloro-2'-methyl-1,1'-biphenyl-2-ol (4.5 g, 17.39 mmol) with 3-chloroperoxybenzoic acid (12.0 g, 69.57 mmol, 77%) followed by potassium carbonate (6.0 g, 43.48 mmol) generally according to the procedure described for Intermediate 9 afforded 2.9 g (61%) of (±)-[7-(4-chloro-2-methylphenyl)-2,3-dihydro-1-benzofuran-2-yl]methanol as a colorless oil. Anal. calcd. for $C_{16}H_{15}ClO_2$: C, 69.95; H, 5.5. Found: C, 69.23; H, 5.42.

Intermediate 183

(±)-[7-(4-chloro-2-methylphenyl)-2,3-dihydro-1-benzofuran-2-yl]methyl 4-methylbenzenesulfonate Treatment of (±)-[7-(4-chloro-2-methylphenyl)-2,3-dihydro-1-benzofuran-2-yl]methanol (2.78 g, 10.11 mmol) with p-toluenesulfonyl chloride (2.31 g, 12.14 mol) generally according to the procedure described for Intermediate 10 gave 4.04 g (93%) of (±)-[7-(4-chloro-2-methylphenyl)-2,3-dihydro-1-benzofuran-2-yl]methyl 4-methylbenzenesulfonate as a yellow oil. Anal. calcd. for $C_{23}H_{21}ClO_4S$: C, 64.4; H, 4.93. Found: C, 64.24; H, 4.93.

Intermediate 184

No compound

Intermediate 185

(+)-[-7-bromo-2,3-dihydro-1-benzofuran-2-yl]methyl 4-methylbenzenesulfonate

Fraction 1 obtained as a white solid from the chiral HPLC separation of 7-bromo-2,3-dihydro-1-benzofuran-2-yl]methyl 4-methylbenzenesulfonate ($R_t$=6.220 min, Chiraicel AD, ethanol). $[\alpha]_D^{25}$=+23.4 (c 10.0 in methanol); mp 96-99° C.

Intermediate 186

(−)-[-7-bromo-2,3-dihydro-1-benzofuran-2-yl]methyl 4-methylbenzenesulfonate

Fraction 2 obtained as a white solid from the chiral HPLC separation of 7-bromo-2,3-dihydro-1-benzofuran-2-yl]methyl 4-methylbenzenesulfonate ($R_t$=6.220 min, Chiraicel AD, ethanol). $[\alpha]_D^{25}$=−22.00 (c 10.0 in methanol); mp 96-99° C.

Intermediate 187

(±)-[7-(2,3-dimethylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with (2,3-dimethylphenyl)boronic acid (0.294 g, 1.96 mmol) generally according to the procedure described for Intermediate 184 provided 0.335 g (62%) of (±)-[7-(2,3-dimethylphenyl)-2,3-dihydro-1-benzofuran-2-yl]methyl 4-methylbenzenesulfonate as a white solid. $R_f$=0.43 (silica, ethyl acetate:hexanes 1:4).

Intermediate 188

(±)-[7-(2,3-dimethoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.30 g, 0.783 mmol) with (2,3-dimethoxylphenyl)boronic acid (0.427 g, 2.35 mmol) generally according to the procedure described for Intermediate 184 provided 0.283 g (82%) of (±)-[7-(2,3-dimethoxylphenyl)-2,3-dihydro-1-benzofuran-2-yl]methyl 4-methylbenzenesulfonate as a white solid. $R_f$=0.43 (silica, ethyl acetate:hexanes 1:4).

Intermediate 189

(±)-[7-(2,3-difluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with (2,3-difluorophenyl)boronic acid (0.618 g, 3.91 mmol) generally according to the procedure described for Intermediate 184 provided 0.090 g (77%) of (±)-[7-(2,3-difluorophenyl)-2,3-dihydro-1-benzofuran-2-yl]methyl 4-methylbenzenesulfonate as a white solid. $R_f$=0.43 (silica, ethyl acetate:hexanes 1:4).

Intermediate 190

(±)-[7-(2,5-dimethylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with (2,5-dimethylphenyl)boronic acid (0.294 g, 1.96 mmol) generally according to the procedure described for Intermediate 184 provided 0.430 g (81%) of (±)-[7-(2,5-dimethylphenyl)-2,3-dihydro-1-benzofuran-2-yl]methyl 4-methylbenzenesulfonate as a white solid. $R_f$=0.43 (silica, ethyl acetate:hexanes 1:4).

Intermediate 191

(±)-[7-(2,5-difluorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with (2,5-difluorophenyl)boronic acid (0.309 g, 1.96 mmol) generally according to the procedure described for Intermediate 184 provided 0.360 g (66%) of (±)-[7-(2,3-difluorophenyl)-2,3-dihydro-1-benzofuran-2-yl]methyl 4-methylbenzenesulfonate as a white solid. $R_f$=0.43 (silica, ethyl acetate: hexanes 1:4).

Intermediate 192

[7-(2,5-dichlorophenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (1.43 g, 3.73 mmol) with (2,5-dichlorophenyl)boronic acid (1.07 g, 5.59 mmol) generally according to the procedure described for Intermediate 184 provided 1.49 g (88%) of (±)[7-(2,5-dichlorophenyl)-2,3-dihydro-1-benzofuran-2-yl]methyl 4-methylbenzenesulfonate as a white solid. $R_f$=0.43 (silica, ethyl acetate: hexanes 1:4.

Intermediate 193

(±)-[7-(2,5-dimethoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with (2,5-dimethoxyphenyl)boronic acid (0.356 g, 1.96 mmol) generally according to the procedure described for Intermediate 184 provided 0.291 g (51%) of (±)-[7-(2,5-dimethoxyphenyl)-2,3-dihydro-1-benzofuran-2-yl]methyl 4-methylbenzenesulfonate as a white solid. $R_f$=0.43 (silica, ethyl acetate:hexanes 1:4).

Intermediate 194

(±)-[7-(5-chloro-2-methylphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with (5-chloro-2-methylphenyl)boronic acid (0.334 g, 1.96 mmol) generally according to the procedure described for Intermediate 184 provided 0.451 g (81%) of (±)-[7-(5-chloro-2-methylphenyl)-2,3-dihydro-1-benzofuran-2-yl]methyl 4-methylbenzenesulfonate as a white solid. $R_f$=0.43 (silica, ethyl acetate:hexanes 1:4).

Intermediate 195

(±)-[7-(5-chloro-2-methoxyphenyl)-2,3-dihydro-1-benzofuran-2-yl]methyl 4-methylbenzenesulfonate Treatment of (±)-(7-bromo-2,3-dihydro-1-benzofuran-2-yl)methyl 4-methylbenzenesulfonate (0.50 g, 1.305 mmol) with (5-chloro-2-methoxyphenyl)boronic acid (0.365 g, 1.96 mmol generally according to the procedure described for Intermediate 184 provided 0.382 g (66%) of (±)-[7-(5-chloro-2-methoxyphenyl)-2,3-dihydro-1-benzofuran-2-yl]methyl 4-methylbenzenesulfonate as a white solid. $R_f$=0.43 (silica, ethyl acetate:hexanes 1:4).

Intermediate 196

(±)-[7-(2,4,6-trichlorophenyl)-2,3-dihydro-1-benzofuran-2-yl]methyl 4-methylbenzenesulfonate Treatment of 2,4,6-trichlorobromobenzene (14.5 g, 55.69 mmol) with 2-methoxybenzeneboronic acid (12.69 g, 83.54 mol), dichlorobis(tri-o-tolylphosphine)-palladium(II) (0.656 g, 0.835 mmol), and potassium carbonate (19.21 g, 139.22 mmol) generally according to the procedure described for Intermediate 37 provided 9.8 g (61%) of 2' 4',6'-trichloro-1,1'-biphenyl-2-yl methyl ether. To a solution of 2'4',6'-trichloro-1,1'-biphenyl-2-yl methyl ether (9.8 g, 34.08 mmol) in dichloromethane (100 mL) cooled to −78° C. was added boron tribromide (9.38 g, 1.0 M in dichloromethane) generally according to the procedure described for Intermediate 163 provided provided 9.2 g of a yellow solid. Treatment of 2',4',6'-trichloro-1,1'-biphenyl-2-ol (9.17 g, 33.52 mmol) with potassium carbonate (18.53 g, 134.1 mmol) and allyl bromide (4.46 g, 36.87 mol), followed by refluxing the resultant allyl ether in mesitylene generally according to the procedure described for Intermediate 8 provided 3-allyl-2',4',6'-trichloro-1,1'-biphenyl-2-ol. Treatment of 3-allyl-2',4',6'-trichloro-1,1'-biphenyl-2-ol. (10.35 g, 33.00 mmol) with 3-chloroperoxybenzoic acid (17.08 g, 99.00 mmol, 77%) followed by potassium carbonate (11.40 g, 82.51 mmol) generally according to the procedure described for Intermediate 9 afforded 10.4 g (95%) of (±)-[7-(2,4,6-trichlorophenyl)-2,3-dihydro-1-benzofuran-2-yl]methanol. Treatment of (±)-[7-(2,4,6-trichlorophenyl)-2,3-dihydro-1-benzofuran-2-yl] methanol (10.38 g, 31.49 mmol) with p-toluenesulfonyl chloride (7.20 g, 37.79 mol) generally according to the procedure described for Intermediate 10 gave 10.5 g (68%) of (±)-[7-(2,6-dichlorophenyl)-2,3-dihydro-1-benzofuran-2-yl]methyl 4-methylbenzenesulfonate as a white solid. mp 178-180° C.

Intermediate 197

(±)-(7-pyridin-3-yl-2,3-dihydro-1-benzofuran-2-yl) methyl 4-methylbenzenesulfonate Treatment of (±)-(7-bromo-2,3-dihydro-1-benzofuran-2-yl)methyl 4-methylbenzenesulfonate (4.0 g, 10.44 mmol) with pyridin-3-ylboronic acid (3.85 g, 31.31 mmol), tetrakis tri-phenylphosphine palladium (0.362 g, 0.052 mmol), and potassium carbonate (3.61 g, 26.09 mmol) generally according to the procedure described for Intermediate 184 provided 2.47 g (62%) of (±)-(7-pyridin-3-yl-2,3-dihydro-1-benzofuran-2-yl)methyl 4-methylbenzenesulfonates a light yellow solid. $R_f$=0.43 (silica, ethyl acetate:hexanes 1:4).

Intermediate 198

(±)-(7-nitro-2,3-dihydro-1-benzofuran-2-yl)methanol

To a solution of 2-nitrophenol (13.9 g, 100 mmol) in N,N-dimethylformamide (300 mL) was added with sodium hydride (4.2 g, 100 mmol 60%) followed by allyl bromide (13.3 g, 110 mmol) and the reaction was allowed to stir at room temperature for 2 hours The reaction mixture was diluted with water (500 mL) to dissolve any solids and extracted with ethyl acetate (3×250 mL). The combined organic layers were washed with water (4×500 mL), saturated aqueous sodium chloride (400 mL), dried (magnesium sulfate) and the solvent removed in vacuo to give 1-(allyloxy)-2-nitrobenzene. The oil was re-dissolved in mesitylene (500 mL) and heated at reflux for 3 d. Removal of the solvent in vacuo provided a crude oil. Purification by flash column chromatography (silica, dichloromethane:hexanes 0.5:9.5) provided 6.8 g, (50%) of 2-allyl-6-nitrophenol as a yellow oil. To a solution of 2-allyl-6-nitrophenol (6.6 g, 36.84 mmol) in dichloromethane (300 mL) was added 3-chloroperoxybenzoic acid (77%, 16.5 g, 73.67 mmol) The reaction mixture was allowed to stir at room temperature for 8 h. The reaction mixture was washed with a 1:1 solution of 10% sodium sulfite:saturated sodium bicarbonate (2×300 mL). The solvent was removed in vacuo to give crude yellow oil. The oil was diluted with methanol (300 mL) and added to a solution of potassium carbonate (15.0 g, 108.5 mmol) the solution was allowed to stir at room temperature 2 h. The solvent was removed in vacuo. The residue was washed with water (1000 mL) and ethyl acetate (500 mL). The aqueous layer was acidified with 1 N aqueous hydrogen chloride and washed with ethyl acetate (500 mL). The combined organics were washed with water (500 mL), saturated aqueous sodium chloride (500 mL), dried (magnesium sulfate) and the solvent removed in vacuo to provide a crude solid. Purification by flash column chromatography (silica, dichloromethane:hexanes 4:10) provided 3.18 g (44%) of (±)-(7-nitro-2,3-dihydro-1-benzofuran-2-yl)methanol as yellow solid. mp 63-65° C.

Intermediate 199

(±)-(7-nitro-2,3-dihydro-1-benzofuran-2-yl)methyl 4-methylbenzenesulfonate

To a solution of (±)-(7-nitro-2,3-dihydro-1-benzofuran-2-yl)methanol (3.14 g, 16.09 mol) in dichloromethane (100 mL) was added diisopropylethyl amine (4.16 g, 32.18 mmol), N,N-dimethylaminopyridine (0.39 g, 3.2 mmol), and p-toluenesulfonyl chloride (4.6 g, 24.13 mmol) the reaction was allowed to stir at room temperature for 12 h. The reaction was diluted with dichloromethane (500 mL), washed with saturated aqueous sodium bicarbonate (200 mL), saturated aqueous sodium chloride (200 mL), dried (magnesium sulfate) and the solvent removed in vacuo to give a crude oil. Purification by flash column chromatography (silica, dichloromethane: hexanes 3:10) afforded 5.2 g (94%) of (±)-(7-nitro-2,3-dihydro-1-benzofuran-2-yl)methyl 4-methylbenzenesulfonate as off-white solid. mp 129-131° C.

Intermediate 200

(±)-(7-amino-2,3-dihydro-1-benzofuran-2-yl)methyl 4-methylbenzenesulfonate

A solution of (±)-(7-amino-2,3-dihydro-1-benzofuran-2-yl)methyl 4-methylbenzenesulfonate (4.8 g, 13.74 mmol) in ethanol (400 mL) and palladium on carbon (1.4 g, 5 wt. %) was shaken under an $H_2$ atmosphere (50 psi) for 12 h. The reaction mixture was filtered (celite) and the solvent removed in vacuo provided 4.4 g (99%) of (±)-(7-amino-2,3-dihydro-1-benzofuran-2-yl)methyl 4-methylbenzenesulfonate as a light brown oil.

Intermediate 201

(±)-{7-[(4-methylphenyl)amino]-2,3-dihydro-1-benzofuran-2-yl}methyl 4-methylbenzenesulfonate Treatment of (±)-(7-anilino-2,3-dihydro-1-benzofuran-2-yl)methyl-4-methylbenzenesulfonate (0.96 g, 3.0 mmol) in toluene (20 mL) with 1-bromo-4-methylbenzene (0.513 g, 3.0 mmol)dichloro[1,1'-bis(diphenylphosphino)ferrocene] palladium(II)dichloromethane (0.061 g, 0.075 mmol), 1,1'-bis(diphenylphosphino)ferrocene (0.125 g, 0.225 mmol), sodium tert-butoxide (0.18 g, 1.875 mmol) the reaction was allowed to reflux 3 h. The solvent was removed in vacuo. The residue was washed with water (100 mL) and ethyl acetate (50 mL). The combined organic layers were washed with saturated aqueous sodium chloride, dried (magnesium sulfate), and the solvent removed in vacuo to provide a crude oil. Purification by flash column chromatography (silica, ethyl acetate:hexanes 3:10) afforded 0.36 g (29%) of (±)-{7-[(4-methylphenyl)amino]-2,3-dihydro-1-benzofuran-2-yl}methyl 4-methylbenzenesulfonate as a yellow solid. mp 118-120° C.

Intermediate 202

(±)-{7-[(4-chlorophenyl)amino]-2,3-dihydro-1-benzofuran-2-yl}methyl 4-methylbenzenesulfonate Treatment of (±)-(7-amino-2,3-dihydro-1-benzofuran-2-yl)methyl 4-methylbenzenesulfonate (0.96 g, 3.0 mmol) with 1-bromo-4-chlorobenzene (0.570 g, 3.0 mmol) generally according to the procedure described for Intermediate 37 provided 0.77 g (57%) of (±)-{7-[(4-chlorophenyl)amino]-2,3-dihydro-1-benzofuran-2-yl}methyl 4-methylbenzenesulfonate as a white solid. mp 132-134° C.

Intermediate 203

(±)-{7-[(3,4-dimethylphenyl)amino]-2,3-dihydro-1-benzofuran-2-yl}methyl 4-methylbenzenesulfonate Treatment of (±)-(7-amino-2,3-dihydro-1-benzofuran-2-yl)methyl 4-methylbenzenesulfonate (0.96 g, 3.0 mmol) with 4-bromo-1,2-dimethylbenzene (0.558 g, 3.0 mmol), generally according to the procedure described for Intermediate 202 provided 0.51 g (38%) (±)-{7-[(3,4-dimethylphenyl)amino]-2,3-dihydro-1-benzofuran-2-yl}methyl 4-methylbenzenesulfonate as a yellow solid. mp 88-90° C.

Intermediate 204

(±)-benzyl {[7-(2,3-dimethoxyphenyl)-2,3-dihydro-1-benzofuran-2-yl]methyl}carbamate Treatment of (±)-benzyl[7-(2,3-dimethoxyphenyl)-2,3-dihydro-1-benzofuran-2-yl]methanamine (2.7 g, 8.39 mmol) with diisopropylethylamine (1.63 g, 12.59 mmol) and benzyl chloroformate (1.72 g, 10.07 mmol) generally according to the procedure described for Intermediate 12 provided 3.21 g (91%) of (±)-benzyl {[7-(2,3-dimethoxyphenyl)-2,3-dihydro-1-benzofuran-2-yl]methyl}carbamate as a colorless oil.

Intermediate 205

(±)-benzyl {[7-(4-chloro-2-methylphenyl)-2,3-dihydro-1-benzofuran-2-yl]methyl}carbamate Treatment of (±)-benzyl[7-(4-chloro-2-methylphenyl)-2,3-dihydro-1-benzofuran-2-yl]methanamine (0.979 g, 3.15 mmol) with diisopropylethylamine (0.612 g, 4.73 mmol) and benzyl chloroformate (0.646 g, 3.79 mmol) generally according to the procedure described for Intermediate 12 provided 1.2 g (96%) of (±)-benzyl[7-(4-chloro-2-methylphenyl)-2,3-dihydro-1-benzofuran-2-yl]carbamate as a colorless oil.

Intermediate 206

(+)-benzyl {[7-(4-chloro-2-methylphenyl)-2,3-dihydro-1-benzofuran-2-yl]methyl}carbamate Fraction 1 obtained as a colorless oil from the chiral HPLC separation of (±)-benzyl [7-(2,3-dimethoxyphenyl)-2,3-dihydro-1-benzofuran-2-yl]carbamate ($R_t$=7.725 min, Chiralcel AD, ethanol:hexane 1:1). $[\alpha]_D^{25}$=+12.8 (c 10.0 in methanol).

Intermediate 207

(−)-benzyl {[7-(4-chloro-2-methylphenyl)-2,3-dihydro-1-benzofuran-2-yl]methyl}carbamate Fraction 2 obtained as a colorless oil from the chiral HPLC separation of (±)-benzyl [7-(2,3-dimethoxyphenyl)-2,3-dihydro-1-benzofuran-2-yl]carbamate ($R_t$=9.542 min, Chiralcel AD, ethanol:hexane 1:1). $[\alpha]_D^{25}$=−4.8 (c 10.0 in methanol).

Intermediate 208

(+)-benzyl {[7-(2,6-difluorophenyl)-2,3-dihydro-1-benzofuran-2-yl]methyl}carbamate Fraction 1 obtained as a colorless oil from the chiral HPLC separation of (±)-benzyl [7-(2,6-difluorophenyl)-2,3-dihydro-1-benzofuran-2-yl]carbamate ($R_t$=4.340 min, Chiralcel AD, isopropanol:hexane 2:8). $[\alpha]_D^{25}$=+18.8 (c 10.0 in methanol).

Intermediate 209

(−)-benzyl {[7-(2,6-difluorophenyl)-2,3-dihydro-1-benzofuran-2-yl]methyl}carbamate Fraction 2 obtained as a colorless oil from the chiral HPLC separation of (±)-benzyl [7-(2,6-difluorophenyl)-2,3-dihydro-1-benzofuran-2-yl]carbamate ($R_t$=5.251 min, Chiralcel AD, isopropanol:hexane 2:8). $[\alpha]_D^{25}$=−16.8 (c 10.0 in methanol).

Intermediate 210

(±)-benzyl {[7-(5-chloro-2-methylphenyl)-2,3-dihydro-1-benzofuran-2-yl]methyl}carbamate Treatment of (±)-benzyl[7-(4-chloro-2-methylphenyl)-2,3-dihydro-1-benzofuran-2-yl]methanamine (3.1 g, 11.32 mmol) with diisopropylethylamine (2.19 g, 16.98 mmol) and benzyl chloroformate (2.37 g, 12.45 mmol) generally according to the procedure described for Intermediate 12 provided 4.12 g (89%) of (±)-benzyl {[7-(5-chloro-2-methylphenyl)-2,3-dihydro-1-benzofuran-2-yl]methyl}carbamate as a colorless oil.

Intermediate 211

(±)-benzyl {[7-(2,4,6-trichlorophenyl)-2,3-dihydro-1-benzofuran-2-yl]methyl}carbamate Treatment of (±)-benzyl[7-(2,4,6-trichlorophenyl)-2,3-dihydro-1-benzofuran-2-yl]methanamine (2.83 g, 8.61 mmol) with diisopropylethylamine (1.67 g, 12.92 mmol) and benzyl chloroformate (1.76 g, 10.33 mmol) generally according to the procedure described for Intermediate 12 provided 3.46 g (87%) of (±)-benzyl {[7-(2,4,6-trichlorophenyl)-2,3-dihydro-1-benzofuran-2-yl]methyl}carbamate as a colorless oil.

Intermediate 212

(±)-benzyl [(7-pyridin-3-yl-2,3-dihydro-1-benzofuran-2-yl)methyl]carbamate

Treatment of (±)-1-(7-pyridin-3-yl-2,3-dihydro-1-benzofuran-2-yl)methanamine (0.770 g, 3.40 mmol) with diisopropylethylamine (0.660 g, 5.1 mmol) and benzyl chloroformate (0.778 g, 4.08 mmol) generally according to the procedure described for Intermediate 12 provided 0.702 g (57%) of (±)-benzyl [(7-pyridin-3-yl-2,3-dihydro-1-benzofuran-2-yl)methyl]carbamate as an amber oil.

Intermediate 213

(±)-benzyl{[7-(2-chlorophenyl)-2,3-dihydro-1-benzofuran-2-yl]methyl}methylcarbamate Treatment of (±)-[(N-methyl-1-[7-(2-chlorophenyl)-2,3-dihydro-1-benzofuran-2-yl]methanamine (0.932 g, 3.4 mmol) with diisopropylethylamine (0.66 g, 5.11 mmol) and benzyl chloroformate (0.778 g, 4.08 mmol) generally according to the procedure described for Intermediate 12 provided 1.25 g (86%) of (±)-benzyl {[7-(2-chlorophenyl)-2,3-dihydro-1-benzofuran-2-yl]methyl}methylcarbamate as a colorless oil.

Intermediate 214

(±)-benzyl{[7-(2-methylphenyl)-2,3-dihydro-1-benzofuran-2-yl]methyl}methylcarbamate Treatment of (±)-[(N-methyl-1-[7-(2-methylphenyl)-2,3-dihydro-1-benzofuran-2-yl]methanamine (0.67 g, 32.64 mmol) with diisopropylethylamine (0.512 g, 3.97 mmol) and benzyl chloroformate (0.605 g, 3.17 mmol) generally according to the procedure described for Intermediate 12 provided 0.790 g (77%) of (±)-benzyl {[7-(2-methylphenyl)-2,3-dihydro-1-benzofuran-2-yl]methyl}methylcarbamate as a colorless oil.

Intermediate 215

(±)-benzyl{[7-(2,6-dichlorophenyl)-2,3-dihydro-1-benzofuran-2-yl]methyl}methylcarbamate Treatment of (±)-[(N-methyl-1-[7-(2,6-dichlorophenyl)-2,3-dihydro-1-benzofuran-2-yl]methanamine (1.1 g, 3.57 mmol) with diisopropylethylamine (0.69 g, 5.35 mmol) and benzyl chloroformate (0.0.82 g, 4.28 mmol) generally according to the procedure described for Intermediate 12 provided 1.6 g (99%) of (±)-benzyl {[7-(2,6-dichlorophenyl)-2,3-dihydro-1-benzofuran-2-yl]methyl}methylcarbamate as a colorless oil.

Intermediate 216

(±)-benzyl{[7-pyridin-3-yl-2,3-dihydro-1-benzofuran-2-yl]methyl}methylcarbamate

Treatment of (±)-(7-bromo-2,3-dihydro-benzofuran-2-yl-methyl)carbamate (0.80 g, 2.21 mmol) with pyridine-3-boronic acid (0.407 g, 3.31 mmol) generally according to the procedure described for Intermediate 37 provided 0.213 g (27%) of (±)-benzyl {[7-pyridine-3-yl-2,3-dihydro-1-benzofuran-2-yl]methyl}methylcarbamate as a colorless oil.

Intermediate 217

(±)-benzyl[7-(2,3-dichlorophenyl)-2,3-dihydro-1-benzofuran-2-yl]methyl}carbamate Treatment of (±)-(7-bromo-2,3-dihydro-benzofuran-2-yl-methyl)carbamate (1.3 g, 3.59 mmol) with 2,3-dichlorophenylboronic acid (1.03 g, 5.38 mmol) generally according to the procedure described for Intermediate 37 provided 0.93 g (63%) of (±)-benzyl{[7-(2,3-dichlorophenyl)-2,3-dihydro-1-benzofuran-2-yl]methylcarbamate as a yellow oil.

Intermediate 218

(±)-benzyl{[7-(2,5-dichlorophenyl)-2,3-dihydro-1-benzofuran-2-yl]methyl}carbamate Treatment of (±)-(7-bromo-2,3-dihydro-benzofuran-2-yl-methyl)carbamate (3.2 g, 8.83 mmol) with 2,5-dichlorophenylboronic acid (2.54 g, 13.24 mmol) generally according to the procedure described for Intermediate 37 provided 0.299 g (27%) of (±)-benzyl {[7-(2,5-dichlorophenyl)-2,3-dihydro-1-benzofuran-2-yl]methyl}carbamate as a yellow oil.

Intermediate 219

(±)-benzyl {[7-(2,4,6-trichlorophenyl)-2,3-dihydro-1-benzofuran-2-yl]methyl}carbamate Treatment of (±)-{[7-(2,4,6-trichlorophenyl)-2,3-dihydro-1-benzofuran-2-yl]methyl}amine (1.1 g, 3.57 mmol) with diisopropylethylamine (0.69 g, 5.35 mmol) and benzyl chloroformate (0.0.82 g, 4.28 mmol) generally according to the procedure described for Intermediate 12 provided 1.6 g (99%) of (±)-benzyl {[7-(2,4,6-trichlorophenyl)-2,3-dihydro-1-benzofuran-2-yl]methyl}carbamate as a colorless oil.

Intermediate 220

(±)-benzyl methyl][7-(2,4,6-trichlorophenyl)-2,3-dihydro-1-benzofuran-2-yl]methyl}carbamate Treatment of (±)-N-methyl-1-[7-(2,4,6-trichlorophenyl)-2,3-dihydro-1-benzofuran-2-yl]methanamine (1.1 g, 3.57 mmol) with diisopropylethylamine (0.69 g, 5.35 mmol) and benzyl chloroformate (0.0.82 g, 4.28 mmol) generally according to the procedure described for Intermediate 12 provided 1.6 g (99%) of (±)-benzyl methyl{[7-(2,4,6-trichlorophenyl)-2,3-dihydro-1-benzofuran-2-yl]methyl}carbamate as a colorless oil.

Intermediate 221

(+)-benzyl {[7-(2,4,6-trichlorophenyl)-2,3-dihydro-1-benzofuran-2-yl]methyl}carbamate Fraction 1 obtained as a colorless oil from the chiral HPLC separation of (±)-benzyl {[7-(2,4,6-trichlorophenyl)-2,3-dihydro-1-benzofuran-2-yl]methyl}carbamate. $[\alpha]_D^{25}$=+7.8 (c 10.0 in methanol).

Intermediate 222

(−)-benzyl {[7-(2,4,6-trichlorophenyl)-2,3-dihydro-1-benzofuran-2-yl]methyl}carbamate Fraction 1 obtained as a colorless oil from the chiral HPLC separation of (±)-benzyl {[7-(2,4,6-trichlorophenyl)-2,3-dihydro-1-benzofuran-2-yl]methyl}carbamate. $[\alpha]_D^{25}$=−6.2 (c 10.0 in methanol).

Intermediate 223

(±)-[7-bromo-5-(trifluoromethyl)-2,3-dihydro-1-benzofuran-2-yl]methyl 4-methylbenzenesulfonate Treatment of (±)-[7-bromo-5-(trifluoromethyl)-2,3-dihydro-1-benzofuran-2-yl]methanol (3.59 g, 12.1 mmol) with p-toluenesulfonyl chloride (3.6 g, 18.2 mmol) generally according to described for Intermediate 10 provided 3.82 g (70%) (±)-[7-bromo-5-(trifluoromethyl)-2,3-dihydro-1-benzofuran-2-yl]methyl 4-methylbenzenesulfonate. mp 95-97° C.

Intermediate 224

(−)-[7-(2-methylphenyl)-2,3-dihydro-1-benzofuran-2-yl]methyl 4-methylbenzenesulfonate Treatment of (−)-[7-bromo-2,3-dihydro-1-benzofuran-2-yl]methyl 4-methylbenzenesulfonate (2.0 g, 5.22 mmol) with 2-methylphenylboronic acid (1.06 g, 7.83 mmol) generally according to described for Intermediate 37 provided 1.71 g (83%) (−)-[7-(2-methylphenyl)-2,3-dihydro-1-benzofuran-2-yl]methyl 4-methylbenzenesulfonate. $[\alpha]_D^{25}$=−44.6 (c 10.0 in methanol).

Intermediate 225

(S)-1-Benzyloxy-3-(5-fluoro-2-methoxy-phenyl)propan-2-ol

To a solution of 4-fluoro-2-bromanisole (12.6 ml, 0.1 mol) in anhydrous tetrahydrofuran at −78° C. was added n-butyllithium (39 ml, 2.5 M in hexane) and the resulting mixture was allowed to stir at −78° C. for 3 h. Copper(I) bromide-dimethylsulfide (10.0 g, 0.05 mol) was then added at −78° C. and the reaction mixture was allowed to warm to 40° C. over 2 h. Benzyl(S)-(+)-glycidyl ether (3.71 ml, 0.025 mol) was added at −60° C. followed by boron trifluoride diethyl etherate (0.15 ml, 1.2 mmol) and the reaction mixture was allowed to warm to room temperature over 12 h. The solvent was removed in vacuo and purification by flash column chromatography (silica, ethyl acetate:hexanes 3:7) afforded 5.0 g (70%) of (S)-1-benzyloxy-3-(5-fluoro-2-methoxy-phenyl) propan-2-ol as a colorless oil. HRMS ESI m/e 308.1666 [M+NH4]+, Calc'd m/e 308.1662 [M+NH4]+; $[\alpha]_D^{25}$=+8.1 (c 0.89% in methanol).

Intermediate 226

(S)-1-Benzyloxy-3-(5-chloro-2-methoxy-phenyl)propan-2-ol

Treatment of 4-chloro-2-bromanisole (21.5 g, 0.1 mol) generally according to the procedure described for Intermediate 225 provided 5.1 g (67%) of (S)-1-benzyloxy-3-(5-chloro-2-methoxy-phenyl)propan-2-ol as a colorless oil. HRMS ESI m/e 307.1096 [M+H]$^+$, Calc'd 307.1101; $[\alpha]_D^{25}$=+6.6 (c 1% in methanol).

Intermediate 227

(S)-1-Benzyloxy-3-(2-methoxy-5-methyl-phenyl)propan-2-ol

Treatment of 2-bromo-4-methylanisole (14.05 ml, 0.1 mol) generally according to the procedure described for Intermediate 225 afforded 6.74 g (96%) of (S)-1-benzyloxy-3-(2-methoxy-5-methyl-phenyl)propan-2-ol as a colorless oil. HRMS EI m/e 286.1565 (M)$^+$, Calc'd. 286.1569; $[\alpha]_D^{25}$=+15.67 (c 9.57 in methanol).

Intermediate 228

(S)-1-Benzyloxy-3-(2-methoxy-phenyl)propan-2-ol

Treatment of 2-bromoanisole (12.1 ml, 0.1 mol) generally according to the procedure described for Intermediate 225 gave 5.4 g (82%) of (S)-1-benzyloxy-3-(2-methoxyphenyl)propan-2-ol as a colorless oil. HRMS EI m/e 272.1413 (M)$^+$, Calc'd. 272.1412. $[\alpha]_D^{25}$=+18.07 (c 7.86 in methanol).

Intermediate 229

(S)-1-Benzyloxy-3-(2',6'-dichlor-5-fluoro-2-methoxybiphenyl-3-yl)propan-2-ol

To a solution of 3-bromo-2',6'-dichloro-5-fluoro-2-methoxy-biphenyl (2.2 g, 6.3 mmol) in anhydrous tetrahydrofuran at 0° C. was added isopropylmagnesium chloride (3.45 ml, 2.0 M in hexane) and the resulting mixture was allowed to stir at 0° C. for 4 h. The reaction mixture was cooled to −30° C. and copper(I) cyanide (0.28 g, 3.1 mmol) in tetrahydrofuran was added and the reaction mixture was allowed to stir at −30° C. for 1 h. Benzyl(S)-(+)-glycidyl ether (0.48 ml, 3.1 mmol) was then added at −30° C. and the reaction mixture was allowed to warm to room temperature for 12 h. The solvent was removed in vacuo and purification by flash column chromatography (silica, ethyl acetate:hexanes 3:7) provided 1.28 g (94%) of (S)-1-benzyloxy-3-(2',6'-dichlor-5-fluoro-2-methoxybiphenyl-3-yl)propan-2-ol as a colorless oil. HRMS ESI m/e 435.0946 [M−H]$^-$, Calc'd 435.0930; $[\alpha]_D^{25}$=+2.8 (c 8.14 in dimethylsulfoxide).

Intermediate 230

(1S)-2-bromo-1-(5-fluoro-2-hydroxybenzyl)ethyl acetate

A solution of (S)-1-benzyloxy-3-(5-fluoro-2-methoxyphenyl)propan-2-ol (5.17 g, 17.8 mmol) in hydrogen bromide (40 ml, 30 wt. % in acetic acid) was heated to 70° C. and allowed to stir for 12 h. The solvent was removed in vacuo and the residue was dissolved in dichloromethane and washed with ammonium hydroxide. The solvent was removed in vacuo and purification by flash column chromatography (silica, ethyl acetate:hexanes 3:7) afforded 3.60 g (70%) of (1S)-2-bromo-1-(5-fluoro-2-hydroxybenzyl)ethyl acetate as a light brown oil. Elemental Analysis for: $C_{11}H_{12}BrFO_3$ Theory: C, 45.38H, 4.15 Found: C, 45.24H, 4.09.

Intermediate 231

(1S)-2-bromo-1-(5-chloro-2-hydroxybenzyl)ethyl acetate

Treatment of (S)-1-benzyloxy-3-(5-chloro-2-methoxyphenyl)propan-2-ol (5.4 g, 17.6 mmol) generally according to the procedure described for Intermediate 230 gave 3.8 g (70%) of (1S)-2-bromo-1-(5-chloro-2-hydroxybenzyl)ethyl acetate as a light brown oil. HRMS EI m/e 305.9647 (M)$^+$.

Intermediate 232

(1S)-2-bromo-1-(2-hydroxy-5-methylbenzyl)ethyl acetate

Treatment of (S)-1-benzyloxy-3-(2-methoxy-5-methylphenyl)propan-2-ol (6.7 g, 23.3 mmol) generally according to the procedure described for Intermediate 230 provided 6.24 g (93%) of (1S)-2-bromo-1-(2-hydroxy-5-methylbenzyl)ethyl acetate as a yellow oil. MS EI m/e 286 (M)$^+$; $[\alpha]_D^{25}$=−2.41 (c 8.29 in methanol).

Intermediate 233

(1S)-2-bromo-1-(2-hydroxybenzyl)ethyl acetate

Treatment of (S)-1-benzyloxy-3-(2-methoxy-phenyl)propan-2-ol (5.40 g, 19.8 mmol) generally according to the procedure described for Intermediate 230 provided 3.42 g (63%) of (1S)-2-bromo-1-(2-hydroxybenzyl)ethyl acetate as a yellow oil. $[\alpha]_D^{25}$=−12.2 (c 1% in methanol). Elemental Analysis for: $C_{16}H_{15}BrO_3$ Theory: C, 48.37H, 4.80 Found: C, 48.48H, 4.78.

Intermediate 234

3-[(2S)-2-(acetyloxy)-3-bromopropyl]-2',6'-dichloro-5-fluorobiphenyl-2-yl acetate Treatment of (S)-1-benzyloxy-3-(2',6'-dichlor-5-fluoro-2-methoxybiphenyl-3-yl)propan-2-ol (1.28 g, 2.9 mmol) generally according to the procedure described for Intermediate 230 provided 1.12 g (80%) of 3-[(2S)-2-(acetyloxy)-3-bromopropyl]-2',6'-dichloro-5-fluorobiphenyl-2-yl acetate as a light yellow oil. HRMS ESI m/e 476.9686 [M+H]$^+$, Calc'd. 476.9671; $[\alpha]_D^{25}$1=+13.2 (c 1% in methanol).

Intermediate 235

(S)-2-(3-Bromo-2-hydroxy-propyl)-4-fluoro-phenol

To a solution of (1S)-2-bromo-1-(5-fluoro-2-hydroxybenzyl)ethyl acetate (3.57 g, 12.2 mmol) in methanol was added hydrogen chloride (1.0 M in diethylether, 49 ml) and the reaction mixture was allowed to stir at room temperature for 12 h. The solvent was removed in vacuo and purification by flash column chromatography (silica, ethyl acetate:hexanes 3:7) afforded 2.95 g (97%) of (S)-2-(3-bromo-2-hydroxypropyl)-4-fluoro-phenol as a colorless oil. HRMS ESI m/e 246.9761 [M−H]$^+$; Calc'd 246.9755. $[\alpha]_D^{25}$=+8.2° (c 0.71% in methanol).

Intermediate 236

(S)-2-(3-Bromo-2-hydroxy-propyl)-4-chloro-phenol

Treatment of (1S)-2-bromo-1-(5-chloro-2-hydroxybenzyl)ethyl acetate (2.47 g, 3.2 mmol) generally according to the procedure described for Intermediate 235 gave 1.68 g (79%) of (S)-2-(3-bromo-2-hydroxy-propyl)-4-chloro-phenol as a yellow oil. $[\alpha]_D^{25}=+9.8°$ (c 1% in methanol), HRMS EI m/e 263.956 (M)$^+$.

Intermediate 237

(S)-2-(3-Bromo-2-hydroxy-propyl)-4-methyl-phenol

Treatment of (1S)-2-bromo-1-(2-hydroxy-5-methylbenzyl)ethyl acetate (6.24 g, 22 mmol) generally according to the procedure described for Intermediate 235 afforded 5.0 g (94%) of (S)-2-(3-bromo-2-hydroxy-propyl)-4-methyl-phenol as a colorless oil. $[\alpha]_D^{25}=+13.8$ (c 1% in methanol), HRMS ESI m/e 243.0020 [M–H]$^-$, Calc'd. 243.0021.

Intermediate 238

(S)-2-(3-Bromo-2-hydroxy-propyl)-phenol

Treatment of (1S)-2-bromo-1-(2-hydroxybenzyl)ethyl acetate (3.42 g, 12.5 mmol) generally according to the procedure described for Intermediate 235 provided 2.71 g (93%) of (S)-2-(3-bromo-2-hydroxy-propyl)-phenol as a light yellow oil. MS ES m/e 229.0 [M–H]$^-$; $[\alpha]_D^{25}=+16.46$ (c 8.14 in methanol).

Intermediate 239

(S)-3-(3-Bromo-2-hydroxy-propyl)-2',6',-dichloro-5-fluoro-biphenyl-2-ol

Treatment of 3-[(2S)-2-(acetyloxy)-3-bromopropyl]-2',6'-dichloro-5-fluorobiphenyl-2-yl acetate (1.6 g, 33.4 mmol) generally according to the procedure described for Intermediate 235 gave 1.48 g (99%) of (S)-3-(3-bromo-2-hydroxy-propyl)-2',6',-dichloro-5-fluoro-biphenyl-2-ol as a light yellow oil. HRMS EI m/e 391.9391 (M)$^+$, Calc'd. 391.9391; $[\alpha]_D^{25}=-4.76$ (c 7.14 in methanol).

Intermediate 240

(R)-2-Bromomethyl-5-fluoro-2,3-dihydro-benzofuran

Treatment of (S)-2-(3-bromo-2-hydroxy-propyl)$_4$-fluoro-phenol (1.97 g, 8 mmol), triphenylphosphine (5.2 g, 20 mmol), and diethylazodicarboxylate (3.11 ml, 20 mmol) generally according to the procedure described for Intermediate 18 afforded 1.40 g (76%) of (R)-2-bromomethyl-5-fluoro-2,3-dihydro-benzofuran as a colorless oil. HRMS ESI m/e 228.9661 [M–H]$^-$. $[\alpha]_D^{25}=-33.0$ (c 1% in methanol).

Intermediate 241

(R)-2-Bromomethyl-5-methyl-2,3-dihydro-benzofuran

Treatment of (S)-2-(3-bromo-2-hydroxy-propyl)-4-methyl-phenol (5.0 g, 20 mmol) generally according to the procedure described for Intermediate 18 gave 3.04 g (70%) of (R)-2-bromomethyl-5-methyl-2,3-dihydro-benzofuran as a yellow oil. HRMS EI m/e 225.9998 (M)$^+$; $[\alpha]_D^{25}=-41.13$ (c 8.86 in methanol).

Intermediate 242

(R)-2-Bromomethyl-2,3-dihydro-benzofuran

Treatment of (S)-2-(3-bromo-2-hydroxy-propyl)-phenol (2.71 g, 12 mmol) generally according to the procedure described for Intermediate 18 provided 1.62 g (65%) of (R)-2-bromomethyl-2,3-dihydro-benzofuran as a yellow oil. $[\alpha]_D^{25}=-37$ (c 1% in methanol); HRMS EI m/e 211.9840 (M)$^+$, Calc'd. 211.9837.

Intermediate 243

(R)-2-Bromomethyl-7-(2',6'-dichloro-phenyl)-5-fluoro-2,3-dihydro-benzofuran

Treatment of (S)-3-(3-bromo-2-hydroxy-propyl)-2',6',-dichloro-5-fluoro-biphenyl-2-ol (1.48 g, 3.7 mmol) generally according to the procedure described for Intermediate 18 afforded 1.16 g (82%) of (R)-2-bromomethyl-7-(2',6'-dichloro-phenyl)-5-fluoro-2,3-dihydro-benzofuran as a colorless oil. HRMS EI m/e 373.9277 (M)$^+$, Calc'd. 373.9277; $[\alpha]_D^{25}=-15.75$ (c 8.0 in methanol).

Intermediate 244

(R)-7-Bromo-2-bromomethyl-5-fluoro-2,3-dihydro-benzofuran

To a solution of (R)-2-bromomethyl-5-fluoro-2,3-dihydro-benzofuran (3.20 g, 14 mmol) in acetic acid was added bromine (2.2 ml, 42 mmol) and the reaction mixture was allowed to stir at room temperature for 12 h. The solvent was removed in vacuo and the residue dissolved in dichloromethane and washed with saturated aqueous sodium sulfite. The solvent was removed in vacuo and purification by flash column chromatography (silica, ethyl acetate:hexanes 1:19) afforded 3.16 g (74%) of as a light yellow oil. HRMS EI m/e 307.8846 (M)$^+$, Calc'd. 307.8848. $[\alpha]_D^{25}=+24.8$ (c 1% in methanol).

Intermediate 245

(R)-2-Bromomethyl-5-fluoro-7-o-toly-2,3-dihydrobenzofuran

Treatment of (R)-7-bromo-2-bromomethyl-5-fluoro-2,3-dihydrobenzofuran (2.57 g, 8.2 mmol) and o-tolyboronic acid (3.4 g, 24 mmol) generally according to the procedure described for Intermediate 37 afforded 2.54 g (95%) of (R)-2-Bromomethyl-5-fluoro-7-o-toly-2,3-dihydrobenzofuran as a colorless oil. HRMS EI m/e 320.0224 (M)$^+$; $[\alpha]_D^{25}=+35.00$ (c 1% in methanol).

Intermediate 246

(R)-2-Bromomethyl-7-(2-chloro-phenyl)-5-fluoro-2,3-dihydrobenzofuran

Treatment of (R)-7-bromo-2-bromomethyl-5-fluoro-2,3-dihydrobenzofuran (0.5 g, 1.6 mmol) and 2-chlorobenzene boronic acid (0.76 g, 4.8 mmol) generally according to the procedure described for Intermediate 37 gave 0.55 g (99%) (R)-2-bromomethyl-7-(2-chloro-phenyl)-5-fluoro-2,3-dihydrobenzofuran as a colorless oil. HRMS EI M+339.9657; $[\alpha]_D^{25}=+29.6$ (c 8.14 in methanol).

Intermediate 247

(R)-2-Bromomethyl-7-(2-methyl-5-chloro-phenyl)-5-fluoro-2,3-dihydrobenzofuran Treatment of (R)-7-bromo-2-bromomethyl-5-fluoro-2,3-dihydrobenzofuran (0.40 g, 1.3 mmol) and 5-chloro-o-toluene boronic acid (0.88 g, 5.2 mmol) generally according to the procedure described for Intermediate 37 provided 0.41 g (90%) of (R)-2-bromomethyl-7-(2-methyl-5-chloro-phenyl)-5-fluoro-2,3-dihydrobenzofuran as a colorless oil. HRMS EI M+353.9829; $[\alpha]_D^{25}=+47.38$ (c 9.29 in methanol).

Intermediate 248

(R)-2-Bromomethyl-7-(2-methyl-4-chloro-phenyl)-5-fluoro-2,3-dihydrobenzofuran Treatment of (R)-7-bromo-2-bromomethyl-5-fluoro-2,3-dihydrobenzofuran (0.42 g, 1.3 mmol) and 4-chloro-o-toluene boronic acid (0.88 g, 5.2 mmol) generally according to the procedure described for Intermediate 37 provided 0.43 g (95%) of (R)-2-bromomethyl-7-(2-methyl-4-chloro-phenyl)-5-fluoro-2,3-dihydrobenzofuran as a colorless oil. HRMS EI M+ 353.9825, Calc'd. 353.9825; $[\alpha]_D^{25}=+39.14$ (c 7.0 in methanol).

Intermediate 249

(R)-2-Azidomethyl-7-(4-chloro-2-methyl-phenyl)-5-fluoro-2,3-dihydrobenzofuran Treatment of (R)-2-Bromomethyl-7-(4-chloro-2-methylphenyl)-5-fluoro-2,3-dihydrobenzofuran (0.4 g, 1.1 mmol) generally according to the procedure described for Intermediate 98 gave 0.30 g (85%) of (R)-2-azidomethyl-7-(4-chloro-2-methyl-phenyl)-5-fluoro-2,3-dihydrobenzofuran as a colorless oil. HRMS EI m/e 317.0719 (M)+, Calc'd. 317.0718; $[\alpha]_D^{25}=+16.76$ (c 8.71 in methanol).

Intermediate 250

(R)-2-Azidomethyl-7-(5-chloro-2-methyl-phenyl)-5-fluoro-2,3-dihydrobenzofuran Treatment of 2-bromomethyl-7-(5-chloro-2-methyl-phenyl)-5-fluoro-2,3-dihydrobenzofuran (0.41 g, 1.2 mmol) generally according to the procedure described for Intermediate 98 gave 0.31 g (85%) of (R)-2-azidomethyl-7-(5-chloro-2-methyl-phenyl)-5-fluoro-2,3-dihydrobenzofuran as a colorless oil. EMS EI m/e 317.0734 (M)+, Calc'd. 317.0733; $[\alpha]_D^{25}=+3.12$ (c 7.71 in methanol).

EXAMPLE 1

(±)-1-(4-phenyl-2,3-dihydro-1-benzofuran-2-yl)methanamine

Treatment of (±)-(4-phenyl-2,3-dihydro-1-benzofuran-2-yl)methyl 4-methylbenzenesulfonate (1.36 g, 3.57 mmol) with sodium azide (0.929 g, 14.29 mmol) generally according to the procedure described for intermediate 98 afforded (±)-(4-phenyl-2,3-dihydro-1-benzofuran-2-yl)methyl azide. The azide was dissolved in ethanol (50 mL) and palladium on carbon (0.083 g, 10 wt. %) was added and the reaction mixture was shaken under an $H_2$ atmosphere (50 psi) for 6 h. The reaction mixture was filtered (celite) and the solvent removed in vacuo to provide a colorless oil. The oil was re-dissolved in isopropanol (3 mL) and hydrogen chloride (1.0 N in diethyl ether, 10.0 mL) was added. The resulting precipitate was filtered, washed (diethyl ether), and dried to afford 0.700 g (94%) of (±)-1-(4-phenyl-2,3-dihydro-1-benzofuran-2-yl)methanamine as a white solid, hydrochloride salt. mp 229-230° C.; Anal. calcd. for $C_{15}H_{15}NOHCl$: C, 68.83; H, 6.16; N, 5.35. Found: C, 66.11; H, 6.25; N, 5.02.

EXAMPLE 2

(+)-1-(4-phenyl-2,3-dihydro-1-benzofuran-2-yl)methanamine

Fraction 1 (0.206 g) obtained from the chiral HPLC separation of (±)-benzyl(4-phenyl-2,3-dihydro-1-benzofuran-2-yl)methylcarbamate (Chiralcel OD, ethanol:water 15:85) was treated with hydrogen bromide (3 mL, 30 wt. % in acetic acid) and the reaction mixture was allowed to stir at room temperature for 30 min. Diethyl ether (20 mL) was added to the reaction mixture and the resulting precipitate was filtered, washed with diethyl ether, and dried to afford 0.082 g (46%) of (+)-1-(4-phenyl-2,3-dihydro-1-benzofuran-2-yl)methanamine as a tan solid, hydrobromide salt. $[\alpha]_D^{25}=+86.92$ (c 10.0 in methanol); mp 225-226° C.; Anal. calcd. for $C_{15}H_{15}NOHBr$: C, 58.84; H, 5.27; N, 4.57. Found: C, 57.02; H, 4.96; N, 4.3.

EXAMPLE 3

(−)-1-(4-phenyl-2,3-dihydro-1-benzofuran-2-yl)methanamine

Treatment of 0.197 g of fraction 2 obtained from the chiral HPLC separation of (±)-benzyl(4-phenyl-2,3-dihydro-1-benzofuran-2-yl)methylcarbamate, (Chiralcel OD, ethanol:water 15:85) with hydrogen bromide (3 mL, 30 wt. % in acetic acid) generally according to the procedure described for Example 2 gave 0.091 g (54%) of (−)-1-(4-phenyl-2,3-dihydro-1-benzofuran-2-yl)methanamine as a tan solid, hydrobromide salt. $[\alpha]_D^{25}=-84.76$ (c 10.0 in methanol); mp 227-228° C.; Anal. calcd. for $C_{15}H_{15}NOHBr$: C, 58.84; H, 5.27; N, 4.57. Found: C, 57.19; H, 5.19; N, 4.18.

EXAMPLE 4

(±)-1-[4-(2-methylphenyl)-2,3-dihydro-1-benzofuran-2-yl]methanamine

Treatment of (±)-[4-(2-methylphenyl)-2,3-dihydro-1-benzofuran-2-yl]methyl 4-methylbenzenesulfonate (1.31 g, 3.32 mmol) with sodium azide (0.863 g, 13.28 mmol) generally according to the procedure described for Intermediate 98 afforded (±)-2-(azidomethyl)-4-(2-methylphenyl)-2,3-dihydro-1-benzofuran. Treatment of the azide with palladium on carbon (0.082 g, 10 wt. %) generally according to the procedure described for Example 1 provided 0.689 g (85%) of (±)-1-[4-(2-methylphenyl)-2,3-dihydro-1-benzofuran-2-yl]methanamine as a white solid, hydrochloride salt. mp 231-234° C.; Anal. calcd. for $C_{16}H_{17}NOHCl.0.2H_2O$: C, 68.79; H, 6.64; N, 5.01. Found: C, 68.49; H, 6.50; N, 4.87.

EXAMPLE 5

(+)-1-[4-(2-methylphenyl)-2,3-dihydro-1-benzofuran-2-yl]methanamine

Treatment of 0.236 g of fraction 1 obtained from the chiral HPLC separation of (±)-benzyl[4-(2-methylphenyl)-2,3-dihydro-1-benzofuran-2-yl]methylcarbamate (Chiralcel OD, methanol) with hydrogen bromide (3 mL, 30 wt. % in acetic acid) generally according to the procedure described for Example 2 gave 0.167 g (83%) of (+)-1-[4-(2-methylphenyl)-2,3-dihydro-1-benzofuran-2-yl]methanamine as a white solid, hydrobromide salt. $[\alpha]_D^{25}$=+89.44 (c 10.0 in methanol); mp 232-233° C.; Anal. calcd. for $C_{16}H_{17}NOHBr$: C, 60.01; H, 5.67; N, 4.37. Found: C, 59.28; H, 5.36; N, 3.8.

EXAMPLE 6

(−)-1-[4-(2-methylphenyl)-2,3-dihydro-1-benzofuran-2-yl]methanamine

Treatment of 0.229 g of fraction 2 obtained from the chiral HPLC separation of (±)-benzyl[4-(2-methylphenyl)-2,3-dihydro-1-benzofuran-2-yl]methylcarbamate (Chiralcel OD, methanol) with hydrogen bromide (3 mL, 30 wt. % in acetic acid) according the procedure described for Example 2 afforded 0.190 g, (97%) of (−)-1-[4-(2-methylphenyl)-2,3-dihydro-1-benzofuran-2-yl]methanamine as a white solid, hydrobromide salt. $[\alpha]_D^{25}$=−83.96 (c 10.0 in methanol); mp 231-233° C.; Anal. calcd. for $C_{16}H_{17}NOHBr$: C, 60.01; H, 5.67; N, 4.37. Found: C, 59.37; H, 5.64; N, 3.98.

EXAMPLE 7

(±)-1-(7-methoxy-2,3-dihydro-1-benzofuran-2-yl)methanamine

Treatment of (±)-(7-methoxy-2,3-dihydro-1-benzofuran-2-yl)methyl 4-methylbenzenesulfonate (1.00 g, 2.99 mmol) with sodium azide (0.78 g, 11.96 mmol) generally according to the procedure described for Intermediate 98 provided (±)-2-(azidomethyl)-7-methoxy-2,3-dihydro-1-benzofuran. Treatment of the azide with palladium on carbon (0.06 g, 10 wt. %) generally according to the procedure described for Example 1 afforded 0.465 g (54%) (±)-1-(7-methoxy-2,3-dihydro-1-benzofuran-2-yl)methanamine as a white solid, hydrochloride salt. mp 168-171° C.; Anal. calcd. for $C_{10}H_{13}NO_2HCl$: C, 55.69; H, 6.54; N, 6.49. Found: C, 55.68; H, 6.52; N, 6.5.

EXAMPLE 8

(±)-(7-cyclopentyl-2,3-dihydro-1-benzofuran-2-yl)methylamine

Treatment of (±)-(7-cyclopentyl-2,3-dihydro-1-benzofuran-2-yl)methanol (4.08 g, 18.7 mmol) with p-toluenesulfonyl chloride (3.92 g, 21.9 mmol) in anhydrous pyridine (76 mL) generally according to the procedure described for Intermediate 10 gave (±)-(7-cyclopentyl-2,3-dihydro-1-benzofuran-2-yl)methyl 4-methylbenzenesulfonate as a tan oil. Treatment of the tosylate with sodium azide (4.39 g, 67.57 mmol) generally according to the procedure described for Intermediate 98 afforded 4.1 g of (±)-2-(azidomethyl)-7-cyclopentyl-2,3-dihydro-1-benzofuran as a yellow oil. Treatment of the azide with palladium on carbon (0.41 g, 10 wt. %) generally according to the procedure described for Example 1 afforded 2.5 g (58%) of (±)-(7-cyclopentyl-2,3-dihydro-1-benzofuran-2-yl)methylamine as a white solid, hydrochloride salt. mp 174° C.; Anal. calcd. for $C_{14}H_{900}N_2HCl$: C, 66.26; H, 7.94; N, 5.52. Found C, 66.13; H, 7.71; N, 5.5.

EXAMPLE 9

(−)-(7-cyclopentyl-2,3-dihydro-1-benzofuran-2-yl)methylamine

Treatment of 0.833 g of fraction 1 obtained from the chiral HPLC separation of (±)-(7-cyclopentyl-2,3-dihydro-1-benzofuran-2-yl)methylcarbamate (Chiralcel OJ, ethanol:hexane 1:1) with hydrogen bromide (12.0 mL, 30 wt. % in acetic acid) generally according to the procedure described for Example 2 gave 0.541 g (76%) of (−)-(7-cyclopentyl-2,3-dihydro-1-benzofuran-2-yl)methylamine as a tan solid, hydrobromide salt. $[\alpha]_D^{25}$=−13.4 (c 10.0 in methanol); mp 208-211° C.; Anal. calcd. for $C_{14}H_{19}NOHBr$: C, 56.39; H, 6.76; N, 4.7. Found: C, 55.83; H, 6.54; N, 4.41.

EXAMPLE 10

(+)-(7-cyclopentyl-2,3-dihydro-1-benzofuran-2-yl)methylamine

Treatment of 0.760 g of fraction 2 obtained from the chiral HPLC separation of (±)-(7-cyclopentyl-2,3-dihydro-1-benzofuran-2-yl)methylcarbamate (Chiralcel OJ, ethanol:hexane 1:1) with hydrogen bromide (11.0 mL, 30 wt. % in acetic acid) generally according to the procedure described for Example 2 afforded 0.468 g (72%) of (+)-(7-cyclopentyl-2,3-dihydro-1-benzofuran-2-yl)methylamine as a tan solid, hydrobromide salt. $[\alpha]_D^{25}$=+11.5 (c 10.0 in methanol); Anal. calcd. for $C_{14}H_{19}NOHBr$: C, 56.39; H, 6.76; N, 4.7. Found: C, 56.03; H, 6.71; N, 4.63.

EXAMPLE 11

(±)-(5-chloro-7-cyclohexyl-2,3-dihydro-1-benzofuran-2-yl)methylamine

Treatment of (±)-(5-chloro-7-cyclohexyl-2,3-dihydro-1-benzofuran-2-yl)methanol (4.5 g, 0.017 mol) with p-toluenesulfonyl chloride (4.8 g, 0.025 mol), diisopropylethylamine (4.36 g, 0.034 mol), and 4-(dimethylamino)pyridine (0.12 g, 0.98 mmol) generally according to the procedure described for Intermediate 45 gave (±)-(5-chloro-7-cyclohexyl-2,3-dihydro-1-benzofuran-2-yl)methyl 4-methylbenzenesulfonate as a colorless oil. Treatment of the tosylate with sodium azide (4.03 g, 61.99 mmol) generally according to the procedure described for Intermediate 98 provided 3.45 g of (±)-2-(azidomethyl)-5-chloro-7-cyclohexyl-2,3-dihydro-1-benzofuran. Treatment of the azide with sulfided platinum on carbon (0.75 g, 5 wt. %) generally according to the procedure described for Example 1 afforded 2.70 g (60%) of (±)-(5-chloro-7-cyclohexyl-2,3-dihydro-1-benzofuran-2-yl)methylamine as a white solid, hydrochloride salt. mp 210-213° C.; Anal. calcd for $C_{15}H_{20}ClNOHCl$: C, 59.61; H, 7.00; N, 4.63. Found: C, 57.29; H, 7.14; N, 4.78.

EXAMPLE 12

(±)-N-[(5-chloro-7-cyclohexyl-2,3-dihydro-1-benzofuran-2-yl)methyl]-N-methylamine To a suspension of lithium aluminum hydride (0.114 g, 3.0 mmol) in tetrahydrofuran (30 mL) was added (±)-methyl(5-chloro-7-cyclohexyl-2,3-dihydro-1-benzofuran-2-yl)methylcarbamate (0.65 g, 2.0 mmol) and the reaction mixture was allowed to stir at room temperature for 30 h. The reaction mixture was quenched with saturated ammonium chloride (50 mL), diluted with tetrahydrofuran (70 mL), and the aqueous layer was extracted with tetrahydrofuran (2×50 mL). The combined organic layers were washed with saturated aqueous sodium bicarbonate (100 mL) and saturated aqueous sodium chloride (100 mL), were dried (sodium sulfate), and the solvent was removed in vacuo to provide a crude oil. Purification by flash column chromatography (silica, dichloromethane:

methanol 97:3) gave a light brown oil. The oil was re-dissolved in tetrahydrofuran (50 mL) and aqueous hydrogen chloride (1 N, 3 mL) was added. The resulting precipitate was filtered and washed with diethyl ether to provide 0.28 g (44%) of (±)-N-[(5-chloro-7-cyclohexyl-2,3-dihydro-1-benzofuran-2-yl)methyl]-N-methylamine as a white solid, hydrochloride salt. mp 125-128° C.; Anal. calcd. for $C_{16}H_{22}ClNOHCl$: C, 60.76; H, 7.33; N, 4.43. Found: C, 60.92; H, 7.46; N, 4.09.

EXAMPLE 13

(±)-(7-tert-butyl-5-methoxy-2,3-dihydro-1-benzofuran-2-yl)methylamine

Treatment of 2-tert-butyl-4-methoxyphenol and 3-tert-butyl-4-methoxyphenol (18.25 g, 0.101 mol) with potassium carbonate (55.28 g, 0.400 mol) and allyl bromide (14.69 g, 0.121 mol) followed by treatment of the resultant allyl ether in refluxing mesitylene generally according to the procedure described for Intermediate 8 provided 2-allyl-6-tert-butyl-4-methoxyphenol and 2-allyl-5-tert-butyl-4-methoxyphenol. Treatment of the phenol with 3-chloroperoxybenzoic acid (49.58 g, 0.287 mol, 77%) and potassium carbonate (33.0 g, 0.238 mol) generally according to the procedure described for Intermediate 9 gave 3.23 g (14%) of (±)-(7-tert-butyl-5-methoxy-2,3-dihydro-1-benzofuran-2-yl)methanol as a white solid. Treatment of the benzofuran with p-toluenesulfonyl chloride (2.86 g, 0.015 mol) generally according to the procedure described for Intermediate 10 afforded (±)-(7-tert-butyl-5-methoxy-2,3-dihydro-1-benzofuran-2-yl)methyl 4-methylbenzenesulfonate. Treatment of the tosylate with sodium azide (1.46 g, 22.5 mmol) generally according to the procedure described for Intermediate 98 gave (±)-2-(azidomethyl)-7-tert-butyl-5-methoxy-2,3-dihydro-1-benzofuran. Treatment of the azide with palladium on carbon (0.14 g, 10 wt. %) generally according to the procedure described for Example 1 afforded 1.5 g (40%) of (±)-(7-tert-butyl-5-methoxy-2,3-dihydro-1-benzofuran-2-yl)methylamine) as a white solid, hydrochloride salt. mp 174-176° C.; Anal calcd. for $C_{14}H_{21}O_2NHCl$: C, 61.87; H, 8.16; N, 5.15. Found C, 61.67; H, 8.37; N, 4.93.

EXAMPLE 14

(±)-[7-chloro-4-(trifluoromethyl)-2,3-dihydro-1-benzofuran-2-yl]methanamine

Treatment of (±)-[7-chloro-4-(trifluoromethyl)-2,3-dihydro-1-benzofuran-2-yl]methyl 4-methylbenzenesulfonate (1.0 g, 2.46 mmol) with sodium azide (0.64 g, 9.83 mmol) generally according to the procedure described for Intermediate 98 provided (±)-2-(azidomethyl)-7-chloro-4-(trifluoromethyl)-2,3-dihydro-1-benzofuran. Treatment of the azide with palladium on carbon (0.060 g, 10 wt. %) generally according to the procedure described for Example 1 afforded 0.350 g (64%) of (±)-1-[7-chloro-4-(trifluoromethyl)-2,3-dihydro-1-benzofuran-2-yl]methanamine as a white solid, hydrochloride salt. mp >250° C.; Anal. calcd. for $C_{10}H_9F_3ClNOHCl$: C, 41.69; H, 3.5; N, 4.86. Found: C, 41.78; H, 3.43; N, 4.77.

EXAMPLE 15

(±)-1-(7-benzyl-2,3-dihydro-1-benzofuran-2-yl)methanamine

Treatment of (±)-(7-benzyl-2,3-dihydro-1-benzofuran-2-yl)methyl 4-methylbenzenesulfonate (6.53 g, 16.6 mmol) with sodium azide (4.30 g, 66.2 mmol) generally according to the procedure described for Intermediate 98 afforded (±)-(7-benzyl-2,3-dihydro-1-benzofuran-2-yl)methyl azide. Treatment of the azide with palladium on carbon (0.40 g, 10 wt. %) generally according to the procedure described for Example 1 gave 3.62 g (79%) of (±)-1-(7-benzyl-2,3-dihydro-1-benzofuran-2-yl)methanamine as a white solid, hydrochloride salt. mp 107-111° C. (dec); Anal. calcd. for $C_{16}H_{17}NOHCl$: C, 69.69; H, 6.58; N, 5.08. Found: C, 68.56; H, 6.66; N, 4.92.

EXAMPLE 16

(+)-1-(7-benzyl-2,3-dihydro-1-benzofuran-2-yl)methanamine

Treatment of 1.528 g of fraction 1 obtained from the chiral HPLC separation of (±)-benzyl(7-benzyl-2,3-dihydro-1-benzofuran-2-yl)methylcarbamate (Chiralcel OD, methanol) with palladium on carbon (0.15 g, 10 wt. %) generally according to the procedure described for Example 1 gave 0.781 g (69%) of (+)-1-(7-benzyl-2,3-dihydro-1-benzofuran-2-yl)methanamine as a white solid, hydrochloride salt. $[\alpha]_D^{25}$= +15.1 (c 10.0 in methanol); mp 128-131° C.; Anal. calcd. for $C_{16}H_{17}NOHCl$: C, 69.69; H, 6.58; N, 5.08. Found: C, 69.14; H, 6.51; N, 5.03.

EXAMPLE 17

(−)-1-(7-benzyl-2,3-dihydro-1-benzofuran-2-yl)methanamine

Treatment of 0.792 g of fraction 2 obtained from the chiral HPLC separation of (±)-benzyl(7-benzyl-2,3-dihydro-1-benzofuran-2-yl)methylcarbamate (Chiralcel OD, methanol) with palladium on carbon (0.08 g, 10 wt. %) generally according to the procedure described for Example 1 gave 0.415 g (71%) of (−)-1-(7-benzyl-2,3-dihydro-1-benzofuran-2-yl)methanamine as a white solid, hydrochloride salt. $[\alpha]_D^{25}$= −15.3 (c 10.0 in methanol); mp 128-131° C.; Anal. calcd. for $C_{16}H_{17}NOHCl$: C, 69.69; H, 6.58; N, 5.08. Found: C, 69.29; H, 6.59; N, 5.06.

EXAMPLE 18

(±)-(7-isopropyl-2,3-dihydro-1-benzofuran-2-yl)methylamine

Treatment of (±)-(7-isopropyl-2,3-dihydro-1-benzofuran-2-yl)methyl 4-methylbenzenesulfonate (5.15 g, 14.9 mmol) with sodium azide (3.87 g, 59.5 mmol) generally according to the procedure described for Intermediate 98 afforded (±)-(7-isopropyl-2,3-dihydro-1-benzofuran-2-yl)methyl azide. Treatment of the azide with palladium on carbon (0.30 g, 10 wt. %) generally according to the procedure described for Example 1 gave 2.35 g (69%) of (±)-(7-isopropyl-2,3-dihydro-1-benzofuran-2-yl)methylamine as a white solid, hydrochloride salt. mp 160-164° C. (dec); Anal. calcd. for $C_{12}H_{17}NOHCl$: C, 63.29; H, 7.97; N, 6.15. Found: C, 63.33; H, 7.98; N, 6.15.

EXAMPLE 19

(−)-(7-isopropyl-2,3-dihydro-1-benzofuran-2-yl)methylamine

Treatment of 0.891 g of fraction 1 obtained from the chiral HPLC separation of (±)-benzyl(7-isopropyl-2,3-dihydro-1-benzofuran-2-yl)methylcarbamate (Chiralcel OJ, ethanol)

with palladium on carbon (0.09 g, 10 wt. %) generally according to the procedure described for Example 1 gave 0.475 g (76%) of (−)-(7-isopropyl-2,3-dihydro-1-benzofuran-2-yl)methylamine as a white solid, hydrochloride salt. $[\alpha]_D^{25}=$ −34.09 (c 10.0 in methanol); mp 176-178° C.; Anal. calcd. for $C_{12}H_{17}NOHCl$: C, 63.29; H, 7.97; N, 6.15. Found: C, 63.32; H, 8.07; N, 6.14.

EXAMPLE 20

(+)-(7-isopropyl-2,3-dihydro-1-benzofuran-2-yl)methylamine

Treatment of 0.776 g of fraction 2 obtained from the chiral HPLC separation of (±)-benzyl(7-isopropyl-2,3-dihydro-1-benzofuran-2-yl)methylcarbamate (Chiralcel OJ, ethanol) with palladium on carbon (0.09 g, 10 wt. %) generally according to the procedure described for Example 1 gave 0.445 g (82%) of (+)-(7-isopropyl-2,3-dihydro-1-benzofuran-2-yl)methylamine as a white solid, hydrochloride salt. $[\alpha]_D^{25}=$ +32.18 (c 10.0 in methanol); mp 176-178° C.; Anal. calcd. for $C_{12}H_{17}NOHCl$: C, 63.29; H, 7.97; N, 6.15. Found: C, 63.86; H, 8.06; N, 6.00.

EXAMPLE 21

(±)-1-(5-chloro-7-isopropyl-4-methyl-2,3-dihydro-1-benzofuran-2-yl)methanamine

Treatment of (±)-(5-chloro-7-isopropyl-4-methyl-2,3-dihydro-1-benzofuran-2-yl)methyl 4-methylbenzenesulfonate (6.64 g, 16.8 mmol) with sodium azide (3.28 g, 50.4 mmol) generally according to the procedure described for Intermediate 98 afforded (±)-2-(azidomethyl)-5-chloro-7-isopropyl-4-methyl-2,3-dihydro-1-benzofuran. To a solution of (±)-2-(azidomethyl)-5-chloro-7-isopropyl-4-methyl-2,3-dihydro-1-benzofuran (4.44 g, 16.71 mmol) in tetrahydrofuran (100 mL) was added triphenylphoshine (5.25 g, 20.05 mmol) followed by water (10 mL) and the reaction mixture was allowed to stir at room temperature for 12 h. The solvent was removed in vacuo to provide a crude solid. Purification by flash column chromatography (silica, 10% ammonium hydroxide in methanol:ethyl acetate 1:9) provided a colorless oil. The oil was re-dissolved in isopropanol (5 mL) and hydrogen chloride (20.0 mL, 1.0 N in diethyl ether) was added. The resulting precipitate was filtered, washed (diethyl ether), and dried to afford 4.08 g (88%) of (±)-1-(5-chloro-7-isopropyl-4-methyl-2,3-dihydro-1-benzofuran-2-yl)methanamine as a white solid, hydrochloride salt. mp >225° C. (dec); Anal. calcd. for $C_{13}H_{18}ClNOHCl$: C, 56.53; H, 6.93; N, 5.07. Found: C, 56.56; H, 6.91; N, 4.94.

EXAMPLE 22

(−)-1-(5-chloro-7-isopropyl-4-methyl-2,3-dihydro-1-benzofuran-2-yl)methanamine

To 1.61 g of fraction 1 obtained from the chiral HPLC separation of (±)-benzyl (5-chloro-7-isopropyl-4-methyl-2,3-dihydro-1-benzofuran-2-yl)methylcarbamate (Chiralpak AD, ethanol) was added hydrogen bromide (20 mL, 30 wt. % in acetic acid) and the resulting solution was allowed to stir at room temperature for 3 h. The reaction mixture was diluted with water and neutralized with 2.0 N aqueous sodium hydroxide. The reaction mixture was extracted with ethyl acetate (2×100 mL), the combined organic layers were washed with water (100 mL) and saturated aqueous sodium chloride (100 mL), were dried (magensium sulfate), and the solvent was removed in vacuo to provide a crude oil. Purification by flash column chromatography (silica, 10% aqueous ammonium hydroxide in methanol:ethyl acetate 1:9) provided a colorless oil. The oil was re-dissolved in isopropanol (2 m]L) and hydrogen chloride (6 mL, 1.0 M in diethyl ether) was added. The rsulting precipitate was filtered, washed (diethyl ether), and dried to give 0.52 g (44%) of (−)-1-(5-chloro-7-isopropyl-4-methyl-2,3-dihydro-1-benzofuran-2-yl)methanamine as a white solid, hydrochloride salt. $[\alpha]_D^{25}=$−53.20 (c 10.0 in methanol); mp >225° C.; Anal. calcd. for $C_{13}H_{18}ClNOHCl$: C, 56.53; H, 6.93; N, 5.07. Found: C, 56.61; H, 7.06; N, 5.07.

EXAMPLE 23

(+)-1-(5-chloro-7-isopropyl-4-methyl-2,3-dihydro-1-benzofuran-2-yl)methanamine

Treatment of 1.49 g of fraction 2 obtained from the chiral HPLC separation of (±)-benzyl(5-chloro-7-isopropyl-4-methyl-2,3-dihydro-1-benzofuran-2-yl)methylcarbamate (Chiralpak AD, ethanol) with hydrogen bromide (20 mL, 30 wt. % in acetic acid) generally according to the procedure described for Example 22 afforded 0.456 g (42%) of (+)-1-(5-chloro-7-isopropyl-4-methyl-2,3-dihydro-1-benzofuran-2-yl)methanamine as a white solid, hydrochloride salt. $[\alpha]_D^{25}=$+51.30 (c 10.0 in methanol); mp >225° C.; Anal. calcd. for $C_{13}H_{18}ClNOHCl$: C, 56.53; H, 6.93; N, 5.07. Found: C, 56.52; H, 7.06; N, 5.03.

EXAMPLE 24

(±)-1-(7-tert-butyl-2,3-dihydro-1-benzofuran-2-yl)methanamine

Treatment of (±)-(7-tert-butyl-2,3-dihydro-1-benzofuran-2-yl)methyl 4-methylbenzenesulfonate (12.43 g, 0.035 mol) with sodium azide (6.73 g, 0.103 mol) generally according to the procedure described for Intermediate 98 afforded (±)-2-(azidomethyl)-7-tert-butyl-2,3-dihydro-1-benzofuran. Treatment of the azide with palladium on carbon (0.750 g, 10 wt. %) generally according to the procedure described for Example 1 gave 5.56 g (67%) of (±)-1-(7-tert-butyl-2,3-dihydro-1-benzofuran-2-yl)methanamine as a white solid, hydrochloride salt. mp 177-180° C. (dec); Anal. Calcd. for $C_{13}H_{19}NOHCl$: C, 64.59; H, 8.34; N, 5.79. Found: C, 64.34; H, 9.19; N, 5.73.

EXAMPLE 25

(−)-1-(7-tert-butyl-2,3-dihydro-1-benzofuran-2-yl)methanamine

Treatment of 1.31 g of fraction 1 obtained from the chiral HPLC separation of (±)-benzyl(7-tert-butyl-2,3-dihydro-1-benzofuran-2-yl)methylcarbamate (Chiralcel OJ, ethanol) with palladium on carbon (0.13 g, 10 wt. %) generally according to the procedure described for Example 1 gave 0.747 g (80%) of (−)-1-(7-tert-butyl-2,3-dihydro-1-benzofuran-2-yl)methanamine as a white solid, hydrochloride salt. $[\alpha]_D^{25}=$−25.4 (c 10.0 in methanol); mp 178-180° C.; Anal. calcd. for $C_{13}H_{19}NOHCl$: C, 64.59; H, 8.34; N, 5.79. Found: C, 64.23; H, 8.75; N, 5.44.

EXAMPLE 26

(+)-1-(7-tert-butyl-2,3-dihydro-1-benzofuran-2-yl)methanamine

Treatment of 2.2 g of fraction 2 obtained from the chiral HPLC separation of (±)-benzyl (7-tert-butyl-2,3-dihydro-1-benzofuran-2-yl)methylcarbamate (Chiralcel OJ, ethanol)

with palladium on carbon (0.22 g, 10 wt. %) generally according to the procedure described for Example 1 gave 1.40 g (89%) of (+)-1-(7-tert-butyl-2,3-dihydro-1-benzofuran-2-yl)methanamine as a white solid, hydrochloride salt. $[\alpha]_D^{25}$= +24.99 (c 10.0 in methanol); mp 177-179° C.; Anal. calcd. for $C_{13}H_{19}NOHCl$: C, 64.59; H, 8.34; N, 5.79. Found: C, 64.87; H, 8.72; N, 5.51.

EXAMPLE 27

(±)-1-(7-tert-butyl-5-chloro-2,3-dihydro-1-benzofuran-2-yl)methanamine

Treatment of (±)-(7-tert-butyl-5-chloro-2,3-dihydro-1-benzofuran-2-yl)methyl 4-methylbenzenesulfonate (13.74 g, 34.8 mmol) with sodium azide (9.05 g, 0.139 mol) generally according to the procedure described for Intermediate 98 afforded (±)-2-(azidomethyl)-7-tert-butyl-5-chloro-2,3-dihydro-1-benzofuran. Treatment of the azide with triphenylphoshine (9.13 g, 34.8 mmol) generally according to the procedure described for Example 21 afforded 4.43 (46 of (±)-1-(7-tert-butyl-5-chloro-2,3-dihydro-1-benzofuran-2-yl)methanamine as a white solid, hydrochloride salt. mp 229-231° C.; Anal. calcd. for $C_{13}H_{18}ClNOHCl$: C, 56.53; H, 6.93; N, 5.07. Found: C, 56.49; H, 6.71; N, 4.86.

EXAMPLE 28

(−)-1-(7-tert-butyl-5-chloro-2,3-dihydro-1-benzofuran-2-yl)methanamine

Treatment of 0.888 g of fraction 1 obtained from the (±)-benzyl(7-tert-butyl-5-chloro-2,3-dihydro-1-benzofuran-2-yl)methylcarbamate (Chiralpak AD, hexane:isopropanol 9:1) with hydrogen bromide (20 mL, 30 wt. % in acetic acid) generally according to the procedure described for Example 2 gave 0.594 g (78%) of (−)-1-(7-tert-butyl-5-chloro-2,3-dihydro-1-benzofuran-2-yl)methanamine as a white solid, hydrobromide salt. $[\alpha]_D^{25}$=−33.16 (c 10.0 in methanol); mp 219-222° C.; Anal. calcd. for $C_{13}H_{18}ClNOHBr$: C, 48.69; H, 5.97; N, 4.37. Found: C, 48.81; H, 6.01; N, 4.24.

EXAMPLE 29

(+)-1-(7-tert-butyl-5-chloro-2,3-dihydro-1-benzofuran-2-yl)methanamine

Treatment of 0.855 g of fraction 2 obtained from the (±)-benzyl(7-tert-butyl-5-chloro-2,3-dihydro-1-benzofuran-2-yl)methylcarbamate (Chiralpak AD, hexane:isopropanol 9:1) with hydrogen bromide (20 mL, 30 wt. % in acetic acid) generally according to the procedure described for Example 2 provided 0.286 g (39%) of (+)-1-(7-tert-butyl-5-chloro-2,3-dihydro-1-benzofuran-2-yl)methanamine as a white solid, hydrobromide salt. $[\alpha]_D^{25}$=+35.32 (c 10.0 in methanol); mp 219-222° C.; Anal. calcd. for $C_{13}H_{18}ClNOHBr$: C, 48.69; H, 5.97; N, 4.37. Found: C, 48.78; H, 5.97; N, 4.28.

EXAMPLE 30

(±)-1-(6-methoxy-2,3-dihydro-1-benzofuran-2-yl)methanamine

Treatment of (±)-(6-methoxy-2,3-dihydro-1-benzofuran-2-yl)methyl 4-methylbenzenesulfonate (1.00 g, 2.99 mmol) with sodium azide (0.78 g, 11.96 mmol) generally according to the procedure described for Intermediate 98 afforded (±)-2-(azidomethyl)-6-methoxy-2,3-dihydro-1-benzofuran. Treatment of the azide with palladium on carbon (0.06 g, 10 wt. %) generally according to the procedure described for Example 1 gave 0.442 g (69%) of (±)-1-(6-methoxy-2,3-dihydro-1-benzofuran-2-yl)methanamine as a white solid, hydrochloride salt. mp >220° C.; Anal. calcd. for $C_{10}H_{13}NO_2HCl$: C, 55.69; H, 6.54; N, 6.49. Found: C, 55.29; H, 6.48; N, 6.38.

EXAMPLE 31

(±)-(6-phenyl-2,3-dihydro-1-benzofuran-2-yl)methanamine

Treatment of (±)-(6-phenyl-2,3-dihydro-1-benzofuran-2-yl)methyl 4-methylbenzenesulfonate (0.280 g, 0.736 mmol) with sodium azide (0.191 g, 2.94 mmol) generally according to the procedure described for Intermediate 98 gave (±)-(6-phenyl-2,3-dihydro-1-benzofuran-2-yl)methyl azide. Treatment of the azide with palladium on carbon (0.026 g, 10 wt. %) generally according to the procedure described for Example 1 provided 0.190 g (90%) of (±)-(6-phenyl-2,3-dihydro-1-benzofuran-2-yl)methanamine as a tan solid, hydrobromide salt. mp 218-221° C. Anal. calcd. for $C_{15}H_{15}NOHBr$: C, 58.84; H, 5.27; N, 4.57. Found: C, 54.80; H, 4.88; N, 4.18.

EXAMPLE 32

(±)-1-{7-[3,5-bis(trifluoromethyl)phenyl]-2,3-dihydro-1-benzofuran-2-yl}methanamine Treatment of {7-[3,5-bis(trifluoromethyl)phenyl]-2,3-dihydro-1-benzofuran-2-yl methyl 4-methylbenzenesulfonate (0.75 g, 1.45 mmol) with sodium azide (0.24 g, 3.62 mmol) generally according to the procedure described for Intermediate 98 provided (±)-2-(azidomethyl)-7-[3,5-bis(trifluoromethyl)phenyl]-2,3-dihydro-1-benzofuran. Treatment of the azide with palladium on carbon (10%, 0.075 g) generally according to the procedure described for Example 1 afforded 0.270 g (47%) of (±)-1-{7-[3,5-bis(trifluoromethyl)phenyl]-2,3-dihydro-1-benzofuran-2-yl}methanamine as a white solid, hydrochloride salt. mp 174-175° C. (dec.); Anal. calcd. for $C_{17}H_{13}F_6NOHCl$: C, 51.34; H, 3.55; N, 3.52. Found: C, 51.25; H, 3.57; N, 3.68.

EXAMPLE 33

(±)-1-[7-(1-naphthyl)-2,3-dihydro-1-benzofuran-2-yl]methanamine

Treatment of (±)-(7-{[(trifluoromethyl)sulfonyl]oxy}-2,3-dihydro-1-benzofuran-2-yl)methyl 4-methylbenzenesulfonate (1.5 g, 3.32 mmol) with 1-naphthaleneboronic acid (0.86 g, 4.97 mmol), tetrakis(triphenylphosphine)palladium (0) (0.38 g, 0.33 mmol), and potassium phosphate (1.41 g, 6.63 mmol) generally according to the procedure described for Intermediate 50 provided (±)-[7-(1-naphthyl)-2,3-dihydro-1-benzofuran-2-yl]methyl 4-methylbenzenesulfonate. Treatment of the tosylate with sodium azide (0.10 g, 1.49 mmol) generally according to the procedure described for Intermediate 98 afforded (±)-2-(azidomethyl)-7-(1-naphthyl)-2,3-dihydro-1-benzofuran. Treatment of the azide with palladium on carbon (0.03 g, 10 wt. %) generally according to the procedure described for Example 1 gave 0.10 g (10%) of (±)-1-[7-(1-naphthyl)-2,3-dihydro-1-benzofuran-2-yl] methanamine as a white solid, hydrochloride salt. mp 120-

124° C.; Anal. calcd. for $C_{19}H_{17}NOHCl \cdot 0.5H_2O$: C, 71.13; H, 5.97; N, 4.37. Found: C, 70.93; H, 5.74; N, 4.58.

EXAMPLE 34

(±)-1-[7-(3-chloro-4-fluorophenyl)-2,3-dihydro-1-benzofuran-2-yl]methanamine

Treatment of (±)-[7-(3-chloro-4-fluorophenyl)-2,3-dihydro-1-benzofuran-2-yl]methyl 4-methylbenzenesulfonate (0.68 g, 1.57 mmol) with sodium azide (0.25 g, 3.92 mmol) generally according to the procedure described for Intermediate 98 gave (±)-2-(azidomethyl)-7-(3-chloro-4-fluorophenyl)-2,3-dihydro-1-benzofuran. Treatment of the azide with palladium on carbon (0.035 g, 10 wt. %) generally according to the procedure described for Example 1 afforded 0.186 g (38%) of (±)-1-[7-(3-chloro-4-fluorophenyl)-2,3-dihydro-1-benzofuran-2-yl]methanamine as a white solid, hydrochloride salt. mp >210° C.; Anal. calcd. for $C_{15}H_{13}ClFNOHCl$: C, 57.34; H, 4.49; N, 4.46. Found: C, 57.38; H, 4.32; N, 4.55.

EXAMPLE 35

(±)-1-[7-(3,5-dichlorophenyl)-2,3-dihydro-1-benzofuran-2-yl]methanamine

Treatment of (±)-[7-(3,5-dichlorophenyl)-2,3-dihydro-1-benzofuran-2-yl]methyl 4-methylbenzenesulfonate (0.22 g, 0.498 mmol) with sodium azide (0.08 g, 1.25 mmol) generally according to the procedure described for Intermediate 98 afforded (±)-2-(azidomethyl)-7-(3,5-dichlorophenyl)-2,3-dihydro-1-benzofuran. Treatment of the azide with triphenylphosphine (0.26 g, 0.997 mol) generally according to the procedure described for Example 21 afforded 0.08 g (49%) of (±)-1-[7-(3,5-dichlorophenyl)-2,3-dihydro-1-benzofuran-2-yl]methanamine as a white solid, hydrochloride salt. mp 165-168° C.; Anal. calcd. for $C_{15}H_{13}Cl_2NOHCl$: C, 54.49; H, 4.27; N, 4.24. Found: C, 54.27; H, 3.95; N, 4.23.

EXAMPLE 36

(±)-1-(7-phenyl-2,3-dihydro-1-benzofuran-2-yl)methanamine

Treatment of (±)-(7-phenyl-2,3-dihydro-1-benzofuran-2-yl)methyl 4-methylbenzenesulfonate (0.40 g, 1.06 mmol) with sodium azide (0.17 g, 2.65 mmol) generally according to the procedure described for Intermediate 98 provided (±)-(7-phenyl-2,3-dihydro-1-benzofuran-2-yl)methyl azide. Treatment of the azide with palladium on carbon (0.025 g, 10 wt. %) generally according to the procedure described for Example 1 afforded 0.181 g (65%) of (±)-1-(7-phenyl-2,3-dihydro-1-benzofuran-2-yl)methanamine as a white solid, hydrochloride salt. mp >200° C. (dec); Anal. calcd. for $C_{15}H_{15}NOHCl \cdot 0.2H_2O$: C, 67.90; H, 6.23; N, 5.2 Found: C, 67.69; H, 6.16; N, 5.3.

EXAMPLE 37

(+)-(1-(7-phenyl-2,3-dihydro-1-benzofuran-2-yl)methanamine

Treatment of 0.40 g of fraction 1 obtained from the chiral HPLC separation of (±)-1-(7-phenyl-2,3-dihydro-1-benzofuran-2-yl)methanamine (Chiralpak AD, ethanol:hexane 1:1) with palladium on carbon (0.040 g, 10 wt. %) generally according to the procedure described for Example 1 gave (+)-(1-(7-phenyl-2,3-dihydro-1-benzofuran-2-yl)methanamine 0.235 g (37%) as a white solid, hydrochloride salt. $[\alpha]_D^{25}=+14.6$ (c 10.0 in methanol); Anal. calcd. for $C_{15}H_{15}NOHCl$: C, 68.83; H, 6.16; N, 5.35. Found: C, 67.54; H, 5.97; N, 5.03.

EXAMPLE 38

(−)-1-(7-phenyl-2,3-dihydro-1-benzofuran-2-yl)methanamine

Treatment of 0.40 g of fraction 2 obtained from the chiral HPLC separation of (±)-1-(7-phenyl-2,3-dihydro-1-benzofuran-2-yl)methanamine (Chiralpak AD, ethanol:hexane 1:1) with palladium on carbon (0.040 g, 10 wt. %) generally according to the procedure described for Example 1 gave 0.212 g (33%) of (−)-1-(7-phenyl-2,3-dihydro-1-benzofuran-2-yl)methanamine as a white solid, hydrochloride salt. $[\alpha]_D^{25}=-17.9$ (c 10.0 in methanol); mp 220-222° C.; Anal. calcd. for $C_{15}H_{15}NOHCl$: C, 68.83; H, 6.16; N, 5.35. Found: C, 67.68; H, 6.07; N, 5.15.

EXAMPLE 39

(±)-1-[7-(2-naphthyl)-2,3-dihydro-1-benzofuran-2-yl]methanamine

Treatment of (±)-[7-(2-naphthyl)-2,3-dihydro-1-benzofuran-2-yl]methyl 4-methylbenzenesulfonate (0.51 g, 1.23 mmol) with sodium azide (0.20 g, 3.08 mmol) generally according to the procedure described for Intermediate 98 provided (±)-2-(azidomethyl)-7-(2-naphthyl)-2,3-dihydro-1-benzofuran. Treatment of the azide with palladium on carbon (0.050 g, 10 wt. %) generally according to the procedure described for Example 1 afforded 0.183 g (48%) of (±)-1-[7-(2-naphthyl)-2,3-dihydro-1-benzofuran-2-yl]methanamine as a white solid, hydrochloride salt. mp 135-140° C.; Anal. calcd. for $C_{19}H_{17}NOHCl \cdot 0.3H_2O$: C, 71.94; H, 5.91 N, 4.42. Found: C, 71.67; H, 5.95; N, 4.25.

EXAMPLE 40

(±)-1-(2',3'-dihydro-2,7'-bi-1-benzofuran-2'-yl)methanamine

Treatment of (±)-(7-{[(trifluoromethyl)sulfonyl]oxy}-2,3-dihydro-1-benzofuran-2-yl)methyl 4-methylbenzenesulfonate (1.5 g, 3.32 mmol) with 2-benzofuranboronic acid (0.81 g, 4.97 mmol), tetrakis(triphenylphosphine)palladium (0) (0.38 g, 0.33 mmol), and potassium phosphate (1.41 g, 6.63 mmol) generally according to the procedure described for Intermediate 50 provided (±)-2',3'-dihydro-2,7'-bi-1-benzofuran-2'-ylmethyl 4-methylbenzenesulfonate. Treatment of the tosylate with sodium azide (0.09 g, 1.32 mmol) generally according to the procedure described for Intermediate 98 afforded (±)-2'-(azidomethyl)-2',3'-dihydro-2,7'-bi-1-benzofuran. Treatment of the azide with palladium on carbon (0.03 g, 10 wt. %) generally according to the procedure described for Example 1 provided 0.12 g (12%) of (±)-1-(2',3'-dihydro-2,7'-bi-1-benzofuran-2'-yl)methanamine as a white solid, hydrochloride salt. mp >220° C. (dec); Anal. calcd. for $C_{19}H_{17}NOHCl \cdot 1.0H_2O$: C, 63.85; H, 5.67; N, 4.38. Found: C, 63.54; H, 5.1; N, 4.3.

EXAMPLE 41

(±)-1-[7-(3-methylphenyl)-2,3-dihydro-1-benzofuran-2-yl]methanamine

Treatment of (±)-[7-(3-methylphenyl)-2,3-dihydro-1-benzofuran-2-yl]methyl 4-methylbenzenesulfonate (0.90 g, 2.27 mmol) with sodium azide (0.44 g, 6.84 mmol) generally according to the procedure described for Intermediate 98 gave (±)-2-(azidomethyl)-7-(3-methylphenyl)-2,3-dihydro-1-benzofuran. Treatment of the azide with palladium on carbon (10%, 0.060 g) generally according to the procedure described for Example 1 afforded 0.444 g (71%) of (±)-1-[7-(3-methylphenyl)-2,3-dihydro-1-benzofuran-2-yl]methanamine as a white solid, hydrochloride salt. mp >210° C. (dec); Anal. calcd. for $C_{16}H_{17}NOHCl.0.2H_2O$: C, 68.79; H, 6.64; N, 5.01. Found: C, 68.54; H, 6.57; N, 4.9.

EXAMPLE 42

(+)-1-[7-(3-methylphenyl)-2,3-dihydro-1-benzofuran-2-yl]methanamine

Treatment of 0.390 g of fraction 1 obtained from the chiral HPLC separation of (±)-benzyl[7-(3-methylphenyl)-2,3-dihydro-1-benzofuran-2-yl]methylcarbamate (Chiralpak AD, ethanol:hexane 1:1) with palladium on carbon (0.039 g, 10 wt. %) generally according to the procedure described for Example 1 gave 0.189 g (66%) of (+)-1-[7-(3-methylphenyl)-2,3-dihydro-1-benzofuran-2-yl]methanamine as a white solid, hydrochloride salt. $[\alpha]_D^{25}$=+28.4 (c 10.0 in methanol); mp 196-198° C.; Anal. calcd. for $C_{16}H_{17}NOHCl$: C, 69.69; H, 6.58; N, 5.08. Found: C, 68.44; H, 6.71; N, 4.81.

EXAMPLE 43

(−)-1-[7-(3-methylphenyl)-2,3-dihydro-1-benzofuran-2-yl]methanamine

Treatment of 0.290 g of fraction 2 obtained from the chiral HPLC separation of (±)-benzyl[7-(3-methylphenyl)-2,3-dihydro-1-benzofuran-2-yl]methylcarbamate (Chiralpak AD, ethanol:hexane 1:1) with palladium on carbon (0.030 g, 10 wt. %) generally according to the procedure described for Example 1 gave 0.178 g (83%) of (−)-1-[7-(3-methylphenyl)-2,3-dihydro-1-benzofuran-2-yl]methanamine as a white solid, hydrochloride salt. $[\alpha]_D^{25}$=−25.6 (c 10.0 in methanol); mp 194-196° C.; Anal. calcd. for $C_{16}H_{17}NOHCl$: C, 69.69; H, 6.58; N, 5.08. Found: C, 68.92; H, 6.62; N, 4.94.

EXAMPLE 44

(±)-1-(7-thien-3-yl-2,3-dihydro-1-benzofuran-2-yl)methanamine

Treatment of (±)-(7-thien-3-yl-2,3-dihydro-1-benzofuran-2-yl)methyl 4-methylbenzenesulfonate (2.2 g, 5.64 mmol) with sodium azide (1.48 g, 22.77 mmol) generally according to the procedure described for Intermediate 98 afforded (±)-(7-thien-3-yl-2,3-dihydro-1-benzofuran-2-yl)methyl azide. Treatment of the azide with palladium on carbon (0.130 g, 10 wt. %) generally according to the procedure described for Example 1 gave 0.838 g (55%) of (±)-1-(7-thien-3-yl-2,3-dihydro-1-benzofuran-2-yl)methanamine as a white solid, hydrochloride salt. mp >200° C.; Anal. calcd. for $C_{13}H_{13}FNOSHCl$: C, 58.31; H, 5.27; N, 5.23. Found: C, 56.4; H, 5.23; N, 4.95.

EXAMPLE 45

(+)-1-(7-thien-3-yl-2,3-dihydro-1-benzofuran-2-yl)methanamine

Treatment of 0.219 g of fraction 1 obtained from the chiral HPLC separation of (±)-benzyl(7-thien-3-yl-2,3-dihydro-1-benzofuran-2-yl)methylcarbamate (Chiralcel AD, water:methanol 1:9) with hydrogen bromide (3.0 mL, 30 wt. % in acetic acid) generally according to the procedure described for Example 2 afforded 0.120 g (64%) of (+)-1-(7-thien-3-yl-2,3-dihydro-1-benzofuran-2-yl)methanamineas a tan solid, hydrobromide salt. $[\alpha]_D^{25}$=+13.8 (c 10.0 in methanol); mp 234-236° C.; Anal. calcd. for $C_{13}H_{13}NOSHBr$: C, 50.01; H, 4.52; N, 4.49. Found: C, 49.37; H, 4.45; N, 4.41.

EXAMPLE 46

(−)-1-(7-thien-3-yl-2,3-dihydro-1-benzofuran-2-yl)methanamine

Treatment of 0.211 g of fraction 2 obtained from the chiral HPLC separation of (±)-benzyl(7-thien-3-yl-2,3-dihydro-1-benzofuran-2-yl)methylcarbamate (Chiralcel AD, water:methanol 1:9) with hydrogen bromide (3.0 mL, 30 wt. % in acetic acid) generally according to the procedure described for Example 2 gave 0.130 g (72%) of (−)-1-(7-thien-3-yl-2,3-dihydro-1-benzofuran-2-yl)methanamine as a white solid, hydrobromide salt. $[\alpha]_D^{25}$=−14.5 (c 10.0 in methanol); mp 234-235° C.; Anal. calcd. for $C_{13}H_{13}NOSHBr$: C, 50.01; H, 4.52; N, 4.49. Found: C, 49.15; H, 4.49; N, 4.38.

EXAMPLE 47

(±)-1-[7-(2-methylphenyl)-2,3-dihydro-1-benzofuran-2-yl]methanamine

Treatment of (±)-[7-(2-methylphenyl)-2,3-dihydro-1-benzofuran-2-yl]methyl 4-methylbenzenesulfonate (7.79 g, 19.74 mmol) with sodium azide (5.13 g, 78.99 mmol) generally according to the procedure described for Intermediate 98 gave (±)-2-(azidomethyl)-7-(2-methylphenyl)-2,3-dihydro-1-benzofuran. Treatment of the azide with palladium on carbon (0.5 g, 10 wt. %) generally according to the procedure described for Example 1 provided 3.63 g (67%) of (±)-1-[7-(2-methylphenyl)-2,3-dihydro-1-benzofuran-2-yl]methanamine as a white solid, hydrochloride salt. mp >200° C.; Anal. calcd. for $C_{16}H_{17}NOHCl$: C, 69.69; H, 6.58; N, 5.08. Found: C, 69.83; H, 6.64; N, 5.

EXAMPLE 48

(+)-1-[7-(2-methylphenyl)-2,3-dihydro-1-benzofuran-2-yl]methanamine

Treatment of 1.61 g of fraction 1 obtained from the chiral HPLC separation of (±)-benzyl[7-(2-methylphenyl)-2,3-dihydro-1-benzofuran-2-yl]methylcarbamate (Chiralcel OJ, ethanol:hexane 1:1) with palladium on carbon (0.161 g, 10 wt. %) generally according to the procedure described for Example 1 gave 0.951 g (80%) of (+)-1-[7-(2-methylphenyl)-2,3-dihydro-1-benzofuran-2-yl]methanamine as a white solid, hydrochloride salt. $[\alpha]_D^{25}$=+16.9 (c 10.0 in methanol); mp 211-212° C.; Anal. calcd. for $C_{16}H_{17}NOHCl$: C, 69.69; H, 6.58; N, 5.08. Found: C, 68.88; H, 6.72; N, 4.92.

EXAMPLE 49

(−)-1-[7-(2-methylphenyl)-2,3-dihydro-1-benzofuran-2-yl]methanamine

Treatment of 1.68 g of fraction 2 obtained from the chiral HPLC separation of (±)-benzyl[7-(2-methylphenyl)-2,3-dihydro-1-benzofuran-2-yl]methylcarbamate (Chiralcel OJ, ethanol:hexane 1:1) with palladium on carbon (0.169 g, 10 wt. %) generally according to the procedure described for Example 1 afforded 1.04 g (84%) of (−)-1-[7-(2-methylphenyl)-2,3-dihydro-1-benzofuran-2-yl]methanamine as a white solid, hydrochloride salt. $[\alpha]_D^{25}=-16.4$ (c 10.0 in methanol); mp 208-209° C.; Anal. calcd. for $C_{16}H_{17}NOHCl$: C, 69.69; H, 6.58; N, 5.08. Found: C, 69.19; H, 6.62; N, 4.91.

EXAMPLE 50

(±)-1-[7-(2-fluorophenyl)-2,3-dihydro-1-benzofuran-2-yl]methanamine

Treatment of (±)-[7-(2-fluorophenyl)-2,3-dihydro-1-benzofuran-2-yl]methyl 4-methylbenzenesulfonate (3.13 g, 7.85 mmol) with sodium azide (2.04 g, 31.42 mmol) generally according to the procedure described for Intermediate 98 afforded (±)-2-(azidomethyl)-7-(2-fluorophenyl)-2,3-dihydro-1-benzofuran. Treatment of the azide with sulfided platinum on carbon (0.21 g, 5 wt. %) generally according to the procedure described for Example 1 provided 1.81 g (83%) of (±)-1-[7-(2-fluorophenyl)-2,3-dihydro-1-benzofuran-2-yl]methanamine as a white solid, hydrochloride salt. mp 244-246° C.; Anal. calcd. for $C_{15}H_{14}FNOHCl$: C, 64.4; H, 5.4; N, 5.01. Found: C, 63.98; H, 5.4; N, 4.89.

EXAMPLE 51

(+)-1-[7-(2-fluorophenyl)-2,3-dihydro-1-benzofuran-2-yl]methanamine

Treatment of 0.542 g of fraction 1 obtained from the chiral HPLC separation of (±)-benzyl[7-(2-fluorophenyl)-2,3-dihydro-1-benzofuran-2-yl]methylcarbamate (Chiralcel OJ, hexane:isopropanol 9:1) with palladium on carbon (0.054 g, 10 wt. %) generally according to the procedure described for Example 1 gave 0.337 g (84%) of (+)-1-[7-(2-fluorophenyl)-2,3-dihydro-1-benzofuran-2-yl]methanamine as a white solid, hydrochloride salt. $[\alpha]_D^{25}=+7.14$ (c 10.0 in dimethylsulfoxide); mp 227-228° C.; Anal. calcd. for $C_{15}H_{14}FNOHCl$: C, 64.4; H, 5.4; N, 5.01. Found: C, 63.96; H, 5.4; N, 4.84.

EXAMPLE 52

(−)-1-[7-(2-fluorophenyl)-2,3-dihydro-1-benzofuran-2-yl]methanamine

Treatment of 0.509 g of fraction 2 obtained from the chiral HPLC separation of (±)-benzyl[7-(2-fluorophenyl)-2,3-dihydro-1-benzofuran-2-yl]methylcarbamate (Chiralcel OJ, hexane:isopropanol 9:1) with palladium on carbon (0.050 g, 10 wt. %) generally according to the procedure described for Example 1 provided 0.318 g (84%) of (−)-1-[7-(2-fluorophenyl)-2,3-dihydro-1-benzofuran-2-yl]methanamine as a white solid, hydrochloride salt. $[\alpha]_D^{25}=-9.48$ (c 10.0 in dimethylsulfoxide); mp 224-225° C.; Anal. calcd. for $C_{15}H_{14}FNOHCl$: C, 64.4; H, 5.4; N, 5.01. Found: C, 63.74; H, 5.21; N, 4.91.

EXAMPLE 53

(±)-1-{7-[2-(trifluoromethyl)phenyl]-2,3-dihydro-1-benzofuran-2-yl}methanamine

Treatment of (7-bromo-2,3-dihydro-1-benzofuran-2-yl)methyl 4-methylbenzenesulfonate (4.0 g, 10.44 mmol) with 2-(trifluoromethyl)phenylboronic acid (2.57 g, 13.6 mmol), dichlorobis(tri-o-tolylphosphine)-palladium(II) (0.426 g, 0.542 mmol), and potassium carbonate (3.61 g, 26.09 mmol) generally according to the procedure described for Intermediate 37 provided (±)-{7-[2-(trifluoromethyl)phenyl]-2,3-dihydro-1-benzofuran-2-yl}methyl 4-methylbenzenesulfonate. Treatment of the tosylate with sodium azide (1.31 g, 20.25 mmol) generally according to the procedure described for Intermediate 98 afforded (±)-2-(azidomethyl)-7-[2-(trifluoromethyl)phenyl]-2,3-dihydro-1-benzofuran. Treatment of the azide with palladium on carbon (0.160 g, 10 wt. %) generally according to the procedure described for Example 1 provided 1.05 g (65%) of (±)-1-{7-[2-(trifluoromethyl)phenyl]-2,3-dihydro-1-benzofuran-2-yl}methanamine as a white solid, hydrochloride salt. mp 204-205° C.; Anal. calcd. for $C_{16}H_{14}F_3NOHCl$: C, 58.25; H, 4.59; N, 4.25. Found: C, 57.57; H, 4.52; N, 4.08.

EXAMPLE 54

(−)-1-{7-[2-(trifluoromethyl)phenyl]-2,3-dihydro-1-benzofuran-2-yl}methanamine

Treatment of 0.350 g of fraction 1 obtained from the chiral HPLC separation of (±)-benzyl {7-[2-(trifluoromethyl)phenyl]-2,3-dihydro-1-benzofuran-2-yl}methylcarbamate (Chiralcel OJ, ethanol:hexane 1:1) with palladium on carbon (0.035 g, 10 wt. %) generally according to the procedure described for Example 1 gave 0.200 g (74%) of (−)-1-{7-[2-(trifluoromethyl)phenyl]-2,3-dihydro-1-benzofuran-2-yl}methanamine as a white solid, hydrochloride salt. $[\alpha]_D^{25}=-23.10$ (c 10.0 in methanol); mp 109-111° C.; Anal. calcd. for $C_{16}H_{14}F_3NOHCl$: C, 58.28; H, 4.59; N, 4.25. Found: C, 58.09; H, 4.35; N, 4.21.

EXAMPLE 55

(+)-1-{7-[2-(trifluoromethyl)phenyl]-2,3-dihydro-1-benzofuran-2-yl}methanamine

Treatment of 0.343 g of fraction 2 obtained from the chiral HPLC separation of (±)-benzyl {7-[2-(trifluoromethyl)phenyl]-2,3-dihydro-1-benzofuran-2-yl}methylcarbamate (Chiralcel OJ, ethanol:hexane 1:1) with palladium on carbon (0.034 g, 10 wt. %) generally according to the procedure described for Example 1 provided 0.165 g (62%) of (+)-1-{7-[2-(trifluoromethyl)phenyl]-2,3-dihydro-1-benzofuran-2-yl}methanamine as a white solid, hydrochloride salt. $[\alpha]_D^{25}=+25.12$ (c 10.0 in methanol); mp 97-100° C.; Anal. calcd. for $C_{16}H_{14}F_3NOHCl$: C, 58.28; H, 4.59; N, 4.25. Found: C, 57.82; H, 4.35; N, 4.15.

EXAMPLE 56

(±)-1-[7-(2,6-dimethylphenyl)-2,3-dihydro-1-benzofuran-2-yl]methanamine

Treatment of (±)-[7-(2,6-dimethylphenyl)-2,3-dihydro-1-benzofuran-2-yl]methyl 4-methylbenzenesulfonate (0.646 g, 1.58 mmol) with sodium azide (0.411 g, 6.33 mmol) generally according to the procedure described for Intermediate 98 afforded (±)-2-(azidomethyl)-7-(2,6-dimethylphenyl)-2,3-dihydro-1-benzofuran. Treatment of the azide with palladium on carbon (0.057 g, 10 wt. %) generally according to the procedure described for Example 1 provided 0.383 g (84%) of (±)-1-[7-(2,6-dimethylphenyl)-2,3-dihydro-1-benzofuran-2-yl]methanamine as a white solid, hydrochloride salt. mp >250° C.; Anal. calcd. for $C_{17}H_{19}NOHCl$: C, 70.46; H, 6.96; N, 4.83. Found: C, 69.06; H, 7.01; N, 4.21.

EXAMPLE 57

(−)-1-[7-(2,6-dimethylphenyl)-2,3-dihydro-1-benzofuran-2-yl]methanamine

Treatment of 0.524 g of fraction 1 obtained from the chiral HPLC separation of (±)-benzyl[7-(2,6-dimethylphenyl)-2,3-dihydro-1-benzofuran-2-yl]methylcarbamate (Chiralcel OJ, methanol:carbon dioxide 3:7) with palladium on carbon (0.052 g, 10 wt. %) generally according to the procedure described for Example 1 gave 0.183 g (47%) of (−)-1-[7-(2,6-dimethylphenyl)-2,3-dihydro-1-benzofuran-2-yl]methanamine as a white solid, hydrochloride salt. $[\alpha]_D^{25}$=−3.98 (c 10.0 in methanol); mp 244-247° C.; Anal. calcd. for $C_{17}H_{19}NOHCl$: C, 70.46; H, 6.96; N, 4.83. Found: C, 69.61; H, 7.00; N, 4.60.

EXAMPLE 58

(+)-1-[7-(2,6-dimethylphenyl)-2,3-dihydro-1-benzofuran-2-yl]methanamine

Treatment of 0.530 g of fraction 2 obtained from the chiral HPLC separation of (±)-benzyl[7-(2,6-dimethylphenyl)-2,3-dihydro-1-benzofuran-2-yl]methylcarbamate (Chiralcel OJ, methanol:carbon dioxide 3:7) with palladium on carbon (0.053 g, 10 wt. %) generally according to the procedure described for Example 1 afforded 0.224 g (57%) of (+)-1-[7-(2,6-dimethylphenyl)-2,3-dihydro-1-benzofuran-2-yl]methanamine as a white solid, hydrochloride salt. $[\alpha]_D^{25}$=+4.28 (c 10.0 in methanol); mp 244-247° C.; Anal. calcd. for $C_{17}H_{19}NOHCl$: C, 70.46; H, 6.96; N, 4.83. Found: C, 69.61; H, 6.87; N, 4.65.

EXAMPLE 59

(±)-1-[7-(2-methoxyphenyl)-2,3-dihydro-1-benzofuran-2-yl]methanamine

Treatment of (±)-(7-bromo-2,3-dihydro-1-benzofuran-2-yl)methyl 4-methylbenzenesulfonate (5.0 g, 13.05 mmol) with 2-methoxyphenylboronic acid (2.57 g, 16.96 mmol), dichlorobis(tri-o-tolylphosphine)-palladium(II) (0.532 g, 0.677 mmol), and potassium carbonate (4.51 g, 32.62 mmol) generally according to the procedure described for Intermediate 37 provided (±)-[7-(2-methoxyphenyl)-2,3-dihydro-1-benzofuran-2-yl]methyl 4-methylbenzenesulfonate. Treatment of the tosylate with sodium azide (0.76 g, 11.69 mmol) generally according to the procedure described for Intermediate 98 gave (±)-2-(azidomethyl)-7-(2-methoxyphenyl)-2,3-dihydro-1-benzofuran. Treatment of the azide with palladium on carbon (0.072 g, 10 wt. %) generally according to the procedure described for Example 1 provided 0.453 g (12%) of (±)-1-[7-(2-methoxyphenyl)-2,3-dihydro-1-benzofuran-2-yl]methanamine as a white solid, hydrochloride salt. mp >250° C.; Anal. calcd. for $C_{16}H_{17}NO_2HCl$: C, 65.86; H, 6.22; N, 4.8. Found: C, 65.72; H, 6.15; N, 4.86.

EXAMPLE 60

(±)-1-[7-(2-chlorophenyl)-2,3-dihydro-1-benzofuran-2-yl]methanamine

Treatment of (±)-[7-(2-chlorophenyl)-2,3-dihydro-1-benzofuran-2-yl]methyl 4-methylbenzenesulfonate (2.6 g, 6.26 mmol) with sodium azide (1.63 g, 25.05 mmol) generally according to the procedure described for Intermediate 98 gave (±)-2-(azidomethyl)-7-(2-chlorophenyl)-2,3-dihydro-1-benzofuran. Treatment of the azide with sulfided platinum on carbon (0.17 g, 5 wt. %) generally according to the procedure described for Example 1 provided 1.05 g (57%) of (±)-1-[7-(2-chlorophenyl)-2,3-dihydro-1-benzofuran-2-yl]methanamine as a white solid, hydrochloride salt. mp >250° C.; Anal. calcd. for $C_{15}H_{14}ClNOHCl$: C, 60.83; H, 5.1; N, 4.73. Found: C, 60.71; H, 5.48; N, 4.55.

EXAMPLE 61

(±)-[7-(2-isopropylphenyl)-2,3-dihydro-1-benzofuran-2-yl]methylamine

Treatment of (±)-(7-bromo-2,3-dihydro-1-benzofuran-2-yl)methyl 4-methylbenzenesulfonate (4.81 g, 12.56 mmol) with 2-(2-isopropylphenyl)-4,4,5,5-tetramethyl-1,3,2-dioxaborolane (4.63 g, 18.84 mmol, Intermediate 35), dichlorobis(tri-o-tolylphosphine)-palladium(II) (0.493 g, 0.627 mmol), and potassium carbonate (4.34 g, 31.38 mmol) generally according to the procedure described for Intermediate 37 provided (±)-[7-(2-isopropylphenyl)-2,3-dihydro-1-benzofuran-2-yl]methyl 4-methylbenzenesulfonate. Treatment of the tosylate with sodium azide (2.10 g, 32.37 mmol) generally according to the procedure described for Intermediate 98 provided (±)-2-(azidomethyl)-7-(2-isopropylphenyl)-2,3-dihydro-1-benzofuran. Treatment of the azide with palladium on carbon (0.22 g, 10 wt. %) generally according to the procedure described for Example 1 provided 2.15 g (56%) of (±)-[7-(2-isopropylphenyl)-2,3-dihydro-1-benzofuran-2-yl]methylamine as a white solid, hydrochloride salt. mp 202-204° C.; Anal. calcd. for $C_{18}H_{21}NOHCl$: C, 71.16; H, 7.30; N, 4.61. Found: C, 70.83; H, 7.34; N, 4.48.

EXAMPLE 62

(+)-[7-(2-isopropylphenyl)-2,3-dihydro-1-benzofuran-2-yl]methylamine

Treatment of 0.760 g of fraction 1 obtained from the chiral HPLC separation of (±)-benzyl[7-(2-isopropylphenyl)-2,3-dihydro-1-benzofuran-2-yl]methylcarbamate (Chiralcel OD, hexane:isopropanol 9:1) with palladium on carbon (0.076 g, 10 wt. %) generally according to the procedure described for Example 1 gave 0.388 g (63%) of (+)-[7-(2-isopropylphenyl)-2,3-dihydro-1-benzofuran-2-yl]methylamine as a white solid, hydrochloride salt. $[\alpha]_D^{25}$=+15.7 (c 10.0 in methanol); mp 205-206° C.; Anal. calcd. for $C_{18}H_{21}NOHCl$: C, 71.16; H, 7.3; N, 4.61. Found: C, 70.78; H, 7.42; N, 4.47.

EXAMPLE 63

(−)-[7-(2-isopropylphenyl)-2,3-dihydro-1-benzofuran-2-yl]methylamine

Treatment of 0.749 g of fraction 2 obtained from the chiral HPLC separation of (±)-benzyl[7-(2-isopropylphenyl)-2,3-dihydro-1-benzofuran-2-yl]methylcarbamate (Chiralcel OD, hexane:isopropanol 9:1) with palladium on carbon (0.075 g, 10 wt. %) generally according to the procedure described for Example 1 provided 0.376 g (66%) of (−)-[7-(2-isopropylphenyl)-2,3-dihydro-1-benzofuran-2-yl]methylamine as a white solid, hydrochloride salt. $[\alpha]_D^{25}$=−16.0 (c 10.0 in methanol); mp 205-206° C.; Anal. calcd. for $C_{18}H_{21}NOHCl$: C, 71.16; H, 7.3; N, 4.61. Found: C, 70.54; H, 7.37; N, 4.61.

EXAMPLE 64

(±)-1-[7-(3-fluorophenyl)-2,3-dihydro-1-benzofuran-2-yl]methanamine

Treatment of (±)-[7-(3-fluorophenyl)-2,3-dihydro-1-benzofuran-2-yl]methyl 4-methylbenzenesulfonate (1.68 g, 4.22 mmol) with sodium azide (1.09 g, 16.88 mmol) generally according to the procedure described for Intermediate 98 afforded (±)-2-(azidomethyl)-7-(3-fluorophenyl)-2,3-dihydro-1-benzofuran. Treatment of the azide with palladium on carbon (0.107 g, 10 wt. %) generally according to the procedure described for Example 1 provided 0.95 g (81%) of (±)-1-[7-(3-fluorophenyl)-2,3-dihydro-1-benzofuran-2-yl]methanamine as a white solid, hydrochloride salt. mp 200-202° C., Anal. calcd. for $C_{15}H_{14}FNOHCl$: C, 64.4; H, 5.4; N, 5.01. Found: C, 63.93; H, 5.48; N, 4.73.

EXAMPLE 65

(±)-1-[7-(3-chlorophenyl)-2,3-dihydro-1-benzofuran-2-yl]methanamine

Treatment of (±)-[7-(3-chlorophenyl)-2,3-dihydro-1-benzofuran-2-yl]methyl 4-methylbenzenesulfonate (3.6 g, 8.66 mmol) with sodium azide (2.25 g, 34.65 mmol) generally according to the procedure described for Intermediate 98 gave (±)-2-(azidomethyl)-7-(3-chlorophenyl)-2,3-dihydro-1-benzofuran. Treatment of the azide with sulfided platinum on carbon (0.125 g, 5 wt. %) generally according to the procedure described for Example 1 provided 1.91 g (74%) of (±)-1-[7-(3-chlorophenyl)-2,3-dihydro-1-benzofuran-2-yl]methanamine as a tan solid, hydrochloride salt. mp 150-154° C.; Anal. calcd. for $C_{15}H_{14}ClNOHCl$: C, 60.83; H, 5.1; N, 4.73. Found: C, 59.17; H, 5.12; N, 4.38.

EXAMPLE 66

(+)-1-[7-(3-chlorophenyl)-2,3-dihydro-1-benzofuran-2-yl]methanamine

Treatment of 0.495 g of fraction 1 obtained from the chiral HPLC separation of (±)-benzyl[7-(3-chlorophenyl)-2,3-dihydro-1-benzofuran-2-yl]methylcarbamate (Chiralpak AS, hexane:isopropanol 9:1) with hydrogen bromide (6.2 mL, 30 wt. % in acetic acid) generally according to the procedure described for Example 2 gave 0.150 g (28%) of (+)-1-[7-(3-chlorophenyl)-2,3-dihydro-1-benzofuran-2-yl]methanamine as a tan solid, hydrobromide salt. $[\alpha]_D^{25}$=+35.7 (c 10.0 in methanol); mp 187-189° C.; Anal. calcd. for $C_{15}H_{14}ClNOHBr$: C, 52.89; H. 4.44; N, 4.11. Found: C, 52.4; H, 4.47; N, 3.97.

EXAMPLE 67

(−)-1-[7-(3-chlorophenyl)-2,3-dihydro-1-benzofuran-2-yl]methanamine

Treatment of 0.542 g of fraction 2 obtained from the chiral HPLC separation of (±)-benzyl[7-(3-chlorophenyl)-2,3-dihydro-1-benzofuran-2-yl]methylcarbamate (Chiralpak AS, hexane:isopropanol 9:1) with hydrogen bromide (6.8 mL, 30 wt. % in acetic acid) generally according to the procedure described for Example 2 afforded 0.232 g (49%) of (−)-1-[7-(3-chlorophenyl)-2,3-dihydro-1-benzofuran-2-yl]methanamine as a white solid, hydrobromide salt. $[\alpha]_D^{25}$=−34.6 (c 10.0 in methanol); mp 189-190° C.; Anal. calcd. for $C_{15}H_{14}ClNOHBr$: C, 52.89; H, 4.44; N, 4.11. Found: C, 52.83; H, 4.47; N, 3.97.

EXAMPLE 68

(±)-1-[7-(3-methoxyphenyl)-2,3-dihydro-1-benzofuran-2-yl]methanamine

Treatment of (±)-[7-(3-methoxyphenyl)-2,3-dihydro-1-benzofuran-2-yl]methyl 4-methylbenzenesulfonate (3.0 g, 7.82 mmol) with sodium azide (0.309 g, 4.48 mmol) generally according to the procedure described for Intermediate 98 gave (±)-2-(azidomethyl)-7-(3-methoxyphenyl)-2,3-dihydro-1-benzofuran. Treatment of the azide with palladium on carbon (0.030 g, 10 wt. %) generally according to the procedure described for Example 1 provided 0.25 g (80%) of (±)-1-[7-(3-methoxyphenyl)-2,3-dihydro-1-benzofuran-2-yl]methanamine as a white solid, hydrochloride salt. mp 152-154° C.; Anal. calcd. for $C_{16}H_{17}NO_2HCl$: C, 65.86; H, 6.22; N, 4.8. Found: C, 65.21; H, 6.17; N, 4.46.

EXAMPLE 69

(±)-1-{7-[3-(trifluoromethyl)phenyl]-2,3-dihydro-1-benzofuran-2-yl}methanamine

Treatment of (±)-{7-[3-(trifluoromethyl)phenyl]-2,3-dihydro-1-benzofuran-2-yl}methyl 4-methylbenzenesulfonate (5.2 g, 11.57 mmol) with sodium azide (3.01 g, 46.3 mmol) generally according to the procedure described for Intermediate 98 gave (±)-2-(azidomethyl)-7-[3-(trifluoromethyl)phenyl]-2,3-dihydro-1-benzofuran. Treatment of the azide with palladium on carbon (0.375 g, 10 wt. %) generally according to the procedure described for Example 1 provided 2.64 g (69%) of (±)-1-{7-[3-(trifluoromethyl)phenyl]-2,3-dihydro-1-benzofuran-2-yl}methanamine as a white solid, hydrochloride salt. mp 172-174° C.; Anal. calcd. for $C_{16}H_{14}F_3NOHCl$: C, 58.28; H, 4.59; N, 4.25. Found: C, 58.09; H, 4.6; N, 4.03.

EXAMPLE 70

(±)-1-[7-(4-methylphenyl)-2,3-dihydro-1-benzofuran-2-yl]methanamine

Treatment of (±)-[7-(4-methylphenyl)-2,3-dihydro-1-benzofuran-2-yl]methyl 4-methylbenzenesulfonate (1.01 g, 2.56 mmol) with sodium azide (0.664 g, 10.24 mmol) generally according to the procedure described for Intermediate 98 gave (±)-2-(azidomethyl)-7-(4-methylphenyl)-2,3-dihydro-1-benzofuran. Treatment of the azide with palladium on carbon (0.03 g, 10 wt. %) generally according to the procedure described for Example 1 provided 0.528 g (75%) of (±)-1-[7-(4-methylphenyl)-2,3-dihydro-1-benzofuran-2-yl]methanamine as a white solid, hydrochloride salt. mp 231-232° C.; Anal. calcd. for $C_{16}H_{17}NOHCl$: C, 69.69; H, 6.58; N, 5.08. Found: C, 66.26; H, 7.0; N, 4.73.

EXAMPLE 71

(+)-1-[7-(4-methylphenyl)-2,3-dihydro-1-benzofuran-2-yl]methanamine

Treatment of 0.198 g of fraction 1 obtained from the chiral HPLC separation of (±)-benzyl[7-(4-methylphenyl)-2,3-dihydro-1-benzofuran-2-yl]methylcarbamate (Chiralpak AD, methanol:water 19:1)) with hydrogen bromide (3.0 mL, 30 wt. % in acetic acid) generally according to the procedure described for Example 2 afforded 0.143 g (84%) of (+)-1-[7-(4-methylphenyl)-2,3-dihydro-1-benzofuran-2-yl]methanamine as a tan solid, hydrobromide salt. $[\alpha]_D^{25}$=+17.42 (c 10.0 in methanol); mp >250° C.; Anal. calcd. for $C_{16}H_{17}NOHBr$: C, 60.01; H, 5.67; N, 4.37. Found: C, 59.58; H, 5.57; N, 4.26.

EXAMPLE 72

(−)-1-[7-(4-methylphenyl)-2,3-dihydro-1-benzofuran-2-yl]methanamine

Treatment of 0.167 g of fraction 2 obtained from the chiral HPLC separation of (±)-benzyl[7-(4-methylphenyl)-2,3-dihydro-1-benzofuran-2-yl]methylcarbamate (Chiralpak AD, methanol:water 19:1) with hydrogen bromide (3.0 mL, 30 wt. % in acetic acid) generally according to the procedure described for Example 2 gave 0.067 g (47%) of (−)-1-[7-(4-methylphenyl)-2,3-dihydro-1-benzofuran-2-yl]methanamine as a white solid, hydrobromide salt. $[\alpha]_D^{25}$=−17.02 (c 10.0 in methanol); mp >250° C.; Anal. calcd. for $C_{16}H_{17}NOHBr$: C, 60.01; H, 5.67; N, 4.37. Found: C, 59.5; H, 5.67; N, 4.23.

EXAMPLE 73

(±)-1-[7-(4-fluorophenyl)-2,3-dihydro-1-benzofuran-2-yl]methanamine

Treatment of (±)-[7-(4-fluorophenyl)-2,3-dihydro-1-benzofuran-2-yl]methyl 4-methylbenzenesulfonate (1.1 g, 3.01 mmol) with sodium azide (0.784 g, 12.04 mmol) generally according to the procedure described for Intermediate 98 afforded (±)-2-(azidomethyl)-7-(4-fluorophenyl)-2,3-dihydro-1-benzofuran. Treatment of the azide with palladium on carbon (0.074 g, 10 wt. %) generally according to the procedure described for Example 1 provided 0.542 g (64%) of (±)-1-[7-(4-fluorophenyl)-2,3-dihydro-1-benzofuran-2-yl] methanamine as a white solid, hydrochloride salt. mp 237-240° C.; Anal. calcd. for $C_{15}H_{14}FNOHCl$: C, 64.4; H, 5.4; N, 5.01. Found: C, 64.26; H, 5.33; N, 4.85.

EXAMPLE 74

(+)-1-[7-(4-fluorophenyl)-2,3-dihydro-1-benzofuran-2-yl]methanamine

Treatment of 0.184 g of fraction 1 obtained from the chiral HPLC separation of (±)-benzyl[7-(4-fluorophenyl)-2,3-dihydro-1-benzofuran-2-yl]methylcarbamate (Chiralcel OD, methanol:water 19:1) with hydrogen bromide (2.0 mL, 30 wt. % in acetic acid) generally according to the procedure described for Example 2 gave 0.08 g (55%) of (+)-1-[7-(4-fluorophenyl)-2,3-dihydro-1-benzofuran-2-yl]methanamine as a white solid, hydrobromide salt. $[\alpha]_D^{25}$=+13.26 (c 10.0 in methanol); mp 207-208° C.; Anal. calcd. for $C_{15}H_{14}FNOHBr$: C, 55.57; H, 4.66; N, 4.32. Found: C, 55.10; H, 4.59; N, 4.22.

EXAMPLE 75

(−)-1-[7-(4-fluorophenyl)-2,3-dihydro-1-benzofuran-2-yl]methanamine

Treatment of 0.173 g of fraction 2 obtained from the chiral HPLC separation of (±)-benzyl[7-(4-fluorophenyl)-2,3-dihydro-1-benzofuran-2-yl]methylcarbamate (Chiralcel OD, methanol:water 19:1) with hydrogen bromide (2.0 mL, 30 wt. % in acetic acid) generally according to the procedure described for Example 2 provided 0.108 g (73%) of (−)-1-[7-(4-fluorophenyl)-2,3-dihydro-1-benzofuran-2-yl]methanamine as a white solid, hydrobromide salt. $[\alpha]_D^{25}$=−12.24 (c 10.0 in methanol); mp 208-210° C.; Anal. calcd. for $C_{15}H_{14}FNOHBr$: C, 55.57; H, 4.66; N, 4.32. Found: C, 55.12; H, 4.62; N, 4.21.

EXAMPLE 76

(±)-1-[7-(4-chlorophenyl)-2,3-dihydro-1-benzofuran-2-yl]methanamine

Treatment of (±)-[7-(4-chlorophenyl)-2,3-dihydro-1-benzofuran-2-yl]methyl 4-methylbenzenesulfonate (1.2 g, 2.89 mmol) with sodium azide (0.752 g, 11.57 mmol) generally according to the procedure described for Intermediate 98 afforded (±)-2-(azidomethyl)-7-(4-fluorophenyl)-2,3-dihydro-1-benzofuran. Treatment of the azide with sulfided platinum on carbon (0.082 g, 5 wt. %) generally according to the procedure described for Example 1 provided 0.592 g (69%) of (±)-1-[7-(4-chlorophenyl)-2,3-dihydro-1-benzofuran-2-yl]methanamine as a white solid, hydrochloride salt. mp 212-214° C.; Anal. calcd. for $C_{15}H_{14}ClNOHCl$: C, 60.83; H, 65.10; N, 4.73. Found: C, 59.99; H, 5.00; N, 4.47.

EXAMPLE 77

(+)-1-[7-(4-chlorophenyl)-2,3-dihydro-1-benzofuran-2-yl]methanamine

Treatment of 0.226 g of fraction 1 obtained from the chiral HPLC separation of (±)-benzyl[7-(4-chlorophenyl)-2,3-dihydro-1-benzofuran-2-yl]methylcarbamate (Chiralcel AD, methanol) with hydrogen bromide (5.7 mL, 30 wt. % in acetic acid) generally according to the procedure described for Example 2 gave 0.113 g (58%) of (+)-1-[7-(4-chlorophenyl)-2,3-dihydro-1-benzofuran-2-yl]methanamine as a white solid, hydrobromide salt. $[\alpha]_D^{25}$=+15.72 (c 10.0 in methanol); mp 229-231° C.; Anal. calcd. for $C_{15}H_{14}ClNOHBr$: C, 52.89; H, 4.44; N, 4.11. Found: C, 52.98; H, 4.43; N, 4.05.

EXAMPLE 78

(−)-1-[7-(4-chlorophenyl)-2,3-dihydro-1-benzofuran-2-yl]methanamine

Treatment of 0.229 g of fraction 2 obtained from the chiral HPLC separation of (±)-benzyl[7-(4-chlorophenyl)-2,3-dihydro-1-benzofuran-2-yl]methylcarbamate (Chiralcel AD, methanol) with hydrogen bromide (5.8 mL, 30 wt. % in acetic acid) generally according to the procedure described for Example 2 provided 0.121 g (61%) of (−)-1-[7-(4-chlorophenyl)-2,3-dihydro-1-benzofuran-2-yl]methanamine as a white solid, hydrobromide salt. $[\alpha]_D^{25}$=−18.40 (c 10.0 in methanol); mp 233-235° C.; Anal. calcd. for $C_{15}H_{14}ClNOHBr$: C, 52.89; H, 4.44; N, 4.11. Found: C, 52.78; H, 4.4; N, 3.98.

EXAMPLE 79

(±)-1-[7-(4-methoxyphenyl)-2,3-dihydro-1-benzofuran-2-yl]methanamine

Treatment of (±)-[7-(4-methoxyphenyl)-2,3-dihydro-1-benzofuran-2-yl]methyl 4-methylbenzenesulfonate (2.1 g, 5.11 mmol) with sodium azide (1.33 g, 20.96 mmol) generally according to the procedure described for Intermediate 98 afforded (±)-2-(azidomethyl)-7-(4-methoxyphenyl)-2,3-dihydro-1-benzofuran. Treatment of the azide with palladium on carbon (0.125 g, 10 wt. %) generally according to the procedure described for Example 1 provided 0.860 g (58%) of (±)-1-[7-(4-methoxyphenyl)-2,3-dihydro-1-benzofuran-2-yl]methanamine as a white solid, hydrochloride salt. mp 176-178° C.; Anal. calcd. for $C_{16}H_{17}NO_2HCl$: C, 65.86; H, 6.22; N, 4.80. Found: C, 65.02; H, 6.13; N, 4.57.

EXAMPLE 80

(+)-1-[7-(4-methoxyphenyl)-2,3-dihydro-1-benzofuran-2-yl]methanamine

Treatment of 0.314 g of fraction 1 obtained from the chiral HPLC separation of (±)-benzyl[7-(4-methoxyphenyl)-2,3-dihydro-1-benzofuran-2-yl]methylcarbamate (Chiralcel AD, methanol) with palladium on carbon (0.031 g, 10 wt. %) generally according to the procedure described for Example 1 provided 0.160 g (68%) of (+)-1-[7-(4-methoxyphenyl)-2,3-dihydro-1-benzofuran-2-yl]methanamine as a white solid, hydrochloride salt. $[\alpha]_D^{25}$=+20.34 (c 10.0 in methanol); mp 183-186° C.; Anal. calcd. for $C_{16}H_{17}NO_2HCl$: C, 65.86; H, 6.22; N, 4.8. Found: C, 62.45; H, 6.11; N, 4.38.

EXAMPLE 81

(−)-1-[7-(4-methoxyphenyl)-2,3-dihydro-1-benzofuran-2-yl]methanamine

Treatment of 0.312 g of fraction 2 obtained from the chiral HPLC separation of (±)-benzyl[7-(4-methoxyphenyl)-2,3-dihydro-1-benzofuran-2-yl]methylcarbamate with hydrogen bromide (12.0 mL, 30 wt. % in acetic acid) generally according to the procedure described for Example 2 provided 0.156 g (58%) of (−)-1-[7-(4-methoxyphenyl)-2,3-dihydro-1-benzofuran-2-yl]methanamine as a white solid, hydrobromide salt. $[\alpha]_D^{25}$=−14.66 (c 10.0 in methanol); mp 185-188° C.; Anal. calcd. for $C_{16}H_{17}NO_2HBr$: C, 57.16; H, 5.4; N, 4.17. Found: C, 56.53; H, 5.48; N, 4.01.

EXAMPLE 82

(±)-1 {7-[4-(trifluoromethyl)phenyl]-2,3-dihydro-1-benzofuran-2-yl}methanamine

Treatment of (±)-{7-[4-(trifluoromethyl)phenyl]-2,3-dihydro-1-benzofuran-2-yl}methyl 4-methylbenzenesulfonate (3.3 g, 7.34 mmol) with sodium azide (1.91 g, 29.38 mmol) generally according to the procedure described for Intermediate 98 gave (±)-2-(azidomethyl)-7-[4-(trifluoromethyl)phenyl]-2,3-dihydro-1-benzofuran. Treatment of the azide with palladium on carbon (0.205 g, 10 wt. %) generally according to the procedure described for Example 1 provided 1.82 g (75%) of (±)-1-{7-[4-(trifluoromethyl)phenyl]-2,3-dihydro-1-benzofuran-2-yl methanamine as a white solid, hydrochloride salt. mp >250° C.; Anal. calcd. for $C_{16}H_{14}F_3NOHCl$: C, 58.28; H, 4.59; N, 4.25. Found: C, 57.47; H, 4.82; N, 3.65.

EXAMPLE 83

(±)-1-[7-(2,4-dichlorophenyl)-2,3-dihydro-1-benzofuran-2-yl]methanamine

Treatment of (±)-[7-(2,4-dichlorophenyl)-2,3-dihydro-1-benzofuran-2-yl]methyl 4-methylbenzenesulfonate (4.2 g, 9.34 mmol) with sodium azide (2.4 g, 37.38 mmol) generally according to the procedure described for Intermediate 98 gave (±)-2-(azidomethyl)-7-(2,4-dichlorophenyl)-2,3-dihydro-1-benzofuran. Treatment of the azide with sulfided platinum on carbon (0.32 g, 5 wt. %) generally according to the procedure described for Example 1 provided 2.16 g (72%) of (±)-1-[7-(2,4-dichlorophenyl)-2,3-dihydro-1-benzofuran-2-yl]methanamine as a white solid, hydrochloride salt. mp 198-200° C.; Anal. calcd. for $C_{15}H_{13}Cl_2NOHCl$: C, 54.49; H, 4.27; N, 4.24. Found: C, 54.5; H, 4.39; N, 4.16.

EXAMPLE 84

(±)-1-(5-chloro-7-phenyl-2,3-dihydro-1-benzofuran-2-yl)methanamine

Treatment of (±)-(5-chloro-7-phenyl-2,3-dihydro-1-benzofuran-2-yl)methyl 4-methylbenzenesulfonate (0.55 g, 1.33 mmol) with sodium azide (0.345 g, 5.31 mmol) generally according to the procedure described for Intermediate 98 provided 0.35 g of (±)-2-(azidomethyl)-5-chloro-7-phenyl-2,3-dihydro-1-benzofuran as a colorless oil. Treatment of the azide with sulfided platinum on carbon (90 mg, 5 wt. %) generally according to the procedure described for Example 1 provided 0.14 g (40%) of (±)-1-(5-chloro-7-phenyl-2,3-dihydro-1-benzofuran-2-yl)methanamine as a white solid, hydrochloride salt. mp 258° C. (dec); Anal. calcd. for $C_{15}H_{14}ClNOHCl$: C, 60.83; H, 5.1; N, 4.73. Found: C, 60.13; H, 4.95; N, 4.6.

EXAMPLE 85

(+)-1-(5-chloro-7-phenyl-2,3-dihydro-1-benzofuran-2-yl)methanamine

Treatment of (±)-1-(5-chloro-7-phenyl-2,3-dihydro-1-benzofuran-2-yl)methanamine (0.8 g, 2.70 mmol) with diisopropylethylamine (1.05 g, 8.10) and benzyl chloroformate (0.83 g, 4.86 mmol) generally according to the procedure described for Intermediate 12 afforded (±)-benzyl(5-chloro-7-phenyl-2,3-dihydro-1-benzofuran-2-yl)methylcarbamate. Chiral HPLC separation of (±)-benzyl(5-chloro-7-phenyl-2,3-dihydro-1-benzofuran-2-yl)methylcarbamate (Chiralpak AD, ethanol) provided two fractions. Fraction 1 ($R_t$=10.875 min, (Chiralpak AD, ethanol); Fraction 2 ($R_t$=15.590 min, (Chiralpak AD, ethanol). Treatment of 0.40 g of fraction 1 obtained from the chiral HPLC separation of (±)-benzyl (5-chloro-7-phenyl-2,3-dihydro-1-benzofuran-2-yl)methylcarbamate (Chiralpak AD, ethanol) with hydrogen bromide (5 mL, 30 wt. % in acetic acid) generally according to the procedure described for Example 2 gave 0.27 g (77%) of (+)-1-(5-chloro-7-phenyl-2,3-dihydro-1-benzofuran-2-yl) methanamine as a white solid, hydrobromide salt. $[\alpha]_D^{25}$=+ 0.7 (c 10.0 in methanol); mp 201-203° C.; Anal. calcd. for $C_{15}H_{14}ClNOHBr$: C, 52.89; H, 4.44; N, 4.11. Found: C, 52.96; H, 4.25; N, 3.88.

EXAMPLE 86

(−)-1-(5-chloro-7-phenyl-2,3-dihydro-1-benzofuran-2-yl)methanamine

Treatment of 0.23 g of fraction 2 obtained from the chiral HPLC separation of (±)-benzyl(5-chloro-7-phenyl-2,3-dihydro-1-benzofuran-2-yl)methylcarbamate (Chiralpak AD, ethanol) with hydrogen bromide (3 mL, 30 wt. % in acetic acid) generally according to the procedure described for Example 2 gave 0.14 g (70%) of (−)-1-(5-chloro-7-phenyl-2,3-dihydro-1-benzofuran-2-yl)methanamine as a white solid, hydrobromide salt. $[\alpha]_D^{25}$=−0.6 (c 10.0 in methanol); mp 201-203° C.; Anal. calcd. for $C_{15}H_{14}ClNOHBr$: C, 52.89; H, 4.44; N, 4.11. Found: C, 52.76; H, 4.38; N, 4.06.

EXAMPLE 87

(±)-1-[5-chloro-7-(2-chlorophenyl)-2,3-dihydro-1-benzofuran-2-yl]methanamine

Treatment of (±)-(5-chloro-7-{[(trifluoromethyl)sulfonyl]oxy}-2,3-dihydro-1-benzofuran-2-yl)methyl 4-methylbenzenesulfonate (1.40 g, 2.88 mmol) with 2-chlorophenylboronic acid (0.67 g, 1.49 mmol), dichloro[1,1'-bis(diphenylphosphino)ferrocene]palladium(II) dichloromethane adduct (0.25 g, 0.30 mmol), and potassium carbonate (0.83 g, 6.0 mmol) generally according to the procedure described for Intermediate 35 provided (±)-[5-chloro-7-(2-chlorophenyl)-2,3-dihydro-1-benzofuran-2-yl]methyl 4-methylbenzenesulfonate. Treatment of the tosylate with sodium azide (1.5 g, 23.1 mmol) generally according to the procedure described for Intermediate 98 provided (±)-2-(azidomethyl)-5-chloro-7-(2-methylphenyl)-2,3-dihydro-1-benzofuran. Treatment of the azide with sulfided platinum on carbon (120 mg, 5 wt. %) generally according to the procedure described for Example 1 gave 0.70 g (80%) of (±)-1-[5-chloro-7-(2-chlorophenyl)-2,3-dihydro-1-benzofuran-2-yl]methanamine as a yellow solid, hydrochloride salt. mp 231-234° C.; Anal. calcd. for $C_{15}H_{13}Cl_2NOHCl$: C, 54.49; H, 4.27; N, 4.24. Found: C, 46.01; H, 4.17; N, 3.25.

EXAMPLE 88

(±)-1-[5-chloro-7-(3-methylphenyl)-2,3-dihydro-1-benzofuran-2-yl]methanamine

Treatment of (±)-2-(azidomethyl)-5-chloro-7-(3-methylphenyl)-2,3-dihydro-1-benzofuran (0.26 g, 0.87 mmol) with sulfided platinum on carbon (85 mg, 5 wt. %) generally according to the procedure described for Example 1 afforded 0.14 g (59%) of (±)-1-[5-chloro-7-(3-methylphenyl)-2,3-dihydro-1-benzofuran-2-yl]methanamine as a white solid, hydrochloride salt. mp 268-271° C.; Anal. calcd. for $C_{16}H_{16}ClNOHCl$: C, 61.95; H, 5.52; N, 4.52. Found: C, 61.01; H, 5.44; N, 4.35.

EXAMPLE 89

(±)-1-[5-chloro-7-(3-chlorophenyl)-2,3-dihydro-1-benzofuran-2-yl]methanamine

Treatment of (±)-[5-chloro-7-(3-chlorophenyl)-2,3-dihydro-1-benzofuran-2-yl]methyl 4-methylbenzenesulfonate (1.00 g, 2.24 mmol) with sodium azide (0.93 g, 14.3 mmol) generally according to the procedure described for Intermediate 98 provided 0.41 g of (±)-2-(azidomethyl)-5-chloro-7-(3-chlorophenyl)-2,3-dihydro-1-benzofuran. Treatment of the azide with sulfided platinum on carbon (100 mg, 5 wt. %) generally according to the procedure described for Example 1 provided 0.31 g (50%) of (±)-1-[5-chloro-7-(3-chlorophenyl)-2,3-dihydro-1-benzofuran-2-yl]methanamine as a white solid, hydrochloride salt. mp 195° C. (dec); Anal. calcd for $C_{15}H_{13}Cl_2NOHCl$: C, 54.49; H, 4.27; N, 4.24. Found: C, 51.59; H, 4.21; N, 4.02.

EXAMPLE 90

(±)-(5-chloro-7-thien-3-yl-2,3-dihydro-1-benzofuran-2-yl)methylamine

Treatment of (±)-(5-chloro-7-thien-3-yl-2,3-dihydro-1-benzofuran-2-yl)methyl 4-methylbenzenesulfonate (0.18 g, 0.43 mmol) with sodium azide (0.11 g, 1.72 mmol) generally according to the procedure described for Intermediate 98 provided 0.13 g of (±)-2-(azidomethyl)-5-chloro-7-thien-3-yl-2,3-dihydro-1-benzofuran. Treatment of the azide with sulfided platinum on carbon (120 mg, 5 wt. %) generally according to the procedure described for Example 1 gave 0.11 g (85%) of (±)-(5-chloro-7-thien-3-yl-2,3-dihydro-1-benzofuran-2-yl)methylamine as a light yellow solid, hydrochloride salt. mp 230° C. (dec); Anal. calcd. for $C_{13}H_{12}ClNOSHCl$: C, 51.66; H, 4.34; N, 4.63. Found: C, 45.27; H, 4.19; N, 3.93.

EXAMPLE 91

(−)-(5-chloro-7-thien-3-yl-2,3-dihydro-1-benzofuran-2-yl)methylamine

Treatment of 0.44 g of fraction 1 obtained from the chiral HPLC separation of (±)-benzyl(5-chloro-7-thien-3-yl-2,3-dihydro-1-benzofuran-2-yl)methylcarbamate (Chiralpak AD, hexane:ethanol 1:1) with hydrogen bromide (5 mL, 30 wt. % in acetic acid) generally according to the procedure described for Example 2 gave 0.20 g (52%) of (−)-(5-chloro-7-thien-3-yl-2,3-dihydro-1-benzofuran-2-yl)methylamine as a white solid, hydrobromide salt. $[\alpha]_D^{25}$=−6.00 (c 10.0 in dimethylsulfoxide); mp 277-280° C.; Anal. calcd. for $C_{13}H_{12}ClNOSHBr$: C, 45.04; H, 3.78; N, 4.04. Found: C, 44.67; H, 3.64; N, 3.84.

EXAMPLE 92

(+)-(5-chloro-7-thien-3-yl-2,3-dihydro-1-benzofuran-2-yl)methylamine

Treatment of 0.40 g of fraction 2 obtained from the chiral HPLC separation of (±)-benzyl(5-chloro-7-thien-3-yl-2,3-dihydro-1-benzofuran-2-yl)methylcarbamate (Chiralpak AD, hexane:ethanol 1:1) with hydrogen bromide (5 mL, 30 wt. % in acetic acid) generally according to the procedure described for Example 2 gave 0.31 g (89%) of (+)-(5-chloro-7-thien-3-yl-2,3-dihydro-1-benzofuran-2-yl)methylamine as a white solid, hydrobromide salt. $[\alpha]_D^{25}$=+5.01 (c 10.0 in dimethylsulfoxide); mp 277-280° C.; Anal. calcd. for $C_{13}H_{12}ClNOSHBr$: C, 45.04; H, 3.78; N, 4.04. Found: C, 44.88; H, 3.69; N, 3.86.

EXAMPLE 93

(+)-N-[(5-chloro-7-thien-3-yl-2,3-dihydro-1-benzofuran-2-yl)methyl]-N-methylamine To a solution of fraction 1 obtained from the chiral HPLC separation of (±)-benzyl (5-chloro-7-thien-3-yl-2,3-dihydro-1-benzofuran-2-yl)methylcarbamate (0.50 g, 1.25 mmol) in tetrahydrofuran (20 mL) was added lithium aluminum hydride (0.30 g, 7.5 mmol, 95 wt. %) and the reaction mixture was allowed to stir at room temperature for 5 h. The reaction mixture was quenched with ethyl aceate (5 mL) and partitioned between tetrahydrofuran (50 mL) and water (20 mL). The organic layer was separated and washed with saturated aqueous sodium bicarbonate (50 mL) and saturated aqueous sodium chloride (50 mL), was dried (magnesium sulfate), and the solvent was removed in vacuo to provide a crude oil. Purification by flash column chromatography (silica, dichloromethane:methanol 39:1) provided a light brown oil. The oil was re-dissolved in THF (50 mL), aqueous hydrogen chloride (1.0 N, 1.5 mL) was added, and the resulting precipitate was filtered and washed with diethyl ether (15 mL) to afford 0.14 g (35%) of (+)-N-[(5-chloro-7-thien-3-yl-2,3-dihydro-1-benzofuran-2-yl)methyl]-N-methylamine as a white solid, hydrochloride salt. $[\alpha]_D^{25}$=+6.6 (c 10.0 in methanol); mp 263-266° C.; Anal. calcd. for $C_{14}H_{14}ClNOSHCl$: C, 53.17; H, 4.78; N, 4.43. Found: C, 52.5; H, 4.88; N, 4.26.

EXAMPLE 94

(−)-N-[(5-chloro-7-thien-3-yl-2,3-dihydro-1-benzofuran-2-yl)methyl]-N-methylamine Treatment of fraction 2 obtained from the chiral HPLC separation of (±)-benzyl (5-chloro-7-thien-3-yl-2,3-dihydro-1-benzofuran-2-yl)methylcarbamate (0.57 g, 1.43 mmol) with lithium aluminum hydride (0.30 g, 7.5 mmol, 95 wt. %) generally according to the procedure described for Example 93 afforded 0.26 g (58%) of (−)-N-[(5-chloro-7-thien-3-yl-2,3-dihydro-1-benzofuran-2-yl)methyl]-N-methylamine as a white solid, hydrochloride salt. $[\alpha]_D^{25}$=−8.2 (c 10.0 in methanol); mp 263-266° C.; Anal. calcd. for $C_{14}H_{14}ClNOSHCl$: C, 53.17; H, 4.78; N, 4.43. Found: C, 53.8; H, 4.85; N, 4.25.

EXAMPLE 95

(±)-1-[5-chloro-7-(2-methylphenyl)-2,3-dihydro-1-benzofuran-2-yl]methanamine

Treatment of (±)-(5-chloro-7-{[(trifluoromethyl)sulfonyl]oxy}-2,3-dihydro-1-benzofuran-2-yl)methyl 4-methylbenzenesulfonate (1.37 g, 2.81 mmol) with 2-methylphenylboronic acid (0.65 g, 4.60 mmol), dichloro[1,1'-bis(diphenylphosphino)ferrocene]palladium(II) dichloromethane adduct (0.25 g, 0.30 mmol), and potassium carbonate (0.83 g, 6.0 mmol) generally according to the procedure described for Intermediate 35 provided (±)-[5-chloro-7-(2-methylphenyl)-2,3-dihydro-1-benzofuran-2-yl]methyl 4-methylbenzenesulfonate. Treatment of the tosylate with sodium azide (1.04 g, 16.1 mmol) generally according to the procedure described for Intermediate 98 provided (±)-2-(azidomethyl)-5-chloro-7-(2-methylphenyl)-2,3-dihydro-1-benzofuran. Treatment of the azide with sulfided platinum on carbon (200 mg, 5 wt. %) generally according to the procedure described for Example 1 gave 0.70 g (80%) of (±)-1-[5-chloro-7-(2-methylphenyl)-2,3-dihydro-1-benzofuran-2-yl]methanamine as a light yellow solid, hydrochloric salt. mp 160-163° C.; Anal. calcd. for $C_{16}H_{16}ClNOHCl$: C, 61.95; H, 5.52; N, 4.52. Found: C, 57.75; H, 5.4; N, 3.95.

EXAMPLE 96

(+)-1-[5-chloro-7-(2-methylphenyl)-2,3-dihydro-1-benzofuran-2-yl]methanamine

Treatment of (±)-1-[5-chloro-7-(2-methylphenyl)-2,3-dihydro-1-benzofuran-2-yl]methanamine (0.65 g, 2.10 mmol) with diisopropylethylamine (0.813 g, 6.29) and benzyl chloroformate (0.71 g, 4.19 mmol) generally according to the procedure described for Intermediate 12 afforded (±)-benzyl [5-chloro-7-(2-methylphenyl)-2,3-dihydro-1-benzofuran-2-yl]methylcarbamate. Chiral HPLC separation of (±)-benzyl [5-chloro-7-(2-methylphenyl)-2,3-dihydro-1-benzofuran-2-yl]methylcarbamate. (Chiralpak AD, ethanol) provided two fractions. Fraction 1 ($R_t$=9.114 min, (Chiralpak AD, ethanol); Fraction 2 ($R_t$=11.426 min, (Chiralpak AD, ethanol). Treatment of 0.27 g of fraction 1 obtained from the chiral HPLC separation of (±)-benzyl [5-chloro-7-(2-methylphenyl)-2,3-dihydro-1-benzofuran-2-yl]methylcarbamate (Chiralpak AD, ethanol) with hydrogen bromide (5 mL, 30 wt. % in acetic acid) generally according to the procedure described for Example 2 gave 0.22 g (94%) of (+)-1-[5-chloro-7-(2-methylphenyl)-2,3-dihydro-1-benzofuran-2-yl]methanamine as a white solid, hydrobromide salt. $[\alpha]_D^{25}$=+1.5 (c 10.0 in methanol); mp 170-172° C.; Anal. calcd. for $C_{16}H_{16}ClNOHBr$: C, 54.18; H, 4.83; N, 3.95. Found: C, 53.28; H, 4.77; N, 3.66.

EXAMPLE 97

(−)-1-[5-chloro-7-(2-methylphenyl)-2,3-dihydro-1-benzofuran-2-yl]methanamine

Treatment of 0.25 g of fraction 2 obtained from the chiral HPLC separation of (±)-benzyl[5-chloro-7-(2-methylphenyl)-2,3-dihydro-1-benzofuran-2-yl]methylcarbamate (Chiralpak AD, ethanol) with hydrogen bromide (4 mL, 30 wt. % in acetic acid) generally according to the procedure described for Example 2 gave 0.17 g (78%) of (−)-1-[5-chloro-7-(2-methylphenyl)-2,3-dihydro-1-benzofuran-2-yl]methanamine as a white solid, hydrobromide salt. $[\alpha]_D^{25}$=−1.6 (c 10.0 in methanol); mp 170-172° C.; Anal. calcd. for $C_{16}H_{16}ClNOHBr$: C, 54.18; H, 4.83; N, 3.95. Found: C, 53.01; H, 4.76; N, 3.78.

EXAMPLE 98

(±)-1-(4-fluoro-7-phenyl-2,3-dihydro-1-benzofuran-2-yl)methanamine

Treatment of (±)-(4-fluoro-7-phenyl-2,3-dihydro-1-benzofuran-2-yl)methyl 4-methylbenzenesulfonate (2.03 g, 5.09 mmol) with sodium azide (1.32 g, 20.38 mmol) generally according to the procedure described for Intermediate 98 provided (±)-2-(azidomethyl)-4-fluoro-7-phenyl-2,3-dihydro-1-benzofuran. Treatment of the azide with palladium on carbon (0.137 g, 10 wt. %) generally according to the procedure described for Example 1 gave 0.610 g (43%) of (±)-1-(4-fluoro-7-phenyl-2,3-dihydro-1-benzofuran-2-yl)methanamine as a white solid, hydrochloride salt. mp 254-257° C.; Anal. calcd. for $C_{15}H_{14}FNOHCl$: C, 64.4; H, 5.40; N, 5.01. Found: C, 64.98; H, 5.48; N, 4.79.

EXAMPLE 99

(±)-1-[4-fluoro-7-(2-methylphenyl)-2,3-dihydro-1-benzofuran-2-yl]methanamine

Treatment of (±)-[4-fluoro-7-(2-methylphenyl)-2,3-dihydro-1-benzofuran-2-yl]methyl 4-methylbenzenesulfonate (1.38 g, 3.35 mmol) with sodium azide (0.87 g, 13.38 mmol) generally according to the procedure described for Intermediate 98 afforded (±)-2-(azidomethyl)-4-fluoro-7-(2-methylphenyl)-2,3-dihydro-1-benzofuran. Treatment of the azide with palladium on carbon (0.083 g, 10 wt. %) generally according to the procedure described for Example 1 provided 0.561 g (57%) of (±)-1-[4-fluoro-7-(2-methylphenyl)-2,3-dihydro-1-benzofuran-2-yl]methanamine as a white solid, hydrochloride salt. mp 228-231° C.; Anal. calcd. for $C_{16}H_{16}FNOHCl$: C, 65.42; H, 5.83; N, 4.77. Found: C, 66.01; H, 5.88; N, 4.51.

EXAMPLE 100

(±)-1-[7-(2-chlorophenyl)-5-fluoro-2,3-dihydro-1-benzofuran-2-yl]methanamine

Treatment of (±)-[7-(2-chlorophenyl)-5-fluoro-2,3-dihydro-1-benzofuran-2-yl]methyl 4-methylbenzenesulfonate (6.65 g, 0.015 mol) with sodium azide (3.99 g, 0.061 mol) generally according to the procedure described for Intermediate 98 afforded (±)-2-(azidomethyl)-7-(2-chlorophenyl)-5-fluoro-2,3-dihydro-1-benzofuran. Treatment of the azide with triphenylphosphine (4.18 g, 0.16 mol) generally according to the procedure described for Example 21 provided 3.37 g (70%) of (±)-1-[7-(2-chlorophenyl)-5-fluoro-2,3-dihydro-1-benzofuran-2-yl]methanamine as a white solid, hydrochloride salt. mp >250° C. (dec); Anal. calcd. for $C_{15}H_{13}ClFNOHCl$: C, 57.34; H, 4.49; N, 4.46. Found: C, 57.45; H, 4.75; N, 4.22.

EXAMPLE 101

(+)-1-[7-(2-chlorophenyl)-5-fluoro-2,3-dihydro-1-benzofuran-2-yl]methanamine

Treatment of 1.22 g of fraction 1 obtained from the chiral HPLC separation of (±)-benzyl[7-(2-chlorophenyl)-5-fluoro-2,3-dihydro-1-benzofuran-2-yl]methylcarbamate (Chiralcel OJ, hexane:ethanol 1:1) with hydrogen bromide (20 mL, 30 wt. % in acetic acid) generally according to the procedure described for Example 22, afforded 0.319 (34%) of (+)-1-[7-(2-chlorophenyl)-5-fluoro-2,3-dihydro-1-benzofuran-2-yl]methanamine as a white solid, hydrochloride salt. $[\alpha]_D^{25}$=+1.18 (c 10.0, methanol); mp 206-209° C.; Anal. calcd. for $C_{15}H_{13}ClFNOHCl$: C, 57.34; H, 4.49; N, 4.46. Found: C, 57.52; H, 4.67; N, 4.44.

EXAMPLE 102

(−)-1-[7-(2-chlorophenyl)-5-fluoro-2,3-dihydro-1-benzofuran-2-yl]methanamine

Treatment of 1.19 g of fraction 2 obtained from the chiral HPLC separation of (±)-benzyl[7-(2-chlorophenyl)-5-fluoro-2,3-dihydro-1-benzofuran-2-yl]methylcarbamate (Chiralcel OJ, hexane:ethanol 1:1) with hydrogen bromide (20 mL, 30 wt. % in acetic acid) generally according to the procedure described for Example 22 provided 0.108 (12%) of (−)-1-[7-(2-chlorophenyl)-5-fluoro-2,3-dihydro-1-benzofuran-2-yl]methanamine as a white solid, hydrochloride salt. mp 206-209° C.; FAB HRMS calcd. for $C_{15}H_{14}ClFNO$ [M+H]$^+$: 278.0748. Found m/z 278.0730.

EXAMPLE 103

(±)-1-(5-fluoro-7-phenyl-2,3-dihydro-1-benzofuran-2-yl)methanamine

Treatment of (±)-(5-fluoro-7-phenyl-2,3-dihydro-1-benzofuran-2-yl)methyl 4-methylbenzenesulfonate (1.50 g, 3.76 mmol) with sodium azide (0.979 g, 15.06 mmol) generally according to the procedure described for Intermediate 98 provided (±)-2-(azidomethyl)-5-fluoro-7-phenyl-2,3-dihydro-1-benzofuran. Treatment of the azide with palladium on carbon (0.101 g, 10 wt. %) generally according to the procedure described for Example 1 provided 0.719 g (68%) of (±)-1-(5-fluoro-7-phenyl-2,3-dihydro-1-benzofuran-2-yl)methanamine as a white solid, hydrochloride salt. mp 255-260° C.; Anal. calcd. for $C_{15}H_{14}FNOHCl$: C, 64.4; H, 5.4; N, 5.01. Found: C, 64.16; H, 5.54; N, 4.73.

EXAMPLE 104

(±)-1-[5-fluoro-7-(2-methylphenyl)-2,3-dihydro-1-benzofuran-2-yl]methanamine

Treatment of (±)-[5-fluoro-7-(2-methylphenyl)-2,3-dihydro-1-benzofuran-2-yl]methyl 4-methylbenzenesulfonate (1.48 g, 3.59 mmol) with sodium azide (0.933 g, 14.35 mmol) generally according to the procedure described for Intermediate 98 gave (±)-2-(azidomethyl)-5-fluoro-7-(2-methylphenyl)-2,3-dihydro-1-benzofuran. Treatment of the azide with palladium on carbon (0.101 g, 10 wt. %) generally according to the procedure described for Example 1 provided 0.555 g (53%) of (±)-1-[5-fluoro-7-(2-methylphenyl)-2,3-dihydro-1-benzofuran-2-yl]methanamine as a white solid, hydrochloride salt. mp 229-234° C.; Anal. calcd. for $C_{16}H_{16}FNOHCl.0.1H_2O$: C, 65.02; H, 5.87; N, 4.74. Found: C, 64.99; H, 5.83; N, 4

EXAMPLE 105

(+)-1-[5-fluoro-7-(2-methylphenyl)-2,3-dihydro-1-benzofuran-2-yl]methanamine

Treatment of 1.51 g of fraction 1 obtained from the chiral HPLC separation of (±)-benzyl[5-fluoro-7-(2-methylphenyl)-2,3-dihydro-1-benzofuran-2-yl]methylcarbamate (Chiralcel OD, hexane:isopropanol 8:2) with palladium on carbon (0.151 g, 10 wt. %) generally according to the procedure described for Example 1 afforded 0.981 g (87%) of (+)-1-[5-fluoro-7-(2-methylphenyl)-2,3-dihydro-1-benzofuran-2-yl]methanamine as a white solid, hydrochloride salt. $[\alpha]_D^{25}$=+12.18 (c 10.0, methanol); mp 227-230° C.; Anal. calcd. for $C_{16}H_{16}FNOHCl$: C, 65.42; H, 5.83; N, 4.77. Found: C, 65.11; H, 5.78; N, 4.62.

EXAMPLE 106

(−)-1-[5-fluoro-7-(2-methylphenyl)-2,3-dihydro-1-benzofuran-2-yl]methanamine

Treatment of 1.65 g of fraction 2 obtained from the chiral HPLC separation of (±)-benzyl[5-fluoro-7-(2-methylphenyl)-2,3-dihydro-1-benzofuran-2-yl]methylcarbamate (Chiralcel OD, hexane:isopropanol 4:1) with palladium on carbon (0.133 g, 10 wt. %) generally according to the procedure described for Example 1 provided 0.966 g (78%) of (−)-1-[5-fluoro-7-(2-methylphenyl)-2,3-dihydro-1-benzofuran-2-yl]methanamine as a white solid, hydrochloride salt. $[\alpha]_D^{25}$=−11.4 (c 10.0, methanol); mp 227-230° C.; Anal. calcd. for $C_{16}H_{16}FNOHCl$: C, 65.42; H, 5.83; N, 4.77. Found: C, 65.28; H, 5.78; N, 4.66.

EXAMPLE 107

(±)-1-[5-fluoro-7-(2-fluorophenyl)-2,3-dihydro-1-benzofuran-2-yl]methanamine

Treatment of (±)-[5-fluoro-7-(2-fluorophenyl)-2,3-dihydro-1-benzofuran-2-yl]methyl 4-methylbenzenesulfonate (1.84 g, 4.42 mmol) with sodium azide (1.15 g, 17.67 mmol) generally according to the procedure described for Intermediate 98 afforded (±)-2-(azidomethyl)-5-fluoro-7-(2-fluorophenyl)-2,3-dihydro-1-benzofuran. Treatment of the azide with palladium on carbon (0.111 g, 10 wt. %) generally according to the procedure described for Example 1 provided 1.02 g (77%) of (±)-1-[5-fluoro-7-(2-methylphenyl)-2,3-dihydro-1-benzofuran-2-yl]methanamine as a white solid, hydrochloride salt. mp 240-247° C. (dec); Anal. calcd. for $C_{15}H_{13}F_2NOHCl$: C, 60.51; H, 4.74; N, 4.7. Found: C, 60.33; H, 4.69; N, 4.4.

EXAMPLE 108

(±)-1-{5-fluoro-7-[2-(trifluoromethyl)phenyl]-2,3-dihydro-1-benzofuran-2-yl}methanamine Treatment of (±)-{5-fluoro-7-[2-(trifluoromethyl)phenyl]-2,3-dihydro-1-benzofuran-2-yl)}methyl 4-methylbenzenesulfonate (5.34 g, 0.011 mol) with sodium azide (2.60 g, 0.04 mol) generally according to the procedure described for Intermediate 98 provided (±)-2-(azidomethyl)-5-fluoro-7-[2-(trifluoromethyl)phenyl]-2,3-dihydro-1-benzofuran. Treatment of the azide with triphenylphosphine (2.89 g, 0.011 mol) generally according to the procedure described for Example 21 afforded 3.25 g (89%) of (±)-1-{5-fluoro-7-[2-(trifluoromethyl)phenyl]-2,3-dihydro-1-benzofuran-2-yl}methanamine as a white solid, hydrochloride salt. mp 196-198° C. (dec); Anal. calcd. for $C_{16}H_{13}F_4NOHCl$: C, 55.26; H, 4.06; N, 4.03. Found: C, 55.88; H, 4.26; N, 3.77.

EXAMPLE 109

(±)-(4,5-difluoro-7-phenyl-2,3-dihydro-1-benzofuran-2-yl)methylamine

Treatment of (±)-(4,5-difluoro-7-phenyl-2,3-dihydro-1-benzofuran-2-yl)methyl azide (0.60 g, 2.09 mmol) in methanol (40 mL) with sulfided platinum on carbon (0.15 g, 5 wt. %) generally according to the procedure described for Example 1 provided 0.60 g (96%) of (±)-(4,5-difluoro-7-phenyl-2,3-dihydro-1-benzofuran-2-yl)methylamine as a pink solid, hydrochloride salt. mp >240° C.; Anal. calcd. for $C_{15}H_{13}F_2NOHCl\, 0.5H_2O$: C, 58.74; H, 4.93; N, 4.57. Found: C, 58.6; H, 4.56; N, 4.33.

EXAMPLE 110

(±)-1-[4,5-difluoro-7-(2-methylphenyl)-2,3-dihydro-1-benzofuran-2-yl]methanamine Treatment of (±)-[4,5-difluoro-7-(2-methylphenyl)-2,3-dihydro-1-benzofuran-2-yl]methyl azide (0.85 g, 2.82 mmol) with sulfided platinum on carbon (0.30 g, 5 wt. %) generally according to the procedure described for Example 1 gave 0.78 g (67%) of (±)-1-[4,5-difluoro-7-(2-methylphenyl)-2,3-dihydro-1-benzofuran-2-yl]methanamine as a grey solid, hydrochloride salt. mp >224-227° C.; Anal. calcd. for $C_{16}H_{15}F_2NOHCl\, 0.4H_2O$: C, 60.25; H, 5.31; N, 4.39. Found: C, 59.98; H, 5.33; N, 4.39.

EXAMPLE 111

(±)-1-(5-chloro-7-methoxy-2,3-dihydro-1-benzofuran-2-yl)methanamine

Treatment of (±)-(5-chloro-7-methoxy-2,3-dihydro-1-benzofuran-2-yl)methyl 4-methylbenzenesulfonate (1.10 g, 2.98 mmol) with sodium azide (1.5 g, 23.1 mmol) generally according to the procedure described for Intermediate 98 provided (±)-2-(azidomethyl)-5-chloro-7-methoxy-2,3-dihydro-1-benzofuran. Treatment of the azide with sulfided platinum on carbon (0.080 g, 5 wt. %) generally according to the procedure described for Example 1 afforded 0.415 g (56%) of (±)-1-(5-chloro-7-methoxy-2,3-dihydro-1-benzofuran-2-yl)methanamine as a white solid, hydrochloride salt. mp 195-198° C.; Anal. calcd. for $C_{10}H_{12}ClNO_2HCl$: C, 48.02; H, 5.24; N, 5.6. Found: C, 46.41; H, 5.09; N, 5.31.

EXAMPLE 112

(±)-1-(5-chloro-2-methyl-7-phenyl-2,3-dihydro-1-benzofuran-2-yl)methanamine

Treatment of (±)-(5-chloro-2-methyl-7-{[(trifluoromethyl)sulfonyl]oxy}-2,3-dihydro-1-benzofuran-2-yl)methyl 4-methylbenzenesulfonate (5.00 g, 10.0 mmol) with phenylboronic acid (1.83 g, 15.0 mmol), dichloro[1,1'-bis(diphenylphosphino)ferrocene]palladium(II) dichloromethane adduct (0.82 g, 1.0 mmol), and potassium carbonate (2.76 g, 20.0 mmol) generally according to the procedure described for Intermediate 35 gave (±)-(5-chloro-2-methyl-7-phenyl-2,3-dihydro-1-benzofuran-2-yl)methyl 4-methylbenzenesulfonate. Treatment of (±)-(5-chloro-2-methyl-7-phenyl-2,3-dihydro-1-benzofuran-2-yl)methyl 4-methylbenzenesulfonate (4.1 g, 9.5 mmol) with sodium azide (3.9 g, 60.0 mmol) generally according to the procedure described for Intermediate 98 afforded (±)-2-(azidomethyl)-5-chloro-2-methyl-7-phenyl-2,3-dihydro-1-benzofuran. Treatment of the azide with sulfided platinum on carbon (0.350 g, 5 wt. %) generally according to the procedure described for Example 1 provided 2.0 g (64%) of (±)-1-(5-chloro-2-methyl-7-phenyl-2,3-dihydro-1-benzofuran-2-yl)methanamine as a white solid, hydrochloride salt. mp 222-225° C.; Anal. calcd. for $C_{16}H_{16}ClNOHCl$: C, 61.95; H, 5.52; N, 4.52. Found: C, 60.82; H, 5.67; N, 4.37.

EXAMPLE 113

(±)-(5-chloro-2-methyl-7-thien-3-yl-2,3-dihydro-1-benzofuran-2-yl)methylamine

Treatment of (±)-(5-chloro-2-methyl-7-{[(trifluoromethyl)sulfonyl]oxy}-2,3-dihydro-1-benzofuran-2-yl)methyl 4-methylbenzenesulfonate (5.00 g, 10.0 mmol), thiophene-3-boronic acid (1.92 g, 15.0 mmol), dichloro[1,1'-bis(diphenylphosphino)ferrocene]palladium(II) dichloromethane adduct (0.82 g, 1.0 mmol), and potassium carbonate (2.76 g, 20.0 mmol) generally according to the procedure described for Intermediate 35 provided (±)-(5-chloro-2-methyl-7-thien-3-yl-2,3-dihydro-1-benzofuran-2-yl)methyl 4-methylbenzenesulfonate. Treatment of the tosylate with sodium azide (2.00 g, 30.7 mmol) generally according to the procedure described for Intermediate 98 gave (±)-2-(azidomethyl)-5-chloro-2-methyl-7-thien-3-yl-2,3-dihydro-1-benzofuran. Treatment of the azide with sulfided platinum on carbon (0.250 g, 5 wt. %) generally according to the procedure described for Example 1 afforded 0.7 g (22%0 of (±)-(5-chloro-2-methyl-7-thien-3-yl-2,3-dihydro-1-benzofuran-2-yl)methylamine as a white solid, hydrochloride salt. mp 295-298° C. (dec); Anal. calcd. for $C_{14}H_{14}ClNOSHCl$: C, 53.17; H, 4.78; N, 4.43. Found: C, 52.80; H, 4.74; N, 4.24.

EXAMPLE 114

(±)-(5-chloro-2-methyl-7-thien-2-yl-2,3-dihydro-1-benzofuran-2-yl)methylamine

Treatment of (±)-(5-chloro-2-methyl-7-{[(trifluoromethyl)sulfonyl]oxy}-2,3-dihydro-1-benzofuran-2-yl)methyl 4-methylbenzenesulfonate (2.90 g, 5.8 mmol), thiophene-2-boronic acid (1.11 g, 8.7 mmol), dichloro[1,1'-bis(diphenylphosphino)ferrocene]palladium(II) dichloromethane adduct (0.47 g, 0.58 mmol), and potassium carbonate (1.6 g, 11.6 mmol) generally according to the procedure described for Intermediate 35 gave (±)-(5-chloro-2-methyl-7-thien-2-yl-2,3-dihydro-1-benzofuran-2-yl)methyl 4-methylbenzenesulfonate. Treatment of the tosylate with sodium azide (2.00 g, 30.7 mmol) generally according to the procedure described for Intermediate 98 provided (±)-2-(azidomethyl)-5-chloro-2-methyl-7-thien-2-yl-2,3-dihydro-1-benzofuran. Treatment of the azide with sulfided platinum on carbon (0.250 g, 5 wt. %) generally according to the procedure described for Example 1 afforded 0.58 g of (±)-(5-chloro-2-methyl-7-thien-2-yl-2,3-dihydro-1-benzofuran-2-yl)methylamine as a white solid, hydrochloride salt. mp 251-252° C.; Anal. calcd. for $C_{14}H_{14}ClNOSHCl$: C, 53.17; H, 4.78; N, 4.43. Found: C, 51.17; H, 4.48; N, 4.32.

EXAMPLE 115

(−)-1-(7-tert-butyl-5-methoxy-2,3-dihydro-1-benzofuran-2-yl)methanamine

Treatment of 0.211 g of fraction 1 obtained from the chiral HPLC separation of (±)-benzyl(7-tert-butyl-5-methoxy-2,3-dihydro-1-benzofuran-2-yl)methylcarbamate ($R_t$=4.39 min, Chiralpak OD, 2-butanol:carbon dioxide 2:8) with palladium on carbon (0.021 g, 10 wt. %) generally according to the procedure described for Example 1 gave 0.098 g (63%) of (−)-1-(7-tert-butyl-5-methoxy-2,3-dihydro-1-benzofuran-2-yl)methanamine as a white solid, hydrochloride salt. mp 157-159° C.; $[\alpha]_D^{25}$=−32.46 (c 10.0 in methanol); Anal. calcd. for $C_{14}H_{21}NO_2HCl$: C, 61.87; H, 8.16; N, 5.15. Found: C, 59.03; H, 7.86; N, 4.77.

EXAMPLE 116

(+)-1-(7-tert-butyl-5-methoxy-2,3-dihydro-1-benzofuran-2-yl)methanamine

Treatment of 0.264 g of fraction 2 obtained from the chiral HPLC separation of (±)-benzyl [(7-tert-butyl-5-methoxy-2,3-dihydro-1-benzofuran-2-yl)methyl]carbamate ($R_t$=5.07 min, Chiralpak OD, 2-butanol:carbon dioxide 2:8) with palladium on carbon (0.026 g, 10 wt. %) generally according to the procedure described for Example 1 gave 0.098 g (50%) of (+)-1-(7-tert-butyl-5-methoxy-2,3-dihydro-1-benzofuran-2-yl)methanamine as a white solid, hydrochloride salt. $[\alpha]_D^{25}$=+31.9 (c 10.0 in methanol); mp 157-159° C.; Anal. calcd. for $C_{14}H_{21}NO_2HCl$: C, 61.87; H, 8.16; N, 5.15. Found: C, 60.04; H, 8.09; N, 4.78.

EXAMPLE 117

(±)-1-{7-[(1E)-3,3-dimethylbut-1-enyl]-2,3-dihydro-1-benzofuran-2-yl}methanamine Treatment of (±)-{7-[(1E)-3,3-dimethylbut-1-enyl]-2,3-dihydro-1-benzofuran-2-yl}methyl 4-methylbenzenesulfonate (6.54 g, 16.92 mmol) with sodium azide (4.37 g, 67.68 mmol) generally according to the procedure described for Intermediate 98 afforded (±)-{7-[(1E)-3,3-dimethylbut-1-enyl]-2,3-dihydro-1-benzofuran-2-yl}methyl azide. Treatment of the azide (1.78 g, 6.92 mmol) with triphenylphosphine (1.81 g, 6.92 mmol) generally according to the procedure described for Example 21 afforded 0.454 g (28%) of (±)-1-{7-[(1E)-3,3-dimethylbut-1-enyl]-2,3-dihydro-1-benzofuran-2-yl}methanamine as a white solid, hydrochloride salt. mp 216-218° C.; Anal. calcd. for $C_{15}H_{21}NOHCl$: C, 67.28; H, 8.28; N, 5.23. Found: C, 66.19; H, 8.27; N, 5.14.

EXAMPLE 118

(±)-1-[7-(3,3-dimethylbutyl)-2,3-dihydro-1-benzofuran-2-yl]methanamine

Treatment of (±)-{7-[(1E)-3,3-dimethylbut-1-enyl]-2,3-dihydro-1-benzofuran-2-yl}methyl azide (1.82 g, 7.07 mmol) with palladium on carbon (0.18 g, 10 wt. %) generally according to the procedure described for Example 1 provided 0.642 g (34%) of (±)-1-[7-(3,3-dimethylbutyl)-2,3-dihydro-1-benzofuran-2-yl]methanamine as a white solid, hydrochloride salt. mp 158-160° C.; Anal. calcd. for $C_{15}H_{23}NOHCl$: C, 66.77; H, 8.97; N, 5.19. Found: C, 66.31; H, 8.56; N, 5.09.

EXAMPLE 119

(±)-1-{7-[(E)-2-phenylvinyl]-2,3-dihydro-1-benzofuran-2-yl}methanamine

Treatment of (±)-{7-[(E)-2-phenylvinyl]-2,3-dihydro-1-benzofuran-2-yl}methyl 4-methylbenzenesulfonate (6.53 g, 16.06 mmol) with sodium azide (4.17 g, 64.25 mmol) generally according to the procedure described for Intermediate 98 afforded (±)-(7-[(E)-2-phenylvinyl]-2,3-dihydro-1-benzofuran-2-yl}methyl azide. Treatment of (±)-{7-[(E)-2-phenylvinyl]-2,3-dihydro-1-benzofuran-2-yl}methyl azide (2.2 g, 7.9 mmol) with triphenylphosphine (2.08 g, 7.9 mmol) generally according to the procedure described for Example 21 afforded 0.675 g (34%) of (±)-1-{7-[(E)-2-phenylvinyl]-2,3-dihydro-1-benzofuran-2-yl}methanamine as a white solid, hydrochloride salt. mp 209-211° C.; Anal. calcd. for $C_{17}H_{17}NOHCl$: C, 70.95; H, 6.3; N, 4.87. Found: C, 69.63; H, 6.46; N, 4.72.

EXAMPLE 120

(±)-1-[7-(2-phenylethyl)-2,3-dihydro-1-benzofuran-2-yl]methanamine

Treatment of (±)-{7-[(E)-2-phenylvinyl]-2,3-dihydro-1-benzofuran-2-yl}methyl azide (2.2 g, 7.9 mmol) with palladium on carbon (0.22 g, 10 wt. %) generally according to the procedure described for Example 1 provided 1.1 g (48%) of (±)-1-[7-(2-phenylethyl)-2,3-dihydro-1-benzofuran-2-yl]methanamine as a white solid, hydrochloride salt. mp 155-157° C.; Anal. calcd. for $C_{17}H_{19}NOHCl$: C, 70.46; H, 6.96; N, 4.83. Found: C, 70.11; H, 7.08; N, 4.62.

EXAMPLE 121

(±)-1-[4-(4-methylphenyl)-2,3-dihydro-1-benzofuran-2-yl]methanamine

Treatment of (±)-(4-bromo-2,3-dihydro-1-benzofuran-2-yl)methyl 4-methylbenzenesulfonate (5.0 g, 13.0 mmol), o-tolylboronic acid (2.66 g, 19.57 mmol), dichlorobis(tri-o-tolylphosphine)-palladium(II) (0.512 g, 0.651 mmol), and potassium carbonate (4.51 g, 32.63 mmol) generally according to the procedure described for Intermediate 37 provided 4.0 g (77%) of (±)-1-[4-(4-methylphenyl)-2,3-dihydro-1-benzofuran-2-yl]methanamine as a yellow oil. Treatment of (±)-(4-bromo-2,3-dihydro-1-benzofuran-2-yl)methyl 4-methylbenzenesulfonate (3.8 g, 9.63 mmol) with sodium azide (2.5 g, 38.53 mmol) generally according to the procedure described for Intermediate 98 gave 2.39 g (94%) of [4-(4-methylphenyl)-2,3-dihydro-1-benzofuran-2-yl]methyl azide. Treatment of the azide with palladium on carbon (0.239 g, 10 wt. %) generally according to the procedure described for Example 1 provided 2.3 g (93%) of (±)-1-[4-(4-methylphenyl)-2,3-dihydro-1-benzofuran-2-yl]methanamine as a white solid, hydrochloride salt. mp 239-241° C.; Anal. calcd. for $C_{16}H_{17}NOHCl$: C, 69.69; H, 6.58; N, 5.08. Found: C, 69:36; H, 6.64; N, 4.93.

EXAMPLE 122

(±)-1-{4-[2-(trifluoromethyl)phenyl]-2,3-dihydro-1-benzofuran-2-yl}methanamine

Treatment of (±)-(4-bromo-2,3-dihydro-1-benzofuran-2-yl)methyl 4-methylbenzenesulfonate (5.0 g, 13.05 mmol) with 2-(trifluoromethyl)phenylboronic acid (3.72 g, 17.57 mmol), dichlorobis(tri-o-tolylphosphine)-palladium(II) (0.512 g, 0.652 mmol), and potassium carbonate (4.5 g, 32.62 mmol) generally according to the procedure described for Intermediate 37 provided 4.5 g (77%) of (±)-{4-[2-(trifluoromethyl)phenyl]-2,3-dihydro-1-benzofuran-2-yl}methyl 4-methylbenzenesulfonate as a yellow oil. Treatment of (±)-{4-[2-(trifluoromethyl)phenyl]-2,3-dihydro-1-benzofuran-2-yl}methyl 4-methylbenzenesulfonate (4.3 g, 9.59 mmol) with sodium azide (2.5 g, 38.46 mmol) generally according to the procedure described for Intermediate 98 gave 2.88 g (94%) of (±)-{4-[2-(trifluoromethyl)phenyl]-2,3-dihydro-1-benzofuran-2-yl}methyl azide. Treatment of the azide with palladium on carbon (0.28 g, 10 wt. %) generally according to the procedure described for Example 1 provided 2.46 g (83%) of (±)-1-{4-[2-(trifluoromethyl)phenyl]-2,3-dihydro-1-benzofuran-2-yl}methanamine as a white solid, hydrochloride salt. mp 213-215° C.; Anal. calcd. for $C_{16}H_{14}F_3NOHCl$: C, 58.28; H, 4.59; N, 4.25. Found: C, 58.13; H, 4.65; N, 4.13.

EXAMPLE 123

(−)-1-{4-[2-(trifluoromethyl)phenyl]-2,3-dihydro-1-benzofuran-2-yl}methanamine

Treatment of 0.825 g of fraction 1 obtained from the chiral HPLC separation of (±)-benzyl({4-[2-(trifluoromethyl)phenyl]-2,3-dihydro-1-benzofuran-2-yl}methyl)carbamate ($R_t$=5.701 min, Chiralcel OJ, ethanol:hexane 1:1) with palladium on carbon (0.082 g, 10 wt. %) generally according to the procedure described for Example 1 gave 0.480 g (76%) of (−)-1-{4-[2-(trifluoromethyl)phenyl]-2,3-dihydro-1-benzofuran-2-yl}methanamine as a white solid, hydrochloride salt. $[\alpha]_D^{25}$=−81.36 (c 10.0 in methanol); mp 203-206° C.; Anal. calcd. for $C_{16}H_{14}F_3NOHCl$: C, 58.28; H, 4.59; N, 4.25. Found: C, 58.12; H, 5.15; N, 3.92.

EXAMPLE 124

(+)-1-{4-[2-(trifluoromethyl)phenyl]-2,3-dihydro-1-benzofuran-2-yl}methanamine

Treatment of 0.800 g of fraction 2 obtained from the chiral HPLC separation of (±)-benzyl({4-[2-(trifluoromethyl)phenyl]-2,3-dihydro-1-benzofuran-2-yl}methyl)carbamate ($R_t$=7.122 min, Chiralcel OJ, ethanol:hexane 1:1) with palladium on carbon (0.080 g, 10 wt. %) generally according to the procedure described for Example 1 gave 0.334 g (54%) of (−)-1-{4-[2-(trifluoromethyl)phenyl]-2,3-dihydro-1-benzofuran-2-yl}methanamine as a white solid, hydrochloride salt. $[\alpha]_D^{25}$=+79.42 (c 10.0 in methanol); mp 203-206° C.; Anal. calcd. for $C_{16}H_{14}F_3NOHCl$: C, 58.28; H, 4.59; N, 4.25. Found: C, 57.98; H, 5.36; N, 3.85.

EXAMPLE 125

(±)-1-[4-(2,6-dimethylphenyl)-2,3-dihydro-1-benzofuran-2-yl]methanamine

Treatment of (±)-[4-(2,6-dimethylphenyl)-2,3-dihydro-1-benzofuran-2-yl]methyl 4-methylbenzenesulfonate (2.27 g, 5.55 mmol) with sodium azide (1.44 g, 22.23 mmol) generally according to the procedure described for Intermediate 98 gave 1.41 g (91%) of (±)-[4-(2,6-dimethylphenyl)-2,3-dihydro-1-benzofuran-2-yl]methyl azide. Treatment of the azide with palladium on carbon (0.141 g, 10 wt. %) generally according to the procedure described for Example 1 provided 1.36 g (93%) of (±)-1-[4-(2,6-dimethylphenyl)-2,3-dihydro-1-benzofuran-2-yl]methanamine as a white solid, hydrochloride salt. mp 254-256° C.; Anal. calcd. for $C_{17}H_{19}NOHCl$: C, 70.46; H, 6.96; N, 4.83. Found: C, 69.03; H, 7.05; N, 4.66.

EXAMPLE 126

(+)-1-[4-(2,6-dimethylphenyl)-2,3-dihydro-1-benzofuran-2-yl]methanamine

Treatment of 0.564 g of fraction 1 obtained from the chiral HPLC separation of (±)-benzyl {[4-(2,6-dimethylphenyl)-2,3-dihydro-1-benzofuran-2-yl]methyl}carbamate ($R_t$=4.818 min, Chiralcel OD, ethanol) with palladium on carbon (0.056 g, 10 wt. %) generally according to the procedure described for Example 1 gave 0.321 g (76%) of (+)-1-[4-(2,6-dimethylphenyl)-2,3-dihydro-1-benzofuran-2-yl]methanamine as a white solid, hydrochloride salt. $[\alpha]_D^{25}$=+89.54 (c 10.0 in methanol); mp >250° C.; Anal. calcd. for $C_{17}H_{19}NOHCl$: C, 70.46; H, 6.96; N, 4.83. Found: C, 68.75; H, 7.1; N, 4.32.

EXAMPLE 127

(−)-1-[4-(2,6-dimethylphenyl)-2,3-dihydro-1-benzofuran-2-yl]methanamine

Treatment of 0.372 g of fraction 2 obtained from the chiral HPLC separation of (±)-benzyl {[4-(2,6-dimethylphenyl)-2,3-dihydro-1-benzofuran-2-yl]methyl}carbamate ($R_t$ 6.985 min, Chiralcel OD, ethanol) with palladium on carbon (0.037 g, 10 wt. %) generally according to the procedure described for Example 1 gave 0.275 g (99%) of (−)-1-[4-(2,6-dimethylphenyl)-2,3-dihydro-1-benzofuran-2-yl]methanamine as a white solid, hydrochloride salt. $[\alpha]_D^{25}$=−91.76 (c 10.0 in methanol); mp >250° C.; Anal. calcd. for $C_{17}H_{19}NOHCl$: C, 70.46; H, 6.96; N, 4.83. Found: C, 68.59; H, 6.85; N, 4.48.

EXAMPLE 128

(+)-1-[7-(2-methoxyphenyl)-2,3-dihydro-1-benzofuran-2-yl]methanamine

Treatment of 0.928 g of fraction 2 obtained from the chiral HPLC separation of (±)-benzyl[7-(2-methoxyphenyl)-2,3-dihydro-1-benzofuran-2-yl]methylcarbamate (Chiralcel OD, hexane:isopropanol 9:1) with palladium on carbon (0.092 g, 10 wt. %) generally according to the procedure described for Example 1 gave 0.549 g (75%) of (+)-1-[7-(2-methoxyphenyl)-2,3-dihydro-1-benzofuran-2-yl]methanamine as a white solid, hydrochloride salt. $[\alpha]_D^{25}$=+9.90 (c 10.0 in methanol); mp 180-184° C.; Anal. calcd. for $C_{16}H_{17}NO_2HCl$: C, 65.86; H, 6.22; N, 4.8. Found: C, 64.46; H, 6.24; N, 4.63.

EXAMPLE 129

(−)-1-[7-(2-chlorophenyl)-2,3-dihydro-1-benzofuran-2-yl]methanamine

To a solution of (+)-benzyl {[7-(2-chlorophenyl)-2,3-dihydro-1-benzofuran-2-yl]methyl}carbamate (0.530 g, 1.34 mmol) in acetonitrile (25 mL) cooled to 0° C. was added iodotrimethylsilane (1.07 g, 5.38 mmol) and the reaction mixture was allowed to stir for 90 min. The reaction mixture was quenched by the addition of aqueous hydrogen chloride (25 mL, 2.0 N) and washed with diethyl ether (50 mL). The aqueous layer was neutralized with aqueous sodium hydroxide (50 mL, 2.5 N) and extracted with dichloromethane (2×100 mL). The combined organic fractions were washed with water (75 mL), saturated aqueous sodium chloride (50 mL), dried (magnesium sulfate), and the solvent removed in vacuo to provide a crude oil. The oil was re-dissolved in isopropanol (2 mL) and hydrogen chloride (5.0 mL, 1.0 M in diethyl ether) was added. The resulting precipitate was filtered, washed (diethyl ether), and dried to afford 0.229 g (58%) of (−)-1-[7-(2-chlorophenyl)-2,3-dihydro-1-benzofuran-2-yl]methanamine as a white solid, hydrochloride salt. $[\alpha]_D^{25}$=−11.06 (c 10.0 in dimethylsulfoxide); mp 186-188° C.; Anal. calcd. for $C_{15}H_{14}ClNOHCl$: C, 60.83; H, 5.1; N, 4.73. Found C, 59.59; H, 5.13; N, 4.48.

EXAMPLE 130

(+)-1-[7-(2-chlorophenyl)-2,3-dihydro-1-benzofuran-2-yl]methanamine

Treatment of (−)-benzyl {[7-(2-chlorophenyl)-2,3-dihydro-1-benzofuran-2-yl]methyl}carbamate (0.480 g, 1.22 mmol) with iodotrimethylsilane (0.975 g, 4.87 mmol) generally according to the procedure described for Example 129 afforded 0.272 g (75%) of (+)-1-[7-(2-chlorophenyl)-2,3-dihydro-1-benzofuran-2-yl]methanamine as a white solid, hydrochloride salt. $[\alpha]_D^{25}$=+9.90 (c 10.0 in dimethylsulfoxide); mp 186-188° C.; Anal. calcd. for $C_{15}H_{14}ClNOHCl$: C, 60.83; H, 5.1; N, 4.73. Found C, 60.53; H, 5.39; N, 4.62.

EXAMPLE 131

(+)-1-[7-(3-fluorophenyl)-2,3-dihydro-1-benzofuran-2-yl]methanamine

Treatment of (+)-benzyl {[7-(3-fluorophenyl)-2,3-dihydro-1-benzofuran-2-yl]methyl}carbamate (0.326 g, 0.864 mmol) with palladium on carbon (0.033 g, 10 wt. %) generally according to the procedure described for Example 1 provided 0.195 g (81%) of (+)-1-[7-(3-fluorophenyl)-2,3-dihydro-1-benzofuran-2-yl]methanamine as a white solid, hydrochloride salt. $[\alpha]_D^{25}$=+18.32 (c 10.0 in methanol); mp 186-188° C.; Anal. calcd. for $C_{15}H_{14}FNOHCl$: C, 64.4; H, 5.4; N, 5.01. Found: C, 63.32; H, 5.1; N, 4.86.

EXAMPLE 132

(−)-1-[7-(3-fluorophenyl)-2,3-dihydro-1-benzofuran-2-yl]methanamine

Treatment of (−)-benzyl {[7-(3-fluorophenyl)-2,3-dihydro-1-benzofuran-2-yl]methyl}carbamate (0.330 g, 0.874 mmol) with palladium on carbon (0.033 g, 10 wt. %) generally according to the procedure described for Example 1 provided 0.135 g (55%) of (−)-1-[7-(3-fluorophenyl)-2,3-dihydro-1-benzofuran-2-yl]methanamine as a white solid, hydrochloride salt. $[\alpha]_D^{25}$=−19.00 (c 10.0 in methanol); mp 186-188° C.; Anal. calcd. for $C_{15}H_{14}FNOHCl$: C, 64.4; H, 5.4; N, 5.01. Found: C, 63.52; H, 5.16; N, 4.91.

EXAMPLE 133

(+)-1-[7-(3-methoxyphenyl)-2,3-dihydro-1-benzofuran-2-yl]methanamine

Treatment of (+)-benzyl {[7-(3-methoxyphenyl)-2,3-dihydro-1-benzofuran-2-yl]methylcarbamate (1.36 g, 3.49 mmol) with palladium on carbon (0.136 g, 10 wt. %) generally according to the procedure described for Example 1 provided 0.70 g (79%) of (+)-1-[7-(3-methoxyphenyl)-2,3-dihydro-1-benzofuran-2-yl]methanamine as a white solid, hydrochloride salt. $[\alpha]_D^{25}$=+32.44 (c 10.0 in methanol); mp 156-158° C.; Anal. calcd. for $C_{16}H_{17}NO_2HCl$: C, 65.86; H, 6.22; N, 4.8. Found: C, 65.25; H, 6.18; N, 4.69.

EXAMPLE 134

(−)-1-[7-(3-methoxyphenyl)-2,3-dihydro-1-benzofuran-2-yl]methanamine

Treatment of (−)-benzyl {[7-(3-methoxyphenyl)-2,3-dihydro-1-benzofuran-2-yl]methyl}carbamate (1.38 g, 3.54 mmol) with palladium on carbon (0.138 g, 10 wt. %) generally according to the procedure described for Example 1 provided 0.558 g (62%) of (−)-1-[7-(3-methoxyphenyl)-2,3-dihydro-1-benzofuran-2-yl]methanamine as a white solid, hydrochloride salt. $[\alpha]_D^{25}$=−32.14 (c 10.0 in methanol); mp 156-158° C.; Anal. calcd. for $C_{16}H_{17}NO_2HCl$: C, 65.86; H, 6.22; N, 4.8. Found: C, 65.03; H, 6.22; N, 4.7.

EXAMPLE 135

(−)-1-{7-[3-(trifluoromethyl)phenyl]-2,3-dihydro-1-benzofuran-2-yl}methanamine

Treatment of 0.680 g of fraction 1 obtained from the chiral HPLC separation of (±)-benzyl({7-[3-(trifluoromethyl)phenyl]-2,3-dihydro-1-benzofuran-2-yl}methyl)carbamate (Chiralpak OJ, isopropanol:carbon dioxide 15:85) with palladium on carbon (0.068 g, 10 wt. %) generally according to the procedure described for Example 1 gave 0.301 g (67%) of (−)-1-{7-[3-(trifluoromethyl)phenyl]-2,3-dihydro-1-benzofuran-2-yl}methanamine as a white solid, hydrochloride salt. $[\alpha]_D^{25}$=−31.74 (c 10.0 in methanol); mp 184-186° C.; Anal. calcd. for $C_{16}H_{14}F_3NOHCl$: C, 58.28; H, 4.59; N, 4.25. Found: C, 58.15; H, 4.57; N, 4.21.

EXAMPLE 136

(+)-1-{7-[3-(trifluoromethyl)phenyl]-2,3-dihydro-1-benzofuran-2-yl}methanamine

Treatment of 0.700 g of fraction 2 obtained from the chiral HPLC separation of (±)-benzyl({7-[3-(trifluoromethyl)phenyl]-2,3-dihydro-1-benzofuran-2-yl}methyl)carbamate (Chiralpak OJ, isopropanol:carbon dioxide 15:85) with palladium on carbon (0.070 g, 10 wt. %) generally according to the procedure described for Example 1 gave 0.328 g (61%) of (+)-1-{7-[3-(trifluoromethyl)phenyl]-2,3-dihydro-1-benzofuran-2-yl}methanamine as a white solid, hydrochloride salt.

[α]$_D^{25}$=+31.66 (c 10.0 in methanol); mp 184-186° C.; Anal. calcd. for C$_{16}$H$_{14}$F$_3$NOHCl: C, 58.28; H, 4.59; N, 4.25. Found: C, 57.96; H, 4.44; N, 4.16.

EXAMPLE 137

(+)-1-{7-[4-(trifluoromethyl)phenyl]-2,3-dihydro-1-benzofuran-2-yl}methanamine

Treatment of 0.720 g of fraction 1 obtained from the chiral HPLC separation of (±)-benzyl({7-[4-(trifluoromethyl)phenyl]-2,3-dihydro-1-benzofuran-2-yl}methyl)carbamate (Chiralpak AD, methanol:water 95:5) with palladium on carbon (0.072 g, 10 wt. %) generally according to the procedure described for Example 1 gave 0.411 g (74%) of (+)-1-{7-[4-(trifluoromethyl)phenyl]-2,3-dihydro-1-benzofuran-2-yl}methanamine as a white solid, hydrochloride salt. [α]$_D^{25}$=+15.90 (c 10.0 in methanol); mp 226-229° C.; Anal. calcd. for C$_{16}$H$_{14}$F$_3$NOHCl: C, 58.28; H, 4.59; N, 4.25. Found: C, 57.31; H, 4.84; N, 4.09.

EXAMPLE 138

(−)-1-{7-[4-(trifluoromethyl)phenyl]-2,3-dihydro-1-benzofuran-2-yl}methanamine

Treatment of 0.740 g of fraction 2 obtained from the chiral HPLC separation of (±)-benzyl({7-[4-(trifluoromethyl)phenyl]-2,3-dihydro-1-benzofuran-2-yl}methyl)carbamate (Chiralpak AD, methanol:water 95:5) with palladium on carbon (0.074 g, 10 wt. %) generally according to the procedure described for Example 1 gave 0.425 g (74%) of (−)-1-{7-[4-(trifluoromethyl)phenyl]-2,3-dihydro-1-benzofuran-2-yl}methanamine as a white solid, hydrochloride salt. [α]$_D^{25}$=−14.98 (c 10.0 in methanol); mp 226-229° C.; Anal. calcd. for C$_{16}$H$_{14}$F$_3$NOHCl: C, 58.28; H, 4.59; N, 4.25. Found: C, 57.48; H, 4.51; N, 4.09.

EXAMPLE 139

(±)-1-[7-(2,6-difluorophenyl)-2,3-dihydro-1-benzofuran-2-yl]methanamine

Treatment of (±)-[7-(2,6-difluorophenyl)-2,3-dihydro-1-benzofuran-2-yl]methanol (3.5 g, 13.35 mmol) with p-toluenesulfonyl chloride (3.05 g, 16.01 mol) generally according to the procedure described for Intermediate 10 gave 3.5 g (64%) of (±)-[7-(2,6-difluorophenyl)-2,3-dihydro-1-benzofuran-2-yl]methyl 4-methylbenzenesulfonate. Treatment of (±)-[7-(2,6-difluorophenyl)-2,3-dihydro-1-benzofuran-2-yl] methyl 4-methylbenzenesulfonate (3.0 g, 7.20 mmol) with sodium azide (1.87 g, 28.8 mmol) generally according to the procedure described for Intermediate 98 gave (±)-[7-(2,6-difluorophenyl)-2,3-dihydro-1-benzofuran-2-yl]methyl azide. Treatment of the azide with palladium on carbon (0.20 g, 10 wt. %) generally according to the procedure described for Example 1 provided 1.69 g (90%) of (±)-1-[7-(2,6-difluorophenyl)-2,3-dihydro-1-benzofuran-2-yl]methanamine as a white solid, hydrochloride salt. mp 219-222° C.; Anal. calcd. for C$_{15}$H$_{13}$F$_2$NOHCl: C, 60.51; H, 4.74; N, 4.7. Found: C, 60.34; H, 4.87; N, 4.58.

EXAMPLE 140

(±)-1-[7-(2,6-dichlorophenyl)-2,3-dihydro-1-benzofuran-2-yl]methanamine

Treatment of (±)-[7-(2,6-dichlorophenyl)-2,3-dihydro-1-benzofuran-2-yl]methyl 4-methylbenzenesulfonate (0.75 g, 1.67 mmol) with sodium azide (0.43 g, 6.67 mmol) generally according to the procedure described for Intermediate 98 afforded 0.48 g (90%) of (±)-[7-(2,6-dichlorophenyl)-2,3-dihydro-1-benzofuran-2-yl]methyl azide. Treatment of the azide with triphenylphosphine (0.393 g, 1.49 mmol) generally according to the procedure described for Example 21 afforded 0.348 g (71%) of (±)-1-[7-(2,6-dichlorophenyl)-2,3-dihydro-1-benzofuran-2-yl]methanamine as a white solid, hydrochloride salt. mp 206-208° C.; Anal. calcd. for C$_{15}$H$_{13}$Cl$_2$NOHCl: C, 54.49; H, 4.27; N, 4.24. Found: C, 54.38; H, 4.36; N, 4.12.

EXAMPLE 141

(−)-1-[7-(2,6-dichlorophenyl)-2,3-dihydro-1-benzofuran-2-yl]methanamine

Treatment of 0.081 g of fraction 1 obtained from the chiral HPLC separation of (±)-benzyl {[7-(2,6-dichlorophenyl)-2,3-dihydro-1-benzofuran-2-yl]methyl}carbamate (Chiralpak AD, ethanol:hexane 1:1) with iodotrimethylsilane (0.153 g, 0.766 mmol) generally according to the procedure described for Example 129 gave 0.039 g (58%) of (−)-1-[7-(2,6-dichlorophenyl)-2,3-dihydro-1-benzofuran-2-yl]methanamine as a white solid, hydrochloride salt. [α]$_D^{25}$=−29.8 (c 10.0 in dimethylsulfoxide); mp 207-209° C.; Anal. calcd. for C$_{15}$H$_{13}$Cl$_2$NOHCl: C, 54.49; H, 4.27; N, 4.24. Found: C, 54.74; H, 3.97; N, 4.23.

EXAMPLE 142

(+)-1-[7-(2,6-dichlorophenyl)-2,3-dihydro-1-benzofuran-2-yl]methanamine

Treatment of 0.132 g of fraction 2 obtained from the chiral HPLC separation of (±)-benzyl {[7-(2,6-dichlorophenyl)-2,3-dihydro-1-benzofuran-2-yl]methyl}carbamate (Chiralpak AD, ethanol:hexane 1:1) with iodotrimethylsilane (0.247 g, 1.23 mmol) generally according to the procedure described for Example 129 gave 0.036 g (56%) of (+)-1-[7-(2,6-dichlorophenyl)-2,3-dihydro-1-benzofuran-2-yl]methanamine as a white solid, hydrochloride salt. [α]$_D^{25}$=+30.0 (c 10.0 in dimethylsulfoxide); mp 207-209° C.; Anal. calcd. for C$_{15}$H$_{13}$Cl$_2$NOHCl: C, 54.49; H, 4.27; N, 4.24. Found: C, 54.43; H, 4.017; N, 4.19.

EXAMPLE 143

(±)-1-[7-(2,4-dimethoxyphenyl)-2,3-dihydro-1-benzofuran-2-yl]methanamine

Treatment of (±)-[7-(2,4-dimethoxyphenyl)-2,3-dihydro-1-benzofuran-2-yl]methyl 4-methylbenzenesulfonate (3.0 g, 6.81 mmol) with sodium azide (1.77 g, 27.26 mmol) generally according to the procedure described for Intermediate 98 afforded (±)-2-(azidomethyl)-7-(2,4-dimethoxyphenyl)-2,3-dihydro-1-benzofuran. Treatment of the azide with palladium on carbon (0.215 g, 10 wt. %) generally according to the procedure described for Example 1 provided 1.57 g (72%) of (±)-1-[7-(2,4-dimethoxyphenyl)-2,3-dihydro-1-benzofuran-2-yl]methanamine as a white solid, hydrochloride salt. mp 175-178° C.; Anal. calcd. for C$_{17}$H$_{19}$NO$_3$HCl: C, 63.45; H, 6.26; N, 4.35. Found: C, 62.59; H, 6.25; N, 4.01.

EXAMPLE 144

(−)-1-[7-(2,4-dimethoxyphenyl)-2,3-dihydro-1-benzofuran-2-yl]methanamine

Treatment of (+)-benzyl {[7-(2,4-dimethoxyphenyl)-2,3-dihydro-1-benzofuran-2-yl]methyl}carbamate (0.660 g, 1.57 mmol) with palladium on carbon (0.066 g, 10 wt. %) generally according to the procedure described for Example 1 afforded 0.242 g (48%) of (−)-1-[7-(2,4-dimethoxyphenyl)-2,3-dihydro-1-benzofuran-2-yl]methanamine as a pale yellow solid, hydrochloride salt. $[\alpha]_D^{25}$=−4.7 (c 10.0 in methanol); mp 166-168° C.; Anal. calcd. for $C_{17}H_{19}NO_3HCl$: C, 63.45; H, 6.26; N, 4.35. Found: C, 60.84; H, 6.51; N, 3.98.

EXAMPLE 145

(+)-1-[7-(2,4-dimethoxyphenyl)-2,3-dihydro-1-benzofuran-2-yl]methanamine

Treatment of (−)-benzyl {[7-(2,4-dimethoxyphenyl)-2,3-dihydro-1-benzofuran-2-yl]methyl}carbamate (0.638 g, 1.52 mmol) with palladium on carbon (0.066 g, 10 wt. %) generally according to the procedure described for Example 1 afforded 0.357 g (73%) of (+)-1-[7-(2,4-dimethoxyphenyl)-2,3-dihydro-1-benzofuran-2-yl]methanamine as a pale yellow solid, hydrochloride salt. $[\alpha]_D^{25}$=+1.16 (c 10.0 in methanol); mp 166-168° C.; Anal. calcd. for $C_{17}H_{19}NO_3HCl$: C, 63.45; H, 6.26; N, 4.35. Found: C, 61.94; H, 6.85; N, 3.76.

EXAMPLE 146

(±)-1-[7-(2,4-difluorophenyl)-2,3-dihydro-1-benzofuran-2-yl]methanamine

Treatment of (±)-[7-(2,4-difluorophenyl)-2,3-dihydro-1-benzofuran-2-yl]methyl 4-methylbenzenesulfonate (4.3 g, 10.37 mmol) with sodium azide (3.03 g, 46.68 mmol) generally according to the procedure described for Intermediate 98 gave 2.91 g (98%) of (±)-[7-(2,4-difluorophenyl)-2,3-dihydro-1-benzofuran-2-yl]methyl azide. Treatment of the azide with palladium on carbon (0.29 g, 10 wt. %) generally according to the procedure described for Example 1 afforded 2.3 g (76%) of (±)-1-[7-(2,4-difluorophenyl)-2,3-dihydro-1-benzofuran-2-yl]methanamine as a white solid, hydrochloride salt. mp 222-224° C.; Anal calcd. for $C_{15}H_{13}F_2NOHCl$: C, 60.51; H, 4.74; N, 4.7. Found C, 60.65; H, 4.76; N, 4.51.

EXAMPLE 147

(+)-1-[7-(2,4-difluorophenyl)-2,3-dihydro-1-benzofuran-2-yl]methanamine

Treatment of (+)-benzyl {[7-(2,4-difluorophenyl)-2,3-dihydro-1-benzofuran-2-yl]methyl}carbamate (1.1 g, 2.78 mmol) with palladium on carbon (0.135 g, 10 wt. %) generally according to the procedure described for Example 1 gave 0.312 g (43%) of (+)-1-[7-(2,4-difluorophenyl)-2,3-dihydro-1-benzofuran-2-yl]methanamine as a white solid, hydrochloride salt. $[\alpha]_D^{25}$=+3.58 (c 10.0 in dimethylsulfoxide); mp 222-224° C.; Anal. calcd. for $C_{15}H_{13}F_2NOHCl$: C, 60.51; H, 4.74; N, 4.7. Found: C, 59.98; H, 4.7; N, 4.64.

EXAMPLE 148

(−)-1-[7-(2,4-difluorophenyl)-2,3-dihydro-1-benzofuran-2-yl]methanamine

Treatment of (−)-benzyl {[7-(2,4-difluorophenyl)-2,3-dihydro-1-benzofuran-2-yl]methyl}carbamate (0.612 g, 1.55 mmol) with palladium on carbon (0.061 g, 10 wt. %) generally according to the procedure described for Example 1 gave 0.268 g (66%) of (−)-1-[7-(2,4-difluorophenyl)-2,3-dihydro-1-benzofuran-2-yl]methanamine as a white solid, hydrochloride salt. $[\alpha]_D^{25}$=−4.66 (c 10.0 in dimethylsulfoxide); mp 222-224° C.; Anal. calcd. for $C_{15}H_{13}F_2NOHCl$: C, 60.51; H, 4.74; N, 4.7. Found: C, 60.34; H, 4.58; N, 4.48.

EXAMPLE 149

(−)-1-[7-(2,4-dichlorophenyl)-2,3-dihydro-1-benzofuran-2-yl]methanamine

Treatment of (+)-benzyl {[7-(2,4-dichlorophenyl)-2,3-dihydro-1-benzofuran-2-yl]methyl}carbamate (2.06 g, 4.81 mmol) with iodotrimethylsilane (3.85 g, 19.24 mmol) generally according to the procedure described for Example 129 gave 0.933 g (85%) of (−)-1-[7-(2,4-dichlorophenyl)-2,3-dihydro-1-benzofuran-2-yl]methanamine as a white solid, hydrochloride salt. $[\alpha]_D^{25}$=−3.34 (c 10.0 in dimethylsulfoxide); mp 203-206° C.; Anal. calcd. for $C_{15}H_{13}Cl_2NOHCl$: C, 54.59; H, 4.27; N, 4.24. Found: C, 53.69; H, 3.96; N, 3.99.

EXAMPLE 150

(+)-1-[7-(2,4-dichlorophenyl)-2,3-dihydro-1-benzofuran-2-yl]methanamine

Treatment of (−)-benzyl {[7-(2,4-dichlorophenyl)-2,3-dihydro-1-benzofuran-2-yl]methyl}carbamate (1.85 g, 4.32 mmol) with iodotrimethylsilane (3.45 g, 17.28 mmol) generally according to the procedure described for Example 129 gave 1.04 g (82%) of (+)-1-[7-(2,4-dichlorophenyl)-2,3-dihydro-1-benzofuran-2-yl]methanamine as a white solid, hydrochloride salt. $[\alpha]_D^{25}$=+2.7 (c 10.0 in dimethylsulfoxide); mp 201-204° C.; Anal. calcd. for $C_{15}H_{13}Cl_2NOHCl$: C, 54.59; H, 4.27; N, 4.24. Found: C, 54.25; H, 4.12; N, 4.16.

EXAMPLE 151

(−)-1-{5-fluoro-7-[2-(trifluoromethyl)phenyl]-2,3-dihydro-1-benzofuran-2-yl}methanamine Treatment of 0.837 g of fraction 1 obtained from the chiral HPLC separation of (±)-benzyl({5-fluoro-7-[2-(trifluoromethyl)phenyl]-2,3-dihydro-1-benzofuran-2-yl}methyl)carbamate ($R_t$=4.965 min, Chiralcel AD, methanol) with iodotrimethylsilane (1.50 g, 7.51 mmol) generally according to the procedure described for Example 129 gave 0.301 g (51%) of (−)-1-{5-fluoro-7-[2-(trifluoromethyl)phenyl]-2,3-dihydro-1-benzofuran-2-yl}methanamine as a white solid, hydrochloride salt. $[\alpha]_D^{25}$=−20.00 (c 10.0 in methanol); mp 183-188° C.; Anal. calcd. for $C_{16}H_{13}F_4NOHCl$: C, 55.26; H, 4.06; N, 4.03. Found: C, 53.42; H, 4.1; N, 4.4.

EXAMPLE 152

(+)-1-{5-fluoro-7-[2-(trifluoromethyl)phenyl]-2,3-dihydro-1-benzofuran-2-yl}methanamine Treatment of 0.751 g of fraction 2 obtained from the chiral HPLC separation of (±)-benzyl({5-fluoro-7-[2-(trifluoromethyl)phenyl]-2,3-dihydro-1-benzofuran-2-yl}methyl)carbamate ($R_t$=6.877 min, Chiralcel AD, methanol) with iodotrimethylsilane (0.675 g, 3.37 mmol) generally according to the procedure described for Example 129 gave 0.211 g (36%) of (+)-1-{5-fluoro-7-[2-(trifluoromethyl)phenyl]-2,3-dihydro-1-benzofuran-2-yl}methanamine as a white solid, hydrochloride salt. $[\alpha]_D^{25}$=+18.98 (c 10.0 in methanol); mp 193-197° C.; Anal. calcd. for $C_{16}H_{13}F_4NOHCl$: C, 55.26; H, 4.06; N, 4.03. Found: C, 51.01; H, 3.76; N, 4.14.

EXAMPLE 153

No compound

EXAMPLE 154

(±)-1-[7-(2,3-dimethylphenyl)-2,3-dihydro-1-benzofuran-2-yl]methanamine

Treatment of (±)-(7-bromo-2,3-dihydro-1-benzofuran-2-yl)methyl 4-methylbenzenesulfonate (0.50 g, 1.305 mmol) with (2,3-dimethyl-phenyl)boronic acid (0.294 g, 1.96 mmol), dichlorobis(tri-o-tolylphosphine)-palladium(II) (0.041 g, 0.052 mmol), and potassium carbonate (0.41 g, 3.25 mmol) generally according to the procedure described for Intermediate 37 provided 0.335 g (62%) of (±)-[7-(2,3-dimethylphenyl)-2,3-dihydro-1-benzofuran-2-yl]methyl 4-methylbenzenesulfonate. Treatment of (±)-[7-(2,3-dimethylphenyl)-2,3-dihydro-1-benzofuran-2-yl]methyl 4-methylbenzenesulfonate with sodium azide (0.134 g, 2.06 mmol) generally according to the procedure described for Intermediate 98 afforded (±)-2-(azidomethyl)-7-(2,3-dichlorophenyl)-2,3-dihydro-1-benzofuran-7 amine. To a solution of (±)-2-(azidomethyl)-7-(2,3-dichlorophenyl)-2,3-dihydro-1-benzofuran-7 amine (0.135 g, 1.483 mmol) in tetrahydrofuran (5 mL) was added polymer supported triphenyl phosphine (0.152 g, 0.58 mmol) and the reaction mixture was allowed to stir at room temperature for 12 h. The reaction mixture was filtered (celite) and the solvent removed in vacuo to provide a colorless oil. The oil was re-dissolved in isopropanol (3 mL) and hydrogen chloride (1.0 N in diethyl ether, 10.0 mL) was added. The resulting precipitate was filtered, washed (diethyl ether), and dried to afford 0.075 g (54%) of (±)-1-[7-(2,3-dimethylphenyl)-2,3-dihydro-1-benzofuran-2-yl]methanamine as a white solid, hydrochloride salt. mp>225° C.:

EXAMPLE 155

(±)-{[7-(2,3-dimethoxyphenyl)-2,3-dihydro-1-benzofuran-2-yl]methyl}amine

The title compound was prepared following the general procedure of Example 154 as a light yellow solid (2.91 g, 58%) from (±)-(7-bromo-2,3-dihydro-1-benzofuran-2-yl) methyl 4-methylbenzenesulfonate (6.0 g, 15.65 mmol) and (2,3-dimethoxyphenyl)boronic acid (4.27 g, 23.49 mmol). mp 219-222° C.

EXAMPLE 156

(−)-{[(7-(2,3-dimethoxyphenyl)-2,3-dihydro-1-benzofuran-2-yl]methyl}amine

Treatment of 1.46 g of fraction 1 obtained from the chiral HPLC separation of (±)-benzyl {[7-(2,3-dimethoxyphenyl)-2,3-dihydro-1-benzofuran-2-yl]methyl}carbamate Chiralcel OD, 2-butanol:carbon dioxide 3:7 with palladium on carbon (0.146 g, 10 wt. %) generally according to the procedure described for Example 1 gave 0.767 g (69%) of (−)-{[(−7-(2, 3-dimethoxyphenyl)-2,3-dihydro-1-benzofuran-2-yl] methyl}amine as a tan solid, hydrochloride salt. $[\alpha]_D^{25}$= −65.6 (c 10.0 in methanol); mp 146-148° C.

EXAMPLE 157

(+)-{[(7-(2,3-dimethoxyphenyl)-2,3-dihydro-1-benzofuran-2-yl]methyl}amine

Treatment of 1.45 g of fraction 2 obtained from the chiral HPLC separation of (±)-benzyl {[7-(2,3-dimethoxyphenyl)-2,3-dihydro-1-benzofuran-2-yl]methyl}carbamate Chiralcel OD, 2-butanol:carbon dioxide 3:7 with palladium on carbon (0.146 g, 10 wt. %) generally according to the procedure described for Example 1 gave 0.86 g (77%) of (+)-{[(7-(2,3-dimethoxyphenyl)-2,3-dihydro-1-benzofuran-2-yl] methyl}amine as a white solid, hydrochloride salt. $[\alpha]_D^{25}$= +61.6 (c 10.0 in methanol); mp 146-148° C.

EXAMPLE 158

(+)-{[7-(4-chloro-2-methylphenyl)-2,3-dihydro-1-benzofuran-2-yl]methyl}amine

Treatment of fraction 1 (0.437 g) obtained from the chiral HPLC separation of (±)-benzyl {[7-(4-chloro-2-methylphenyl)-2,3-dihydro-1-benzofuran-2-yl]methyl}carbamate (Chiralcel AD, ethanol:hexane 1:10) in acetonitrile (25 mL) was cooled to 0° C. and treated with iodotrimethylsilane (0.883 g, 4.413 mmol) and the reaction mixture was allowed to stir at for 1 h. The solvent was removed in vacuo and the residue quenched with aqueous hydrogen chloride (2.0 N) (300 mL) and washed with diethyl ether (300 mL). The aqueous layer was separated, treated with 10% potassium hydroxide and dichloromethane (600 mL). The combined organic layers were washed with water (200 mL) and saturated aqueous sodium chloride (200 mL), was dried (magnesium sulfate), and the solvent was removed in vacuo to provide 0.20 g (60%) of (+){[-7-(4-chloro-2-methylphenyl)-2,3-dihydro-1-benzofuran-2-yl]methyl}amine (0.437 g, 1.07 mmol) as a white solid, hydrochloride salt. $[\alpha]_D^{25}$=+10.2 (c 10.0 in methanol); mp 190-191° C.

EXAMPLE 159

(−)-{[7-(4-chloro-2-methylphenyl)-2,3-dihydro-1-benzofuran-2-yl]methyl}amine

The title compound was prepared (0.224 g, 74%) following the general procedure of Example 158 as a white solid, hydrochloride salt from (−)-benzyl {[7-(4-chloro-2-methylphenyl)-2,3-dihydro-1-benzofuran-2-yl]methyl}carbamate (0.40 g, 0.981 mmol) and iodotrimethylsilane (0.785 g, 3.92 mmol). $[\alpha]_D^{25}$=−13.0 (c 10.0 in methanol); mp 190-191° C.

EXAMPLE 160

(±)-{[7-(2,3-difluorophenyl)-2,3-dihydro-1-benzofuran-2-yl]methyl}amine

The title compound was prepared (0.051 g, 26%) following the general procedure of Example 154 as a light yellow solid, hydrochloride salt from (±)-(7-bromo-2,3-dihydro-1-benzofuran-2-yl)methyl 4-methylbenzenesulfonate (0.50 g, 1.31 mmol) and (2,3-difluoroyphenyl)boronic acid (0.618 g, 3.91 mmol). mp 219-222° C.

EXAMPLE 161

(±)-{[7-(2,5-dimethylphenyl)-2,3-dihydro-1-benzofuran-2-yl]methyl}amine

The title compound was prepared (0.075 g, 40%) following the general procedure of Example 154 as a white solid, hydrochloride salt from (±)-(7-bromo-2,3-dihydro-1-benzofuran-2-yl)methyl 4-methylbenzenesulfonate (0.50 g, 1.31 mmol) and (2,5-dimethylphenyl)boronic acid (0.618 g, 3.91 mmol). mp >225° C.

EXAMPLE 162

(±)-{[7-(2,5-dimethoxyphenyl)-2,3-dihydro-1-benzofuran-2-yl]methyl}amine

The title compound was prepared (0.043 g, 35%) following the general procedure of Example 154 as a white solid, hydrochloride salt from (±)-(7-bromo-2,3-dihydro-1-benzofuran-2-yl)methyl 4-methylbenzenesulfonate (0.50 g, 1.31 mmol) and (2,5-dimethoxyphenyl)boronic acid (0.356 g, 1.96 mmol). mp 128-132° C.

EXAMPLE 163

(±)-{[7-(2,5-dichlorophenyl)-2,3-dihydro-1-benzofuran-2-yl]methyl}amine

The title compound was prepared (0.56 g, 45%) following the general procedure of Example 154 as a white solid, hydrochloride salt from (±)-(7-bromo-2,3-dihydro-1-benzofuran-2-yl)methyl 4-methylbenzenesulfonate (1.43 g, 1.31 mmol) and (2,5-dichlorophenyl)boronic acid (1.07 g, 5.59 mmol). mp 203-205° C.

EXAMPLE 164

(+)-{[7-(2,5-dichlorophenyl)-2,3-dihydro-1-benzofuran-2-yl]methyl}amine

Treatment of 0.771 g of fraction 2 obtained from the chiral HPLC separation of (±)-benzyl {[7-(2,5-dichlorophenyl)-2,3-dihydro-1-benzofuran-2-yl]methyl}carbamate with trimethylsilyl iodide (1.44 g, 7.20 mmol) generally according to the procedure described for Example 158 gave 0.202 g (59%) of (+)-{[(7-(2,5-dichlorophenyl)-2,3-dihydro-1-benzofuran-2-yl]methyl}amine as a white solid, hydrochloride salt $[\alpha]_D^{25}$=+16.0 (c 10.0 in methanol); mp 181-183° C.

EXAMPLE 165

(−)-{[7-(2,5-dichlorophenyl)-2,3-dihydro-1-benzofuran-2-yl]methyl}amine

Treatment of 0.710 g of fraction 1 obtained from the chiral HPLC separation of (±)-benzyl {[7-(2,5-dichlorophenyl)-2,3-dihydro-1-benzofuran-2-yl]methyl}carbamate with trimethylsilyl iodide (1.33 g, 6.63 mmol) generally according to the procedure described for Example 158 gave 0.202 g (45%) of (−)-{[(−7-(2,5-dichlorophenyl)-2,3-dihydro-1-benzofuran-2-yl]methyl}amine as a white solid, hydrochloride salt. $[\alpha]_D^{25}$=−14.4 (c 10.0 in methanol); mp 184-186° C.

EXAMPLE 166

(±)-{[7-(2,4,6-trichlorophenyl)-2,3-dihydro-1-benzofuran-2-yl]methyl}amine

Treatment of 2,4,6-trichlorobromobenzene (14.5 g, 55.69 mmol) with 2-methoxybenzeneboronic acid (12.69 g, 83.54 mol), dichlorobis(tri-o-tolylphosphine)-palladium(II) (0.656 g, 0.835 mmol), and potassium carbonate (19.21 g, 139.22 mmol) generally according to the procedure described for Intermediate 37 provided 9.8 g (61%) of 2'4',6'-trichloro-1,1'-biphenyl-2-yl methyl ether. To a solution of 2' 4',6'-trichloro-1,1'-biphenyl-2-yl methyl ether (9.8 g, 34.08 mmol) in dichloromethane (100 mL) cooled to −78° C. was added boron tribromide (9.38 g, 1.0 M in dichloromethane) generally according to the procedure described for Intermediate 163 provided 9.2 g of 2',4',6'-trichlorobiphenyl-2-ol as a yellow solid. Treatment of 2',4',6'-trichloro-1,1'-biphenyl-2-ol (9.17 g, 33.52 mmol) with potassium carbonate (18.53 g, 134.1 mmol) and allyl bromide (4.46 g, 36.87 mol), followed by refluxing the resultant allyl ether in mesitylene generally according to the procedure described for Intermediate 8 provided 3-allyl-2',4',6'-trichloro-1,1'-biphenyl-2-ol. Treatment of 3-allyl-2',4',6'-trichloro-1,1'-biphenyl-2-ol. (10.35 g, 33.00 mmol) with 3-chloroperoxybenzoic acid (17.08 g, 99.00 mmol, 77%) followed by potassium carbonate (11.40 g, 82.51 mmol) generally according to the procedure described for Intermediate 9 afforded 10.4 g (95%) of (±)-[7-(2,4,6-trichlorophenyl)-2,3-dihydro-1-benzofuran-2-yl]methanol. Treatment of (±)-[7-(2,4,6-trichlorophenyl)-2,3-dihydro-1-benzofuran-2-yl]methanol (10.38 g, 31.49 mmol) with p-toluenesulfonyl chloride (7.20 g, 37.79 mol) generally according to the procedure described for Intermediate 10 gave 10.5 g (68%) of (±)-[7-(2,4,6-trichlorophenyl)-2,3-dihydro-1-benzofuran-2-yl]methyl 4-methylbenzenesulfonate as a white solid. Treatment of (±)-[7-(2,4,6-trichlorophenyl)-2,3-dihydro-1-benzofuran-2-yl]methyl 4-methylbenzenesulfonate (1.38 g, 2.85 mmol) with sodium azide (0.74 g, 11.4 mmol) generally according to the procedure described for Intermediate 98 afforded 0.93 g, (92%) of (±)-2-(azidomethyl)-7-(2,4,6-trichlorophenyl)-2,3-dihydro-1-benzofuran. To a solution of (±)-2-(azidomethyl)-7-(2,4,6-trichlorophenyl)-2,3-dihydro-1-benzofuran in tetrahydrofuran (75 mL) was added polymer-supported triphenylphosphine (1.36 g, 5.24 mmol) and the reaction was allowed to stir at room temperature 12 h. The reaction mixture was filtered (celite) and the solvent removed in vacuo to provide a crude oil. Purification by flash column chromatography (silica, 10% aqueous ammonium hydroxide in methanol:ethyl acetate 1:9) provided a colorless oil. The oil was re-dissolved in isopropanol (2 mL) and hydrogen chloride (6 mL, 1.0 M in diethyl ether) was added. The resulting precipitate was filtered, washed (diethyl ether), and dried to give 0.53 g (56%) of (±)-{[7-(2,4,6-trichlorophenyl)-2,3-dihydro-1-benzofuran-2-yl]methyl}amine as a white solid, hydrochloride salt. mp> 225° C.

EXAMPLE 167

(±)-{[7-(4-chloro-2-methylphenyl)-2,3-dihydro-1-benzofuran-2-yl]methyl}amine

The title compound was prepared (1.01 g, 13%) following the general procedure of Example 154 as a white solid, hydrochloride salt from 1-bromo-4-chloro-2-methyl-benzene (5.0 g, 24.33 mmol) and (2-methoxyphenyl)boronic acid (4.8 g, 31.63 mmol). mp 175-177° C.

EXAMPLE 168

(±)-{[7-(5-chloro-2-methylphenyl)-2,3-dihydro-1-benzofuran-2-yl]methyl}amine

The title compound was prepared (0.68 g, 31%) following the general procedure of Example 154 as a white solid, hydrochloride salt from (±)-(7-bromo-2,3-dihydro-1-benzofuran-2-yl)methyl 4-methylbenzenesulfonate (0.50 g, 1.31 mmol) and (5-chloro-2-methylphenyl)boronic acid (0.334 g, 1.96 mmol). mp 146-150° C.

EXAMPLE 169

(±)-{[7-(5-chloro-2-methoxyphenyl)-2,3-dihydro-1-benzofuran-2-yl]methyl}amine

The title compound was prepared (0.68 g, 35%) following the general procedure of Example 154 as a white solid, hydrochloride salt from (±)-(7-bromo-2,3-dihydro-1-benzofuran-2-yl)methyl 4-methylbenzenesulfonate (0.50 g, 1.31 mmol) and (5-chloro-2-methyoxlphenyl)boronic acid (0.365 g, 1.96 mmol). mp 149-152° C.

EXAMPLE 170

(±)-[(7-pyridin-3-yl-2,3-dihydro-1-benzofuran-2-yl)methyl]amine

The title compound was prepared (0.770 g, 69%) following the general procedure of Example 154 as a light brown solid, hydrochloride salt from (±)-(7-bromo-2,3-dihydro-1-benzofuran-2-yl)methyl 4-methylbenzenesulfonate (4.0 g, 10.44 mmol) and pyridine-3-ylboronic acid (3.85 g, 31.31 mmol). mp 158-162° C.

EXAMPLE 171

(+)-{[7-pyridin-3-yl-2,3-dihydro-1-benzofuran-2-yl]methyl}amine

The title compound was prepared (0.17 g, 78%) following the general procedure of Example 129 as a yellow solid, hydrochloride salt from (+)-benzyl {[7-pyridin-3-yl-2,3-dihydro-1-benzofuran-2-yl]methyl}carbamate (0.30 g, 0.832 mmol) and trimethylsilyl iodide (0.66 g, 3.33 mmol). $[\alpha]_D^{25}$=+27.2 (c 10.0 in methanol); mp 168-171° C.

EXAMPLE 172

(−)-{[7-pyridin-3-yl-2,3-dihydro-1-benzofuran-2-yl]methyl}amine

The title compound was prepared (0.172 g, 78%) following the general procedure of Example 129 as a light yellow solid, hydrochloride salt from (+)-benzyl {[7-pyridin-3-yl-2,3-dihydro-1-benzofuran-2-yl]methyl}carbamate (0.33 g, 0.91 mmol) and trimethylsilyl iodide (0.73 g, 3.64 mmol). $[\alpha]_D^{25}$=−20.4 (c 10.0 in methanol); mp 168-171° C.

EXAMPLE 173

(±)-N-[2-(aminomethyl)-2,3-dihydro-1-benzofuran-7-yl]-N-phenylamine

To a solution of (±)-(7-anilino-2,3-dihydro-1-benzofuran-2-yl)methyl 4-methylbenzenesulfonate (0.5 g, 1.5 mmol) in toluene (20 mL) was added bromobenzene (0.23 g, 1.5 mmol), dichloro[1,1'-bis(diphenylphosphino)ferrocene]palladium(II) dichloromethane adduct (0.061 g, 0.075 mmol), 1,1'-bis(diphenylphosphino)ferrocene (0.125 g, 0.225 mmol), and sodium tert-butoxide (0.18 g, 1.875 mmol) and the reaction mixture was allowed to reflux 3 h. The solvent was removed in vacuo. The residue was washed with water (100 mL) and ethyl acetate (50 mL). The combined organic layers were washed with saturated aqueous sodium chloride, dried (magnesium sulfate), and the solvent removed in vacuo to provide a crude oil. Purification by flash column chromatography (silica, ethyl acetate:hexanes 3:10) afforded (±)-(7-anilino-2,3-dihydro-1-benzofuran-2-yl)methyl 4-methylbenzenesulfonate. Treatement of (±)-(7-anilino-2,3-dihydro-1-benzofuran-2-yl)methyl 4-methylbenzenesulfonate with sodium azide (0.18 g, 2.78 mmol) generally according to the procedure described for Intermediate 98 afforded (±)-2-(azidomethyl)-N-phenyl-2,3-dihydro-1-benzofuran-7-amine. Treatment of the azide with polymer-supported triphenylphosphine (1.09 g, 4.17 mmol) generally according to the procedure described for Example 21 provided 0.042 g, (46%) of (±)-2-(aminomethyl)-N-phenyl-2,3-dihydro-1-benzofuran-7-amine as a white solid, fumarate salt. mp 216-218° C.

EXAMPLE 174

(±)-N-[2-(aminomethyl)-2,3-dihydro-1-benzofuran-7-yl]-N-(4-methylphenyl)amine

The title compound was prepared (0.171 g, 15%) following the general procedure of Example 173 as a white solid, fumarate salt from (±)-(7-anilino-2,3-dihydro-1-benzofuran-2-yl)methyl 4-methylbenzenesulfonate (0.96 g, 3.0 mmol) and 4-bromotoluene (0.51 g, 3.0 mmol). mp 226-228° C.

EXAMPLE 175

(±)-N-[2-(aminomethyl)-2,3-dihydro-1-benzofuran-7-yl]-N-(4-chlorophenyl)amine

The title compound was prepared (0.158 g, 18%) following the general procedure of Example 173 as a white solid, fumarate salt from (±)-(7-anilino-2,3-dihydro-1-benzofuran-2-yl)methyl 4-methylbenzenesulfonate (0.96 g, 3.0 mol) and 1-bromo-4-chlorobenzene (0.57 g, 3.0 mmol). mp 223-224° C.

EXAMPLE 176

(±)-N-[2-(aminomethyl)-2,3-dihydro-1-benzofuran-7-yl]-N-(4-methoxyphenyl)amine

The title compound was prepared (0.048 g, 5%) following the general procedure of Example 173 as a yellow solid, fumarate salt from (±)-(7-anilino-2,3-dihydro-1-benzofuran-2-yl)methyl 4-methylbenzenesulfonate (0.96 g, 3.0 mmol) and 1-bromo-4-methoxybenzene (0.896 g, 3.0 mmol). mp 178-180° C.

EXAMPLE 177

(±)-N-[2-(aminomethyl)-2,3-dihydro-1-benzofuran-7-yl]-N-[4-(trifluoromethyl)phenyl]amine The title compound was prepared (0.227 g, 18%) following the general procedure of Example 173 as a white solid, fumarate salt from (±)-(7-anilino-2,3-dihydro-1-benzofuran-2-yl)methyl 4-methylbenzenesulfonate (0.96 g, 3.0 mmol) and 1-bromo-4-(trifluoromethyl)benzene (0.675 g, 3.0 mmol). mp 218-220° C.

EXAMPLE 178

(±)-N-[2-(aminomethyl)-2,3-dihydro-1-benzofuran-7-yl]-N-(4-fluorophenyl)amine

The title compound was prepared (0.066 g, 7%) following the general procedure of Example 173 as a white solid, fumarate salt from (±)-(7-anilino-2,3-dihydro-1-benzofuran-2-yl)

methyl 4-methylbenzenesulfonate (0.96 g, 3.0 mmol) and 1-bromo-4-fluorobenzene (0.52 g, 3.0 mmol). mp 234-236° C.

EXAMPLE 179

(±)-N-[2-(aminomethyl)-2,3-dihydro-1-benzofuran-7-yl]-N-(3,4-dichlorophenyl)amine The title compound was prepared (0.171 g, 15%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-3,4-dichlorobenzene (0.68 g, 3.0 mmol). mp 229-231° C.

EXAMPLE 180

(±)-N-[2-(aminomethyl)-2,3-dihydro-1-benzofuran-7-yl]-N-(2,4-dimethylphenyl)amine The title compound was prepared (0.234 g, 24%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-2,4-dimethylbenzene (0.55 g, 3.0 mmol). mp 232-234° C.

EXAMPLE 181

(±)-N-[2-(aminomethyl)-2,3-dihydro-1-benzofuran-7-yl]-N-(3,4-dimethylphenyl)amine The title compound was prepared (0.115 g, 12%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-3,4-dimethylbenzene (0.55 g, 3.0 mmol). mp 232-234° C.

EXAMPLE 182

(±)-N-[2-(aminomethyl)-2,3-dihydro-1-benzofuran-7-yl]-N-(3-methylphenyl)amine

The title compound was prepared (0.16 g, 17%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 3-bromotoluene (0.51 g, 3.0 mmol). mp 217-218° C.

EXAMPLE 183

(±)-N-[2-(aminomethyl)-2,3-dihydro-1-benzofuran-7-yl]-N-(3-fluorophenyl)amine

The title compound was prepared (0.266 g, 28%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 4-bromo-3-fluorobenzene (0.525 g, 3.0 mmol). mp 219-221° C.

EXAMPLE 184

(±)-N-2-(aminomethyl)-N-[3-(trifluoromethyl)phenyl]-2,3-dihydro-1-benzofuran-7-amine The title compound was prepared (0.195 g, 18%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-3-(trifluoromethyl)benzene (0.675 g, 3.0 mmol). mp 212-214° C.

EXAMPLE 185

(±)-N-[2-(aminomethyl)-2,3-dihydro-1-benzofuran-7-yl]-N-(4-methoxy-3-methylphenyl)amine The title compound was prepared (0.03 g, 3%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 5-bromo-2-methoxytoluene (0.603 g, 3.0 mmol). mp 205-207° C.

EXAMPLE 186

(±)-N-[2-(aminomethyl)-2,3-dihydro-1-benzofuran-7-yl]-N-(3,5-difluorophenyl)amine The title compound was prepared (0.185 g, 19%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-3,5-difluorobenzene (0.57 g, 3.0 mmol). mp 229-231° C.

EXAMPLE 187

(±)-N-[2-(aminomethyl)-2,3-dihydro-1-benzofuran-7-yl]-N-(3-trifluoromethoxy)phenyl]amine The title compound was prepared (0.144 g, 11%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-3-(trifluoromethoxy)benzene (0.723 g, 3.0 mmol). mp 199-201° C.

EXAMPLE 188

(±)-N-[2-(aminomethyl)-2,3-dihydro-1-benzofuran-7-yl]-N-(3-chloro-4-methylphenyl)amine The title compound was prepare (0.282 g, 27%) d following the general procedure of Example 173 as a white solid, fumarate salt from (±)-(7-anilino-2,3-dihydro-1-benzofuran-2-yl)methyl 4-methylbenzenesulfonate (0.96 g, 3.0 mmol) and 4-bromo-2-chlorotoluene (0.63 g, 3.0 mmol). mp 225-227° C.

EXAMPLE 189

(±)-N-[2-(aminomethyl)-2,3-dihydro-1-benzofuran-7-yl]-N-(3,5-dichlorophenyl)amine The title compound was prepared (0.065 g, 6%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-3,5-dichlorophenylbenzene (0.678 g, 3.0 mmol). mp >250° C.

EXAMPLE 190

(±)-N-[2-(aminomethyl)-2,3-dihydro-1-benzofuran-7-yl]-N-(3-chlorophenyl)amine

The title compound was prepared (0.284 g, 28%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 4-bromo-3-chlorophenylbenzene (0.57 g, 3.0 mmol). mp 220-222° C.

EXAMPLE 191

(±)-N-[2-(aminomethyl)-2,3-dihydro-1-benzofuran-7-yl]-N-(4-chloro-3-methylphenyl)amine The title compound was prepared (0.298 g, 28%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 5-bromo-3-chlorotoluene (0.629 g, 3.0 mmol). mp 225-227° C.

EXAMPLE 192

(±)-N-[2-(aminomethyl)-2,3-dihydro-1-benzofuran-7-yl]-N-(3,5-dimethylphenyl)amine The title compound was prepared (0.178 g, 18%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-3,5-dimethylbenzene (0.57 g, 3.0 mmol). mp >250° C.

EXAMPLE 193

(±)-N-[2-(aminomethyl)-2,3-dihydro-1-benzofuran-7-yl]-N-(3-chloro-4-fluorophenyl)amine The title compound was prepared (0.167 g, 16%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-3-chloro-4-fluorobenzene (0.63 g, 3.0 mmol). mp 244-245° C.

EXAMPLE 194

(±)-N-[2-(aminomethyl)-2,3-dihydro-1-benzofuran-7-yl]-N-(2-fluorophenyl)amine

The title compound was prepared (0.070 g, 7%) following the general procedure of Example 173 as a white solid, fumarate salt from (±)-(7-anilino-2,3-dihydro-1-benzofuran-2-yl) methyl 4-methylbenzenesulfonate (0.96 g, 3.0 mmol) and 1-bromo-2-fluorobenzene (0.52 g, 3.0 mmol). mp 203-205° C.

EXAMPLE 195

(±)-{[5-fluoro-7-(2-methoxyphenyl)-2,3-dihydro-1-benzofuran-2-yl]methyl}amine

The title compound was prepared (0.16 g, 88%) following the general procedure of Example 154 as a white solid, hydrochloride salt from (±)-(7-bromo-5-fluoro-2,3-dihydro-1-benzofuran-2-yl)methyl 4-methylbenzenesulfonate 1.0 g, 2.5 mmol) and (2-methoxyphenyl)boronic acid (0.57 g, 3.7 mmol). mp 219-220° C.

EXAMPLE 196

(±)-{[5-fluoro-7-(3-fluorophenyl)-2,3-dihydro-1-benzofuran-2-yl]methyl}amine

The title compound was prepared (0.136 g, 46%) following the general procedure of Example 154 as a white solid, hydrochloride salt from (±)-(7-bromo-5-fluoro-2,3-dihydro-1-benzofuran-2-yl)methyl 4-methylbenzenesulfonate 0.40 g, 1.0 mmol) and (3-fluorophenyl)boronic acid (0.22 g, 1.50 mmol). mp 193-194° C.

EXAMPLE 197

(±)-{[5-fluoro-7-(3-methoxyphenyl)-2,3-dihydro-1-benzofuran-2-yl]methyl}amine

The title compound was prepared (0.175 g, 64%) following the general procedure of Example 154 as a white solid, hydrochloride salt from (±)-(7-bromo-5-fluoro-2,3-dihydro-1-benzofuran-2-yl)methyl 4-methylbenzenesulfonate 0.4 g, 0.996 mmol) and (3-methoxyphenyl)boronic acid (0.23 g, 1.51 mmol). mp 172-175° C.

EXAMPLE 198

(±)-{[5-fluoro-7-(3-methylphenyl)-2,3-dihydro-1-benzofuran-2-yl]methyl}amine

The title compound was prepared (0.178 g, 68%) following the general procedure of Example 154 as a white solid, hydrochloride salt from (±)-(7-bromo-5-fluoro-2,3-dihydro-1-benzofuran-2-yl)methyl 4-methylbenzenesulfonate (0.4 g, 0.996 mmol) and (3-methylphenyl)boronic acid (0.21 g, 1.51 mmol). mp 228-230° C.

EXAMPLE 199

(±)-{[5-fluoro-7-(4-fluorophenyl)-2,3-dihydro-1-benzofuran-2-yl]methyl}amine

The title compound was prepared (0.160 g, 54%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 1.0 mmol) and (4-fluorophenyl)boronic acid (0.22 g, 1.50 mmol). mp 241-243° C.

EXAMPLE 200

(±)-{[5-fluoro-7-(4-chlorophenyl)-2,3-dihydro-1-benzofuran-2-yl]methyl}amine

The title compound was prepared (0.173 g, 55%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 1.0 mmol) and (4-chlorophenyl)boronic acid (0.25 g, 1.50 mmol). mp 221-225° C.

EXAMPLE 201

(±)-{[5-fluoro-7-(4-methylphenyl)-2,3-dihydro-1-benzofuran-2-yl]methyl}amine

The title compound was prepared (0.211 g, 72%) following the general procedure of Example 154 as a white solid, hydrochloride salt from (±)-(7-bromo-5-fluoro-2,3-dihydro-1-benzofuran-2-yl)methyl 4-methylbenzenesulfonate (0.4 g, 0.996 mmol) and (4-methylphenyl)boronic acid (0.20 g, 1.51 mmol). mp 180-183° C.

EXAMPLE 202

(±)-{[5-fluoro-7-(4-methoxyphenyl)-2,3-dihydro-1-benzofuran-2-yl]methyl}amine

The title compound was prepared (0.209 g, 68%) following the general procedure of Example 154 as a white solid, hydrochloride salt from (±)-(7-bromo-5-fluoro-2,3-dihydro-1-benzofuran-2-yl)methyl 4-methylbenzenesulfonate 0.4 g, 0.996 mmol) and (4-methoxyphenyl)boronic acid (0.23 g, 1.51 mmol). mp 175-176° C.

EXAMPLE 203

(±)-[(5-fluoro-7-thien-3-yl-2,3-dihydro-1-benzofuran-2-yl)methyl]amine

The title compound was prepared (0.233 g, 82%) following the general procedure of Example 154 as a white solid, hydrochloride salt from (±)-(7-bromo-5-fluoro-2,3-dihydro-1-benzofuran-2-yl)methyl 4-methylbenzenesulfonate (0.4 g, 0.996 mmol) and 3-thienylboronic acid (0.19 g, 1.51 mmol). mp 272-274° C.

EXAMPLE 204

(±)-{[5-fluoro-7-(3-furyl)-2,3-dihydro-1-benzofuran-2-yl]methyl}amine

The title compound was prepared (0.076 g, 33%) following the general procedure of Example 154 as a yellow solid, hydrochloride salt from (±)-(7-bromo-5-fluoro-2,3-dihydro-1-benzofuran-2-yl)methyl 4-methylbenzenesulfonate (0.4 g, 0.996 mmol) and 3-furylboronic acid (0.18 g, 1.51 mmol). mp 236-239° C.

EXAMPLE 205

(±)-[(5-fluoro-7-pyridin-2-yl-2,3-dihydro-1-benzofuran-2-yl)methyl]amine

The title compound was prepared (0.060 g, 11%) following the general procedure of Example 154 as a white solid, hydrochloride salt from (±)-(7-bromo-5-fluoro-2,3-dihydro-1-benzofuran-2-yl)methyl 4-methylbenzenesulfonate (0.60 g, 1.49 mmol) and 2-(tri-tert-butylstannyl)pyridine (2.6 g, 7.0 mmol 85%). mp 196-198° C.

EXAMPLE 206

(±)-[(5-fluoro-7-pyridin-3-yl-2,3-dihydro-1-benzofuran-2-yl)methyl]amine

The title compound was prepared (0.072 g, 13%) following the general procedure of Example 154 as a white solid, hydrochloride salt from (±)-(7-bromo-5-fluoro-2,3-dihydro-1-benzofuran-2-yl)methyl 4-methylbenzenesulfonate (0.60 g, 1.49 mmol) and pyridin-3-ylboronic acid (0.55 g, 4.5 mmol). mp 173-175° C.

EXAMPLE 207

(−)-[(5-fluoro-7-pyridin-3-yl-2,3-dihydro-1-benzofuran-2-yl)methyl]amine

Treatment of 0.58 g of fraction 2 obtained from the chiral HPLC separation of (±)-benzyl {[7-(2,5-dichlorophenyl)-2,3-dihydro-1-benzofuran-2-yl]methyl}carbamate with hydrogen bromide (6 mL, 30 wt. % in acetic acid) generally according to the procedure described for Example 2 gave 0.181 g (15%) of (−)-{[5-fluoro-7-pyridin-3-yl-2,3-dihydro-1-benzofuran-2-yl]methyl}amine as a white solid, hydrochloride salt. $[\alpha]_D^{25}$=−16.74 (c 10.0 in methanol); mp 88-90° C.

EXAMPLE 208

(+)-{[5-fluoro-7-pyridin-3-yl-2,3-dihydro-1-benzofuran-2-yl]methyl}amine

Treatment of 0.59 g of fraction 1 obtained from the chiral HPLC separation of (±)-benzyl {[7-(2,5-dichlorophenyl)-2,3-dihydro-1-benzofuran-2-yl]methyl}carbamate with hydrogen bromide (6 mL, 30 wt. % in acetic acid) generally according to the procedure described for Example 2 gave 0.181 g (15%) of (+)-{[5-fluoro-7-pyridin-3-yl-2,3-dihydro-1-benzofuran-2-yl]methyl}amine as a white solid, hydrochloride salt. $[\alpha]_D^{25}$=+13.71 (c 10.0 in methanol); mp 86-89° C.

EXAMPLE 209

(±)-[(5-fluoro-7-pyridin-4-yl-2,3-dihydro-1-benzofuran-2-yl)methyl]amine

The title compound was prepared (0.029 g, 5%) following the general procedure of Example 154 as a off-white solid, fumarate salt from (±)-(7-bromo-5-fluoro-2,3-dihydro-1-benzofuran-2-yl)methyl 4-methylbenzenesulfonate (0.40 g, 0.996 mmol) and pyridin-4-ylboronic acid (0.18 g, 1.5 mmol). mp 170-171° C.

EXAMPLE 210

(±)-[(5-fluoro-7-pyrimidin-5-yl-2,3-dihydro-1-benzofuran-2-yl)methyl]amine

The title compound was prepared (0.010 g, 5%) following the general procedure of Example 154 as a white solid, fumarate salt from (±)-(7-bromo-5-fluoro-2,3-dihydro-1-benzofuran-2-yl)methyl 4-methylbenzenesulfonate (0.40 g, 0.996 mmol) and pyrimidin-5-ylboronic acid (0.52 g, 4.0 mmol). mp 65° C. (dec).

EXAMPLE 211

(±)-{[7-(2,3-dichlorophenyl)-5-fluoro-2,3-dihydro-1-benzofuran-2-yl]methyl}amine The title compound was prepared (0.076 g, 35%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 0.996 mmol) and 2,3-dichlorophenylboronic acid (0.856 g, 4.5 mmol). mp 185-187° C.

EXAMPLE 212

(±)-{[7-(2,3-dimethoxyphenyl)-5-fluoro-2,3-dihydro-1-benzofuran-2-yl]methyl}amine The title compound was prepared (0.143 g, 40%) following the general procedure of Example 154 as a white solid, hydrochloride salt from (±)-(7-bromo-5-fluoro-2,3-dihydro-1-benzofuran-2-yl)methyl 4-methylbenzenesulfonate (0.50 g, 1.25 mmol) and 2,3-dimethoxyphenylboronic acid (0.68 g, 3.0 mmol). mp 90-93° C.

EXAMPLE 213

(−)-{[7-(2,3-dimethoxyphenyl)-5-fluoro-2,3-dihydro-1-benzofuran-2-yl]methyl}amine Treatment of 0.60 g of fraction 1 obtained from the chiral HPLC separation of (±)-benzyl {[7-(2,3-dimethoxyphenyl)-2,3-dihydro-1-benzofuran-2-yl]methyl}carbamate with trimethylsilyl iodide (1.10 g, 5.6 mmol) generally according to the procedure described for Example 129 gave 0.341 g (73%) of (−)-{[7-(2,3-dimethoxyphenyl)-5-fluoro-2,3-dihydro-1-benzofuran-2-yl]methyl}amine as a white solid, hydrochloride salt. $[\alpha]_D^{25}=-54.27$ (c 10.0 in methanol); mp 173-175° C.

EXAMPLE 214

(+)-{[7-(2,3-dimethoxyphenyl)-5-fluoro-2,3-dihydro-1-benzofuran-2-yl]methyl}amine Treatment of 0.80 g of fraction 2 obtained from the chiral HPLC separation of (±)-benzyl {[7-(2,3-dimethoxyphenyl)-2,3-dihydro-1-benzofuran-2-yl]methyl}carbamate with trimethylsilyl iodide (1.44 g, 7.2 mmol) generally according to the procedure described for Example 129 gave 0.253 g (41%) of (+)-{[7-(2,3-dimethoxyphenyl)-5-fluoro-2,3-dihydro-1-benzofuran-2-yl]methyl}amine as a white solid, hydrochloride salt. $[\alpha]_D^{25}=+53.38$ (c 10.0 in methanol); mp 166-167° C.

EXAMPLE 215

(±)-{[7-(2,4-difluorophenyl)-5-fluoro-2,3-dihydro-1-benzofuran-2-yl]methyl}amine The title compound was prepared (0.163 g, 52%) following the general procedure of Example 154 as a off-white solid, hydrochloride salt from (±)-(7-bromo-5-fluoro-2,3-dihydro-1-benzofuran-2-yl)methyl 4-methylbenzenesulfonate (0.40 g, 0.996 mmol) and 2,4-difluorophenylboronic acid (0.708 g, 4.5 mmol). mp 218-220° C.

EXAMPLE 216

(±)-{[7-(2,4-dichlorophenyl)-5-fluoro-2,3-dihydro-1-benzofuran-2-yl]methyl}amine The title compound was prepared (0.049 g, 14%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 0.996 mmol) and 2,4-dichlorophenylboronic acid (0.856 g, 4.5 mmol). mp 107-109° C.

EXAMPLE 217

(−)-{[5-fluoro-7-(2,4-dichlorophenyl)-2,3-dihydro-1-benzofuran-2-yl]methyl}amine Treatment of 0.50 g of fraction 1 obtained from the chiral HPLC separation of (±)-benzyl {[7-(2,4-dichloroyphenyl)-2,3-dihydro-1-benzofuran-2-yl]methyl carbamate with trimethylsilyl iodide (1.12 g, 4.40 mmol) generally according to the procedure described for Example 129 gave 0.234 g (60%) of (−)-{[5-chloro-7-(2,4-dichlorophenyl)-2,3-dihydro-1-benzofuran-2-yl]methyl}amine as a white solid, hydrochloride salt. $[\alpha]_D^{25}=-2.07$ (c 10.0 in methanol); mp 175-178° C.

EXAMPLE 218

(+)-{[5-fluoro-7-(2,4-dichlorophenyl)-2,3-dihydro-1-benzofuran-2-yl]methyl}amine Treatment of 0.50 g of fraction 2 obtained from the chiral HPLC separation of (±)-benzyl {[7-(2,4-dichlorophenyl)-2,3-dihydro-1-benzofuran-2-yl]methyl}carbamate with trimethylsilyl iodide (1.12 g, 4.40 mmol) generally according to the procedure described for Example 129 gave 0.220 g (56%) of (+)-{[5-chloro-7-(2,4-dichlorophenyl)-2,3-dihydro-1-benzofuran-2-yl]methyl}amine as a white solid, hydrochloride salt. $[\alpha]_D^{25}=+1.80$ (c 10.0 in methanol); mp 203-205° C.

EXAMPLE 219

(±)-{[7-(2,4-dimethoxyphenyl)-5-fluoro-2,3-dihydro-1-benzofuran-2-yl]methyl}amine The title compound was prepared (0.068 g, 20%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 0.996 mmol) and 2,4-dimethoxyphenylboronic acid (0.819 g, 4.5 mmol). mp 141-143° C.

EXAMPLE 220

(±)-{[7-(2,5-difluorophenyl)-5-fluoro-2,3-dihydro-1-benzofuran-2-yl]methyl}amine The title compound was prepared (0.068 g, 20%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 0.996 mmol) and 2,5-difluorophenylboronic acid (0.473 g, 3.0 mmol). mp 203-205° C.

EXAMPLE 221

(±)-{[7-(2,5-dichlorophenyl)-5-fluoro-2,3-dihydro-1-benzofuran-2-yl]methyl}amine The title compound was prepared (0.098 g, 28%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 0.996 mmol) and 2,5-dichlorophenylboronic acid (0.57 g, 3.0 mmol). mp 165-166° C.

EXAMPLE 222

(±)-{[7-(2,5-dimethylphenyl)-5-fluoro-2,3-dihydro-1-benzofuran-2-yl]methyl}amine The title compound was prepared (0.026 g, 9%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 0.996 mmol) and 2,5-dimethylphenylboronic acid (0.45 g, 3.0 mmol). mp 153-155° C.

EXAMPLE 223

(±)-{[7-(2,5-dimethoxyphenyl)-5-fluoro-2,3-dihydro-1-benzofuran-2-yl]methyl}amine The title compound was prepared (0.064 g, 19%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 0.996 mmol) and 2,5-dimethoxyphenylboronic acid (0.54 g, 3.0 mmol). mp 120-122° C.

EXAMPLE 224

(±)-{[5-fluoro-7-(5-methoxy-2-methylphenyl)-2,3-dihydro-1-benzofuran-2-yl]methyl}amine The title compound was prepared (0.083 g, 26%) following the general procedure of Example 154 as a white solid, hydrochloride salt from (±)-(7-bromo-5-fluoro-2,3-dihydro-1-benzofuran-2-yl)methyl 4-methylbenzenesulfonate (0.41 g, 1.0 mmol) (5-methoxy-2-methylphenyl)boronic acid (0.5 g, 3.0 mmol). mp 233-235° C.

EXAMPLE 225

(±)-{[5-fluoro-7-(2-methoxy-5-methylphenyl)-2,3-dihydro-1-benzofuran-2-yl]methyl}amine The title compound was prepared (0.017 g, 5%) following the general procedure of Example 154 as a white solid, hydrochloride salt from (±)-(7-bromo-5-fluoro-2,3-dihydro-1-benzofuran-2-yl)methyl 4-methylbenzenesulfonate (0.40 g, 1.0 mmol) (2-methoxy-5-methylphenyl)boronic acid (0.51 g, 3.0 mmol). mp 110-111° C.

EXAMPLE 226

(±)-{[7-(2,6-difluorophenyl)-5-fluoro-2,3-dihydro-1-benzofuran-2-yl]methyl}amine The title compound was prepared (0.140 g, 9%) following the general procedure of Example 166 as a white solid, hydrochloride salt from (2,6-difluorophenyl)boronic acid (4.0 g, 23.5 mmol) and (2-bromo-1,3-difluorobenzene (3.1 g, 15.7 mmol). mp 235-237° C.

EXAMPLE 227

(±)-{[7-(2,6-dimethylphenyl)-5-fluoro-2,3-dihydro-1-benzofuran-2-yl]methyl}amine The title compound was prepared (0.109 g, 3%) following the general procedure of Example 166 as a white solid, hydrochloride salt from (2,6-dimethylphenyl)boronic acid (4.0 g, 23.0 mmol) and 2-bromo-1,3-dimethylbenzene (2.9 g, 15.6 mmol). mp 241-243° C.

EXAMPLE 228

(+)-{[7-(2,6-dimethylphenyl)-5-fluoro-2,3-dihydro-1-benzofuran-2-yl]methyl}amine Treatment of 0.50 g of fraction 1 obtained from the chiral HPLC separation of (±)-[7-(2,6-dimethylphenyl)-5-fluoro-2,3-dihydro-1-benzofuran-2-yl]methyl 4-methylbenzenesulfonate with sodium azide (0.38 g, 58.5 mmol) generally according to the procedure described for Example 1 gave 0.28 g (80%) of (+)-2-(azidomethyl)-7-(2,6-dimethylphenyl)-5-fluoro-2,3-dihydro-1-benzofuran as a colorless oil. Treatment of the azide with triphenyl phosphine (0.74 g, 2.82 mmol) generally according to the procedure described for Example 154 afforded a white solid, hydrochloride salt; $[\alpha]_D^{25}$=+10.83 (c 10.0 in methanol); mp 192-194° C.

EXAMPLE 229

(−)-{[7-(2,6-dimethylphenyl)-5-fluoro-2,3-dihydro-1-benzofuran-2-yl]methyl}amine Treatment of 0.50 g of fraction 2 obtained from the chiral HPLC separation of (±)-[7-(2,6-dimethylphenyl)-5-fluoro-2,3-dihydro-1-benzofuran-2-yl]methyl 4-methylbenzenesulfonate with sodium azide (0.38 g, 58.5 mmol) generally according to the procedure described for Example 1 gave 0.22 g (63%) of (−)-2-(azidomethyl)-7-(2,6-dimethylphenyl)-5-fluoro-2,3-dihydro-1-benzofuran as a colorless oil. Treatment of the azide with triphenyl phosphine (0.58 g, 2.22 mmol) generally according to the procedure described for Example 154 afforded a white solid, hydrochloride salt; $[\alpha]_D^{25}$=−6.6 (c 10.0 in methanol); mp 180-183° C.

EXAMPLE 230

(±)-{[7-(2,6-dichlorophenyl)-5-fluoro-2,3-dihydro-1-benzofuran-2-yl]methyl}amine The title compound was prepared (0.21 g, 5%) following the general procedure of Example 166 as a white solid, hydrochloride salt from (5-fluoro-2-methoxyphenyl)boronic acid (3.0 g, 17.6 mmol) and 2-bromo-1,3-dichlorobenzene (2.65 g, 12.0 mmol). mp 204-205° C.

EXAMPLE 231

(±)-N-{[7-(2,6-dichlorophenyl)-5-fluoro-2,3-dihydro-1-benzofuran-2-yl]methyl}cyclopropanamine The title compound was prepared (0.035 g, 30%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.14 g, 0.30 mmol) and cyclopropylamine (0.17 g, 3.0 mmol). mp 112-113° C.

EXAMPLE 232

(±)-1-cyclopropyl-N-{[7-(2,6-dichlorophenyl)-5-fluoro-2,3-dihydro-1-benzofuran-2-yl]methyl}methanamine The title compound was prepared (0.066 g, 54%) following the general procedure of Example 390 as a white solid, hydrochloride salt from (±)-([5-fluoro-7-(2,6-dichlorophenyl)-2,3- dihydro-1-benzofuran-2-yl]methyl 4-methylbenzenesulfonate (0.14 g, 0.30 mmol) and (aminomethyl)cyclopropane (0.21 g, 3.0 mmol). mp 130-133° C.

EXAMPLE 233

(±)-N-{[7-(2,6-dichlorophenyl)-5-fluoro-2,3-dihydro-1-benzofuran-2-yl]methyl}cyclobutanamine The title compound was prepared (0.074 g, 61%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.14 g, 0.30 mmol) and cyclobutylamine (0.21 g, 3.0 mmol). mp 128-130° C.

EXAMPLE 234

(±)-N-{[7-(2,6-dichlorophenyl)-5-fluoro-2,3-dihydro-1-benzofuran-2-yl]methyl}ethanamine The title compound was prepared (0.068 g, 56%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.15 g, 0.32 mmol) and ethylamine (0.138 g, 3.2 mmol). mp 138.140° C.

EXAMPLE 235

(±)-N-{[7-(2,6-dichlorophenyl)-5-fluoro-2,3-dihydro-1-benzofuran-2-yl]methyl}propan-1-amine The title compound was prepared (0.092 g, 84%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.13 g, 0.28 mmol) and propylamine (0.165 g, 2.80 mmol). mp >250° C.

EXAMPLE 236

(±)-N-{[7-(2,6-dichlorophenyl)-5-fluoro-2,3-dihydro-1-benzofuran-2-yl]methyl}propan-2-amine The title compound was prepared (0.065 g, 66%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.14 g, 0.3 mmol) and isopropylamine (0.18 g, 3.0 mmol). mp 134-135° C.

EXAMPLE 237

(±)-{[7-(2,6-dichlorophenyl)-5-fluoro-2,3-dihydro-1-benzofuran-2-yl]methyl}dimethylamine The title compound was prepared (0.069 g, 61%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.14 g, 0.3 mmol) and dimethylamine (0.14 g, 3.0 mmol). mp 199-201° C.

EXAMPLE 238

(±)-1-{[7-(2,6-dichlorophenyl)-5-fluoro-2,3-dihydro-1-benzofuran-2-yl]methyl}piperidine The title compound was prepared (0.074 g, 69%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.12 g, 0.26 mmol) and piperidine (0.22 g, 2.6 mmol). mp 184-186° C.

EXAMPLE 239

(±)-1-{[7-(2,6-dichlorophenyl)-5-fluoro-2,3-dihydro-1-benzofuran-2-yl]methyl}morpholine The title compound was prepared (0.069 g, 61%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.14 g, 0.30 mmol) and morpholine (0.26 g, 3.0 mmol). mp 196-199° C.

EXAMPLE 240

(±)-1-{[7-(2,6-dichlorophenyl)-5-fluoro-2,3-dihydro-1-benzofuran-2-yl]methyl}pyrrolidine The title compound was prepared (0.069 g, 61%) following the general procedure of Example 390 as a white solid, hydrochloride salt from (±)-([5-fluoro-7-(2,6-dichlorophenyl)-2,3-dihydro-1-benzofuran-2-yl]methyl 4-methylbenzenesulfonate (0.13 g, 0.28 mmol) and pyrrolidine (0.20 g, 2.8 mmol). mp 65-67° C.

EXAMPLE 241

(±)-{[5-chloro-7-(2-fluorophenyl)-2,3-dihydro-1-benzofuran-2-yl]methyl}amine

The title compound was prepared (0.017 g, 39%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and (2-fluorophenyl)boronic acid (0.6 g, 4.3 mmol). mp 235-237° C.

EXAMPLE 242

(±)-{[5-chloro-7-(2-methoxyphenyl)-2,3-dihydro-1-benzofuran-2-yl]methyl}amine

The title compound was prepared (0.017 g, 10%) following the general procedure of Example 154 as a white solid, hydrochloride salt from (±)-(7-bromo-5-chloro-2,3-dihydro-1-benzofuran-2-yl)methyl 4-methylbenzenesulfonate (1.1 g, 2.42 mmol) and (2-methoxyphenyl)boronic acid (1.55 g, 9.68 mmol). mp 240-242° C.

EXAMPLE 243

(±)-{[5-chloro-7-(3-furyl)-2,3-dihydro-1-benzofuran-2-yl]methyl}amine

The title compound was prepared (0.017 g, 9%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 3-furylboronic acid (0.54 g, 4.82 mmol). mp>250° C.

EXAMPLE 244

(±)-{[5-chloro-7-(2,3-difluorophenyl)-2,3-dihydro-1-benzofuran-2-yl]methyl}amine The title compound was prepared (0.131 g, 56%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,3-difluorophenylboronic acid (0.76 g, 4.81 mmol). mp 216-218° C.

EXAMPLE 245

(−)-{[5-chloro-7-(2,3-difluorophenyl)-2,3-dihydro-1-benzofuran-2-yl]methyl}amine Treatment of 0.66 g of fraction 1 obtained from the chiral HPLC separation of (±)-benzyl {[5-chloro-7-(2,3-difluorophenyl)-2,3-dihydro-1-benzofuran-2-yl]methyl}carbamate with hydrogen bromide (15 mL, 30 wt. % in acetic acid) generally according to the procedure described for Example 2 gave a crude salt. The salt was washed with saturated sodium bicarbonate (200 mL) and extracted with ethyl acetate (2×200 mL). The combined organic layers were washed with saturated aqueous sodium chloride (100 mL), dried (sodium sulfate), and the solvent was removed in vacuo to provide a colorless oil. The oil was re-dissolved in isopropanol (3 mL) and hydrogen chloride (1.0 N in diethyl ether, 10.0 mL) was added. The resulting precipitate was filtered, washed (diethyl ether), and dried to afford 0.391 g (76%) of (−)-{[5-chloro-7-(2,3-difluorophenyl)-2,3-dihydro-1-benzofuran-2-yl]methyl}amine as a white solid, hydrochloride salt. $[\alpha]_D^{25}=-13.8$ (c 10.0 in methanol); mp 225-227° C.

EXAMPLE 246

(±)-{[5-chloro-7-(2,3-difluorophenyl)-2,3-dihydro-1-benzofuran-2-yl]methyl}amine Treatment of 0.63 g of fraction 2 obtained from the chiral HPLC separation of (±)-benzyl {[5-chloro-7-(2,3-difluorophenyl)-2,3-dihydro-1-benzofuran-2-yl]methyl}carbamate with hydrogen bromide (15 mL, 30 wt. % in acetic acid) generally according to the procedure described for Example 245 gave 0.387 g (66%) of (+)-{[5-chloro-7-(2,3-difluorophenyl)-2,3-dihydro-1-benzofuran-2-yl]methyl}amine as a white solid, hydrochloride salt. $[\alpha]_D^{25}=+10.6$ (c 10.0 in methanol); mp 225-227° C.

EXAMPLE 247

(±)-{[5-chloro-7-(2,3-dichlorophenyl)-2,3-dihydro-1-benzofuran-2-yl]methyl}amine The title compound was prepared (0.160 g, 55%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,3-dichlorophenylboronic acid (0.92 g, 4.81 mmol). mp 245-246° C.

EXAMPLE 248

(±)-{[5-chloro-7-(2,3-dimethylphenyl)-2,3-dihydro-1-benzofuran-2-yl]methyl}amine The title compound was prepared (0.072 g, 31%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,3-dimethylphenylboronic acid (0.70 g, 4.81 mmol). mp 223-225° C.

EXAMPLE 249

(±)-{[5-chloro-7-(2,3-dimethoxyphenyl)-2,3-dihydro-1-benzofuran-2-yl]methyl}amine The title compound was prepared (0.137 g, 47%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,3-dimethoxyphenylboronic acid (0.88 g, 4.81 mmol). mp 120-122° C.

EXAMPLE 250

(±)-{[5-chloro-7-(2,4-difluorophenyl)-2,3-dihydro-1-benzofuran-2-yl]methyl}amine The title compound was prepared (0.134 g, 57%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,4-difluorophenylboronic acid (0.76 g, 4.81 mmol). mp 216-218° C.

EXAMPLE 251

(±)-{[5-chloro-7-(2,4-dichlorophenyl)-2,3-dihydro-1-benzofuran-2-yl]methyl}amine The title compound was prepared (0.10 g, 42%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,4-dichlorophenylboronic acid (0.92 g, 4.81 mmol). mp 202-204° C.

EXAMPLE 252

(−)-{[5-chloro-7-(2,4-dichlorophenyl)-2,3-dihydro-1-benzofuran-2-yl]methyl}amine Treatment of 0.67 g of fraction 1 obtained from the chiral HPLC separation of (±)-benzyl {[5-chloro-7-(2,4-dichlorophenyl)-2,3-dihydro-1-benzofuran-2-yl]methyl}carbamate with hydrogen bromide (15 mL, 30 wt. % in acetic acid) generally according to the procedure described for Example 245 gave 0.465 g (88%) of (−)-{[5-chloro-7-(2,4-dichlorophenyl)-2,3-dihydro-1-benzofuran-2-yl]methyl}amine as a white solid, hydrochloride salt. $[\alpha]_D^{25}=-8.5$ (c 10.0 in methanol); mp 237-239° C.

EXAMPLE 253

(+)-{[5-chloro-7-(2,4-dichlorophenyl)-2,3-dihydro-1-benzofuran-2-yl]methyl}amine Treatment of 0.42 g of fraction 2 obtained from the chiral HPLC separation of (±)-benzyl {[5-chloro-7-(2,4-dichlorophenyl)-2,3-dihydro-1-benzofuran-2-yl]methyl}carbamate with hydrogen bromide (15 mL, 30 wt. % in acetic acid) generally according to the procedure described for Example 245 gave 0.275 g (83%) of (+)-{[5-chloro-7-(2,4-dichlorophenyl)-2,3-dihydro-1-benzofuran-2-yl]

EXAMPLE 254

(±)-{[5-chloro-7-(2,4-dimethoxyphenyl)-2,3-dihydro-1-benzofuran-2-yl]methyl}amine The title compound was prepared (0.075 g, 45%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,4-dimethoxyphenylboronic acid (0.88 g, 4.81 mmol). mp 220-222° C.

EXAMPLE 255

(±)-{[5-chloro-7-(2,5-difluorophenyl)-2,3-dihydro-1-benzofuran-2-yl]methyl}amine The title compound was prepared (0.118 g, 42%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,5-difluorophenylboronic acid (0.76 g, 4.81 mmol). mp 242-244° C.

EXAMPLE 256

(±)-{[5-chloro-7-(2,5-dichlorophenyl)-2,3-dihydro-1-benzofuran-2-yl]methyl}amine The title compound was prepared (0.137 g, 52%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,5-dichlorophenylboronic acid (0.92 g, 4.81 mmol). mp 160-162° C.

EXAMPLE 257

(±)-{[5-chloro-7-(5-chloro-2-methoxyphenyl)-2,3-dihydro-1-benzofuran-2-yl]methyl}amine The title compound was prepared (0.159 g, 56%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and (5-chloro-2-methoxyphenyl)boronic acid (0.90 g, 4.81 mmol). mp 174-176° C.

EXAMPLE 258

(±)-{[5-chloro-7-(3,4-difluorophenyl)-2,3-dihydro-1-benzofuran-2-yl]methyl}amine The title compound was prepared (0.121 g, 44%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 3,4-difluorophenylboronic acid (0.76 g, 4.81 mmol). mp >250° C.

EXAMPLE 259

(±)-{[5-chloro-7-(3-chloro-4-fluorophenyl)-2,3-dihydro-1-benzofuran-2-yl]methyl}amine The title compound was prepared (0.068 g, 47%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 3-chloro-4-fluorophenylboronic acid (0.84 g, 4.81 mmol). mp 214-243° C.

EXAMPLE 260

(±)-{[5-chloro-7-(2,6-dimethylphenyl)-2,3-dihydro-1-benzofuran-2-yl]methyl}amine The title compound was prepared (0.246 g, 53%) following the general procedure of Example 154 as a white solid, hydrochloride salt from (±)-(7-bromo-5-chloro-2,3-dihydro-1-benzofuran-2-yl)methyl 4-methylbenzenesulfonate (0.505 g, 1.21 mmol) and 2,6-dimethylphenylboronic acid (2.8 g, 18.66 mmol). mp 173-175° C.

EXAMPLE 261

(−)-{[5-chloro-7-(2,6-dimethylphenyl)-2,3-dihydro-1-benzofuran-2-yl]methyl}amine Treatment of 0.67 g of fraction 1 obtained from the chiral HPLC separation of (±)-benzyl {[5-chloro-7-(2,6-dimethylphenyl)-2,3-dihydro-1-benzofuran-2-yl]methyl}carbamate with hydrogen bromide (15 mL, 30 wt. % in acetic acid) generally according to the procedure described for Example 245 provided 0.226 g (44%) of (−)-{[5-chloro-7-(2,6-dimethylphenyl)-2,3-dihydro-1-benzofuran-2-yl]methyl}amine as a white solid, hydrochloride salt. $[\alpha]_D^{25}=$ −16.9 (c 10.0 in methanol); mp 200-202° C.

EXAMPLE 262

(+)-{[5-chloro-7-(2,6-dimethylphenyl)-2,3-dihydro-1-benzofuran-2-yl]methyl}amine Treatment of 0.66 g of fraction 2 obtained from the chiral HPLC separation of (±)-benzyl {[5-chloro-7-(2,6-dimethylphenyl)-2,3-dihydro-1-benzofuran-2-yl]methyl}carbamate with hydrogen bromide (15 mL, 30 wt. % in acetic acid) generally according to the procedure described for Example 245 afforded 0.339 g (67%) of (+)-{[5-chloro-7-(2,6-dimethylphenyl)-2,3-dihydro-1-benzofuran-2-yl]methyl}amine as a white solid, hydrochloride salt. $[\alpha]_D^{25}=$ +14.9 (c 10.0 in methanol); mp 204-206° C.

EXAMPLE 263

(±)-{[5-chloro-7-(2,6-dichlorophenyl)-2,3-dihydro-1-benzofuran-2-yl]methyl}amine The title compound was prepared (0.072 g, 8%) following the general procedure of Example 166 as a white solid, hydrochloride salt from (5-chloro-2-methoxyphenyl)boronic acid (5.0 g, 26.88 mmol) and 2-bromo-1,3-dichlorobenzene (12.14 g, 53.76 mmol). mp 234-236° C.

EXAMPLE 264

(±)-{[5-chloro-7-(2,6-dichlorophenyl)-2,3-dihydro-1-benzofuran-2-yl]methyl}amine Treatment of 0.80 g of fraction 2 obtained from the chiral HPLC separation of (±)-benzyl {[5-chloro-7-(2,6-dichlorophenyl)-2,3-dihydro-1-benzofuran-2-yl]methyl}carbamate with trimethylsilyl iodide (1.46 g, 7.20

--- methyl}amine as a white solid, hydrochloride salt; $[\alpha]_D^{25}=$ +10.1 (C 10.0 in methanol); mp 240-242° C.

mmol) generally according to the procedure described for Example 158 afforded 0.341 g (56%) of (+)-{[5-chloro-7-(2,6-dichlorophenyl)-2,3-dihydro-1-benzofuran-2-yl]methyl}amine as a white solid, hydrochloride salt. $[\alpha]_D^{25}=$ +33.61 (c 10.0 in methanol); mp >250° C.

EXAMPLE 265

(−)-{[5-chloro-7-(2,6-dichlorophenyl)-2,3-dihydro-1-benzofuran-2-yl]methyl}amine Treatment of 0.60 g of fraction 1 obtained from the chiral HPLC separation of (±)-benzyl-{[5-chloro-7-(2,6-dichlorophenyl)-2,3-dihydro-1-benzofuran-2-yl]methyl}carbamate with trimethylsilyl iodide (1.09 g, 5.60 mmol) generally according to the procedure described for Example 158 gave 0.253 g (55%) of (−)-{[5-chloro-7-(2,6-dichlorophenyl)-2,3-dihydro-1-benzofuran-2-yl]methyl}amine as a white solid, hydrochloride salt. $[\alpha]_D^{25}=$ −31.76 (c 10.0 in methanol); mp >250° C.

EXAMPLE 266

(±)-{[(5-chloro-7-pyridin-3-yl-2,3-dihydro-1-benzofuran-2-yl)methyl]amine

The title compound was prepared (0.162 g, 45%) following the general procedure of Example 154 as a white solid, hydrochloride salt from (±)-(7-bromo-5-chloro-2,3-dihydro-1-benzofuran-2-yl)methyl 4-methylbenzenesulfonate (0.50 g, 1.20 mmol) and pyridin-3-ylboronic acid (0.50 g, 3.86 mmol). mp >250° C.

EXAMPLE 267

(±)-N-{[5-chloro-7-(2,6-dimethylphenyl)-2,3-dihydro-1-benzofuran-2-yl]methyl}cyclopropanamine The title compound was prepared (0.056 g, 34%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and cyclopropylamine (0.39 g, 6.77 mmol). mp 214-216° C.

EXAMPLE 268

(±)-N-{[5-chloro-7-(2,6-dimethylphenyl)-2,3-dihydro-1-benzofuran-2-yl]methyl}(cyclopropylmethyl)amine The title compound was prepared (0.058 g, 45%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and (aminomethyl)cyclopropane (0.50 g, 6.77 mmol). mp 203-205° C.

EXAMPLE 269

(±)-N-{[5-chloro-7-(2,6-dimethylphenyl)-2,3-dihydro-1-benzofuran-2-yl]methyl}cyclobutanamine The title compound was prepared (0.027 g, 21%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and cyclobutylamine (0.49 g, 6.77 mmol). mp 203-205° C.

EXAMPLE 270

No compound

EXAMPLE 271

(±)-N-{[5-chloro-7-(2,6-dimethylphenyl)-2,3-dihydro-1-benzofuran-2-yl]methyl}ethanamine The title compound was prepared (0.079 g, 66%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and ethylamine (0.14 g, 3.38 mmol). mp 230-232° C.

EXAMPLE 272

(±)-N-{[5-chloro-7-(2,6-dimethylphenyl)-2,3-dihydro-1-benzofuran-2-yl]methyl}propan-2-amine The title compound was prepared (0.064 g, 52%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and isopropylamine (0.40 g, 6.76 mmol). mp 213-215° C.

EXAMPLE 273

No compound

EXAMPLE 274

(±)-{[5-chloro-7-(2,6-dimethylphenyl)-2,3-dihydro-1-benzofuran-2-yl]methyl}dimethylamine The title compound was prepared (0.068 g, 57%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and dimethylamine (0.18 g, 6.76 mmol). mp 220-222° C.

EXAMPLE 275

(±)-1-{[5-chloro-7-(2,6-dimethylphenyl)-2,3-dihydro-1-benzofuran-2-yl]methyl}piperidine The title compound was prepared (0.095 g, 72%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and piperidine (0.58 g, 6.76 mmol). mp >235° C.

EXAMPLE 276

(±)-4-{[5-chloro-7-(2,6-dimethylphenyl)-2,3-dihydro-1-benzofuran-2-yl]methyl}morpholine The title compound was prepared (0.09 g, 68%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and morpholine (0.58 g, 6.76 mmol). mp 228-230° C.

EXAMPLE 277

(±)-4-{[5-chloro-7-(2,6-dimethylphenyl)-2,3-dihydro-1-benzofuran-2-yl]methyl}thiomorpholine The title compound was prepared (0.55 g, 39%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and thiomorpholine (0.72 g, 6.76 mmol). mp 224-226° C.

EXAMPLE 278

(±)-N-{[5-chloro-7-(2,6-dimethylphenyl)-2,3-dihydro-1-benzofuran-2-yl]methyl}propan-1-amine The title compound was prepared (0.094 g, 76%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and propylamine (0.40 g, 6.76 mmol) mp 200-202° C.

EXAMPLE 279

(±)-1-{[5-chloro-7-(2,6-dimethylphenyl)-2,3-dihydro-1-benzofuran-2-yl]methyl}piperazine The title compound was prepared (0.118 g, 81%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and piperazine (0.58 g, 6.76 mmol). mp 190-192° C.

EXAMPLE 280

(±)-1-{[5-chloro-7-(2,6-dimethylphenyl)-2,3-dihydro-1-benzofuran-2-yl]methyl}pyrrolidine The title compound was prepared (0.094 g, 73%) following the general procedure of Example 390 as a white solid, hydrochloride salt from (±)-([5-chloro-7-(2,6-dimethylphenyl)-2,3-dihydro-1-benzofuran-2-yl]methyl 4-methylbenzenesulfonate (0.15 g, 0.338 mmol) and pyrrolidine (0.48 g, 6.76 mmol). mp 245-247° C.

EXAMPLE 281

(±)-{[(5-methyl-7-phenyl-2,3-dihydro-1-benzofuran-2-yl)methyl]amine

Treatment of 2-bromo-4-methylphenol (19.09 g, 102 mmol) with potassium carbonate (56.0 g, 400 mmol) and allyl bromide (15.96 g, 130 mmol), followed by refluxing the resultant allyl ether in mesitylene generally according to the procedure described for Intermediate 8 provided 2-allyl-6-bromo-4-methylphenol. Treatment of 2-allyl-6-bromo-4-methylphenol (5.21 g, 23.0 mmol) with 3-chloroperoxybenzoic acid (9.13 g, 34.50 mmol, 77%) followed by potassium carbonate (7.9 g, 57.5 mmol) generally according to the procedure described for Intermediate 9 afforded 2.14 g (43%) of (±)-(7-bromo-5-methyl-2,3-dihydro-1-benzofuran-2-yl)methanol. Treatment of (±)-(7-bromo-5-methyl-2,3-dihydro-1-benzofuran-2-yl)methanol (2.41 g, 10.0 mmol) with p-toluenesulfonyl chloride (2.1 g, 11.0 mol) generally according to the procedure described for Intermediate 10 gave 3.31 g (84%) of (±)-(7-bromo-5-methyl-2,3-dihydro-1-benzofuran-2-yl)methyl 4-methylbenzenesulfonate as a yellow oil. Treatment of (±)-(7-bromo-5-methyl-2,3-dihydro-1-benzofuran-2-yl)methyl 4-methylbenzenesulfonate (0.25 g, 0.63 mmol) and phenylboronic acid (0.23 g, 1.89 mmol) generally according to the procedure described for Intermediate 154 afforded 0.23 g, (93%) of (±)-(5-methyl-7-phenyl-2,3-dihydro-1-benzofuran-2-yl)methyl 4-methylbenzenesulfonate. Treatment of the tosylate with sodium azide (0.19 g, 3.0 mmol) generally according to the procedure described for Intermediate 98 afforded 0.15 g (97%) of (±)-2-(azidomethyl)-5-methyl-7-phenyl-2,3-dihydro-1-benzofuran. Treatment of (±)-2-(azidomethyl)-5-methyl-7-phenyl-2,3-dihydro-1-benzofuran with polymer-supported triphenylphosphine (0.297 g, 1.13 mmol) according to the procedure described in Example 21 afforded 0.106 g (61%) of (±)-[(5-methyl-7-phenyl-2,3-dihydro-1-benzofuran-2-yl)methyl]amine as a white solid, hydrochloride salt. mp 227-228° C.

EXAMPLE 282

(±)-{[7-(2-methylphenyl)-5-methyl-2,3-dihydro-1-benzofuran-2-yl]methyl}amine

The title compound was prepared (0.111 g, 49%) following the general procedure of Example 154 as a white solid, hydrochloride salt from (±)-(7-bromo-5-methyl-2,3-dihydro-1-benzofuran-2-yl)methyl 4-methylbenzenesulfonate (0.30 g, 0.76 mmol) and 2-methylphenylboronic acid (0.32 g, 3.00 mmol). mp 260-263° C.

EXAMPLE 283

(±)-{[7-(2-fluorophenyl)-5-methyl-2,3-dihydro-1-benzofuran-2-yl]methyl}amine

The title compound was prepared (0.136 g, 46%) following the general procedure of Example 154 as a white solid, hydrochloride salt from (±)-(7-bromo-5-methyl-2,3-dihydro-1-benzofuran-2-yl)methyl 4-methylbenzenesulfonate (0.40 g, 1.00 mmol) and 2-fluorophenylboronic acid (0.42 g, 3.00 mmol). mp 232-234° C.

EXAMPLE 284

(±)-{[7-(2-methoxyphenyl)-5-methyl-2,3-dihydro-1-benzofuran-2-yl]methyl}amine

The title compound was prepared (0.136 g, 44%) following the general procedure of Example 154 as a white solid, hydrochloride salt from (±)-(7-bromo-5-methyl-2,3-dihydro-1-benzofuran-2-yl)methyl 4-methylbenzenesulfonate (0.40 g, 1.00 mmol) and 2-methoxyphenylboronic acid (0.46 g, 3.00 mmol). mp 194-195° C.

EXAMPLE 285

No compound

EXAMPLE 286

(±)-{[7-(2-chlorophenyl)-5-methyl-2,3-dihydro-1-benzofuran-2-yl]methyl}amine

The title compound was prepared (0.135 g, 58%) following the general procedure of Example 154 as a white solid, hydrochloride salt from (±)-(7-bromo-5-methyl-2,3-dihydro-1- benzofuran-2-yl)methyl 4-methylbenzenesulfonate (0.30 g, 0.76 mmol) and 2-chlorophenylboronic acid (0.35 g, 2.28 mmol). mp 260-263° C.

EXAMPLE 287

(±)-({5-methyl-7-[2-(trifluoromethyl)phenyl[-2,3-dihydro-7-benzofuran-2-yl}methyl)amine The title compound was prepared (0.135 g, 58%) following the general procedure of Example 154 as a white solid, hydrochloride salt from (±)-(7-bromo-5-methyl-2,3-dihydro-1-benzofuran-2-yl)methyl 4-methylbenzenesulfonate (0.31 g, 0.76 mmol) and 2-(trifluoromethyl)phenylboronic acid (0.36 g, 2.28 mmol). mp 211-213° C.

EXAMPLE 288

(±)-{[7-(3-chlorophenyl)-5-methyl-2,3-dihydro-1-benzofuran-2-yl]methyl}amine

The title compound was prepared (0.028 g, 9%) following the general procedure of Example 154 as a white solid, hydrochloride salt from (±)-(7-bromo-5-methyl-2,3-dihydro-1-benzofuran-2-yl)methyl 4-methylbenzenesulfonate (0.40 g, 1.00 mmol) and 3-chlorophenylboronic acid (0.47 g, 3.00 mmol). mp 90-93° C.

EXAMPLE 289

(±)-{[7-(3-methylphenyl)-5-methyl-2,3-dihydro-1-benzofuran-2-yl]methyl}amine

The title compound was prepared (0.107 g, 37%) following the general procedure of Example 154 as a white solid, hydrochloride salt from (±)-(7-bromo-5-methyl-2,3-dihydro-1-benzofuran-2-yl)methyl 4-methylbenzenesulfonate (0.40 g, 1.00 mmol) and 3-methylphenylboronic acid (0.41 g, 3.00 mmol). mp 235-237° C.

EXAMPLE 290

(±)-{[7-(4-methylphenyl)-5-methyl-2,3-dihydro-1-benzofuran-2-yl]methyl}amine

The title compound was prepared (0.116 g, 38%) following the general procedure of Example 154 as a white solid, hydrochloride salt from (±)-(7-bromo-5-methyl-2,3-dihydro-1-benzofuran-2-yl)methyl 4-methylbenzenesulfonate (0.40 g, 1.00 mmol) and 4-methylphenylboronic acid (0.46 g, 3.00 mmol). mp 172-173° C.

EXAMPLE 291

(±)-{[7-(4-fluorophenyl)-5-methyl-2,3-dihydro-1-benzofuran-2-yl]methyl}amine

The title compound was prepared (0.112 g, 39%) following the general procedure of Example 154 as a white solid, hydrochloride salt from (±)-(7-bromo-5-methyl-2,3-dihydro-1-benzofuran-2-yl)methyl 4-methylbenzenesulfonate (0.40 g, 1.00 mmol) and 4-fluorophenylboronic acid (0.42 g, 3.00 mmol). mp 225-227° C.

EXAMPLE 292

(±)-{[7-(4-chlorophenyl)-5-methyl-2,3-dihydro-1-benzofuran-2-yl]methyl}amine

The title compound was prepared (0.097 g, 31%) following the general procedure of Example 154 as a white solid, hydrochloride salt from (±)-(7-bromo-5-methyl-2,3-dihydro-1-benzofuran-2-yl)methyl 4-methylbenzenesulfonate (0.40 g, 1.00 mmol) and 4-chlorophenylboronic acid (0.47 g, 3.00 mmol). mp 250-252° C.

EXAMPLE 293

(±)-{[7-(4-methoxyphenyl)-5-methyl-2,3-dihydro-1-benzofuran-2-yl]methyl}amine

The title compound was prepared (0.116 g, 38%) following the general procedure of Example 154 as a white solid, hydrochloride salt from (±)-(7-bromo-5-methyl-2,3-dihydro-1-benzofuran-2-yl)methyl 4-methylbenzenesulfonate (0.40 g, 1.00 mmol) and 4-methoxyphenylboronic acid (0.49 g, 3.00 mmol). mp 207-209° C.

EXAMPLE 294

(±)-{[7-(2,3-dimethoxyphenyl)-5-methyl-2,3-dihydro-1-benzofuran-2-yl]methyl}amine The title compound was prepared (0.164 g, 44%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.26 mmol) and 2,3 dimethoxyphenylboronic acid (0.69 g, 3.75 mmol). mp 97-99° C.

EXAMPLE 295

(−)-{[7-(2,3-dimethoxyphenyl)-5-methyl-2,3-dihydro-1-benzofuran-2-yl]methyl}amine Treatment of 0.59 g of fraction 1 obtained from the chiral HPLC separation of (±)-benzyl {[7-(2,3-dimethoxyphenyl)-5-methyl-2,3-dihydro-1-benzofuran-2-yl]methyl}carbamate with trimethylsilyl iodide (1.08 g, 5.44 mmol) generally according to the procedure described for Example 158 gave 0.316 g (69%) of (−)-{[7-(2,3-dimethoxyphenyl)-5-methyl-2,3-dihydro-1-benzofuran-2-yl]methyl}amine as a white solid, hydrochloride salt. $[\alpha]_D^{25}=-73.6$ (c 10.0 in methanol); mp 120-123° C.

EXAMPLE 296

(+)-{[7-(2,3-dimethoxyphenyl)-5-methyl-2,3-dihydro-1-benzofuran-2-yl]methyl}amine Treatment of 0.52 g of fraction 2 obtained from the chiral HPLC separation of (±)-benzyl {[7-(2,3-dimethoxyphenyl)-5-methyl-2,3-dihydro-1-benzofuran-2-yl]methyl}carbamate with trimethylsilyl iodide (0.956 g, 4.80 mmol) generally according to the procedure described for Example 158 afforded 0.127 g (32%) of (+)-{[7-(2,3-dimethoxyphenyl)-5-methyl-2,3-dihydro-1-benzofuran-2-yl]methyl}amine as a white solid, hydrochloride salt. $[\alpha]_D^{25}=+74.51$ (c 10.0 in methanol); mp 98-100° C.

EXAMPLE 297

(±)-{[7-(2,4-dichlorophenyl)-5-methyl-2,3-dihydro-1-benzofuran-2-yl]methyl}amine The title compound was prepared (0.124 g, 29%) following the general procedure of Example 154 as a white solid, hydrochloride salt from (±)-(7-bromo-5-methyl-2,3-dihydro-1- benzofuran-2-yl)methyl 4-methylbenzenesulfonate (0.50 g, 1.26 mmol) and 2,4 dichlorophenylboronic acid (0.72 g, 3.8 mmol). mp 172-173° C.

EXAMPLE 298

(−)-{[7-(2,4-dichlorophenyl)-5-methyl-2,3-dihydro-1-benzofuran-2-yl]methyl}amine Treatment of 0.50 g of fraction 1 obtained from the chiral HPLC separation of (±)-benzyl {[7-(2,4-dichlorophenyl)-5-methyl-2,3-dihydro-1-benzofuran-2-yl]methyl}carbamate with trimethylsilyl iodide (0.905 g, 4.52 mmol) generally according to the procedure described for Example 129 provided 0.275 g (71%) of (−)-{[7-(2,4-dichlorophenyl)-5-methyl-2,3-dihydro-1-benzofuran-2-yl]methyl}amine as a white solid, hydrochloride salt. $[\alpha]_D^{25}=-8.0$ (c 10.0 in methanol); mp 173-176° C.

EXAMPLE 299

(+)-{[7-(2,4-dichlorophenyl)-5-methyl-2,3-dihydro-1-benzofuran-2-yl]methyl}amine Treatment of 0.48 g of fraction 2 obtained from the chiral HPLC separation of (±)-benzyl {[7-(2,4-dichlorophenyl)-5-methyl-2,3-dihydro-1-benzofuran-2-yl]methyl}carbamate with trimethylsilyl iodide (0.868 g, 4.34 mmol) generally according to the procedure described for Example 129 afforded 0.254 g (68%) of (+)-{[7-(2,4-dichlorophenyl)-5-methyl-2,3-dihydro-1-benzofuran-2-yl]methyl}amine as a white solid, hydrochloride salt. $[\alpha]_D^{25}=+7.25$ (c 10.0 in methanol); mp 173-176° C.

EXAMPLE 300

(±)-{[7-(2,5-dichlorophenyl)-5-methyl-2,3-dihydro-1-benzofuran-2-yl]methyl}amine The title compound was prepared (0.121 g, 28%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.26 mmol) and 2,5-dichlorophenylboronic acid (0.72 g, 3.8 mmol). mp 155-156° C.

EXAMPLE 301

(±)-{[7-(2,6-dimethylphenyl)-5-methyl-2,3-dihydro-1-benzofuran-2-yl]methyl}amine The title compound was prepared (0.030 g, 11%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.26 mmol) and 2,6 dimethylphenylboronic acid (0.76 g, 4.00 mmol). mp 234-235° C.

EXAMPLE 302

(±)-{[7-(2,6-dichlorophenyl)-5-methyl-2,3-dihydro-1-benzofuran-2-yl]methyl}amine The title compound was prepared (0.030 g, 21%) following the general procedure of Example 154 as a white solid, hydrochloride salt from (±)-(7-bromo-5-methyl-2,3-dihydro-1-benzofuran-2-yl)methyl 4-methylbenzenesulfonate (0.56 g, 1.41 mmol) and 2,6 dichlorophenylboronic acid (2.17 g, 14.10 mmol). mp 193-195° C.

EXAMPLE 303

(−)-{[7-(2,6-dichlorophenyl)-5-methyl-2,3-dihydro-1-benzofuran-2-yl]methyl}amine Treatment of 0.72 g of fraction 1 obtained from the chiral HPLC separation of (±)-benzyl {[7-(2,6-dichlorophenyl)-5-methyl-2,3-dihydro-1-benzofuran-2-yl]methyl}carbamate with trimethylsilyl iodide (1.28 g, 7.20 mmol) generally according to the procedure described for Example 158 gave 0.227 g (41%) of (−)-{[7-(2,6-dichlorophenyl)-5-methyl-2,3-dihydro-1-benzofuran-2-yl]methyl}amine as a white solid, hydrochloride salt. $[\alpha]_D^{25}=-28.9$ (c 10.0 in methanol); mp 222-224° C.

EXAMPLE 304

(+)-{[7-(2,6-dichlorophenyl)-5-methyl-2,3-dihydro-1-benzofuran-2-yl]methyl}amine Treatment of 0.65 g of fraction 2 obtained from the chiral HPLC separation of (±)-benzyl {[7-(2,6-dichlorophenyl)-5-methyl-2,3-dihydro-1-benzofuran-2-yl]methyl}carbamate with trimethylsilyl iodide (1.18 g, 6.00 mmol) generally according to the procedure described for Example 158 gave 0.259 g (51%) of (+)-{[7-(2,6-dichlorophenyl)-5-methyl-2,3-dihydro-1-benzofuran-2-yl]methyl}amine as a white solid, hydrochloride; $[\alpha]_D^{25}=+33.82$ (c 10.0 in methanol); salt. mp 222-224° C.

EXAMPLE 305

(±)-{[5-ethyl-7-(2-methylphenyl)-2,3-dihydro-1-benzofuran-2-yl]methyl}amine

To a solution of 4-ethylphenol (10.0 g, 82.0 mmol) in acetonitrile (250 mL) cooled to 0° C. was slowly added N-bromosuccinimide (16.0 g, 90 mmol) and the reaction mixture was allowed to stir at 0° C. for 1 h. The solvent was removed in vacuo and the reaction mixture was diluted with ice water (500 mL) and diethyl ether (500 mL). A solid precipitate was removed via filtration and the aqueous phase was separated and extracted with ethyl ether (2×200 mL). The combined organic extracts were washed with saturated aqueous sodium chloride (400 mL), dried (magnesium sulfate) and the solvent was removed in vacuo to give a crude oil. Purification by flash column chromatography (silica, ethyl acetate:hexanes 1:9) gave 8.35 g (51%). Treatment of 2-bromo-4-ethylphenol (8.35 g, 41.0 mmol) with potassium carbonate (14.3 g, 100 mmol) and allyl bromide (6.57 g, 130 mmol), followed by refluxing the resultant allyl ether in mesitylene generally according to the procedure described for Intermediate 8 provided 2-allyl-6-bromo-4-ethylphenol. Treatment of 2-allyl-6-bromo-4-ethylphenol (5.18, 22.0 mmol) with 3-chloroperoxybenzoic acid (8.60 g, 33.0 mmol, 77%) followed by potassium carbonate (7.4 g, 55.0 mmol) generally according to the procedure described for Intermediate 9 afforded 3.94 g (70%) of (±)-(7-bromo-5-ethyl-2,3-dihydro-1-benzofuran-2-yl)methanol. Treatment of (±)-(7-bromo-5-ethyl-2,3-dihydro-1-benzofuran-2-yl)methanol (3.94 g, 15.0 mmol) with p-toluenesulfonyl chloride (3.5 g, 18.0 mol) generally according to the procedure described for Intermediate 10 gave 5.78 g (92%) of (±)-(7-bromo-5-ethyl-2,3-dihydro-1-benzofuran-2-yl)methyl 4-methylbenzenesulfonate as a colorless oil. Treatment of (±)-(7-bromo-5-ethyl-2,3-dihydro-1-benzofuran-2-yl)methyl 4-methylbenzenesulfonate (0.30 g, 0.73 mmol) and 2-methylphenylboronic acid (0.30 g, 2.19 mmol) generally according to the procedure described for Intermediate 35 afforded 0.30 g, (97%) of (±)-(5-ethyl-7-phenyl-2,3-dihydro-1-benzofuran-2-yl)methyl 4-methylbenzenesulfonate. Treatment of the tosylate with sodium azide (0.23 g, 3.55 mmol) generally according to the procedure described for Intermediate 98 afforded 0.16 g (77%) of (±)-2-(azidomethyl)-5-ethyl-7-phenyl-2,3-dihydro-1-benzofuran. Treatment of (±)-2-(azidomethyl)-5-ethyl-7-phenyl-2,3-dihydro-1-benzofuran with polymer-supported triphenylphosphine (0.786 g, 0.869 mmol) according to the procedure described in Example 154 afforded 0.009 g (4%) of (±)-[(5-ethyl-7-phenyl-2,3-dihydro-1-benzofuran-2-yl)methyl]amine as a white solid, hydrochloride salt. mp 198° C. (dec).

EXAMPLE 306

(±)-{[5-ethyl-7-(2-chlorophenyl)-2,3-dihydro-1-benzofuran-2-yl]methyl}amine

The title compound was prepared (0.174 g, 74%) following the general procedure of Example 154 as a white solid, hydrochloride salt from (±)-(7-bromo-5-ethyl-2,3-dihydro-1-benzofuran-2-yl)methyl 4-methylbenzenesulfonate (0.3 g, 0.73 mmol) and 2-chlorophenylboronic acid (0.34 g, 2.19 mmol). mp 268-271° C.

EXAMPLE 307

(±)-{[5-isopropyl-7-(2-methylphenyl)-2,3-dihydro-1-benzofuran-2-yl]methyl}amine

To a solution of 4-isopropylphenol (13.38 g, 98.0 mmol) with N-bromosuccinimide (17.5 g, 98 mmol) generally according to the procedure described for Example 305 afforded 13.78 g (65%) of 2-bromo-4-isopropylphenol. Treatment of 2-bromo-4-isopropylphenol (13.74 g, 41.0 mmol) with potassium carbonate (22.0 g, 160 mmol) and allyl bromide (9.23 g, 76.8 mmol), followed by refluxing the resultant allyl ether in mesitylene generally according to the procedure described for Intermediate 8 provided 2-allyl-6-bromo-4-isopropylphenol. Treatment of 2-allyl-6-bromo-4-isopropylphenol (6.85 g, 27.0 mmol) with 3-chloroperoxybenzoic acid (7.72 g, 27.0 mmol, 77%) followed by potassium carbonate (9.3 g, 67.5.0 mmol) generally according to the procedure described for Intermediate 9 afforded 1.12 g, (17%) of (±)-(7-bromo-5-isopropyl-2,3-dihydro-1-benzofuran-2-yl)methanol. Treatment of (±)-(7-bromo-5-isopropyl-2,3-dihydro-1-benzofuran-2-yl)methanol (1.12 g, 4.6 mmol) with p-toluenesulfonyl chloride (1.32 g, 6.9 mmol) generally according to the procedure described for Intermediate 10 gave 1.90 g (97%) of (±)-(7-bromo-5-isopropyl-2,3-dihydro-1-benzofuran-2-yl)methyl 4-methylbenzenesulfonate as a colorless oil. Treatment of (±)-(7-bromo-5-isopropyl-2,3-dihydro-1-benzofuran-2-yl)methyl 4-methylbenzenesulfonate (0.4 g, 0.94 mmol) and 2-methylphenylboronic acid (0.38 g, 2.82 mmol) generally according to the procedure described for Intermediate 35 afforded 0.19 g, (46%) of (5-isopropyl-7-phenyl-2,3-dihydro-1-benzofuran-2-yl)methyl 4-methylbenzenesulfonate. Treatment of the tosylate with sodium azide (0.141 g, 2.17 mmol) generally according to the procedure described for Intermediate 98 afforded 0.11 g (83%) of (±)-2-(azidomethyl)-5-isopropyl-7-phenyl-2,3-dihydro-1-benzofuran. Treatment of (±)-2-(azidomethyl)-5-isopropyl-7-phenyl-2,3-dihydro-1-benzofuran with polymer-supported triphenylphosphine (0.188 g, 0.716 mmol) according to the procedure described in Example 154 afforded 0.055 g (48%) of (±)-[(5-isopropyl-7-phenyl-2,3-dihydro-1-benzofuran-2-yl)methyl]amine as a white solid, hydrochloride salt. mp 221-222° C. (dec).

EXAMPLE 308

(±)-{[5-isopropyl-7-(2-chlorophenyl)-2,3-dihydro-1-benzofuran-2-yl]methyl}amine

The title compound was prepared (0.096 g, 30%) following the general procedure of Example 154 as a white solid, hydrochloride salt from (±)-(7-bromo-5-isopropyl-2,3-dihydro-1-benzofuran-2-yl)methyl 4-methylbenzenesulfonate (0.4 g, 0.94 mmol) and 2-chlorophenylboronic acid (0.44 g, 2.81 mmol). mp 257-260° C.

EXAMPLE 309

(±)-{[5-cyclopentyl-7-(2-methylphenyl)-2,3-dihydro-1-benzofuran-2-yl]methyl}amine To a solution of 4-cyclopentylphenol (3.0 g, 18.0 mmol) in acetonitrile (30 mL) cooled to 0° C. was slowly added N-bromosuccinimide (3.29 g, 18 mmol) generally according to the procedure described for Example 309 afforded 3.75 g (84%) of 2-bromo-4-cyclopentylphenol Treatment of 2-bromo-4-cyclopentylphenol (3.75 g, 16.0 mmol) with potassium carbonate (5.4.0 g, 40 mmol) and allyl bromide (2.38 g, 20.8 mmol), followed by refluxing the resultant allyl ether in mesitylene generally according to the procedure described for Intermediate 8 provided 2-allyl-6-bromo-4-cyclopentylphenol. Treatment of 2-allyl-6-bromo-4-cyclopentylphenol (3.0 g, 10.0 mmol) with 3-chloroperoxybenzoic acid (3.49 g, 12.0 mmol, 77%) followed by potassium carbonate (3.7 g, 25.0 mmol) generally according to the procedure described for Intermediate 9 afforded 1.68 g, (53%) of (±)-(7-bromo-5-cyclopentyl-2,3-dihydro-1-benzofuran-2-yl)methanol.
Treatment of (±)-(7-bromo-5-cyclopentyl-2,3-dihydro-1-benzofuran-2-yl)methanol (1.68 g, 4.6 mmol) with p-toluenesulfonyl chloride (0.96 g, 5.0 mmol) generally according to the procedure described for Intermediate 10 gave 1.78 g (70%) of (±)-(7-bromo-5-cyclopentyl-2,3-dihydro-1-benzofuran-2-yl)methyl 4-methylbenzenesulfonate as a colorless oil. Treatment of (±)-(7-bromo-5-cyclopentyl-2,3-dihydro-1-benzofuran-2-yl)methyl 4-methylbenzenesulfonate (0.5 g, 1.1 mmol) and 2-methylphenylboronic acid (0.45 g, 3.3 mmol) generally according to the procedure described for Intermediate 35 afforded 0.51 g, (99%) of (5-cyclopentyl-7-phenyl-2,3-dihydro-1-benzofuran-2-yl)methyl 4-methylbenzenesulfonate. Treatment of the tosylate with sodium azide (0.239 g, 3.67 mmol) generally according to the procedure described for Intermediate 98 afforded 0.16 g (65%) of (±)-2-(azidomethyl)-5-isopropyl-7-phenyl-2,3-dihydro-1-benzofuran. Treatment of (±)-2-(azidomethyl)-5-cyclopentyl-7-phenyl-2,3-dihydro-1-benzofuran with polymer-supported triphenylphosphine (0.24 g, 0.48 mmol) according to the procedure described in Example 154 afforded 0.126 g (50%) of (±)-[(5-cyclopentyl-7-phenyl-2,3-dihydro-1-benzofuran-2-yl)methyl]amine as a white solid, hydrochloride salt. mp 190-193° C. (dec).

EXAMPLE 310

(±)-{[5-cyclopentyl-7-(2-chlorophenyl)-2,3-dihydro-1-benzofuran-2-yl]methyl}amine The title compound was prepared (0.171 g, 42%) following the general procedure of Example 154 as a white solid, hydrochloride salt from (±)-(7-bromo-5-cyclopentyl-2,3-dihydro- 1-benzofuran-2-yl)methyl 4-methylbenzenesulfonate (0.50 g, 1.10 mmol) and 2-chlorophenylboronic acid (0.52 g, 3.30 mmol). mp 268-271° C.

EXAMPLE 311

(±)-2-(aminomethyl)-7-(2-methylphenyl)-2,3-dihydro-1-benzofuran-5-carbonitrile

Treatment of 3-bromo-4-hydroxybenzonitrile (10.0 g, 50.0 mmol) with potassium carbonate (27.9 g, 200 mmol) and allyl bromide (7.96 g, 66.0 mmol), followed by refluxing the resultant allyl ether in mesitylene generally according to the procedure described for Intermediate 8 provided 3-allyl-5-bromo-4-hydroxybenzonitrile. Treatment of 3-allyl-5-bromo-4-hydroxybenzonitrile (4.63 g, 19.0 mmol) with 3-chloroperoxybenzoic acid (6.2 g, 35.93 mmol, 77%) followed by potassium carbonate (6.56 g, 47.5 mmol) generally according to the procedure described for Intermediate 9 afforded 1.30 g (426) of (±)-7-bromo-2-(hydroxymethyl)-2,3-dihydro-1-benzofuran-5-carbonitrile. Treatment of (±)-7-bromo-2-(hydroxymethyl)-2,3-dihydro-1-benzofuran-5-carbonitrile (1.3 g, 5.0 mmol) with p-toluenesulfonyl chloride (1.02 g, 5.4 mol) generally according to the procedure described for Intermediate 10 gave 1.5 g (72%) of (±)-(7-bromo-5-cyano-2,3-dihydro-1-benzofuran-2-yl)methyl 4-methylbenzenesulfonate as a white solid. Treatment of (±)-(7-bromo-5-cyano-2,3-dihydro-1-benzofuran-2-yl)methyl 4-methylbenzenesulfonate (0.30 g, 0.73 mmol) and 2-methylphenylboronic acid (0.3 g, 2.20 mmol) generally according to the procedure described for Intermediate 35 afforded 0.33 g, (99%) of (±)-[5-cyano-7-(2-methylphenyl)-2,3-dihydro-1-benzofuran-2-yl]methyl 4-methylbenzenesulfonate. Treatment of the tosylate with sodium azide (0.26 g, 4.0 mmol) generally according to the procedure described for Intermediate 98 afforded 0.17 g (74%) of (±)-2-(azidomethyl)-7-(2-methylphenyl)-2,3-dihydro-1-benzofuran-5-carbonitrile. Treatment of the azide with polymer-supported triphenylphosphine (0.24 g, 0.67 mmol) according to the procedure described in Example 154 afforded 0.118 g (53%) of (±)-2-(aminomethyl)-7-(2-methylphenyl)-2,3-dihydro-1-benzofuran-5-carbonitrile as a white solid, hydrochloride salt. mp 127-129° C.

EXAMPLE 312

(±)-2-(aminomethyl)-7-(2-chlorophenyl)-2,3-dihydro-1-benzofuran-5-carbonitrile

The title compound was prepared (0.27 g, 57%) following the general procedure of Example 154 as a white solid, hydrochloride salt from (±)-(7-bromo-5-cyano-2,3-dihydro-1-benzofuran-2-yl)methyl 4-methylbenzenesulfonate (0.60 g, 1.50 mmol) and 2-chlorophenylboronic acid (0.69 g, 4.50 mmol). mp 173-175° C.

EXAMPLE 313

(±)-{[5-(trifluoromethyl)-7-(2-fluorophenyl)-2,3-dihydro-1-benzofuran-2-yl]methyl}amine To a solution of 4-(trifluoromethyl)phenol (5.0 g, 30.86 mmol) in carbon tetrachloride (100 mL) cooled to 0° C. was added dropwise over 4 hours bromine (4.94 g, 30.86 mmol) in carbon tetrachloride (25 mL) and the reaction mixture was allowed to stir at 0° C. for 24 h. The reaction mixture was washed with 10% aqueous sodium bisulfite (100 mL) and dichloromethane (300 mL). The aqueous phase was separated and extracted with dichloromethane (2×100 mL). The combined organic extracts were washed with saturated aqueous sodium chloride (400 mL), dried (magnesium sulfate) and the solvent was removed in vacuo to give a crude oil. Purification by flash column chromatography (silica, ethyl acetate:hexanes 2:8) gave 4.69 g (63%). Treatment of 2-bromo-4-(trifluoromethyl)phenol (4.69 g, 19.5 mmol) with sodium hydride (0.86 g, 21.0 mmol 60%) and allyl bromide (2.5 g, 21.0 mmol), followed by refluxing the resultant allyl ether in mesitylene generally according to the procedure described for Intermediate 8 provided 2-allyl-6-bromo-4-(trifluoromethyl)phenol. Treatment of 2-allyl-6-bromo-4-(trifluoromethyl)phenol (3.66 g, 13.0 mmol) with 3-chloroperoxybenzoic acid (5.84 g, 26.0 mmol, 77%) followed by potassium carbonate (2.5 g, 19.5 mmol) generally according to the procedure described for Intermediate 9 afforded 3.50 g (91%) of (±)-(7-bromo-5-(trifluoromethyl)-2,3-dihydro-1-benzofuran-2-yl)methanol. Treatment of (±)-(7-bromo-5-(trifluoromethyl-2,3-dihydro-1-benzofuran-2-yl)methanol (3.5 g, 11.78 mmol) with p-toluenesulfonyl chloride (3.6 g, 17.67 mol) generally according to the procedure described for Intermediate 10 gave 5.0 g (94%) of (±)-(7-bromo-5-(trifluoromethyl)-2,3-dihydro-1-benzofuran-2-yl)methyl 4-methylbenzenesulfonate as a white solid. Treatment of (±)-(7-bromo-5-(trifluoromethyl)-2,3-dihydro-1-benzofuran-2-yl)methyl 4-methylbenzenesulfonate (0.30 g, 0.66 mmol) and 2-fluorophenylboronic acid (0.26 g, 2.13 mmol) generally according to the procedure described for Intermediate 35 afforded 0.11 g, (81%) of (±)-[7-(2-fluorophenyl)-5-(trifluoromethyl)-2,3-dihydro-1-benzofuran-2-yl]methyl 4-methylbenzenesulfonate. Treatment of the tosylate with sodium azide (0.21 g, 3.2 mmol) generally according to the procedure described for Intermediate 98 afforded 0.16 g (88%) of (±)-2-(azidomethyl)-5-(trifluoromethyl)-7-(2-fluorophenyl)-2,3-dihydro-1-benzofuran. Treatment of (±)-2-(azidomethyl)-5-(trifluoromethyl)-7-(2-fluorophenyl)-2,3-dihydro-1-benzofuran with polymer-supported triphenylphosphine (0.20 g, 0.76 mmol) according to the procedure described in Example 154 afforded 0.053 g (24%) of (±)-[(5-(trifluoromethyl)-7-(phenyl)-1-2,3-dihydro-1-benzofuran-2-yl)methyl]amine as a white solid, hydrochloride salt. mp >250° C.

EXAMPLE 314

(±)-{[5-(trifluoromethyl)-7-(2-methylphenyl)-2,3-dihydro-1-benzofuran-2-yl]methyl}amine The title compound was prepared (0.148 g, 65%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2-methylphenylboronic acid (0.36 g, 2.64 mmol). mp 253-255° C.

EXAMPLE 315

(±)-{[5-(trifluoromethyl)-7-(2-chlorophenyl)-2,3-dihydro-1-benzofuran-2-yl]methyl}amine The title compound was prepared (0.27 g, 57%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.325 g, 0.72 mmol) and 2-chlorophenylboronic acid (0.169 g, 2.88 mmol). mp 192-194° C.

EXAMPLE 316

(±)-{[5-(trifluoromethyl)-7-(2-methoxyphenyl)-2,3-dihydro-1-benzofuran-2-yl]methyl}amine The title compound was prepared (0.21 g, 87%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2-methoxyphenylboronic acid (0.40 g, 2.64 mmol). mp 203-205° C.

EXAMPLE 317

(±)-{[5-(trifluoromethyl)-7-(2-(trifluoromethyl)phenyl)-2,3-dihydro-1-benzofuran-2-yl]methyl}amine The title compound was prepared (0.088 g, 33%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2-(trifluoromethyl)phenylboronic acid (0.50 g, 2.64 mmol). mp 195-197° C.

EXAMPLE 318

(±)-{[5-(trifluoromethyl)-7-(3-methylphenyl)-2,3-dihydro-1-benzofuran-2-yl]methyl}amine The title compound was prepared (0.092 g, 40%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3-methylphenylboronic acid (0.50 g, 2.64 mmol). mp >250° C.

EXAMPLE 319

(±)-{[5-(trifluoromethyl)-7-(3-fluorophenyl)-2,3-dihydro-1-benzofuran-2-yl]methyl}amine The title compound was prepared (0.068 g, 30%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3-fluorophenylboronic acid (0.50 g, 2.64 mmol). mp >250° C.

EXAMPLE 320

(±)-{[5-(trifluoromethyl)-7-(3-chlorophenyl)-2,3-dihydro-1-benzofuran-2-yl]methyl}amine The title compound was prepared (0.102 g, 42%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3-chlorophenylboronic acid (0.41 g, 2.64 mmol). 238-240 mp ° C.

EXAMPLE 321

(±)-{[5-(trifluoromethyl)-7-(3-methoxyphenyl)-2,3-dihydro-1-benzofuran-2-yl]methyl}amine The title compound was prepared (0.125 g, 52%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3-methoxyphenylboronic acid (0.40 g, 2.64 mmol). mp 202-204° C.

EXAMPLE 322

(±)-{[5-(trifluoromethyl)-7-(3-(trifluoromethyl)phenyl)-2,3-dihydro-1-benzofuran-2-yl]methyl}amine The title compound was prepared (0.038 g, 14%) following the general procedure of Example 154 as a off-white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3-(trifluoromethyl)phenylboronic acid (0.50 g, 2.64 mmol). mp 225-227° C.

EXAMPLE 323

(±)-{[5-(trifluoromethyl)-7-(4-methylphenyl)-2,3-dihydro-1-benzofuran-2-yl]methyl}amine The title compound was prepared (0.102 g, 46%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 4-methylphenylboronic acid (0.36 g, 2.64 mmol). mp 248-250° C.

EXAMPLE 324

(±)-{[5-(trifluoromethyl)-7-(4-fluorophenyl)-2,3-dihydro-1-benzofuran-2-yl]methyl}amine The title compound was prepared (0.119 g, 52%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 4-fluorophenylboronic acid (0.37 g, 2.64 mmol). mp >250° C.

EXAMPLE 325

(±)-{[5-(trifluoromethyl)-7-(4-chlorophenyl)-2,3-dihydro-1-benzofuran-2-yl]methyl}amine The title compound was prepared (0.036 g, 15%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 4-chlorophenylboronic acid (0.42 g, 2.64 mmol). mp >250° C.

EXAMPLE 326

(±)-{[5-(trifluoromethyl)-7-(4-methoxyphenyl)-2,3-dihydro-1-benzofuran-2-yl]methyl}amine The title compound was prepared (0.130 g, 54%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 4-methoxyphenylboronic acid (0.40 g, 2.64 mmol). mp 248-250° C.

EXAMPLE 327

(±)-{[5-(trifluoromethyl)-7-(4-(trifluoromethyl)phenyl)-2,3-dihydro-1-benzofuran-2-yl]methyl}amine The title compound was prepared (0.105 g, 40%) following the general procedure of Example 154 as white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 4-(trifluoromethyl)phenylboronic acid (0.50 g, 2.64 mmol). mp >250° C.

EXAMPLE 328

(±)-{[7-(2,3-dimethylphenyl)-5-(trifluoromethyl)-2,3-dihydro-1-benzofuran-2-yl]methyl}amine The title compound was prepared (0.124 g, 58%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,3-dimethylphenylboronic acid (0.40 g, 2.64 mmol). mp 198-200° C.

EXAMPLE 329

(±)-{[7-(2,3-difluorophenyl)-5-(trifluoromethyl)-2,3-dihydro-1-benzofuran-2-yl]methyl}amine The title compound was prepared (0.059 g, 25%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,3-difluorophenylboronic acid (0.30 g, 1.90 mmol). mp. 217-218° C.

EXAMPLE 330

(±)-{[7-(2,3-dichlorophenyl)-5-(trifluoromethyl)-2,3-dihydro-1-benzofuran-2-yl]methyl}amine The title compound was prepared (0.045 g, 17%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,3-dichlorophenylboronic acid (0.50 g, 2.64 mmol). mp 152-155° C.

EXAMPLE 331

(±)-{[7-(2,3-dimethoxyphenyl)-5-(trifluoromethyl)-2,3-dihydro-1-benzofuran-2-yl]methyl}amine The title compound was prepared (0.080 g, 31%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,3-dimethoxyphenylboronic acid (0.48 g, 2.64 mmol). mp 178-180° C.

EXAMPLE 332

(±)-{[7-(2,4-difluorophenyl)-5-(trifluoromethyl)-2,3-dihydro-1-benzofuran-2-yl]methyl}amine The title compound was prepared (0.163 g, 67%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,4-difluorophenylboronic acid (0.30 g, 1.90 mmol). mp 237-239° C.

EXAMPLE 333

(±)-{[7-(2,4-dimethoxyphenyl)-5-(trifluoromethyl)-2,3-dihydro-1-benzofuran-2-yl]methyl}amine The title compound was prepared (0.098 g, 38%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,4-dimethoxyphenylboronic acid (0.48 g, 2.64 mmol). mp 210-212° C.

EXAMPLE 334

(±)-{[7-(3,4-difluorophenyl)-5-(trifluoromethyl)-2,3-dihydro-1-benzofuran-2-yl]methyl}amine The title compound was prepared (0.063 g, 26%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3,4-difluorophenylboronic acid (0.42 g, 2.64 mmol). mp 237-239° C.

EXAMPLE 335

(±)-{[7-(3-chloro-4-fluorophenyl)-5-(trifluoromethyl)-2,3-dihydro-1-benzofuran-2-yl]methyl}amine The title compound was prepared (0.044 g, 19%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3-chloro-4-fluorophenylboronic acid (0.465 g, 2.64 mmol). mp >250° C.

EXAMPLE 336

(±)-{[7-(2,5-difluorophenyl)-5-(trifluoromethyl)-2,3-dihydro-1-benzofuran-2-yl]methyl}amine The title compound was prepared (0.063 g, 26%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,5-difluorophenylboronic acid (0.42 g, 2.64 mmol). mp >250° C.

EXAMPLE 337

(±)-{[7-(2,5-dichlorophenyl)-5-(trifluoromethyl)-2,3-dihydro-1-benzofuran-2-yl]methyl}amine The title compound was prepared (0.128 g, 48%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,5-dichlorophenylboronic acid (0.503 g, 2.64 mmol). mp 203-205° C.

EXAMPLE 338

(±)-{[7-(2,6-dimethylphenyl)-5-(trifluoromethyl)-2,
3-dihydro-1-benzofuran-2-yl]methyl}amine The title compound was prepared (0.012 g, 4%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 2,6-dimethylphenylboronic acid (0.40 g, 2.64 mmol). mp 198-200° C.

EXAMPLE 339

(±)-{[7-(4-butylphenyl)-5-(trifluoromethyl)-2,3-dihydro-1-benzofuran-2-yl]methyl}amine The title compound was prepared (0.122 g, 48%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 4-butylphenylboronic acid (0.28 g, 1.57 mmol). mp 190-192° C.

EXAMPLE 340

(±)-4-[2-(aminomethyl)-5-(trifluoromethyl)-2,3-dihydro-1-benzofuran-7-yl]benzonitrile The title compound was prepared (0.102 g, 35%) following the general procedure of Example 154 as a white solid from (±)-(7-bromo-5-(trifluoromethyl)-2,3-dihydro-1-benzofuran-2-yl)methyl 4-methylbenzenesulfonate (0.30 g, 0.66 mmol) and 4-cyanophenylboronic acid (0.23 g, 1.57 mmol). mp 238-239° C.

EXAMPLE 341

(±)-{[7-(3-furyl)-5-(trifluoromethyl)-2,3-dihydro-1-benzofuran-2-yl]methyl}amine The title compound was prepared (0.053 g, 25%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3-furylphenylboronic acid (0.22 g, 1.96 mmol). mp >250° C.

EXAMPLE 342

(±)-{[7-thien-3-yl-5-(trifluoromethyl)-2,3-dihydro-1-benzofuran-2-yl]methyl}amine The title compound was prepared (0.164 g, 73%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and 3-thienylboronic acid (0.34 g, 2.64 mmol). mp >250° C.

EXAMPLE 343

(±)-{[7-pyridin-3-yl-5-(trifluoromethyl)-2,3-dihydro-1-benzofuran-2-yl]methyl}amine The title compound was prepared (0.081 g, 30%) following the general procedure of Example 154 as a white solid, hydrochloride salt from (±)-(7-bromo-5-(trifluoromethyl)-2,3-dihydro-1-benzofuran-2-yl)methyl 4-methylbenzenesulfonate (0.30 g, 0.66 mmol) and pyridine-3-ylboronic acid (0.24 g, 1.95 mmol). mp 200-202° C.

EXAMPLE 344

(±)-[(5,7-diphenyl-2,3-dihydro-1-benzofuran-2-yl)methyl]amine

Treatment of 3-bromo-4-hydroxybiphenyl (15.7 g, 63.0 mmol) with potassium carbonate (34.84 g, 252.0 mmol) and allyl bromide (9.15 g, 75.63 mmol), followed by refluxing the resultant allyl ether in mesitylene generally according to the procedure described for Intermediate 8 provided 3-allyl-5-bromobiphenyl-4-ol. Treatment of 3-allyl-5-bromobiphenyl-4-ol (17.8 g, 61.5 mmol) with 3-chloroperoxybenzoic acid (31.87 g, 184.67 mmol, 77%) followed by potassium carbonate (21.27 g, 153.89 mmol) generally according to the procedure described for Intermediate 9 afforded 15.8 g (84%) of (±)-(7-bromo-5-phenyl-2,3-dihydro-1-benzofuran-2-yl)methanol. Treatment of (±)-(7-bromo-5-phenyl-2,3-dihydro-1-benzofuran-2-yl)methanol (15.8 g, 51.77 mmol) with p-toluenesulfonyl chloride (14.79 g, 77.65 mmol) generally according to the procedure described for Intermediate 10 gave 18.8 g (79%) of (±)-(7-bromo-5-phenyl-2,3-dihydro-1-benzofuran-2-yl)methyl 4-methylbenzenesulfonate as a white solid. Treatment of (±)-(7-bromo-5-methyl-2,3-dihydro-1-benzofuran-2-yl)methyl 4-methylbenzenesulfonate (1.5 g, 3.26 mmol) and phenylboronic acid (0.59 g, 4.89 mmol) generally according to the procedure described for Intermediate 35 afforded 1.17 g, (78%) of (±)-(5,7-diphenyl-2,3-dihydro-1-benzofuran-2-yl)methyl 4-methylbenzenesulfonate. Treatment of the tosylate with sodium azide (0.342 g, 5.26 mmol) generally according to the procedure described for Intermediate 98 afforded 0.39 g (91%) of (±)-2-(azidomethyl)-5,7-diphenyl-2,3-dihydro-1-benzofuran. Treatment of (±)-2-(azidomethyl)-5,7-diphenyl-2,3-dihydro-1-benzofuran with polymer-supported triphenylphosphine (0.314 g, 1.21 mmol) according to the procedure described in Example 154 afforded 0.34 g (99%) of (±)-(5,7-diphenyl-2,3-dihydro-1-benzofuran-2-yl)methylamine as a white solid, hydrochloride salt. mp >250° C.

EXAMPLE 345

(±)-{[7-(2-chlorophenyl)-5-phenyl-2,3-dihydro-1-benzofuran-2-yl]methyl}amine

The title compound was prepared (0.157 g, 39%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.09 mmol) and 2-chlorophenylboronic acid (0.255 g, 1.63 mmol). mp >250° C.

EXAMPLE 346

(±)-{[7-(3-chlorophenyl)-5-phenyl-2,3-dihydro-1-benzofuran-2-yl]methyl}amine

The title compound was prepared (0.166 g, 41%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.09 mmol) and 3-chlorophenylboronic acid (0.255 g, 1.63 mmol). mp 240-242° C.

EXAMPLE 347

(±)-{[7-(4-chlorophenyl)-5-phenyl-2,3-dihydro-1-benzofuran-2-yl]methyl}amine

The title compound was prepared (0.092 g, 22%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.09 mmol) and 4-chlorophenylboronic acid (0.255 g, 1.63 mmol). mp 200-203° C.

EXAMPLE 348

(±)-{[7-(2-fluorophenyl)-5-phenyl-2,3-dihydro-1-benzofuran-2-yl]methyl}amine

The title compound was prepared (0.153 g, 39%) following the general procedure of Example 154 as a light yellow solid, hydrochloride salt from (±)-(7-bromo-5-methyl-2,3-dihydro-1-benzofuran-2-yl)methyl 4-methylbenzenesulfonate (0.50 g, 1.09 mmol) and 2-fluorophenylboronic acid (0.228 g, 1.63 mmol). mp >250° C.

EXAMPLE 349

(±)-{[7-(3-fluorophenyl)-5-phenyl-2,3-dihydro-1-benzofuran-2-yl]methyl}amine

The title compound was prepared following the general procedure of Example 154 as a light yellow solid, hydrochloride salt (0.107 g, 28%) from (±)-(7-bromo-5-methyl-2,3-dihydro-1-benzofuran-2-yl)methyl 4-methylbenzenesulfonate (0.50 g, 1.09 mmol) and 3-fluorophenylboronic acid (0.228 g, 1.63 mmol). mp >250° C.

EXAMPLE 350

(±)-{[7-(4-fluorophenyl)-5-phenyl-2,3-dihydro-1-benzofuran-2-yl]methyl}amine

The title compound was prepared (0.106 g, 27%) following the general procedure of Example 154 as a light yellow solid, hydrochloride salt from (±)-(7-bromo-5-methyl-2,3-dihydro-1-benzofuran-2-yl)methyl 4-methylbenzenesulfonate (0.50 g, 1.09 mmol) and 4-fluorophenylboronic acid (0.228 g, 1.63 mmol). mp >250° C.

EXAMPLE 351

(±)-{[7-(2-methylphenyl)-5-phenyl-2,3-dihydro-1-benzofuran-2-yl]methyl}amine

The title compound was prepared (0.148 g, 39%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.09 mmol) and 2-methylphenylboronic acid (0.222 g, 1.63 mmol). mp 225-227° C.

EXAMPLE 352

(±)-{[7-(3-methylphenyl)-5-phenyl-2,3-dihydro-1-benzofuran-2-yl]methyl}amine

The title compound was prepared (0.080 g, 21%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.09 mmol) and 3-methylphenylboronic acid (0.222 g, 1.63 mmol). mp 246-249° C.

EXAMPLE 353

(±)-{[7-(4-methylphenyl)-5-phenyl-2,3-dihydro-1-benzofuran-2-yl]methyl}amine

The title compound was prepared (0.094 g, 25%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.09 mmol) and 4-methylphenylboronic acid (0.222 g, 1.63 mmol). mp 159-162° C.

EXAMPLE 354

(±)-{[7-(2,4-difluorophenyl)-5-phenyl-2,3-dihydro-1-benzofuran-2-yl]methyl}amine The title compound was prepared (0.157 g, 38%) following the general procedure of Example 154 as white solid, hydrochloride salt from (±)-(7-bromo-5-methyl-2,3-dihydro-1-benzofuran-2-yl)methyl 4-methylbenzenesulfonate (0.50 g, 1.09 mmol) and (2,4-difluorophenyl)boronic acid (0.258 g, 1.63 mmol). mp 159-162° C.

EXAMPLE 355

(±)-{[7-(2,5-dichlorophenyl)-5-phenyl-2,3-dihydro-1-benzofuran-2-yl]methyl}amine The title compound was prepared (0.168 g, 38%) following the general procedure of Example 154 as a white solid, hydrochloride salt from (±)-(7-bromo-5-methyl-2,3-dihydro-1-benzofuran-2-yl)methyl 4-methylbenzenesulfonate (0.50 g, 1.09 mmol) and (2,5-dichlorophenyl)boronic acid (0.312 g, 1.63 mmol). mp 159-162° C.

EXAMPLE 356

(±)-{[7-(2-fluorophenyl)-5-methoxy-2,3-dihydro-1-benzofuran-2-yl]methyl}amine

The title compound was prepared (0.121 g, 49%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.21 mmol) and 2-fluorophenylboronic acid (0.68 g, 4.84 mmol). mp >250° C.

EXAMPLE 357

(±)-{[7-(2-chlorophenyl)-5-methoxy-2,3-dihydro-1-benzofuran-2-yl]methyl}amine

The title compound was prepared (0.121 g, 46%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.21 mmol) and 2-chlorophenylboronic acid (0.75 g, 4.84 mmol). mp 179-181° C.

EXAMPLE 358

(±)-{[7-(2-methylphenyl)-5-methoxy-2,3-dihydro-1-benzofuran-2-yl]methyl}amine

The title compound was prepared (0.118 g, 48%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.21 mmol) and 2-methylphenylboronic acid (0.66 g, 4.84 mmol). mp 187-189° C.

EXAMPLE 359

(±)-{[7-(2-methoxyphenyl)-5-methoxy-2,3-dihydro-1-benzofuran-2-yl]methyl}amine

The title compound was prepared (0.181 g, 33%) following the general procedure of Example 154 as a white solid, hydrochloride salt from (±)-(7-bromo-5-methoxy-2,3-dihydro-1-benzofuran-2-yl)methyl 4-methylbenzenesulfonate (1.0 g, 2.42 mmol) and 2-methoxyphenylboronic acid (1.55 g, 9.68 mmol). mp 190-192° C.

EXAMPLE 360

(±)-{[5-methoxy-7-(3-thienyl)-2,3-dihydro-1-benzofuran-2-yl]methyl}amine

The title compound was prepared (0.110 g, 46%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.21 mmol) and 3-thienylboronic acid (0.62 g, 4.84 mmol). mp 230-232° C.

EXAMPLE 361

(±)-{[7-(2,3-difluorophenyl)-5-methoxy-2,3-dihydro-1-benzofuran-2-yl]methyl}amine The title compound was prepared (0.141 g, 54%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,3 difluorophenylboronic acid (0.76 g, 4.84 mmol). mp 224-226° C.

EXAMPLE 362

(±)-{[7-(2,3-dichlorophenyl)-5-methoxy-2,3-dihydro-1-benzofuran-2-yl]methyl}amine The title compound was prepared (0.087 g, 30%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,3 dichlorophenylboronic acid (0.92 g, 4.84 mmol). mp 159-161° C.

EXAMPLE 363

(±)-{[7-(2,3-dimethylphenyl)-5-methoxy-2,3-dihydro-1-benzofuran-2-yl]methyl}amine The title compound was prepared (0.132 g, 52%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,3 dimethylphenylboronic acid (0.70 g, 4.84 mmol). mp 129-130° C.

EXAMPLE 364

(±)-{[7-(2,4-difluorophenyl)-5-methoxy-2,3-dihydro-1-benzofuran-2-yl]methyl}amine The title compound was prepared (0.164 g, 63%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,4 difluorophenylboronic acid (0.76 g, 4.84 mmol). mp 226-228° C.

EXAMPLE 365

(±)-{[7-(2,4-dichlorophenyl)-5-methoxy-2,3-dihydro-1-benzofuran-2-yl]methyl}amine The title compound was prepared (0.091 g, 32%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,4 dichlorophenylboronic acid (0.92 g, 4.84 mmol). mp 180-182° C.

EXAMPLE 366

(±)-{[7-(2,5-difluorophenyl)-5-methoxy-2,3-dihydro-1-benzofuran-2-yl]methyl}amine The title compound was prepared (0.148 g, 56%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,5 difluorophenylboronic acid (0.76 g, 4.84 mmol). mp 118-120° C.

EXAMPLE 367

(±)-{[7-(2,5-dichlorophenyl)-5-methoxy-2,3-dihydro-1-benzofuran-2-yl]methyl}amine The title compound was prepared (0.048 g, 16%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,5 dichlorophenylboronic acid (0.92 g, 4.84 mmol). mp 140-142° C.

EXAMPLE 368

(+)-{[7-(2,5-dichlorophenyl)-5-methoxy-2,3-dihydro-1-benzofuran-2-yl]methyl}amine Treatment of 0.50 g of fraction 1 obtained from the chiral HPLC separation of (±)-benzyl {[7-(2,5-dichlorophenyl)-5-methoxy-2,3-dihydro-1-benzofuran-2-yl]methyl}carbamate with hydrogen bromide (14 mL, 30 wt. % in acetic acid) generally according to the procedure described for Example 245 gave 0.297 g (75%) of (+)-{[7-(2,5-dichlorophenyl)-5-methoxy-2,3-dihydro-1-benzofuran-2-yl]methyl}amine as a white solid, hydrochloride salt. $[\alpha]_D^{25}$=+6.62 (c 10.0 in methanol); mp 148-150° C.

EXAMPLE 369

(−)-{[7-(2,5-dichlorophenyl)-5-methoxy-2,3-dihydro-1-benzofuran-2-yl]methyl}amine Treatment of 0.135 g of fraction 2 obtained from the chiral HPLC separation of (±)-benzyl {[7-(2,5-dichlorophenyl)-5-methoxy-2,3-dihydro-1-benzofuran-2-yl]methyl}carbamate with hydrogen bromide (3 mL, 30 wt. % in acetic acid) generally according to the procedure described for Example 245 gave 0.047 g (44%) of (−)-{[7-(2,5-dichlorophenyl)-5-methoxy-2,3-dihydro-1-benzofuran-2-yl]methyl}amine a white solid, hydrochloride salt. $[\alpha]_D^{25}$=−6.73 (c 10.0 in methanol); mp 148-150° C.

EXAMPLE 370

(±)-{[7-(2,5-dimethylphenyl)-5-methoxy-2,3-dihydro-1-benzofuran-2-yl]methyl}amine The title compound was prepared (0.134 g, 53%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,5 dimethylphenylboronic acid (0.70 g, 4.84 mmol). mp 214-216° C.

EXAMPLE 371

(±)-{[7-(2,5-dimethoxyphenyl)-5-methoxy-2,3-dihydro-1-benzofuran-2-yl]methyl}amine The title compound was prepared (0.070 g, 24%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,5 dimethoxyphenylboronic acid (0.88 g, 4.84 mmol). mp 128-130° C.

EXAMPLE 372

(±)-{[7-(5-chloro-2-methoxyphenyl)-5-methoxy-2,3-dihydro-1-benzofuran-2-yl]methyl}amine The title compound was prepared (0.169 g, 60%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 5-chloro-2-methoxyphenylboronic acid (0.90 g, 4.84 mmol). mp 172-174° C.

EXAMPLE 373

(±)-{[7-(3-chloro-4-fluorophenyl)-5-methoxy-2,3-dihydro-1-benzofuran-2-yl]methyl}amine The title compound was prepared (0.178 g, 65%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 3-chloro-4-fluorophenylboronic acid (0.84 g, 4.84 mmol). mp 220-222° C.

EXAMPLE 374

(±)-{[7-(2,6-dimethylphenyl)-5-methoxy-2,3-dihydro-1-benzofuran-2-yl]methyl}amine The title compound was prepared (0.170 g, 67%) following the general procedure of Example 154 as a white solid, hydrochloride salt from (±)-(7-bromo-5-methoxy-2,3-dihydro-1-benzofuran-2-yl)methyl 4-methylbenzenesulfonate (0.50 g, 1.26 mmol) and 2,6 dimethylphenylboronic acid (0.92 g, 4.84 mmol). mp 212-214° C.

EXAMPLE 375

(±)-{[7-fluoro-5-(2-methylphenyl)-2,3-dihydro-1-benzofuran-2-yl]methyl}amine

Treatment of 4-bromo-2-fluorophenol (25.0 g, 130.9 mmol) with potassium carbonate (72.35 g, 523.53 mmol) and allyl bromide (19.00 g, 157.06 mmol), followed by refluxing the resultant allyl ether in mesitylene generally according to the procedure described for Intermediate 8 provided 2-allyl-4-bromo-6-fluorophenol. Treatment of 2-allyl-4-bromo-6-fluorophenol (25.6 g, 110.8 mmol) with 3-chloroperoxybenzoic acid (57.36 g, 332.38 mmol, 77%) followed by potassium carbonate (38.28 g, 277.0 mmol) generally according to the procedure described for Intermediate 9 afforded 19.1 g (70%) of (±)-(7-fluoro-5-bromo-2,3-dihydro-1-benzofuran-2-yl)methanol. Treatment of (±)-(7-fluoro-5-bromo-2,3-dihydro-1-benzofuran-2-yl)methanol (18.61 g, 75.3 mmol) with p-toluenesulfonyl chloride (17.22 g, 90.34 mmol) generally according to the procedure described for Intermediate 10 gave 22.6 g (75%) of (±)-(7-fluoro-5-bromo-2,3-dihydro-1-benzofuran-2-yl)methyl 4-methylbenzenesulfonate as a white solid. Treatment of (±)-(7-fluoro-5-bromo-2,3-dihydro-1-benzofuran-2-yl)methyl 4-methylbenzenesulfonate (0.5 g, 1.25 mmol) and 2-methylphenylboronic acid (0.254 g, 1.87 mmol) generally according to the procedure described for Intermediate 35 afforded 0.282 g, (55%) of (±)-([7-fluoro-5-(2-methylphenyl)-2,3-dihydro-1-benzofuran-2-yl]methyl 4-methylbenzenesulfonate. Treatment of the tosylate with sodium azide (0.19 g, 3.0 mmol) generally according to the procedure described for Intermediate 98 afforded 0.17 g (99%) of (±)-2-(azidomethyl)-7-fluoro-5-(2-methylphenyl)-2,3-dihydro-1-benzofuran. Treatment of (±)-2-(azidomethyl)-7-fluoro-5-(2-methylphenyl)-2,3-dihydro-1-benzofuran with polymer-supported triphenylphosphine (0.30 g, 3.0 mmol) according to the procedure described in Example 154 afforded 0.038 g (22%) of (±)-([7-fluoro-5-(2-methylphenyl)-2,3-dihydro-1-benzofuran-2-yl]methyl]amine as a white solid, hydrochloride salt. mp >250° C.

EXAMPLE 376

(±)-{[7-fluoro-5-(2-chlorophenyl)-2,3-dihydro-1-benzofuran-2-yl]methyl}amine

The title compound was prepared (0.026 g, 24%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 2-chlorophenylboronic acid (0.292 g, 1.89 mmol). mp >250° C.

EXAMPLE 377

(±)-{[7-fluoro-5-(2-fluorophenyl)-2,3-dihydro-1-benzofuran-2-yl]methyl}amine

The title compound was prepared (0.055 g, 38%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 2-fluorophenylboronic acid (0.292 g, 1.89 mmol). mp >250° C.

EXAMPLE 378

(±)-({7-fluoro-5-[2-(trifluoromethyl)phenyl]-2,3-dihydro-1-benzofuran-2-yl}methyl)amine The title compound was prepared (0.059 g, 38%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and [2-(trifluoromethyl)phenyl]boronic acid (0.355 g, 1.89 mmol). mp 189-194° C. (dec).

EXAMPLE 379

(±)-{[7-fluoro-5-(2-methoxyphenyl)-2,3-dihydro-1-benzofuran-2-yl]methyl}amine

The title compound was prepared (0.050 g, 38%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 2-methoxyphenylboronic acid (0.284 g, 1.89 mmol). mp 203-207° C. (dec).

EXAMPLE 380

(±)-{[7-fluoro-5-(3-methylphenyl)-2,3-dihydro-1-benzofuran-2-yl]methyl}amine

The title compound was prepared (0.057 g, 40%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 3-methylphenylboronic acid (0.254 g, 1.89 mmol). mp >250° C.

EXAMPLE 381

(±)-{[7-fluoro-5-(3-fluorophenyl)-2,3-dihydro-1-benzofuran-2-yl]methyl}amine

The title compound was prepared (0.071 g, 52%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 3-fluorophenylboronic acid (0.292 g, 1.89 mmol). mp >250° C.

EXAMPLE 382

(±)-{[7-fluoro-5-(3-chlorophenyl)-2,3-dihydro-1-benzofuran-2-yl]methyl}amine

The title compound was prepared (0.065 g, 44%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 3-chlorophenylboronic acid (0.292 g, 1.89 mmol). mp >250° C.

EXAMPLE 383

(±)-({7-fluoro-5-[3-(trifluoromethyl)phenyl]-2,3-dihydro-1-benzofuran-2-yl}methyl)amine The title compound was prepared (0.055 g, 37%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 3-(trifluoromethyl)phenylboronic acid (0.355 g, 1.89 mmol). mp >250° C.

EXAMPLE 384

(±)-{[7-fluoro-5-(3-methoxyphenyl)-2,3-dihydro-1-benzofuran-2-yl]methyl}amine

The title compound was prepared (0.042 g, 32%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 3-methoxyphenylboronic acid (0.284 g, 1.89 mmol). mp >250° C.

EXAMPLE 385

(±)-{[7-fluoro-5-(4-methylphenyl)-2,3-dihydro-1-benzofuran-2-yl]methyl}amine

The title compound was prepared (0.061 g, 50%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 4-methylphenylboronic acid (0.254 g, 1.89 mmol). mp >250° C.

EXAMPLE 386

(±)-{[7-fluoro-5-(4-chlorophenyl)-2,3-dihydro-1-benzofuran-2-yl]methyl}amine

The title compound was prepared (0.085 g, 55%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 4-chlorophenylboronic acid (0.292 g, 1.89 mmol). mp >250° C.

EXAMPLE 387

(±)-{[7-fluoro-5-(4-fluorophenyl)-2,3-dihydro-1-benzofuran-2-yl]methyl}amine

The title compound was prepared (0.060 g, 47%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 4-fluorophenylboronic acid (0.292 g, 1.89 mmol). mp >250° C.

EXAMPLE 388

(±)-({7-fluoro-5-[4-(trifluoromethyl)phenyl]-2,3-dihydro-1-benzofuran-2-yl}methyl)amine The title compound was prepared (0.041 g, 26%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and [4-(trifluoromethyl)phenyl]boronic acid (0.355 g, 1.89 mmol). mp >250° C.

EXAMPLE 389

(±)-{[7-fluoro-5-(4-methoxyphenyl)-2,3-dihydro-1-benzofuran-2-yl]methyl}amine

The title compound was prepared (0.66 g, 51%) following the general procedure of Example 154 as a white solid, hydrochloride salt from of (±)-(7-fluoro-5-bromo-2,3-dihydro-1-benzofuran-2-yl)methyl 4-methylbenzenesulfonate. (0.50 g, 1.25 mmol) and 4-methoxyphenylboronic acid (0.284 g, 1.89 mmol). mp >250° C.

EXAMPLE 390

(±)-N-{[7-(2,6-dichlorophenyl)-2,3-dihydro-1-benzofuran-2-yl]methyl}ethanamine

To a solution of (±)-7-(2,6-dichlorophenyl)-2,3-dihydro-1-benzofuran-2-yl 4-methylbenzenesulfonate (0.2 g, 0.46 mmol) in dimethylsulfoxide (5 mL) was added ethylamine (0.20 g, 4.4 mmol) and the reaction mixture was allowed to stir at 60° C. for 12 h. The reaction was diluted with water (10 mL) and ethyl acetate (2×10 mL). The combined organic layers were washed with water (3×20 mL) and saturated aqueous sodium chloride (20 mL), dried (magnesium sulfate) and the solvent was removed in vacuo to give an oil. The oil was re-dissolved in isopropanol (0.5 mL) and hydrogen chloride (0.5 mL, 1.0 M in diethyl ether) was added. The resulting precipitate was filtered, washed (diethyl ether), to give 0.084 g (57%) of (±)-N-{[7-(2,6-dichlorophenyl)-2,3-dihydro-1-benzofuran-2-yl]methyl}ethanamine as a white solid, hydrochloride salt. mp 195-197° C.

EXAMPLE 391

(±)-N-{[7-(2,6-dichlorophenyl)-2,3-dihydro-1-benzofuran-2-yl]methyl}cyclopropanamine The title compound was prepared (0.057 g, 39%) following the general procedure of Example 390 as a white solid, hydrochloride salt from (±)-7-(2,6-dichlorophenyl)-2,3-dihydro-1-benzofuran-2-yl 4-methylbenzenesulfonate (0.2 g, 0.46 mmol) and cyclopropylamine (0.254 g, 4.40 mmol). mp 182-184° C.

EXAMPLE 392

(±)-N-{[7-(2,6-dichlorophenyl)-2,3-dihydro-1-benzofuran-2-yl]methyl}cyclobutanamine The title compound was prepared (0.077 g, 39%) following the general procedure of Example 390 as a white solid, hydrochloride salt from (±)-7-(2,6-dichlorophenyl)-2,3-dihydro-1-benzofuran-2-yl 4-methylbenzenesulfonate (0.2 g, 0.46 mmol) and cyclobutylamine (0.317 g, 4.40 mmol). mp 185-188° C.

EXAMPLE 393

(±)-N-{[7-(2,6-dichlorophenyl)-2,3-dihydro-1-benzofuran-2-yl]methyl}propan-2-amine The title compound was prepared (0.054 g, 35%) following the general procedure of Example 390 as a white solid, hydrochloride salt from (±)-7-(2,6-dichlorophenyl)-2,3-dihydro-1-benzofuran-2-yl 4-methylbenzenesulfonate (0.2 g, 0.46 mmol) and isopropylamine (0.258 g, 4.40 mmol). mp 182-184° C.

EXAMPLE 394

No compound

EXAMPLE 395

(±)-{[6-fluoro-7-(2-methylphenyl)-2,3-dihydro-1-benzofuran-2-yl]methyl}amine

Treatment of 1-bromo-2-methylbenzene (10.06 g, 58.84 mmol) with (2-fluoro-6-methyoxyphenyl)boronic acid (5.0 g, 29.42 mol tetrakis(triphenylphosphine)palladium(0) (2.5 g, 2.16 mmol), and sodium carbonate (6.2 g, 58.84 mmol) generally according to the procedure described for Intermediate 37 provided 2.35 g (37%) of 6-fluoro-2'-methylbiphenyl-2-yl methyl ether. A solution of 6-fluoro-2'-methylbiphenyl-2-yl methyl ether (2.35 g, 10.86 mmol) in hydrogen bromide (40 mL, 30 wt. % in acetic acid) was heated to 55° C. for 12 h. The reaction mixture was concentrated under in vacuo and the crude residue diluted with ethyl acetate (200 mL). The organic layer was carefully extracted with saturated bicarbonate solution (3×200 mL) was dried (magnesium sulfate), and the solvent was removed in vacuo to provide a crude oil. Treatment of 6-fluoro-2'-methybiphenyl-2-ol (2.17 g, 10.84 mmol) with sodium hydride (0.65 g, 16.26 mmol, 60 wt. %) and allyl bromide (0.96 g, 16.26 mmol), followed by refluxing the resultant allyl ether in mesitylene generally according to the procedure described for Intermediate 8 provided 3-allyl-6-fluoro-2'-methylbiphenyl-2-ol. Treatment of 3-allyl-6-fluoro-2'-methylbiphenyl-2-ol (1.77 g, 7.3 mmol) with 3-chloroperoxybenzoic acid (3.2 g, 10.96 mmol, 77%) followed by potassium carbonate (1.2 g, 8.76 mmol) generally according to the procedure described for Intermediate 9 afforded 1.5 g (80%) of (±)-[6-fluoro-7-(2-methylphenyl)-2, 3-dihydro-1-benzofuran-2-yl]methanol. Treatment of (±)-[6-fluoro-7-(2-methylphenyl)-2,3-dihydro-1-benzofuran-2-yl] methanol (1.5 g, 5.81 mmol) with p-toluenesulfonyl chloride (1.66 g, 8.71 mol) generally according to the procedure described for Intermediate 10 gave 2.17 g (90%) of (±)-[6-fluoro-7-(2-methylphenyl)-2,3-dihydro-1-benzofuran-2-yl] methyl 4-methylbenzenesulfonate as a white solid. Treatment of (±)-[6-fluoro-7-(2-methylphenyl)-2,3-dihydro-1-benzofuran-2-yl]methyl 4-methylbenzenesulfonate (0.23 g, 0.56 mmol) with sodium azide (0.23 g, 3.54 mmol) generally according to the procedure described for Intermediate 98 afforded 0.135 g, (86%) of (±)-2-(azidomethyl)-6-fluoro-7-(2-methylphenyl)-2,3-dihydro-1-benzofuran. Treatment of (±)-2-(azidomethyl)-6-fluoro-7-(2-methylphenyl)-2,3-dihydro-1-benzofuran (0.135 g, 0.4 mmol) in tetrahydrofuran (10 mL) with polymer-supported triphenylphosphine (0.30 g, 0.9 mmol) generally according to the procedure described for Example 154 provided 0.11 g (67%) of (±)-{[6-fluoro-7-(2-methylphenyl)-2,3-dihydro-1-benzofuran-2-yl] methyl}amine as a white solid, hydrochloride salt. mp 216-218° C.

EXAMPLE 396

(+)-{[6-fluoro-7-(2-methylphenyl)-2,3-dihydro-1-benzofuran-2-yl]methyl}amine

Treatment of 0.66 g of fraction 1 obtained from the chiral HPLC separation of (±)-benzyl {[6-fluoro-7-(2-methylphenyl)-2,3-dihydro-1-benzofuran-2-yl]methyl}carbamate with hydrogen bromide (5 mL, 30 wt. % in acetic acid) generally according to the procedure described for Example 245 gave 0.276 g (76%) of (+)-{[6-fluoro-7-(2-methylphenyl)-2,3-dihydro-1-benzofuran-2-yl]methyl}amine as a white solid, hydrochloride salt. mp 216-218° C.

EXAMPLE 397

(−)-{[6-fluoro-7-(2-methylphenyl)-2,3-dihydro-1-benzofuran-2-yl]methyl}amine

Treatment of 0.66 g of fraction 2 obtained from the chiral HPLC separation of (±)-benzyl {[(6-fluoro-7-(2-methylphenyl)-2,3-dihydro-1-benzofuran-2-yl]methyl}carbamate with hydrogen bromide (5 mL, 30 wt. % in acetic acid) generally according to the procedure described for Example 245 gave 0.192 g (52%) of (−)-{[6-fluoro-7-(2-methylphenyl)-2,3-dihydro-1-benzofuran-2-yl]methyl}amine as a white solid, hydrochloride salt. mp 216-218° C.

EXAMPLE 398

(±)-{[7-(2-chlorophenyl)-6-fluoro-2,3-dihydro-1-benzofuran-2-yl]methyl}amine

Treatment of 1-bromo-2-chlorobenzene (5.63 g, 29.4 mmol) with (2-fluoro-6-methyoxyphenyl)boronic acid (5.0 g, 29.42 mol) generally according to the procedure described for Intermediate 37 afforded 2.0 g (29%) of 6-fluoro-2'-chlorobiphenyl-2-yl methyl ether. Treatment of 6-fluoro-2'-chlorobiphenyl-2-yl methyl ether with hydrogen bromide (50 mL, 30 wt. % in acetic acid) generally according to the procedure described for Example 395 afforded a brown oil. The oil was reacted with sodium hydride (0.34 g, 14.35 mmol) and allyl bromide (1.74 g, 14.35 mmol) followed by refluxing the resultant allyl ether in mesitylene generally according to the procedure described for Intermediate 8 to provide 3-allyl-6-chloro-2'-chlorobiphenyl-2-ol. Treatment of 3-allyl-6-fluoro-2'-methylbiphenyl-2-ol (1.2 g, 4.56 mmol) with m-chloroperoxybenzoic acid (2.36 g, 13.68 mmol, 77%) and potassium carbonate (1.575 g, 11.4 mmol) generally according to the procedure described for Intermediate 9 afforded 0.7 g (55%) of (±)-[7-(2-chlorophenyl)-6-fluoro-2,3-dihydro-1-benzofuran-2-yl]methanol. Treatment (±)-[7-(2-chlorophenyl)-6-fluoro-2,3-dihydro-1-benzofuran-2-yl]methanol (1.5 g, 5.81 mmol) with p-toluenesulfonyl chloride (1.66 g, 8.71 mol) generally according to the procedure described for Intermediate 10 gave 0.9 g (82%) of (±)-[6-fluoro-7-(2-chlorophenyl)-2,3-dihydro-1-benzofuran-2-yl]methyl 4-methylbenzenesulfonate as a white solid. Treatment of (±)-[6-fluoro-7-(2-chlorophenyl)-2,3-dihydro-1-benzofuran-2-yl]methyl 4-methylbenzenesulfonate (0.50 g, 1.15 mmol) with sodium azide (0.4 g, 6.15 mmol) generally according to the procedure described for Intermediate 98 afforded 0.35 g, (99%) of (±)-2-(azidomethyl)-7-(2-chlorophenyl)-6-fluoro-2,3-dihydro-1-benzofuran. Treatment of (±)-2-(azidomethyl)-7-(2-chlorophenyl)-6-fluoro-2,3-dihydro-1-benzofuran (0.35 g, 1.15 mmol) in tetrahydrofuran (10 mL) with polymer-supported triphenylphosphine (0.60 g, 2.3 mmol) generally according to the procedure described for Example 154 provided 0.170 g (47%) of (±)-{[6-fluoro-7-(2-chlorophenyl)-2,3-dihydro-1-benzofuran-2-yl]methyl}amine as a white solid, hydrochloride salt. mp 248-250° C.

EXAMPLE 399

(±)-{[6-chloro-7-(2-methylphenyl)-2,3-dihydro-1-benzofuran-2-yl]methyl}amine

Treatment of 1-bromo-2-methylbenzene (5.0 g, 26.88 mmol) with (2-chloro-6-methyoxyphenyl)boronic acid (13.8 g, 80.6 mol) generally according to the procedure described for Intermediate 37 afforded 3.85 g (62%) of 6-chloro-2'-methylbiphenyl-2-yl methyl ether. Treatment of 6-chloro-2'-methylbiphenyl-2-yl methyl ether with hydrogen bromide (100 mL, 30 wt. % in acetic acid) generally according to the procedure described for Example 395 afforded brown oil. The oil was reacted with sodium hydride (0.61 g, 25.38 mmol) and allyl bromide (3.07 g, 25.38 mmol) followed by refluxing the resultant allyl ether in mesitylene generally according to the procedure described for Intermediate 8 provided 3-allyl-6-chloro-2'-methylbiphenyl-2-ol. Treatment of 3-allyl-6-chloro-2'-methylbiphenyl-2-ol (4.38 g, 16.92 mmol) with m-chloroperoxybenzoic acid (4.38 g, 25.38 mmol, 77%) and potassium carbonate (2.81 g, 20.30 mmol) generally according to the procedure described for Intermediate 9 afforded 2.4 g (52%) of (±)-[7-(2-methylphenyl)-6-chloro-2,3-dihydro-1-benzofuran-2-yl]methanol. Treatment (±)-[7-(2-methylphenyl)-6-chloro-2,3-dihydro-1-benzofuran-2-yl]methanol (2.4 g, 8.73 mmol) with p-toluenesulfonyl chloride (2.50 g, 13.1 mmol) generally according to the procedure described for Intermediate 10 gave 3.2 g (85%) of (±)-[6-chloro-7-(2-methylphenyl)-2,3-dihydro-1-benzofuran-2-yl]methyl 4-methylbenzenesulfonate as a colorless oil. Treatment of (±)-[6-chloro-7-(2-methylphenyl)-2,3-dihydro-1-benzofuran-2-yl]methyl 4-methylbenzenesulfonate (0.21 g, 0.49 mmol) with sodium azide (0.35 g, 5.38 mmol) generally according to the procedure described for Intermediate 98 afforded 0.14 g, (99%) of (±)-2-(azidomethyl)-7-(2-methylphenyl)-6-chloro-2,3-dihydro-1-benzofuran. Treatment of (±)-2-(azidomethyl)-7-(2-methylphenyl)-6-chloro-2,3-dihydro-1-benzofuran (0.14 g, 0.468 mmol) in tetrahydrofuran (10 m]L) with polymer-supported triphenylphosphine (0.24 g, 0.936 mmol) generally according to the procedure described for Example 154 provided 0.028 g (18%) of (±)-{[6-chloro-7-(2-methylphenyl)-2,3-dihydro-1-benzofuran-2-yl]methyl}amine as a white solid, hydrochloride salt. mp 204-206° C.

EXAMPLE 400

(±)-{[6-chloro-7-(2-chlorophenyl)-2,3-dihydro-1-benzofuran-2-yl]methyl}amine

Treatment of 1-bromo-2-chlorobenzene (5.0 g, 26.88 mmol) with (2-chloro-6-methyoxyphenyl)boronic acid (15.6 g, 80.64 mol) generally according to the procedure described for Intermediate 37 afforded 5.0 g (73%) of 6-chloro-2'-chlorobiphenyl-2-yl methyl ether. Treatment of 6-chloro-2'-methylbiphenyl-2-yl methyl ether with hydrogen bromide (60 mL, 30 wt. % in acetic acid) generally according to the procedure described for Example 395 afforded a brown oil. The oil was reacted with sodium hydride (1.05 g, 26.35 mmol) and allyl bromide (3.19 g, 26.35 mmol) followed by refluxing the resultant allyl ether in mesitylene generally according to the procedure described for Intermediate 8 provided 3-allyl-6-chloro-2'-chlorobiphenyl-2-ol. Treatment of 3-allyl-6-chloro-2'-chlorobiphenyl-2-ol (2.8 g, 10.03 mmol) with m-chloroperoxybenzoic acid (4.6 g, 15.0 mmol, 77%) and potassium carbonate (1.6 g, 12.0 mmol) generally according to the procedure described for Intermediate 9 afforded 2.2 g (74%) of (±)-[7-(2-chlorophenyl)-6-chloro-2,3-dihydro-1-benzofuran-2-yl]methanol. Treatment (±)-[7-(2-chlorophenyl)-6-chloro-2,3-dihydro-1-benzofuran-2-yl]methanol (1.6 g, 5.42 mmol) with p-toluenesulfonyl chloride (1.55 g, 8.13 mmol) generally according to the procedure described for Intermediate 10 gave 2.1 g (86%) of (±)-[6-chloro-7-(2-chlorophenyl)-2,3-dihydro-1-benzofuran-2-yl]methyl 4-methylbenzenesulfonate as a colorless oil. Treatment of (±)-[6-chloro-7-(2-chlorophenyl)-2,3-dihydro-1-benzofuran-2-yl]methyl 4-methylbenzenesulfonate (0.2 g, 0.44 mmol) with sodium azide (0.2 g, 3.08 mmol) generally according to the procedure described for Intermediate 98 afforded 0.14 g, (99%) of (±)-2-(azidomethyl)-7-(2-chlorophenyl)-6-chloro-2,3-dihydro-1-benzofuran. Treatment of (±)-2-(azidomethyl)-7-(2-chlorophenyl)-6-chloro-2,3-dihydro-1-benzofuran (0.14 g, 0.43 mmol) in tetrahydrofuran (10 mL) with polymer-supported triphenylphosphine (0.3 g, 1.14 mmol) generally according to the procedure described for Example 154 provided 0.036 g (24%) of (±)-{[6-chloro-7-(2-chlorophenyl)-2,3-dihydro-1-benzofuran-2-yl]methyl}amine as a white solid, hydrochloride salt. mp 221-223° C.

EXAMPLE 401

(±)-{[6-fluoro-7-(2-methylphenyl)-2,3-dihydro-1-benzofuran-2-yl]methyl}methylamine The title compound was prepared (0.053 g, 72%) following the general procedure of Example 390 as a white solid, hydrochloride salt from (±)-[6-fluoro-7-(2-methylphenyl)-2,3-dihydro-1-benzofuran-2-yl]methyl 4-methylbenzenesulfonate (0.1 g, 0.24 mmol) and methylamine (0.31 g, 10.0 mmol). mp 200-202° C.

EXAMPLE 402

(±)-{[6-fluoro-7-(2-chlorophenyl)-2,3-dihydro-1-benzofuran-2-yl]methyl}methylamine The title compound was prepared (0.12 g, 40%) following the general procedure of Example 390 as a white solid, hydrochloride salt from (±)-[6-fluoro-7-(2-chlorophenyl)-2,3-dihydro-1-benzofuran-2-yl]methyl 4-methylbenzenesulfonate (0.4 g, 0.92 mmol) and methylamine (0.55 g, 17.7 mmol). mp 170-173° C.

EXAMPLE 403

(±)-{[6-chloro-7-(2-methylphenyl)-2,3-dihydro-1-benzofuran-2-yl]methyl}methylamine The title compound was prepared (0.02 g, 27%) following the general procedure of Example 390 as a white solid, hydrochloride salt from (±)-[6-chloro-7-(2-methylphenyl)-2,3-dihydro-1-benzofuran-2-yl]methyl 4-methylbenzenesulfonate (0.1 g, 0.23 mmol) and methylamine (0.24 g, 7.8 mmol). mp 158-160° C.

EXAMPLE 404

(±)-{[6-chloro-7-(2-chlorophenyl)-2,3-dihydro-1-benzofuran-2-yl]methyl}methylamine The title compound was prepared (0.056 g, 73%) following the general procedure of Example 390 as a white solid, hydrochloride salt from (±)-[6-chloro-7-(2-chlorophenyl)-2,3-dihydro-1-benzofuran-2-yl]methyl 4-methylbenzenesulfonate (0.1 g, 0.23 mmol) and methylamine (0.24 g, 7.8 mmol). mp 155-157° C.

EXAMPLE 405

No compound

EXAMPLE 406

(±)-[(N-methyl-1-[7-(2-methylphenyl)-2,3-dihydro-1-benzofuran-2-yl]methanamine

The title compound was prepared (0.055 g, 24%) following the general procedure of Example 154 as a white solid, hydrochloride salt from (±)-[(7-bromo-2,3-dihydro-1-benzofuran-2-yl)methyl]methylamine (0.20 g, 0.826 mmol) and 2-methylphenylboronic acid (0.168 g, 1.24 mmol). mp 166-169° C.

EXAMPLE 407

(−)-N-methyl-1-[7-(2-methylphenyl)-2,3-dihydro-1-benzofuran-2-yl]methanamine

Treatment of 0.325 g of fraction 1 obtained from the chiral HPLC separation of (±)-benzyl methyl {[7-(2-methylphenyl)-2,3-dihydro-1-benzofuran-2-yl]methyl}carbamate with trimethylsilyl iodide (0.671 g, 3.3 mmol) generally according to the procedure described for Example 158 gave 0.193 g (80%) of (−)-N-methyl-1-[7-(2-methylphenyl)-2,3-dihydro-1-benzofuran-2-yl]methanamine as a white solid, hydrochloride salt. $[\alpha]_D^{25}=-22.2$ (c 10.0 in methanol); mp 182-185° C.

EXAMPLE 408

(+)-N-methyl-1-[7-(2-methylphenyl)-2,3-dihydro-1-benzofuran-2-yl]methanamine

Treatment of 0.32 g of fraction 2 obtained from the chiral HPLC separation of (±)-benzyl methyl {[7-(2-methylphenyl)-2,3-dihydro-1-benzofuran-2-yl]methyl}carbamate with trimethylsilyl iodide (0.67 g, 3.3 mmol) generally according to the procedure described for Example 158 gave 0.192 g (80%) of (+)-N-methyl-1-[7-(2-methylphenyl)-2,3-dihydro-1-benzofuran-2-yl]methanamine as a white solid, hydrochloride salt. $[\alpha]_D^{25}=+26.4$ (c 10.0 in methanol); mp 182-185° C.

EXAMPLE 409

(±)-[(N-methyl-1-[7-(2-chlorophenyl)-2,3-dihydro-1-benzofuran-2-yl]methanamine

The title compound was prepared (0.078 g, 40%) following the general procedure of Example 154 as a white solid, hydrochloride salt from (±)-[(7-bromo-2,3-dihydro-1-benzofuran-2-yl)methyl]methylamine (0.20 g, 0.826 mmol) and 2-chlorophenylboronic acid (0.194 g, 1.24 mmol). mp 163-165° C.

EXAMPLE 410

(+)-N-methyl-1-[7-(2-chlorophenyl)-2,3-dihydro-1-benzofuran-2-yl]methanamine

Treatment of 2.71 g of fraction 2 obtained from the chiral HPLC separation of (±)-benzyl methyl {[7-(2-chlorophenyl)-2,3-dihydro-1-benzofuran-2-yl]methyl}carbamate with trimethylsilyl iodide (5.32 g, 26.57 mmol) generally according to the procedure described for Example 158 gave 1.23 g (60%) of (+)-N-methyl-1-[7-(2-chlorolphenyl)-2,3-dihydro-1-benzofuran-2-yl]methanamine as a white solid, hydrochloride salt. $[\alpha]_D^{25}=+13.2$ (c 10.0 in methanol); mp 154-157° C.

EXAMPLE 411

(−)-N-methyl-1-[7-(2-chlorophenyl)-2,3-dihydro-1-benzofuran-2-yl]methanamine

Treatment of 3.01 g of fraction 1 obtained from the chiral HPLC separation of (±)-benzyl methyl {[7-(2-chlorophenyl)-2,3-dihydro-1-benzofuran-2-yl]methyl}carbamate with trimethylsilyl iodide (5.91 g, 29.52 mmol) generally according to the procedure described for Example 158 gave 1.80 g (76%) of (+)-N-methyl-1-[7-(2-chlorolphenyl)-2,3-dihydro-1-benzofuran-2-yl]methanamine as a white solid, hydrochloride salt. $[\alpha]_D^{25}$=−13.2 (c 10.0 in methanol); mp 154-157° C.

EXAMPLE 412

(±)-[(N-methyl-1-[7-(2-fluorophenyl)-2,3-dihydro-1-benzofuran-2-yl]methanamine

The title compound was prepared (0.147 g, 66%) following the general procedure of Example 390 as a white solid, hydrochloride salt from (±)-[7-(2-fluorophenyl)-2,3-dihydro-1-benzofuran-2-yl]methyl 4-methylbenzenesulfonate (0.300 g, 0.753 mmol) and methylamine (0.92 g, 29.5 mmol). mp 148-150° C.

EXAMPLE 413

(±)-[(N-methyl-1-[7-(2-methoxyphenyl)-2,3-dihydro-1-benzofuran-2-yl]methanamine

The title compound was prepared (0.250 g, 76%) following the general procedure of Example 154 as a white solid, hydrochloride salt from (±)-[7-(2-methoxyphenyl)-2,3-dihydro-1-benzofuran-2-yl]methyl 4-methylbenzenesulfonate (0.501 g, 1.22 mmol) and methylamine (4.56 g, 150.0 mmol). mp 157-159° C.

EXAMPLE 414

(±)-[(N-methyl-1-[7-(3-methylphenyl)-2,3-dihydro-1-benzofuran-2-yl]methanamine

The title compound was prepared (0.059 g, 26%) following the general procedure of Example 154 as a white solid, hydrochloride salt from (±)-[(7-bromo-2,3-dihydro-1-benzofuran-2-yl)methyl]methylamine (0.200 g, 0.826 mmol) and 3-methylphenylboronic acid (0.169 g, 1.24 mmol). mp 157-159° C.

EXAMPLE 415

(±)-[(N-methyl-1-[7-(3-fluorophenyl)-2,3-dihydro-1-benzofuran-2-yl]methanamine

The title compound was prepared (0.38 g, 53%) following the general procedure of Example 154 as a white solid, hydrochloride salt from (±)-[(7-bromo-2,3-dihydro-1-benzofuran-2-yl)methyl]methylamine (0.200 g, 0.826 mmol) and 3-fluorophenylboronic acid (0.173 g, 1.24 mmol). mp 160-163° C.

EXAMPLE 416

(±)-[(N-methyl-1-[7-(3-chlorophenyl)-2,3-dihydro-1-benzofuran-2-yl]methanamine

The title compound was prepared (0.59 g, 53%) following the general procedure of Example 154 as a white solid, hydrochloride salt from (±)-[(7-bromo-2,3-dihydro-1-benzofuran-2-yl)methyl]methylamine (0.200 g, 0.826 mmol) and 3-chlorophenylboronic acid (0.194 g, 1.24 mmol). mp 177-178° C.

EXAMPLE 417

(±)-[(N-methyl-1-[7-(3-methoxyphenyl)-2,3-dihydro-1-benzofuran-2-yl]methanamine

The title compound was prepared (0.41 g, 49%) following the general procedure of Example 154 as a white solid, hydrochloride salt from (±)-[(7-bromo-2,3-dihydro-1-benzofuran-2-yl)methyl]methylamine (0.200 g, 0.826 mmol) and 3-methoxyphenylboronic acid (0.188 g, 1.24 mmol). mp 148-151° C.

EXAMPLE 418

(±)-[(N-methyl-1-[7-(4-methylphenyl)-2,3-dihydro-1-benzofuran-2-yl]methanamine

The title compound was prepared (0.071 g, 34%) following the general procedure of Example 154 as a white solid, hydrochloride salt from (±)-[(7-bromo-2,3-dihydro-1-benzofuran-2-yl)methyl]methylamine (0.200 g, 0.826 mmol) and 4-methylphenylboronic acid (0.168 g, 1.24 mmol). mp 210-213° C.

EXAMPLE 419

(±)-[(N-methyl-1-[7-(4-fluorophenyl)-2,3-dihydro-1-benzofuran-2-yl]methanamine

The title compound was prepared (0.049 g, 21%) following the general procedure of Example 154 as a white solid, hydrochloride salt from (±)-[(7-bromo-2,3-dihydro-1-benzofuran-2-yl)methyl]methylamine (0.200 g, 0.826 mmol) and 4-fluorophenylboronic acid (0.173 g, 1.24 mmol). mp 209-211° C.

EXAMPLE 420

(±)-[(N-methyl-1-[7-(4-chlorophenyl)-2,3-dihydro-1-benzofuran-2-yl]methanamine

The title compound was prepared (0.037 g, 16%) following the general procedure of Example 154 as a white solid, hydrochloride salt from (±)-[(7-bromo-2,3-dihydro-1-benzofuran-2-yl)methyl]methylamine (0.200 g, 0.826 mmol) and 4-chlorophenylboronic acid (0.193 g, 1.24 mmol). mp 227-230° C.

EXAMPLE 421

(±)-[(N-methyl-1-[7-(4-methoxyphenyl)-2,3-dihydro-1-benzofuran-2-yl]methanamine

The title compound was prepared (0.052 g, 23%) following the general procedure of Example 154 as a white solid, hydrochloride salt from (±)-[(7-bromo-2,3-dihydro-1-benzofuran-2-yl)methyl]methylamine (0.200 g, 0.826 mmol) and 4-methoxyphenylboronic acid (0.188 g, 1.24 mmol). mp 214-217° C.

EXAMPLE 422

(±)-[(N-methyl-1-[7-(2,3-dimethylphenyl)-2,3-dihydro-1-benzofuran-2-yl]methanamine The title compound was prepared (0.046 g, 65%) following the general procedure of Example 390 as a white solid, hydrochloride salt from (±)-[7-(2,3-dimethylphenyl)-2,3-dihydro-1-benzofuran-2-yl]methyl 4-methylbenzenesulfonate (0.095 g, 0.23 mmol) and methylamine (0.072 g, 2.3 mmol). mp 197-199° C.

EXAMPLE 423

(±)-[(N-methyl-1-[7-(2,3-dimethoxyphenyl)-2,3-dihydro-1-benzofuran-2-yl]methanamine The title compound was prepared (0.137 g, 63%) following the general procedure of Example 390 as a white solid, hydrochloride salt from (±)-[7-(2,3-dimethoxyphenyl)-2,3-dihydro-1-benzofuran-2-yl]methyl 4-methylbenzenesulfonate (0.283 g, 0.64 mmol) and methylamine (0.199 g, 6.42 mmol). mp 163-166° C.

EXAMPLE 424

(±)-[(N-methyl-1-[7-(2,4-difluorophenyl)-2,3-dihydro-1-benzofuran-2-yl]methanamine The title compound was prepared (0.137 g, 68%) following the general procedure of Example 390 as a white solid, hydrochloride salt from (±)-[7-(2,4-difluorophenyl)-2,3-dihydro-1-benzofuran-2-yl]methyl 4-methylbenzenesulfonate (0.366 g, 0.88 mmol) and methylamine (0.273 g, 8.80 mmol). mp 156-160° C.

EXAMPLE 425

(±)-[(N-methyl-1-[7-(2,4-dichlorophenyl)-2,3-dihydro-1-benzofuran-2-yl]methanamine The title compound was prepared (0.137 g, 47%) following the general procedure of Example 390 as a white solid, hydrochloride salt from (±)-[7-(2,4-dichlorophenyl)-2,3-dihydro-1-benzofuran-2-yl]methyl 4-methylbenzenesulfonate (0.125 g, 0.278 mmol) and methylamine (0.086 g, 2.78 mmol). mp 190-192° C.

EXAMPLE 426

(±)-[(N-methyl-1-[7-(2,4-dimethoxyphenyl)-2,3-dihydro-1-benzofuran-2-yl]methanamine The title compound was prepared (0.272 g, 82%) following the general procedure of Example 390 as a white solid, hydrochloride salt from (±)-[7-(2,4-dimethoxyphenyl)-2,3-dihydro-1-benzofuran-2-yl]methyl 4-methylbenzenesulfonate (0.435 g, 0.987 mmol) and methylamine (0.306 g, 9.87 mmol). mp 185-188° C.

EXAMPLE 427

(±)-[(N-methyl-1-[7-(2,5-dimethylphenyl)-2,3-dihydro-1-benzofuran-2-yl]methanamine The title compound was prepared (0.091 g, 65%) following the general procedure of Example 390 as a white solid, hydrochloride salt from (±)-[7-(2,5-dimethylphenyl)-2,3-dihydro-1-benzofuran-2-yl]methyl 4-methylbenzenesulfonate (0.091 g, 0.22 mmol) and methylamine (0.069 g, 2.22 mmol). mp 186-189° C.

EXAMPLE 428

(±)-[(N-methyl-1-[7-(2,5-difluorophenyl)-2,3-dihydro-1-benzofuran-2-yl]methanamine The title compound was prepared (0.027 g, 60%) following the general procedure of Example 390 as a white solid, hydrochloride salt from (±)-[7-(2,5-difluorophenyl)-2,3-dihydro-1-benzofuran-2-yl]methyl 4-methylbenzenesulfonate (0.060 g, 0.14 mmol) and methylamine (0.045 g, 1.4 mmol). mp 172-174° C.

EXAMPLE 429

(±)-[(N-methyl-1-[7-(2,5-dichlorophenyl)-2,3-dihydro-1-benzofuran-2-yl]methanamine The title compound was prepared (0.068 g, 83%) following the general procedure of Example 390 as a white solid, hydrochloride salt from (±)-[7-(2,5-dichlorophenyl)-2,3-dihydro-1-benzofuran-2-yl]methyl 4-methylbenzenesulfonate (0.120 g, 0.26 mmol) and methylamine (1.24 g, 40.0 mmol). mp 147-149° C.

EXAMPLE 430

(±)-[(N-methyl-1-[7-(5-chloro-2-methoxyphenyl)-2,3-dihydro-1-benzofuran-2-yl]methanamine The title compound was prepared (0.058 g, 79%) following the general procedure of Example 390 as a white solid, hydrochloride salt from (±)-[7-(5-chloro-2-methoxyphenyl)-2,3-dihydro-1-benzofuran-2-yl]methyl 4-methylbenzenesulfonate (0.095 g, 0.213 mmol) and methylamine (0.045 g, 2.1 mmol). mp 201-203° C.

EXAMPLE 431

(±)-[(N-methyl-1-[7-(5-chloro-2-methylphenyl)-2,3-dihydro-1-benzofuran-2-yl]methanamine The title compound was prepared (0.051 g, 65%) following the general procedure of Example 390 as a white solid, hydrochloride salt from (±)-[7-(5-chloro-2-methylphenyl)-2,3-dihydro-1-benzofuran-2-yl]methyl 4-methylbenzenesulfonate (0.103 g, 0.24 mmol) and methylamine (0.074 g, 2.4 mmol). mp 178-182° C.

EXAMPLE 432

(±)-[(N-methyl-1-[7-(2,6-dimethylphenyl)-2,3-dihydro-1-benzofuran-2-yl]methanamine The title compound was prepared (0.039 g, 63%) following the general procedure of Example 390 as a white solid, hydrochloride salt from (±)-[7-(2,6-dimethylphenyl)-2,3-dihydro-1-benzofuran-2-yl]methyl 4-methylbenzenesulfonate (0.084 g, 0.205 mmol) and methylamine (1.86 g, 60.0 mmol). mp> 250° C.

EXAMPLE 433

(±)-[(N-methyl-1-[7-(2,6-dichlorophenyl)-2,3-dihydro-1-benzofuran-2-yl]methanamine The title compound was prepared (0.351 g, 77%) following the general procedure of Example 390 as a white solid, hydrochloride salt from [7-(2,6-dichlorophenyl)-2,3-dihydro-1-benzofuran-2-yl]methyl 4-methylbenzenesulfonate (0.595 g, 1.324 mmol) and methylamine (1.86 g, 60.0 mmol). 190-192 mp ° C.

EXAMPLE 434

(−)-{[7-(2,6-dichlorophenyl)-2,3-dihydro-1-benzofuran-2-yl]methyl}methylamine

Treatment of 0.607 g of fraction 1 obtained from the chiral HPLC separation of (±)-benzyl {7-(2,6-dichlorophenyl)-2,3-dihydro-1-benzofuran-2-yl]methyl}methylcarbamate with trimethylsilyl iodide (1.09 g, 5.49 mmol) generally according to the procedure described for Example 158 gave 0.409 g (86%) of (−)-{[7-(2,6-dichlorophenyl)-2,3-dihydro-1-benzofuran-2-yl]methyl}methylamine as a white solid, hydrochloride salt. $[\alpha]_D^{25}$=−11.6 (c 10.0 in methanol); mp 195-197° C.

EXAMPLE 435

(+)-{[7-(2,6-dichlorophenyl)-2,3-dihydro-1-benzofuran-2-yl]methyl}methylamine

Treatment of 0.625 g of fraction 1 obtained from the chiral HPLC separation of (±)-benzyl {7-(2,6-dichlorophenyl)-2,3-dihydro-1-benzofuran-2-yl]methyl}methylcarbamate with trimethylsilyl iodide (1.131 g, 5.65 mmol) generally according to the procedure described for Example 158 gave 0.369 g (76%) of (+)-{[7-(2,6-dichlorophenyl)-2,3-dihydro-1-benzofuran-2-yl]methyl}methylamine. $[\alpha]_D^{25}$=+11.2 (c 10.0 in methanol); mp 195-197° C.

EXAMPLE 436

(±)-N-methyl-1-(7-pyridin-3-yl-2,3-dihydro-1-benzofuran-2-yl)methanamine

The title compound was prepared (0.367 g, 70%) following the general procedure of Example 390 as a white solid, hydrochloride salt from (7-pyridin-3-yl-2,3-dihydro-1-benzofuran-2-yl)methyl 4-methylbenzenesulfonate (0.730 g, 1.91 mmol) and methylamine (1.14 g, 36.7 mmol). mp 212-215° C.

EXAMPLE 437

(±)-[(N-methyl-1-[7-(2,3-difluorophenyl)-2,3-dihydro-1-benzofuran-2-yl]methanamine The title compound was prepared (0.094 g, 84%) following the general procedure of Example 390 as a white solid, hydrochloride salt from (±)-[7-(2,3-difluorophenyl)-2,3-dihydro-1-benzofuran-2-yl]methyl 4-methylbenzenesulfonate (0.095 g, 0.23 mmol) and methylamine (0.072 g, 2.3 mmol); mp 166-168° C.

EXAMPLE 438

(±)-{[5-fluoro-7-(2-fluorophenyl)-2,3-dihydro-1-benzofuran-2-yl]methyl}methylamine The title compound was prepared (0.060 g, 40%) following the general procedure of Example 390 as a white solid, hydrochloride salt from (±)-[5-fluoro-7-(2-fluorophenyl)-2,3-dihydro-1-benzofuran-2-yl]methyl 4-methylbenzenesulfonate (0.2 g, 0.48 mmol) and methylamine (0.149 g, 4.80 mmol). mp 140-141° C.

EXAMPLE 439

(±)-{[5-fluoro-7-(2-chlorophenyl)-2,3-dihydro-1-benzofuran-2-yl]methyl}methylamine The title compound was prepared (0.075 g, 52%) following the general procedure of Example 390 as a white solid, hydrochloride salt from (±)-[5-fluoro-7-(2-chlorophenyl)-2,3-dihydro-1-benzofuran-2-yl]methyl 4-methylbenzenesulfonate (0.19 g, 0.44 mmol) and methylamine (0.136 g, 4.40 mmol). mp 141-143.

EXAMPLE 440

(±)-{[5-fluoro-7-(2-methylphenyl)-2,3-dihydro-1-benzofuran-2-yl]methyl}methylamine The title compound was prepared (0.038 g, 34%) following the general procedure of Example 390 as a white solid, hydrochloride salt from (±)-[5-fluoro-7-(2-methylphenyl)-2,3-dihydro-1-benzofuran-2-yl]methyl 4-methylbenzenesulfonate (0.15 g, 0.36 mmol) and methylamine (0.112 g, 3.60 mmol). mp 102-104° C.

EXAMPLE 441

(−)-{[5-fluoro-7-(2-methylphenyl)-2,3-dihydro-1-benzofuran-2-yl]methyl}methylamine Treatment of 0.22 g of fraction 2 obtained from the chiral HPLC separation of (±)-benzyl {[5-fluoro-7-(2-methylphenyl)-2,3-dihydro-1-benzofuran-2-yl]methyl}methylcarbamate with trimethylsilyl iodide (0.416 g, 2.08 mmol) generally according to the procedure described for Example 158 gave 0.125 g (79%) of (−)-{[5-fluoro-7-(2-methylphenyl)-2,3-dihydro-1-benzofuran-2-yl]methyl}methylamine as a white solid, hydrochloride salt. $[\alpha]_D^{25}$=−18.58 (c 10.0 in methanol); mp 123-124° C.

EXAMPLE 442

(+)-{[5-fluoro-7-(2-methylphenyl)-2,3-dihydro-1-benzofuran-2-yl]methyl}methylamine Treatment of 0.28 g of fraction 1 obtained from the chiral HPLC separation of (±)-benzyl {[5-fluoro-7-(2-methylphenyl)-2,3-dihydro-1-benzofuran-2-yl]methyl}methylcarbamate with trimethylsilyl iodide (0.528 g, 2.64 mmol) generally according to the procedure described for Example 158 gave 0.124 g (61%) of (+)-{[5-fluoro-7-(2-methylphenyl)-2,3-dihydro-1-benzofuran-2-yl]methyl}methylamine as a white solid, hydrochloride salt. $[\alpha]_D^{25}$=+14.25 (c 10.0 in methanol); mp 123-124° C.

EXAMPLE 443

(±)-{[5-fluoro-7-(2-methoxyphenyl)-2,3-dihydro-1-benzofuran-2-yl]methyl}methylamine The title compound was prepared (0.075 g, 37%) following the general procedure of Example 390 as a white solid, hydrochloride salt from (±)-[5-fluoro-7-(2-methoxyphenyl)-2,3-dihydro-1-benzofuran-2-yl]methyl 4-methylbenzenesulfonate (0.27 g, 0.6 mmol) and methylamine (0.198 g, 6.0 mmol). mp 175-176° C.

EXAMPLE 444

(±)-{[7-(2,3-dimethoxyphenyl)-5-fluoro-2,3-dihydro-1-benzofuran-2-yl]methyl}methylamine The title compound was prepared (0.103 g, 74%) following the general procedure of Example 390 as a white solid, hydrochloride salt from (±)-[7-(2,3-dimethoxyphenyl)-5-fluoro-2,3-dihydro-1-benzofuran-2-yl]methyl 4-methylbenzenesulfonate (0.18 g, 0.39 mmol) and methylamine (0.139 g, 3.9 mmol). mp 85-89° C.

EXAMPLE 445

(±)-[7-(2,4-dichlorophenyl)-5-fluoro-2,3-dihydro-1-benzofuran-2-yl]methyl}methylamine The title compound was prepared (0.041 g, 40%) following the general procedure of Example 390 as a white solid, hydrochloride salt from (±)-[7-(2,4-dichlorophenyl)-5-fluoro-2,3- dihydro-1-benzofuran-2-yl]methyl 4-methylbenzene-sulfonate (0.13 g, 0.278 mmol) and methylamine (0.086 g, 2.78 mmol). mp 146-148° C.

EXAMPLE 446

(−)-[7-(2,4-dichlorophenyl)-5-fluoro-2,3-dihydro-1-benzofuran-2-yl]methyl}methylamine Treatment of 0.48 g of fraction 2 obtained from the chiral HPLC separation of (±)-benzyl {[7-(2,4-dichlorophenyl)-5-fluoro-2,3-dihydro-1-benzofuran-2-yl]methyl methylcarbamate with trimethylsilyl iodide (0.834 g, 4.17 mmol) generally according to the procedure described for Example 158 gave 0.200 g (53%) of (−)-[7-(2,4-dichlorophenyl)-5-fluoro-2,3-dihydro-1-benzofuran-2-yl]methyl}methylamine as a white solid, hydrochloride salt. $[\alpha]_D^{25}$=−8.87 (c 10.0 in methanol); mp 162-163° C.

EXAMPLE 447

(+)-[7-(2,4-dichlorophenyl)-5-fluoro-2,3-dihydro-1-benzofuran-2-yl]methyl}methylamine Treatment of 0.48 g of fraction 1 obtained from the chiral HPLC separation of (±)-benzyl {[7-(2,4-dichlorophenyl)-5-fluoro-2,3-dihydro-1-benzofuran-2-yl] methyl}methylcarbamate with trimethylsilyl iodide (0.834 g, 4.17 mmol) generally according to the procedure described for Example 158 gave 0.200 g (53%) of (+)-[7-(2,4-dichlorophenyl)-5-fluoro-2,3-dihydro-1-benzofuran-2-yl] methyl}methylamine as a white solid, hydrochloride salt. $[\alpha]_D^{25}$=+8.61 (c 10.0 in methanol); mp 161-163° C.

EXAMPLE 448

(±)-{[7-(2,5-difluorophenyl)-5-fluoro-2,3-dihydro-1-benzofuran-2-yl]methyl}methylamine The title compound was prepared (0.73 g, 44%) following the general procedure of Example 390 as a white solid, hydrochloride salt from (±)-[7-(2,5-difluorophenyl)-5-fluoro-2,3-dihydro-1-benzofuran-2-yl]methyl 4-methylbenzene-sulfonate (0.22 g, 0.51 mmol) and methylamine (0.155 g, 5.1 mmol). mp 185-187° C.

EXAMPLE 449

(±)-{[7-(2,5-dichlorophenyl)-5-fluoro-2,3-dihydro-1-benzofuran-2-yl]methyl}methylamine The title compound was prepared (0.123 g, 80%) following the general procedure of Example 390 as a white solid, hydrochloride salt from (±)-[7-(2,5-dichlorophenyl)-5-fluoro-2,3-dihydro-1-benzofuran-2-yl]methyl 4-methylbenzene-sulfonate (0.2 g, 0.43 mmol) and methylamine (0.133 g, 4.3 mmol). mp 166-168° C.

EXAMPLE 450

(+)-{[5-fluoro-7-(2,5-dichlorophenyl)-2,3-dihydro-1-benzofuran-2-yl]methyl}methylamine Treatment of 0.53 g of fraction 1 obtained from the chiral HPLC separation of (±)-benzyl {[7-(2,5-dichlorophenyl)-5-fluoro-2,3-dihydro-1-benzofuran-2-yl] methyl}methylcarbamate with trimethylsilyl iodide (0.92 g, 4.60 mmol) generally according to the procedure described for Example 158 gave 0.204 g (49%) of (+)-{[5-fluoro-7-(2,5-dichlorophenyl)-2,3-dihydro-1-benzofuran-2-yl] methyl}methylamine as a white solid, hydrochloride salt. $[\alpha]_D^{25}$=+14.00 (c 10.0 in methanol); mp 118-120° C.

EXAMPLE 451

(−)-{[5-fluoro-7-(2,5-dichlorophenyl)-2,3-dihydro-1-benzofuran-2-yl]methyl}methylamine Treatment of 0.54 g of fraction 2 obtained from the chiral HPLC separation of (±)-benzyl {[7-(2,5-dichlorophenyl)-5-fluoro-2,3-dihydro-1-benzofuran-2-yl]methyl methylcarbamate with trimethylsilyl iodide (0.96 g, 4.80 mmol) generally according to the procedure described for Example 158 gave 0.275 g (65%) of (−)-{[5-fluoro-7-(2,5-dichlorophenyl)-2,3-dihydro-1-benzofuran-2-yl]methyl}methylamine as a white solid, hydrochloride salt. $[\alpha]_D^{25}$=−22.30 (c 10.0 in methanol); mp 110-112° C.

EXAMPLE 452

(±)-{[7-(2,5-dimethylphenyl)-5-fluoro-2,3-dihydro-1-benzofuran-2-yl]methyl}methylamine The title compound was prepared (0.76 g, 48%) following the general procedure of Example 390 as a white solid, hydrochloride salt from (±)-[7-(2,5-dimethylphenyl)-5-fluoro-2,3-dihydro-1-benzofuran-2-yl]methyl 4-methylbenzene-sulfonate (0.21 g, 0.49 mmol) and methylamine (0.152 g, 4.9 mmol). mp 186-188° C.

EXAMPLE 453

(±)-{[7-(2,6-dimethylphenyl)-5-fluoro-2,3-dihydro-1-benzofuran-2-yl]methyl}methylamine The title compound was prepared (0.148 g, 65%) following the general procedure of Example 390 as a white solid, hydrochloride salt from (±)-[7-(2,6-dimethylphenyl)-5-fluoro-2,3-dihydro-1-benzofuran-2-yl]methyl 4-methylbenzene-sulfonate (0.3 g, 0.70 mmol) and methylamine (0.22 g, 7.0 mmol). mp 175-178° C.

EXAMPLE 454

(±)-{[7-(2,6-dichlorophenyl)-5-fluoro-2,3-dihydro-1-benzofuran-2-yl]methyl}methylamine The title compound was prepared (0.081 g, 52%) following the general procedure of Example 390 as a white solid, hydrochloride salt from (±)-[7-(2,6-dichlorophenyl)-5-fluoro-2,3-dihydro-1-benzofuran-2-yl]methyl 4-methylbenzene-sulfonate (0.2 g, 0.43 mmol) and methylamine (0.133 g, 4.3 mmol). mp 196-198° C.

EXAMPLE 456

(±)-{[5-fluoro-7-(5-methoxy-2-methylphenyl)-2,3-dihydro-1-benzofuran-2-yl]methyl}methylamine The title compound was prepared (0.73 g, 50%) following the general procedure of Example 390 as a white solid, hydrochloride salt from (±)-[5-fluoro-7-(5-methoxy-2-methylphenyl)-2,3-dihydro-1-benzofuran-2-yl]methyl 4-methylbenzenesulfonate (0.19 g, 0.40 mmol) and methylamine (0.124 g, 4.0 mmol). mp 173-174° C.

EXAMPLE 457

(±)-{[5-fluoro-7-(2-methoxy-5-methylphenyl)-2,3-dihydro-1-benzofuran-2-yl]methyl}methylamine The title compound was prepared (0.77 g, 48%) following the general procedure of Example 390 as a white solid, hydrochloride salt from (±)-[5-fluoro-7-(2-methoxy-5-methylphenyl)-2,3-dihydro-1-benzofuran-2-yl]methyl 4-methylbenzenesulfonate (0.21 g, 0.45 mmol) and methylamine (0.139 g, 4.5 mmol). mp 197-199° C.

EXAMPLE 458

(±)-{[7-(5-chloro-2-methoxyphenyl)-5-fluoro-2,3-dihydro-1-benzofuran-2-yl]methyl}methylamine The title compound was prepared (0.62 g, 38%) following the general procedure of Example 390 as a white solid, hydrochloride salt from (±)-[7-(5-chloro-2-methoxyphenyl)-5-fluoro-2,3-dihydro-1-benzofuran-2-yl]methyl 4-methylbenzenesulfonate (0.21 g, 0.45 mmol) and methylamine (0.139 g, 4.5 mmol). mp 189-190° C.

EXAMPLE 459

(±)-[(5-fluoro-7-pyridin-3-yl-2,3-dihydro-1-benzofuran-2-yl)methyl]methylamine

The title compound was prepared (0.056 g, 34%) following the general procedure of Example 390 as a white solid, hydrochloride salt from (±)-[5-fluoro-7-pyridin-3-yl-2,3-dihydro-1-benzofuran-2-yl]methyl 4-methylbenzenesulfonate (0.20 g, 0.50 mmol) and methylamine (0.155 g, 5.0 mmol). mp 255-257° C.

EXAMPLE 460

(±)-[(5-chloro-7-(2-methoxyphenyl)-2,3-dihydro-1-benzofuran-2-yl]methyl}methylamine The title compound was prepared (0.037 g, 29%) following the general procedure of Example 390 as a white solid, hydrochloride salt from (±)-[5-chloro-7-(2-methoxyphenyl)-2,3-dihydro-1-benzofuran-2-yl]methyl 4-methylbenzenesulfonate (0.39 g, 0.88 mmol) and methylamine (0.271 g, 8.8 mmol). mp 100-102° C.

EXAMPLE 461

(±)-{[5-chloro-7-(2,6-dimethylphenyl)-2,3-dihydro-1-benzofuran-2-yl]methyl}methylamine The title compound was prepared (0.155 g, 62%) following the general procedure of Example 390 as a white solid, hydrochloride salt from (±)-[5-chloro-7-(2,6-dimethylphenyl)-2,3-dihydro-1-benzofuran-2-yl]methyl 4-methylbenzenesulfonate (0.333 g, 0.74 mmol) and methylamine (0.231 g, 7.4 mmol). mp 229-231° C.

EXAMPLE 462

(±)-[(5-chloro-7-(2-fluorophenyl)-2,3-dihydro-1-benzofuran-2-yl]methyl}methylamine The title compound was prepared (0.037 g, 34%) following the general procedure of Example 390 as a white solid, hydrochloride salt from (±)-[5-chloro-7-(2-fluorophenyl)-2,3-dihydro-1-benzofuran-2-yl]methyl 4-methylbenzenesulfonate (0.142 g, 0.33 mmol) and methylamine (0.102 g, 3.3 mmol). mp 159-161° C.

EXAMPLE 463

(±)-{[5-chloro-7-(2,3-difluorophenyl)-2,3-dihydro-1-benzofuran-2-yl]methyl}methylamine The title compound was prepared (0.068 g, 60%) following the general procedure of Example 390 as a white solid, hydrochloride salt from (±)-[5-chloro-7-(2,3-difluorophenyl)-2,3-dihydro-1-benzofuran-2-yl]methyl 4-methylbenzenesulfonate (0.148 g, 0.329 mmol) and methylamine (0.102 g, 3.29 mmol). mp 177-179° C.

EXAMPLE 464

(±)-{[5-chloro-7-(2,3-dichlorophenyl)-2,3-dihydro-1-benzofuran-2-yl]methyl}methylamine The title compound was prepared (0.051 g, 40%) following the general procedure of Example 390 as a white solid, hydrochloride salt from (±)-[5-chloro-7-(2,3-dichlorophenyl)-2,3-dihydro-1-benzofuran-2-yl]methyl 4-methylbenzenesulfonate (0.165 g, 0.341 mmol) and methylamine (0.106 g, 3.41 mmol). mp 219-221° C.

EXAMPLE 465

(±)-{[5-chloro-7-(2,3-dimethylphenyl)-2,3-dihydro-1-benzofuran-2-yl]methyl}methylamine The title compound was prepared (0.054 g, 47%) following the general procedure of Example 390 as a white solid, hydrochloride salt from (±)-[5-chloro-7-(2,3-dimethylphenyl)-2,3-dihydro-1-benzofuran-2-yl]methyl 4-methylbenzenesulfonate (0.149 g, 0.33 mmol) and methylamine (0.102 g, 3.3 mmol). mp 148-150° C.

EXAMPLE 466

(±)-{[5-chloro-7-(2,3-dimethoxyphenyl)-2,3-dihydro-1-benzofuran-2-yl]methyl}methylamine The title compound was prepared (0.046 g, 34%) following the general procedure of Example 390 as a white solid, hydrochloride salt from (±)-[5-chloro-7-(2,3-dimethoxyphenyl)-2,3-dihydro-1-benzofuran-2-yl]methyl 4-methylbenzenesulfonate (0.172 g, 0.36 mmol) and methylamine (0.112 g, 3.6 mmol). mp 105-107° C.

EXAMPLE 467

(±)-{[5-chloro-7-(2,4-difluorophenyl)-2,3-dihydro-1-benzofuran-2-yl]methyl}methylamine The title compound was prepared (0.059 g, 48%) following the general procedure of Example 390 as a white solid, hydrochloride salt from (±)-[5-chloro-7-(2,4-difluorophenyl)-2,3-dihydro-1-benzofuran-2-yl]methyl 4-methylbenzenesulfonate (0.162 g, 0.36 mmol) and methylamine (0.112 g, 3.6 mmol). mp 163-165° C.

EXAMPLE 468

(±)-{[5-chloro-7-(2,4-dichlorophenyl)-2,3-dihydro-1-benzofuran-2-yl]methyl}methylamine The title compound was prepared (0.059 g, 57%) following the general procedure of Example 390 as a white solid, hydrochloride salt from (±)-[5-chloro-7-(2,4-dichlorophenyl)-2,3-dihydro-1-benzofuran-2-yl]methyl 4-methylbenzenesulfonate (0.135 g, 0.28 mmol) and methylamine (0.086 g, 2.8 mmol). mp 202-204° C.

EXAMPLE 469

(±)-{[5-chloro-7-(2,4-dimethoxyphenyl)-2,3-dihydro-1-benzofuran-2-yl]methyl}methylamine The title compound was prepared (0.052 g, 68%) following the general procedure of Example 390 as a white solid, hydrochloride salt from (±)-[5-chloro-7-(2,4-dimethoxyphenyl)-2,3-dihydro-1-benzofuran-2-yl]methyl 4-methylbenzenesulfonate (0.099 g, 0.21 mmol) and methylamine (0.065 g, 2.1 mmol). mp 206-208° C.

EXAMPLE 470

(±)-{[5-chloro-7-(2,5-difluorophenyl)-2,3-dihydro-1-benzofuran-2-yl]methyl}methylamine The title compound was prepared (0.090 g, 67%) following the general procedure of Example 390 as a white solid, hydrochloride salt from (±)-[5-chloro-7-(2,5-difluorophenyl)-2,3-dihydro-1-benzofuran-2-yl]methyl 4-methylbenzenesulfonate (0.175 g, 0.39 mmol) and methylamine (0.120 g, 3.9 mmol). mp 189-191° C.

EXAMPLE 471

(±)-{[5-chloro-7-(2,5-dichlorophenyl)-2,3-dihydro-1-benzofuran-2-yl]methyl}methylamine The title compound was prepared (0.027 g, 23%) following the general procedure of Example 390 as a white solid, hydrochloride salt from (±)-[5-chloro-7-(2,5-dichlorophenyl)-2,3-dihydro-1-benzofuran-2-yl]methyl 4-methylbenzenesulfonate (0.152 g, 0.31 mmol) and methylamine (0.086 g, 3.1 mmol). mp 185-187° C.

EXAMPLE 472

(±)-{[5-chloro-7-(5-chloro-2-methoxyphenyl)-2,3-dihydro-1-benzofuran-2-yl]methyl}methylamine The title compound was prepared (0.027 g, 21%) following the general procedure of Example 390 as a white solid, hydrochloride salt from (±)-[5-chloro-7-(5-chloro-2-methoxyphenyl)-2,3-dihydro-1-benzofuran-2-yl]methyl 4-methylbenzenesulfonate (0.165 g, 0.34 mmol) and methylamine (0.107 g, 3.4 mmol). mp 193-195° C.

EXAMPLE 473

(±)-{[5-chloro-7-(3,4-difluorophenyl)-2,3-dihydro-1-benzofuran-2-yl]methyl}methylamine The title compound was prepared (0.09 g, 79%) following the general procedure of Example 390 as a white solid, hydrochloride salt from (±)-[5-chloro-7-(3,4-difluorophenyl)-2,3-dihydro-1-benzofuran-2-yl]methyl 4-methylbenzenesulfonate (0.149 g, 0.33 mmol) and methylamine (0.102 g, 3.3 mmol). mp 235-237° C.

EXAMPLE 474

(±)-[5-chloro-7-(3-chloro-4-fluorophenyl)-2,3-dihydro-1-benzofuran-2-yl]methyl}methylamine The title compound was prepared (0.032 g, 48%) following the general procedure of Example 390 as a white solid, hydrochloride salt from (±)-[5-chloro-7-(3-chloro-4-fluorophenyl)-2,3-dihydro-1-benzofuran-2-yl]methyl 4-methylbenzenesulfonate (0.086 g, 0.18 mmol) and methylamine (0.057 g, 1.8 mmol). mp 202-204° C.

EXAMPLE 475

(±)-{[7-(2-fluorophenyl)-5-methyl-2,3-dihydro-1-benzofuran-2-yl]methyl}methylamine The title compound was prepared (0.03 g, 28%) following the general procedure of Example 390 as a white solid, hydrochloride salt from (±)-[7-(2-fluorophenyl) 5-methyl-2,3-dihydro-1-benzofuran-2-yl]methyl 4-methylbenzenesulfonate (0.14 g, 0.34 mmol) and methylamine (0.105 g, 3.4 mmol). mp 153-155° C.

EXAMPLE 476

(±)-{[7-(2-chlorophenyl)-5-methyl-2,3-dihydro-1-benzofuran-2-yl]methyl}methylamine The title compound was prepared (0.060 g, 28%) following the general procedure of Example 390 as a white solid, hydrochloride salt from (±)-[7-(2-chlorophenyl) 5-methyl-2,3-dihydro-1-benzofuran-2-yl]methyl 4-methylbenzenesulfonate (0.22 g, 0.50 mmol) and methylamine (0.155 g, 5.0 mmol). mp 194-196° C.

EXAMPLE 477

(±)-{[7-(2-methoxyphenyl)-5-methyl-2,3-dihydro-1-benzofuran-2-yl]methyl}methylamine The title compound was prepared (0.041 g, 32%) following the general procedure of Example 390 as a white solid, hydrochloride salt from (±)-[7-(2-methoxyphenyl) 5-methyl-2,3-dihydro-1-benzofuran-2-yl]methyl 4-methylbenzenesulfonate (0.17 g, 0.40 mmol) and methylamine (0.124 g, 4.0 mmol). mp 165-166° C.

EXAMPLE 478

(±)-{[7-(3-methylphenyl)-5-methyl-2,3-dihydro-1-benzofuran-2-yl]methyl}methylamine The title compound was prepared (0.075 g, 60%) following the general procedure of Example 390 as a white solid, hydrochloride salt from (±)-[7-(3-methylphenyl) 5-methyl-2,3-dihydro-1-benzofuran-2-yl]methyl 4-methylbenzenesulfonate (0.17 g, 0.42 mmol) and methylamine (0.129 g, 4.2 mmol). mp 165-167° C.

EXAMPLE 479

(±)-{[7-(3-chlorophenyl)-5-methyl-2,3-dihydro-1-benzofuran-2-yl]methyl}methylamine The title compound was prepared (0.016 g, 13%) following the general procedure of Example 390 as a white solid, hydrochloride salt from (±)-[7-(3-chlorophenyl) 5-methyl-2,3-dihydro-1-benzofuran-2-yl]methyl 4-methylbenzenesulfonate (0.16 g, 0.37 mmol) and methylamine (0.115 g, 3.7 mmol). mp 181-182° C.

EXAMPLE 480

(±)-{[7-(4-methylphenyl)-5-methyl-2,3-dihydro-1-benzofuran-2-yl]methyl}methylamine The title compound was prepared (0.049 g, 44%) following the general procedure of Example 390 as a white solid, hydrochloride salt from (±)-[7-(4-methylphenyl) 5-methyl-2,3-dihydro-1-benzofuran-2-yl]methyl 4-methylbenzenesulfonate (0.15 g, 0.37 mmol) and methylamine (0.114 g, 3.7 mmol). mp 184-185° C.

EXAMPLE 481

(±)-{[7-(4-chlorophenyl)-5-methyl-2,3-dihydro-1-benzofuran-2-yl]methyl}methylamine The title compound was prepared (0.026 g, 21%) following the general procedure of Example 390 as a white solid, hydrochloride salt from (±)-[7-(4-chlorophenyl) 5-methyl-2,3-dihydro-1-benzofuran-2-yl]methyl 4-methylbenzenesulfonate (0.16 g, 0.37 mmol) and methylamine (0.115 g, 3.7 mmol). mp 210-213° C.

EXAMPLE 482

(±)-{[7-(4-fluorophenyl)-5-methyl-2,3-dihydro-1-benzofuran-2-yl]methyl}methylamine The title compound was prepared (0.028 g, 25%) following the general procedure of Example 390 as a white solid, hydrochloride salt from (±)-[7-(4-fluorophenyl) 5-methyl-2,3-dihydro-1-benzofuran-2-yl]methyl 4-methylbenzenesulfonate (0.15 g, 0.36 mmol) and methylamine (0.112 g, 3.6 mmol). mp 206-208° C.

EXAMPLE 483

(±)-{[7-(4-methoxyphenyl)-5-methyl-2,3-dihydro-1-benzofuran-2-yl]methyl}methylamine The title compound was prepared (0.075 g, 52%) following the general procedure of Example 390 as a white solid, hydrochloride salt from (±)-[7-(4-methoxyphenyl) 5-methyl-2,3-dihydro-1-benzofuran-2-yl]methyl 4-methylbenzenesulfonate (0.19 g, 0.45 mmol) and methylamine (0.112 g, 4.5 mmol). mp 235-238° C.

EXAMPLE 484

(±)-{[7-(2,3-dimethoxyphenyl)-5-methyl-2,3-dihydro-1-benzofuran-2-yl]methyl}methylamine The title compound was prepared (0.094 g, 44%) following the general procedure of Example 390 as a white solid, hydrochloride salt from (±)-[7-(2,3-dimethoxyphenyl) 5-methyl-2,3-dihydro-1-benzofuran-2-yl]methyl 4-methylbenzenesulfonate (0.18 g, 0.40 mmol) and methylamine (0.123 g, 4.0 mmol). mp 85-89° C.

EXAMPLE 485

(±)-{[7-(2,4-dichlorophenyl)-5-methyl-2,3-dihydro-1-benzofuran-2-yl]methyl}methylamine The title compound was prepared (0.029 g, 14%) following the general procedure of Example 390 as a white solid, hydrochloride salt from (±)-[7-(2,4-dichlorophenyl) 5-methyl-2,3-dihydro-1-benzofuran-2-yl]methyl 4-methylbenzenesulfonate (0.26 g, 0.56 mmol) and methylamine (0.174 g, 5.6 mmol). mp 169-171° C.

EXAMPLE 486

(±)-{[7-(2,5-dichlorophenyl)-5-methyl-2,3-dihydro-1-benzofuran-2-yl]methyl}methylamine The title compound was prepared (0.034 g, 27%) following the general procedure of Example 390 as a white solid, hydrochloride salt from (±)-[7-(2,5-dichlorophenyl) 5-methyl-2,3-dihydro-1-benzofuran-2-yl]methyl 4-methylbenzenesulfonate (0.16 g, 0.34 mmol) and methylamine (0.107 g, 3.4 mmol). mp 158-160° C.

EXAMPLE 487

(+)-{[7-(2,5-dichlorophenyl)-5-methyl-2,3-dihydro-1-benzofuran-2-yl]methyl}methylamine Treatment of 0.51 g of fraction 1 obtained from the chiral HPLC separation of (±)-benzyl {[7-(2,5-dichlorophenyl)-5-methyl-2,3-dihydro-1-benzofuran-2-yl]methyl}methylcarbamate with trimethylsilyl iodide (0.88 g, 4.4 mmol) generally according to the procedure described for Example 158 gave 0.256 g (64%) of (+)-{[7-(2,5-dichlorophenyl)-5-methyl-2,3-dihydro-1-benzofuran-2-yl]methyl}methylamine as a white solid, hydrochloride salt. $[\alpha]_D^{25}=+14.0$ (c 10.0 in methanol); mp 192-194° C.

EXAMPLE 488

(−)-{[7-(2,5-dichlorophenyl)-5-methyl-2,3-dihydro-1-benzofuran-2-yl]methyl}methylamine Treatment of 0.50 g of fraction 2 obtained from the chiral HPLC separation of (±)-benzyl {[7-(2,5-dichlorophenyl)-5-methyl-2,3-dihydro-1-benzofuran-2-yl]methyl}methylcarbamate with trimethylsilyl iodide (0.88 g, 4.4 mmol) generally according to the procedure described for Example 158 gave 0.132 g (33%) of (−)-{[7-(2,5-dichlorophenyl)-5-methyl-2,3-dihydro-1-benzofuran-2-yl]methyl}methylamine as a white solid, hydrochloride salt. $[\alpha]_D^{25}=-12.99$ (c 10.0 in methanol); mp 192-194° C.

EXAMPLE 489

(±)-{[7-(2,6-dimethylphenyl)-5-methyl-2,3-dihydro-1-benzofuran-2-yl]methyl}methylamine The title compound was prepared (0.035 g, 46%) following the general procedure of Example 390 as a white solid, hydrochloride salt from (±)-[7-(2,6-dimethylphenyl) 5-methyl-2,3-

EXAMPLE 490

(±)-{[7-(2,6-dichlorophenyl)-5-methyl-2,3-dihydro-1-benzofuran-2-yl]methyl}methylamine The title compound was prepared (0.073 g, 78%) following the general procedure of Example 390 as a white solid, hydrochloride salt from (±)-[7-(2,6-dichlorophenyl) 5-methyl-2,3-dihydro-1-benzofuran-2-yl]methyl 4-methylbenzenesulfonate (0.12 g, 0.26 mmol) and methylamine (0.080 g, 2.6 mmol). mp 192-195° C.

EXAMPLE 491

(±)-{[7-(2-fluorophenyl)-5-methoxy-2,3-dihydro-1-benzofuran-2-yl]methyl}methylamine The title compound was prepared (0.039 g, 51%) following the general procedure of Example 390 as a white solid, hydrochloride salt from (±)-{[7-(2-fluorophenyl)-5-methoxy-2,3-dihydro-1-benzofuran-2-yl]methyl}4-methylbenzenesulfonate (0.102 g, 0.24 mmol) and methylamine (0.074 g, 2.4 mmol). mp 110-112° C.

EXAMPLE 492

(±)-{[7-(2-chlorophenyl)-5-methoxy-2,3-dihydro-1-benzofuran-2-yl]methyl}methylamine The title compound was prepared (0.040 g, 52%) following the general procedure of Example 390 as a white solid, hydrochloride salt from (±)-{[7-(2-chlorophenyl)-5-methoxy-2,3-dihydro-1-benzofuran-2-yl]methyl}4-methylbenzenesulfonate (0.102 g, 0.23 mmol) and methylamine (0.071 g, 2.3 mmol). mp 185-186° C.

EXAMPLE 493

(±)-{[7-(2-methylphenyl)-5-methoxy-2,3-dihydro-1-benzofuran-2-yl]methyl}methylamine The title compound was prepared (0.055 g, 54%) following the general procedure of Example 390 as a white solid, hydrochloride salt from (±)-{[7-(2-methylphenyl)-5-methoxy-2,3-dihydro-1-benzofuran-2-yl]methyl}4-methylbenzenesulfonate (0.135 g, 0.32 mmol) and methylamine (0.099 g, 3.2 mmol). mp 167-169° C.

EXAMPLE 494

(±)-{[7-(2,3-difluorophenyl)-5-methoxy-2,3-dihydro-1-benzofuran-2-yl]methyl}methylamine The title compound was prepared (0.017 g, 18%) following the general procedure of Example 390 as a white solid, hydrochloride salt from (±)-{[7-(2,3-difluorophenyl)-5-methoxy-2,3-dihydro-1-benzofuran-2-yl]methyl}4-methylbenzenesulfonate (0.12 g, 0.27 mmol) and methylamine (0.082 g, 2.7 mmol). mp 148-150° C.

EXAMPLE 495

(±)-{[7-(2,3-dichlorophenyl)-5-methoxy-2,3-dihydro-1-benzofuran-2-yl]methyl}methylamine The title compound was prepared (0.053 g, 68%) following the general procedure of Example 390 as a white solid, hydrochloride salt from (±)-{[7-(2,3-dichlorophenyl)-5-methoxy-2,3-dihydro-1-benzofuran-2-yl]methyl}4-methylbenzenesulfonate (0.135 g, 0.28 mmol) and methylamine (0.087 g, 2.8 mmol). mp 178-180° C.

EXAMPLE 496

(±)-{[7-(2,3-dimethylphenyl)-5-methoxy-2,3-dihydro-1-benzofuran-2-yl]methyl}methylamine The title compound was prepared (0.064 g, 64%) following the general procedure of Example 390 as a white solid, hydrochloride salt from (±)-{[7-(2,3-dimethylphenyl)-5-methoxy-2,3-dihydro-1-benzofuran-2-yl]methyl}4-methylbenzenesulfonate (0.132 g, 0.30 mmol) and methylamine (0.093 g, 3.0 mmol). mp 177-179° C.

EXAMPLE 497

(±)-{[7-(2,4-difluorophenyl)-5-methoxy-2,3-dihydro-1-benzofuran-2-yl]methyl}methylamine The title compound was prepared (0.062 g, 61%) following the general procedure of Example 390 as a white solid, hydrochloride salt from (±)-{[7-(2,4-difluorophenyl)-5-methoxy-2,3-dihydro-1-benzofuran-2-yl]methyl}4-methylbenzenesulfonate (0.132 g, 0.29 mmol) and methylamine (0.092 g, 2.9 mmol). mp 179-181° C.

EXAMPLE 498

(±)-{[7-(2,5-difluorophenyl)-5-methoxy-2,3-dihydro-1-benzofuran-2-yl]methyl}methylamine The title compound was prepared (0.027 g, 27%) following the general procedure of Example 390 as a white solid, hydrochloride salt from (±)-{[7-(2,5-difluorophenyl)-5-methoxy-2,3-dihydro-1-benzofuran-2-yl]methyl}4-methylbenzenesulfonate (0.129 g, 0.29 mmol) and methylamine (0.090 g, 2.9 mmol). mp 163-165° C.

EXAMPLE 499

(±)-{[7-(2,5-dichlorophenyl)-5-methoxy-2,3-dihydro-1-benzofuran-2-yl]methyl}methylamine The title compound was prepared (0.061 g, 56%) following the general procedure of Example 390 as a white solid, hydrochloride salt from (±)-{[7-(2,5-dichlorophenyl)-5-methoxy-2,3-dihydro-1-benzofuran-2-yl]methyl}4-methylbenzenesulfonate (0.139 g, 0.29 mmol) and methylamine (0.090 g, 2.9 mmol). mp 179-181° C.

EXAMPLE 500

(±)-{[7-(2,5-dimethylphenyl)-5-methoxy-2,3-dihydro-1-benzofuran-2-yl]methyl}methylamine The title compound was prepared (0.064 g, 62%) following the general procedure of Example 390 as a white solid, hydrochloride salt from (±)-{[7-(2,5-dimethylphenyl)-5-methoxy-2,3-dihydro-1-benzofuran-2-yl]methyl}4-methylbenzenesulfonate (0.135 g, 0.31 mmol) and methylamine (0.096 g, 3.1 mmol). mp 202-204° C.

EXAMPLE 501

(±)-{[7-(2,5-dimethoxyphenyl)-5-methoxy-2,3-dihydro-1-benzofuran-2-yl]methyl}methylamine The title compound was prepared (0.032 g, 27%) following the general procedure of Example 390 as a white solid, hydrochloride salt from (±)-{[7-(2,5-dimethoxyphenyl)-5-methoxy-2,3-dihydro-1-benzofuran-2-yl]methyl}4-methylbenzenesulfonate (0.152 g, 0.32 mmol) and methylamine (0.100 g, 3.2 mmol). mp 144-145° C.

EXAMPLE 502

(±)-{[7-(5-chloro-2-methoxyphenyl)-5-methoxy-2,3-dihydro-1-benzofuran-2-yl]methyl}methylamine The title compound was prepared (0.067 g, 58%) following the general procedure of Example 390 as a white solid, hydrochloride salt from (±)-{[7-(5-chloro-2-methoxyphenyl)-5-methoxy-2,3-dihydro-1-benzofuran-2-yl]methyl}4-methylbenzenesulfonate (0.148 g, 0.31 mmol) and methylamine (0.097 g, 3.1 mmol). mp 169-171° C.

EXAMPLE 503

(±)-{[7-(3-chloro-4-fluorophenyl)-5-methoxy-2,3-dihydro-1-benzofuran-2-yl]methyl}methylamine The title compound was prepared (0.052 g, 46%) following the general procedure of Example 390 as a white solid, hydrochloride salt from (±)-{[7-(3-chloro-4-fluorophenyl)-5-methoxy-2,3-dihydro-1-benzofuran-2-yl]methyl}4-methylbenzenesulfonate (0.14 g, 0.31 mmol) and methylamine (0.097 g, 3.1 mmol). mp 197-199° C.

EXAMPLE 504

(±)-{[7-(2,6-dimethylphenyl)-5-methoxy-2,3-dihydro-1-benzofuran-2-yl]methyl}methylamine The title compound was prepared (0.076 g, 57%) following the general procedure of Example 390 as a white solid, hydrochloride salt from (±)-{[7-(2,6-dimethylphenyl)-5-methoxy-2,3-dihydro-1-benzofuran-2-yl]methyl}4-methylbenzenesulfonate (0.175 g, 0.40 mmol) and methylamine (0.12 g, 4.0 mmol). mp 170-172° C.

EXAMPLE 505

(±)-{[7-(2-chlorophenyl)-5-phenyl-2,3-dihydro-1-benzofuran-2-yl]methyl}methylamine The title compound was prepared (0.066 g, 84%) following the general procedure of Example 390 as a white solid, hydrochloride salt from (±)-{[7-(2-chlorophenyl)-5-phenyl-2,3-dihydro-1-benzofuran-2-yl]methyl}4-methylbenzenesulfonate (0.10 g, 0.20 mmol) and methylamine (0.30 g, 9.8 mmol). 192-194 mp ° C.

EXAMPLE 506

(±)-{[7-(3-chlorophenyl)-5-phenyl-2,3-dihydro-1-benzofuran-2-yl]methyl}methylamine The title compound was prepared (0.055 g, 69%) following the general procedure of Example 390 as a white solid, hydrochloride salt from (±)-{[7-(3-chlorophenyl)-5-phenyl-2,3-dihydro-1-benzofuran-2-yl]methyl}4-methylbenzenesulfonate (0.10 g, 0.20 mmol) and methylamine (0.30 g, 9.8 mmol). mp 211-214° C.

EXAMPLE 507

(±)-{[7-(4-chlorophenyl)-5-phenyl-2,3-dihydro-1-benzofuran-2-yl]methyl}methylamine The title compound was prepared (0.056 g, 71%) following the general procedure of Example 390 as a white solid, hydrochloride salt from (±)-{[7-(4-chlorophenyl)-5-phenyl-2,3-dihydro-1-benzofuran-2-yl]methyl}4-methylbenzenesulfonate (0.10 g, 0.20 mmol) and methylamine (0.30 g, 9.8 mmol). mp >250° C.

EXAMPLE 508

(±)-{[7-(2-fluorophenyl)-5-phenyl-2,3-dihydro-1-benzofuran-2-yl]methyl}methylamine The title compound was prepared (0.065 g, 83%) following the general procedure of Example 390 as a white solid, hydrochloride salt from (±)-{[7-(2-fluorophenyl)-5-phenyl-2,3-dihydro-1-benzofuran-2-yl]methyl}4-methylbenzenesulfonate (0.10 g, 0.21 mmol) and methylamine (0.30 g, 9.8 mmol). mp 204-206° C.

EXAMPLE 509

(±)-{[7-(3-fluorophenyl)-5-phenyl-2,3-dihydro-1-benzofuran-2-yl]methyl}methylamine The title compound was prepared (0.058 g, 74%) following the general procedure of Example 390 as a white solid, hydrochloride salt from (±)-{[7-(3-fluorophenyl)-5-phenyl-2,3-dihydro-1-benzofuran-2-yl]methyl}4-methylbenzenesulfonate (0.10 g, 0.21 mmol) and methylamine (0.30 g, 9.8 mmol). mp >250° C.

EXAMPLE 510

(±)-{[7-(4-fluorophenyl)-5-phenyl-2,3-dihydro-1-benzofuran-2-yl]methyl}methylamine The title compound was prepared (0.040 g, 51%) following the general procedure of Example 390 as a white solid, hydrochloride salt from (±)-{[7-(4-fluorophenyl)-5-phenyl-2,3-dihydro-1-benzofuran-2-yl]methyl}4-methylbenzenesulfonate (0.10 g, 0.21 mmol) and methylamine (0.30 g, 9.8 mmol). mp >250° C.

EXAMPLE 511

(±)-{[7-(2-methylphenyl)-5-phenyl-2,3-dihydro-1-benzofuran-2-yl]methyl}methylamine The title compound was prepared (0.055 g, 70%) following the general procedure of Example 390 as a white solid, hydrochloride salt from (±)-{[7-(2-methylphenyl)-5-phenyl-2,3-dihydro-1-benzofuran-2-yl]methyl}4-methylbenzenesulfonate (0.10 g, 0.21 mmol) and methylamine (0.30 g, 9.8 mmol). mp 232-235° C.

EXAMPLE 512

(±)-{[7-(3-methylphenyl)-5-phenyl-2,3-dihydro-1-benzofuran-2-yl]methyl}methylamine The title compound was prepared (0.055 g, 70%) following the general procedure of Example 390 as a white solid, hydrochloride salt from (±)-{[7-(3-methylphenyl)-5-phenyl-2,3-dihydro-1-benzofuran-2-yl]methyl}4-methylbenzenesulfonate (0.10 g, 0.21 mmol) and methylamine (0.30 g, 9.8 mmol). mp 230-234° C.

EXAMPLE 513

(±)-{[7-(4-methylphenyl)-5-phenyl-2,3-dihydro-1-benzofuran-2-yl]methyl}methylamine The title compound was prepared (0.051 g, 65%) following the general procedure of Example 390 as a white solid, hydrochloride salt from (±)-{[7-(4-methylphenyl)-5-phenyl-2,3-dihydro-1-benzofuran-2-yl]methyl}4-methylbenzenesulfonate (0.10 g, 0.213 mmol) and methylamine (0.30 g, 9.8 mmol). mp >250° C.

EXAMPLE 514

(±)-{[7-(2-methoxyphenyl)-5-phenyl-2,3-dihydro-1-benzofuran-2-yl]methyl}methylamine The title compound was prepared (0.060 g, 76%) following the general procedure of Example 390 as a white solid, hydrochloride salt from (±)-{[7-(2-methoxyphenyl)-5-phenyl-2,3-dihydro-1-benzofuran-2-yl]methyl}4-methylbenzenesulfonate (0.10 g, 0.21 mmol) and methylamine (0.30 g, 9.8 mmol). mp 140-143° C.

EXAMPLE 515

(±)-{[7-(3-methoxyphenyl)-5-phenyl-2,3-dihydro-1-benzofuran-2-yl]methyl}methylamine The title compound was prepared (0.053 g, 67%) following the general procedure of Example 390 as a white solid, hydrochloride salt from (±)-{[7-(3-methoxyphenyl)-5-phenyl-2,3-dihydro-1-benzofuran-2-yl]methyl}4-methylbenzenesulfonate (0.10 g, 0.21 mmol) and methylamine (0.30 g, 9.8 mmol). mp 206-209° C.

EXAMPLE 516

(±)-{[7-(4-methoxyphenyl)-5-phenyl-2,3-dihydro-1-benzofuran-2-yl]methyl}methylamine The title compound was prepared (0.081 g, 99%) following the general procedure of Example 390 as a white solid, hydrochloride salt from (±)-{[7-(4-methoxyphenyl)-5-phenyl-2,3-dihydro-1-benzofuran-2-yl]methyl}4-methylbenzenesulfonate (0.10 g, 0.21 mmol) and methylamine (0.30 g, 9.8 mmol). mp >250° C.

EXAMPLE 517

(±)-{[7-(2,4-difluorophenyl)-5-phenyl-2,3-dihydro-1-benzofuran-2-yl]methyl}methylamine The title compound was prepared (0.047 g, 59%) following the general procedure of Example 390 as a white solid, hydrochloride salt from (±)-{[7-(2,4-difluorophenyl)-5-phenyl-2,3-dihydro-1-benzofuran-2-yl]methyl}4-methylbenzenesulfonate (0.10 g, 0.20 mmol) and methylamine (0.30 g, 9.8 mmol). mp 188-191° C.

EXAMPLE 518

(±)-{[N-methyl-1-[7-phenyl-5-(trifluoromethyl)-2,3-dihydro-1-benzofuran-2-yl]methanamine The title compound was prepared (0.031 g, 67%) following the general procedure of Example 390 as a white solid, hydrochloride salt from (±)-[7-phenyl-5-(trifluoromethyl)-2,3-dihydro-1-benzofuran-2-yl]methyl 4-methylbenzenesulfonate (0.060 g, 0.13 mmol) and methylamine (0.12 g, 3.9 mmol). mp 189-190° C.

EXAMPLE 519

(±)-N-methyl-1-[7-(3-methylphenyl)-5-(trifluoromethyl)-2,3-dihydro-1-benzofuran-2-yl]methanamine The title compound was prepared (0.026 g, 67%) following the general procedure of Example 390 as a white solid, hydrochloride salt from [7-(3-methylphenyl)-5-(trifluoromethyl)-2,3-dihydro-1-benzofuran-2-yl]methyl 4-methylbenzenesulfonate (0.050 g, 0.11 mmol) and methylamine (0.12 g, 3.9 mmol). mp 228-230° C.

EXAMPLE 520

(±)-N-methyl-1-[7-(3-fluorophenyl)-5-(trifluoromethyl)-2,3-dihydro-1-benzofuran-2-yl]methanamine The title compound was prepared (0.026 g, 60%) following the general procedure of Example 390 as a white solid, hydrochloride salt from [7-(3-fluorophenyl)-5-(trifluoromethyl)-2,3-dihydro-1-benzofuran-2-yl]methyl 4-methylbenzenesulfonate (0.055 g, 0.18 mmol) and methylamine (0.12 g, 3.9 mmol). mp 238-240° C.

EXAMPLE 521

(±)-N-methyl-1-[7-(2,3-difluorophenyl)-5-(trifluoromethyl)-2,3-dihydro-1-benzofuran-2-yl]methanamine The title compound was prepared (0.015 g, 19%) following the general procedure of Example 390 as a white solid, hydrochloride salt from [7-(2,3-difluorophenyl)-5-(trifluoromethyl)-2,3-dihydro-1-benzofuran-2-yl]methyl 4-methylbenzenesulfonate (0.10 g, 0.21 mmol) and methylamine (0.12 g, 3.9 mmol). mp 123-125° C.

EXAMPLE 522

(±)-N-methyl-1-[7-(3,4-difluorophenyl)-5-(trifluoromethyl)-2,3-dihydro-1-benzofuran-2-yl]methanamine The title compound was prepared (0.035 g, 48%) following the general procedure of Example 390 as a white solid, hydrochloride salt from [7-(3,4-difluorophenyl)-5-(trifluoromethyl)-2,3-dihydro-1-benzofuran-2-yl]methyl 4-methylbenzenesulfonate (0.093 g, 0.19 mmol) and methylamine (0.12 g, 3.9 mmol). mp 235-237° C.

EXAMPLE 523

(±)-N-methyl-1-[7-(2,5-difluorophenyl)-5-(trifluoromethyl)-2,3-dihydro-1-benzofuran-2-yl]methanamine The title compound was prepared (0.045 g, 58%) following the general procedure of Example 390 as a white solid, hydrochloride salt from [7-(2,5-difluorophenyl)-5-(trifluoromethyl)-2,3-dihydro-1-benzofuran-2-yl]methyl 4-methylbenzenesulfonate (0.10 g, 0.21 mmol) and methylamine (0.12 g, 3.9 mmol). mp 138-140° C.

EXAMPLE 524

(±)-N-methyl-1-[7-(2,3-dichlorophenyl)-5-(trifluoromethyl)-2,3-dihydro-1-benzofuran-2-yl]methanamine The title compound was prepared (0.039 g, 49%) following the general procedure of Example 390 as a white solid, hydrochloride salt from [7-(2,3-dichlorophenyl)-5-(trifluoromethyl)-2,3-dihydro-1-benzofuran-2-yl]methyl 4-methylbenzenesulfonate (0.10 g, 0.19 mmol) and methylamine (0.12 g, 3.9 mmol). mp 238-240° C.

EXAMPLE 525

(±)-{[7-(3-chloro-4-fluorophenyl)-5-(trifluoromethyl)-2,3-dihydro-1-benzofuran-2-yl]methyl}methylamine The title compound was prepared (0.014 g, 19%) following the general procedure of Example 390 as a white solid, hydrochloride salt from [7-(3-chloro-4-fluorophenyl)-5-(trifluoromethyl)-2,3-dihydro-1-benzofuran-2-yl]methyl 4-methylbenzenesulfonate (0.095 g, 0.19 mmol) and methylamine (0.12 g, 3.9 mmol). mp 229-230° C.

EXAMPLE 526

(±)-N-methyl-1-[7-(2,4-dimethoxyphenyl)-5-(trifluoromethyl)-2,3-dihydro-1-benzofuran-2-yl]methanamine The title compound was prepared (0.048 g, 76%) following the general procedure of Example 390 as a white solid, hydrochloride salt from [7-(2,4-dimethoxyphenyl)-5-(trifluoromethyl)-2,3-dihydro-1-benzofuran-2-yl]methyl 4-methylbenzenesulfonate (0.080 g, 0.16 mmol) and methylamine (0.12 g, 3.9 mmol). mp 234-236° C.

EXAMPLE 527

(±)-{[7-[3,5-bis(trifluoromethyl)phenyl]-5-(trifluoromethyl)-2,3-dihydro-1-benzofuran-2-yl]methyl}methylamine The title compound was prepared (0.033 g, 58%) following the general procedure of Example 390 as a white solid, hydrochloride salt from [7-[3,5-bis(trifluoromethyl)phenyl]-5-(trifluoromethyl)-2,3-dihydro-1-benzofuran-2-yl]methyl 4-methylbenzenesulfonate (0.070 g, 0.12 mmol) and methylamine (0.12 g, 3.9 mmol). mp 205-207° C.

EXAMPLE 528

(±)-{[7-fluoro-5-(2-methylphenyl)-2,3-dihydro-1-benzofuran-2-yl]methyl}methylamine The title compound was prepared (0.075 g, 75%) following the general procedure of Example 390 as a white solid, hydrochloride salt from (±)-[7-fluoro-5-(2-methylphenyl)-2,3-dihydro-1-benzofuran-2-yl]methyl 4-methylbenzenesulfonate (0.141 g, 0.32 mmol) and methylamine (0.20 g, 6.4 mmol). mp 212-217° C. (dec).

EXAMPLE 529

(±)-{[7-fluoro-5-(2-chlorophenyl)-2,3-dihydro-1-benzofuran-2-yl]methyl}methylamine The title compound was prepared (0.068 g, 47%) following the general procedure of Example 390 as a white solid, hydrochloride salt from (±)-[7-fluoro-5-(2-chlorophenyl)-2,3-dihydro-1-benzofuran-2-yl]methyl 4-methylbenzenesulfonate (0.199 g, 0.46 mmol) and methylamine (0.28 g, 9.2 mmol). mp 217-222° C. (dec).

EXAMPLE 530

(±)-{[7-fluoro-5-(2-fluorophenyl)-2,3-dihydro-1-benzofuran-2-yl]methyl}methylamine The title compound was prepared (0.132 g, 92%) following the general procedure of Example 390 as a white solid, hydrochloride salt from (±)-[7-fluoro-5-(2-fluorophenyl)-2,3-dihydro-1-benzofuran-2-yl]methyl 4-methylbenzenesulfonate (0.20 g, 0.48 mmol) and methylamine (0.30 g, 9.6 mmol). mp>250° C. (dec).

EXAMPLE 531

(±)-{7-fluoro-5-[2-(trifluoromethyl)phenyl]-2,3-dihydro-1-benzofuran-2-yl}methyl)methylamine The title compound was prepared (0.02 g, 18%) following the general procedure of Example 390 as a white solid, hydrochloride salt from (±)-[{7-fluoro-5-[2-(trifluoromethyl)phenyl]-2,3-dihydro-1-benzofuran-2-yl}methyl 4-methylbenzenesulfonate (0.21 g, 0.45 mmol) and methylamine (0.28 g, 9.0 mmol). mp 196-200° C. (dec).

EXAMPLE 532

(±)-{7-fluoro-5-[2-methoxyphenyl]-2,3-dihydro-1-benzofuran-2-yl}methyl)methylamine The title compound was prepared (0.13 g, 92%) following the general procedure of Example 390 as a white solid, hydrochloride salt from (±)-[{7-fluoro-5-[2-methoxyphenyl]-2,3-dihydro-1-benzofuran-2-yl}methyl 4-methylbenzenesulfonate (0.18 g, 0.42 mmol) and methylamine (0.26 g, 8.4 mmol). mp 223-226° C. (dec).

EXAMPLE 533

(±)-{7-fluoro-5-[3-methylphenyl]-2,3-dihydro-1-benzofuran-2-yl}methyl)methylamine The title compound was prepared (0.14 g, 99%) following the general procedure of Example 390 as a white solid, hydrochloride salt from (±)-[{7-fluoro-5-[3-methylphenyl]-2,3-dihydro-1-benzofuran-2-yl}methyl 4-methylbenzenesulfonate (0.20 g, 0.48 mmol) and methylamine (0.30 g, 9.6 mmol). mp 245-250° C.

EXAMPLE 534

(±)-{7-fluoro-5-[3-chlorophenyl]-2,3-dihydro-1-benzofuran-2-yl}methyl)methylamine The title compound was prepared (0.11 g, 81%) following the general procedure of Example 390 as a white solid, hydrochloride salt from (±)-[{7-fluoro-5-[3-chlorophenyl]-2,3-dihydro-1-benzofuran-2-yl}methyl 4-methylbenzenesulfonate (0.21 g, 0.49 mmol) and methylamine (0.30 g, 9.6 mmol). mp 225-232° C.

EXAMPLE 535

(±)-{[7-fluoro-5-(3-fluorophenyl)-2,3-dihydro-1-benzofuran-2-yl]methyl}methylamine The title compound was prepared (0.12 g, 88%) following the general procedure of Example 390 as a white solid, hydrochloride salt from (±)-[7-fluoro-5-(3-fluorophenyl)-2,3-dihydro-1-benzofuran-2-yl]methyl 4-methylbenzenesulfonate (0.19 g, 0.45 mmol) and methylamine (0.28 g, 9.1 mmol). mp>250° C.

EXAMPLE 536

(±)-{7-fluoro-5-[3-(trifluoromethyl)phenyl]-2,3-dihydro-1-benzofuran-2-yl}methyl)methylamine The title compound was prepared (0.034 g, 23%) following the general procedure of Example 390 as a white solid, hydrochloride salt from (±)-[{7-fluoro-5-[3-(trifluoromethyl)phenyl]-2,3-dihydro-1-benzofuran-2-yl}methyl 4-methylbenzenesulfonate (0.19 g, 0.42 mmol) and methylamine (0.26 g, 8.5 mmol). mp 215-219° C.

EXAMPLE 537

(±)-{7-fluoro-5-[3-methoxyphenyl]-2,3-dihydro-1-benzofuran-2-yl}methyl)methylamine The title compound was prepared (0.13 g, 99%) following the general procedure of Example 390 as a white solid, hydrochloride salt from (±)-[{7-fluoro-5-[3-methoxyphenyl]-2,3-dihydro-1-benzofuran-2-yl}methyl 4-methylbenzenesulfonate (0.18 g, 0.42 mmol) and methylamine (0.26 g, 8.3 mmol). mp 214-217° C.

EXAMPLE 538

(±)-{7-fluoro-5-[4-methylphenyl]-2,3-dihydro-1-benzofuran-2-yl}methyl)methylamine The title compound was prepared (0.11 g, 88%) following the general procedure of Example 390 as a white solid, hydrochloride salt from (±)-[{7-fluoro-5-[4-methylphenyl]-2,3-dihydro-1-benzofuran-2-yl}methyl 4-methylbenzenesulfonate (0.17 g, 0.41 mmol) and methylamine (0.26 g, 8.3 mmol). mp>250° C.

EXAMPLE 539

(±)-{7-fluoro-5-[4-chlorophenyl]-2,3-dihydro-1-benzofuran-2-yl}methyl)methylamine The title compound was prepared (0.14 g, 91%) following the general procedure of Example. 390 as a white solid, hydrochloride salt from (±)-[{7-fluoro-5-[4-chlorophenyl]-2,3-dihydro-1-benzofuran-2-yl}methyl 4-methylbenzenesulfonate (0.21 g, 0.49 mmol) and methylamine (0.30 g, 9.8 mmol). mp >250° C.

EXAMPLE 540

(±)-{[7-fluoro-5-(4-fluorophenyl)-2,3-dihydro-1-benzofuran-2-yl]methyl}methylamine The title compound was prepared (0.12 g, 96%) following the general procedure of Example 390 as a white solid, hydrochloride salt from (±)-[7-fluoro-5-(4-fluorophenyl)-2,3-dihydro-1-benzofuran-2-yl]methyl 4-methylbenzenesulfonate (0.18 g, 0.43 mmol) and methylamine (0.27 g, 8.6 mmol). mp>250° C.

EXAMPLE 541

(±)-{7-fluoro-5-[4-(trifluoromethyl)phenyl]-2,3-dihydro-1-benzofuran-2-yl}methyl)methylamine The title compound was prepared (0.14 g, 87%) following the general procedure of Example 390 as a white solid, hydrochloride salt from (±)-[{7-fluoro-5-[4-(trifluoromethyl)phenyl]-2,3-dihydro-1-benzofuran-2-yl}methyl 4-methylbenzenesulfonate (0.21 g, 0.45 mmol) and methylamine (0.28 g, 9.0 mmol). mp >250° C.

EXAMPLE 542

(±)-{7-fluoro-5-[4-methoxyphenyl]-2,3-dihydro-1-benzofuran-2-yl}methyl)methylamine The title compound was prepared (0.12 g, 92%) following the general procedure of Example 390 as a white solid, hydrochloride salt from (±)-[{7-fluoro-5-[4-methoxyphenyl]-2,3-dihydro-1-benzofuran-2-yl}methyl 4-methylbenzenesulfonate (0.18 g, 0.42 mmol) and methylamine (0.26 g, 8.4 mmol). mp >250° C.

EXAMPLE 543

(+){[7-(2,6-dichlorophenyl)-5-fluoro-2,3-dihydro-1-benzofuran-2-yl]methyl}methylamine Treatment of 0.71 g of fraction 1 obtained from the chiral HPLC separation of (±)-[7-(2,6-dichlorophenyl)-5-fluoro-2,3-dihydro-1-benzofuran-2-yl]methyl 4-methylbenzenesulfonate with methylamine (0.47 g, 15.0 mmol) generally according to the procedure described for Example 390 gave 0.42 g (76%) of (+)-{[(7-(2,6-dichlorophenyl)-5-fluoro-2,3-dihydro-1-benzofuran-2-yl]methyl}methylamine as a white solid, hydrochloride salt. $[\alpha]_D^{25}$=+7.89 (c 10.0 in methanol); mp 140-142° C.

EXAMPLE 544

(−){[7-(2,6-dichlorophenyl)-5-fluoro-2,3-dihydro-1-benzofuran-2-yl]methyl}methylamine Treatment of 0.79 g of fraction 2 obtained from the chiral HPLC separation of (±)-[7-(2,6-dichlorophenyl)-5-fluoro-2,3-dihydro-1-benzofuran-2-yl]methyl 4-methylbenzenesulfonate with methylamine (0.52 g, 16.9 mmol) generally according to the procedure described for Example 390 gave 0.39 g (64%) of (−)-{[(7-(2,6-dichlorophenyl)-5-fluoro-2,3-

EXAMPLE 545

(R)-[7-(2-chloro-phenyl)-5-fluoro-2,3-dihydro-benzofuran-2-ylmethyl]-methyl-amine Treatment of (R)-2-bromomethyl-7-(2-chloro-phenyl)-5-fluoro-2,3-dihydrobenzofuran (0.55 g, 1.6 mmol) generally according to the procedure described for Example 390 gave 0.36 g (77%) of (R)-[7-(2-chloro-phenyl)-5-fluoro-2,3-dihydro-benzofuran-2-ylmethyl]-methyl-amine as a white foam, hydrochloride salt. $[\alpha]_D^{25}$=+11.57 (c 7.43 in methanol); Anal. calcd. for $C_{16}H_{15}ClFNOHCl$: C, 58.55; H, 4.91; N, 4.27; Found: C, 56.86; H, 5.27; N, 3.91.

EXAMPLE 546

(R)-[7-(2,6-dichloro-phenyl)-5-fluoro-2,3-dihydro-benzofuran-2-ylmethyl]ethylamine Treatment of (R)-2-bromomethyl-7-(2,6-dichloro-phenyl)-5-fluoro-2,3-dihydrobenzofuran (0.42 g, 1.1 mmol) generally according to the procedure described for Example 390 afforded 0.28 g (74%) of (R)-[7-(2,6-dichloro-phenyl)-5-fluoro-2,3-dihydro-benzofuran-2-ylmethyl]ethylamine as a white foam, hydrochloride salt. MS ES [M+H]+340.1; $[\alpha]_D^{25}$=−7.12 (c 7.86 in methanol); Anal. calcd. for $C_{17}H_{16}Cl_2FNOHCl$: C, 54.21; H, 4.55; N, 3.72. Found: C, 51.85; H, 4.88; N, 3.50.

EXAMPLE 547

(R)-[7-(2,6-dichloro-phenyl)-5-Fluoro-2,3-dihydro-benzofuran-2-ylmethyl]dimethylamine Treatment of (R)-2-bromomethyl-7-(2,6-dichloro-phenyl)-5-fluoro-2,3-dihydrobenzofuran (0.41 g, 1.1 mmol) and N,N-dimethylamine (2.0 M in tetrahydrofuran, 5.4 ml) generally according to the procedure described for Example 390 afforded 0.29 g (80%) of (R)-[7-(2,6-dichloro-phenyl)-5-fluoro-2,3-dihydro-benzofuran-2-ylmethyl]-dimethyl-amine as a white solid, hydrochloride salt. mp 156-158° C.; $[\alpha]_D^{25}$=−21.04 (c 7.71 in methanol); Anal. calcd. for $C_{17}H_{16}Cl_2FNOHCl$: C, 54.21; H, 4.55; N, 3.72. Found: C, 53.98; H, 4.62; N, 3.56.

EXAMPLE 548

{[(2R)-7-(5-chloro-2-methylphenyl)-5-fluoro-2,3-dihydro-1-benzofuran-2-yl]methyl}amine Treatment of (R)-2-azidomethyl-7-(5-chloro-2-methylphenyl)-5-fluoro-2,3-dihydro-benzofuran (0.40 g, 1.2 mmol) generally according to the procedure described for Example 21 gave {[(2R)-7-(5-chloro-2-methylphenyl)-5-fluoro-2,3-dihydro-1-benzofuran-2-yl]methyl}amine as a white solid, hydrochloride salt. mp 148-150° C.; $[\alpha]_D^{25}$=+1.45 (c 8.29 in methanol); Anal. calcd. for $C_{16}H_{15}ClFNOHCl$: C, 58.55; H, 4.91; N, 4.27. Found: C, 58.55; H, 4.78; N, 3.88.

EXAMPLE 549

{[(2R)-7-(4-chloro-2-methylphenyl)-5-fluoro-2,3-dihydro-1-benzofuran-2-yl]methyl}amine Treatment of (R)-2-azidomethyl-7-(4-chloro-2-methylphenyl)-5-fluoro-2,3-dihydrobenzo-furan (0.40 g, 1.2 mmol) generally according to the procedure described for Example 21 provided 0.29 g (80%) of {[(2R)-7-(4-chloro-2-methylphenyl)-5-fluoro-2,3-dihydro-1-benzofuran-2-yl]methyl}amine as a white solid, hydrochloride salt. mp 183-185° C.; $[\alpha]_D^{25}$=+7.22 (c 9.14 in methanol); Anal. calcd. for $C_{16}H_{15}ClFNOHCl$: C, 58.55; H, 4.91; N, 4.27. Found: C, 58.55; H, 4.87; N, 4.52.

EXAMPLE 550

(−)-{[7-(2,6-dichlorophenyl)-5-fluoro-2,3-dihydro-1-benzofuran-2-yl]methyl}amine Treatment of 0.95 g of fraction 1 obtained from the chiral HPLC separation of (±)-benzyl {[7-(2,6-dichlorophenyl)-5-fluoro-2,3-dihydro-1-benzofuran-2-yl]methyl}carbamate with hydrogen bromide (20 mL, 30 wt. % in acetic acid) generally according to the procedure described for Example 245 gave 0.38 g (57%) of (−)-{[7-(2,6-dichlorophenyl)-5-fluoro-2,3-dihydro-1-benzofuran-2-yl]methyl}amine as a white solid, hydrochloride salt. $[\alpha]_D^{25}$=−21.12 (c 10.0 in methanol); mp 228-230° C.

EXAMPLE 551

(+)-{[7-(2,6 dichlorophenyl)-5-fluoro-2,3-dihydro-1-benzofuran-2-yl]methyl}amine Treatment of 1.3 g of fraction 2 obtained from the chiral HPLC separation of (±)-benzyl {[7-(2,6-dichlorophenyl)-5-fluoro-2,3-dihydro-1-benzofuran-2-yl]methyl}carbamate trimethylsilyl iodide (2.33 g, 11.6 mmol) generally according to the procedure described for Example 158 gave 0.78 g (77%) of (+)-{[7-(2,6-dichlorophenyl)-5-fluoro-2,3-dihydro-1-benzofuran-2-yl]methyl}amine as a white solid, hydrochloride salt. $[\alpha]_D^{25}$=16.46 (c 10.0 in methanol); mp 217-220° C.

EXAMPLE 552

(±)-{2-[6-chloro-7-(2-chlorophenyl)-2,3-dihydro-1 benzofuran-2-yl]ethyl}amine

To a solution of (±)-[6-chloro-7-(2-chlorophenyl)-2,3-dihydro-1-benzofuran-2-yl]methanol (0.5 g, 1.69 mmol) in toluene (10 mL) was added triphenylphosphine (0.66 g, 2.54 mmol), diethyl azodicarboxylate (0.44 g, 2.54 mmol), and 2-hydroxy-2-methylpropanenitrile (0.21 g, 2.53 mmol) and the reaction mixture was allowed to stir at room temperature for 48 h. The solvent was removed in vacuo to provide a crude oil. Purification by flash column chromatography (silica, ethyl acetate:hexanes 1:9-3:7) provided 0.22 g (43%) of (±)-{2-[6-chloro-7-(2-chlorophenyl)-2,3-dihydro-1-benzofuran-2-yl]propanenitrile. To a solution of the nitrile in tetrahydrofuran (10 mL) was added borane-tetrahydrofuran (8 mL) and the reaction mixture was heated to reflux for 3 h. The reaction mixture was quenched with 1.0 N aqueous hydrogen chloride (100 mL) and then neutralized with 1.0 N aqueous sodium hydroxide (100 mL). The aqueous layer was extracted with ethyl acetate (2×200 mL) and the combined organic extracts were washed with saturated aqueous sodium chloride (100 mL), dried (magnesium sulfate) and the solvent removed in vacuo. Purification by flash column chromatography (silica, 10% ammonium hydroxide in methanol:dichloromethane 1:9) provided 0.1 g (19%) of (±)-{2-[6-chloro-7-(2-chlorophenyl)-2,3-dihydro-1-benzofuran-2-yl]ethyl}amine as a white solid, hydrochloride salt. mp 211-213° C.

EXAMPLE 553

(±)-{2-[7-(2,6-dichlorophenyl)-5-fluoro-2,3-dihydro-1-benzofuran-2-yl]ethyl}amine Treatment of (±)-[7-(2,6-dichlorophenyl)-5-fluoro-2,3-dihydro-1-benzofuran-2-yl]methanol (0.5 g, 1.9 mmol) with triphenylphosphine (1.23 g, 4.67 mmol), diethyl azodicarboxylate (0.82 g, 4.68 mmol), and 2-hydroxy-2-methylpropanenitrile (0.40 g, 4.68 mmol) generally according to the procedure described for Example 552 afforded 0.106 g (15%) of (±)-{2-[7-(2,6-dichlorophenyl)-5-fluoro-2,3-dihydro-1-benzofuran-2-yl]ethyl}amine as a white solid, hydrochloride salt. mp 212-213° C.

EXAMPLE 554

(±)-{2-[7-(2-methoxyphenyl)-5-methoxy-2,3-dihydro-1-benzofuran-2-yl]ethyl}amine

To a solution of (±)-[5-methoxy-7-(2-methoxyphenyl)-2,3-dihydro-1-benzofuran-2-yl]methyl 4-methylbenzenesulfonate (0.25 g, 0.57 mmol) in dimethylsulfoxide (20 mL) was added sodium cyanide (0.07 g, 1.43 mmol) and the reaction mixture was allowed to stir at 50° C. for 1 h. The reaction was quenched by the addition of water (10 mL) and extracted with ethyl acetate (2×10 mL). The combined organics were washed with water (3×20 mL), saturated aqueous sodium chloride (20 mL), dried (magnesium sulfate) and the solvent was removed in vacuo to give a crude oil. Purification by flash column chromatography (silica, ethyl acetate:hexanes 2:8) gave (±)-[5-methoxy-7-(2-methoxyphenyl)-2,3-dihydro-1-benzofuran-2-yl]acetonitrile as a colorless oil. The oil was dissolved in ethanol (30 mL), 28% aqueous ammonium hydroxide (20 mL), and treated with rhodium on alumina (0.1 g, 5 wt. %) generally according to procedure described for Example 1 to afford 0.025 g (13%) of (±)-{2-[5-methoxy-7-(2-methoxyphenyl)-2,3-dihydro-1-benzofuran-2-yl]ethyl}amine as a yellow solid, hydrochloride salt. mp 240-242° C.

EXAMPLE 555

(±)-{N-methyl-1-[(7-(2,4,6-trichlorophenyl)-2,3-dihydro-1-benzofuran-2-yl]methanamine The title compound was prepared (0.424 g, 80%) following the general procedure of Example 390 as a white solid, hydrochloride salt from (±)-[7-(2,4,6-trichlorophenyl)-2,3-dihydro-1-benzofuran-2-yl]methyl 4-methylbenzenesulfonate (0.68 g, 1.4 mmol) and methylamine (3.1 g, 50.0 mmol). mp 169-172° C.

EXAMPLE 556

(+)-N-methyl-1-[(7-(2,4,6-trichlorophenyl)-2,3-dihydro-1-benzofuran-2-yl]methanamine Treatment of 1.48 g of fraction 2 obtained from the chiral HPLC separation of (±)-benzyl {[7-(2,4,6-trichlorophenyl)-2,3-dihydro-1-benzofuran-2-yl]methyl}methylcarbamate with trimethylsilyl iodide (2.48 g, 12.4 mmol) generally according to the procedure described for Example 158 provided 0.125 g (11%) of (+)-{N-methyl-1-[(7-(2,4,6-trichlorophenyl)-2,3-dihydro-1-benzofuran-2-yl]methanamine as a white solid, hydrochloride salt. $[\alpha]_D^{25}$=+7.8 (c 10.0 in methanol); mp 93-98° C.

EXAMPLE 557

(−)-{N-methyl-1-[(7-(2,4,6-trichlorophenyl)-2,3-dihydro-1-benzofuran-2-yl]methanamine Treatment of 1.41 g of fraction 1 obtained from the chiral HPLC separation of (±)-benzyl {[7-(2,4,6-trichlorophenyl)-2,3-dihydro-1-benzofuran-2-yl]methyl}methylcarbamate with trimethylsilyl iodide (2.36 g, 11.8 mmol) generally according to the procedure described for Example 158 gave 0.17 g (15%) of (−)-{N-methyl-1-[(7-(2,4,6-trichlorophenyl)-2,3-dihydro-1-benzofuran-2-yl]methanamine as a white solid, hydrochloride salt. $[\alpha]_D^{25}$=−6.2 (c 10.0 in methanol); mp 93-98° C.

EXAMPLE 558

(+)-{[7-(2,6-dimethylphenyl)-5-fluoro-2,3-dihydro-1-benzofuran-2-yl]methyl}methylamine The title compound was prepared (0.147 g, 65%) following the general procedure of Example 390 as a white solid, hydrochloride salt from (+)-[7-(2,6-dimethylphenyl)-5-fluoro-2,3-dihydro-1-benzofuran-2-yl]methyl 4-methylbenzenesulfonate (0.50 g, 1.2 mmol) and methylamine (0.372 g, 12.0 mmol). $[\alpha]_D^{25}$=+1.6 (c 10.0 in methanol); mp 169-170° C.

EXAMPLE 559

(−)-{[7-(2,6-dimethylphenyl)-5-fluoro-2,3-dihydro-1-benzofuran-2-yl]methyl}methylamine The title compound was prepared (0.298 g, 79%) following the general procedure of Example 390 as a white solid, hydrochloride salt from (−)-[7-(2,6-dimethylphenyl)-5-fluoro-2,3-dihydro-1-benzofuran-2-yl]methyl 4-methylbenzenesulfonate (0.50 g, 1.2 mmol) and methylamine (0.372 g, 12.0 mmol). $[\alpha]_D^{25}$=−3.0 (c 10.0 in methanol); mp 171-173° C.

EXAMPLE 560

(−)-{[7-(2,6-dimethylphenyl)-5-methoxy-2,3-dihydro-1-benzofuran-2-yl]methyl}methylamine Treatment of 0.56 g of fraction 1 obtained from the chiral HPLC separation of (±)-benzyl {[7-(2,6-dimethylphenyl)-5-methoxy-2,3-dihydro-1-benzofuran-2-yl]methyl}methylcarbamate with palladium on carbon (0.1 g, 10 wt. %) generally according to the procedure described for Example 1 gave 0.323 g (74%) of (−)-{[7-(2,6-dimethylphenyl)-5-methoxy-2,3-dihydro-1-benzofuran-2-yl]methyl}methylamine as a white solid, hydrochloride salt. $[\alpha]_D^{25}$=−5.9 (c 10.0 in methanol); mp 158-160° C.

EXAMPLE 561

(+)-{[7-(2,6-dimethylphenyl)-5-methoxy-2,3-dihydro-1-benzofuran-2-yl]methyl}methylamine Treatment of 0.55 g of fraction 2 obtained from the chiral HPLC separation of (±)-benzyl {[7-(2,6-dimethylphenyl)-5-methoxy-2,3-dihydro-1-benzofuran-2-yl]methyl}methylcarbamate with palladium on carbon (0.1 g, 10 wt. %) generally according to the procedure described for Example 1 gave 0.225 g (53%) of (+) {[7-(2,6-dimethylphenyl)-5-methoxy-2,3-dihydro-1-benzofuran-2-yl]methyl}methylamine as a white solid, hydrochloride salt. $[\alpha]_D^{25}$=+4.51 (c 10.0 in methanol); mp 158-160° C.

EXAMPLE 562

(+)-{[5-chloro-7-(2,5-dichlorophenyl)-2,3-dihydro-1-benzofuran-2-yl]methyl}methylamine Treatment of 0.9 g of fraction 1 obtained from the chiral HPLC separation of (±)-benzyl {[7-(2,5-dichlorophenyl)-5-chloro-2,3-dihydro-1-benzofuran-2-yl]methyl}methylcarbamate with hydrogen bromide (20 mL, 30 wt. % in acetic acid) generally according to the procedure described for Example 245 gave 0.598 g (84%) of (+)-{[5-chloro-7-(2,5-dichlorophenyl)-2,3-dihydro-1-benzofuran-2-yl]methyl}methylamine as a white solid, hydrochloride salt. $[\alpha]_D^{25}=+14.27$ (c 10.0 in methanol); mp 181-183° C.

EXAMPLE 563

(−)-{[5-chloro-7-(2,5-dichlorophenyl)-2,3-dihydro-1-benzofuran-2-yl]methyl}methylamine Treatment of 0.9 g of fraction 2 obtained from the chiral HPLC separation of (±)-benzyl {[7-(2,5-dichlorophenyl)-5-chloro-2,3-dihydro-1-benzofuran-2-yl]methyl}methylcarbamate with hydrogen bromide (20 mL, 30 wt. % in acetic acid) generally according to the procedure described for Example 245 gave 0.49 g (68%) of (−)-{[5-chloro-7-(2,5-dichlorophenyl)-2,3-dihydro-1-benzofuran-2-yl]methyl}methylamine as a white solid, hydrochloride salt. $[\alpha]_D^{25}=-7.8$ (c 10.0 in methanol); mp 187-189° C.

EXAMPLE 564

(−)-{[5-chloro-7-(2,6-dimethylphenyl)-2,3-dihydro-1-benzofuran-2-yl]methyl}methylamine Treatment of 0.65 g of fraction 1 obtained from the chiral HPLC separation of (±)-benzyl {[5-chloro-7-(2,6-dimethylphenyl)-2,3-dihydro-1-benzofuran-2-yl]methyl}methylcarbamate with hydrogen bromide (15 mL, 30 wt. % in acetic acid) generally according to the procedure described for Example 245 gave 0.395 g (78%) of (−)-{[5-chloro-7-(2,6-dimethylphenyl)-2,3-dihydro-1-benzofuran-2-yl]methyl}methylamine as a white solid, hydrochloride salt. $[\alpha]_D^{25}=-8.4$ (c 10.0 in methanol); mp 229-231° C.

EXAMPLE 565

(+)-{[5-chloro-7-(2,6-dimethylphenyl)-2,3-dihydro-1-benzofuran-2-yl]methyl}methylamine Treatment of 0.65 g of fraction 2 obtained from the chiral HPLC separation of (±)-benzyl {[5-chloro-7-(2,6-dimethylphenyl)-2,3-dihydro-1-benzofuran-2-yl]methyl}methylcarbamate with hydrogen bromide (15 mL, 30 wt. % in acetic acid) generally according to the procedure described for Example 245 gave 0.37 g (74%) of (+)-{[5-chloro-7-(2,6-dimethylphenyl)-2,3-dihydro-1-benzofuran-2-yl]methyl}methylamine as a white solid, hydrochloride salt. $[\alpha]_D^{25}=+11.6$ (c 10.0 in methanol); mp 229-231° C.

EXAMPLE 566

(+)-{[7-(2,3-dimethoxyphenyl)-5-methyl-2,3-dihydro-1-benzofuran-2-yl]methyl}methylamine Treatment of 0.8 g of fraction 2 obtained from the chiral HPLC separation of (±)-benzyl {[7-(2,3-dimethoxyphenyl)-5-methyl-2,3-dihydro-1-benzofuran-2-yl]methyl}methylcarbamate with trimethylsilyl iodide (1.05 g, 5.2 mmol) generally according to the procedure described for Example 158 gave 0.16 g (28%) of (+)-{[7-(2,3-dimethoxyphenyl)-5-methyl-2,3-dihydro-1-benzofuran-2-yl]methyl}amine as a light yellow foam, hydrochloride salt. $[\alpha]_D^{25}=+38.89$ (c 10.0 in methanol).

EXAMPLE 567

(−)-{[7-(2,3-dimethoxyphenyl)-5-methyl-2,3-dihydro-1-benzofuran-2-yl]methyl}methylamine Treatment of 0.67 g of fraction 1 obtained from the chiral HPLC separation of (±)-benzyl {[7-(2,3-dimethoxyphenyl)-5-methyl-2,3-dihydro-1-benzofuran-2-yl]methyl}methylcarbamate with trimethylsilyl iodide (1.05 g, 5.2 mmol) generally according to the procedure described for Example 158 gave 0.14 g (29%) of (−)-{[7-(2,3-dimethoxyphenyl)-5-methyl-2,3-dihydro-1-benzofuran-2-yl]methyl}methylamine as a light yellow foam, hydrochloride salt. $[\alpha]_D^{25}=-38.0$ (c 10.0 in methanol).

EXAMPLE 568

(−)-{[7-(2,3-dimethoxyphenyl)-5-fluoro-2,3-dihydro-1-benzofuran-2-yl]methyl}methylamine Treatment of 0.88 g of fraction 1 obtained from the chiral HPLC separation of (±)-benzyl {[7-(2,3-dimethoxyphenyl)-5-fluoro-2,3-dihydro-1-benzofuran-2-yl]methyl}methylcarbamate with trimethylsilyl iodide (1.55 g, 7.7 mmol) generally according to the procedure described for Example 158 gave 0.37 g (54%) of (−)-{[7-(2,3-dimethoxyphenyl)-5-fluoro-2,3-dihydro-1-benzofuran-2-yl]methyl}methylamine as a light yellow foam, hydrochloride salt; $[\alpha]_D^{25}=-26.4$ (c 10.0 in methanol).

EXAMPLE 569

(+)-{[7-(2,3-dimethoxyphenyl)-5-fluoro-2,3-dihydro-1-benzofuran-2-yl]methyl}methylamine Treatment of 1.4 g of fraction 2 obtained from the chiral HPLC separation of (±)-benzyl {[7-(2,3-dimethoxyphenyl)-5-fluoro-2,3-dihydro-1-benzofuran-2-yl]methyl}methylcarbamate with trimethylsilyl iodide (2.53 g, 12.6 mmol) generally according to the procedure described for Example 158 gave 0.53 g (48%) of (+)-{[7-(2,3-dimethoxyphenyl)-5-fluoro-2,3-dihydro-1-benzofuran-2-yl]methyl}methylamine as a light yellow foam, hydrochloride salt; $[\alpha]_D^{25}=25.2$ (c 10.0 in methanol).

EXAMPLE 570

Alternative synthesis of 2R-(−)-7-(2,6-dichlorophenyl)-5-fluoro-2,3-dihydro-2-aminomethylbenzofuran hydrochloride

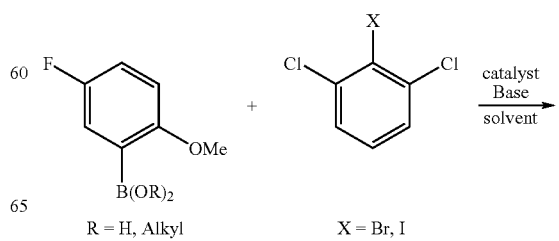

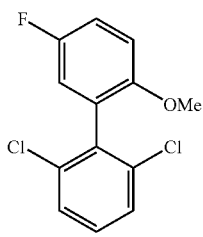

To a solution of NaOH (54 g, 1.35 mol) in water (400 mL) heated to 60° C. was added dimethoxyethane (400 mL), then dichlorobromobenzene (Aldrich, 60 g, 0.267 mol) and boronic acid (50 g, 0.294 mol). To the resulting stirred emulsion, solid $Pd(PPh_3)_4$ (9.5 g, 8.2 mmol) was added and washed down with 100 mL of DME. The greenish mixture was heated at reflux (ca. 80° C.) while stirred mechanically. The course of reaction was monitored by HPLC. After 2 hr, 9.0 g (0.053 mol) of additional boronic acid and 2.0 g (1.7 mmol) of the catalyst were added to the reaction mixture and the heating was continued for 16 hr longer. More boronic acid (5.8 g, 0.034 mol) and the catalyst (0.5 g, 0.4 mmol) were added at that point and the mixture was kept at reflux for 7 hr longer (23 hr was total reaction time).

The heating was stopped and 600 mL of heptane and 300 mL of water were added. The mixture was allowed to cool to room temperature and then was filtered through Celite. The layers were separated, the organic layer was washed with water, three times with brine, dried with $MgSO_4$ and filtered through a pad of Magnesol. The clear colorless solution was concentrated on a rotary evaporator to a colorless oil (weight 72 g). The oil was triturated with 120 mL of heptane which caused crystallization of a white solid. The mixture was left in a refrigerator overnight, the separated crystals were filtered and dried in air. Yield 51 g, 93% pure. The major impurity was determined to be the homo-coupling product 13. Additional recrystallization of the material from heptane gave crystals of 98% purity. Yield 45 g (62%) as white crystals.

1-Methoxy-2-bromo-4-fluoro-2',6'-dichlorobiphenyl

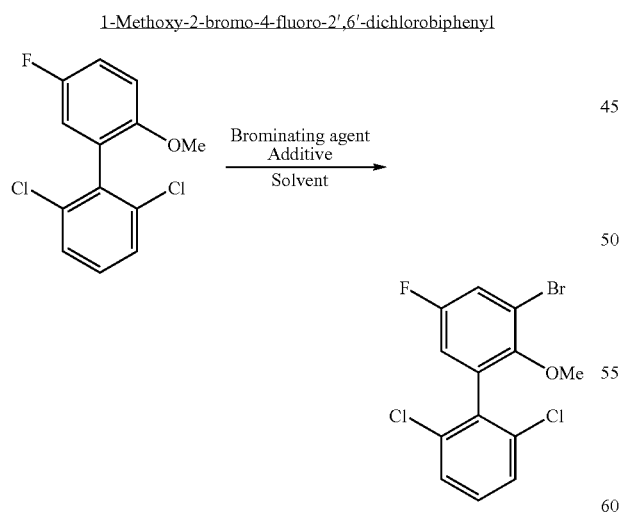

To a magnetically stirred solution of the arene (38.0 g, 0.140 mol) in 190 mL of dioxane placed into a 500-mL round-bottom flask equipped with a temperature probe, cone, sulfuric acid (38 mL) was added slowly (exothermic mixing, temperature rose to 37° C., the solution turned yellow). To the warm solution (the arene would crystallize out of the mixture if it was allowed to cool down), solid NBS (26.7 g, 0.150 mol) was added in one portion (no exothermic heating was observed here). The resulting solution was heated in a mantle at 50° C. The reaction progress monitored by HPLC. After 18 hr, only trace amount of the starting arene was detected.

The reaction mixture was allowed to cool to room temperature (r.t.), then it was poured onto 400 g of ice (could use lesser amount as it did not melt completely). Heptane (100 mL) was added and the mixture was transferred to the separatory funnel. The aqueous layer was separated and extracted with additional portions of heptane (2×100 mL) (toluene could be used instead of heptane as the product started to crystallize; toluene was added to the organic solution to get the product back into the solution). Combined organic solutions were washed once with water (30 mL), then aq. $Na_2S_2O_3$ solution (to remove unreacted NBS, reaction with KI-starch indicator paper), and, finally, with 1 M aq. NaOH solution (2×30 mL) (upon NaOH treatment the mixture turned from yellow to dark-brown but all the color went into the aqueous phase). Light-yellow clear organic solution was dried with $MgSO_4$, filtered through a cotton plug and evaporated in vacuum (bath temp. 60° C.). The resulting yellow oil was re-dissolved in 55 mL of heptane.

The first batch of crystals (25.5 g) slowly separated from the heptane solution at r.t. and was filtered and dried in air. Purity 98% (HPLC @ 215 nm), white crystals. M.p. 67-69° C.

The second batch of the product (13.9 g) was isolated from the mother liquor by chilling it in a dry-ice-acetone bath, filtering off the precipitated solid and drying it in a vacuum desiccator over $CaSO_4$. Purity 97% (HPLC area % at 215 nm), white amorphous powder. M.p. 47-56° C.

Total yield 39.4 g (80%). $^1H$ NMR (300 MHz, $CDCl_3$) δ: 7.42 (m, J=8.1 Hz, 2H)[10], 7.39 (dd, J=3.0, 7.7 Hz, 1H), 7.30 (dd, J=8.1 Hz, 1H), 6.86 (dd, J=3.0, 8.0 Hz, 1H), 3.56 (s, 3H). Protons at 7.42 and 7.30 ppm form a second-order A2B spin system with JAB=8.1 Hz (determined by NMR simulation). EI MS, m/z.

2-[5-Fluoro-3-(2,6-dichlorophenyl)-2-methoxybenzyl]oxirane

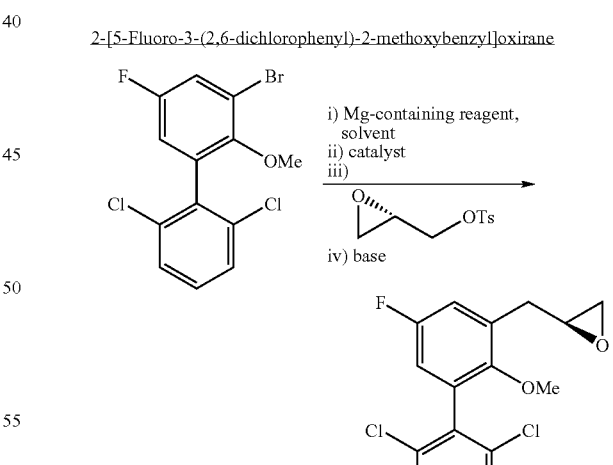

Generation of the Grignard reagent. Aryl bromide (25.0 g, 71.4 mmol) was placed into a 500-mL flask equipped with a magnetic stirrer, nitrogen inlet, temperature probe and a rubber septum. The flask was purged excessively with nitrogen, then left under positive nitrogen pressure. Dry THF (100 mL) was transferred into the flask via a syringe. The solution was chilled in an ice bath to 2° C.

A solution of i-PrMgCl in ThF (1.9 M, Aldrich, 39.5 mL, 75 mmol) was added slowly to the solution in the flask via a syringe (20 min addition time, the temperature was maintained between 2 and 6° C.). The resulting yellowish solution was left in the bath for 18 hr allowing it to reach room temperature. (The reaction is monitored by HPLC analysis of an aliquote quenched by water. Care should be taken not to introduce oxygen into the reaction flask while sampling the solution.)

Reaction with glycidyl tosylate. The solution of the Grignard reagent was chilled to −30° C. by placing the flask in a bath with partially frozen dichloroethane (M.p. −45° C.). CuCN (0.45 g, 5.0 mmol, 7 mol %; Aldrich) was added to the flask via syringe as a slurry in dry THF. The resulting mixture was stirred for 1 hr at −30° C., then (S)-(+)-glycidyl tosylate (15.5 g, 68 mmol, Aldrich) dissolved in 10 mL of dry THF was added to the solution (addition time 30 min, reaction mixture temperature was maintained between −22 and −29° C.). The reaction was left stirring at −31° C. for 2 hr, then the DCE bath was replaced with a partially frozen o-xylene bath (o-xylene M.p. −25° C.). Over the next 3 hr the temperature was allowed to reach −18° C. HPLC analysis of the quenched aliquot showed complete disappearance of glycidyl tosylate.

To the cold reaction mixture, 100 mL of aq. $NH_4Cl$ solution (prepared by 1:1 dilution of the saturated solution with water) was added. The phases were separated. The aqueous layer was extracted with 50 mL of NTBE. Combined organic solutions were washed with 30 mL of brine.

Closure of the epoxide. To the solution of the intermediate hydroxytosylate was added aq. solution of NaOH prepared by mixing 20 mL of 10 M stock solution (200 mmol) with 30 mL of water. The resulting bi-phasic mixture was stirred rapidly with a magnetic stirrer so that the mixture was broken into fine emulsion. After 18 hr at room temp, (checked by HPLC) the mixture was transferred to a separatory funnel and the phases were separated. The aqueous phase was extracted with 100 mL of MTBE, combined organic solutions were washed with brine and dried with $MgSO_4$. After filtration through a paper filter, light-yellow solution was evaporated in vacuum to give a mixture the epoxide and des-bromo-arene as a light-yellow oil which solidified upon cooling to room temp. Weight 23.06 g. The mixture was used in the subsequent step without purification.

The epoxide (22.6 g of the crude mixture from the previous step, ca. 67 mmol), phthalimide (10.3 g, 70 mmol) and its potassium salt (12.9 g, 70 mmol) were placed in a 250 round-bottom flask equipped with a magnetic stirrer, a nitrogen inlet, and a temperature probe. Dry DMF (100 mL) was added to the mixture. The reaction flask was briefly purged with nitrogen and then was being heated at 75° C. with stirring for 20 hr (the progress was monitored by HPLC). Once no starting epoxide was detected, the mixture was allowed to cool to room temp, and then mixed with 200 mL of ice-water slush. The product was extracted with MTBE (2×100 mL). The organic solution was washed with solution prepared from 2 parts of 1 M aq. NaOH, 3 parts brine, and 5 parts water (2×100 mL), then with brine until neutral pH (Note: The product may start crystallizing during the extractions and washes. In that case it was brought back into solution by adding THF to the mixture). The resulting organic solution was dried with $MgSO_4$, filtered through a paper filter and evaporated in vacuum. The product started to crystallize during the evaporation. The volume of the solvent was reduced to ca. 40 mL, then the residue was triturated with 200 mL of hexanes. The white solid was filtered, washed with hexanes and dried in air.

Yield 23.25 g (74% over 3 steps, based on the amount of glycidyl tosylate). M.p. 165-168° C. $^1$H NMR (300 MHz, $CDCl_3$) δ: 7.86 (m, 2H), 7.72 (m, 2H), 7.43 (m, 1H), 7.41 (m, 1H), 7.27 (m, 1H), 7.08 (dd, J=3.0, 8.8 Hz, 1H), 6.79 (dd, J=3.0 Hz, 8.1 Hz, 1H), 4.23 (d$^5$, J=3.3, 4.3, 5.7, 7.9, 8.5 Hz, 1H), 3.85 (dd, J=3.3, 14.1 Hz, 1H), 3.80 (dd, J=8.5, 14.1 Hz, 1H), 3.42 (s, 3H), 2.96 (dd, J=4.3, 13.9 Hz, 1H), 2.92 (dd, J=7.9, 13.9 Hz, 1H), 2.80 (d, J=5.7 Hz, 1H). ES MS, m/z: 474 (M+H)$^+$, $Cl_2$ isotope pattern. Analytical purity: 97% (HPLC area % at 215 nm).

2S-3-[5-Fluoro-3-(2,6-dichlorophenyl)-2-methoxyphenyl]-1-N-phthalimidopropan-2-ylmethanesulfonate

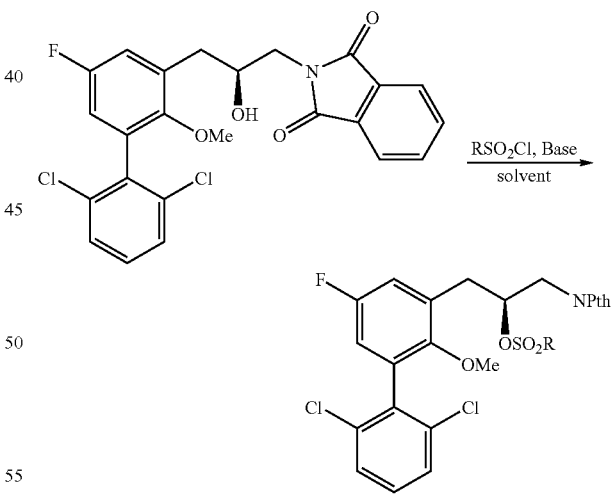

2S-3-[5-Fluoro-3-(2,6-dichlorophenyl)-2-methoxyphenyl]-1-N-phthalimidopropan-2-ol

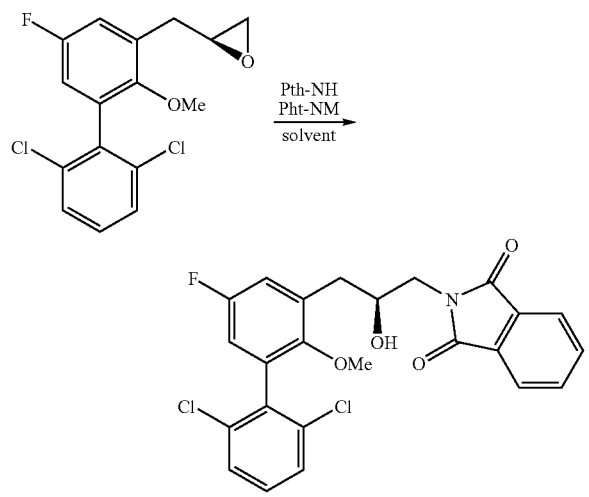

In a 500 mL Erlenmeyer flask equipped with a magnetic stirrer, temperature probe and an addition funnel (suspended over the flask without attaching) was placed the product of the preceding step, 2S-3-[5-Fluoro-3-(2,6-dichlorophenyl)-2-methoxyphenyl]-1-N-phthalimidopropan-2-ol, (22.0 g, 46.4 mmol), $CH_2Cl_2$ (200 mL) and triethylamine (9.7 mL, 70 mmol). Into the addition funnel was placed $CH_2Cl_2$ (20 mL) and methanesulfonyl chloride (5.4 mL, 70 mL). The solution of MsCl was added dropwise (addition time 10 min) to the stirred solution in the flask (exothermic reaction, temp, rose to 32° C. by the end of addition). The reaction mixture was allowed to stir at room temp, for 2 hr (checked by HPLC). White solid separated from the solution over that time.

Water (100 mL) was added to the reaction mixture while stirring it rapidly. About 120 mL of DCM was distilled off on a rotary evaporator. The residue was triturated with 200 mL of hexanes. The solid was filtered and washed excessively with water and hexanes. The cake was dried on the filter for 1 hr then overnight in a vacuum desiccator oven.

Yield 25.2 g (98%) as a white fluffy crystals. M.p. >200° C. (decomp.) $^1$H NMR (300 MHz, CDCl$_3$) δ: 7.86 (m, 2H), 7.72 (m, 2H), 7.43 (m, 2H), 7.29 (m, 1H), 7.09 (dd, J=3.1, 8.5 Hz, 1H), 6.82 (dd, J=3.1, 8.3 Hz, 1H), 5.28 (m, 1H), 4.09 (dd, J=8.6, 14.6 Hz, 1H), 3.90 (dd, J=3.3, 14.6 Hz, 1H), 3.45 (s, 3H), 3.18 (dd, J=5.4, 14.0 Hz, 1H), 3.09 (dd, J=7.8, 14.0 Hz, 1H), 2.65 (s, 3H). $^{13}$C NMR (100 MHz, dmso-J$_6$) δ: 167.6, 157.6 (d, J=242 Hz), 152.4 (d, J=2 Hz), 134.8, 134.4, 134.3 (d, J=16 Hz), 131.6, 131.4 (d, J=20 Hz), 131.4, 130.8, 128.3, 123.1, 118.7 (d, J=22 Hz), 116.7 (d, J=24 Hz), 78.5, 60.5, 40.8, 37.6, 33.2. ES MS, m/z: 552 (M+H)$^+$, Cl$_2$ isotope pattern. Analytical purity 99.6% (HPLC area % at 215 nm).

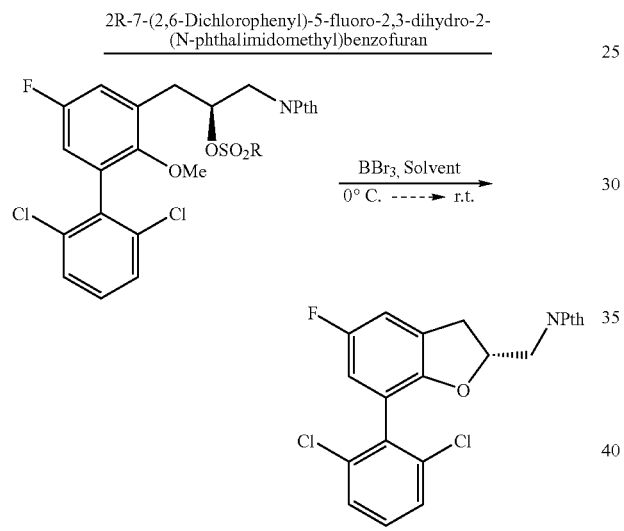

The product of the preceding step, 2S-3-[5-Fluoro-3-(2,6-dichlorophenyl)-2-methoxyphenyl]-1-N-phthalimidopropan-2-yl methanesulfonate, (22.1 g, 40.0 mmol) and dichloromethane (200 mL) were placed into a 500-mL flask equipped with a magnetic stirrer, a temperature probe, a nitrogen inlet and a 50-mL addition runnel. The flask and the addition runnel were purged briefly with nitrogen (Oust in case). The slurry in the flask was chilled in an ice bath to 4° C. A 1M solution of BBr$_3$ in CH$_2$Cl$_2$ (Aldrich, 42 mL, 42 mmol) was placed into the addition runnel and was added dropwise to the stirred contents of the flask (addition time 12 min, temp, drifted from 4 to 10° C.). The stirring was continued allowing the temperature of the reaction mixture to reach 16° C. over 2-hr period and then at room temp (19° C.) for 3 hr longer. The reaction progress was monitored by HPLC (1% of unreacted starting material remained, area % at 215 nm). 1M The reaction mixture was quenched by slowly pouring it into the solution prepared from NaHCO$_3$ (11 g, 131 mmol) and 200 mL of water (the reaction went fairly slow, no exotherm was observed, no excessive foaming either). Precipitate formed initially in the organic layer but dissolved after ca. 20 min of rapid stirring. After 30 min of stirring, the layers were separated. Aqueous layer was extracted with dichloromethane (2×50 mL). Combined organic solutions were washed with 100 mL of water, then dried with MgSO$_4$ The drying agent was filtered off and washed with ethyl acetate. The volume of the filtrate was reduced to about 50 mL on rotary evaporator. The product separated as white or light-yellow solid. The slurry was triturated with 40 mL of a 50:50 hexanes-MTBE mixture, the solid was filtered, washed with the above mixture of solvents and dried on the filter.

Yield 14.4 g (82%) as a light-yellow solid. M.p. 222.5-224.5° C. $^1$H NMR (400 MHz, dmso-J$_6$) δ: 7.85 (m, 4H), 7.53 (m, 2H), 7.41 (m, 1H), 7.19 (dd, J=2.7, 8.2 Hz, 1H), 6.86 (dd, J=2.7, 9.3 Hz, 1H), 5.09 (m, 1H), 3.79 (m, 2H), 3.43 (dd, J=9.3, 16.6 Hz, 1H), 3.15 (dd, J=5.9, 16.6 Hz, 1H). $^{13}$C NMR (100 MHz, dmso-4) δ: 167.8, 156.4 (d, 3=237 Hz), 152.2, 134.5, 134.4 (d, J=30 Hz), 133.5, 131.5, 130.6, 128.6 (d, J=9.4 Hz), 128.1 (d, J=3.6 Hz), 123.1, 118.2, 118.1, 114.9 (d, J=9.3 Hz), 112.9 (d, J=25 Hz), 80.0, 41.1, 33.2. ES MS, m/z: 442 MH$^+$, Cl$_2$ isotope pattern. Analytical purity: 99.9% (HPLC area % at 215 nm).

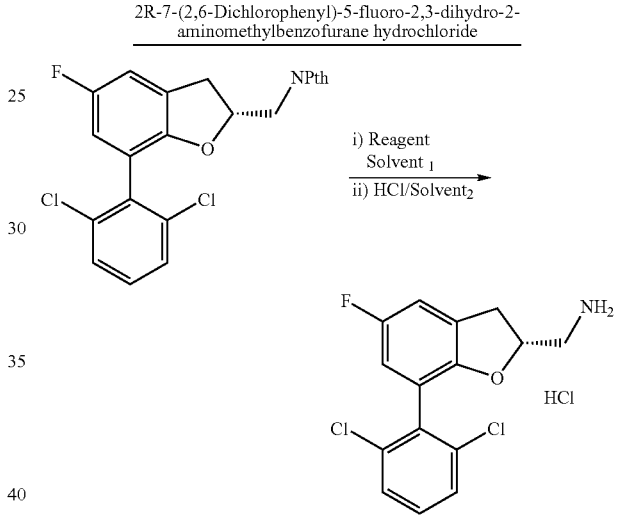

The product of the preceding step, 2R-7-(2,6-Dichlorophenyl)-5-fluoro-2,3-dihydro-2-(N-phthalimidomethyl)benzofuran, (12.9 g, 29.2 mmol) was mixed with 70 mL of isopropanol and 15 mL of water. Hydrazine hydrate (55% hydrazine content, Aldrich, 5 mL, 90 mmol) was then added and the reaction mixture was magnetically stirred and heated at gentle reflux for 2 hr. (In case by-product phthalyl hydrazide crystallizes out and gets in a way of stirring it is re-dissolved by adding 3:1 mixture of isopropanol-water. It is very little soluble in isopropanol alone.) Dissolution of the staring material and formation of a clear solution was an indication that the reaction is done. It was confirmed by HPLC analysis before working up the reaction mixture.

To the hot solution was added 40 mL of 1 M aqueous NaOH and 100 mL of water. The product was extracted with MTBE (3×50 mL). Combined extracts were washed with 60 mL of 0.2 M aq. NaOH, then with water (2×50 mL) and finally with brine (50 mL). Resulting clear solution was dried over Na$_2$SO$_4$ for 1 hr, filtered through a paper filter and evaporated in vacuum to afford a light-yellow oil (it was slightly opalescent).

The oil was dissolved in 50 mL of EtOAc and to the solution was added rapidly 2 M solution of HCl in diethyl ether (Aldrich, 15 mL, 30 mmol). The salt precipitated rapidly (exothermic) and froze in a single chunk. It was broken up by shaking it with 100 mL of ether, then the slurry was stirred for 30 min in an ice bath. The salt was filtered, washed with 100 mL of ether, dried first on the filter in the stream of air until the filter reached room temp, and then overnight in a vacuum desiccator over $CaSO_4$.

Yield 9.4 g (92%) as white crystals. M.p. 231-233° C. $^1$H NMR (400 MHz, dmso-d$^6$) δ: 8.25 (broad s, 3H), 7.57 (m, J=8.1 Hz, 2H), 7.45 (dd, J=8.1 Hz, 1H), 7.24 (dd, J=2.6, 8.1 Hz, 1H), 6.90 (dd, J=2.6, 9.6 Hz, 1H), 5.05 (d$^4$, J=9.2, 7.9, 7.0, 4.5 Hz, 1H), 3.45 (dd, J=9.2, 16.6 Hz, 1H), 3.17 (dd, J=7.0, 16.6 Hz), 3.10 (dd, J=13.4, 4.5 Hz, 1H), 3.04 (dd, J=13.4, 7.9 Hz, 1H). Protons at 7.57 and 7.45 ppm form a second-order $A_2B$ spin system with $J_{AB}$=8.1 Hz (determined by NMR simulation). $^{13}$C NMR (400 MHz, dmso-J$_6$) δ: 156.4 (d, J=257 Hz), 151.9, 134.5, 134.2, 133.5, 130.5, 128.7 (d, J=11 Hz), 128.2 (d, J=21 Hz), 118.3 (d, J=9 Hz), 115.0 (d, J=25 Hz), 112.9 (d, J=25 Hz), 80.0,42.1,32.8. ES MS, m/z: 312 (M+H), $Cl_2$ isotope pattern. Enantiomeric purity: 99.4% ee (chiral HPLC on Chiracel OD-H 0.46×25 cm, 1 ml/min 90% heptane/DIEA, 10% ethanol, area % at 280 nm). Analytical purity: 99.8% (HPLC on Prodigy ODS3 0.46×15 cm, 1 ml/min water/TFA-MeCN/TFA 100 min gradient 0-100%, area % at 215 nm). Seventeen impurities in the range of 0.003-0.06 area % were detected totaling 0.19%. For $C_{15}H_{13}Cl_3FNO$ found C, 51.59%, H, 3.81%, N, 3.87%, anionic Cl, 10.49%; calc'd C, 51.68%, H, 3.76%, N, 4.02%, anionic Cl, 10.17%.

EXAMPLE 571

Determination of Binding Affinity and Agonist Activity of Compounds of Formula 1

The ability of the compounds of this invention to act as $5HT_{2C}$ agonists and partial agonists was established using several standard pharmacological test procedures; the procedures used and results obtained are provided below. In the test procedures, 5-HT stands for 5-hydroxytryptamine, mCPP stands for meta-chlorophenylpiperazine, and DOI stands for 1-(2,5-dimethoxy-4-iodophenyl)isopropylamine.

To evaluate the affinity of various compounds of Formula 1 for activity at the $5-HT_{2C}$ receptor, a CHO (Chinese Hamster Ovary) cell line transfected with the cDNA expressing the human 5-hydroxytryptamine-2C (h5-$HT_{2C}$) receptor was maintained in DMEM (Dulbecco's Modified Eagle Media) supplied with fetal calf serum, glutamine, and the markers: guaninephosphoribosyl transferase (GTP) and hypoxanthin-ethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10-25 µL volumes. Bovine Serum Albumin (BSA) was used as the standard in the protein determination by the method of Lowry et al., (J. Biol. Chem., 193:265 (1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1-2 mg per ml of suspension. The preparation membrane suspension (many times concentrated) was aliquoted in 1 ml volumes and stored at −70 C until used in subsequent binding experiments.

Binding measurements were performed in a 96 well microtiter plate format, in a total volume of 200 µL. To each well was added: 60 µL of incubation buffer made in 50 mM Tris.HCl buffer, pH 7.4 and containing 4 mM $CaCl_2$; 20 µL of [$^{125}$I] DOI (S.A., 2200 Ci/mmol, NEN Life Science).

The dissociation constant, KD of [$^{125}$I] DOI at the human serotonin 5-$HT_{2C}$ receptor was 0.4 nM by saturation binding with increasing concentrations of [$^{125}$I] DOI. The reaction was initiated by the final addition of 100 µL of tissue suspension containing 50 µg of receptor protein. Nonspecific binding is measured in the presence of 1 µM unlabeled DOI added in 20.0 µL volume. Test compounds were added in 20.0 µL. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 µL Microscint-20 scintillant in a Packard TopCount® equipped with six (6) photomultiplier detectors.

Specific binding is defined as the total radioactivity bound less the amount bound in the presence of 1 µM unlabeled DOI. Binding in the presence of varying concentrations of test drugs is expressed as percent of specific binding in the absence of drug. These results are then plotted as log % bound vs log concentration of test drug. Non linear regression analysis of data points yields both the $IC_{50}$ and the $K_i$ values of test compounds with 95% confidence limits. Alternatively, a linear regression line of decline of data points is plotted, from which the $IC_{50}$ value can be read off the curve and the $K_i$ value determined by solving the following equation:

$$K_i = \frac{IC_{50}}{1 + L/K_D}$$

where L is the concentration of the radioactive ligand used and the $K_D$ is the dissociation constant of the ligand for the receptor, both expressed in nM.

The following $K_i$'s (95% confidence interval) are provided for various reference compounds:

| Compound | $K_i$ |
|---|---|
| Ritanserin | 2.0 (1.3-3.1) nM |
| Ketanserin | 94.8 (70.7-127.0) nM |
| Mianserin | 2.7 (1.9-3.8) nM |
| Clozapine | 23.2 (16.0-34.0) nM |
| Methiothepin | 4.6 (4.0-6.0) nM |
| Methysergide | 6.3 (4.6-8.6) nM |
| Loxapine | 33.0 (24.0-47.0) nM |
| mCPP | 6.5 (4.8-9.0) nM |
| DOI | 6.2 (4.9-8.0) nM |

The ability of the compounds of Formula 1 to produce an agonist response at brain 5-$HT_{2C}$ was assessed by determining their effect on calcium mobilization using the following procedure: CHO cells stably expressing the human 5-$HT_{2C}$ receptor were cultured in Dulbecco's modified Eagle's medium (DMEM) supplemented with 10% fetal bovine serum and non-essential amino acids. Cells were plated at a density of 40K cells/well in 96-well clear-bottom black-wall plates 24 hours prior to the evaluation of 5-HT$_{2C}$ receptor-stimulated calcium mobilization. For calcium studies, cells were loaded with the calcium indicator dye Fluo-3-AM in Hank's buffered saline (FBS) for 60 minutes at 37° C. Cells were washed with BBS at room temperature and transferred to the fluorometric imaging plate reader (FLIPR, Molecular Devices, Sunnyvale, Calif.) for acquisition of calcium images. Excitation at 488 nm was achieved with an Argon ion laser and a 510-560 nm emission filter was used. Fluorescence images and relative intensities were captured at 1 second intervals and cells were stimulated by addition of agonist after 10 baseline measurements using the internal fluidics module of the FLIPR. An increase in fluorescence counts corresponds to an increase in intracellular calcium.

For the evaluation of agonist pharmacology the calcium changes in response to different concentrations of agonist were determined using a maximum minus minimum calculation of the raw fluorescence count data. Calcium changes were then expressed as a percentage of the response observed with a maximally effective concentration of 5-HT. $EC_{50}$ values were estimated by non-linear regression analysis of the log-concentration % maximum 5-HT response curves using the 4-parameter logistic function. Preferred compounds are those with an $EC_{50}$ of ≦about 1000 nM, preferably ≦about 100 nM, more preferably ≦about 20 nM, still more preferably ≦about 5 nM, and most preferably ≦about 2 nM.

The following $EC_{50}$'s are provided for various reference compounds:

| Compound | $EC_{50}$ |
|---|---|
| 5-HT | 0.5 nM |
| DOI | 0.5 nM |
| mCPP | 5.4 nM |

The results of the standard experimental test procedures described in the preceding paragraphs were as follows:

| | 5-HT$_{2C}$ Affinity | 5-HT$_{2C}$ Function | |
|---|---|---|---|
| Compound | $K_i$ (nM) | $EC_{50}$ (nM) | Emax (%) |
| Example 1 | 43 | 926 | 90 |
| Example 2 | 16 | 61 | 90 |
| Example 3 | 204 | | |
| Example 4 | 26 | 562 | 100 |
| Example 5 | 9 | 208 | 90 |
| Example 6 | 84 | | |
| Example 7 | 160 | | |
| Example 8 | 9 | 188 | 85 |
| Example 9 | 10 | 194 | 85 |
| Example 10 | 42 | 179 | 60 |
| Example 11 | 106 | | |
| Example 12 | 127 | | |
| Example 13 | 133 | | |
| Example 14 | 78 | | |
| Example 15 | 222 | | |
| Example 16 | 274 | 451 | 65 |
| Example 17 | 66 | 100 | 70 |
| Example 18 | 5 | 9.6 | 100 |
| Example 19 | 2 | 66 | 100 |
| Example 20 | 24 | 178 | 70 |
| Example 21 | 9 | 86 | 85 |
| Example 22 | 5 | 25 | 90 |
| Example 23 | 9 | 73 | 80 |
| Example 24 | 36 | | |
| Example 25 | 18 | 10 | 90 |
| Example 26 | 71 | 79 | 100 |
| Example 27 | 39 | 2015 | 80 |

-continued

| | 5-HT$_{2C}$ Affinity | 5-HT$_{2C}$ Function | |
|---|---|---|---|
| Compound | $K_i$ (nM) | $EC_{50}$ (nM) | Emax (%) |
| Example 28 | 16 | 77 | 90 |
| Example 29 | 35 | 229 | 80 |
| Example 30 | 191 | | |
| Example 31 | 1372 | | |
| Example 32 | 419 | | |
| Example 33 | 32 | | |
| Example 34 | 37 | | |
| Example 35 | 141 | | |
| Example 36 | 15 | | |
| Example 37 | 1 | 1 | 100 |
| Example 38 | 56 | 540 | 100 |
| Example 39 | 43 | | |
| Example 40 | 122 | | |
| Example 41 | 25 | | |
| Example 42 | 17 | 162 | 100 |
| Example 43 | 100 | 748 | 80 |
| Example 44 | 3 | 7 | 100 |
| Example 45 | 2 | 5 | 90 |
| Example 46 | 54 | | |
| Example 47 | 0.4 | 5.4 | 100 |
| Example 48 | 0.3 | 2.4 | 100 |
| Example 49 | 10 | 132 | 80 |
| Example 50 | 1 | 14 | 100 |
| Example 51 | 1 | | |
| Example 52 | 13 | | |
| Example 53 | 1 | 45 | 80 |
| Example 54 | 0.5 | 9 | 85 |
| Example 55 | 3 | 48 | 70 |
| Example 56 | 1 | 60 | 100 |
| Example 57 | 1 | 12 | 80 |
| Example 58 | 9 | 313 | 60 |
| Example 59 | 2 | 127 | 100 |
| Example 60 | 0.3 | 12 | 100 |
| Example 61 | 37 | 1092 | 30 |
| Example 62 | 40 | 130 | 70 |
| Example 63 | 52 | | |
| Example 64 | 13 | 70 | 100 |
| Example 65 | 11 | 187 | 100 |
| Example 66 | 5 | 250 | 100 |
| Example 67 | 83 | 5763 | 70 |
| Example 68 | 5 | 144 | 90 |
| Example 69 | 96 | | |
| Example 70 | 2 | 22 | 100 |
| Example 71 | 1 | 1.4 | 100 |
| Example 72 | 33 | 511 | 85 |
| Example 73 | 5 | 41 | 100 |
| Example 74 | 3 | 11 | 100 |
| Example 75 | 103 | | |
| Example 76 | 3 | 25 | 90 |
| Example 77 | 2 | 8 | 100 |
| Example 78 | 41 | 161 | 90 |
| Example 79 | 2 | 24 | 95 |
| Example 80 | 1 | 17 | 90 |
| Example 81 | 24 | 294 | 50 |
| Example 82 | 15 | 275 | 95 |
| Example 83 | 1 | 7.9 | 100 |
| Example 84 | 11 | | |
| Example 85 | 5 | 557 | 100 |
| Example 86 | 75 | 963 | 90 |
| Example 87 | 0.8 | 20 | 90 |
| Example 88 | 48 | | |
| Example 89 | 40 | | |
| Example 90 | 8 | | |
| Example 91 | 5 | 45 | 100 |
| Example 92 | 62 | | |
| Example 93 | 13 | 874 | 80 |
| Example 94 | 176 | | |
| Example 95 | 1 | 65 | 100 |
| Example 96 | 1 | 27 | 100 |
| Example 97 | 4 | 577 | 60 |
| Example 98 | 60 | | |
| Example 99 | 21 | 838 | 60 |
| Example 100 | 0.2 | 120 | 100 |
| Example 101 | 0.2 | 0.32 | 100 |
| Example 102 | 8 | 32 | 65 |

| Compound | 5-HT$_{2C}$ Affinity K$_i$ (nM) | 5-HT$_{2C}$ Function EC$_{50}$ (nM) | Emax (%) |
|---|---|---|---|
| Example 103 | 7 | 996 | 80 |
| Example 104 | 1 | 241 | 100 |
| Example 105 | 1 | 4 | 95 |
| Example 106 | 16 | 91 | 50 |
| Example 107 | 1 | 93 | 100 |
| Example 108 | 4 | 39 | 95 |
| Example 109 | 25 | 3220 | 40 |
| Example 110 | 9 | 1002 | 70 |
| Example 111 | 26 | | |
| Example 112 | 55 | | |
| Example 113 | 130 | | |
| Example 114 | 471 | | |
| Example 115 | 79 | | |
| Example 116 | 527 | | |
| Example 117 | 263 | | |
| Example 118 | 319 | | |
| Example 119 | 78 | | |
| Example 120 | 128 | | |
| Example 121 | 44 | 681 | 60 |
| Example 122 | 95 | 931 | 70 |
| Example 123 | 207 | | |
| Example 124 | 53 | | |
| Example 125 | 276 | | |
| Example 126 | 17 | 2715 | 40 |
| Example 127 | 20 | | |
| Example 128 | 41 | 24 | 70 |
| Example 129 | 0.3 | 0.2 | 100 |
| Example 130 | 4.8 | 54 | 80 |
| Example 131 | 1.5 | 34 | 90 |
| Example 132 | 20 | 1484 | 50 |
| Example 133 | 3.6 | 66 | 80 |
| Example 134 | 483 | | |
| Example 135 | 131 | | |
| Example 136 | 124 | | |
| Example 137 | 1.2 | 473 | 90 |
| Example 138 | 7.4 | 3802 | 60 |
| Example 139 | 2.5 | 6 | 90 |
| Example 140 | 0.3 | 0.72 | 90 |
| Example 141 | 0.07 | 0.03 | 90 |
| Example 142 | 1.6 | 101 | 80 |
| Example 143 | 6.3 | 1 | 90 |
| Example 144 | 6.1 | 4 | 90 |
| Example 145 | 91 | | |
| Example 146 | 2.4 | 5 | 90 |
| Example 147 | 1.3 | 7 | 90 |
| Example 148 | 12 | 290 | 70 |
| Example 149 | 0.15 | 0.97 | 100 |
| Example 150 | 4.1 | 74 | 100 |
| Example 151 | 1.1 | 27 | 100 |
| Example 152 | 6.6 | 202 | 70 |
| Example 154 | 6.2 | 65 | 90 |
| Example 155 | 9 | 43 | 90 |
| Example 156 | 4.7 | 6 | 90 |
| Example 157 | 58 | | |
| Example 158 | 1.1 | 42 | 100 |
| Example 159 | 12 | 636 | 80 |
| Example 160 | | 32 | 100 |
| Example 161 | 8 | 32 | 90 |
| Example 162 | 13 | 24 | 100 |
| Example 163 | 0.23 | 2 | 90 |
| Example 164 | 0.28 | 0.3 | 100 |
| Example 165 | 18 | 80 | 70 |
| Example 166 | 8 | 0.2 | 90 |
| Example 167 | 3.1 | 21 | 90 |
| Example 168 | 2 | 1 | 100 |
| Example 169 | 14 | 50 | 100 |
| Example 170 | 3.3 | 14 | 90 |
| Example 171 | 0.88 | 0.7 | 100 |
| Example 172 | 185 | | |
| Example 173 | 326 | | |
| Example 174 | 203 | | |
| Example 175 | 384 | | |
| Example 176 | 488 | | |
| Example 177 | 353 | | |
| Example 178 | 310 | | |
| Example 179 | 435 | | |
| Example 180 | 290 | | |
| Example 181 | 146 | | |
| Example 182 | 279 | | |
| Example 183 | 178 | | |
| Example 184 | 185 | | |
| Example 185 | 159 | | |
| Example 186 | 171 | | |
| Example 187 | 247 | | |
| Example 188 | 579 | | |
| Example 189 | 363 | | |
| Example 190 | 186 | | |
| Example 191 | 270 | | |
| Example 192 | 142 | | |
| Example 193 | 246 | | |
| Example 194 | 127 | | |
| Example 195 | 0.48 | 9 | 80 |
| Example 196 | 108 | | |
| Example 197 | 63 | | |
| Example 198 | 17 | 903 | 60 |
| Example 199 | 19 | 416 | 80 |
| Example 200 | 12 | 369 | 80 |
| Example 201 | 8 | 396 | 80 |
| Example 202 | 11 | 105 | 80 |
| Example 203 | 8.5 | 187 | 80 |
| Example 204 | 1.3 | 336 | 90 |
| Example 205 | 3 | 280 | 80 |
| Example 206 | 1.7 | 4 | 90 |
| Example 207 | 128 | 112 | 80 |
| Example 208 | 1.9 | 0.36 | 100 |
| Example 209 | 2.3 | 57 | 90 |
| Example 210 | 36 | | |
| Example 211 | 19 | 672 | 70 |
| Example 212 | 2.4 | 11 | 90 |
| Example 213 | | 9 | 100 |
| Example 214 | | 79 | 70 |
| Example 215 | 5 | 80 | 80 |
| Example 216 | 0.7 | 0.2 | 100 |
| Example 217 | 0.4 | 143 | 70 |
| Example 218 | 0.7 | 0.2 | 90 |
| Example 219 | 7 | 79 | 90 |
| Example 220 | 8 | 30 | 90 |
| Example 221 | 1.4 | 2 | 90 |
| Example 222 | 18 | 120 | 80 |
| Example 223 | 10 | 30 | 80 |
| Example 224 | 18 | 455 | 70 |
| Example 225 | 1.2 | 3 | 90 |
| Example 226 | 1.3 | 30 | 90 |
| Example 227 | 1.5 | 3 | 95 |
| Example 228 | | 313 | 70 |
| Example 229 | 0.4 | 6 | 100 |
| Example 230 | 0.6 | 48 | 90 |
| Example 231 | | 0.4 | 80 |
| Example 232 | | 114 | 50 |
| Example 233 | | 614 | 20 |
| Example 234 | | 11 | 90 |
| Example 235 | | 49 | 50 |
| Example 236 | | 123 | 70 |
| Example 237 | 0.57 | 3 | 80 |
| Example 238 | | 529 | 40 |
| Example 239 | | 1433 | 40 |
| Example 240 | | 89 | 70 |
| Example 241 | 0.3 | 29 | 90 |
| Example 242 | 3 | 48 | 90 |
| Example 243 | 0.25 | 50 | 90 |
| Example 244 | 0.74 | 52 | 90 |
| Example 245 | 2 | 57 | 100 |
| Example 246 | 23 | 1491 | 90 |
| Example 247 | 15 | 164 | 90 |
| Example 248 | 9 | 225 | 80 |
| Example 249 | 4 | 21 | 90 |
| Example 250 | 2.5 | 72 | 90 |
| Example 251 | 0.38 | 8 | 90 |
| Example 252 | 1.1 | 3 | 100 |
| Example 253 | 8.6 | 251 | 90 |

-continued

| Compound | 5-HT$_{2C}$ Affinity K$_i$ (nM) | 5-HT$_{2C}$ Function EC$_{50}$ (nM) | Emax (%) |
|---|---|---|---|
| Example 254 | 0.89 | 11 | 90 |
| Example 255 | 5 | 79 | 90 |
| Example 256 | 0.74 | 4 | 100 |
| Example 257 | 28 | 194 | 80 |
| Example 258 | 42 | 734 | 80 |
| Example 259 | 69 | | |
| Example 260 | 0.13 | 22 | 90 |
| Example 261 | 0.5 | 67 | 90 |
| Example 262 | | 471 | 70 |
| Example 263 | 1.8 | 0.8 | 100 |
| Example 266 | 4.9 | 3 | 90 |
| Example 267 | | 730 | 80 |
| Example 268 | | 961 | 50 |
| Example 269 | | 5124 | 20 |
| Example 271 | | 594 | 90 |
| Example 272 | | 845 | 70 |
| Example 274 | | 330 | 70 |
| Example 278 | | 726 | 60 |
| Example 279 | | 155 | 70 |
| Example 280 | | 288 | 70 |
| Example 281 | 3.8 | 35 | 90 |
| Example 282 | 1.7 | 43 | 90 |
| Example 283 | 1.2 | 6 | 100 |
| Example 284 | 0.8 | 7 | 100 |
| Example 286 | 0.76 | 6 | 100 |
| Example 287 | 0.13 | 21 | 90 |
| Example 288 | 7.1 | 38 | 100 |
| Example 289 | 1 | 44 | 100 |
| Example 290 | 1.7 | 58 | 80 |
| Example 291 | 0.4 | 22 | 100 |
| Example 292 | 4.9 | 66 | 100 |
| Example 293 | 3.8 | 7 | 90 |
| Example 294 | 0.11 | 8 | 90 |
| Example 295 | | 8 | 90 |
| Example 296 | | 50 | 80 |
| Example 297 | 0.56 | 0.73 | 100 |
| Example 298 | 11 | 30 | 90 |
| Example 299 | 0.19 | 0.1 | 100 |
| Example 300 | 0.1 | 3 | 90 |
| Example 301 | 2 | 31 | 90 |
| Example 302 | 0.3 | 2 | 100 |
| Example 303 | 0.2 | | |
| Example 304 | 1.7 | | |
| Example 305 | 1.1 | | |
| Example 306 | 0.58 | 0.64 | 100 |
| Example 307 | 1 | 49 | 90 |
| Example 308 | 0.9 | 24 | 90 |
| Example 309 | 8 | 107 | 90 |
| Example 310 | 13 | 137 | 90 |
| Example 311 | 25 | 63 | 90 |
| Example 312 | 15 | 25 | 90 |
| Example 313 | 164 | 70 | 90 |
| Example 314 | 18 | 42 | 90 |
| Example 315 | 25 | 19 | 90 |
| Example 316 | 64 | | |
| Example 317 | 84 | | |
| Example 318 | 98 | | |
| Example 319 | 83 | | |
| Example 320 | 107 | | |
| Example 321 | 59 | | |
| Example 322 | 427 | | |
| Example 323 | 161 | | |
| Example 324 | 60 | | |
| Example 325 | 320 | | |
| Example 326 | 34 | 228 | 80 |
| Example 327 | 255 | | |
| Example 328 | 61 | | |
| Example 329 | 87 | | |
| Example 330 | 88 | | |
| Example 331 | 38 | 271 | 80 |
| Example 332 | 37 | 111 | 80 |
| Example 333 | 13 | 70 | 90 |
| Example 334 | 324 | | |
| Example 335 | 192 | | |

-continued

| Compound | 5-HT$_{2C}$ Affinity K$_i$ (nM) | 5-HT$_{2C}$ Function EC$_{50}$ (nM) | Emax (%) |
|---|---|---|---|
| Example 336 | 45 | 123 | 90 |
| Example 337 | 34 | 48 | 90 |
| Example 338 | 14 | 44 | 90 |
| Example 339 | 328 | | |
| Example 340 | 88 | | |
| Example 341 | 36 | 231 | 90 |
| Example 342 | 28 | 590 | 80 |
| Example 343 | 12 | 49 | 90 |
| Example 344 | 275 | 2916 | 60 |
| Example 345 | 98 | | |
| Example 346 | 5000 | | |
| Example 347 | 5000 | | |
| Example 348 | 529 | | |
| Example 349 | 760 | | |
| Example 350 | 497 | | |
| Example 351 | 87 | | |
| Example 352 | 876 | | |
| Example 353 | 845 | | |
| Example 354 | 610 | | |
| Example 355 | 385 | | |
| Example 356 | 0.63 | 63 | 100 |
| Example 357 | 18 | 2 | 100 |
| Example 358 | 7 | | |
| Example 359 | 10 | 8 | 90 |
| Example 361 | 33 | 73 | 90 |
| Example 362 | 36 | 343 | 70 |
| Example 363 | 26 | 225 | 70 |
| Example 364 | 0.9 | 62 | 85 |
| Example 365 | 24 | 15 | 100 |
| Example 366 | 13 | 394 | 80 |
| Example 367 | 0.21 | 3 | 100 |
| Example 368 | 1.4 | 4 | 90 |
| Example 369 | | 283 | 90 |
| Example 370 | 30 | 190 | 80 |
| Example 371 | 14 | 64 | 80 |
| Example 372 | 23 | 224 | 80 |
| Example 373 | 61 | 859 | 60 |
| Example 374 | 0.6 | 19 | 100 |
| Example 375 | 71 | | |
| Example 376 | 88 | | |
| Example 377 | 194 | | |
| Example 378 | 201 | | |
| Example 379 | 453 | | |
| Example 380 | 424 | | |
| Example 381 | 923 | | |
| Example 382 | 801 | | |
| Example 383 | 1758 | | |
| Example 384 | 1255 | | |
| Example 385 | 1354 | | |
| Example 386 | 1025 | | |
| Example 387 | 1549 | | |
| Example 388 | 1580 | | |
| Example 389 | 1620 | | |
| Example 390 | 1.8 | 2 | 80 |
| Example 391 | | 0.2 | 80 |
| Example 393 | 21.5 | 45 | 60 |
| Example 395 | 0.3 | 0.4 | 90 |
| Example 396 | 0.3 | | |
| Example 397 | 1.6 | | |
| Example 398 | 0.04 | 0.1 | 100 |
| Example 400 | 0.5 | | |
| Example 401 | 0.38 | 0.7 | 90 |
| Example 402 | 0.24 | 0.1 | 90 |
| Example 404 | 0.4 | | |
| Example 406 | 0.51 | 9 | 100 |
| Example 407 | 8.5 | 149 | 60 |
| Example 408 | 0.46 | 6 | 90 |
| Example 409 | 3 | 22 | 90 |
| Example 410 | 0.08 | 0.05 | 90 |
| Example 411 | 2.6 | 57 | 80 |
| Example 412 | 5.3 | 34 | 90 |
| Example 413 | 21 | 8 | 90 |
| Example 414 | 3.4 | 781 | 60 |
| Example 415 | 1.1 | 109 | 70 |

| Compound | 5-HT$_{2C}$ Affinity K$_i$ (nM) | 5-HT$_{2C}$ Function EC$_{50}$ (nM) | Emax (%) | Compound | 5-HT$_{2C}$ Affinity K$_i$ (nM) | 5-HT$_{2C}$ Function EC$_{50}$ (nM) | Emax (%) |
|---|---|---|---|---|---|---|---|
| Example 416 | 1.6 | 467 | 70 | Example 494 | 35 | 475 | 60 |
| Example 417 | 3.7 | 183 | 60 | Example 495 | 41 | 338 | 60 |
| Example 418 | 1.1 | 59 | 80 | Example 496 | 46 | 510 | 60 |
| Example 419 | 3.8 | 1359 | 80 | Example 497 | 37 | 315 | 70 |
| Example 420 | 7.0 | 504 | 80 | Example 498 | 35 | 326 | 70 |
| Example 421 | 1.5 | 93 | 70 | Example 499 | 3.6 | 57 | 90 |
| Example 422 |  | 443 | 80 | Example 500 | 86 | 256 | 80 |
| Example 423 | 6.1 | 28 | 70 | Example 501 | 45 | 70 | 70 |
| Example 424 |  | 49 | 90 | Example 502 | 60 |  |  |
| Example 425 |  | 9 | 100 | Example 503 | 78 |  |  |
| Example 426 |  | 17 | 100 | Example 504 | 1.2 | 27 | 90 |
| Example 427 |  | 298 | 80 | Example 505 | 371 |  |  |
| Example 428 |  | 69 | 80 | Example 506 | 1601 |  |  |
| Example 429 | 2.8 | 16 | 92 | Example 507 | 2726 |  |  |
| Example 430 |  | 448 | 80 | Example 508 | 1795 |  |  |
| Example 431 |  | 63 | 90 | Example 509 | 5000 |  |  |
| Example 432 |  | 72 | 80 | Example 510 | 5000 |  |  |
| Example 433 | 3.5 | 1 | 100 | Example 511 | 248 |  |  |
| Example 434 | 0.03 | 7 | 90 | Example 512 | 810 |  |  |
| Example 435 |  | 82 | 80 | Example 513 | 1148 |  |  |
| Example 436 |  | 55 | 90 | Example 514 | 242 |  |  |
| Example 437 |  | 30 | 80 | Example 515 | 965 |  |  |
| Example 438 | 2.4 | 68 | 70 | Example 516 | 1581 |  |  |
| Example 439 | 0.45 | 6 | 90 | Example 517 | 2140 |  |  |
| Example 440 | 1.2 | 9 | 100 | Example 518 | 40 | 384 | 80 |
| Example 441 | 10 | 531 | 70 | Example 519 | 488 |  |  |
| Example 442 | 0.2 | 6 | 90 | Example 520 | 372 |  |  |
| Example 443 | 4.8 | 5 | 90 | Example 521 | 246 |  |  |
| Example 444 |  | 37 | 80 | Example 522 | 474 |  |  |
| Example 445 | 0.48 | 1 | 90 | Example 523 | 61 |  |  |
| Example 446 |  | 460 | 70 | Example 524 | 136 |  |  |
| Example 447 |  | 3 | 90 | Example 525 | 559 |  |  |
| Example 448 | 7 | 78 | 70 | Example 526 | 25 | 50 | 90 |
| Example 449 | 1 | 2 | 90 | Example 527 | 4744 |  |  |
| Example 450 | 0.27 | 0.8 | 100 | Example 528 | 1093 |  |  |
| Example 451 | 0.31 | 137 | 80 | Example 529 | 616 |  |  |
| Example 452 | 24 | 153 | 80 | Example 530 | 915 |  |  |
| Example 453 |  | 24 | 80 | Example 531 | 409 |  |  |
| Example 454 | 0.26 | 0.39 | 90 | Example 532 | 3355 |  |  |
| Example 456 | 4.1 | 50 | 100 | Example 533 | 1516 |  |  |
| Example 457 | 38 | 740 | 50 | Example 534 | 1049 |  |  |
| Example 458 | 17 | 212 | 80 | Example 535 | 1091 |  |  |
| Example 459 | 24 | 16 | 90 | Example 536 | 1119 |  |  |
| Example 460 |  | 215 | 90 | Example 537 | 1695 |  |  |
| Example 461 |  | 34 | 80 | Example 538 | 380 |  |  |
| Example 462 |  | 79 | 80 | Example 539 | 209 |  |  |
| Example 463 | 21 | 89 | 80 | Example 540 | 486 |  |  |
| Example 464 |  | 462 | 70 | Example 541 | 316 |  |  |
| Example 465 |  | 496 | 60 | Example 542 | 372 |  |  |
| Example 466 |  | 55 | 70 | Example 543 |  | 0.2 | 100 |
| Example 467 |  | 257 | 80 | Example 544 |  | 73 | 70 |
| Example 468 |  | 73 | 80 | Example 545 | 0.14 | 0.1 | 100 |
| Example 469 |  | 21 | 80 | Example 546 | 2.3 |  |  |
| Example 470 |  | 289 | 70 | Example 547 | 1.8 |  |  |
| Example 471 |  | 14 | 90 | Example 548 | 2.3 |  |  |
| Example 472 |  | 353 | 80 | Example 549 | 3.1 |  |  |
| Example 475 | 3.2 | 25 | 80 | Example 550 | 0.37 | 0.4 | 100 |
| Example 476 | 0.2 | 5 | 100 | Example 551 | 0.55 | 17 | 90 |
| Example 477 | 6.7 | 9 | 80 | Example 552 | 0.3 |  |  |
| Example 478 | 11 | 225 | 70 | Example 554 | 41 | 2 | 70 |
| Example 479 | 0.5 | 71 | 80 | Example 555 | 0.6 | 4 | 80 |
| Example 480 | 4.4 | 251 | 70 | Example 558 |  | 265 | 70 |
| Example 481 | 1.5 | 75 | 80 | Example 559 | 0.3 | 7 | 90 |
| Example 482 | 7 | 143 | 80 | Example 560 | 0.35 | 2 | 100 |
| Example 483 | 5 | 58 | 80 | Example 561 | 2.7 | 21 | 80 |
| Example 484 | 0.51 | 43 | 70 | Example 562 | 0.48 | 2 | 90 |
| Example 485 | 3 | 32 | 90 | Example 563 |  | 135 | 70 |
| Example 486 | 0.2 | 5 | 90 | Example 564 |  | 43 | 90 |
| Example 487 | 0.06 | 3 | 100 | Example 565 |  | 287 | 70 |
| Example 488 | 0.34 | 132 | 90 | Example 566 |  | 3 | 70 |
| Example 489 | 3 | 39 | 90 | Example 567 |  | 9 | 60 |
| Example 490 | 1 | 6 | 100 | Example 568 |  | 4 | 80 |
| Example 491 | 22 | 200 | 80 | Example 569 |  | 6 | 60 |
| Example 492 | 3.1 | 7 | 80 |  |  |  |  |
| Example 493 | 11 | 8 | 90 |  |  |  |  |

The compounds of this invention thus have affinity for and agonist or partial agonist activity at brain serotonin $5HT_{2C}$ receptors. They are therefore of interest for the treatment of the central nervous system conditions described previously herein.

The entire disclosure of each patent, patent application, and publication cited or described in this document is hereby incorporated by reference.

What is claimed:

1. A compound of Formula 1:

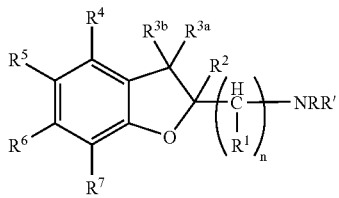

Formula 1 or pharmaceutically acceptable salt thereof;
wherein:
R and R' are, independently, hydrogen, alkyl of 1 to 6 carbon atoms, cycloalkyl of 3 to 6 carbon atoms, or alkylcycloalkyl of 4 to 12 carbon atoms having 3 to 6 carbons in the cycloalkyl ring;
alternatively R and R' can be taken together with the nitrogen to which they are attached to form a ring containing 2-5 carbon atoms, wherein one of the ring carbon atoms is optionally replaced by nitrogen, sulfur or oxygen;
$R^1$, $R^2$, $R^{3a}$ and $R^{3b}$ are, independently, hydrogen or lower alkyl;
$R^4$, $R^5$, and $R^6$ are, independently, hydrogen, halogen, cyano, hydroxyl, carboxyl, alkyl of 1 to 8 carbon atoms, perfluoroalkyl of 1 to 6 carbon atoms, alkoxy of 1 to 6 carbon atoms, perfluoroalkoxy of 1 to 6 carbon atoms, aryl of 6 and 10 carbon atoms, aryloxy of 6 and 10 carbon atoms, 5 to 10 membered heteroaryl having 1 to 3 heteroatoms each independently selected from nitrogen, oxygen or sulfur, alkenyl of 2 to 8 carbon atoms, alkanoyl of 2 to 6 carbon atoms, alkanoyloxy of 2 to 6 carbon atoms, carboalkoxy of 2 to 6 carbon atoms, carboxamido, alkanamido of 2 to 6 carbon atoms, alkanesulfonamido of 1 to 6 carbon atoms, amino, monoalkylamino of 1 to 6 carbon atoms, dialkylamino of 1 to 6 carbon atoms per alkyl moiety, cycloalkyl of 3 to 8 carbon atoms, or 3 to 8 membered heterocycloalkyl having 1 to 3 heteroatoms each independently selected from nitrogen, oxygen or sulfur, wherein the cycloalkyl and heterocycloalkyl groups are saturated or partially saturated; and
n is 1 or 2;
$R^7$ is branched alkyl of 3 to 8 carbon atoms, branched alkenyl of 3 to 8 carbon atoms, or —Y—$R^8$, wherein Y is a direct bond, and $R^8$ is aryl of 6 and 10 carbon atoms substituted with 1 to 5 groups independently selected from halogen, hydroxyl, cyano, alkyl of 1 to 6 carbon atoms, perfluoroalkyl of 1 to 6 carbon atoms, alkoxy of 1 to 6 carbon atoms, or perfluoroalkoxy of 1 to 6 carbon atoms, 5 to 10 membered heteroaryl, cycloalkyl of 3 to 8 carbon atoms, or 3 to 8 membered heterocycloalkyl, wherein the cycloalkyl and heterocycloalkyl groups are saturated or partially saturated; and
wherein, unless otherwise indicated, any aryl, heteroaryl, cycloalkyl or heterocycloalkyl may optionally be substituted with 1 to 5 substituents independently selected from halogen, hydroxyl, cyano, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

2. The compound of claim 1 wherein:
R' is hydrogen; and
R is hydrogen, alkyl of 1 to 6 carbon atoms, or perfluoroalkyl of 1 to 6 carbon atoms.

3. The compound of claim 1 wherein R and R' are, independently, hydrogen or alkyl of 1 to 6 carbon atoms.

4. The compound according to claim 1 wherein $R^7$ is —Y—$R^8$, wherein Y is a direct bond, and $R^8$ is aryl of 6 and 10 carbon atoms substituted with 1 to 5 groups independently selected from halogen, hydroxyl, cyano, alkyl of 1 to 6 carbon atoms, perfluoroalkyl of 1 to 6 carbon atoms, alkoxy of 1 to 6 carbon atoms, or perfluoroalkoxy of 1 to 6 carbon atoms, 5 to 10 membered heteroaryl, cycloalkyl of 3 to 8 carbon atoms, or 3 to 8 membered heterocycloalkyl as defined in claim 1, and $R^4$, $R^5$, and $R^6$ are, independently, hydrogen, halogen, alkyl of 1 to 8 carbon atoms, perfluoroalkyl of 1 to 3 carbon atoms, alkoxy of 1 to 3 carbon atoms, alkenyl of 2 to 8 carbon atoms, cycloalkyl of 3 to 8 carbon atoms, 3 to 8 membered heterocycloalkyl, aryl of 6 and 10 carbon atoms, or 5 to 10 membered heteroaryl, and wherein any aryl, heteroaryl, cycloalkyl or heterocycloalkyl may optionally be substituted with 1 to 5 substituents independently selected from halogen, hydroxyl, cyano, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

5. The compound of claim 1 wherein $R^4$, $R^5$, $R^6$ are, independently, hydrogen, halogen, alkyl of 1 to 3 carbon atoms, alkoxy of 1 to 3 carbon atoms, perfluoroalkyl of 1 to 3 carbon atoms, or perfluoroalkoxy of 1 to 3 carbon atoms.

6. The compound of claim 1 wherein at least one of $R^4$ and $R^5$ is halogen, alkyl of 1 to 6 carbon atoms, perfluoroalkyl of 1 to 3 carbon atoms, or alkoxy of 1 to 6 carbon atoms.

7. The compound of claim 1 wherein $R^7$ is phenyl, substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

8. The compound of claim 7 wherein $R^7$ is phenyl, substituted with 1 to 3 substituents independently selected from halogen, alkyl of 1 to 3 carbon atoms, perfluoroalkyl of 1 to 3 carbon atoms, or alkoxy of 1 to 3 carbon atoms.

9. A compound of claim 8 wherein n is 1.

10. The compound of claim 9 wherein $R^7$ is phenyl, substituted with 1 to 3 substituents selected from fluoro, chloro, methyl, methoxy or trifluoromethyl.

11. The compound of claim 10 wherein $R^5$ is halo and each of R, R', $R^1$, and $R^2$ are hydrogen.

12. The compound of claim 11 wherein $R^{3a}$ and $R^{3b}$ are both hydrogen.

13. The compound of claim 1, wherein $R^7$ is selected from the group consisting of:
4-methoxy-2-methylphenyl,
2-chloro-4-(trifluoromethyl)phenyl,
2-chloro-4-methoxyphenyl,
2-chloro-4-(trifluoromethoxy)phenyl,
({7-[4-methoxy-2-(trifluoromethyl)phenyl,
4-ethoxy-2-methylphenyl,
4-ethoxy-2-(trifluoromethyl)phenylamine,
4-chloro-2-(trifluoromethyl)phenyl,
4-fluoro-2-(trifluoromethyl)phenyl,
2-ethyl-4-methoxyphenyl,
2,4-dichlorophenyl, 2,4-dimethylphenyl,
4-isopropyl-2-methoxyphenyl,
4-isopropoxy-2-(trifluoromethyl)phenyl,
2-chloro-4-isopropoxyphenyl,
4-chloro-2-methylphenyl,
2,6-difluorophenyl,
2-chloro-6-fluorophenyl,
2-fluoro-6-(trifluoromethyl)phenyl,
2,6-bis(trifluoromethyl)phenyl,
2,3-dichlorophenyl,
3-chloro-2-fluorophenyl,
2-chloro-3-methylphenyl,
2,6-dichloro-4-methoxyphenyl, and
5-fluoro-2-methoxyphenyl.

14. The compound of claim 1 wherein $R^4$ or $R^5$ is aryl of 6 and 10 carbon atoms, said aryl optionally substituted with 1 to 5 substituents independently selected from halogen, hydroxyl, alkyl of 1 to 6 carbon atoms, perfluoroalkyl of 1 to 6 carbon atoms, alkoxy of 1 to 6 carbon atoms, or perfluoroalkoxy of 1 to 6 carbon atoms.

15. The compound of claim 1 which is:
(±)-1-[7-(2,3-dimethylphenyl)-2,3-dihydro-1-benzofuran-2-yl]methanamine,
(±)-{[7-(2,3-dimethoxyphenyl)-2,3-dihydro-1-benzofuran-2-yl]methyl}amine,
(−)-{[(7-(2,3-dimethoxyphenyl)-2,3-dihydro-1-benzofuran-2-yl]methyl}amine,
(+)-{[(7-(2,3-dimethoxyphenyl)-2,3-dihydro-1-benzofuran-2-yl]methyl}amine,
(+)-{[7-(4-chloro-2-methylphenyl)-2,3-dihydro-1-benzofuran-2-yl]methyl}amine,
(−)-{[7-(4-chloro-2-methylphenyl)-2,3-dihydro-1-benzofuran-2-yl]methyl}amine,
(±)-{[7-(2,3-difluorophenyl)-2,3-dihydro-1-benzofuran-2-yl]methyl}amine,
(±)-{[7-(2,5-dimethylphenyl)-2,3-dihydro-1-benzofuran-2-yl]methyl}amine,
(±)-{[7-(2,5-dimethoxyphenyl)-2,3-dihydro-1-benzofuran-2-yl]methyl}amine,
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(−)-{[7-(2,5-dichlorophenyl)-2,3-dihydro-1-benzofuran-2-yl]methyl}amine,
(±)-{[7-(2,4,6-trichlorophenyl)-2,3-dihydro-1-benzofuran-2-yl]methyl}amine,
(±)-{[7-(4-chloro-2-methylphenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(±)-{[7-(5-chloro-2-methoxyphenyl)-2,3-dihydro-1-benzofuran-2-yl]methyl}amine,
(±)-[(7-pyridin-3-yl-2,3-dihydro-1-benzofuran-2-yl)methyl]amine,
(+)-{[7-pyridin-3-yl-2,3-dihydro-1-benzofuran-2-yl]methyl}amine,
(−)-{[7-pyridin-3-yl-2,3-dihydro-1-benzofuran-2-yl]methyl}amine,
(±)-{[5-fluoro-7-(2-methoxyphenyl)-2,3-dihydro-1-benzofuran-2-yl]methyl}amine,
(±)-{[5-fluoro-7-(3-fluorophenyl)-2,3-dihydro-1-benzofuran-2-yl]methyl}amine,
(±)-{[5-fluoro-7-(3-methoxyphenyl)-2,3-dihydro-1-benzofuran-2-yl]methyl}amine,
(±)-{[5-fluoro-7-(3-methylphenyl)-2,3-dihydro-1-benzofuran-2-yl]methyl}amine,
(±)-{[5-fluoro-7-(4-fluorophenyl)-2,3-dihydro-1-benzofuran-2-yl]methyl}amine,
(±)-{[5-fluoro-7-(4-chlorophenyl)-2,3-dihydro-1-benzofuran-2-yl]methyl}amine,
(±)-{[5-fluoro-7-(4-methylphenyl)-2,3-dihydro-1-benzofuran-2-yl]methyl}amine,
(±)-{[5-fluoro-7-(4-methoxyphenyl)-2,3-dihydro-1-benzofuran-2-yl]methyl}amine,
(±)-[(5-fluoro-7-thien-3-yl-2,3-dihydro-1-benzofuran-2-yl)methyl]amine,
(±)-{[5-fluoro-7-(3-furyl)-2,3-dihydro-1-benzofuran-2-yl]methyl}amine,
(±)-[(5-fluoro-7-pyridin-2-yl-2,3-dihydro-1-benzofuran-2-yl)methyl]amine,
(±)-[(5-fluoro-7-pyridin-3-yl-2,3-dihydro-1-benzofuran-2-yl)methyl]amine,
(−)-[(5-fluoro-7-pyridin-3-yl-2,3-dihydro-1-benzofuran-2-yl)methyl]amine,
(+)-{[5-fluoro-7-pyridin-3-yl-2,3-dihydro-1-benzofuran-2-yl]methyl}amine,
(±)-[(5-fluoro-7-pyridin-4-yl-2,3-dihydro-1-benzofuran-2-yl)methyl]amine,
(±)-[(5-fluoro-7-pyrimidin-5-yl-2,3-dihydro-1-benzofuran-2-yl)methyl]amine,
(±)-{[7-(2,3-dichlorophenyl)-5-fluoro-2,3-dihydro-1-benzofuran-2-yl]methyl}amine,
(±)-{[7-(2,3-dimethoxyphenyl)-5-fluoro-2,3-dihydro-1-benzofuran-2-yl]methyl}amine,
(−)-{[7-(2,3-dimethoxyphenyl)-5-fluoro-2,3-dihydro-1-benzofuran-2-yl]methyl}amine,
(+)-{[7-(2,3-dimethoxyphenyl)-5-fluoro-2,3-dihydro-1-benzofuran-2-yl]methyl}amine,
(±)-{[7-(2,4-difluorophenyl)-5-fluoro-2,3-dihydro-1-benzofuran-2-yl]methyl}amine,
(±)-{[7-(2,4-dichlorophenyl)-5-fluoro-2,3-dihydro-1-benzofuran-2-yl]methyl}amine,
(−)-{[5-fluoro-7-(2,4-dichlorophenyl)-2,3-dihydro-1-benzofuran-2-yl]methyl}amine,
(+)-{[5-fluoro-7-(2,4-dichlorophenyl)-2,3-dihydro-1-benzofuran-2-yl]methyl}amine,
(±)-{[7-(2,4-dimethoxyphenyl)-5-fluoro-2,3-dihydro-1-benzofuran-2-yl]methyl}amine,
(±)-{[7-(2,5-difluorophenyl)-5-fluoro-2,3-dihydro-1-benzofuran-2-yl]methyl}amine,
(±)-{[7-(2,5-dichlorophenyl)-5-fluoro-2,3-dihydro-1-benzofuran-2-yl]methyl}amine,
(±)-{[7-(2,5-dimethylphenyl)-5-fluoro-2,3-dihydro-1-benzofuran-2-yl]methyl}amine,
(±)-{[7-(2,5-dimethoxyphenyl)-5-fluoro-2,3-dihydro-1-benzofuran-2-yl]methyl}amine,
(±)-{[5-fluoro-7-(5-methoxy-2-methylphenyl)-2,3-dihydro-1-benzofuran-2-yl]methyl}amine,
(±)-{[5-fluoro-7-(2-methoxy-5-methylphenyl)-2,3-dihydro-1-benzofuran-2-yl]methyl}amine,
(±)-{[7-(2,6-difluorophenyl)-5-fluoro-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(+)-{[7-(2,6-dimethylphenyl)-5-fluoro-2,3-dihydro-1-benzofuran-2-yl]methyl}amine,
(−)-{[7-(2,6-dimethylphenyl)-5-fluoro-2,3-dihydro-1-benzofuran-2-yl]methyl}amine,
(±)-{[7-(2,6-dichlorophenyl)-5-fluoro-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine, (±)-1-cyclopropyl-N-{[7-(2,6-dichlorophenyl)-5-fluoro-2,3-dihydro-1-benzofuran-2-yl]methyl}methanamine,
(±)-N-{[7-(2,6-dichlorophenyl)-5-fluoro-2,3-dihydro-1-benzofuran-2-yl]methyl}cyclobutanamine,
(±)-N-{[7-(2,6-dichlorophenyl)-5-fluoro-2,3-dihydro-1-benzofuran-2-yl]methyl}ethanamine,
(±)-N-{[7-(2,6-dichlorophenyl)-5-fluoro-2,3-dihydro-1-benzofuran-2-yl]methyl}propan-1-amine,
(±)-N-{[7-(2,6-dichlorophenyl)-5-fluoro-2,3-dihydro-1-benzofuran-2-yl]methyl}propan-2-amine,
(±)-{[7-(2,6-dichlorophenyl)-5-fluoro-2,3-dihydro-1-benzofuran-2-yl]methyl}dimethylamine,
(±)-1-{[7-(2,6-dichlorophenyl)-5-fluoro-2,3-dihydro-1-benzofuran-2-yl]methyl}piperidine
(±)-1-{[7-(2,6-dichlorophenyl)-5-fluoro-2,3-dihydro-1-benzofuran-2-yl]methyl}morpholine
(±)-1-{[7-(2,6-dichlorophenyl)-5-fluoro-2,3-dihydro-1-benzofuran-2-yl]methyl}pyrrolidine
(±)-{[5-chloro-7-(2-fluorophenyl)-2,3-dihydro-1-benzofuran-2-yl]methyl}amine,
(±)-{[5-chloro-7-(2-methoxyphenyl)-2,3-dihydro-1-benzofuran-2-yl]methyl}amine,
(±)-{[5-chloro-7-(3-furyl)-2,3-dihydro-1-benzofuran-2-yl]methyl}amine,
(±)-{[5-chloro-7-(2,3-difluorophenyl)-2,3-dihydro-1-benzofuran-2-yl]methyl}amine,
(−)-{[5-chloro-7-(2,3-difluorophenyl)-2,3-dihydro-1-benzofuran-2-yl]methyl}amine,
(+)-{[5-chloro-7-(2,3-difluorophenyl)-2,3-dihydro-1-benzofuran-2-yl]methyl}amine,
(±)-{[5-chloro-7-(2,3-dichlorophenyl)-2,3-dihydro-1-benzofuran-2-yl]methyl}amine,
(±)-{[5-chloro-7-(2,3-dimethylphenyl)-2,3-dihydro-1-benzofuran-2-yl]methyl}amine,
(±)-{[5-chloro-7-(2,3-dimethoxyphenyl)-2,3-dihydro-1-benzofuran-2-yl]methyl}amine,
(±)-{[5-chloro-7-(2,4-difluorophenyl)-2,3-dihydro-1-benzofuran-2-yl]methyl}amine,
(±)-{[5-chloro-7-(2,4-dichlorophenyl)-2,3-dihydro-1-benzofuran-2-yl]methyl}amine,
(−)-{[5-chloro-7-(2,4-dichlorophenyl)-2,3-dihydro-1-benzofuran-2-yl]methyl}amine,
(+)-{[5-chloro-7-(2,4-dichlorophenyl)-2,3-dihydro-1-benzofuran-2-yl]methyl}amine,
(±)-{[5-chloro-7-(2,4-dimethoxyphenyl)-2,3-dihydro-1-benzofuran-2-yl]methyl}amine,
(±)-{[5-chloro-7-(2,5-difluorophenyl)-2,3-dihydro-1-benzofuran-2-yl]methyl}amine,
(±)-{[5-chloro-7-(2,5-dichlorophenyl)-2,3-dihydro-1-benzofuran-2-yl]methyl}amine,
(±)-{[5-chloro-7-(5-chloro-2-methoxyphenyl)-2,3-dihydro-1-benzofuran-2-yl]methyl}amine,
(±)-{[5-chloro-7-(3,4-difluorophenyl)-2,3-dihydro-1-benzofuran-2-yl]methyl}amine,
(±)-{[5-chloro-7-(3-chloro-4-fluorophenyl)-2,3-dihydro-1-benzofuran-2-yl]methyl}amine,
(±)-{[5-chloro-7-(2,6-dimethylphenyl)-2,3-dihydro-1-benzofuran-2-yl]methyl}amine,
(−)-{[5-chloro-7-(2,6-dimethylphenyl)-2,3-dihydro-1-benzofuran-2-yl]methyl}amine,
(+)-{[5-chloro-7-(2,6-dimethylphenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(+)-{[5-chloro-7-(2,6-dichlorophenyl)-2,3-dihydro-1-benzofuran-2-yl]methyl}amine,
(−)-{[5-chloro-7-(2,6-dichlorophenyl)-2,3-dihydro-1-benzofuran-2-yl]methyl}amine,
(±)-{[(5-chloro-7-pyridin-3-yl-2,3-dihydro-1-benzofuran-2-yl]methyl}amine,
(±)-N-{[5-chloro-7-(2,6-dimethylphenyl)-2,3-dihydro-1-benzofuran-2-yl]methyl}cyclopropanamine,
(±)-N-{[5-chloro-7-(2,6-dimethylphenyl)-2,3-dihydro-1-benzofuran-2-yl]methyl}(cyclopropylmethyl)amine,
(±)-N-{[5-chloro-7-(2,6-dimethylphenyl)-2,3-dihydro-1-benzofuran-2-yl]methyl}cyclobutanamine,
(±)-N-{[5-chloro-7-(2,6-dimethylphenyl)-2,3-dihydro-1-benzofuran-2-yl]methyl}ethanamine,
(±)-N-{[5-chloro-7-(2,6-dimethylphenyl)-2,3-dihydro-1-benzofuran-2-yl]methyl}propan-2-amine,
(±)-{[5-chloro-7-(2,6-dimethylphenyl)-2,3-dihydro-1-benzofuran-2-yl]methyl}dimethylamine,
(±)-1-{[5-chloro-7-(2,6-dimethylphenyl)-2,3-dihydro-1-benzofuran-2-yl]methyl}piperidine
(±)-4-{[5-chloro-7-(2,6-dimethylphenyl)-2,3-dihydro-1-benzofuran-2-yl]methyl}morpholine
(±)-4-{[5-chloro-7-(2,6-dimethylphenyl)-2,3-dihydro-1-benzofuran-2-yl]methyl}thiomorpholine
(±)-N-{[5-chloro-7-(2,6-dimethylphenyl)-2,3-dihydro-1-benzofuran-2-yl]methyl}propan-1-amine,
(±)-1-{[5-chloro-7-(2,6-dimethylphenyl)-2,3-dihydro-1-benzofuran-2-yl]methyl}piperazine
(±)-1-{[5-chloro-7-(2,6-dimethylphenyl)-2,3-dihydro-1-benzofuran-2-yl]methyl}pyrrolidine
(±)-{[7-(2-methylphenyl)-5-methyl-2,3-dihydro-1-benzofuran-2-yl]methyl}amine,
(±)-{[7-(2-fluorophenyl)-5-methyl-2,3-dihydro-1-benzofuran-2-yl]methyl}amine,
(±)-{[7-(2-methoxyphenyl)-5-methyl-2,3-dihydro-1-benzofuran-2-yl]methyl}amine,
(±)-{[7-(2-chlorophenyl)-5-methyl-2,3-dihydro-1-benzofuran-2-yl]methyl}amine,
(±)-({5-methyl-7-[2-(trifluoromethyl)phenyl]-2,3-dihydro-1-benzofuran-2-yl}methyl)amine,
(±)-{[7-(3-chlorophenyl)-5-methyl-2,3-dihydro-1-benzofuran-2-yl]methyl}amine,
(±)-{[7-(3-methylphenyl)-5-methyl-2,3-dihydro-1-benzofuran-2-yl]methyl}amine,
(±)-{[7-(4-methylphenyl)-5-methyl-2,3-dihydro-1-benzofuran-2-yl]methyl}amine,
(±)-{[7-(4-fluorophenyl)-5-methyl-2,3-dihydro-1-benzofuran-2-yl]methyl}amine,
(±)-{[7-(4-chlorophenyl)-5-methyl-2,3-dihydro-1-benzofuran-2-yl]methyl}amine,
(±)-{[7-(4-methoxyphenyl)-5-methyl-2,3-dihydro-1-benzofuran-2-yl]methyl}amine,
(±)-{[7-(2,3-dimethoxyphenyl)-5-methyl-2,3-dihydro-1-benzofuran-2-yl]methyl}amine,
(−)-{[7-(2,3-dimethoxyphenyl)-5-methyl-2,3-dihydro-1-benzofuran-2-yl]methyl}amine,
(+)-{[7-(2,3-dimethoxyphenyl)-5-methyl-2,3-dihydro-1-benzofuran-2-yl]methyl}amine,
(±)-{[7-(2,4-dichlorophenyl)-5-methyl-2,3-dihydro-1-benzofuran-2-yl]methyl}amine,
(−)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dimethylphenyl)-5-methyl-2,3-dihydro-1-benzofuran-2-yl]methyl}amine, (±)-{[7-(2,6-dichlorophenyl)-5-methyl-2,3-dihydro-1-benzofuran-2-yl]methyl}amine,
(−)-{[7-(2,6-dichlorophenyl)-5-methyl-2,3-dihydro-1-benzofuran-2-yl]methyl}amine,
(+)-{[7-(2,6-dichlorophenyl)-5-methyl-2,3-dihydro-1-benzofuran-2-yl]methyl}amine,
(±)-{[5-ethyl-7-(2-methylphenyl)-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[5-isopropyl-7-(2-methylphenyl)-2,3-dihydro-1-benzofuran-2-yl]methyl}amine,
(±)-{[5-isopropyl-7-(2-chlorophenyl)-2,3-dihydro-1-benzofuran-2-yl]methyl}amine,
(±)-{[5-cyclopentyl-7-(2-methylphenyl)-2,3-dihydro-1-benzofuran-2-yl]methyl}amine,
(±)-{[5-cyclopentyl-7-(2-chlorophenyl)-2,3-dihydro-1-benzofuran-2-yl]methyl}amine,
(±)-{[5-isocyano-7-(2-methylphenyl)-2,3-dihydro-1-benzofuran-2-yl]methyl}amine,
(±)-{[5-isocyano-7-(2-chlorophenyl)-2,3-dihydro-1-benzofuran-2-yl]methyl}amine,
(±)-{[5-(trifluoromethyl)-7-(2-fluorophenyl)-2,3-dihydro-1-benzofuran-2-yl]methyl}amine,
(±)-{[5-(trifluoromethyl)-7-(2-methylphenyl)-2,3-dihydro-1-benzofuran-2-yl]methyl}amine,
(±)-{[5-(trifluoromethyl)-7-(2-chlorophenyl)-2,3-dihydro-1-benzofuran-2-yl]methyl}amine,
(±)-{[5-(trifluoromethyl)-7-(2-methoxyphenyl)-2,3-dihydro-1-benzofuran-2-yl]methyl}amine,
(±)-{[5-(trifluoromethyl)-7-(2-(trifluoromethyl)phenyl)-2,3-dihydro-1-benzofuran-2-yl]methyl}amine,
(±)-{[5-(trifluoromethyl)-7-(3-methylphenyl)-2,3-dihydro-1-benzofuran-2-yl]methyl}amine,
(±)-{[5-(trifluoromethyl)-7-(3-fluorophenyl)-2,3-dihydro-1-benzofuran-2-yl]methyl}amine,
(±)-{[5-(trifluoromethyl)-7-(3-chlorophenyl)-2,3-dihydro-1-benzofuran-2-yl]methyl}amine,
(±)-{[5-(trifluoromethyl)-7-(3-methoxyphenyl)-2,3-dihydro-1-benzofuran-2-yl]methyl}amine,
(±)-{[5-(trifluoromethyl)-7-(3-(trifluoromethyl)phenyl)-2,3-dihydro-1-benzofuran-2-yl]methyl}amine,
(±)-{[5-(trifluoromethyl)-7-(4-methylphenyl)-2,3-dihydro-1-benzofuran-2-yl]methyl}amine,
(±)-{[5-(trifluoromethyl)-7-(4-fluorophenyl)-2,3-dihydro-1-benzofuran-2-yl]methyl}amine,
(±)-{[5-(trifluoromethyl)-7-(4-chlorophenyl)-2,3-dihydro-1-benzofuran-2-yl]methyl}amine,
(±)-{[5-(trifluoromethyl)-7-(4-methoxyphenyl)-2,3-dihydro-1-benzofuran-2-yl]methyl}amine,
(±)-{[5-(trifluoromethyl)-7-(4-(trifluoromethyl)phenyl)-2,3-dihydro-1-benzofuran-2-yl]methyl}amine,
(±)-{[7-(2,3-dimethylphenyl)-5-(trifluoromethyl)-2,3-dihydro-1-benzofuran-2-yl]methyl}amine,
(±)-{[7-(2,3-difluorophenyl)-5-(trifluoromethyl)-2,3-dihydro-1-benzofuran-2-yl]methyl}amine,
(±)-{[7-(2,3-dichlorophenyl)-5-(trifluoromethyl)-2,3-dihydro-1-benzofuran-2-yl]methyl}amine,
(±)-{[7-(2,3-dimethoxyphenyl)-5-(trifluoromethyl)-2,3-dihydro-1-benzofuran-2-yl]methyl}amine,
(±)-{[7-(2,4-difluorophenyl)-5-(trifluoromethyl)-2,3-dihydro-1-benzofuran-2-yl]methyl}amine,
(±)-{[7-(2,4-dimethoxyphenyl)-5-(trifluoromethyl)-2,3-dihydro-1-benzofuran-2-yl]methyl}amine,
(±)-{[7-(3,4-difluorophenyl)-5-(trifluoromethyl)-2,3-dihydro-1-benzofuran-2-yl]methyl}amine,
(±)-{[7-(3-chloro-4-fluorophenyl)-5-(trifluoromethyl)-2,3-dihydro-1-benzofuran-2-yl]methyl}amine,
(±)-{[7-(2,5-difluorophenyl)-5-(trifluoromethyl)-2,3-dihydro-1-benzofuran-2-yl]methyl}amine,
(±)-{[7-(2,5-dichlorophenyl)-5-(trifluoromethyl)-2,3-dihydro-1-benzofuran-2-yl]methyl}amine,
(±)-{[7-(2,6-dimethylphenyl)-5-(trifluoromethyl)-2,3-dihydro-1-benzofuran-2-yl]methyl}amine,
(±)-{[7-(4-butylphenyl)-5-(trifluoromethyl)-2,3-dihydro-1-benzofuran-2-yl]methyl}amine,
(±)-{[7-(3-furyl)-5-(trifluoromethyl)-2,3-dihydro-1-benzofuran-2-yl]methyl}amine,
(±)-{[7-thien-3-yl-5-(trifluoromethyl)-2,3-dihydro-1-benzofuran-2-yl]methyl}amine,
(±)-{[7-pyridin-3-yl-5-(trifluoromethyl)-2,3-dihydro-1-benzofuran-2-yl]methyl}amine,
(±)-{[7-(2-chlorophenyl)-5-phenyl-2,3-dihydro-1-benzofuran-2-yl]methyl}amine,
(±)-{[7-(3-chlorophenyl)-5-phenyl-2,3-dihydro-1-benzofuran-2-yl]methyl}amine,
(±)-{[7-(4-chlorophenyl)-5-phenyl-2,3-dihydro-1-benzofuran-2-yl]methyl}amine,
(±)-{[7-(2-fluorophenyl)-5-phenyl-2,3-dihydro-1-benzofuran-2-yl]methyl}amine,
(±)-{[7-(3-fluorophenyl)-5-phenyl-2,3-dihydro-1-benzofuran-2-yl]methyl}amine,
(±)-{[7-(4-fluorophenyl)-5-phenyl-2,3-dihydro-1-benzofuran-2-yl]methyl}amine,
(±)-{[7-(2-methylphenyl)-5-phenyl-2,3-dihydro-1-benzofuran-2-yl]methyl}amine,
(±)-{[7-(3-methylphenyl)-5-phenyl-2,3-dihydro-1-benzofuran-2-yl]methyl}amine,
(±)-{[7-(4-methylphenyl)-5-phenyl-2,3-dihydro-1-benzofuran-2-yl]methyl}amine,
(±)-{[7-(2,4-difluorophenyl)-5-phenyl-2,3-dihydro-1-benzofuran-2-yl]methyl}amine,
(±)-{[7-(2,5-dichlorophenyl)-5-phenyl-2,3-dihydro-1-benzofuran-2-yl]methyl}amine,
(±)-{[7-(2-fluorophenyl)-5-methoxy-2,3-dihydro-1-benzofuran-2-yl]methyl}amine,
(±)-{[7-(2-chlorophenyl)-5-methoxy-2,3-dihydro-1-benzofuran-2-yl]methyl}amine,
(±)-{[7-(2-methylphenyl)-5-methoxy-2,3-dihydro-1-benzofuran-2-yl]methyl}amine,
(±)-{[7-(2-methoxyphenyl)-5-methoxy-2,3-dihydro-1-benzofuran-2-yl]methyl}amine,
(±)-{[5-methoxy-7-(3-thienyl)-2,3-dihydro-1-benzofuran-2-yl]methyl}amine,
(±)-{[7-(2,3-difluorophenyl)-5-methoxy-2,3-dihydro-1-benzofuran-2-yl]methyl}amine,
(±)-{[7-(2,3-dichlorophenyl)-5-methoxy-2,3-dihydro-1-benzofuran-2-yl]methyl}amine,
(±)-{[7-(2,3-dimethylphenyl)-5-methoxy-2,3-dihydro-1-benzofuran-2-yl]methyl}amine,
(±)-{[7-(2,4-difluorophenyl)-5-methoxy-2,3-dihydro-1-benzofuran-2-yl]methyl}amine,
(±)-{[7-(2,4-dichlorophenyl)-5-methoxy-2,3-dihydro-1-benzofuran-2-yl]methyl}amine,
(±)-{[7-(2,5-difluorophenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(−)-{[7-(2,5-dichlorophenyl)-5-methoxy-2,3-dihydro-1-benzofuran-2-yl]methyl}amine, (±)-{[7-(2,5-dimethylphenyl)-5-methoxy-2,3-dihydro-1-benzofuran-2-yl]methyl}amine,
(±)-{[7-(2,5-dimethoxylphenyl)-5-methoxy-2,3-dihydro-1-benzofuran-2-yl]methyl}amine,
(±)-{[7-(5-chloro-2-methoxyphenyl)-5-methoxy-2,3-dihydro-1-benzofuran-2-yl]methyl}amine,
(±)-{[7-(3-chloro-4-fluorophenyl)-5-methoxy-2,3-dihydro-1-benzofuran-2-yl]methyl}amine,
(±)-{[7-(2,6-dimethylphenyl)-5-methoxy-2,3-dihydro-1-benzofuran-2-yl]methyl}amine,
(±)-N-{[7-(2,6-dichlorophenyl)-2,3-dihydro-1-benzofuran-2-yl]methyl}ethanamine,
(±)-N-{[7-(2,6-dichlorophenyl)-2,3-dihydro-1-benzofuran-2-yl]methyl}cyclopropanamine,
(±)-N-{[7-(2,6-dichlorophenyl)-2,3-dihydro-1-benzofuran-2-yl]methyl}cyclobutanamine,
(±)-N-{[7-(2,6-dichlorophenyl)-2,3-dihydro-1-benzofuran-2-yl]methyl}propan-2-amine,
(±)-{[6-fluoro-7-(2-methylphenyl)-2,3-dihydro-1-benzofuran-2-yl]methyl}amine,
(+)-{[6-fluoro-7-(2-methylphenyl)-2,3-dihydro-1-benzofuran-2-yl]methyl}amine,
(−)-{[6-fluoro-7-(2-methylphenyl)-2,3-dihydro-1-benzofuran-2-yl]methyl}amine,
(±)-{[{[7-(2-chlorophenyl)-6-fluoro-2,3-dihydro-1-benzofuran-2-yl]methyl}amine,
(±)-{[6-chloro-7-(2-methylphenyl)-2,3-dihydro-1-benzofuran-2-yl]methyl}amine,
(±)-{[6-chloro-7-(2-chlorophenyl)-2,3-dihydro-1-benzofuran-2-yl]methyl}amine,
(±)-{[6-fluoro-7-(2-methylphenyl)-2,3-dihydro-1-benzofuran-2-yl]methyl}methylamine,
(±)-{[6-fluoro-7-(2-chlorophenyl)-2,3-dihydro-1-benzofuran-2-yl]methyl}methylamine,
(±)-{[6-chloro-7-(2-methylphenyl)-2,3-dihydro-1-benzofuran-2-yl]methyl}methylamine,
(±)-{[6-chloro-7-(2-chlorophenyl)-2,3-dihydro-1-benzofuran-2-yl]methyl}methylamine,
(±)-[(N-methyl-1-[7-(2-methylphenyl)-2,3-dihydro-1-benzofuran-2-yl]methanamine,
(−)-N-methyl-1-[7-(2-methylphenyl)-2,3-dihydro-1-benzofuran-2-yl]methanamine,
(+)-N-methyl-1-[7-(2-methylphenyl)-2,3-dihydro-1-benzofuran-2-yl]methanamine,
(±)-[(N-methyl-1-[7-(2-chlorophenyl)-2,3-dihydro-1-benzofuran-2-yl]methanamine,
(+)-N-methyl-1-[7-(2-chlorophenyl)-2,3-dihydro-1-benzofuran-2-yl]methanamine,
(−)-N-methyl-1-[7-(2-chlorophenyl)-2,3-dihydro-1-benzofuran-2-yl]methanamine,
(±)-[(N-methyl-1-[7-(2-fluorophenyl)-2,3-dihydro-1-benzofuran-2-yl]methanamine,
(±)-[(N-methyl-1-[7-(2-methoxyphenyl)-2,3-dihydro-1-benzofuran-2-yl]methanamine,
(±)-[(N-methyl-1-[7-(3-methylphenyl)-2,3-dihydro-1-benzofuran-2-yl]methanamine,
(±)-[(N-methyl-1-[7-(3-fluorophenyl)-2,3-dihydro-1-benzofuran-2-yl]methanamine,
(±)-[(N-methyl-1-[7-(3-chlorophenyl)-2,3-dihydro-1-benzofuran-2-yl]methanamine,
(±)-[(N-methyl-1-[7-(3-methoxyphenyl)-2,3-dihydro-1-benzofuran-2-yl]methanamine,
(±)-[(N-methyl-1-[7-(4-methylphenyl)-2,3-dihydro-1-benzofuran-2-yl]methanamine,
(±)-[(N-methyl-1-[7-(4-fluorophenyl)-2,3-dihydro-1-benzofuran-2-yl]methanamine,
(±)-[(N-methyl-1-[7-(4-chlorophenyl)-2,3-dihydro-1-benzofuran-2-yl]methanamine,
(±)-[(N-methyl-1-[7-(4-methoxyphenyl)-2,3-dihydro-1-benzofuran-2-yl]methanamine,
(±)-[(N-methyl-1-[7-(2,3-dimethylphenyl)-2,3-dihydro-1-benzofuran-2-yl]methanamine,
(±)-[(N-methyl-1-[7-(2,3-dimethoxyphenyl)-2,3-dihydro-1-benzofuran-2-yl]methanamine,
(±)-[(N-methyl-1-[7-(2,4-difluorophenyl)-2,3-dihydro-1-benzofuran-2-yl]methanamine,
(±)-[(N-methyl-1-[7-(2,4-dichlorophenyl)-2,3-dihydro-1-benzofuran-2-yl]methanamine,
(±)-[(N-methyl-1-[7-(2,4-dimethoxyphenyl)-2,3-dihydro-1-benzofuran-2-yl]methanamine,
(±)-[(N-methyl-1-[7-(2,5-dimethylphenyl)-2,3-dihydro-1-benzofuran-2-yl]methanamine,
(±)-[(N-methyl-1-[7-(2,5-difluorophenyl)-2,3-dihydro-1-benzofuran-2-yl]methanamine,
(±)-[(N-methyl-1-[7-(2,5-dichlorophenyl)-2,3-dihydro-1-benzofuran-2-yl]methanamine,
(±)-[(N-methyl-1-[7-(5-chloro-2-methoxyphenyl)-2,3-dihydro-1-benzofuran-2-yl]methanamine,
(±)-[(N-methyl-1-[7-(5-chloro-2-methylphenyl)-2,3-dihydro-1-benzofuran-2-yl]methanamine,
(±)-[(N-methyl-1-[7-(2,6-dimethylphenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(+)-{[7-(2,6-dichlorophenyl)-2,3-dihydro-1-benzofuran-2-yl]methyl}methylamine,
(±)-N-methyl-1-(7-pyridin-3-yl-2,3-dihydro-1-benzofuran-2-yl)methanamine,
(±)-[(N-methyl-1-[7-(2,3-difluorophenyl)-2,3-dihydro-1-benzofuran-2-yl]methanamine,
(±)-{[5-fluoro-7-(2-fluorophenyl)-2,3-dihydro-1-benzofuran-2-yl]methyl}methylamine,
(±)-{[5-fluoro-7-(2-chlorophenyl)-2,3-dihydro-1-benzofuran-2-yl]methyl}methylamine,
(±)-{[5-fluoro-7-(2-methylphenyl)-2,3-dihydro-1-benzofuran-2-yl]methyl}methylamine,
(−)-{[5-fluoro-7-(2-methylphenyl)-2,3-dihydro-1-benzofuran-2-yl]methyl}methylamine,
(+)-{[5-fluoro-7-(2-methylphenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-{[7-(2,3-dimethoxyphenyl)-5-fluoro-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(−)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-difluorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(−)-{[5-fluoro-7-(2,5-dichlorophenyl)-2,3-dihydro-1-benzofuran-2-yl]methyl}methylamine,
(±)-{[7-(2,5-dimethylphenyl)-5-fluoro-2,3-dihydro-1-benzofuran-2-yl]methyl}methylamine, (±)-{[7-(2,6-dimethylphenyl)-5-fluoro-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-{[5-fluoro-7-(5-methoxy-2-methylphenyl)-2,3-dihydro-1-benzofuran-2-yl]methyl}methylamine,
(±)-{[5-fluoro-7-(2-methoxy-5-methylphenyl)-2,3-dihydro-1-benzofuran-2-yl]methyl}methylamine,
(±)-{[7-(5-chloro-2-methoxyphenyl)-5-fluoro-2,3-dihydro-1-benzofuran-2-yl]methyl}methylamine,
(±)-[(5-fluoro-7-pyridin-3-yl-2,3-dihydro-1-benzofuran-2-yl)methyl]methylamine,
(±)-[(5-chloro-7-(2-methoxyphenyl)-2,3-dihydro-1-benzofuran-2-yl]methyl}methylamine,
(±)-{[5-chloro-7-(2,6-dimethylphenyl)-2,3-dihydro-1-benzofuran-2-yl]methyl}methylamine,
(±)-[(5-chloro-7-(2-fluorophenyl)-2,3-dihydro-1-benzofuran-2-yl]methyl}methylamine,
(±)-{[5-chloro-7-(2,3-difluorophenyl)-2,3-dihydro-1-benzofuran-2-yl]methyl}methylamine,
(±)-{[5-chloro-7-(2,3-dichlorophenyl)-2,3-dihydro-1-benzofuran-2-yl]methyl}methylamine,
(±)-{[5-chloro-7-(2,3-dimethylphenyl)-2,3-dihydro-1-benzofuran-2-yl]methyl}methylamine,
(±)-{[5-chloro-7-(2,3-dimethoxyphenyl)-2,3-dihydro-1-benzofuran-2-yl]methyl}methylamine,
(±)-{[5-chloro-7-(2,4-difluorophenyl)-2,3-dihydro-1-benzofuran-2-yl]methyl}methylamine,
(±)-{[5-chloro-7-(2,4-dichlorophenyl)-2,3-dihydro-1-benzofuran-2-yl]methyl}methylamine,
(±)-{[5-chloro-7-(2,4-dimethoxyphenyl)-2,3-dihydro-1-benzofuran-2-yl]methyl}methylamine,
(±)-{[5-chloro-7-(2,5-difluorophenyl)-2,3-dihydro-1-benzofuran-2-yl]methyl}methylamine,
(±)-{[5-chloro-7-(2,5-dichlorophenyl)-2,3-dihydro-1-benzofuran-2-yl]methyl}methylamine,
(±)-{[5-chloro-7-(5-chloro-2-methoxyphenyl)-2,3-dihydro-1-benzofuran-2-yl]methyl}methylamine,
(±)-{[5-chloro-7-(3,4-difluorophenyl)-2,3-dihydro-1-benzofuran-2-yl]methyl}methylamine,
(±)-[5-chloro-7-(3-chloro-4-fluorophenyl)-2,3-dihydro-1-benzofuran-2-yl]methyl}methylamine,
(±)-{[7-(2-fluorophenyl)-5-methyl-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2-methoxyphenyl)-5-methyl-2,3-dihydro-1-benzofuran-2-yl]methyl}methylamine,
(±)-{[7-(3-methylphenyl)-5-methyl-2,3-dihydro-1-benzofuran-2-yl]methyl}methylamine,
(±)-{[7-(3-chlorophenyl)-5-methyl-2,3-dihydro-1-benzofuran-2-yl]methyl}methylamine,
(±)-{[7-(4-methylphenyl)-5-methyl-2,3-dihydro-1-benzofuran-2-yl]methyl}methylamine,
(±)-{[7-(4-chlorophenyl)-5-methyl-2,3-dihydro-1-benzofuran-2-yl]methyl}methylamine,
(±)-{[7-(4-fluorophenyl)-5-methyl-2,3-dihydro-1-benzofuran-2-yl]methyl}methylamine,
(±)-{[7-(4-methoxyphenyl)-5-methyl-2,3-dihydro-1-benzofuran-2-yl]methyl}methylamine,
(±)-{[7-(2,3-dimethoxyphenyl)-5-methyl-2,3-dihydro-1-benzofuran-2-yl]methyl}methylamine,
(±)-{[7-(2,4-dichlorophenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(−)-{[7-(2,5-dichlorophenyl)-5-methyl-2,3-dihydro-1-benzofuran-2-yl]methyl}methylamine,
(±)-{[7-(2,6-dimethylphenyl)-5-methyl-2,3-dihydro-1-benzofuran-2-yl]methyl}methylamine,
(±)-{[7-(2,6-dichlorophenyl)-5-methyl-2,3-dihydro-1-benzofuran-2-yl]methyl}methylamine,
(±)-{[7-(2-fluorophenyl)-5-methoxy-2,3-dihydro-1-benzofuran-2-yl]methyl}methylamine,
(±)-{[7-(2-chlorophenyl)-5-methoxy-2,3-dihydro-1-benzofuran-2-yl]methyl}methylamine,
(±)-{[7-(2-methylphenyl)-5-methoxy-2,3-dihydro-1-benzofuran-2-yl]methyl}methylamine,
(±)-{[7-(2,3-difluorophenyl)-5-methoxy-2,3-dihydro-1-benzofuran-2-yl]methyl}methylamine,
(±)-{[7-(2,3-dichlorophenyl)-5-methoxy-2,3-dihydro-1-benzofuran-2-yl]methyl}methylamine,
(±)-{[7-(2,3-dimethylphenyl)-5-methoxy-2,3-dihydro-1-benzofuran-2-yl]methyl}methylamine,
(±)-{[7-(2,4-difluorophenyl)-5-methoxy-2,3-dihydro-1-benzofuran-2-yl]methyl}methylamine,
(±)-{[7-(2,5-difluorophenyl)-5-methoxy-2,3-dihydro-1-benzofuran-2-yl]methyl}methylamine,
(±)-{[7-(2,5-dichlorophenyl)-5-methoxy-2,3-dihydro-1-benzofuran-2-yl]methyl}methylamine,
(±)-{[7-(2,5-dimethylphenyl)-5-methoxy-2,3-dihydro-1-benzofuran-2-yl]methyl}methylamine,
(±)-{[7-(2,5-dimethoxyphenyl)-5-methoxy-2,3-dihydro-1-benzofuran-2-yl]methyl}methylamine,
(±)-{[7-(5-chloro-2-methoxyphenyl)-5-methoxy-2,3-dihydro-1-benzofuran-2-yl]methyl}methylamine,
(±)-{[7-(3-chloro-4-fluorophenyl)-5-methoxy-2,3-dihydro-1-benzofuran-2-yl]methyl}methylamine,
(±)-{[7-(2,6-dimethylphenyl)-5-methoxy-2,3-dihydro-1-benzofuran-2-yl]methyl}methylamine,
(±)-{[7-(2-chlorophenyl)-5-phenyl-2,3-dihydro-1-benzofuran-2-yl]methyl}methylamine,
(±)-{[7-(3-chlorophenyl)-5-phenyl-2,3-dihydro-1-benzofuran-2-yl]methyl}methylamine,
(±)-{[7-(4-chlorophenyl)-5-phenyl-2,3-dihydro-1-benzofuran-2-yl]methyl}methylamine,
(±)-{[7-(2-fluorophenyl)-5-phenyl-2,3-dihydro-1-benzofuran-2-yl]methyl}methylamine,
(±)-{[7-(3-fluorophenyl)-5-phenyl-2,3-dihydro-1-benzofuran-2-yl]methyl}methylamine,
(±)-{[7-(4-fluorophenyl)-5-phenyl-2,3-dihydro-1-benzofuran-2-yl]methyl}methylamine,
(±)-{[7-(2-methylphenyl)-5-phenyl-2,3-dihydro-1-benzofuran-2-yl]methyl}methylamine,
(±)-{[7-(3-methylphenyl)-5-phenyl-2,3-dihydro-1-benzofuran-2-yl]methyl}methylamine,
(±)-{[7-(4-methylphenyl)-5-phenyl-2,3-dihydro-1-benzofuran-2-yl]methyl}methylamine,
(±)-{[7-(2-methoxyphenyl)-5-phenyl-2,3-dihydro-1-benzofuran-2-yl]methyl}methylamine,
(±)-{[7-(3-methoxyphenyl)-5-phenyl-2,3-dihydro-1-benzofuran-2-yl]methyl}methylamine,
(±)-{[7-(4-methoxyphenyl)-5-phenyl-2,3-dihydro-1-benzofuran-2-yl]methyl}methylamine,
(±)-{[7-(2,4-difluorophenyl)-5-phenyl-2,3-dihydro-1-benzofuran-2-yl]methyl}methylamine,
(±)-N-methyl-1-[7-(3-methylphenyl)-5-(trifluoromethyl)-2,3-dihydro-1-benzofuran-2-yl]methanamine,
(±)-N-methyl-1-[7-(3-fluorophenyl)-5-(trifluoromethyl)-2,3-dihydro-1-benzofuran-2-yl]methanamine, (±)-N-methyl-1-[7-(2,3-difluorophenyl)-5-(trifluoromethyl)-2,3-dihydro-1-benzofuran-2-yl]methanamine,
(±)-N-methyl-1-[7-(3,4-difluorophenyl)-5-(trifluoromethyl)-2,3-dihydro-1-benzofuran-2-yl]methanamine,
(±)-N-methyl-1-[7-(2,5-difluorophenyl)-5-(trifluoromethyl)-2,3-dihydro-1-benzofuran-2-yl]methanamine,
(±)-N-methyl-1-[7-(2,3-dichlorophenyl)-5-(trifluoromethyl)-2,3-dihydro-1-benzofuran-2-yl]methanamine,
(±)-{[7-(3-chloro-4-fluorophenyl)-5-(trifluoromethyl)-2,3-dihydro-1-benzofuran-2-yl]methyl}methylamine,
(±)-N-methyl-1-[7-(2,4-dimethoxyphenyl)-5-(trifluoromethyl)-2,3-dihydro-1-benzofuran-2-yl]methanamine,
(±)-{[7-[3,5-bis(trifluoromethyl)phenyl]-5-(trifluoromethyl)-2,3-dihydro-1-benzofuran-2-yl]methyl}methylamine,
(+){[7-(2,6-dichlorophenyl)-5-fluoro-2,3-dihydro-1-benzofuran-2-yl]methyl}methylamine,
(−){[7-(2,6-dichlorophenyl)-5-fluoro-2,3-dihydro-1-benzofuran-2-yl]methyl}methylamine,
(R)-[7-(2-chloro-phenyl)-(5-Fluoro-2,3-dihydro-benzofuran-2-ylmethyl)methyl-amine,
(R)-[7-(2,6-dichloro-phenyl)-5-Fluoro-2,3-dihydro-benzofuran-2-ylmethyl]ethylamine,
(R)-[7-(2,6-dichloro-phenyl)-5-Fluoro-2,3-dihydro-benzofuran-2-ylmethyl]dimethylamine,
{[(2R)-7-(5-chloro-2-methylphenyl)-5-fluoro-2,3-dihydro-1-benzofuran-2-yl]methyl}amine,
{[(2R)-7-(4-chloro-2-methylphenyl)-5-fluoro-2,3-dihydro-1-benzofuran-2-yl]methyl}amine,
(−)-{[7-(2,6-dichlorophenyl)-5-fluoro-2,3-dihydro-1-benzofuran-2-yl]methyl}amine,
(+)-{[7-(2,6 dichlorophenyl)-5-fluoro-2,3-dihydro-1-benzofuran-2-yl]methyl}amine,
(±)-{[2-[6-chloro-7-(2-chlorophenyl)-2,3-dihydro-1-benzofuran-2-yl]ethyl}amine,
(±)-{[2-[7-(2,6-dichlorophenyl)-5-fluoro-2,3-dihydro-1-benzofuran-2-yl]ethyl}amine,
(±)-{[2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(+)-{N-methyl-1-[(7-(2,4,6-trichlorophenyl)-2,3-dihydro-1-benzofuran-2-yl]methanamine,
(−)-{N-methyl-1-[(7-(2,4,6-trichlorophenyl)-2,3-dihydro-1-benzofuran-2-yl]methanamine,
(+)-{[7-(2,6-dimethylphenyl)-5-fluoro-2,3-dihydro-1-benzofuran-2-yl]methyl}methylamine,
(−)-{[7-(2,6-dimethylphenyl)-5-fluoro-2,3-dihydro-1-benzofuran-2-yl]methyl}methylamine,
(−)-{[7-(2,6-dimethylphenyl)-5-methoxy-2,3-dihydro-1-benzofuran-2-yl]methyl}methylamine,
(+)-{[7-(2,6-dimethylphenyl)-5-methoxy-2,3-dihydro-1-benzofuran-2-yl]methyl}methylamine,
(+)-{[5-chloro-7-(2,5-dichlorophenyl)-2,3-dihydro-1-benzofuran-2-yl]methyl}methylamine,
(−)-{[5-chloro-7-(2,5-dichlorophenyl)-2,3-dihydro-1-benzofuran-2-yl]methyl}methylamine,
(−)-{[5-chloro-7-(2,6-dimethylphenyl)-2,3-dihydro-1-benzofuran-2-yl]methyl}methylamine,
(+)-{[5-chloro-7-(2,6-dimethylphenyl)-2,3-dihydro-1-benzofuran-2-yl]methyl}methylamine,
(+)-{[7-(2,3-dimethoxyphenyl)-5-methyl-2,3-dihydro-1-benzofuran-2-yl]methyl}methylamine,
(−)-{[7-(2,3-dimethoxyphenyl)-5-methyl-2,3-dihydro-1-benzofuran-2-yl]methyl}methylamine,
(−)-{[7-(2,3-dimethoxyphenyl)-5-fluoro-2,3-dihydro-1-benzofuran-2-yl]methyl}methylamine, or
(+)-{[7-(2,3-dimethoxyphenyl)-5-fluoro-2,3-dihydro-1-benzofuran-2-yl]methyl}methylamine;

or a pharmaceutically acceptable salt thereof.

16. The compound of claim 15 which is:
(±)-1-[7-(2,3-dimethylphenyl)-2,3-dihydro-1-benzofuran-2-yl]methanamine,
(±)-{[7-(2,3-dimethoxyphenyl)-2,3-dihydro-1-benzofuran-2-yl]methyl}amine,
(−)-{[(7-(2,3-dimethoxyphenyl)-2,3-dihydro-1-benzofuran-2-yl]methyl}amine,
(+)-{[(7-(2,3-dimethoxyphenyl)-2,3-dihydro-1-benzofuran-2-yl]methyl}amine,
(+)-{[7-(4-chloro-2-methylphenyl)-2,3-dihydro-1-benzofuran-2-yl]methyl}amine,
(−)-{[7-(4-chloro-2-methylphenyl)-2,3-dihydro-1-benzofuran-2-yl]methyl}amine,
(±)-{[7-(2,3-difluorophenyl)-2,3-dihydro-1-benzofuran-2-yl]methyl}amine,
(±)-{[7-(2,5-dimethylphenyl)-2,3-dihydro-1-benzofuran-2-yl]methyl}amine,
(±)-{[7-(2,5-dimethoxyphenyl)-2,3-dihydro-1-benzofuran-2-yl]methyl}amine,
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(−)-{[7-(2,5-dichlorophenyl)-2,3-dihydro-1-benzofuran-2-yl]methyl}amine,
(±)-{[7-(2,4,6-trichlorophenyl)-2,3-dihydro-1-benzofuran-2-yl]methyl}amine,
(±)-{[7-(4-chloro-2-methylphenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(±)-{[7-(5-chloro-2-methoxyphenyl)-2,3-dihydro-1-benzofuran-2-yl]methyl}amine,
(±)-[(7-pyridin-3-yl-2,3-dihydro-1-benzofuran-2-yl)methyl]amine,
(+)-{[7-pyridin-3-yl-2,3-dihydro-1-benzofuran-2-yl]methyl}amine,
(−)-{[7-pyridin-3-yl-2,3-dihydro-1-benzofuran-2-yl]methyl}amine,
(±)-{[5-fluoro-7-(2-methoxyphenyl)-2,3-dihydro-1-benzofuran-2-yl]methyl}amine,
(±)-{[5-fluoro-7-(3-fluorophenyl)-2,3-dihydro-1-benzofuran-2-yl]methyl}amine,
(±)-{[5-fluoro-7-(3-methoxyphenyl)-2,3-dihydro-1-benzofuran-2-yl]methyl}amine,
(±)-{[5-fluoro-7-(3-methylphenyl)-2,3-dihydro-1-benzofuran-2-yl]methyl}amine,
(±)-{[5-fluoro-7-(4-fluorophenyl)-2,3-dihydro-1-benzofuran-2-yl]methyl}amine,
(±)-{[5-fluoro-7-(4-chlorophenyl)-2,3-dihydro-1-benzofuran-2-yl]methyl}amine,
(±)-{[5-fluoro-7-(4-methylphenyl)-2,3-dihydro-1-benzofuran-2-yl]methyl}amine,
(±)-{[5-fluoro-7-(4-methoxyphenyl)-2,3-dihydro-1-benzofuran-2-yl]methyl}amine,
(±)-[(5-fluoro-7-thien-3-yl-2,3-dihydro-1-benzofuran-2-yl)methyl]amine,
(±)-{[5-fluoro-7-(3-furyl)-2,3-dihydro-1-benzofuran-2-yl]methyl}amine,
(±)-[(5-fluoro-7-pyridin-2-yl-2,3-dihydro-1-benzofuran-2-yl)methyl]amine,
(±)-[(5-fluoro-7-pyridin-3-yl-2,3-dihydro-1-benzofuran-2-yl)methyl]amine, (−)-[(5-fluoro-7-pyridin-3-yl-2,3-dihydro-1-benzofuran-2-yl)methyl]amine,
(+)-{[5-fluoro-7-pyridin-3-yl-2,3-dihydro-1-benzofuran-2-yl]methyl}amine,
(±)-[(5-fluoro-7-pyridin-4-yl-2,3-dihydro-1-benzofuran-2-yl)methyl]amine,
(±)-[(5-fluoro-7-pyrimidin-5-yl-2,3-dihydro-1-benzofuran-2-yl)methyl]amine,
(±)-{[7-(2,3-dichlorophenyl)-5-fluoro-2,3-dihydro-1-benzofuran-2-yl]methyl}amine,
(±)-{[7-(2,3-dimethoxyphenyl)-5-fluoro-2,3-dihydro-1-benzofuran-2-yl]methyl}amine,
(−)-{[7-(2,3-dimethoxyphenyl)-5-fluoro-2,3-dihydro-1-benzofuran-2-yl]methyl}amine,
(+)-{[7-(2,3-dimethoxyphenyl)-5-fluoro-2,3-dihydro-1-benzofuran-2-yl]methyl}amine,
(±)-{[7-(2,4-difluorophenyl)-5-fluoro-2,3-dihydro-1-benzofuran-2-yl]methyl}amine,
(±)-{[7-(2,4-dichlorophenyl)-5-fluoro-2,3-dihydro-1-benzofuran-2-yl]methyl}amine,
(−)-{[5-fluoro-7-(2,4-dichlorophenyl)-2,3-dihydro-1-benzofuran-2-yl]methyl}amine,
(+)-{[5-fluoro-7-(2,4-dichlorophenyl)-2,3-dihydro-1-benzofuran-2-yl]methyl}amine,
(±)-{[7-(2,4-dimethoxyphenyl)-5-fluoro-2,3-dihydro-1-benzofuran-2-yl]methyl}amine,
(±)-{[7-(2,5-difluorophenyl)-5-fluoro-2,3-dihydro-1-benzofuran-2-yl]methyl}amine,
(±)-{[7-(2,5-dichlorophenyl)-5-fluoro-2,3-dihydro-1-benzofuran-2-yl]methyl}amine,
(±)-{[7-(2,5-dimethylphenyl)-5-fluoro-2,3-dihydro-1-benzofuran-2-yl]methyl}amine,
(±)-{[7-(2,5-dimethoxyphenyl)-5-fluoro-2,3-dihydro-1-benzofuran-2-yl]methyl}amine,
(±)-{[5-fluoro-7-(5-methoxy-2-methylphenyl)-2,3-dihydro-1-benzofuran-2-yl]methyl}amine,
(±)-{[5-fluoro-7-(2-methoxy-5-methylphenyl)-2,3-dihydro-1-benzofuran-2-yl]methyl}amine,
(±)-{[7-(2,6-difluorophenyl)-5-fluoro-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(+)-{[7-(2,6-dimethylphenyl)-5-fluoro-2,3-dihydro-1-benzofuran-2-yl]methyl}amine,
(−)-{[7-(2,6-dimethylphenyl)-5-fluoro-2,3-dihydro-1-benzofuran-2-yl]methyl}amine,
(±)-{[7-(2,6-dichlorophenyl)-5-fluoro-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine,
(±)-1-cyclopropyl-N-{[7-(2,6-dichlorophenyl)-5-fluoro-2,3-dihydro-1-benzofuran-2-yl]methyl}methanamine,
(±)-N-{[7-(2,6-dichlorophenyl)-5-fluoro-2,3-dihydro-1-benzofuran-2-yl]methyl}cyclobutanamine,
(±)-N-{[7-(2,6-dichlorophenyl)-5-fluoro-2,3-dihydro-1-benzofuran-2-yl]methyl}ethanamine,
(±)-N-{[7-(2,6-dichlorophenyl)-5-fluoro-2,3-dihydro-1-benzofuran-2-yl]methyl}propan-1-amine,
(±)-N-{[7-(2,6-dichlorophenyl)-5-fluoro-2,3-dihydro-1-benzofuran-2-yl]methyl}propan-2-amine,
(±)-{[7-(2,6-dichlorophenyl)-5-fluoro-2,3-dihydro-1-benzofuran-2-yl]methyl}dimethylamine,
(±)-1-{[7-(2,6-dichlorophenyl)-5-fluoro-2,3-dihydro-1-benzofuran-2-yl]methyl}piperidine
(±)-1-{[7-(2,6-dichlorophenyl)-5-fluoro-2,3-dihydro-1-benzofuran-2-yl]methyl}morpholine
(±)-1-{[7-(2,6-dichlorophenyl)-5-fluoro-2,3-dihydro-1-benzofuran-2-yl]methyl}pyrrolidine
(±)-{[5-chloro-7-(2-fluorophenyl)-2,3-dihydro-1-benzofuran-2-yl]methyl}amine,
(±)-{[5-chloro-7-(2-methoxyphenyl)-2,3-dihydro-1-benzofuran-2-yl]methyl}amine,
(±)-{[5-chloro-7-(3-furyl)-2,3-dihydro-1-benzofuran-2-yl]methyl}amine,
(±)-{[5-chloro-7-(2,3-difluorophenyl)-2,3-dihydro-1-benzofuran-2-yl]methyl}amine,
(−)-{[5-chloro-7-(2,3-difluorophenyl)-2,3-dihydro-1-benzofuran-2-yl]methyl}amine,
(+)-{[5-chloro-7-(2,3-difluorophenyl)-2,3-dihydro-1-benzofuran-2-yl]methyl}amine,
(±)-{[5-chloro-7-(2,3-dichlorophenyl)-2,3-dihydro-1-benzofuran-2-yl]methyl}amine,
(±)-{[5-chloro-7-(2,3-dimethylphenyl)-2,3-dihydro-1-benzofuran-2-yl]methyl}amine,
(±)-{[5-chloro-7-(2,3-dimethoxyphenyl)-2,3-dihydro-1-benzofuran-2-yl]methyl}amine,
(±)-{[5-chloro-7-(2,4-difluorophenyl)-2,3-dihydro-1-benzofuran-2-yl]methyl}amine,
(±)-{[5-chloro-7-(2,4-dichlorophenyl)-2,3-dihydro-1-benzofuran-2-yl]methyl}amine,
(−)-{[5-chloro-7-(2,4-dichlorophenyl)-2,3-dihydro-1-benzofuran-2-yl]methyl}amine,
(+)-{[5-chloro-7-(2,4-dichlorophenyl)-2,3-dihydro-1-benzofuran-2-yl]methyl}amine,
(±)-{[5-chloro-7-(2,4-dimethoxyphenyl)-2,3-dihydro-1-benzofuran-2-yl]methyl}amine,
(±)-{[5-chloro-7-(2,5-difluorophenyl)-2,3-dihydro-1-benzofuran-2-yl]methyl}amine,
(±)-{[5-chloro-7-(2,5-dichlorophenyl)-2,3-dihydro-1-benzofuran-2-yl]methyl}amine,
(±)-{[5-chloro-7-(5-chloro-2-methoxyphenyl)-2,3-dihydro-1-benzofuran-2-yl]methyl}amine,
(±)-{[5-chloro-7-(3,4-difluorophenyl)-2,3-dihydro-1-benzofuran-2-yl]methyl}amine,
(±)-{[5-chloro-7-(3-chloro-4-fluorophenyl)-2,3-dihydro-1-benzofuran-2-yl]methyl}amine,
(±)-{[5-chloro-7-(2,6-dimethylphenyl)-2,3-dihydro-1-benzofuran-2-yl]methyl}amine,
(−)-{[5-chloro-7-(2,6-dimethylphenyl)-2,3-dihydro-1-benzofuran-2-yl]methyl}amine,
(+)-{[5-chloro-7-(2,6-dimethylphenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(±)-{[(5-chloro-7-pyridin-3-yl-2,3-dihydro-1-benzofuran-2-yl)methyl]amine,
(±)-N-{[5-chloro-7-(2,6-dimethylphenyl)-2,3-dihydro-1-benzofuran-2-yl]methyl}cyclopropanamine,
(±)-N-{[5-chloro-7-(2,6-dimethylphenyl)-2,3-dihydro-1-benzofuran-2-yl]methyl}(cyclopropylmethyl)amine,
(±)-N-{[5-chloro-7-(2,6-dimethylphenyl)-2,3-dihydro-1-benzofuran-2-yl]methyl}cyclobutanamine,
(±)-N-{[5-chloro-7-(2,6-dimethylphenyl)-2,3-dihydro-1-benzofuran-2-yl]methyl}ethanamine,
(±)-N-{[5-chloro-7-(2,6-dimethylphenyl)-2,3-dihydro-1-benzofuran-2-yl]methyl}propan-2-amine,
(±)-{[5-chloro-7-(2,6-dimethylphenyl)-2,3-dihydro-1-benzofuran-2-yl]methyl}dimethylamine,
(±)-N-{[5-chloro-7-(2,6-dimethylphenyl)-2,3-dihydro-1-benzofuran-2-yl]methyl}propan-1-amine,
(±)-1-{[5-chloro-7-(2,6-dimethylphenyl)-2,3-dihydro-1-benzofuran-2-yl]methyl}piperazine (±)-1-{[5-chloro-7-(2,6-dimethylphenyl)-2,3-dihydro-1-benzofuran-2-yl]methyl}pyrrolidine
(±)-{[7-(2-methylphenyl)-5-methyl-2,3-dihydro-1-benzofuran-2-yl]methyl}amine,
(±)-{[7-(2-fluorophenyl)-5-methyl-2,3-dihydro-1-benzofuran-2-yl]methyl}amine,
(±)-{[7-(2-methoxyphenyl)-5-methyl-2,3-dihydro-1-benzofuran-2-yl]methyl}amine,
(±)-{[7-(2-chlorophenyl)-5-methyl-2,3-dihydro-1-benzofuran-2-yl]methyl}amine,
(±)-({5-methyl-7-[2-(trifluoromethyl)phenyl]-2,3-dihydro-1-benzofuran-2-yl}methyl)amine,
(±)-{[7-(3-chlorophenyl)-5-methyl-2,3-dihydro-1-benzofuran-2-yl]methyl}amine,
(±)-{[7-(3-methylphenyl)-5-methyl-2,3-dihydro-1-benzofuran-2-yl]methyl}amine,
(±)-{[7-(4-methylphenyl)-5-methyl-2,3-dihydro-1-benzofuran-2-yl]methyl}amine,
(±)-{[7-(4-fluorophenyl)-5-methyl-2,3-dihydro-1-benzofuran-2-yl]methyl}amine,
(±)-{[7-(4-chlorophenyl)-5-methyl-2,3-dihydro-1-benzofuran-2-yl]methyl}amine,
(±)-{[7-(4-methoxyphenyl)-5-methyl-2,3-dihydro-1-benzofuran-2-yl]methyl}amine,
(±)-{[7-(2,3-dimethoxyphenyl)-5-methyl-2,3-dihydro-1-benzofuran-2-yl]methyl}amine,
(−)-{[7-(2,3-dimethoxyphenyl)-5-methyl-2,3-dihydro-1-benzofuran-2-yl]methyl}amine,
(+)-{[7-(2,3-dimethoxyphenyl)-5-methyl-2,3-dihydro-1-benzofuran-2-yl]methyl}amine,
(±)-{[7-(2,4-dichlorophenyl)-5-methyl-2,3-dihydro-1-benzofuran-2-yl]methyl}amine,
(−)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dimethylphenyl)-5-methyl-2,3-dihydro-1-benzofuran-2-yl]methyl}amine,
(±)-{[7-(2,6-dichlorophenyl)-5-methyl-2,3-dihydro-1-benzofuran-2-yl]methyl}amine,
(−)-{[7-(2,6-dichlorophenyl)-5-methyl-2,3-dihydro-1-benzofuran-2-yl]methyl}amine,
(+)-{[7-(2,6-dichlorophenyl)-5-methyl-2,3-dihydro-1-benzofuran-2-yl]methyl}amine,
(±)-{[5-ethyl-7-(2-methylphenyl)-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[5-isopropyl-7-(2-methylphenyl)-2,3-dihydro-1-benzofuran-2-yl]methyl}amine,
(±)-{[5-isopropyl-7-(2-chlorophenyl)-2,3-dihydro-1-benzofuran-2-yl]methyl}amine,
(±)-{[5-cyclopentyl-7-(2-methylphenyl)-2,3-dihydro-1-benzofuran-2-yl]methyl}amine,
(±)-{[5-cyclopentyl-7-(2-chlorophenyl)-2,3-dihydro-1-benzofuran-2-yl]methyl}amine,
(±)-{[5-isocyano-7-(2-methylphenyl)-2,3-dihydro-1-benzofuran-2-yl]methyl}amine,
(±)-{[5-isocyano-7-(2-chlorophenyl)-2,3-dihydro-1-benzofuran-2-yl]methyl}amine,
(±)-{[5-(trifluoromethyl)-7-(2-fluorophenyl)-2,3-dihydro-1-benzofuran-2-yl]methyl}amine,
(±)-{[5-(trifluoromethyl)-7-(2-methylphenyl)-2,3-dihydro-1-benzofuran-2-yl]methyl}amine,
(±)-{[5-(trifluoromethyl)-7-(2-chlorophenyl)-2,3-dihydro-1-benzofuran-2-yl]methyl}amine,
(±)-{[5-(trifluoromethyl)-7-(2-methoxyphenyl)-2,3-dihydro-1-benzofuran-2-yl]methyl}amine,
(±)-{[5-(trifluoromethyl)-7-(2-(trifluoromethyl)phenyl)-2,3-dihydro-1-benzofuran-2-yl]methyl}amine,
(±)-{[5-(trifluoromethyl)-7-(3-methylphenyl)-2,3-dihydro-1-benzofuran-2-yl]methyl}amine,
(±)-{[5-(trifluoromethyl)-7-(3-fluorophenyl)-2,3-dihydro-1-benzofuran-2-yl]methyl}amine,
(±)-{[5-(trifluoromethyl)-7-(3-chlorophenyl)-2,3-dihydro-1-benzofuran-2-yl]methyl}amine,
(±)-{[5-(trifluoromethyl)-7-(3-methoxyphenyl)-2,3-dihydro-1-benzofuran-2-yl]methyl}amine,
(±)-{[5-(trifluoromethyl)-7-(3-(trifluoromethyl)phenyl)-2,3-dihydro-1-benzofuran-2-yl]methyl}amine,
(±)-{[5-(trifluoromethyl)-7-(4-methylphenyl)-2,3-dihydro-1-benzofuran-2-yl]methyl}amine,
(±)-{[5-(trifluoromethyl)-7-(4-fluorophenyl)-2,3-dihydro-1-benzofuran-2-yl]methyl}amine,
(±)-{[5-(trifluoromethyl)-7-(4-chlorophenyl)-2,3-dihydro-1-benzofuran-2-yl]methyl}amine,
(±)-{[5-(trifluoromethyl)-7-(4-methoxyphenyl)-2,3-dihydro-1-benzofuran-2-yl]methyl}amine,
(±)-{[5-(trifluoromethyl)-7-(4-(trifluoromethyl)phenyl)-2,3-dihydro-1-benzofuran-2-yl]methyl}amine,
(±)-{[7-(2,3-dimethylphenyl)-5-(trifluoromethyl)-2,3-dihydro-1-benzofuran-2-yl]methyl}amine,
(±)-{[7-(2,3-difluorophenyl)-5-(trifluoromethyl)-2,3-dihydro-1-benzofuran-2-yl]methyl}amine,
(±)-{[7-(2,3-dichlorophenyl)-5-(trifluoromethyl)-2,3-dihydro-1-benzofuran-2-yl]methyl}amine,
(±)-{[7-(2,3-dimethoxyphenyl)-5-(trifluoromethyl)-2,3-dihydro-1-benzofuran-2-yl]methyl}amine,
(±)-{[7-(2,4-difluorophenyl)-5-(trifluoromethyl)-2,3-dihydro-1-benzofuran-2-yl]methyl}amine,
(±)-{[7-(2,4-dimethoxyphenyl)-5-(trifluoromethyl)-2,3-dihydro-1-benzofuran-2-yl]methyl}amine,
(±)-{[7-(3,4-difluorophenyl)-5-(trifluoromethyl)-2,3-dihydro-1-benzofuran-2-yl]methyl}amine,
(±)-{[7-(3-chloro-4-fluorophenyl)-5-(trifluoromethyl)-2,3-dihydro-1-benzofuran-2-yl]methyl}amine,
(±)-{[7-(2,5-difluorophenyl)-5-(trifluoromethyl)-2,3-dihydro-1-benzofuran-2-yl]methyl}amine,
(±)-{[7-(2,5-dichlorophenyl)-5-(trifluoromethyl)-2,3-dihydro-1-benzofuran-2-yl]methyl}amine,
(±)-{[7-(2,6-dimethylphenyl)-5-(trifluoromethyl)-2,3-dihydro-1-benzofuran-2-yl]methyl}amine,
(±)-{[7-(4-butylphenyl)-5-(trifluoromethyl)-2,3-dihydro-1-benzofuran-2-yl]methyl}amine,
(±)-{[7-(3-furyl)-5-(trifluoromethyl)-2,3-dihydro-1-benzofuran-2-yl]methyl}amine,
(±)-{[7-thien-3-yl-5-(trifluoromethyl)-2,3-dihydro-1-benzofuran-2-yl]methyl}amine,
(±)-{[7-pyridin-3-yl-5-(trifluoromethyl)-2,3-dihydro-1-benzofuran-2-yl]methyl}amine,
(±)-{[7-(2-chlorophenyl)-5-phenyl-2,3-dihydro-1-benzofuran-2-yl]methyl}amine,
(±)-{[7-(3-chlorophenyl)-5-phenyl-2,3-dihydro-1-benzofuran-2-yl]methyl}amine,
(±)-{[7-(4-chlorophenyl)-5-phenyl-2,3-dihydro-1-benzofuran-2-yl]methyl}amine,
(±)-{[7-(2-fluorophenyl)-5-phenyl-2,3-dihydro-1-benzofuran-2-yl]methyl}amine,
(±)-{[7-(3-fluorophenyl)-5-phenyl-2,3-dihydro-1-benzofuran-2-yl]methyl}amine, (±)-{[7-(4-fluorophenyl)-5-phenyl-2,3-dihydro-1-benzofuran-2-yl]methyl}amine,
(±)-{[7-(2-methylphenyl)-5-phenyl-2,3-dihydro-1-benzofuran-2-yl]methyl}amine,
(±)-{[7-(3-methylphenyl)-5-phenyl-2,3-dihydro-1-benzofuran-2-yl]methyl}amine,
(±)-{[7-(4-methylphenyl)-5-phenyl-2,3-dihydro-1-benzofuran-2-yl]methyl}amine,
(±)-{[7-(2,4-difluorophenyl)-5-phenyl-2,3-dihydro-1-benzofuran-2-yl]methyl}amine,
(±)-{[7-(2,5-dichlorophenyl)-5-phenyl-2,3-dihydro-1-benzofuran-2-yl]methyl}amine,
(±)-{[7-(2-fluorophenyl)-5-methoxy-2,3-dihydro-1-benzofuran-2-yl]methyl}amine,
(±)-{[7-(2-chlorophenyl)-5-methoxy-2,3-dihydro-1-benzofuran-2-yl]methyl}amine,
(±)-{[7-(2-methylphenyl)-5-methoxy-2,3-dihydro-1-benzofuran-2-yl]methyl}amine,
(±)-{[7-(2-methoxyphenyl)-5-methoxy-2,3-dihydro-1-benzofuran-2-yl]methyl}amine,
(±)-{[7-(2,3-difluorophenyl)-5-methoxy-2,3-dihydro-1-benzofuran-2-yl]methyl}amine,
(±)-{[7-(2,3-dichlorophenyl)-5-methoxy-2,3-dihydro-1-benzofuran-2-yl]methyl}amine,
(±)-{[7-(2,3-dimethylphenyl)-5-methoxy-2,3-dihydro-1-benzofuran-2-yl]methyl}amine,
(±)-{[7-(2,4-difluorophenyl)-5-methoxy-2,3-dihydro-1-benzofuran-2-yl]methyl}amine,
(±)-{[7-(2,4-dichlorophenyl)-5-methoxy-2,3-dihydro-1-benzofuran-2-yl]methyl}amine,
(±)-{[7-(2,5-difluorophenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(−)-{[7-(2,5-dichlorophenyl)-5-methoxy-2,3-dihydro-1-benzofuran-2-yl]methyl}amine,
(±)-{[7-(2,5-dimethylphenyl)-5-methoxy-2,3-dihydro-1-benzofuran-2-yl]methyl}amine,
(±)-{[7-(2,5-dimethoxyphenyl)-5-methoxy-2,3-dihydro-1-benzofuran-2-yl]methyl}amine,
(±)-{[7-(5-chloro-2-methoxyphenyl)-5-methoxy-2,3-dihydro-1-benzofuran-2-yl]methyl}amine,
(±)-{[7-(3-chloro-4-fluorophenyl)-5-methoxy-2,3-dihydro-1-benzofuran-2-yl]methyl}amine,
(±)-{[7-(2,6-dimethylphenyl)-5-methoxy-2,3-dihydro-1-benzofuran-2-yl]methyl}amine,
(±)-N-{[7-(2,6-dichlorophenyl)-2,3-dihydro-1-benzofuran-2-yl]methyl}ethanamine,
(±)-N-{[7-(2,6-dichlorophenyl)-2,3-dihydro-1-benzofuran-2-yl]methyl}cyclopropanamine,
(±)-N-{[7-(2,6-dichlorophenyl)-2,3-dihydro-1-benzofuran-2-yl]methyl}propan-2-amine,
(±)-{[6-fluoro-7-(2-methylphenyl)-2,3-dihydro-1-benzofuran-2-yl]methyl}amine,
(+)-{[6-fluoro-7-(2-methylphenyl)-2,3-dihydro-1-benzofuran-2-yl]methyl}amine,
(−)-{[6-fluoro-7-(2-methylphenyl)-2,3-dihydro-1-benzofuran-2-yl]methyl}amine,
(±)-{[{[7-(2-chlorophenyl)-6-fluoro-2,3-dihydro-1-benzofuran-2-yl]methyl}amine,
(±)-{[6-chloro-7-(2-chlorophenyl)-2,3-dihydro-1-benzofuran-2-yl]methyl}amine,
(±)-{[6-fluoro-7-(2-methylphenyl)-2,3-dihydro-1-benzofuran-2-yl]methyl}methylamine,
(±)-{[6-fluoro-7-(2-chlorophenyl)-2,3-dihydro-1-benzofuran-2-yl]methyl}methylamine,
(±)-{[6-chloro-7-(2-chlorophenyl)-2,3-dihydro-1-benzofuran-2-yl]methyl}methylamine,
(±)-[(N-methyl-1-[7-(2-methylphenyl)-2,3-dihydro-1-benzofuran-2-yl]methanamine,
(−)-N-methyl-1-[7-(2-methylphenyl)-2,3-dihydro-1-benzofuran-2-yl]methanamine,
(+)-N-methyl-1-[7-(2-methylphenyl)-2,3-dihydro-1-benzofuran-2-yl]methanamine,
(±)-[(N-methyl-1-[7-(2-chlorophenyl)-2,3-dihydro-1-benzofuran-2-yl]methanamine,
(+)-N-methyl-1-[7-(2-chlorophenyl)-2,3-dihydro-1-benzofuran-2-yl]methanamine,
(−)-N-methyl-1-[7-(2-chlorophenyl)-2,3-dihydro-1-benzofuran-2-yl]methanamine,
(±)-[(N-methyl-1-[7-(2-fluorophenyl)-2,3-dihydro-1-benzofuran-2-yl]methanamine,
(±)-[(N-methyl-1-[7-(2-methoxyphenyl)-2,3-dihydro-1-benzofuran-2-yl]methanamine,
(±)-[(N-methyl-1-[7-(3-methylphenyl)-2,3-dihydro-1-benzofuran-2-yl]methanamine,
(±)-[(N-methyl-1-[7-(3-fluorophenyl)-2,3-dihydro-1-benzofuran-2-yl]methanamine,
(±)-[(N-methyl-1-[7-(3-chlorophenyl)-2,3-dihydro-1-benzofuran-2-yl]methanamine,
(±)-[(N-methyl-1-[7-(3-methoxyphenyl)-2,3-dihydro-1-benzofuran-2-yl]methanamine,
(±)-[(N-methyl-1-[7-(4-methylphenyl)-2,3-dihydro-1-benzofuran-2-yl]methanamine,
(±)-[(N-methyl-1-[7-(4-fluorophenyl)-2,3-dihydro-1-benzofuran-2-yl]methanamine,
(±)-[(N-methyl-1-[7-(4-chlorophenyl)-2,3-dihydro-1-benzofuran-2-yl]methanamine,
(±)-[(N-methyl-1-[7-(4-methoxyphenyl)-2,3-dihydro-1-benzofuran-2-yl]methanamine,
(±)-[(N-methyl-1-[7-(2,3-dimethylphenyl)-2,3-dihydro-1-benzofuran-2-yl]methanamine,
(±)-[(N-methyl-1-[7-(2,3-dimethoxyphenyl)-2,3-dihydro-1-benzofuran-2-yl]methanamine,
(±)-[(N-methyl-1-[7-(2,4-difluorophenyl)-2,3-dihydro-1-benzofuran-2-yl]methanamine,
(±)-[(N-methyl-1-[7-(2,4-dichlorophenyl)-2,3-dihydro-1-benzofuran-2-yl]methanamine,
(±)-[(N-methyl-1-[7-(2,4-dimethoxyphenyl)-2,3-dihydro-1-benzofuran-2-yl]methanamine,
(±)-[(N-methyl-1-[7-(2,5-dimethylphenyl)-2,3-dihydro-1-benzofuran-2-yl]methanamine,
(±)-[(N-methyl-1-[7-(2,5-difluorophenyl)-2,3-dihydro-1-benzofuran-2-yl]methanamine,
(±)-[(N-methyl-1-[7-(2,5-dichlorophenyl)-2,3-dihydro-1-benzofuran-2-yl]methanamine,
(±)-[(N-methyl-1-[7-(5-chloro-2-methoxyphenyl)-2,3-dihydro-1-benzofuran-2-yl]methanamine,
(±)-[(N-methyl-1-[7-(5-chloro-2-methylphenyl)-2,3-dihydro-1-benzofuran-2-yl]methanamine,
(±)-[(N-methyl-1-[7-(2,6-dimethylphenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(+)-{[7-(2,6-dichlorophenyl)-2,3-dihydro-1-benzofuran-2-yl]methyl}methylamine,
(±)-N-methyl-1-(7-pyridin-3-yl-2,3-dihydro-1-benzofuran-2-yl)methanamine, (±)-[(N-methyl-1-[7-(2,3-difluorophenyl)-2,3-dihydro-1-benzofuran-2-yl]methanamine,
(±)-{[5-fluoro-7-(2-fluorophenyl)-2,3-dihydro-1-benzofuran-2-yl]methyl}methylamine,
(±)-{[5-fluoro-7-(2-chlorophenyl)-2,3-dihydro-1-benzofuran-2-yl]methyl}methylamine,
(±)-{[5-fluoro-7-(2-methylphenyl)-2,3-dihydro-1-benzofuran-2-yl]methyl}methylamine,
(−)-{[5-fluoro-7-(2-methylphenyl)-2,3-dihydro-1-benzofuran-2-yl]methyl}methylamine,
(+)-{[5-fluoro-7-(2-methylphenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-{[7-(2,3-dimethoxyphenyl)-5-fluoro-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(−)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-difluorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(−)-{[5-fluoro-7-(2,5-dichlorophenyl)-2,3-dihydro-1-benzofuran-2-yl]methyl}methylamine,
(±)-{[7-(2,5-dimethylphenyl)-5-fluoro-2,3-dihydro-1-benzofuran-2-yl]methyl}methylamine,
(±)-{[7-(2,6-dimethylphenyl)-5-fluoro-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-{[5-fluoro-7-(5-methoxy-2-methylphenyl)-2,3-dihydro-1-benzofuran-2-yl]methyl}methylamine,
(±)-{[5-fluoro-7-(2-methoxy-5-methylphenyl)-2,3-dihydro-1-benzofuran-2-yl]methyl}methylamine,
(±)-{[7-(5-chloro-2-methoxyphenyl)-5-fluoro-2,3-dihydro-1-benzofuran-2-yl]methyl}methylamine,
(±)-[(5-fluoro-7-pyridin-3-yl-2,3-dihydro-1-benzofuran-2-yl)methyl]methylamine,
(±)-[(5-chloro-7-(2-methoxyphenyl)-2,3-dihydro-1-benzofuran-2-yl]methyl}methylamine,
(±)-{[5-chloro-7-(2,6-dimethylphenyl)-2,3-dihydro-1-benzofuran-2-yl]methyl}methylamine,
(±)-[(5-chloro-7-(2-fluorophenyl)-2,3-dihydro-1-benzofuran-2-yl]methyl}methylamine,
(±)-{[5-chloro-7-(2,3-difluorophenyl)-2,3-dihydro-1-benzofuran-2-yl]methyl}methylamine,
(±)-{[5-chloro-7-(2,3-dichlorophenyl)-2,3-dihydro-1-benzofuran-2-yl]methyl}methylamine,
(±)-{[5-chloro-7-(2,3-dimethylphenyl)-2,3-dihydro-1-benzofuran-2-yl]methyl}methylamine,
(±)-{[5-chloro-7-(2,3-dimethoxyphenyl)-2,3-dihydro-1-benzofuran-2-yl]methyl}methylamine,
(±)-{[5-chloro-7-(2,4-difluorophenyl)-2,3-dihydro-1-benzofuran-2-yl]methyl}methylamine,
(±)-{[5-chloro-7-(2,4-dichlorophenyl)-2,3-dihydro-1-benzofuran-2-yl]methyl}methylamine,
(±)-{[5-chloro-7-(2,4-dimethoxyphenyl)-2,3-dihydro-1-benzofuran-2-yl]methyl}methylamine,
(±)-{[5-chloro-7-(2,5-difluorophenyl)-2,3-dihydro-1-benzofuran-2-yl]methyl}methylamine,
(±)-{[5-chloro-7-(2,5-dichlorophenyl)-2,3-dihydro-1-benzofuran-2-yl]methyl}methylamine,
(±)-{[5-chloro-7-(5-chloro-2-methoxyphenyl)-2,3-dihydro-1-benzofuran-2-yl]methyl}methylamine,
(±)-{[7-(2-fluorophenyl)-5-methyl-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2-methoxyphenyl)-5-methyl-2,3-dihydro-1-benzofuran-2-yl]methyl}methylamine,
(±)-{[7-(3-methylphenyl)-5-methyl-2,3-dihydro-1-benzofuran-2-yl]methyl}methylamine,
(±)-{[7-(3-chlorophenyl)-5-methyl-2,3-dihydro-1-benzofuran-2-yl]methyl}methylamine,
(±)-{[7-(4-methylphenyl)-5-methyl-2,3-dihydro-1-benzofuran-2-yl]methyl}methylamine,
(±)-{[7-(4-chlorophenyl)-5-methyl-2,3-dihydro-1-benzofuran-2-yl]methyl}methylamine,
(±)-{[7-(4-fluorophenyl)-5-methyl-2,3-dihydro-1-benzofuran-2-yl]methyl}methylamine,
(±)-{[7-(4-methoxyphenyl)-5-methyl-2,3-dihydro-1-benzofuran-2-yl]methyl}methylamine,
(±)-{[7-(2,3-dimethoxyphenyl)-5-methyl-2,3-dihydro-1-benzofuran-2-yl]methyl}methylamine,
(±)-{[7-(2,4-dichlorophenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(−)-{[7-(2,5-dichlorophenyl)-5-methyl-2,3-dihydro-1-benzofuran-2-yl]methyl}methylamine,
(±)-{[7-(2,6-dimethylphenyl)-5-methyl-2,3-dihydro-1-benzofuran-2-yl]methyl}methylamine,
(±)-{[7-(2,6-dichlorophenyl)-5-methyl-2,3-dihydro-1-benzofuran-2-yl]methyl}methylamine,
(±)-{[7-(2-fluorophenyl)-5-methoxy-2,3-dihydro-1-benzofuran-2-yl]methyl}methylamine,
(±)-{[7-(2-chlorophenyl)-5-methoxy-2,3-dihydro-1-benzofuran-2-yl]methyl}methylamine,
(±)-{[7-(2-methylphenyl)-5-methoxy-2,3-dihydro-1-benzofuran-2-yl]methyl}methylamine,
(±)-{[7-(2,3-difluorophenyl)-5-methoxy-2,3-dihydro-1-benzofuran-2-yl]methyl}methylamine,
(±)-{[7-(2,3-dichlorophenyl)-5-methoxy-2,3-dihydro-1-benzofuran-2-yl]methyl}methylamine,
(±)-{[7-(2,3-dimethylphenyl)-5-methoxy-2,3-dihydro-1-benzofuran-2-yl]methyl}methylamine,
(±)-{[7-(2,4-difluorophenyl)-5-methoxy-2,3-dihydro-1-benzofuran-2-yl]methyl}methylamine,
(±)-{[7-(2,5-difluorophenyl)-5-methoxy-2,3-dihydro-1-benzofuran-2-yl]methyl}methylamine,
(±)-{[7-(2,5-dichlorophenyl)-5-methoxy-2,3-dihydro-1-benzofuran-2-yl]methyl}methylamine,
(±)-{[7-(2,5-dimethylphenyl)-5-methoxy-2,3-dihydro-1-benzofuran-2-yl]methyl}methylamine,
(±)-{[7-(2,5-dimethoxyphenyl)-5-methoxy-2,3-dihydro-1-benzofuran-2-yl]methyl}methylamine,
(±)-{[7-(5-chloro-2-methoxyphenyl)-5-methoxy-2,3-dihydro-1-benzofuran-2-yl]methyl}methylamine,
(±)-{[7-(3-chloro-4-fluorophenyl)-5-methoxy-2,3-dihydro-1-benzofuran-2-yl]methyl}methylamine,
(±)-{[7-(2,6-dimethylphenyl)-5-methoxy-2,3-dihydro-1-benzofuran-2-yl]methyl}methylamine,
(±)-{[7-(2-chlorophenyl)-5-phenyl-2,3-dihydro-1-benzofuran-2-yl]methyl}methylamine, (±)-{[7-(3-chlorophenyl)-5-phenyl-2,3-dihydro-1-benzofuran-2-yl]methyl}methylamine,
(±)-{[7-(4-chlorophenyl)-5-phenyl-2,3-dihydro-1-benzofuran-2-yl]methyl}methylamine,
(±)-{[7-(2-fluorophenyl)-5-phenyl-2,3-dihydro-1-benzofuran-2-yl]methyl}methylamine,
(±)-{[7-(3-fluorophenyl)-5-phenyl-2,3-dihydro-1-benzofuran-2-yl]methyl}methylamine,
(±)-{[7-(4-fluorophenyl)-5-phenyl-2,3-dihydro-1-benzofuran-2-yl]methyl}methylamine,
(±)-{[7-(2-methylphenyl)-5-phenyl-2,3-dihydro-1-benzofuran-2-yl]methyl}methylamine,
(±)-{[7-(3-methylphenyl)-5-phenyl-2,3-dihydro-1-benzofuran-2-yl]methyl}methylamine,
(±)-{[7-(4-methylphenyl)-5-phenyl-2,3-dihydro-1-benzofuran-2-yl]methyl}methylamine,
(±)-{[7-(2-methoxyphenyl)-5-phenyl-2,3-dihydro-1-benzofuran-2-yl]methyl}methylamine,
(±)-{[7-(3-methoxyphenyl)-5-phenyl-2,3-dihydro-1-benzofuran-2-yl]methyl}methylamine,
(±)-{[7-(4-methoxyphenyl)-5-phenyl-2,3-dihydro-1-benzofuran-2-yl]methyl}methylamine,
(±)-{[7-(2,4-difluorophenyl)-5-phenyl-2,3-dihydro-1-benzofuran-2-yl]methyl}methylamine,
(±)-N-methyl-1-[7-(3-methylphenyl)-5-(trifluoromethyl)-2,3-dihydro-1-benzofuran-2-yl]methanamine,
(±)-N-methyl-1-[7-(3-fluorophenyl)-5-(trifluoromethyl)-2,3-dihydro-1-benzofuran-2-yl]methanamine,
(±)-N-methyl-1-[7-(2,3-difluorophenyl)-5-(trifluoromethyl)-2,3-dihydro-1-benzofuran-2-yl]methanamine,
(±)-N-methyl-1-[7-(3,4-difluorophenyl)-5-(trifluoromethyl)-2,3-dihydro-1-benzofuran-2-yl]methanamine,
(±)-N-methyl-1-[7-(2,5-difluorophenyl)-5-(trifluoromethyl)-2,3-dihydro-1-benzofuran-2-yl]methanamine,
(±)-N-methyl-1-[7-(2,3-dichlorophenyl)-5-(trifluoromethyl)-2,3-dihydro-1-benzofuran-2-yl]methanamine,
(±)-{[7-(3-chloro-4-fluorophenyl)-5-(trifluoromethyl)-2,3-dihydro-1-benzofuran-2-yl]methyl}methylamine,
(±)-N-methyl-1-[7-(2,4-dimethoxyphenyl)-5-(trifluoromethyl)-2,3-dihydro-1-benzofuran-2-yl]methanamine,
(±)-{[7-[3,5-bis(trifluoromethyl)phenyl]-5-(trifluoromethyl)-2,3-dihydro-1-benzofuran-2-yl]methyl}methylamine,
(+){[7-(2,6-dichlorophenyl)-5-fluoro-2,3-dihydro-1-benzofuran-2-yl]methyl}methylamine,
(−){[7-(2,6-dichlorophenyl)-5-fluoro-2,3-dihydro-1-benzofuran-2-yl]methyl}methylamine,
(R)-[7-(2-chloro-phenyl)-(5-Fluoro-2,3-dihydro-benzofuran-2-ylmethyl)methyl-amine,
(R)-[7-(2,6-dichloro-phenyl)-5-Fluoro-2,3-dihydro-benzofuran-2-ylmethyl]ethylamine,
(R)-[7-(2,6-dichloro-phenyl)-5-Fluoro-2,3-dihydro-benzofuran-2-ylmethyl]dimethylamine,
{[(2R)-7-(5-chloro-2-methylphenyl)-5-fluoro-2,3-dihydro-1-benzofuran-2-yl]methyl}amine,
{[(2R)-7-(4-chloro-2-methylphenyl)-5-fluoro-2,3-dihydro-1-benzofuran-2-yl]methyl}amine,
(−)-{[7-(2,6-dichlorophenyl)-5-fluoro-2,3-dihydro-1-benzofuran-2-yl]methyl}amine,
(+)-{[7-(2,6 dichlorophenyl)-5-fluoro-2,3-dihydro-1-benzofuran-2-yl]methyl}amine,
(±)-{[2-[6-chloro-7-(2-chlorophenyl)-2,3-dihydro-1-benzofuran-2-yl]ethyl}amine,
(±)-{[2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(+)-{[7-(2,6-dimethylphenyl)-5-fluoro-2,3-dihydro-1-benzofuran-2-yl]methyl}methylamine,
(−)-{[7-(2,6-dimethylphenyl)-5-fluoro-2,3-dihydro-1-benzofuran-2-yl]methyl}methylamine,
(−)-{[7-(2,6-dimethylphenyl)-5-methoxy-2,3-dihydro-1-benzofuran-2-yl]methyl}methylamine,
(+)-{[7-(2,6-dimethylphenyl)-5-methoxy-2,3-dihydro-1-benzofuran-2-yl]methyl}methylamine,
(+)-{[5-chloro-7-(2,5-dichlorophenyl)-2,3-dihydro-1-benzofuran-2-yl]methyl}methylamine,
(−)-{[5-chloro-7-(2,5-dichlorophenyl)-2,3-dihydro-1-benzofuran-2-yl]methyl}methylamine,
(−)-{[5-chloro-7-(2,6-dimethylphenyl)-2,3-dihydro-1-benzofuran-2-yl]methyl}methylamine,
(+)-{[5-chloro-7-(2,6-dimethylphenyl)-2,3-dihydro-1-benzofuran-2-yl]methyl}methylamine,
(+)-{[7-(2,3-dimethoxyphenyl)-5-methyl-2,3-dihydro-1-benzofuran-2-yl]methyl}methylamine,
(−)-{[7-(2,3-dimethoxyphenyl)-5-methyl-2,3-dihydro-1-benzofuran-2-yl]methyl}methylamine,
(−)-{[7-(2,3-dimethoxyphenyl)-5-fluoro-2,3-dihydro-1-benzofuran-2-yl]methyl}methylamine, or
(+)-{[7-(2,3-dimethoxyphenyl)-5-fluoro-2,3-dihydro-1-benzofuran-2-yl]methyl}methylamine;
or a pharmaceutically acceptable salt thereof.

17. The compound of claim 16 which is:
(±)-1-[7-(2,3-dimethylphenyl)-2,3-dihydro-1-benzofuran-2-yl]methanamine,
(±)-{[7-(2,3-dimethoxyphenyl)-2,3-dihydro-1-benzofuran-2-yl]methyl}amine,
(−)-{[(7-(2,3-dimethoxyphenyl)-2,3-dihydro-1-benzofuran-2-yl]methyl}amine,
(+)-{[7-(4-chloro-2-methylphenyl)-2,3-dihydro-1-benzofuran-2-yl]methyl}amine,
(−)-{[7-(4-chloro-2-methylphenyl)-2,3-dihydro-1-benzofuran-2-yl]methyl}amine,
(±)-{[7-(2,3-difluorophenyl)-2,3-dihydro-1-benzofuran-2-yl]methyl}amine,
(±)-{[7-(2,5-dimethylphenyl)-2,3-dihydro-1-benzofuran-2-yl]methyl}amine,
(±)-{[7-(2,5-dimethoxyphenyl)-2,3-dihydro-1-benzofuran-2-yl]methyl}amine,
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(−)-{[7-(2,5-dichlorophenyl)-2,3-dihydro-1-benzofuran-2-yl]methyl}amine,
(±)-{[7-(2,4,6-trichlorophenyl)-2,3-dihydro-1-benzofuran-2-yl]methyl}amine,
(±)-{[7-(4-chloro-2-methylphenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(±)-{[7-(5-chloro-2-methoxyphenyl)-2,3-dihydro-1-benzofuran-2-yl]methyl}amine,
(±)-[(7-pyridin-3-yl-2,3-dihydro-1-benzofuran-2-yl)methyl]amine,
(+)-{[7-pyridin-3-yl-2,3-dihydro-1-benzofuran-2-yl]methyl}amine,
(±)-{[5-fluoro-7-(2-methoxyphenyl)-2,3-dihydro-1-benzofuran-2-yl]methyl}amine,
(±)-{[5-fluoro-7-(3-methylphenyl)-2,3-dihydro-1-benzofuran-2-yl]methyl}amine,
(±)-{[5-fluoro-7-(4-fluorophenyl)-2,3-dihydro-1-benzofuran-2-yl]methyl}amine, (±)-{[5-fluoro-7-(4-chlorophenyl)-2,3-dihydro-1-benzo-
furan-2-yl]methyl}amine,
(±)-{[5-fluoro-7-(4-methylphenyl)-2,3-dihydro-1-benzo-
furan-2-yl]methyl}amine,
(±)-{[5-fluoro-7-(4-methoxyphenyl)-2,3-dihydro-1-ben-
zofuran-2-yl]methyl}amine,
(±)-[(5-fluoro-7-thien-3-yl-2,3-dihydro-1-benzofuran-2-
yl)methyl]amine,
(±)-{[5-fluoro-7-(3-furyl)-2,3-dihydro-1-benzofuran-2-
yl]methyl}amine,
(±)-[(5-fluoro-7-pyridin-2-yl-2,3-dihydro-1-benzofuran-
2-yl)methyl]amine,
(±)-[(5-fluoro-7-pyridin-3-yl-2,3-dihydro-1-benzofuran-
2-yl)methyl]amine,
(−)-[(5-fluoro-7-pyridin-3-yl-2,3-dihydro-1-benzofuran-
2-yl)methyl]amine,
(+)-{[5-fluoro-7-pyridin-3-yl-2,3-dihydro-1-benzofuran-
2-yl]methyl}amine,
(±)-[(5-fluoro-7-pyridin-4-yl-2,3-dihydro-1-benzofuran-
2-yl)methyl]amine,
(±)-{[7-(2,3-dichlorophenyl)-5-fluoro-2,3-dihydro-1-
benzofuran-2-yl]methyl}amine,
(±)-{[7-(2,3-dimethoxyphenyl)-5-fluoro-2,3-dihydro-1-
benzofuran-2-yl]methyl}amine,
(−)-{[7-(2,3-dimethoxyphenyl)-5-fluoro-2,3-dihydro-1-
benzofuran-2-yl]methyl}amine,
(+)-{[7-(2,3-dimethoxyphenyl)-5-fluoro-2,3-dihydro-1-
benzofuran-2-yl]methyl}amine,
(±)-{[7-(2,4-difluorophenyl)-5-fluoro-2,3-dihydro-1-ben-
zofuran-2-yl]methyl}amine,
(±)-{[7-(2,4-dichlorophenyl)-5-fluoro-2,3-dihydro-1-
benzofuran-2-yl]methyl}amine,
(−)-{[5-fluoro-7-(2,4-dichlorophenyl)-2,3-dihydro-1-
benzofuran-2-yl]methyl}amine,
(+)-{[5-fluoro-7-(2,4-dichlorophenyl)-2,3-dihydro-1-
benzofuran-2-yl]methyl}amine,
(±)-{[7-(2,4-dimethoxyphenyl)-5-fluoro-2,3-dihydro-1-
benzofuran-2-yl]methyl}amine,
(±)-{[7-(2,5-difluorophenyl)-5-fluoro-2,3-dihydro-1-ben-
zofuran-2-yl]methyl}amine,
(±)-{[7-(2,5-dichlorophenyl)-5-fluoro-2,3-dihydro-1-
benzofuran-2-yl]methyl}amine,
(±)-{[7-(2,5-dimethylphenyl)-5-fluoro-2,3-dihydro-1-
benzofuran-2-yl]methyl}amine,
(±)-{[7-(2,5-dimethoxyphenyl)-5-fluoro-2,3-dihydro-1-
benzofuran-2-yl]methyl}amine,
(±)-{[5-fluoro-7-(5-methoxy-2-methylphenyl)-2,3-dihy-
dro-1-benzofuran-2-yl]methyl}amine,
(±)-{[5-fluoro-7-(2-methoxy-5-methylphenyl)-2,3-dihy-
dro-1-benzofuran-2-yl]methyl}amine,
(±)-{[7-(2,6-difluorophenyl)-5-fluoro-2,3-dihydro-1-ben-
zofuran-2-yl]methyl}amine,
(±)-{[7-(2,6-dimethylphenyl)-5-fluoro-2,3-dihydro-1-
benzofuran-2-yl]methyl}amine,
(+)-{[7-(2,6-dimethylphenyl)-5-fluoro-2,3-dihydro-1-
benzofuran-2-yl]methyl}amine,
(−)-{[7-(2,6-dimethylphenyl)-5-fluoro-2,3-dihydro-1-
benzofuran-2-yl]methyl}amine,
(±)-{[7-(2,6-dichlorophenyl)-5-fluoro-2,3-dihydro-1-
benzofuran-2-yl]methyl}amine,
(±)-N-{[7-(2,6-dichlorophenyl)-5-fluoro-2,3-dihydro-1-
benzofuran-2-yl]methyl}cyclopropanamine,
(±)-1-cyclopropyl-N-{[7-(2,6-dichlorophenyl)-5-fluoro-
2,3-dihydro-1-benzofuran-2-yl]methyl}methanamine,
(±)-N-{[7-(2,6-dichlorophenyl)-5-fluoro-2,3-dihydro-1-
benzofuran-2-yl]methyl}cyclobutanamine,
(±)-N-{[7-(2,6-dichlorophenyl)-5-fluoro-2,3-dihydro-1-
benzofuran-2-yl]methyl}ethanamine,
(±)-N-{[7-(2,6-dichlorophenyl)-5-fluoro-2,3-dihydro-1-
benzofuran-2-yl]methyl}propan-1-amine,
(±)-N-{[7-(2,6-dichlorophenyl)-5-fluoro-2,3-dihydro-1-
benzofuran-2-yl]methyl}propan-2-amine,
(±)-{[7-(2,6-dichlorophenyl)-5-fluoro-2,3-dihydro-1-
benzofuran-2-yl]methyl}dimethylamine,
(±)-1-{[7-(2,6-dichlorophenyl)-5-fluoro-2,3-dihydro-1-
benzofuran-2-yl]methyl}piperidine
(±)-1-{[7-(2,6-dichlorophenyl)-5-fluoro-2,3-dihydro-1-
benzofuran-2-yl]methyl}morpholine
(±)-1-{[7-(2,6-dichlorophenyl)-5-fluoro-2,3-dihydro-1-
benzofuran-2-yl]methyl}pyrrolidine
(±)-{[5-chloro-7-(2-fluorophenyl)-2,3-dihydro-1-benzo-
furan-2-yl]methyl}amine,
(±)-{[5-chloro-7-(2-methoxyphenyl)-2,3-dihydro-1-ben-
zofuran-2-yl]methyl}amine,
(±)-{[5-chloro-7-(3-furyl)-2,3-dihydro-1-benzofuran-2-
yl]methyl}amine,
(±)-{[5-chloro-7-(2,3-difluorophenyl)-2,3-dihydro-1-
benzofuran-2-yl]methyl}amine,
(−)-{[5-chloro-7-(2,3-difluorophenyl)-2,3-dihydro-1-
benzofuran-2-yl]methyl}amine,
(+)-{[5-chloro-7-(2,3-difluorophenyl)-2,3-dihydro-1-
benzofuran-2-yl]methyl}amine,
(±)-{[5-chloro-7-(2,3-dichlorophenyl)-2,3-dihydro-1-
benzofuran-2-yl]methyl}amine,
(±)-{[5-chloro-7-(2,3-dimethylphenyl)-2,3-dihydro-1-
benzofuran-2-yl]methyl}amine,
(±)-{[5-chloro-7-(2,3-dimethoxyphenyl)-2,3-dihydro-1-
benzofuran-2-yl]methyl}amine,
(±)-{[5-chloro-7-(2,4-difluorophenyl)-2,3-dihydro-1-
benzofuran-2-yl]methyl}amine,
(±)-{[5-chloro-7-(2,4-dichlorophenyl)-2,3-dihydro-1-
benzofuran-2-yl]methyl}amine,
(−)-{[5-chloro-7-(2,4-dichlorophenyl)-2,3-dihydro-1-
benzofuran-2-yl]methyl}amine,
(+)-{[5-chloro-7-(2,4-dichlorophenyl)-2,3-dihydro-1-
benzofuran-2-yl]methyl}amine,
(±)-{[5-chloro-7-(2,4-dimethoxyphenyl)-2,3-dihydro-1-
benzofuran-2-yl]methyl}amine,
(±)-{[5-chloro-7-(2,5-difluorophenyl)-2,3-dihydro-1-
benzofuran-2-yl]methyl}amine,
(±)-{[5-chloro-7-(2,5-dichlorophenyl)-2,3-dihydro-1-
benzofuran-2-yl]methyl}amine,
(±)-{[5-chloro-7-(5-chloro-2-methoxyphenyl)-2,3-dihy-
dro-1-benzofuran-2-yl]methyl}amine,
(±)-{[5-chloro-7-(3,4-difluorophenyl)-2,3-dihydro-1-
benzofuran-2-yl]methyl}amine,
(±)-{[5-chloro-7-(2,6-dimethylphenyl)-2,3-dihydro-1-
benzofuran-2-yl]methyl}amine,
(−)-{[5-chloro-7-(2,6-dimethylphenyl)-2,3-dihydro-1-
benzofuran-2-yl]methyl}amine,
(+)-{[5-chloro-7-(2,6-dimethylphenyl)-2,3-dihydro-1-
benzofuran-2-yl]methyl}amine,
(±)-{[5-chloro-7-(2,6-dichlorophenyl)-2,3-dihydro-1-
benzofuran-2-yl]methyl}amine,
(±)-{[(5-chloro-7-pyridin-3-yl-2,3-dihydro-1-benzofu-
ran-2-yl)methyl]amine,
(±)-N-{[5-chloro-7-(2,6-dimethylphenyl)-2,3-dihydro-1-
benzofuran-2-yl]methyl}cyclopropanamine,
(±)-N-{[5-chloro-7-(2,6-dimethylphenyl)-2,3-dihydro-1-
benzofuran-2-yl]methyl}(cyclopropylmethyl)amine,
(±)-N-{[5-chloro-7-(2,6-dimethylphenyl)-2,3-dihydro-1-
benzofuran-2-yl]methyl}cyclobutanamine, (±)-N-{[5-chloro-7-(2,6-dimethylphenyl)-2,3-dihydro-1-benzofuran-2-yl]methyl}ethanamine,
(±)-N-{[5-chloro-7-(2,6-dimethylphenyl)-2,3-dihydro-1-benzofuran-2-yl]methyl}propan-2-amine,
(±)-{[5-chloro-7-(2,6-dimethylphenyl)-2,3-dihydro-1-benzofuran-2-yl]methyl}dimethylamine,
(±)-N-{[5-chloro-7-(2,6-dimethylphenyl)-2,3-dihydro-1-benzofuran-2-yl]methyl}propan-1-amine,
(±)-1-{[5-chloro-7-(2,6-dimethylphenyl)-2,3-dihydro-1-benzofuran-2-yl]methyl}piperazine
(±)-1-{[5-chloro-7-(2,6-dimethylphenyl)-2,3-dihydro-1-benzofuran-2-yl]methyl}pyrrolidine
(±)-{[7-(2-methylphenyl)-5-methyl-2,3-dihydro-1-benzofuran-2-yl]methyl}amine,
(±)-{[7-(2-fluorophenyl)-5-methyl-2,3-dihydro-1-benzofuran-2-yl]methyl}amine,
(±)-{[7-(2-methoxyphenyl)-5-methyl-2,3-dihydro-1-benzofuran-2-yl]methyl}amine,
(±)-{[7-(2-chlorophenyl)-5-methyl-2,3-dihydro-1-benzofuran-2-yl]methyl}amine,
(±)-({5-methyl-7-[2-(trifluoromethyl)phenyl]-2,3-dihydro-1-benzofuran-2-yl}methyl)amine,
(±)-{[7-(3-chlorophenyl)-5-methyl-2,3-dihydro-1-benzofuran-2-yl]methyl}amine,
(±)-{[7-(3-methylphenyl)-5-methyl-2,3-dihydro-1-benzofuran-2-yl]methyl}amine,
(±)-{[7-(4-methylphenyl)-5-methyl-2,3-dihydro-1-benzofuran-2-yl]methyl}amine,
(±)-{[7-(4-fluorophenyl)-5-methyl-2,3-dihydro-1-benzofuran-2-yl]methyl}amine,
(±)-{[7-(4-chlorophenyl)-5-methyl-2,3-dihydro-1-benzofuran-2-yl]methyl}amine,
(±)-{[7-(4-methoxyphenyl)-5-methyl-2,3-dihydro-1-benzofuran-2-yl]methyl}amine,
(±)-{[7-(2,3-dimethoxyphenyl)-5-methyl-2,3-dihydro-1-benzofuran-2-yl]methyl}amine,
(−)-{[7-(2,3-dimethoxyphenyl)-5-methyl-2,3-dihydro-1-benzofuran-2-yl]methyl}amine,
(+)-{[7-(2,3-dimethoxyphenyl)-5-methyl-2,3-dihydro-1-benzofuran-2-yl]methyl}amine,
(±)-{[7-(2,4-dichlorophenyl)-5-methyl-2,3-dihydro-1-benzofuran-2-yl]methyl}amine,
(−)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dimethylphenyl)-5-methyl-2,3-dihydro-1-benzofuran-2-yl]methyl}amine,
(±)-{[7-(2,6-dichlorophenyl)-5-methyl-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[5-isopropyl-7-(2-methylphenyl)-2,3-dihydro-1-benzofuran-2-yl]methyl}amine,
(±)-{[5-isopropyl-7-(2-chlorophenyl)-2,3-dihydro-1-benzofuran-2-yl]methyl}amine,
(±)-{[5-cyclopentyl-7-(2-methylphenyl)-2,3-dihydro-1-benzofuran-2-yl]methyl}amine,
(±)-{[5-cyclopentyl-7-(2-chlorophenyl)-2,3-dihydro-1-benzofuran-2-yl]methyl}amine,
(±)-{[5-isocyano-7-(2-methylphenyl)-2,3-dihydro-1-benzofuran-2-yl]methyl}amine,
(±)-{[5-isocyano-7-(2-chlorophenyl)-2,3-dihydro-1-benzofuran-2-yl]methyl}amine,
(±)-{[5-(trifluoromethyl)-7-(2-fluorophenyl)-2,3-dihydro-1-benzofuran-2-yl]methyl}amine,
(±)-{[5-(trifluoromethyl)-7-(2-methylphenyl)-2,3-dihydro-1-benzofuran-2-yl]methyl}amine,
(±)-{[5-(trifluoromethyl)-7-(2-chlorophenyl)-2,3-dihydro-1-benzofuran-2-yl]methyl}amine,
(±)-{[5-(trifluoromethyl)-7-(4-methoxyphenyl)-2,3-dihydro-1-benzofuran-2-yl]methyl}amine,
(±)-{[7-(2,3-dimethoxyphenyl)-5-(trifluoromethyl)-2,3-dihydro-1-benzofuran-2-yl]methyl}amine,
(±)-{[7-(2,4-difluorophenyl)-5-(trifluoromethyl)-2,3-dihydro-1-benzofuran-2-yl]methyl}amine,
(±)-{[7-(2,4-dimethoxyphenyl)-5-(trifluoromethyl)-2,3-dihydro-1-benzofuran-2-yl]methyl}amine,
(±)-{[7-(2,5-difluorophenyl)-5-(trifluoromethyl)-2,3-dihydro-1-benzofuran-2-yl]methyl}amine,
(±)-{[7-(2,5-dichlorophenyl)-5-(trifluoromethyl)-2,3-dihydro-1-benzofuran-2-yl]methyl}amine,
(±)-{[7-(2,6-dimethylphenyl)-5-(trifluoromethyl)-2,3-dihydro-1-benzofuran-2-yl]methyl}amine,
(±)-{[7-(3-furyl)-5-(trifluoromethyl)-2,3-dihydro-1-benzofuran-2-yl]methyl}amine,
(±)-{[7-thien-3-yl-5-(trifluoromethyl)-2,3-dihydro-1-benzofuran-2-yl]methyl}amine,
(±)-{[7-pyridin-3-yl-5-(trifluoromethyl)-2,3-dihydro-1-benzofuran-2-yl]methyl}amine,
(±)-{[7-(2-fluorophenyl)-5-methoxy-2,3-dihydro-1-benzofuran-2-yl]methyl}amine,
(±)-{[7-(2-chlorophenyl)-5-methoxy-2,3-dihydro-1-benzofuran-2-yl]methyl}amine,
(±)-{[7-(2-methoxyphenyl)-5-methoxy-2,3-dihydro-1-benzofuran-2-yl]methyl}amine,
(±)-{[7-(2,3-difluorophenyl)-5-methoxy-2,3-dihydro-1-benzofuran-2-yl]methyl}amine,
(±)-{[7-(2,3-dichlorophenyl)-5-methoxy-2,3-dihydro-1-benzofuran-2-yl]methyl}amine,
(±)-{[7-(2,3-dimethylphenyl)-5-methoxy-2,3-dihydro-1-benzofuran-2-yl]methyl}amine,
(±)-{[7-(2,4-difluorophenyl)-5-methoxy-2,3-dihydro-1-benzofuran-2-yl]methyl}amine,
(±)-{[7-(2,4-dichlorophenyl)-5-methoxy-2,3-dihydro-1-benzofuran-2-yl]methyl}amine,
(±)-{[7-(2,5-difluorophenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(−)-{[7-(2,5-dichlorophenyl)-5-methoxy-2,3-dihydro-1-benzofuran-2-yl]methyl}amine,
(±)-{[7-(2,5-dimethylphenyl)-5-methoxy-2,3-dihydro-1-benzofuran-2-yl]methyl}amine,
(±)-{[7-(2,5-dimethoxyphenyl)-5-methoxy-2,3-dihydro-1-benzofuran-2-yl]methyl}amine,
(±)-{[7-(5-chloro-2-methoxyphenyl)-5-methoxy-2,3-dihydro-1-benzofuran-2-yl]methyl}amine,
(±)-{[7-(3-chloro-4-fluorophenyl)-5-methoxy-2,3-dihydro-1-benzofuran-2-yl]methyl}amine,
(±)-{[7-(2,6-dimethylphenyl)-5-methoxy-2,3-dihydro-1-benzofuran-2-yl]methyl}amine,
(±)-N-{[7-(2,6-dichlorophenyl)-2,3-dihydro-1-benzofuran-2-yl]methyl}ethanamine,
(±)-N-{[7-(2,6-dichlorophenyl)-2,3-dihydro-1-benzofuran-2-yl]methyl}cyclopropanamine,
(±)-N-{[7-(2,6-dichlorophenyl)-2,3-dihydro-1-benzofuran-2-yl]methyl}propan-2-amine, (±)-{[6-fluoro-7-(2-methylphenyl)-2,3-dihydro-1-benzofuran-2-yl]methyl}amine,
(±)-{[{[7-(2-chlorophenyl)-6-fluoro-2,3-dihydro-1-benzofuran-2-yl]methyl}amine,
(±)-{[6-fluoro-7-(2-methylphenyl)-2,3-dihydro-1-benzofuran-2-yl]methyl}methylamine,
(±)-{[6-fluoro-7-(2-chlorophenyl)-2,3-dihydro-1-benzofuran-2-yl]methyl}methylamine,
(±)-[(N-methyl-1-[7-(2-methylphenyl)-2,3-dihydro-1-benzofuran-2-yl]methanamine,
(−)-N-methyl-1-[7-(2-methylphenyl)-2,3-dihydro-1-benzofuran-2-yl]methanamine,
(+)-N-methyl-1-[7-(2-methylphenyl)-2,3-dihydro-1-benzofuran-2-yl]methanamine,
(±)-[(N-methyl-1-[7-(2-chlorophenyl)-2,3-dihydro-1-benzofuran-2-yl]methanamine,
(+)-N-methyl-1-[7-(2-chlorophenyl)-2,3-dihydro-1-benzofuran-2-yl]methanamine,
(−)-N-methyl-1-[7-(2-chlorophenyl)-2,3-dihydro-1-benzofuran-2-yl]methanamine,
(±)-[(N-methyl-1-[7-(2-fluorophenyl)-2,3-dihydro-1-benzofuran-2-yl]methanamine,
(±)-[(N-methyl-1-[7-(2-methoxyphenyl)-2,3-dihydro-1-benzofuran-2-yl]methanamine,
(±)-[(N-methyl-1-[7-(3-methylphenyl)-2,3-dihydro-1-benzofuran-2-yl]methanamine,
(±)-[(N-methyl-1-[7-(3-fluorophenyl)-2,3-dihydro-1-benzofuran-2-yl]methanamine,
(±)-[(N-methyl-1-[7-(3-chlorophenyl)-2,3-dihydro-1-benzofuran-2-yl]methanamine,
(±)-[(N-methyl-1-[7-(3-methoxyphenyl)-2,3-dihydro-1-benzofuran-2-yl]methanamine,
(±)-[(N-methyl-1-[7-(4-methylphenyl)-2,3-dihydro-1-benzofuran-2-yl]methanamine,
(±)-[(N-methyl-1-[7-(4-fluorophenyl)-2,3-dihydro-1-benzofuran-2-yl]methanamine,
(±)-[(N-methyl-1-[7-(4-chlorophenyl)-2,3-dihydro-1-benzofuran-2-yl]methanamine,
(±)-[(N-methyl-1-[7-(4-methoxyphenyl)-2,3-dihydro-1-benzofuran-2-yl]methanamine,
(±)-[(N-methyl-1-[7-(2,3-dimethylphenyl)-2,3-dihydro-1-benzofuran-2-yl]methanamine,
(±)-[(N-methyl-1-[7-(2,3-dimethoxyphenyl)-2,3-dihydro-1-benzofuran-2-yl]methanamine,
(±)-[(N-methyl-1-[7-(2,4-difluorophenyl)-2,3-dihydro-1-benzofuran-2-yl]methanamine,
(±)-[(N-methyl-1-[7-(2,4-dichlorophenyl)-2,3-dihydro-1-benzofuran-2-yl]methanamine,
(±)-[(N-methyl-1-[7-(2,4-dimethoxyphenyl)-2,3-dihydro-1-benzofuran-2-yl]methanamine,
(±)-[(N-methyl-1-[7-(2,5-dimethylphenyl)-2,3-dihydro-1-benzofuran-2-yl]methanamine,
(±)-[(N-methyl-1-[7-(2,5-difluorophenyl)-2,3-dihydro-1-benzofuran-2-yl]methanamine,
(±)-[(N-methyl-1-[7-(2,5-dichlorophenyl)-2,3-dihydro-1-benzofuran-2-yl]methanamine,
(±)-[(N-methyl-1-[7-(5-chloro-2-methoxyphenyl)-2,3-dihydro-1-benzofuran-2-yl]methanamine,
(±)-[(N-methyl-1-[7-(5-chloro-2-methylphenyl)-2,3-dihydro-1-benzofuran-2-yl]methanamine,
(±)-[(N-methyl-1-[7-(2,6-dimethylphenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(+)-{[7-(2,6-dichlorophenyl)-2,3-dihydro-1-benzofuran-2-yl]methyl}methylamine,
(±)-N-methyl-1-(7-pyridin-3-yl-2,3-dihydro-1-benzofuran-2-yl)methanamine,
(±)-[(N-methyl-1-[7-(2,3-difluorophenyl)-2,3-dihydro-1-benzofuran-2-yl]methanamine,
(±)-{[5-fluoro-7-(2-fluorophenyl)-2,3-dihydro-1-benzofuran-2-yl]methyl}methylamine,
(±)-{[5-fluoro-7-(2-chlorophenyl)-2,3-dihydro-1-benzofuran-2-yl]methyl}methylamine,
(±)-{[5-fluoro-7-(2-methylphenyl)-2,3-dihydro-1-benzofuran-2-yl]methyl}methylamine,
(−)-{[5-fluoro-7-(2-methylphenyl)-2,3-dihydro-1-benzofuran-2-yl]methyl}methylamine,
(+)-{[5-fluoro-7-(2-methylphenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-{[7-(2,3-dimethoxyphenyl)-5-fluoro-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(−)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-difluorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(−)-{[5-fluoro-7-(2,5-dichlorophenyl)-2,3-dihydro-1-benzofuran-2-yl]methyl}methylamine,
(±)-{[7-(2,5-dimethylphenyl)-5-fluoro-2,3-dihydro-1-benzofuran-2-yl]methyl}methylamine,
(±)-{[7-(2,6-dimethylphenyl)-5-fluoro-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-{[5-fluoro-7-(5-methoxy-2-methylphenyl)-2,3-dihydro-1-benzofuran-2-yl]methyl}methylamine,
(±)-{[5-fluoro-7-(2-methoxy-5-methylphenyl)-2,3-dihydro-1-benzofuran-2-yl]methyl}methylamine,
(±)-{[7-(5-chloro-2-methoxyphenyl)-5-fluoro-2,3-dihydro-1-benzofuran-2-yl]methyl}methylamine,
(±)-[(5-fluoro-7-pyridin-3-yl-2,3-dihydro-1-benzofuran-2-yl)methyl]methylamine,
(±)-[(5-chloro-7-(2-methoxyphenyl)-2,3-dihydro-1-benzofuran-2-yl]methyl}methylamine,
(±)-{[5-chloro-7-(2,6-dimethylphenyl)-2,3-dihydro-1-benzofuran-2-yl]methyl}methylamine,
(±)-[(5-chloro-7-(2-fluorophenyl)-2,3-dihydro-1-benzofuran-2-yl]methyl}methylamine,
(±)-{[5-chloro-7-(2,3-difluorophenyl)-2,3-dihydro-1-benzofuran-2-yl]methyl}methylamine,
(±)-{[5-chloro-7-(2,3-dichlorophenyl)-2,3-dihydro-1-benzofuran-2-yl]methyl}methylamine,
(±)-{[5-chloro-7-(2,3-dimethylphenyl)-2,3-dihydro-1-benzofuran-2-yl]methyl}methylamine,
(±)-{[5-chloro-7-(2,3-dimethoxyphenyl)-2,3-dihydro-1-benzofuran-2-yl]methyl}methylamine,
(±)-{[5-chloro-7-(2,4-difluorophenyl)-2,3-dihydro-1-benzofuran-2-yl]methyl}methylamine,
(±)-{[5-chloro-7-(2,4-dichlorophenyl)-2,3-dihydro-1-benzofuran-2-yl]methyl}methylamine, (±)-{[5-chloro-7-(2,4-dimethoxyphenyl)-2,3-dihydro-1-benzofuran-2-yl]methyl}methylamine,
(±)-{[5-chloro-7-(2,5-difluorophenyl)-2,3-dihydro-1-benzofuran-2-yl]methyl}methylamine,
(±)-{[5-chloro-7-(2,5-dichlorophenyl)-2,3-dihydro-1-benzofuran-2-yl]methyl}methylamine,
(±)-{[5-chloro-7-(5-chloro-2-methoxyphenyl)-2,3-dihydro-1-benzofuran-2-yl]methyl}methylamine,
(±)-{[7-(2-fluorophenyl)-5-methyl-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2-methoxyphenyl)-5-methyl-2,3-dihydro-1-benzofuran-2-yl]methyl}methylamine,
(±)-{[7-(3-methylphenyl)-5-methyl-2,3-dihydro-1-benzofuran-2-yl]methyl}methylamine,
(±)-{[7-(3-chlorophenyl)-5-methyl-2,3-dihydro-1-benzofuran-2-yl]methyl}methylamine,
(±)-{[7-(4-methylphenyl)-5-methyl-2,3-dihydro-1-benzofuran-2-yl]methyl}methylamine,
(±)-{[7-(4-chlorophenyl)-5-methyl-2,3-dihydro-1-benzofuran-2-yl]methyl}methylamine,
(±)-{[7-(4-fluorophenyl)-5-methyl-2,3-dihydro-1-benzofuran-2-yl]methyl}methylamine,
(±)-{[7-(4-methoxyphenyl)-5-methyl-2,3-dihydro-1-benzofuran-2-yl]methyl}methylamine,
(±)-{[7-(2,3-dimethoxyphenyl)-5-methyl-2,3-dihydro-1-benzofuran-2-yl]methyl}methylamine,
(±)-{[7-(2,4-dichlorophenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(−)-{[7-(2,5-dichlorophenyl)-5-methyl-2,3-dihydro-1-benzofuran-2-yl]methyl}methylamine,
(±)-{[7-(2,6-dimethylphenyl)-5-methyl-2,3-dihydro-1-benzofuran-2-yl]methyl}methylamine,
(±)-{[7-(2,6-dichlorophenyl)-5-methyl-2,3-dihydro-1-benzofuran-2-yl]methyl}methylamine,
(±)-{[7-(2-fluorophenyl)-5-methoxy-2,3-dihydro-1-benzofuran-2-yl]methyl}methylamine,
(±)-{[7-(2-chlorophenyl)-5-methoxy-2,3-dihydro-1-benzofuran-2-yl]methyl}methylamine,
(±)-{[7-(2-methylphenyl)-5-methoxy-2,3-dihydro-1-benzofuran-2-yl]methyl}methylamine,
(±)-{[7-(2,3-difluorophenyl)-5-methoxy-2,3-dihydro-1-benzofuran-2-yl]methyl}methylamine,
(±)-{[7-(2,3-dichlorophenyl)-5-methoxy-2,3-dihydro-1-benzofuran-2-yl]methyl}methylamine,
(±)-{[7-(2,3-dimethylphenyl)-5-methoxy-2,3-dihydro-1-benzofuran-2-yl]methyl}methylamine,
(±)-{[7-(2,4-difluorophenyl)-5-methoxy-2,3-dihydro-1-benzofuran-2-yl]methyl}methylamine,
(±)-{[7-(2,5-difluorophenyl)-5-methoxy-2,3-dihydro-1-benzofuran-2-yl]methyl}methylamine,
(±)-{[7-(2,5-dichlorophenyl)-5-methoxy-2,3-dihydro-1-benzofuran-2-yl]methyl}methylamine,
(±)-{[7-(2,5-dimethylphenyl)-5-methoxy-2,3-dihydro-1-benzofuran-2-yl]methyl}methylamine,
(±)-{[7-(2,5-dimethoxyphenyl)-5-methoxy-2,3-dihydro-1-benzofuran-2-yl]methyl}methylamine,
(±)-{[7-(2,6-dimethylphenyl)-5-methoxy-2,3-dihydro-1-benzofuran-2-yl]methyl}methylamine,
(±)-N-methyl-1-[7-(2,4-dimethoxyphenyl)-5-(trifluoromethyl)-2,3-dihydro-1-benzofuran-2-yl]methanamine,
(+){[7-(2,6-dichlorophenyl)-5-fluoro-2,3-dihydro-1-benzofuran-2-yl]methyl}methylamine,
(−){[7-(2,6-dichlorophenyl)-5-fluoro-2,3-dihydro-1-benzofuran-2-yl]methyl}methylamine,
(R)-[7-(2-chloro-phenyl)-(5-Fluoro-2,3-dihydro-benzofuran-2-ylmethyl)methyl-amine,
(−)-{[7-(2,6-dichlorophenyl)-5-fluoro-2,3-dihydro-1-benzofuran-2-yl]methyl}amine,
(+)-{[7-(2,6 dichlorophenyl)-5-fluoro-2,3-dihydro-1-benzofuran-2-yl]methyl}amine,
(±)-{[2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(+)-{[7-(2,6-dimethylphenyl)-5-fluoro-2,3-dihydro-1-benzofuran-2-yl]methyl}methylamine,
(−)-{[7-(2,6-dimethylphenyl)-5-fluoro-2,3-dihydro-1-benzofuran-2-yl]methyl}methylamine,
(−)-{[7-(2,6-dimethylphenyl)-5-methoxy-2,3-dihydro-1-benzofuran-2-yl]methyl}methylamine,
(+)-{[7-(2,6-dimethylphenyl)-5-methoxy-2,3-dihydro-1-benzofuran-2-yl]methyl}methylamine,
(+)-{[5-chloro-7-(2,5-dichlorophenyl)-2,3-dihydro-1-benzofuran-2-yl]methyl}methylamine,
(−)-{[5-chloro-7-(2,5-dichlorophenyl)-2,3-dihydro-1-benzofuran-2-yl]methyl}methylamine,
(−)-{[5-chloro-7-(2,6-dimethylphenyl)-2,3-dihydro-1-benzofuran-2-yl]methyl}methylamine,
(+)-{[5-chloro-7-(2,6-dimethylphenyl)-2,3-dihydro-1-benzofuran-2-yl]methyl}methylamine,
(+)-{[7-(2,3-dimethoxyphenyl)-5-methyl-2,3-dihydro-1-benzofuran-2-yl]methyl}methylamine,
(−)-{[7-(2,3-dimethoxyphenyl)-5-methyl-2,3-dihydro-1-benzofuran-2-yl]methyl}methylamine,
(−)-{[7-(2,3-dimethoxyphenyl)-5-fluoro-2,3-dihydro-1-benzofuran-2-yl]methyl}methylamine, or
(+)-{[7-(2,3-dimethoxyphenyl)-5-fluoro-2,3-dihydro-1-benzofuran-2-yl]methyl}methylamine;
or a pharmaceutically acceptable salt thereof.

18. The compound of claim 17 which is:
(−)-{[(7-(2,3-dimethoxyphenyl)-2,3-dihydro-1-benzofuran-2-yl]methyl}amine,
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(±)-{[7-(2,4,6-trichlorophenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(±)-[(7-pyridin-3-yl-2,3-dihydro-1-benzofuran-2-yl)methyl]amine,
(+)-{[7-pyridin-3-yl-2,3-dihydro-1-benzofuran-2-yl]methyl}amine,
(±)-{[5-fluoro-7-(2-methoxyphenyl)-2,3-dihydro-1-benzofuran-2-yl]methyl}amine,
(±)-[(5-fluoro-7-pyridin-3-yl-2,3-dihydro-1-benzofuran-2-yl)methyl]amine,
(+)-{[5-fluoro-7-pyridin-3-yl-2,3-dihydro-1-benzofuran-2-yl]methyl}amine,
(±)-{[7-(2,3-dimethoxyphenyl)-5-fluoro-2,3-dihydro-1-benzofuran-2-yl]methyl}amine,
(−)-{[7-(2,3-dimethoxyphenyl)-5-fluoro-2,3-dihydro-1-benzofuran-2-yl]methyl}amine,
(±)-{[7-(2,4-dichlorophenyl)-5-fluoro-2,3-dihydro-1-benzofuran-2-yl]methyl}amine, (+)-{[5-fluoro-7-(2,4-dichlorophenyl)-2,3-dihydro-1-benzofuran-2-yl]methyl}amine,
(±)-{[7-(2,5-dichlorophenyl)-5-fluoro-2,3-dihydro-1-benzofuran-2-yl]methyl}amine,
(±)-{[5-fluoro-7-(2-methoxy-5-methylphenyl)-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(−)-{[7-(2,6-dimethylphenyl)-5-fluoro-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine,
(±)-N-{[7-(2,6-dichlorophenyl)-5-fluoro-2,3-dihydro-1-benzofuran-2-yl]methyl}ethanamine,
(±)-{[7-(2,6-dichlorophenyl)-5-fluoro-2,3-dihydro-1-benzofuran-2-yl]methyl}dimethylamine,
(±)-{[5-chloro-7-(2,4-dichlorophenyl)-2,3-dihydro-1-benzofuran-2-yl]methyl}amine,
(−)-{[5-chloro-7-(2,4-dichlorophenyl)-2,3-dihydro-1-benzofuran-2-yl]methyl}amine,
(±)-{[5-chloro-7-(2,4-dimethoxyphenyl)-2,3-dihydro-1-benzofuran-2-yl]methyl}amine,
(±)-{[5-chloro-7-(2,5-dichlorophenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(±)-{[(5-chloro-7-pyridin-3-yl-2,3-dihydro-1-benzofuran-2-yl)methyl]amine,
(±)-{[7-(2-fluorophenyl)-5-methyl-2,3-dihydro-1-benzofuran-2-yl]methyl}amine,
(±)-{[7-(2-methoxyphenyl)-5-methyl-2,3-dihydro-1-benzofuran-2-yl]methyl}amine,
(±)-{[7-(2-chlorophenyl)-5-methyl-2,3-dihydro-1-benzofuran-2-yl]methyl}amine,
(±)-{[7-(4-methoxyphenyl)-5-methyl-2,3-dihydro-1-benzofuran-2-yl]methyl}amine,
(±)-{[7-(2,3-dimethoxyphenyl)-5-methyl-2,3-dihydro-1-benzofuran-2-yl]methyl}amine,
(−)-{[7-(2,3-dimethoxyphenyl)-5-methyl-2,3-dihydro-1-benzofuran-2-yl]methyl}amine,
(±)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dichlorophenyl)-5-methyl-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[5-(trifluoromethyl)-7-(2-chlorophenyl)-2,3-dihydro-1-benzofuran-2-yl]methyl}amine,
(±)-{[7-(2-chlorophenyl)-5-methoxy-2,3-dihydro-1-benzofuran-2-yl]methyl}amine,
(±)-{[7-(2-methoxyphenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(±)-{[7-(2,6-dimethylphenyl)-5-methoxy-2,3-dihydro-1-benzofuran-2-yl]methyl}amine,
(±)-N-{[7-(2,6-dichlorophenyl)-2,3-dihydro-1-benzofuran-2-yl]methyl}ethanamine,
(±)-N-{[7-(2,6-dichlorophenyl)-2,3-dihydro-1-benzofuran-2-yl]methyl}cyclopropanamine,
(±)-{[6-fluoro-7-(2-methylphenyl)-2,3-dihydro-1-benzofuran-2-yl]methyl}amine,
(±)-{[{[7-(2-chlorophenyl)-6-fluoro-2,3-dihydro-1-benzofuran-2-yl]methyl}amine,
(±)-{[6-fluoro-7-(2-methylphenyl)-2,3-dihydro-1-benzofuran-2-yl]methyl}methylamine,
(±)-{[6-fluoro-7-(2-chlorophenyl)-2,3-dihydro-1-benzofuran-2-yl]methyl}methylamine,
(±)-[(N-methyl-1-[7-(2-methylphenyl)-2,3-dihydro-1-benzofuran-2-yl]methanamine,
(+)-N-methyl-1-[7-(2-methylphenyl)-2,3-dihydro-1-benzofuran-2-yl]methanamine,
(+)-N-methyl-1-[7-(2-chlorophenyl)-2,3-dihydro-1-benzofuran-2-yl]methanamine,
(±)-[(N-methyl-1-[7-(2-methoxyphenyl)-2,3-dihydro-1-benzofuran-2-yl]methanamine,
(±)-[(N-methyl-1-[7-(2,4-dichlorophenyl)-2,3-dihydro-1-benzofuran-2-yl]methanamine,
(±)-[(N-methyl-1-[7-(2,4-dimethoxyphenyl)-2,3-dihydro-1-benzofuran-2-yl]methanamine,
(±)-[(N-methyl-1-[7-(2,5-dichlorophenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(±)-{[5-fluoro-7-(2-chlorophenyl)-2,3-dihydro-1-benzofuran-2-yl]methyl}methylamine,
(±)-{[5-fluoro-7-(2-methylphenyl)-2,3-dihydro-1-benzofuran-2-yl]methyl}methylamine,
(+)-{[5-fluoro-7-(2-methylphenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-[(5-fluoro-7-pyridin-3-yl-2,3-dihydro-1-benzofuran-2-yl)methyl]methylamine,
(±)-{[5-chloro-7-(2,5-dichlorophenyl)-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2-methoxyphenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(±)-{[7-(2,6-dichlorophenyl)-5-methyl-2,3-dihydro-1-benzofuran-2-yl]methyl}methylamine,
(±)-{[7-(2-chlorophenyl)-5-methoxy-2,3-dihydro-1-benzofuran-2-yl]methyl}methylamine,
(±)-{[7-(2-methylphenyl)-5-methoxy-2,3-dihydro-1-benzofuran-2-yl]methyl}methylamine,
(−)-{[7-(2,6-dichlorophenyl)-5-fluoro-2,3-dihydro-1-benzofuran-2-yl]methyl}amine,
(+)-{[7-(2,6 dichlorophenyl)-5-fluoro-2,3-dihydro-1-benzofuran-2-yl]methyl}amine, (±)-{[2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(−)-{[7-(2,6-dimethylphenyl)-5-fluoro-2,3-dihydro-1-benzofuran-2-yl]methyl}methylamine,
(−)-{[7-(2,6-dimethylphenyl)-5-methoxy-2,3-dihydro-1-benzofuran-2-yl]methyl}methylamine,
(+)-{[5-chloro-7-(2,5-dichlorophenyl)-2,3-dihydro-1-benzofuran-2-yl]methyl}methylamine,
(+)-{[7-(2,3-dimethoxyphenyl)-5-methyl-2,3-dihydro-1-benzofuran-2-yl]methyl}methylamine,
(−)-{[7-(2,3-dimethoxyphenyl)-5-methyl-2,3-dihydro-1-benzofuran-2-yl]methyl}methylamine,
(−)-{[7-(2,3-dimethoxyphenyl)-5-fluoro-2,3-dihydro-1-benzofuran-2-yl]methyl}methylamine, or
(+)-{[7-(2,3-dimethoxyphenyl)-5-fluoro-2,3-dihydro-1-benzofuran-2-yl]methyl}methylamine;
or a pharmaceutically acceptable salt thereof.

19. The compound of claim 18 which is:
(±)-{[7-(2,5-dichlorophenyl)-2,3-dihydro-1-benzofuran-2-yl]methyl}amine,
(+)-{[7-(2,5-dichlorophenyl)-2,3-dihydro-1-benzofuran-2-yl]methyl}amine,
(±)-{[7-(2,4,6-trichlorophenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(+)-{[7-pyridin-3-yl-2,3-dihydro-1-benzofuran-2-yl]methyl}amine,
(±)-[(5-fluoro-7-pyridin-3-yl-2,3-dihydro-1-benzofuran-2-yl)methyl]amine,
(+)-{[5-fluoro-7-pyridin-3-yl-2,3-dihydro-1-benzofuran-2-yl]methyl}amine,
(±)-{[7-(2,4-dichlorophenyl)-5-fluoro-2,3-dihydro-1-benzofuran-2-yl]methyl}amine,
(+)-{[5-fluoro-7-(2,4-dichlorophenyl)-2,3-dihydro-1-benzofuran-2-yl]methyl}amine,
(±)-{[7-(2,5-dichlorophenyl)-5-fluoro-2,3-dihydro-1-benzofuran-2-yl]methyl}amine,
(±)-{[5-fluoro-7-(2-methoxy-5-methylphenyl)-2,3-dihydro-1-benzofuran-2-yl]methyl}amine,
(±)-{[7-(2,6-dimethylphenyl)-5-fluoro-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine,
(±)-{[7-(2,6-dichlorophenyl)-5-fluoro-2,3-dihydro-1-benzofuran-2-yl]methyl}dimethylamine,
(−)-{[5-chloro-7-(2,4-dichlorophenyl)-2,3-dihydro-1-benzofuran-2-yl]methyl}amine,
(±)-{[5-chloro-7-(2,5-dichlorophenyl)-2,3-dihydro-1-benzofuran-2-yl]methyl}amine,
(±)-{[5-chloro-7-(2,6-dichlorophenyl)-2,3-dihydro-1-benzofuran-2-yl]methyl}amine,
(±)-{[(5-chloro-7-pyridin-3-yl-2,3-dihydro-1-benzofuran-2-yl)methyl]amine,
(±)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[7-(2,5-dichlorophenyl)-5-methyl-2,3-dihydro-1-benzofuran-2-yl]methyl}amine,
(±)-{[7-(2,6-dichlorophenyl)-5-methyl-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-{[7-(2-chlorophenyl)-5-methoxy-2,3-dihydro-1-benzofuran-2-yl]methyl}amine,
(±)-{[7-(2,5-dichlorophenyl)-5-methoxy-2,3-dihydro-1-benzofuran-2-yl]methyl}amine,
(+)-{[7-(2,5-dichlorophenyl)-5-methoxy-2,3-dihydro-1-benzofuran-2-yl]methyl}amine,
(±)-N-{[7-(2,6-dichlorophenyl)-2,3-dihydro-1-benzofuran-2-yl]methyl}ethanamine,
(±)-N-{[7-(2,6-dichlorophenyl)-2,3-dihydro-1-benzofuran-2-yl]methyl}cyclopropanamine,
(±)-{[6-fluoro-7-(2-methylphenyl)-2,3-dihydro-1-benzofuran-2-yl]methyl}amine,
(±)-{[{[7-(2-chlorophenyl)-6-fluoro-2,3-dihydro-1-benzofuran-2-yl]methyl}amine,
(±)-{[6-fluoro-7-(2-methylphenyl)-2,3-dihydro-1-benzofuran-2-yl]methyl}methylamine,
(±)-{[6-fluoro-7-(2-chlorophenyl)-2,3-dihydro-1-benzofuran-2-yl]methyl}methylamine,
(+)-N-methyl-1-[7-(2-chlorophenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(−)-{[7-(2,6-dichlorophenyl)-2,3-dihydro-1-benzofuran-2-yl]methyl}methylamine,
(±)-{[5-fluoro-7-(2-methoxyphenyl)-2,3-dihydro-1-benzofuran-2-yl]methyl}methylamine,
(±)-[7-(2,4-dichlorophenyl)-5-fluoro-2,3-dihydro-1-benzofuran-2-yl]methyl}methylamine,
(+)-[7-(2,4-dichlorophenyl)-5-fluoro-2,3-dihydro-1-benzofuran-2-yl]methyl}methylamine,
(±)-{[7-(2,5-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine,
(±)-{[7-(2-chlorophenyl)-5-methyl-2,3-dihydro-1-benzofuran-2-yl]methyl}methylamine,
(±)-{[7-(2,5-dichlorophenyl)-5-methyl-2,3-dihydro-1-benzofuran-2-yl]methyl}methylamine,
(+)-{[7-(2,5-dichlorophenyl)-5-methyl-2,3-dihydro-1-benzofuran-2-yl]methyl}methylamine,
(−)-{[7-(2,6-dichlorophenyl)-5-fluoro-2,3-dihydro-1-benzofuran-2-yl]methyl}amine,
(±)-{[2-[7-(2-methoxyphenyl)-5-methoxy-2,3-dihydro-1-benzofuran-2-yl]ethyl}amine,
(±)-{N-methyl-1-[(7-(2,4,6-trichlorophenyl)-2,3-dihydro-1-benzofuran-2-yl]methanamine,
(−)-{[7-(2,6-dimethylphenyl)-5-methoxy-2,3-dihydro-1-benzofuran-2-yl]methyl}methylamine,
(+)-{[5-chloro-7-(2,5-dichlorophenyl)-2,3-dihydro-1-benzofuran-2-yl]methyl}methylamine,
(+)-{[7-(2,3-dimethoxyphenyl)-5-methyl-2,3-dihydro-1-benzofuran-2-yl]methyl}methylamine, or
(−)-{[7-(2,3-dimethoxyphenyl)-5-fluoro-2,3-dihydro-1-benzofuran-2-yl]methyl}methylamine;
or a pharmaceutically acceptable salt thereof.

20. The compound of claim 19 which is:
(+)-{[7-(2,5-dichlorophenyl)-2,3-dihydro-1-benzofuran-2-yl]methyl}amine,
(±)-{[7-(2,4,6-trichlorophenyl)-2,3-dihydro-1-benzofuran-2-yl]methyl}amine,
(±)-{[7-(5-chloro-2-methylphenyl)-2,3-dihydro-1-benzofuran-2-yl]methyl}amine,
(+)-{[7-pyridin-3-yl-2,3-dihydro-1-benzofuran-2-yl]methyl}amine, (+)-{[5-fluoro-7-pyridin-3-yl-2,3-dihydro-1-benzofuran-2-yl]methyl}amine,
(±)-{[7-(2,4-dichlorophenyl)-5-fluoro-2,3-dihydro-1-benzofuran-2-yl]methyl}amine,
(+)-{[5-fluoro-7-(2,4-dichlorophenyl)-2,3-dihydro-1-benzofuran-2-yl]methyl}amine,
(±)-N-{[7-(2,6-dichlorophenyl)-5-fluoro-2,3-dihydro-1-benzofuran-2-yl]methyl}cyclopropanamine,
(±)-{[5-chloro-7-(2,6-dichlorophenyl)-2,3-dihydro-1-benzofuran-2-yl]methyl}amine,
(±)-{[7-(2,4-dichlorophenyl)-5-methyl-2,3-dihydro-1-benzofuran-2-yl]methyl}amine,
(+)-{[7-(2,4-dichlorophenyl)-5-methyl-2,3-dihydro-1-benzofuran-2-yl]methyl}amine,
(±)-{[5-ethyl-7-(2-chlorophenyl)-2,3-dihydro-1-benzofuran-2-yl]methyl}amine,
(±)-N-{[7-(2,6-dichlorophenyl)-2,3-dihydro-1-benzofuran-2-yl]methyl}cyclopropanamine,
(±)-{[6-fluoro-7-(2-methylphenyl)-2,3-dihydro-1-benzofuran-2-yl]methyl}amine,
(±)-{[{[7-(2-chlorophenyl)-6-fluoro-2,3-dihydro-1-benzofuran-2-yl]methyl}amine,
(±)-{[6-fluoro-7-(2-methylphenyl)-2,3-dihydro-1-benzofuran-2-yl]methyl}methylamine,
(±)-{[6-fluoro-7-(2-chlorophenyl)-2,3-dihydro-1-benzofuran-2-yl]methyl}methylamine,
(+)-N-methyl-1-[7-(2-chlorophenyl)-2,3-dihydro-1-benzofuran-2-yl]methanamine,
(±)-[(N-methyl-1-[7-(2,6-dichlorophenyl)-2,3-dihydro-1-benzofuran-2-yl]methanamine,
(±)-[7-(2,4-dichlorophenyl)-5-fluoro-2,3-dihydro-1-benzofuran-2-yl]methyl}methylamine,
(+)-{[5-fluoro-7-(2,5-dichlorophenyl)-2,3-dihydro-1-benzofuran-2-yl]methyl}methylamine,
(±)-{[7-(2,6-dichlorophenyl)-5-fluoro-2,3-dihydro-1-benzofuran-2-yl]methyl}methylamine, or
(−)-{[7-(2,6-dichlorophenyl)-5-fluoro-2,3-dihydro-1-benzofuran-2-yl]methyl}amine;
or a pharmaceutically acceptable salt thereof.

21. The compound of claim 2 which is:
(±)-(7-cyclopentyl-2,3-dihydro-1-benzofuran-2-yl)methylamine,
(±)-(7-isopropyl-2,3-dihydro-1-benzofuran-2-yl)methylamine,
(±)-1-(7-tert-butyl-2,3-dihydro-1-benzofuran-2-yl)methanamine,
(±)-1-{7-[3,5-bis(trifluoromethyl)phenyl]-2,3-dihydro-1-benzofuran-2-yl}methanamine,
(±)-1-[7-(3-chloro-4-fluorophenyl)-2,3-dihydro-1-benzofuran-2-yl]methanamine,
(±)-1-[7-(3,5-dichlorophenyl)-2,3-dihydro-1-benzofuran-2-yl]methanamine,
(±)-1-[7-(3-methylphenyl)-2,3-dihydro-1-benzofuran-2-yl]methanamine,
(±)-1-(7-thien-3-yl-2,3-dihydro-1-benzofuran-2-yl)methanamine,
(±)-1-[7-(2-methylphenyl)-2,3-dihydro-1-benzofuran-2-yl]methanamine,
(±)-1-[7-(2-fluorophenyl)-2,3-dihydro-1-benzofuran-2-yl]methanamine,
(±)-1-{7-[2-(trifluoromethyl)phenyl]-2,3-dihydro-1-benzofuran-2-yl}methanamine,
(±)-1-[7-(2,6-dimethylphenyl)-2,3-dihydro-1-benzofuran-2-yl]methanamine,
(±)-1-[7-(2-methoxyphenyl)-2,3-dihydro-1-benzofuran-2-yl]methanamine,
(±)-1-[7-(2-chlorophenyl)-2,3-dihydro-1-benzofuran-2-yl]methanamine,
(±)-[7-(2-isopropylphenyl)-2,3-dihydro-1-benzofuran-2-yl]methanamine,
(±)-1-[7-(3-fluorophenyl)-2,3-dihydro-1-benzofuran-2-yl]methanamine,
(±)-1-[7-(3-chlorophenyl)-2,3-dihydro-1-benzofuran-2-yl]methanamine,
(±)-1-[7-(3-methoxyphenyl)-2,3-dihydro-1-benzofuran-2-yl]methanamine,
(±)-1-{7-[3-(trifluoromethyl)phenyl]-2,3-dihydro-1-benzofuran-2-yl}methanamine,
(±)-1-[7-(4-methylphenyl)-2,3-dihydro-1-benzofuran-2-yl]methanamine,
(±)-1-[7-(4-fluorophenyl)-2,3-dihydro-1-benzofuran-2-yl]methanamine,
(±)-1-[7-(4-chlorophenyl)-2,3-dihydro-1-benzofuran-2-yl]methanamine,
(±)-1-[7-(4-methoxyphenyl)-2,3-dihydro-1-benzofuran-2-yl]methanamine,
(±)-1-{7-[4-(trifluoromethyl)phenyl]-2,3-dihydro-1-benzofuran-2-yl}methanamine,
(±)-1-[7-(2,4-dichlorophenyl)-2,3-dihydro-1-benzofuran-2-yl]methanamine,
(±)-1-[7-(2-chlorophenyl)-5-fluoro-2,3-dihydro-1-benzofuran-2-yl]methanamine,
(±)-1-[7-(2,6-difluorophenyl)-2,3-dihydro-1-benzofuran-2-yl]methanamine,
(±)-1-[7-(2,6-dichlorophenyl)-2,3-dihydro-1-benzofuran-2-yl]methanamine,
(±)-1-[7-(2,4-dimethoxyphenyl)-2,3-dihydro-1-benzofuran-2-yl]methanamine,
(±)-1-[7-(2,4-difluorophenyl)-2,3-dihydro-1-benzofuran-2-yl]methanamine,
or a pharmaceutically acceptable salt thereof.

22. The compound of claim 2 which is:
(±)-(5-chloro-7-cyclohexyl-2,3-dihydro-1-benzofuran-2-yl)methylamine,
(±)-N-[(5-chloro-7-cyclohexyl-2,3-dihydro-1-benzofuran-2-yl)methyl]-N-methylamine,
(±)-1-[5-chloro-7-(2-chlorophenyl)-2,3-dihydro-1-benzofuran-2-yl]methanamine,
(±)-1-[5-chloro-7-(3-methylphenyl)-2,3-dihydro-1-benzofuran-2-yl]methanamine,
(±)-1-[5-chloro-7-(3-chlorophenyl)-2,3-dihydro-1-benzofuran-2-yl]methanamine,
(±)-(5-chloro-7-thien-3-yl-2,3-dihydro-1-benzofuran-2-yl)methylamine,
(±)-1-[5-chloro-7-(2-methylphenyl)-2,3-dihydro-1-benzofuran-2-yl]methanamine,
(±)-1-[4-fluoro-7-(2-methylphenyl)-2,3-dihydro-1-benzofuran-2-yl]methanamine,
(±)-1-[5-fluoro-7-(2-methylphenyl)-2,3-dihydro-1-benzofuran-2-yl]methanamine,
(±)-1-[5-fluoro-7-(2-fluorophenyl)-2,3-dihydro-1-benzofuran-2-yl]methanamine,
(±)-1-{[5-fluoro-7-[2-(trifluoromethyl)phenyl]-2,3-dihydro-1-benzofuran-2-yl}methanamine,
(±)-1-[4,5-difluoro-7-(2-methylphenyl)-2,3-dihydro-1-benzofuran-2-yl]methanamine,
(±)-1-(5-chloro-2-methyl-7-phenyl-2,3-dihydro-1-benzofuran-2-yl)methanamine,
(±)-(5-chloro-2-methyl-7-thien-3-yl-2,3-dihydro-1-benzofuran-2-yl)methylamine,
(±)-(5-chloro-2-methyl-7-thien-2-yl-2,3-dihydro-1-benzofuran-2-yl)methylamine, or
or a pharmaceutically acceptable salt thereof.

23. The compound of claim 2 which is:
(−)-(7-cyclopentyl-2,3-dihydro-1-benzofuran-2-yl)methylamine,
(+)-(7-cyclopentyl-2,3-dihydro-1-benzofuran-2-yl)methylamine,
(−)-1-[7-(3-methylphenyl)-2,3-dihydro-1-benzofuran-2-yl]methanamine,
(−)-1-(7-thien-3-yl-2,3-dihydro-1-benzofuran-2-yl)methanamine,
(+)-[7-(2-isopropylphenyl)-2,3-dihydro-1-benzofuran-2-yl]methylamine,
(−)-[7-(2-isopropylphenyl)-2,3-dihydro-1-benzofuran-2-yl]methylamine,
(−)-1-[7-(3-chlorophenyl)-2,3-dihydro-1-benzofuran-2-yl]methanamine,
(−)-1-[7-(4-fluorophenyl)-2,3-dihydro-1-benzofuran-2-yl]methanamine,
(+)-(5-chloro-7-thien-3-yl-2,3-dihydro-1-benzofuran-2-yl)methylamine,
(−)-N-[(5-chloro-7-thien-3-yl-2,3-dihydro-1-benzofuran-2-yl)methyl]-N-methylamine,
(−)-1-[7-(3-fluorophenyl)-2,3-dihydro-1-benzofuran-2-yl]methanamine,
(−)-1-[7-(3-methoxyphenyl)-2,3-dihydro-1-benzofuran-2-yl]methanamine,
(−)-1-{[7-[3-(trifluoromethyl)phenyl]-2,3-dihydro-1-benzofuran-2-yl}methanamine,
(+)-1-{[7-[3-(trifluoromethyl)phenyl]-2,3-dihydro-1-benzofuran-2-yl}methanamine, or
(−)-1-{[7-[4-(trifluoromethyl)phenyl]-2,3-dihydro-1-benzofuran-2-yl}methanamine;
or a pharmaceutically acceptable salt thereof.

24. The compound of claim 2 which is:
(+)-1-[7-(3-methylphenyl)-2,3-dihydro-1-benzofuran-2-yl]methanamine,
(+)-1-(7-thien-3-yl-2,3-dihydro-1-benzofuran-2-yl)methanamine,
(−)-1-[7-(2-methylphenyl)-2,3-dihydro-1-benzofuran-2-yl]methanamine,
(−)-1-[7-(2-fluorophenyl)-2,3-dihydro-1-benzofuran-2-yl]methanamine,
(+)-1-{7-[2-(trifluoromethyl)phenyl]-2,3-dihydro-1-benzofuran-2-yl}methanamine,
(+)-1-[7-(2,6-dimethylphenyl)-2,3-dihydro-1-benzofuran-2-yl]methanamine,
(+)-1-[7-(3-chlorophenyl)-2,3-dihydro-1-benzofuran-2-yl]methanamine,
(−)-1-[7-(4-methylphenyl)-2,3-dihydro-1-benzofuran-2-yl]methanamine,
(−)-1-[7-(4-chlorophenyl)-2,3-dihydro-1-benzofuran-2-yl]methanamine,
(−)-1-[7-(4-methoxyphenyl)-2,3-dihydro-1-benzofuran-2-yl]methanamine,
(−)-(5-chloro-7-thien-3-yl-2,3-dihydro-1-benzofuran-2-yl)methylamine,
(+)-N-[(5-chloro-7-thien-3-yl-2,3-dihydro-1-benzofuran-2-yl)methyl]-N-methylamine,
(−)-1-[5-chloro-7-(2-methylphenyl)-2,3-dihydro-1-benzofuran-2-yl]methanamine,
(−)-1-[7-(2-chlorophenyl)-5-fluoro-2,3-dihydro-1-benzofuran-2-yl]methanamine,
(−)-1-[5-fluoro-7-(2-methylphenyl)-2,3-dihydro-1-benzofuran-2-yl]methanamine,
(+)-1-[7-(2-methoxyphenyl)-2,3-dihydro-1-benzofuran-2-yl]methanamine,
(+)-1-[7-(3-fluorophenyl)-2,3-dihydro-1-benzofuran-2-yl]methanamine,
(+)-1-[7-(3-methoxyphenyl)-2,3-dihydro-1-benzofuran-2-yl]methanamine,
(+)-1-{7-[4-(trifluoromethyl)phenyl]-2,3-dihydro-1-benzofuran-2-yl}methanamine,
(+)-1-[7-(2,6-dichlorophenyl)-2,3-dihydro-1-benzofuran-2-yl]methanamine,
(+)-1-[7-(2,4-dimethoxyphenyl)-2,3-dihydro-1-benzofuran-2-yl]methanamine,
(+)-1-[7-(2,4-dichlorophenyl)-2,3-dihydro-1-benzofuran-2-yl]methanamine, or
(+)-1-{[5-fluoro-7-[2-(trifluoromethyl)phenyl]-2,3-dihydro-1-benzofuran-2-yl}methanamine;
or a pharmaceutically acceptable salt thereof.

25. The compound of claim 2 which is:
(+)-1-[7-(2-methylphenyl)-2,3-dihydro-1-benzofuran-2-yl]methanamine,
(+)-1-[7-(2-fluorophenyl)-2,3-dihydro-1-benzofuran-2-yl]methanamine,
(−)-1-{7-[2-(trifluoromethyl)phenyl]-2,3-dihydro-1-benzofuran-2-yl}methanamine,
(−)-1-[7-(2,6-dimethylphenyl)-2,3-dihydro-1-benzofuran-2-yl]methanamine,
(+)-1-[7-(4-methylphenyl)-2,3-dihydro-1-benzofuran-2-yl]methanamine,
(+)-1-[7-(4-fluorophenyl)-2,3-dihydro-1-benzofuran-2-yl]methanamine,
(+)-1-[7-(4-chlorophenyl)-2,3-dihydro-1-benzofuran-2-yl]methanamine,
(+)-1-[7-(4-methoxyphenyl)-2,3-dihydro-1-benzofuran-2-yl]methanamine,
(+)-1-[5-chloro-7-(2-methylphenyl)-2,3-dihydro-1-benzofuran-2-yl]methanamine,
(+)-1-[7-(2-chlorophenyl)-5-fluoro-2,3-dihydro-1-benzofuran-2-yl]methanamine,
(+)-1-[5-fluoro-7-(2-methylphenyl)-2,3-dihydro-1-benzofuran-2-yl]methanamine,
(−)-1-[7-(2-chlorophenyl)-2,3-dihydro-1-benzofuran-2-yl]methanamine,
(+)-1-[7-(2-chlorophenyl)-2,3-dihydro-1-benzofuran-2-yl]methanamine,
(−)-1-[7-(2,6-dichlorophenyl)-2,3-dihydro-1-benzofuran-2-yl]methanamine,
(−)-1-[7-(2,4-dimethoxyphenyl)-2,3-dihydro-1-benzofuran-2-yl]methanamine,
(+)-1-[7-(2,4-difluorophenyl)-2,3-dihydro-1-benzofuran-2-yl]methanamine,
(−)-1-[7-(2,4-difluorophenyl)-2,3-dihydro-1-benzofuran-2-yl]methanamine,
(−)-1-[7-(2,4-dichlorophenyl)-2,3-dihydro-1-benzofuran-2-yl]methanamine, or
(−)-1-{5-fluoro-7-[2-(trifluoromethyl)phenyl]-2,3-dihydro-1-benzofuran-2-yl}methanamine;
or a pharmaceutically acceptable salt thereof.

26. The compound of claim 2 which is: (±)-{[7-(2,6-dichlorophenyl)-5-fluoro-2,3-dihydro-1-benzofuran-2-yl]methyl}amine, or pharmaceutically acceptable salt thereof.

27. The compound of claim 2 which is: (±)-{[7-(2,6-dichlorophenyl)-5-fluoro-2,3-dihydro-1-benzofuran-2-yl]methyl}amine, or pharmaceutically acceptable salt thereof.

28. The compound of claim 2 which is: (−)-{[7-(2,6-dichlorophenyl)-5-fluoro-2,3-dihydro-1-benzofuran-2-yl]methyl}amine, or pharmaceutically acceptable salt thereof.

29. The compound of claim 28 wherein the pharmaceutically acceptable salt is a hydrochloride salt.

30. The compound of claim 27 wherein the pharmaceutically acceptable salt is a hydrochloride salt.

31. The compound of claim 26 wherein the pharmaceutically acceptable salt is a hydrochloride salt.

\* \* \* \* \*